(12) United States Patent
Gluchowski et al.

(10) Patent No.: US 6,211,198 B1
(45) Date of Patent: *Apr. 3, 2001

(54) DIHYDROPYRIDINES AND NEW USES THEREOF

(75) Inventors: Charles Gluchowski, Wayne; John M. Wetzel, Elmwood Park; George Chiu, Bridgewater; Mohammed R. Marzabadi, Ridgewood; Wai C. Wong, Newark; Dhanapalan Nagarathnam, Ramsey, all of NJ (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/098,699

(22) Filed: Jun. 15, 1998

Related U.S. Application Data

(60) Division of application No. 08/211,764, filed as application No. PCT/US94/23852 on Apr. 5, 1994, now Pat. No. 5,767,131, which is a continuation-in-part of application No. 08/166,367, filed on Dec. 10, 1993, now abandoned, which is a continuation-in-part of application No. 08/120,169, filed on Sep. 10, 1993, now abandoned, which is a continuation-in-part of application No. 08/043,212, filed on Apr. 5, 1993, now abandoned.

(51) Int. Cl.$^7$ .................. A61K 31/4545; C07D 401/12
(52) U.S. Cl. ............................. 514/318; 546/194
(58) Field of Search ............... 514/318; 546/194

(56) References Cited

U.S. PATENT DOCUMENTS 4,652,573   3/1987   Minaskanian et al. ............... 514/356

(List continued on next page.)

FOREIGN PATENT DOCUMENTS 35 12 995   10/1985 (DE).

(List continued on next page.)

OTHER PUBLICATIONS

Archibald, J.L., et al., "Antihypertensive Ureidopiperidines" *Journal of Medical Chemistry* (1980) 23: 857–861.

(List continued on next page.)

*Primary Examiner*—Jane Fan
(74) *Attorney, Agent, or Firm*—John P. White; Cooper & Dunham LLP

(57) ABSTRACT

The invention provides a method of treating benign prostatic hyperplasia in a subject which comprises administering to the subject a therapeutically effective amount of a compound having the structure:

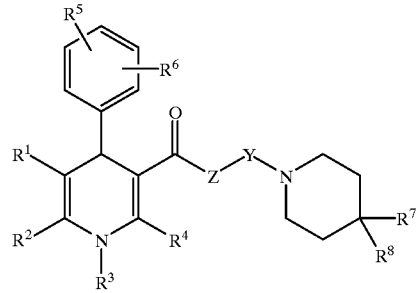

wherein Y is —$(CH_2)_n$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$—, where h and k are independently the same or different and are 1, 2, 3 or 4; wherein Z is O, NH, or $CH_2$; wherein $R^1$ is a linear or branched chain alkyl, alkoxyalkyl or arylalkyl group; wherein $R^2$ and $R^4$ are independently the same or different and are H, or a linear or branched chain alkyl group; wherein $R^3$ is H, a linear or branched chain alkyl, alkoxy, alkoxyalkyl or acyl group; and wherein $R^5$ and $R^6$ are independently the same or different and are H, OH, Cl, Br, F, $NO_2$, CN, $CF_3$, or $NH_2$, or a linear or branched chain alkyl, alkoxy, alkoxycarbonyl, acyl, alkylsulfoxide, alkylsulfone, or mono- or dialkylamino group. Other active compounds containing one, two or three rings are also disclosed as well as pharmaceutical compositions prepared therefrom and methods of use in the treatment of BPH, inhibition of cholesterol synthesis, and reduction of intraocular pressure.

16 Claims, 4 Drawing Sheets

Reaction Scheme 1 (Method A)

U.S. PATENT DOCUMENTS

| | | | |
|---|---|---|---|
| 4,707,486 | 11/1987 | Flockerzi et al. | 514/318 |
| 4,853,393 | 8/1989 | Poindexter et al. | 514/356 |
| 4,895,846 | 1/1990 | Poindexter et al. | 514/252 |
| 4,937,242 | 6/1990 | Matsui et al. | 514/235.8 |
| 4,975,440 | 12/1990 | Flockerzi et al. | 514/318 |
| 4,994,461 | 2/1991 | Ulrich | 514/252 |
| 5,017,586 | 5/1991 | Schlager | 514/318 |
| 5,158,963 | 10/1992 | Nakanishi et al. | 514/356 |
| 5,326,772 | 7/1994 | Klemm et al. | 514/318 |
| 5,403,847 | 4/1995 | Gluchowski et al. | 514/318 |

FOREIGN PATENT DOCUMENTS

| | | |
|---|---|---|
| 37 09 796 | 11/1987 | (DE) . |
| 0071819 | 2/1983 | (EP) . |
| 0176956 | 4/1986 | (EP) . |
| 0197488 | 10/1986 | (EP) . |
| 0255710 | 2/1988 | (EP) . |
| 0289746 | 11/1988 | (EP) . |
| 9109846 | 7/1991 | (WO) . |
| 9118599 | 12/1991 | (WO) . |
| 9200741 | 1/1992 | (WO) . |

OTHER PUBLICATIONS

Boer, R., et al., "(+)–Niguldipine Binds With Very High Affinity to $Ca^{2+}$ Channels and to a Subtype of $\alpha_1$–Adrenoreceptors" *European Journal of Pharmacology—Molecular Pharmacology Section* (1989) 172: 131–145, The Netherlands.

Isaacs, J.T., "Importance of the Natural History of benign Prostactic Hyperplasia In The Evaluation of Pharmacologic Intervention" *The Prostate* (1990) Supplement 3, pp. 1–7.

Hieble, J.P., et al., "In Vitro Characterization of the $\alpha$–Adrenoreceptors in Human Prostate" *European Journal of Pharmacology* (1985) 107: 111–117.

Herbert Lepor, "Role of Alpha–Adrenergic Blockers in the Treatment of Benign Prostatic Hyperplasia" *The Prostate* (1990) Supplement 3: 75–84.

D.L. Murray and I.H. Leopold, "Alpha–adrenergic receptors in rabbit eyes" *Journal of Ocular Pharmacology* (Spring 1985) 1(1): 3–18.

Yamada, S., et al. "Alpha–1 Adrenoceptors in Human Prostate: Characterization and Alteration in Benign Prostatic Hypertrophy" *Journal of Pharmacology and Experimental Therapeutics* (1987) 242: 326–330.

DIHYDROPYRIDINES AND NEW USES THEREOF

This application is a divisional of U.S. Ser. No. 08/211,764, filed Feb. 23, 1996, now U.S. Pat. No. 5,767,131, issued Jun. 16, 1998, which is a 371 national stage filing of PCT/US94/03852, filed Apr. 5, 1994, which is a continuation-in-part of U.S. Ser. No. 08/166,367, filed Dec. 10, 1993, now abandoned, which is a continuation-in-part of U.S. Ser. No. 08/120,169, filed Sep. 10, 1993, now abandoned, which is a continuation-in-part of U.S. Ser. No. 08/043,212, filed Apr. 5, 1993, now abandoned, the contents of which are hereby incorporated by reference into this application.

BACKGROUND OF THE INVENTION

Benign Prostatic Hyperplasia (BPH), also called Benign Prostatic Hypertrophy, is a progressive condition which is characterized by a nodular enlargement of prostatic tissue resulting in obstruction of the urethra. This results in increased frequency of urination, nocturia, a poor urine stream and hesitancy or delay in starting the urine flow. Chronic consequences of BPH can include hypertrophy of bladder smooth muscle, a decompensated bladder and an increased incidence of urinary tract infection. The specific biochemical, histological and pharmacological properties of the prostate adenoma leading to the bladder outlet obstruction are not yet known. However, the development of BPH is considered to be an inescapable phenomenon for the aging male population. BPH is observed in approximately 70% of males over the age of 70. Currently, in the United States, the method of choice for treating BPH is surgery (Lepor, H., Urol. Clinics North Amer., 17, 651 (1990)). Over 400,000 prostatectomies are performed annually (data from 1986). A medicinal alternative to surgery is clearly very desirable. The limitations of surgery for treating BPH include the morbidity rate of an operative procedure in elderly men, persistence or recurrence of obstructive and irritative symptoms, as well as the significant cost of surgery.

$\alpha$-Adrenergic receptors are specific neuroreceptor proteins located in the peripheral and central nervous systems on tissues throughout the body. These receptors are important switches for controlling many physiological functions and, thus, represent important targets for drug development. In fact, many $\alpha$-adrenergic drugs have been developed over the past 40 years. Examples include clonidine, phenoxybenzamine and prazosin (treatment of hypertension), naphazoline (nasal decongestant), and apraclonidine (treating glaucoma). $\alpha$-Adrenergic drugs can be broken down into two distinct classes: agonists (clonidine and naphazoline are agonists), which mimic the receptor activation properties of the endogenous neurotransmitter norepinephrine, and antagonists (phenoxybenzamine and prazosin are antagonists), which act to block the effects of norepinephrine. Many of these drugs are effective but also produce unwanted side effects (for example, clonidine produces dry mouth and sedation in addition to its antihypertensive effects).

During the past 15 years a more precise understanding of $\alpha$-adrenergic receptors and their drugs has evolved through increased scientific scrutiny. Prior to 1977, only one $\alpha$-adrenergic receptor was known to exist. Between 1977 and 1988, it was accepted by the scientific community that at least two $\alpha$-adrenergic receptors—$\alpha_1$ and $\alpha_2$—existed in the central and peripheral nervous systems. Since 1988, new techniques in molecular biology have led to the identification of at least six $\alpha$-adrenergic receptors which exist throughout the central and peripheral nervous systems: $\alpha_{1A}$, $\alpha_{1B}$, $\alpha_{1C}$, $\alpha_{2A}$, $\alpha_{2B}$ and $\alpha_{2C}$ (Bylund, D. B., FASEB J., 6, 832 (1992)). It is not known precisely which physiological responses in the body are controlled by each of these receptors. In addition, many $\alpha$-adrenergic drugs that were developed before 1992 are not selective for any particular $\alpha$-adrenergic receptor. Many of these drugs produce untoward side effects which may be attributed to their poor $\alpha$-adrenergic receptor selectivity.

Since the mid 1970's, nonselective $\alpha$-antagonists have been prescribed to treat BPH. In 1976, M. Caine, et al. (Brit. J. Urol., 48, 255 (1976)), reported that the nonselective $\alpha$-antagonist phenoxybenzamine was useful in relieving the symptoms of BPH. This drug may produce its effects by interacting with $\alpha$-receptors located on the prostate. However, this drug also produces significant side effects which severely limit its use in treating patients on a chronic basis. More recently, the $\alpha$-adrenergic antagonists prazosin and terazosin have also been found to be useful for treating BPH. However, these drugs also produce untoward side effects.

This invention relates to uses for dihydropyridine derivatives previously reported in Flockerzi, D., et. al., U.S. Pat. No. 4,707,486, issued Nov. 17, 1987, and Zimmerman, P., et.al., PCT International Patent Application WO 91/09846, published Jul. 11, 1991, including methods of treatment of BPH. This invention also relates to novel dihydropyridine derivatives. This invention further relates to potent and selective alpha 1C antagonists without significant calcium channel activity.

BRIEF DESCRIPTION OF THE DRAWINGS

A more complete understanding of the invention and many of its advantages will become apparent by reference to the detailed description which follows when considered in conjunction with the accompanying drawings, wherein.

SUMMARY OF THE INVENTION

Figure 1:
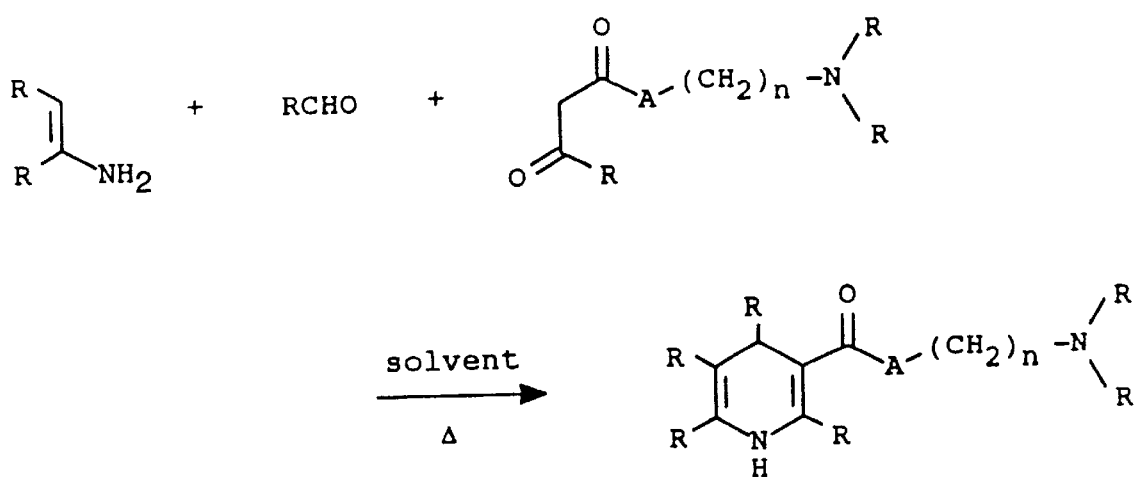
FIG. 1 illustrates condensation to form dihydropyridines by Reaction Scheme 1 (Method A).
Figure 2:
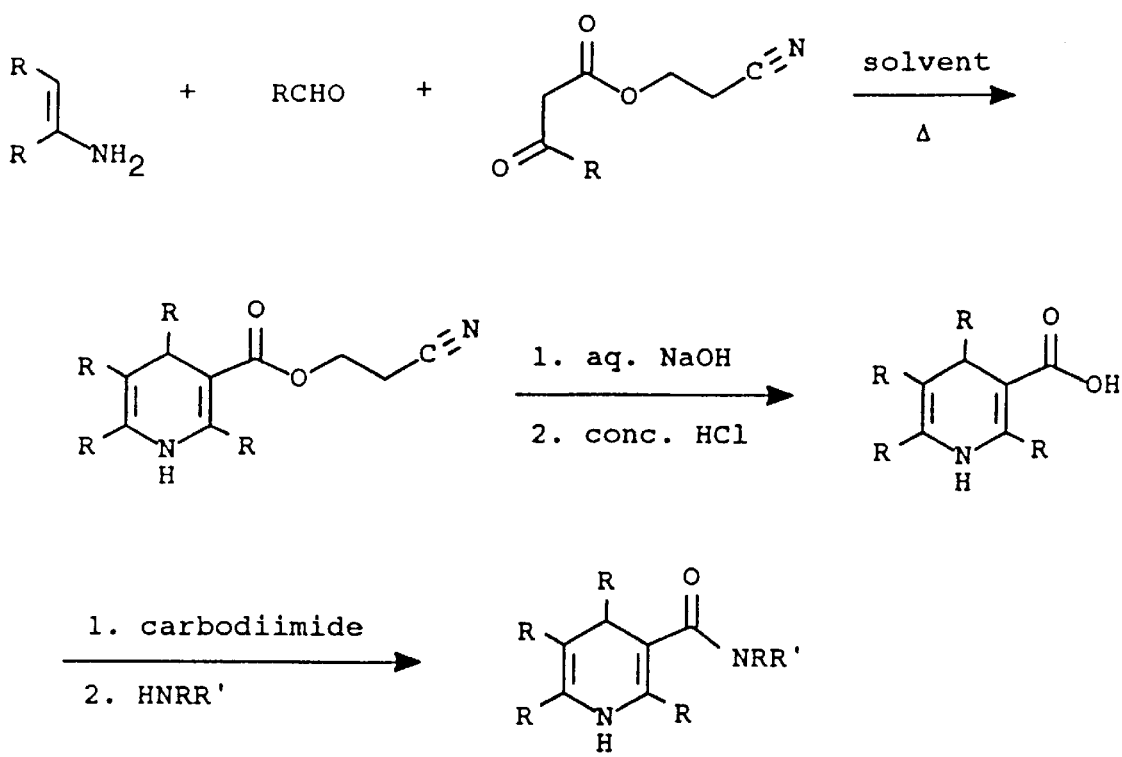
FIG. 2 illustrates condensation to form dihydropyridines by Reaction Scheme 2 (Method B).
Figure 3:
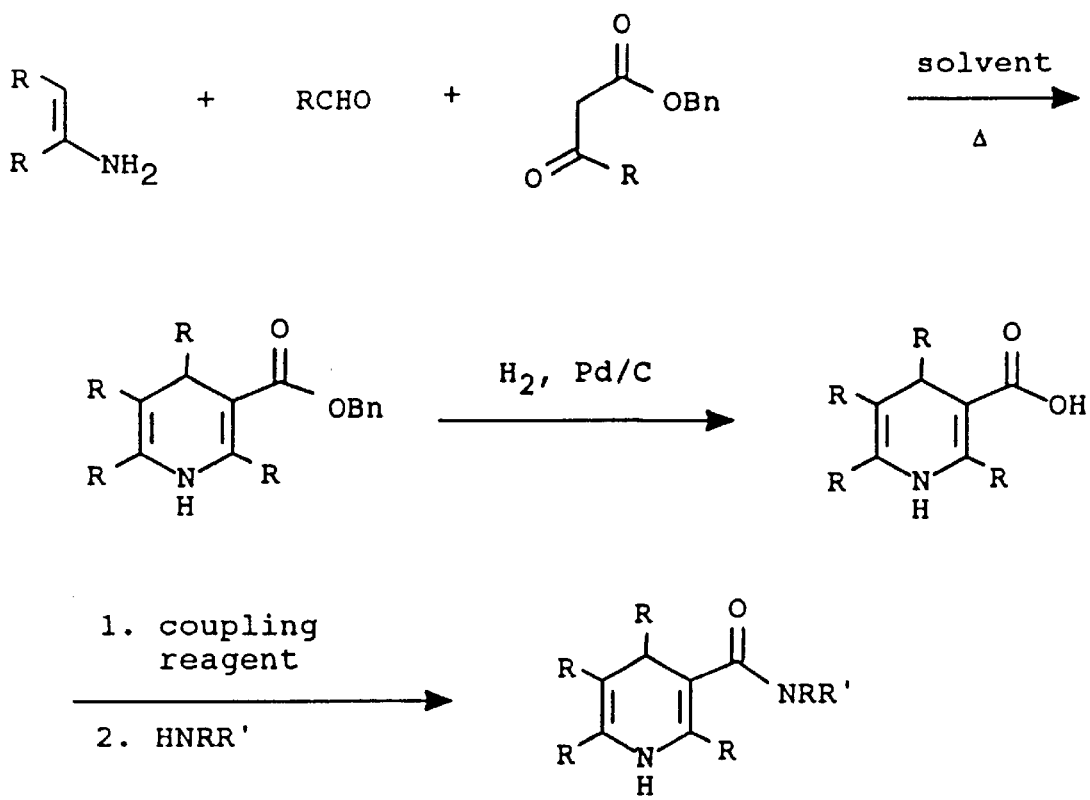
FIG. 3 illustrates condensation to form dihydropyridines by Reaction Scheme 3 (Method C).
Figure 4:
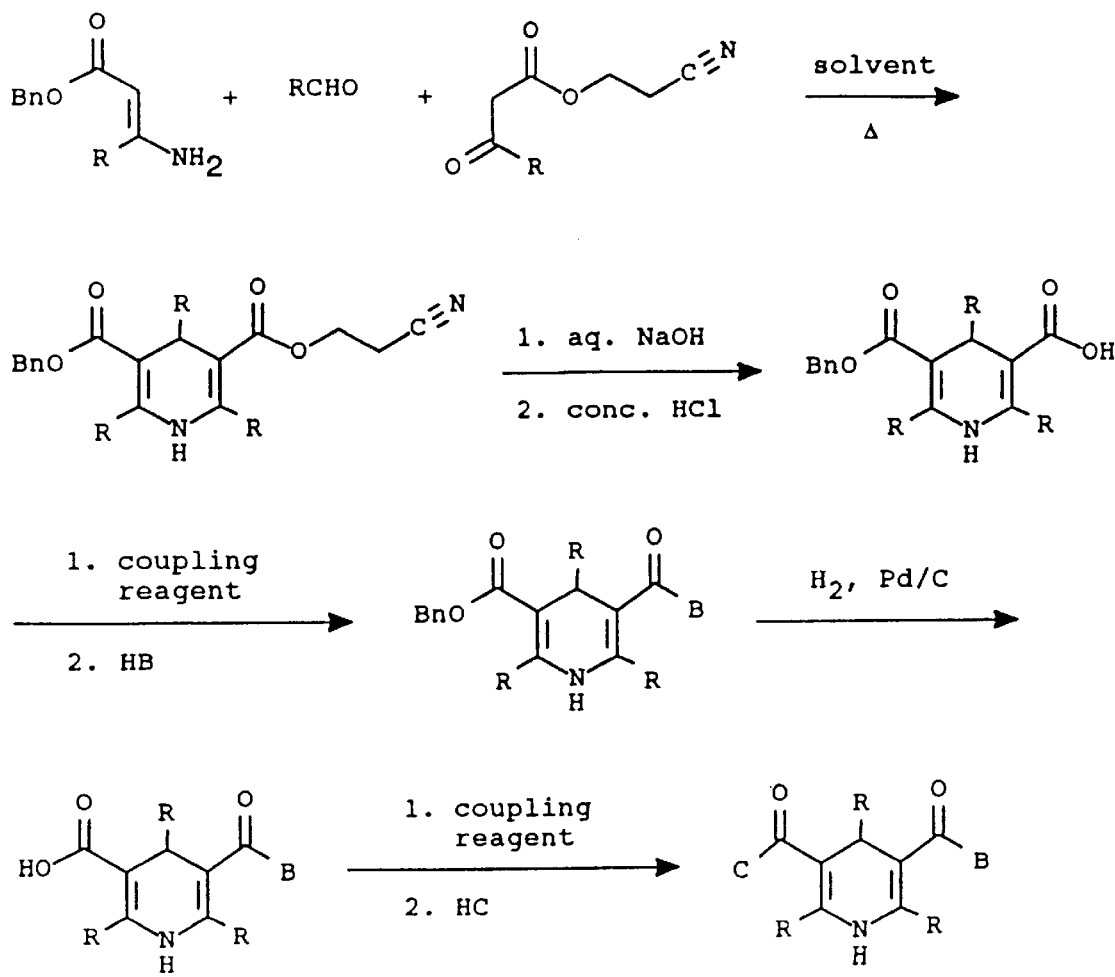
FIG. 4 illustrates condensation to form dihydropyridines by Reaction Scheme 4 (Method D).

The present invention provides a method of treating benign prostatic hyperplasia in a subject which comprises administering to the subject a therapeutically effective amount of a compound having the structure:

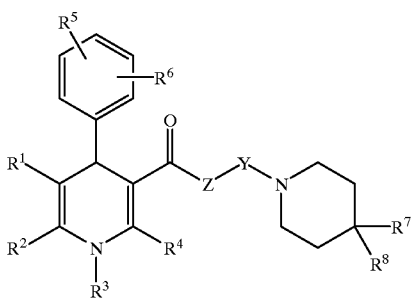

wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH or CH$_2$; wherein R$^1$ is a linear or branched chain alkyl, alkoxyalkyl or arylalkyl group; wherein R$^2$ and R$^4$ are independently the same or different and are H, or a linear or branched chain alkyl group; wherein R$^3$ is H, a linear or branched chain alkyl, alkoxy, alkoxyalkyl or acyl group; wherein R$^5$ and R$^6$ are independently the same or different and are H, OH, Cl, Br, I, F, NO$_2$, N$_3$, CN, CF$_3$ or NH$_2$, or a linear or branched chain alkyl, alkoxy, alkoxycarbonyl, acyl, alkylsulfoxide, alkylsulfone or mono- or dialkylamino group; and wherein R$^7$ and R$^8$ are independently the same or different and are H, CN, CF$_3$, OH, OR, OCOR, NH$_2$, NHR, NR$_2$, or NHCOR, where R is a linear chain alkyl group, a benzyl group, a linear or branched chain alkyl or cycloalkyl group, or are a heteroaryl group comprising a pyridyl, indolyl, indolylalkyl, quinolinyl, isoquinolinyl, pyrryl, furyl, or thiophene group, or an aryl group having the structure:

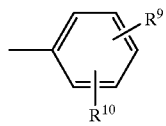

wherein R$^9$ and R$^{10}$ are independently the same or different and are H, Cl, Br, F, OH, OR', OCOR', OCOOR', OCONHR', NH$_2$, NHR', NR'$_2$, NHCOR', NHCOOR' or NHCONHR', where R' is a linear or branched chain alkyl group.

The invention still further provides a method of treating diseases mediated by a, receptors in a subject which comprises administering to the subject a therapeutically effective amount of a compound having the structure:

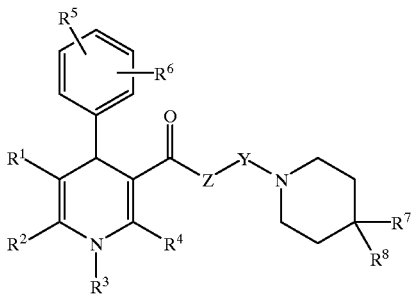

wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein R$^1$ is a linear or branched chain alkyl, alkoxyalkyl or arylalkyl group; wherein R$^2$ and R$^4$ are independently the same or different and are H, or a linear or branched chain alkyl group; wherein R$^3$ is H, a linear or branched chain alkyl, alkoxy, alkoxyalkyl or acyl group; wherein R$^5$ and R$^6$ are independently the same or different and are H, OH, Cl, Br, F, NO$_2$, CN, CF$_3$ or NH$_2$, or a linear or branched chain alkyl, alkoxy, alkoxycarbonyl, acyl, alkylsulfoxide, alkylsulfone or mono-or dialkylamino group; and wherein R$^7$ and R$^8$ are independently the same or different and are H, CN, CF$_3$, OH, OR", OCOR", NH$_2$, NHR", NR"$_2$ or NHCOR", where R" is a linear chain alkyl group, a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

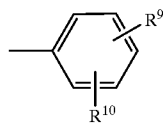

wherein R$^9$ and R$^{10}$ are independently the same or different and are H, Cl, Br, F, OH, OR''', OCOR''', OCOOR''', OCONHR''', NH$_2$, NHR''', NR'''$_2$, NHCOR''', NHCOOR''' or NHCONHR''', where R''' is a linear or branched chain alkyl group.

The invention further provides a compound having the structure:

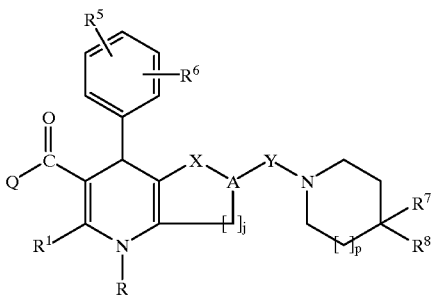

wherein Q is OH, OR", SH, SR''', NH$_2$, NHR''', NR$_2$''', NR"OH, NR"OR''' or a linear or branched chain alkyl group, or an arylalkyl group, or an alkenyl or alkynyl group, or an aryl group, where R" is H, a linear or branched chain alkyl group, trialkylsilylalkyl, cyanoalkyl or an aryl group, and R''' is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or (CH$_2$)$_v$W, where W is NH$_2$, NHR', NR$_2$', NHOH, N$^+$R$_3$'Z$^-$, NHCOR', N$_3$, NO$_2$, or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein X is C=O, $CH_2$, $CR^a_2$, NH, $NR^a$, NCHO, $NCOR^a$, NOH, O or S, where R' is a methyl, ethyl or propyl group; wherein $R^5$ and $R^6$ are independently the same or different and are H, OH, Cl, Br, I, F, $NO_2$, CN, $NH_2$, $N_3$ or $CF_3$, or a linear or branched chain alkyl, alkoxy, alkoxycarbonyl, acyl, alkylsulfoxide, alkylsulfone, or mono- or dialkylamino group, or together constitute a methylenedioxy group; wherein A is CH; wherein Y is —$(CH_2)_k$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$—, where h and k are independently the same or different and are 1, 2, 3 or 4; wherein j is 1 or 2; wherein p is 0, 1 or 2; and wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_q$OH or $COO(CH_2)_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

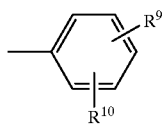

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5.

The invention further provides a compound having the structure:

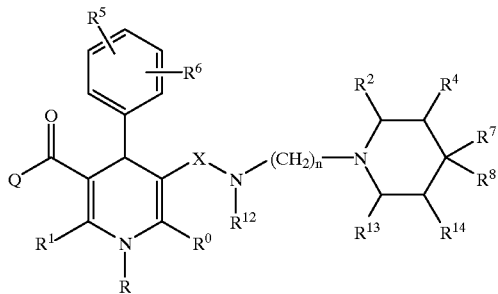

wherein X is C=O, $CH_2$, $CR^a_2$, NH, $NR^a$, NCHO, $NCOR^a$, NOH, O or S, where $R^a$ is a methyl, ethyl or propyl group; wherein Q is OH, OR'', SH, SR''', $NH_2$, NHR''', $NR_2'''$, NR''OH, NR''OR''' or a linear or branched chain alkyl group, or an arylalkyl group, or an alkenyl or alkynyl group, or an aryl group, where R'' is H, a linear or branched chain alkyl group, trialkylsilylalkyl, cyanoalkyl or an aryl group, and R''' is a linear or branched chain alkyl group, or an aryl group; wherein R is H, a linear or branched chain alkyl or acyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where W is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein R is H, a linear or branched chain alkyl or acyl group, or an aryl group; wherein $R^2_1$ $R^{13}$, and $R^{14}$ are independently the same or different and are H, or a linear or branched chain alkyl, hydroxyalkyl, alkoxyalkyl, amino alkyl, or aryl group; wherein $R^4$ is a linear or branched chain alkyl, alkoxyalkyl, hydroxyalkyl, or a linear or branched chain alkenylalkyl group; wherein $R^5$ and $R^6$ are independently the same or different and are H, OH, Cl, Br, I, F, $NO_2$, CN, $NH_2$, $N_3$, $CF_3$, a linear or branched chain alkyl, alkoxy, alkoxycarbonyl, acyl, alkylsulfoxide, alkylsulfoxide, or mono- or dialkylamino group, or together constitute a methylenedioxy group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_q$OH or $COO(CH_2)_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

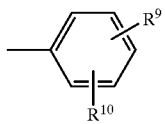

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{12}$ is H or a linear chain alkyl group; and wherein n is 2, 3 or 4.

A general objective of the invention is to provide a method of treating diseases mediated by a, receptors in a subject which comprises administering to the subject a therapeutically effective amount of a compound having the structure:

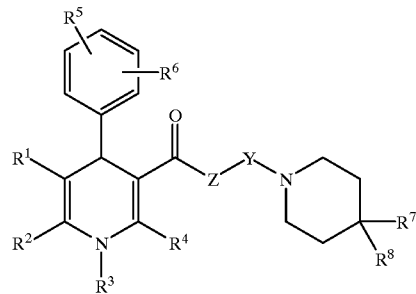

wherein Y is —$(CH_2)_n$—, where n is 1, 2, 3, 4, or 5; —$(CH_2)_h$—O—$(CH_2)_k$—, where h and k are independently the same or different and are 2, 3, or 4; —$(CH_2)_h$—CH=CH—$(CH_2)_k$—; or —$(CH_2)_h$—C≡C—$(CH_2)_k$—, where h and k are independently the same or different and are 1, 2, 3, or 4; wherein Z is O, NH, NCHO, NCOR, NR, NOR, or CH$_2$, where R is a methyl, ethyl, or propyl group; wherein R$^1$ is a linear or branched chain alkyl, alkoxyalkyl, or arylalkyl group; wherein R$^2$ and R$^4$ are independently the same or different and are H, or a linear or branched chain alkyl group; wherein R$^3$ is H, a linear or branched chain alkyl, alkoxy, alkoxyalkyl, or acyl group; wherein R$^5$ and R$^6$ are independently the same or different and are H, OH, Cl, Br, F, NO$_2$, CN, CF$_3$, or NH$_2$, or a linear or branched chain alkyl, alkoxy, alkoxycarbonyl, acyl, alkylsulfoxide, alkylsulfone, or mono- or dialkylamino group; and wherein R$^7$ and R$^8$ are independently the same or different and are H, CN, CF$_3$, OH, OR", OCOR", NH$_2$, NHR", NR"$_2$, or NHCOR", where R" is a linear chain alkyl group, a benzyl group, a linear or branched chain alkyl or cycloalkyl group, or are a heteroaryl group comprising a pyridyl, indolyl, indolylalkyl, quinolinyl, isoquinolinyl, pyrryl, furyl, or thiophene group, or an aryl group having the structure:

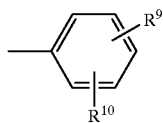

wherein R$^9$ and R$^{10}$ are independently the same or different and are H, Cl, Br, F, OH, OR''', OCOR''', OCOOR''', OCONHR''', NH$_2$, NHR''', NR'''$_2$, NHCOR''', NHCOOR''', NHCONHR''', where R''' is a linear or branched chain alkyl group.

In addition, the present invention provides a compound useful for the treatment of benign prostatic hyperplasia and other disorders having the structure:

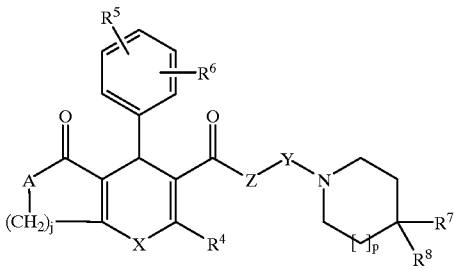

wherein A and X are independently the same or different and are CH$_2$, CR$_2$, NH, NR, NCHO, NCOR, NOH, O, or S, where R is a methyl, ethyl, or propyl group; wherein Y is —(CH$_2$)$_n$—, where n is 1, 2, 3, 4, or 5; —(CH$_2$)$_h$—O—(CH$_2$)$_k$—, where h and k are independently the same or different and are 2, 3, or 4; —(CH$_2$)$_h$—CH=CH—(CH$_2$)$_k$—; or —(CH$_2$)$_h$—C≡C—(CH$_2$)$_k$— where h and k are independently the same or different and are 1, 2, 3, or 4; wherein Z is O, NH, NCHO, NCOR', NR', NOR', or CH$_2$, where R' is a methyl, ethyl, or propyl group; wherein j is 1 or 2; wherein p is 0, 1, or 2; wherein R$^4$ is H, or a linear or branched chain, or cyclic alkyl group; wherein R$^5$ and R$^6$ are independently the same or different and are H, OH, Cl, Br, I, F, NO$_2$, CN, NH$_2$, or CF$_3$, or a linear or branched chain alkyl, alkoxy, alkoxycarbonyl, acyl, alkylsulfoxide, alkylsulfone, or mono- or dialkylamino group, or together constitute a methylenedioxy group; and wherein R$^7$ and R$^8$ are independently the same or different and are H, CN, CF$_3$, OH, OR", OCOR", NH$_2$, NHR", NR"$_2$, or NHCOR", where R" is a linear chain alkyl group, a benzyl group, a linear or branched chain alkyl or cycloalkyl group, or are a heteroaryl group comprising a pyridyl, indolyl, indolylalkyl, quinolinyl, isoquinolinyl, pyrryl, furyl, or thiophene group, or an aryl group having the structure:

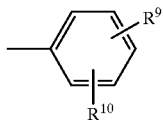

wherein R$^9$ and R$^{10}$ are independently the same or different and are H, Cl, Br, F, OH, OR''', OCOR''', OCOOR''', OCONHR''', NH$_2$, NHR''', NR'''$_2$, NHCOR''', NHCOOR''', NHCONHR''', where R''' is a linear or branched chain alkyl group.

DETAILED DESCRIPTION OF THE INVENTION

The present invention provides a method of treating benign prostatic hyperplasia in a subject which comprises administering to the subject a therapeutically effective amount of a compound having the structure:

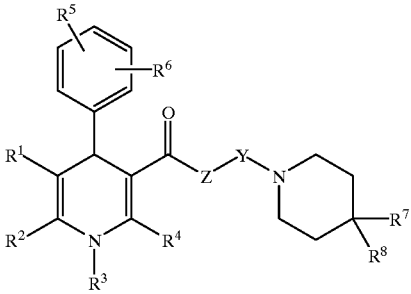

wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH or CH$_2$; wherein R$^1$ is a linear or branched chain alkyl, alkoxyalkyl or arylalkyl group; wherein R$^2$ and R$^4$ are independently the same or different and are H, or a linear or branched chain alkyl group; wherein R$^3$ is H, a linear or branched chain alkyl, alkoxy, alkoxyalkyl or acyl group; wherein R$^5$ and R$^6$ are independently the same or different and are H, OH, Cl, Br, I, F, NO$_2$, N$_3$, CN, CF$_3$ or NH$_2$, or a linear or branched chain alkyl, alkoxy, alkoxycarbonyl, acyl, alkylsulfoxide, alkylsulfone or mono- or dialkylamino group; and wherein R$^7$ and R$^8$ are independently the same or different and are H, CN, CF$_3$, OH, OR, OCOR, NH$_2$, NHR, NR$_2$, or NHCOR, where R is a linear chain alkyl group, a benzyl group, a linear or branched chain alkyl or cycloalkyl group, or are a heteroaryl group comprising a pyridyl, indolyl, indolylalkyl, quinolinyl, isoquinolinyl, pyrryl, furyl, or thiophene group, or an aryl group having the structure:

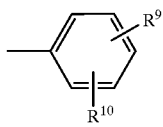

wherein R$^9$ and R$^{10}$ are independently the same or different and are H, Cl, Br, F, OH, OR', OCOR', OCOOR', OCONHR', NH$_2$, NHR', NR'$_2$, NHCOR', NHCOOR' or NHCONHR', where R' is a linear or branched chain alkyl group.

The invention also provides a method of lowering intraocular pressure in a subject which comprises administering to the subject a therapeutically effective amount of a compound having the structure:

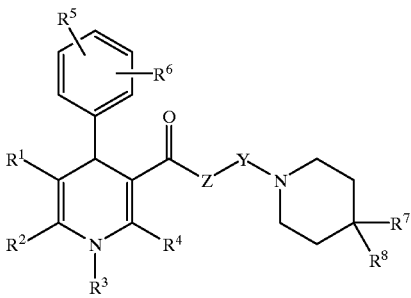

wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein R$^1$ is a linear or branched chain alkyl, alkoxyalkyl or arylalkyl group; wherein R$^2$ and R$^4$ are independently the same or different and are H, or a linear or branched chain alkyl group; wherein R$^3$ is H, a linear or branched chain alkyl, alkoxy, alkoxyalkyl or acyl group; wherein R$^5$ and R$^6$ are independently the same or different and are H, OH, Cl, Br, I, F, NO$_2$, N$_3$, CN, CF$_3$ or NH$_2$, or a linear or branched chain alkyl, alkoxy, alkoxycarbonyl, acyl, alkylsulfoxide, alkylsulfone or mono- or dialkylamino group; wherein R$^7$ and R$^8$ are independently the same or different and are H, CN, CF$_3$, OH, OR', OCOR', NH$_2$, NHR', NR'$_2$ or NHCOR', where R' is a linear chain alkyl group, or a benzyl group, or are a linear or branched chain alkyl or cycloalkyl group, a heteroaryl group comprising a pyridyl, indolyl, indolylalkyl, quinolinyl, isoquinolinyl, pyrryl, furyl or thiophene group, or an aryl group having the structure:

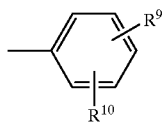

wherein R$^9$ and R$^{10}$ are independently the same or different and are H, Cl, Br, F, OH, OR", OCOR", OCOOR", OCONHR", NH$_2$, NHR", NR"$_2$, NHCOR", NHCOOR" or NHCONHR", where R" is a linear or branched chain alkyl group.

The invention further provides a method of inhibiting cholesterol synthesis in a subject which comprises administering to the subject a therapeutically effective amount of a compound having the structure:

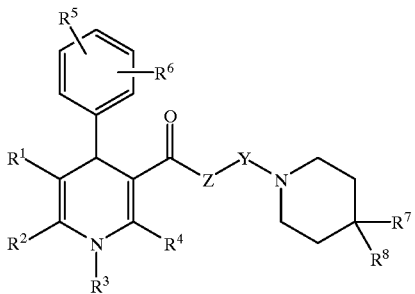

wherein A is CH$_2$, CR$_2$, NH, NR, NCHO, NCOR, NOH, O or S, where R is a methyl, ethyl or propyl group; Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—where h and k are independently the same or different and are 1, 2, 3 or 4; wherein Z is O, NH, NCHO, NCOR', NR', NOR' or CH$_2$, where R' is a methyl, ethyl or propyl group; wherein R$^1$ is a linear or branched chain alkyl, alkoxyalkyl or arylalkyl group; wherein R$^2$ and R$^4$ are independently the same or different and are H, or a linear or branched chain alkyl group; wherein R$^3$ is H, a linear or branched chain alkyl, alkoxy, alkoxyalkyl or acyl group; wherein R$^5$ and R$^6$ are independently the same or different and are H, OH, Cl, Br, F, NO$_2$, CN, CF$_3$ or NH$_2$, or a linear or branched chain alkyl, alkoxy, alkoxycarbonyl, acyl, alkylsulfoxide, alkylsulfone or mono- or dialkylamino group; and wherein R$^7$ and R$^8$ are independently the same or different and are H, CN, CF$_3$, OH, OR", OCOR", NH$_2$, NHR", NR"$_2$, or NHCOR", where R" is a linear chain alkyl group, a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

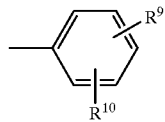

wherein R$^9$ and R$^{10}$ are independently the same or different and are H, Cl, Br, F, OH, OR", OCOR", OCOOR", OCONHR", NH$_2$, NHR", NR"$_2$, NHCOR", NHCOOR" or NHCONHR", where R" is a linear or branched chain alkyl group.

The invention still further provides a method of treating diseases mediated by a, receptors in a subject which comprises administering to the subject a therapeutically effective amount of a compound having the structure:

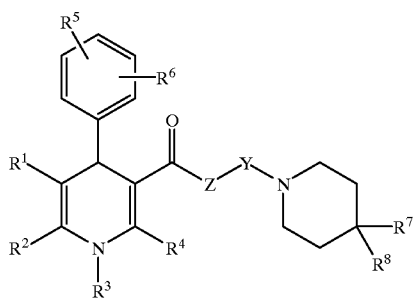

wherein Y is —(CH$_2$)$_n$—, where n is 1, 2, 3, 4, or 5; —(CH$_2$)$_h$—O—(CH$_2$)$_k$—, where h and k are independently the same or different and are 2, 3, or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3, or 4; wherein Z is O, NH, NCHO, NCOR, NR, NOR, or CH$_2$, where R is a methyl, ethyl or propyl group; wherein R$^1$ is a linear or branched chain alkyl, alkoxyalkyl, or arylalkyl group; wherein R$^2$ and R$^4$ are independently the same or different and are H, or a linear or branched chain alkyl group; wherein R$^3$ is H, a linear or branched chain alkyl, alkoxy, alkoxyalkyl or acyl group; wherein R$^5$ and R$^6$ are independently the same or different and are H, OH, Cl, Br, F, NO$_2$, CN, CF$_3$ or NH$_2$, or a linear or branched chain alkyl, alkoxy, alkoxycarbonyl, acyl, alkylsulfoxide, alkylsulfone, or mono- or dialkylamino group; and wherein R$^7$ and R$^8$ are independently the same or different and are H, CN, CF$_3$, OH, OR", OCOR", NH$_2$, NHR", NR"$_2$, or NHCOR", where R" is a linear chain alkyl group, a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

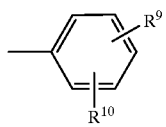

wherein R$^9$ and R$^{10}$ are independently the same or different and are H, Cl, Br, F, OH, OR", OCOR", OCOOR", OCONHR", NH$_2$, NHR", NR"$_2$, NHCOR", NHCOOR" or NHCONHR", where R" is a linear or branched chain alkyl group.

The invention provides a compound having the structure:

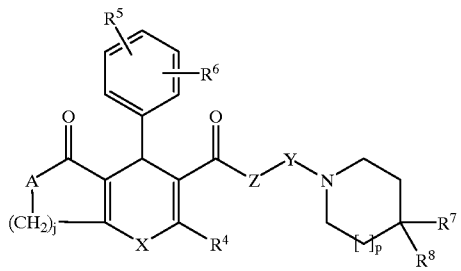

wherein A and X are independently the same or different and are CH$_2$, CR$_2$, NH, NR, NCHO, NCOR, NOH, O, or S, where R is a methyl, ethyl, or propyl group; wherein Y is —(CH$_2$)$_n$—, where n is 1, 2, 3, 4, or 5; —(CH$_2$)$_h$—O—(CH$_2$)$_k$—, where h and k are independently the same or different and are 2, 3, or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR', NR', NOR', or CH$_2$, where R' is a methyl, ethyl, or propyl group; wherein j is 1 or 2; wherein p is 0, 1, or 2; wherein R$^4$ is H, or a linear, cyclic or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^5$ and R$^6$ are independently the same or different and are H, OH, Cl, Br, I, F, NO$_2$, CN, NH$_2$, N$_3$ or CF$_3$, or a linear or branched chain alkyl, alkoxy, alkoxycarbonyl, acyl, alkylsulfoxide, alkylsulfone, or mono- or dialkylamino group, or together constitute a methylenedioxy group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

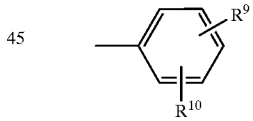

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5. As used herein, the term "pharmaceutically acceptable counterion" shall refer to any anion present in or compatible with mammalian tissue physiology, and includes among others chloride, bromide, iodide, acetate, carbonate, bicarbonate, tartrate, citrate, ascorbate, succinate, maleate, lactate, phosphate, sulfate, hydrogen phosphate, hydrogen sulfate or benzoate. In one embodiment, the invention provides a compound having the structure:

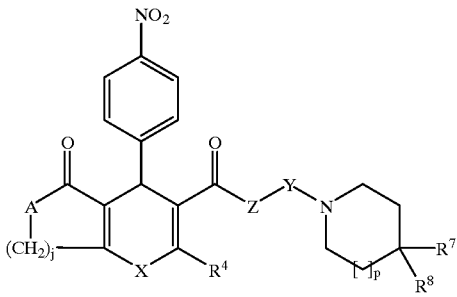

wherein A and X are independently the same or different and are $CH_2$, $CR_2$, NH, NR, NCHO, NCOR, NOH, O or S, where R is a methyl, ethyl or propyl group; wherein Y is —$(CH_2)_n$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$—, where h and k are independently the same or different and are 1, 2, 3 or 4; wherein Z is O, NH, NCHO, NCOR', NR', NOR' or $CH_2$, where R' is a methyl, ethyl or propyl group; wherein p is 0, 1 or 2; wherein $R^4$ is H, a linear, cyclic or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_t$W, where W is $NH_2$, NHR', $NR_2'$, NHOH, $N^+R_3'Z^-$, NHCOR', $N_3$, $NO_2$, or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

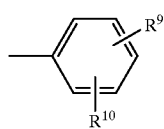

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5. In another embodiment, the invention provides a compound having the structure:

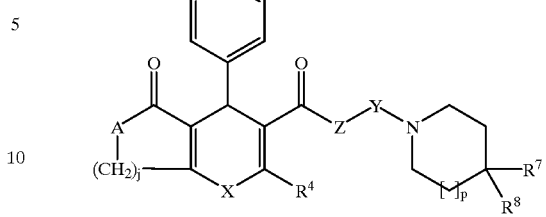

wherein A and X are independently the same or different and are $CH_2$, $CR_2$, NH, NR, NCHO, NCOR, NOH, O or S, where R is a methyl, ethyl or propyl group; wherein Y is —$(CH_2)_n$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$—, where h and k are independently the same or different and are 1, 2, 3 or 4; wherein Z is O, NH, NCHO, NCOR', NR', NOR' or $CH_2$, where R' is a methyl, ethyl or propyl group; wherein j is 1 or 2; wherein p is 0 or 2; wherein $R^4$ is H, a linear, cyclic or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_t$W, where W is $NH_2$, NHR', $NR_2'$, NHOH, $N^+R_3'Z^-$, NHCOR', $N_3$, $NO_2$, or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_qOH$ or $COO(CH_2)_q$ OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

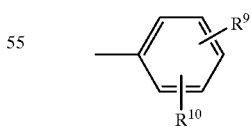

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group and q is 2, 3 or 4 or 5.

The invention provides a compound having the structure:

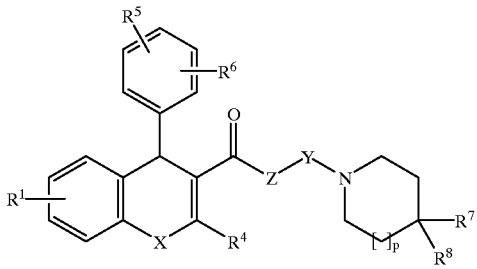

wherein X is $CH_2$, $CR_2$, NH, NR, NCHO, NCOR, NOH, O or S, where R is a methyl, ethyl or propyl group; wherein Y is $—(CH_2)_n—$, where n is 1, 2, 3, 4 or 5; $—(CH_2)_h—O—(CH_2)_k—$, where h and k are independently the same or different and are 2, 3 or 4; $—(CH_2)_h—CH=CH—(CH_2)_k—$; or $—(CH_2)_h—C\equiv C—(CH_2)_k—$, where h and k are independently the same or different and are 1, 2, 3 or 4; wherein Z is O, NH, NCHO, NCOR', NR', NOR' or $CH_2$, where R' is a methyl, ethyl or propyl group; wherein j is 1 or 2; wherein p is 0, 1 or 2; wherein $R^1$ is H, Cl, Br, I, F, $NO_2$, CN, OH, $OR''^2$, $OCOR''^2$, $NH_2$, $NR''^2$, $NHCOR''_2$, or $CF_3$, where $R''^2$ is a linear or branched chain alkyl group, or an aryl group; wherein $R^4$ is H, a linear, cyclic or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_v W^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^5$ and $R^6$ are independently the same or different and are H, OH, Cl, Br, I, F, $NO_2$, CN, $NH_2$, $N_3$ or $CF_3$, or a linear or branched chain alkyl, alkoxy, alkoxycarbonyl, acyl, alkylsulfoxide, alkylsulfone or mono- or dialkylamino group, or together constitute a methylenedioxy group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

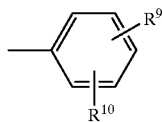

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group and q is 2, 3, 4 or 5. In one embodiment, the invention provides a compound having the structure:

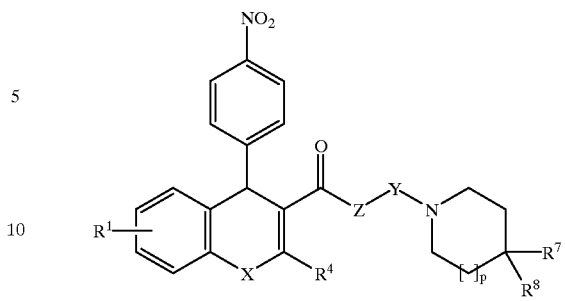

wherein X is $CH_2$, $CR_2$, NH, NR, NCHO, NCOR, NOH, O or S, where R is a methyl, ethyl or propyl group; wherein Y is $—(CH_2)_n—$, where n is 1, 2, 3, 4 or 5; $—(CH_2)_h—O—(CH_2)_k—$, where h and k are independently the same or different and are 2, 3 or 4; $—(CH_2)_h—CH=CH—(CH_2)_k—$; or $—(CH_2)_h—C\equiv C—(CH_2)_k—$, where h and k are independently the same or different and are 1, 2, 3 or 4; wherein Z is O, NH, NCHO, NCOR', NR', NOR' or $CH_2$, where R' is a methyl, ethyl or propyl group; wherein j is 1 or 2; wherein p is 0, 1 or 2; wherein $R^1$ is H, Cl, Br, I, F, $NO_2$, CN, OH, $OR''^2$ $OCOR''^2$, $NH_2$, $NR''^2$, $NHCOR''_2$, or $CF_3$, where $R''^2$ is a linear or branched chain alkyl group, or an aryl group; wherein $R^4$ is H, a linear, cyclic or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_v W^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_qOH$ or $COO(CH_2)_q$ OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

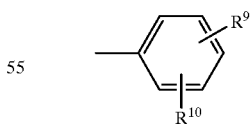

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group and q is 2, 3, 4 or 5. In another embodiment, the invention provides a compound having the structure:

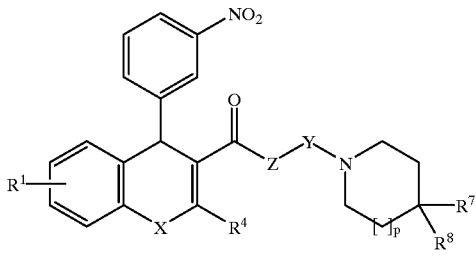

wherein X is $CH_2$, $CR_2$, NH, NR, NCHO, NCOR, NOH, O or S, where R is a methyl, ethyl or propyl group; wherein Y is —$(CH_2)_n$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$—, where h and k are independently the same or different and are 1, 2, 3 or 4; wherein Z is O, NH, NCHO, NCOR', NR', NOR' or $CH_2$, where R' is a methyl, ethyl or propyl group; wherein j is 1 or 2; wherein p is 0, 1 or 2; wherein $R^1$ is H, Cl, Br, I, F, $NO_2$, CN, OH, OR", OCOR", $NH_2$, NR", NHCOR" or $CF_3$, where R" is a linear or branched chain alkyl group, or an aryl group; wherein $R^4$ is H, a linear, cyclic or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_t$W, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', COO$(CH_2)_q$OH or COO$(CH_2)_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

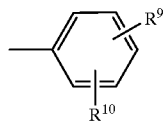

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5.

The invention also provides a compound having the structure:

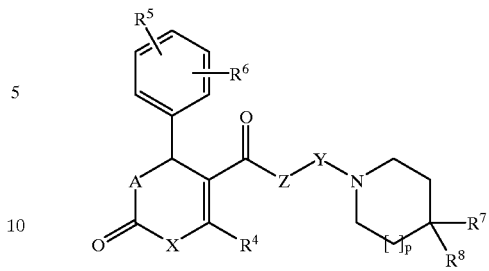

wherein A and X are independently the same or different and are $CH_2$, $CR_2$, NH, NR, NCHO, NCOR, NOH, O or S, where R is a methyl, ethyl or propyl group; wherein Y is —$(CH_2)_n$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$—, where h and k are independently the same or different and are 1, 2, 3 or 4; wherein Z is O, NH, NCHO, NCOR', NR', NOR' or $CH_2$, where R' is a methyl, ethyl or propyl group; wherein j is 1 or 2; wherein p is 0, 1 or 2; wherein $R^4$ is H, a linear, cyclic or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_t$W, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', NR2', NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^5$ and $R^6$ are independently the same or different and are H, OH, Cl, Br, I, F, $NO_2$, CN, $NH_2$, $N_3$ or $CF_3$, or a linear or branched chain alkyl, alkoxy, alkoxycarbonyl, acyl, alkylsulfoxide, alkylsulfone, or mono- or dialkylamino group, or together constitute a methylenedioxy group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', COO$(CH_2)_q$OH or COO$(CH_2)_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

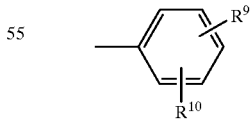

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5. In one embodiment, the invention provides a compound having the structure:

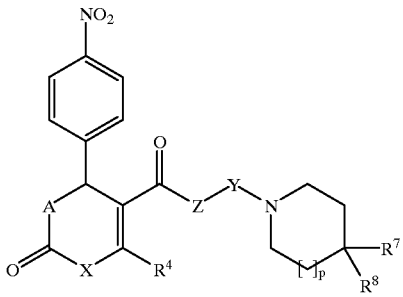

wherein A and X are independently the same or different and are $CH_2$, $CR_2$, NH, NR, NCHO, NCOR, NOH, O or S, where R is a methyl, ethyl or propyl group; wherein Y is —$(CH_2)_n$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$—, where h and k are independently the same or different and are 1, 2, 3 or 4; wherein Z is O, NH, NCHO, NCOR', NR', NOR' or $CH_2$, where R' is a methyl, ethyl or propyl group; wherein j is 1 or 2; wherein p is 0, 1 or 2; wherein $R^4$ is H, a linear, cyclic or branched chain alkyl, an alkoxyalkyl, azidoalkyl, aminoalkoxyalkyl, azidoalkoxyalkyl, alkoxyalkyl, trihaloalkoxyalkyl, aminoalkyl, hydroxyalkyl or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^7$ and $R^8$ are independently the same or different and are H, CN, $CF_3$, OH, OR', OCOR', $NH_2$, NHR', $NR_2'$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

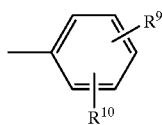

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5. In another embodiment, the invention provides a compound having the structure:

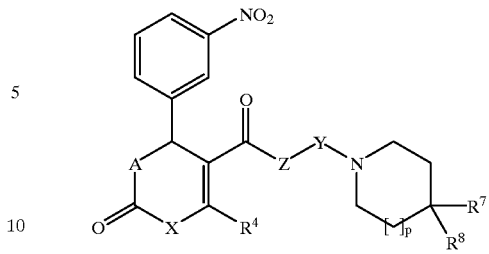

wherein A and X are independently the same or different and are $CH_2$, $CR_2$, NH, NR, NCHO, NCOR, NOH, O or S, where R is a methyl, ethyl or propyl group; wherein Y is —$(CH_2)_n$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$—, where h and k are independently the same or different and are 1, 2, 3 or 4; wherein Z is O, NH, NCHO, NCOR', NR', NOR' or $CH_2$, where R' is a methyl, ethyl or propyl group; wherein j is 1 or 2; wherein p is 0, 1 or 2; wherein $R^4$ is H, or a linear or branched chain, or cyclic alkyl group; and wherein $R^7$ and $R^8$ are independently the same or different and are H, CN, $CF_3$, OH, OR', OCOR', $NH_2$, NHR', $NR_2'$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

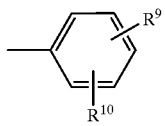

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5.

The invention further provides a compound having the structure:

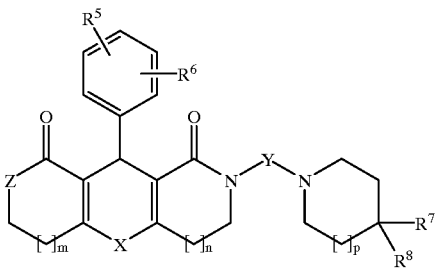

wherein X is $CH_2$, $CR_2$, NH, NR, NCHO, NCOR, NOH, O or S, where R is a methyl, ethyl or propyl group; wherein Y is —$(CH_2)_h$—, where h is 1, 2, 3, 4 or 5; —$(CH_2)_h$—O—$(CH_2)_k$—, where h and k are independently the same or different and are 2, 3 or 4; —$(CH_2)1h$—CH=CH—$(CH_2)_k$—; or —$(CH_2)_h$—C≡C—$(CH_2)_k$—, where h and k are independently the same or different and are 1, 2, 3 or 4; wherein Z is O, NH, NCHO, NCOR', NR', NOR' or CH$_2$, where R' is a methyl, ethyl or propyl group; wherein j is 1 or 2; wherein p is 0, 1 or 2; wherein m and n are independently the same or different and are 0 or 1; wherein R$^5$ and R$^6$ are independently the same or different and are H, OH, Cl, Br, I, F, NO$_2$, CN, NH$_2$, N$_3$ or CF$_3$, or a linear or branched chain alkyl, alkoxy, alkoxycarbonyl, acyl, alkylsulfoxide, alkylsulfone, or mono- or dialkylamino group, or together constitute a methylenedioxy group; and wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

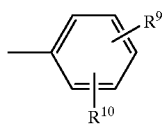

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5. In one embodiment, the invention provides a compound having the structure:

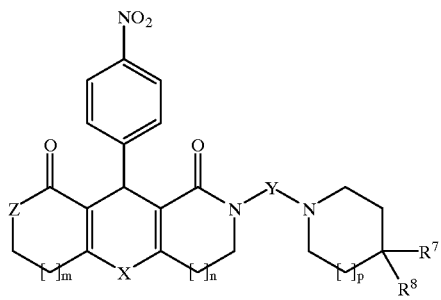

wherein X is CH$_2$, CR$_2$, NH, NR, NCHO, NCOR, NOH, O or S, where R is a methyl, ethyl or propyl group; wherein Y is —(CH$_2$)$_h$—, where h is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR', NR', NOR' or CH$_2$, where R' is a methyl, ethyl or propyl group; wherein j is 1 or 2; wherein p is 0, 1 or 2; wherein m and n are independently the same or different and are 0 or 1; and wherein R$^7$ and R$^8$ are independently the same or different and are H, CN, CF$_3$, OH, OR''', OCOR''', NH$_2$, NHR''', NR'''$_2$, or NHCOR''', where R''' is a linear chain alkyl group, a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

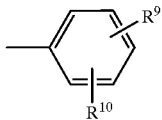

wherein R$^9$ and R$^{10}$ are independently the same or different and are H, Cl, Br, F, OH, OR$^{iv}$, OCOR$^{iv}$, OCOOR', OCONHR$^{iv}$, NH$_2$, NHR$^{iv}$, NR$^{iv}$$_2$, NHCOR$^{iv}$, NHCOOR$^{iv}$ or NHCONHR$^{iv}$, where R$^{iv}$ is a linear or branched chain alkyl group. In another embodiment, the invention provides a compound having the structure:

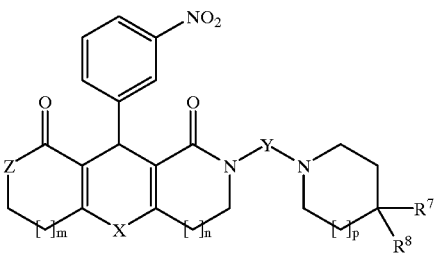

wherein X is CH$_2$, CR$_2$, NH, NR, NCHO, NCOR, NOH, O or S, where R is a methyl, ethyl or propyl group; wherein Y is (CH$_2$)$_h$—, where h is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C(CH$_2$)$_k$— where h and k are independently the same or different and are 1, 2, 3 or 4; wherein Z is O, NH, NCHO, NCOR', NR', NOR' or CH$_2$, where R' is a methyl, ethyl or propyl group; wherein m, n, and p are independently the same or different and are 0 or 1; and wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$ OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

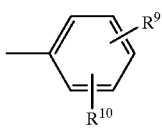

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOR$^{iv}$ or NHCONHR$^{iv}$, where R' is a linear or branched chain alkyl group, and R$^{iv}$ is a linear or branched chain alkyl group, and q is 2, 3, 4 or 5.

The invention further provides a compound having the structure:

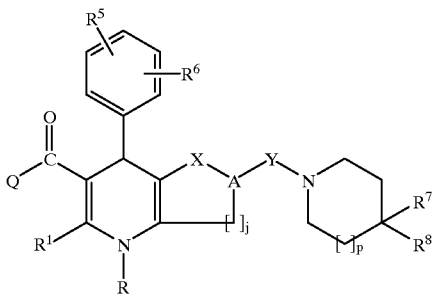

wherein Q is OH, OR", SH, SR'", NH$_2$, NHR'", NR$_2$'", NR"OH, NR"OR'" or a linear or branched chain alkyl group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or (CH$_2$)$_t$W, where W is NH$_2$, NHR', NR$_2$', NHOH, N$^+$R$_3$'Z$^-$, NHCOR', N$_3$, NO$_2$, or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein X is C=O, CH$_2$, CR$^a{}_2$, NH, NR$^a$, NCHO, NCOR$^a$, NOH, O or S, where R' is a methyl, ethyl or propyl group; wherein R$^5$ and R$^6$ are independently the same or different and are H, OH, Cl, Br, I, F, NO$_2$, CN, NH$_2$, N$_3$ or CF$_3$, or a linear or branched chain alkyl, alkoxy, alkoxycarbonyl, acyl, alkylsulfoxide, alkylsulfone, or mono- or dialkylamino group, or together constitute a methylenedioxy group; wherein A is CH; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein j is 1 or 2; wherein p is 0, 1 or 2; and wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

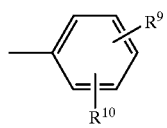

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}{}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5. In one embodiment, the invention provides a compound having the structure:

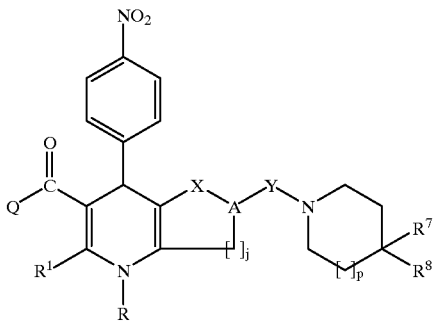

wherein Q is OH, OR", SH, SR'", NH$_2$, NHR'", NR$_2$'", NR"OH, NR"OR'" or a linear or branched chain alkyl group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or (CH$_2$)$_t$W, where W is NH$_2$, NHR', NR$_2$', NHOH, N$^+$R$_3$'Z$^-$, NHCOR', N$_3$, NO$_2$, or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein X is C=O, CH$_2$, CR$^a{}_2$, NH, NR$^a$, NCHO, NCOR$^a$, NOH, O or S, where R' is a methyl, ethyl or propyl group; wherein R is H or a linear or branched chain alkyl or acyl group; wherein A is CH; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein j is 1 or 2; wherein p is 0, 1 or 2; and wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

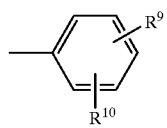

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}{}_2$, NHCOR$^{iv}$, NHCOOR$^{iv}$ or NHCONHR$^{iv}$, where R' is a linear or branched chain alkyl group, and $R^{iv}$ is a linear or branched chain alkyl group, and q is 2, 3, 4 or 5. In another embodiment, the invention provides a compound having the structure:

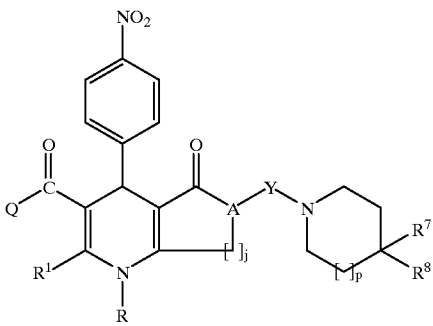

wherein Q is OH, OR", SH, SR'", $NH_2$, NHR'", $NR_2$'", NR"OH, NR"OR'" or a linear or branched chain alkyl group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R is H, a linear or branched chain alkyl or acyl group, or an aryl group; wherein $R^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_tW$, where W is $NH_2$, NHR', $NR_2$', NHOH, $N^+R_3'Z^-$, NHCOR', $N_3$, $NO_2$, or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2$', NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein A is CH; wherein Y is —$(CH_2)_n$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$—, where h and k are independently the same or different and are 1, 2, 3 or 4; wherein j is 1 or 2; wherein p is 0, 1 or 2; and wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2$', COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

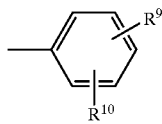

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5. In another embodiment, the invention provides a compound having the structure:

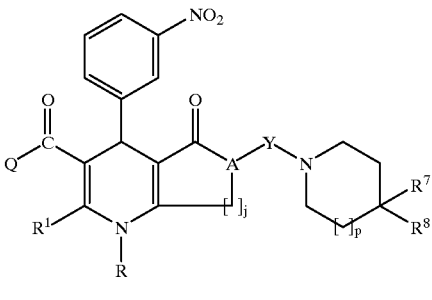

wherein Q is OH, OR", SH, SR'", $NH_2$, NHR'", $NR_2$'", NR"OH, NR"OR'" or a linear or branched chain alkyl group, or an arylalkyl group, or an alkenyl or alkynyl group, or an aryl group, where R" is H, a linear or branched chain alkyl group, or an aryl group; wherein R is H, a linear or branched chain alkyl or acyl group, or an aryl group; wherein $R^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_tW$, where W is $NH_2$, NHR', $NR_2$', NHOH, $N^+R_3'Z^-$, NHCOR', $N_3$, $NO_2$, or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2$', NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein A is CH; wherein Y is —$(CH_2)_n$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$—, where h and k are independently the same or different and are 1, 2, 3 or 4; wherein j is 1 or 2; wherein p is 0, 1 or 2; and wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2$', COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

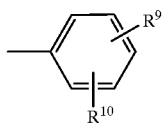

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5.

The invention still further provides a compound having the structure:

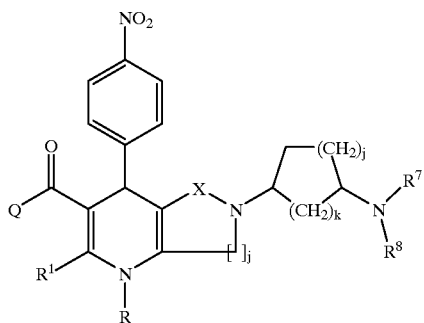

wherein X is C=O, CH$_2$, CR$^a_2$, NH, NR$^a$, NCHO, NCOR$^a$, NOH, O or S, where R$^a$ is a methyl, ethyl or propyl group; wherein Q is OH, OR'', SH, SR''', NH$_2$, NHR''', NR$_2$''', NR''OH, NR''OR''' or a linear or branched chain alkyl group, or an arylalkyl group, or an alkenyl or alkynyl group, or an aryl group, where R'' is H, a linear or branched chain alkyl group, trialkylsilylalkyl, cyanoalkyl or an aryl group, and R''' is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or (CH$_2$)$_t$W, where W is NH$_2$, NHR', NR$_2$', NHOH, N$^+$R$_3$'Z$^-$, NHCOR', N$_3$, NO$_2$, or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^7$ and R$^8$ are independently the same or different and are a linear or branched chain alkyl group, or an aryl group; wherein i is 1 or 2; and wherein j and k are independently the same or different and are 0, 1, 2 or 3. In one embodiment, the invention provides a compound having the structure:

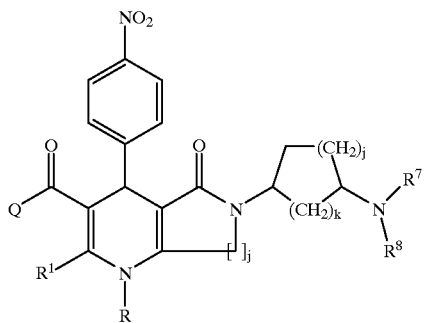

wherein Q is OH, OR'', SH, SR''', NH$_2$, NHR''', NR$_2$''', NR''OH, NR''OR''' or a linear or branched chain alkyl group, or an arylalkyl group, or an alkenyl or alkynyl group, or an aryl group, where R'' is H, a linear or branched chain alkyl group, trialkylsilylalkyl, cyanoalkyl or an aryl group, and R''' is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or (CH$_2$)$_t$W, where W is NH$_2$, NHR', NR$_2$', NHOH, N$^+$R$_3$'Z, NHCOR', N$_3$, NO$_2$ or CH2W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^7$ and R$^8$ are independently the same or different and are a linear or branched chain alkyl group, or an aryl group; wherein i is 1 or 2; and wherein j and k are independently the same or different and are 0, 1, 2 or 3.

The invention provides a compound having the structure:

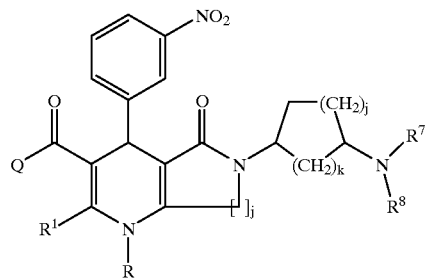

wherein Q is OH, OR'', SH, SR''', NH$_2$, NHR''', NR$_2$''', NR''OH, NR''OR''' or a linear or branched chain alkyl group, or an arylalkyl group, or an alkenyl or alkynyl group, or an aryl group, where R'' is H, a linear or branched chain alkyl group, trialkylsilylalkyl, cyanoalkyl or an aryl group, and R''' is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^7$ and R$^8$ are independently the same or different and are a linear or branched chain alkyl group, or an aryl group; wherein i is 1 or 2; and wherein j and k are independently the same or different and are 0, 1, 2 or 3. In one embodiment, the invention provides a compound having the structure:

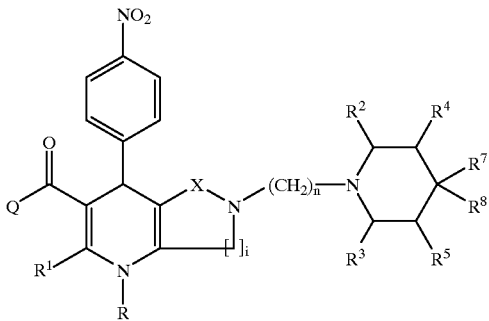

wherein X is C=O, CH$_2$, CR$^a_2$, NH, NR$^a$, NCHO$^a$, NCOR', NOH, O or S, where R$^a$ is a methyl, ethyl or propyl group; wherein Q is OH, OR", SH, SR''', NH$_2$, NHR''', NR$_2$''', NR"OH, NR"OR''' or a linear or branched chain alkyl group, or an arylalkyl group, or an alkenyl or alkynyl group, or an aryl group, where R" is H, a linear or branched chain alkyl group, trialkylsilylalkyl, cyanoalkyl or an aryl group, and R''' is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^2$ and R$^3$ are independently the same or different and are a linear or branched chain alkyl group, or an aryl group; wherein R$^4$ and R$^5$ are independently the same or different and are a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

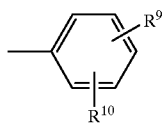

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein i is 1 or 2; and wherein n is 2, 3 or 4. In another embodiment, the invention provides a compound having the structure:

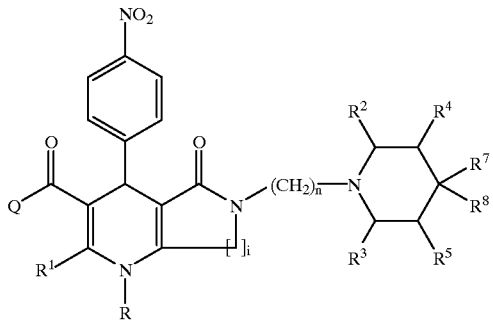

wherein Q is OH, OR", SH, SR''', NH$_2$, NHR''', NR$_2$''', NR"OH, NR"OR''' or a linear or branched chain alkyl group, or an arylalkyl group, or an alkenyl or alkynyl group, or an aryl group, where R" is H, a linear or branched chain alkyl group, trialkylsilylalkyl, cyanoalkyl or an aryl group, and R''' is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^2$ and R$^3$ are independently the same or different and are a linear or branched chain alkyl group, or an aryl group; wherein R$^4$ and R$^5$ are independently the same or different and are a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

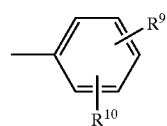

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein i is 1 or 2; and wherein n is 2, 3 or 4.

In another embodiment, the invention provides a compound having the structure:

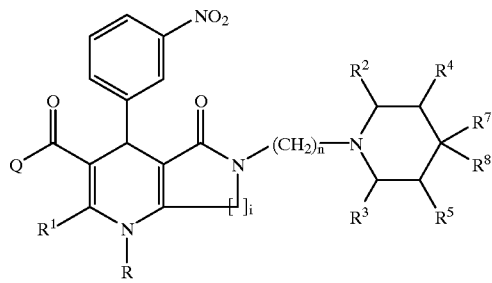

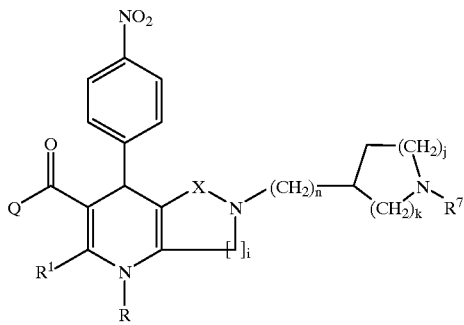

wherein Q is OH, OR", SH, SR'", NH$_2$, NHR'", NR$_2$'", NR"OH, NR"OR'" or a linear or branched chain alkyl group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_tW$, where W is NH$_2$, NHR', NR$_2$', NHOH, N$^+$R$_3$'Z$^-$, NHCOR', N$_3$, NO$_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^2$ and R$^3$ are independently the same or different and are a linear or branched chain alkyl group, or an aryl group; wherein R$^4$ and R$^5$ are independently the same or different and are a linear or branched chain alkyl, alkoxymethyl, or alkoxyethyl group, or a hydroxymethyl or hydroxyethyl group, or a linear or branched chain alkenylalkyl group; wherein R7 and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

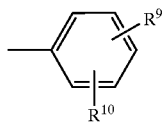

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein i is 1 or 2; and wherein n is 2, 3 or 4.

The invention also provides a compound having the structure:

wherein Q is OH, OR", SH, SR'", NH$_2$, NHR'", NR$_2$'", NR"OH, NR"OR'" or a linear or branched chain alkyl group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_tW$, where W is NH$_2$, NHR', NR$_2$', NHOH, N$^+$R$_3$'Z$^-$, NHCOR', N$_3$, NO$_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^7$ is an aryl or diarylalkyl group; wherein i is 1 or 2; wherein n is 2, 3 or 4; and wherein j and k are independently the same or different and are 0, 1, 2, 3 or 4. In one embodiment, the invention provides a compound having the structure:

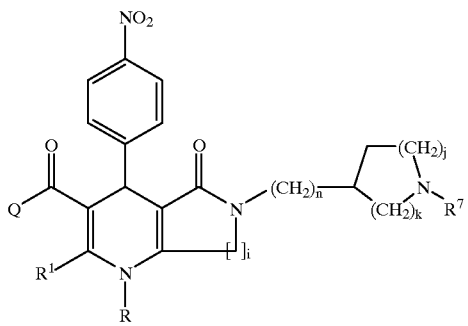

wherein Q is OH, OR", SH, SR'", NH$_2$, NHR'", NR$_2$'", NR"OH, NR"OR'" or a linear or branched chain alkyl group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_tW$, where W is NH$_2$, NHR', NR$_2$', NHOH, N$^+$R$_3$'Z$^-$, NHCOR', N$_3$, NO$_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^7$ is an aryl or diarylalkyl group; wherein i is 1 or 2; wherein n is 2, 3 or 4; and wherein j and k are independently the same or different and are 0, 1, 2, 3 or 4.

The invention further provides a compound having the structure:

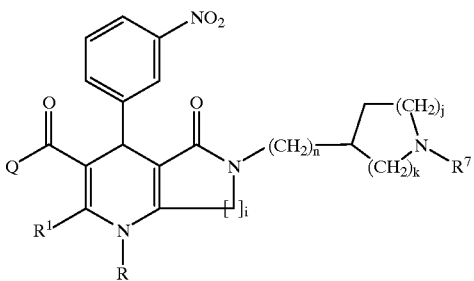

wherein Q is OH, OR'', SH, SR''', $NH_2$, NHR''', $NR_2'''$, NR''OH, NR''OR''' or a linear or branched chain alkyl it group, or an arylalkyl group, or an alkenyl or alkynyl group, or an aryl group, where R'' is H, a linear or branched chain alkyl group, trialkylsilylalkyl, cyanoalkyl or an aryl group, and R''' is a linear or branched chain alkyl group, or an aryl group; wherein R is H, a linear or branched chain alkyl or acyl group, or an aryl group; wherein $R^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where $R^1$ is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^7$ is an aryl or diarylalkyl group; wherein i is 1 or 2; wherein n is 2, 3 or 4; and wherein j and k are independently the same or different and are 0, 1, 2, 3 or 4.

The invention further provides a compound having the structure:

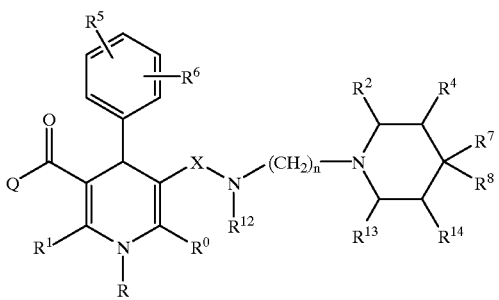

wherein X is C=O, $CH_2$, $CR^a{}_2$, NH, $NR^a$, NCHO, $NCOR^a$, NOH, O or S, where R is a methyl, ethyl or propyl group;

wherein Q is OH, OR'', SH, SR''', $NH_2$, NHR''', $NR_2'''$, NR''OH, NR''OR''' or a linear or branched chain alkyl group, or an arylalkyl group, or an alkenyl or alkynyl group, or an aryl group, where R'' is H, a linear or branched chain alkyl group, trialkylsilylalkyl, cyanoalkyl or an aryl group, and R''' is a linear or branched chain alkyl group, or an aryl group; wherein R is H, a linear or branched chain alkyl or acyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_tW$, where W is $NH_2$, NHR', $NR_2'$, NHOH, $N^+R_3'Z^-$, NHCOR', $N_3$, $NO_2$ or $CH_2W(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein R is H, a linear or branched chain alkyl or acyl group, or an aryl group; wherein $R^2$, $R^{13}$, and $R^{14}$ are independently the same or different and are H, or a linear or branched chain alkyl, hydroxyalkyl, alkoxyalkyl, amino alkyl, or aryl group; wherein $R^4$ is a linear or branched chain alkyl, alkoxyalkyl, hydroxyalkyl, or a linear or branched chain alkenylalkyl group; wherein $R^5$ and $R^6$ are independently the same or different and are H, OH, Cl, Br, I, F, $NO_2$, CN, $NH_2$, $N_3$, $CF_3$, a linear or branched chain alkyl, alkoxy, alkoxycarbonyl, acyl, alkylsulfoxide, alkylsulfoxide, or mono- or dialkylamino group, or together constitute a methylenedioxy group; wherein $R^7$ and $R^8$ are independently the same or different and are H, CN, $CF_3$, OH, OR', OCOR', $NH_2$, NHR', $NR_2'$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

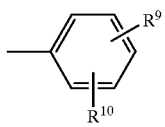

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}{}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{12}$ is H or a linear chain alkyl group; and wherein n is 2, 3 or 4. In one embodiment, the invention provides a compound having the structure:

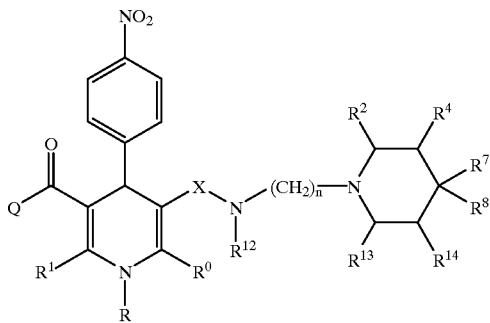

wherein X is C=O, CH$_2$, CR$^a_2$, NH, NR$^a$, NCHO, NCOR$^a$, NOH, O or S, where R is a methyl, ethyl or propyl group; wherein Q is OH, OR", SH, SR'", NH$_2$, NHR'", NR$_2$'", NR"OH, NR"OR'" or a linear or branched chain alkyl group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R is H, a linear or branched chain alkyl or acyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^2$, R$^{13}$, and R$^{14}$ are independently the same or different and are H, or a linear or branched chain alkyl, hydroxyalkyl, alkoxyalkyl, amino alkyl, or aryl group; wherein R$^4$ is a linear or branched chain alkyl, alkoxyalkyl, hydroxyalkyl, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

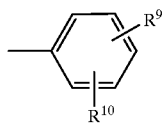

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; and wherein n is 2, 3 or 4. In another embodiment, the invention provides a compound having the structure:

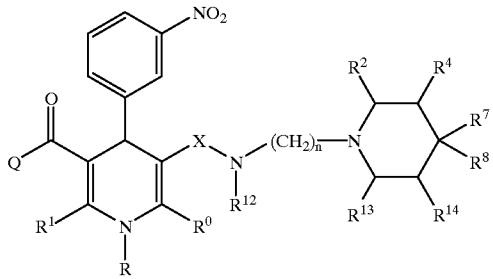

wherein X is C=O, CH$_2$, CR$^a_2$, NH, NR$^a$, NCHO, NCOR$^a$, NOH, O or S, where R is a methyl, ethyl or propyl group; wherein Q is OH, OR", SH, SR'", NH$_2$, NHR'", NR$_2$'", NR"OH, NR"OR'" or a linear or branched chain alkyl group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R is H, a linear or branched chain alkyl or acyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^2$, R$^{13}$, and R$^{14}$ are independently the same or different and are H, or a linear or branched chain alkyl, hydroxyalkyl, alkoxyalkyl, amino alkyl or aryl group; wherein R$^4$ is a linear or branched chain alkyl, alkoxyalkyl, hydroxyalkyl, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

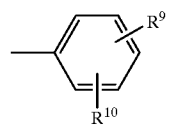

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; and wherein n is 2, 3 or 4.

The invention also provides a compound having the structure:

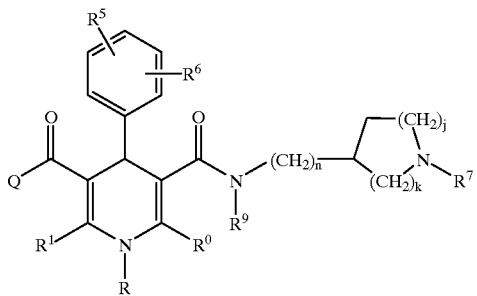

wherein Q is OH, OR", SH, SR'", NH$_2$, NHR'", NR$_2$'", NR"OH, NR"OR'" or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R$^1$ is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^5$ and R$^6$ are independently the same or different and are H, OH, Cl, Br, I, F, NO$_2$, CN, NH$_2$, N$_3$, CF$_3$, a linear or branched chain alkyl, alkoxy, alkoxycarbonyl, acyl, alkylsulfoxide, alkylsulfoxide, or mono- or dialkylamino group, or together constitute a methylenedioxy group; wherein R$^7$ is an aryl or diarylalkyl group; wherein R$^9$ is H or a linear chain alkyl group; wherein j and k are independently the same or different and are 0, 1, 2 or 3; and wherein n is 2, 3 or 4. In one embodiment, the invention provides a compound having the structure:

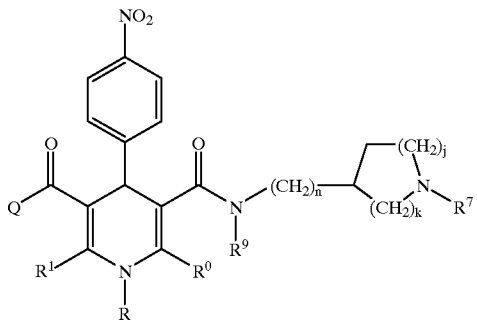

wherein Q is OH, OR", SH, SR'", NH$_2$, NHR'", NR$_2$'", NR"OH, NR"OR'" or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^7$ is an aryl or diarylalkyl group; wherein R$^9$ is a H or linear chain alkyl group; wherein j and k are independently the same or different and are 0, 1, 2 or 3; and wherein n is 2, 3 or 4. In another embodiment, the invention provides a compound having the structure:

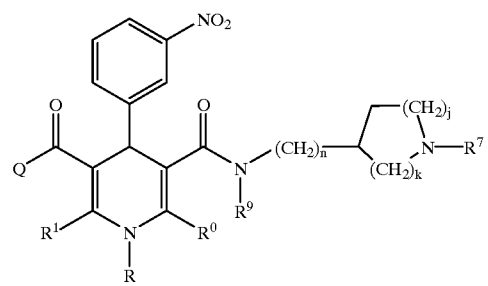

wherein Q is OH, OR", SH, SR'", NH$_2$, NHR'", NR$_2$'", NR"OH, NR"OR'" or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$$^1$, NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R is H or a linear or branched chain alkyl or acyl group, or an aryl group; wherein R$^7$ is an aryl or diarylalkyl group; wherein R$^9$ is H or a linear chain alkyl group; and wherein j and k are independently the same or different and are 0, 1, 2 or 3.

The invention provides a compound having the structure:

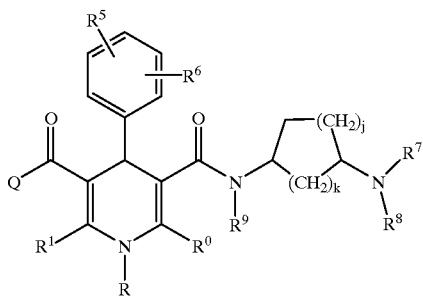

wherein Q is OH, OR", SH, SR''', NH$_2$, NHR''', NR$_2$''', NR"OH, NR"OR''' or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R''' is a linear or branched chain alkyl group, or an aryl group; wherein R is H, a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_tW$, where W is NH$_2$, NHR', NR$_2$', NHOH, N$^+$R$_3$'Z$^-$, NHCOR', N$_3$, NO$_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^5$ and R$^6$ are independently the same or different and are H, OH, Cl, Br, I, F, NO$_2$, CN, NH$_2$, N$_3$, CF$_3$, a linear or branched chain alkyl, alkoxy, alkoxycarbonyl, acyl, alkylsulfoxide, alkylsulfoxide, or mono- or dialkylamino group, or together constitute a methylenedioxy group; wherein R$^7$ is an aryl or diarylalkyl group; wherein R$^9$ is a linear chain alkyl group; and wherein j and k are independently the same or different and are 0, 1, 2 or 3. In one embodiment, the invention provides a compound having the structure:

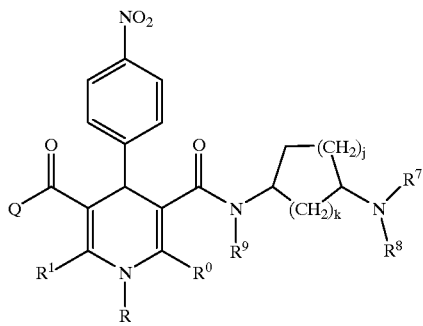

wherein Q is OH, OR", SH, SR''', NH$_2$, NHR''', NR$_2$''', NR"OH, NR"OR''' or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R''' is a linear or branched chain alkyl group, or an aryl group; wherein R is H, a linear or branched chain alkyl or acyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is NH$_2$, NHR', NR$_2$', NHOH, N$^+$R$_3$'Z$^-$, NHCOR', N$_3$, NO$_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^9$ is a linear chain alkyl group; and wherein j and k are independently the same or different and are 0, 1, 2 or 3.

The invention also provides a compound having the structure:

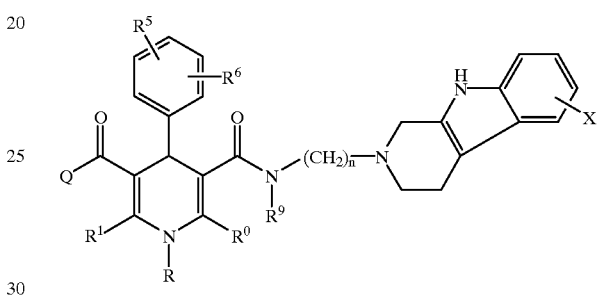

wherein Q is OH, OR", SH, SR''', NH$_2$, NHR''', NR$_2$''', NR"OH, NR"OR''' or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R''' is a linear or branched chain alkyl group, or an aryl group; wherein R is H, a linear or branched chain alkyl or acyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is NH$_2$, NHR', NR$_2$', NHOH, N$^+$R$_3$'Z$^-$, NHCOR', N$_3$, NO$_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein X is H, OH, Cl, Br, I, F, NO$_2$, CN, NH$_2$, or CF$_3$, or a linear or branched chain alkyl, alkoxy, alkoxycarbonyl, acyl, alkylsulfoxide, alkylsulfoxide, or mono- or dialkylamino group; wherein R is H or a linear or branched chain alkyl or acyl group, or an aryl group; wherein R$^0$ and R$^1$ are independently the same or different and are H, or a linear or branched chain alkyl, alkoxyalkyl, azidoalkyl, aminoalkoxyalkyl, azidoalkoxyalkyl, trihaloalkoxyalkyl, aminoalkyl, or hydroxylalkyl group, or an aryl group; wherein R$^5$ and R$^6$ are independently the same or different and are H, OH, Cl, Br, I, F, NO$_2$, N$_3$, CN, NH$_2$, or CF$_3$, or a linear or branched chain alkyl, alkoxy, alkoxycarbonyl, acyl, alkylsulfoxide, alkylsulfoxide, or mono- or dialkylamino group, or together constitute a methylenedioxy group; wherein R$^9$ is H or a linear chain alkyl group; and wherein n is 2, 3 or 4. In one embodiment, the invention provides a compound having the structure:

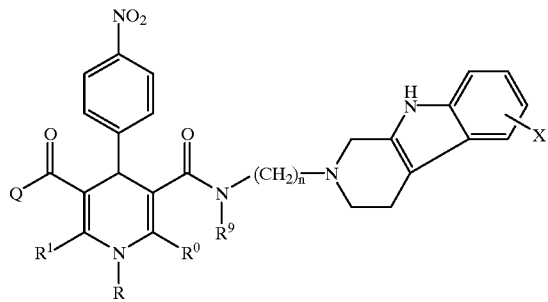

wherein Q is OH, OR", SH, SR'", NH$_2$, NHR'", NR$_2$'", NR"OH, NR"OR'" or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R is H, a linear or branched chain alkyl or acyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein X is H, OH, Cl, Br, I, F, NO$_2$, CN, NH$_2$, or CF$_3$, or a linear or branched chain alkyl, alkoxy, alkoxycarbonyl, acyl, alkylsulfoxide, alkylsulfoxide, or mono- or dialkylamino group; wherein R is H or a linear or branched chain alkyl or acyl group, or an aryl group; wherein $R^0$ and $R^1$ are independently the same or different and are H, or a linear or branched chain alkyl, alkoxyalkyl, azidoalkyl, aminoalkoxyalkyl, azidoalkoxyalkyl, trihaloalkoxyalkyl, aminoalkyl, or hydroxylalkyl group, or an aryl group; wherein $R^9$ is H or a linear chain alkyl group; and wherein n is 2, 3 or 4. In another embodiment, the invention provides a compound having the structure:

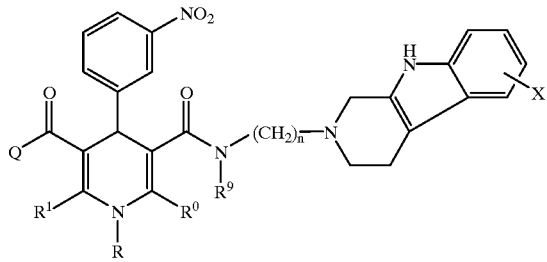

wherein Q is OH, OR", SH, SR'", NH$_2$, NHR'", NR$_2$'", NR"OH, NR"OR'" or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R is H, a linear or branched chain alkyl or acyl group, or an aryl group; wherein X is H, OH, Cl, Br, I, F, NO$_2$, CN, NH$_2$, or CF$_3$, or a linear or branched chain alkyl, alkoxy, alkoxycarbonyl, acyl, alkylsulfoxide, alkylsulfoxide, or mono- or dialkylamino group; wherein R is H or a linear or branched chain alkyl or acyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein $R^9$ is H or a linear chain alkyl group; and wherein n is 2, 3 or 4.

The invention provides a compound having the structure:

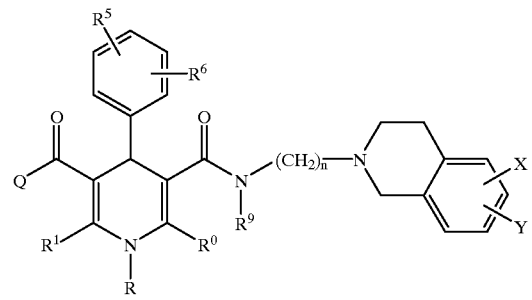

wherein Q is OH, OR", SH, SR'", NH$_2$, NHR'", NR$_2$'", NR"OH, NR"OR'" or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein X and Y are independently the same or different and are H, OH, Cl, Br, I, F, NO$_2$, CN, NH$_2$, or CF$_3$, or a linear or branched chain alkyl, alkoxy, alkoxycarbonyl, acyl, alkylsulfoxide, alkylsulfoxide, or mono- or dialkylamino group; wherein R is H or a linear or branched chain alkyl or acyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein $R^5$ and $R^6$ are independently the same or different and are H, OH, Cl, Br, I, F, NO$_2$, N$_3$, CN, NH$_2$, or CF$_3$, or a linear or branched chain alkyl, alkoxy, alkoxycarbonyl, acyl, alkylsulfoxide, alkylsulfoxide, or mono- or dialkylamino group, or together constitute a methylenedioxy group; wherein $R^9$ is H or a linear chain alkyl group; and wherein n is 2, 3 or 4. In one embodiment, the invention provides a compound having the structure:

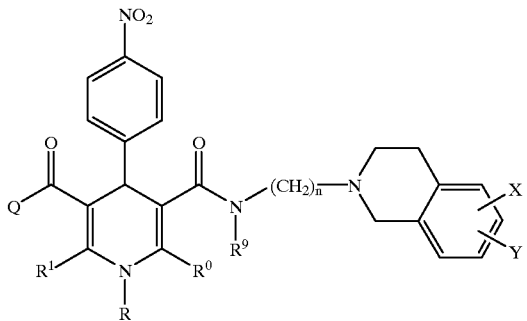

wherein Q is OH, OR", SH, SR'", $NH_2$, NHR'", $NR_2$'", NR"OH, NR"OR'" or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein X and Y are independently the same or different and are H, OH, Cl, Br, I, F, $NO_2$, CN, $NH_2$, or $CF_3$, or a linear or branched chain alkyl, alkoxy, alkoxycarbonyl, acyl, alkylsulfoxide, alkylsulfoxide, or mono- or dialkylamino group; wherein R is H or a linear or branched chain alkyl or acyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2$', NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2$', NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein X and Y are independently the same or different and are H, OH, Cl, Br, I, F, $NO_2$, CN, $NH_2$, or $CF_3$, or a linear or branched chain alkyl, alkoxy, alkoxycarbonyl, acyl, alkylsulfoxide, alkylsulfoxide, or mono- or dialkylamino group; wherein $R^9$ is H or a linear chain alkyl group; and wherein n is 2, 3 or 4. In another embodiment, the invention provides a compound having the structure:

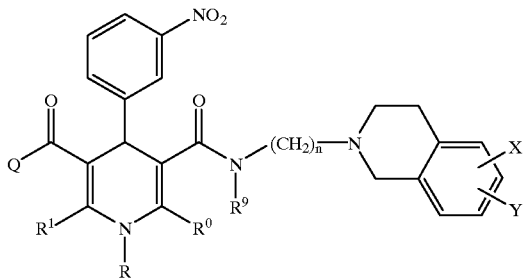

wherein Q is OH, OR", SH, SR'", $NH_2$, NHR'", $NR_2$'", NR"OH, NR"OR'" or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein X and Y are independently the same or different and are H, OH, Cl, Br, I, F, $NO_2$, CN, $NH_2$, or $CF_3$, or a linear or branched chain alkyl, alkoxy, alkoxycarbonyl, acyl, alkylsulfoxide, alkylsulfoxide, or mono- or dialkylamino group; wherein R is H or a linear or branched chain alkyl or acyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2$', NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2$', NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^9$ is H or a linear chain alkyl group; and wherein n is 2, 3 or 4.

The invention further provides a compound having the structure:

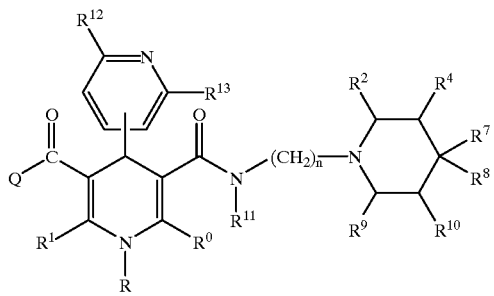

wherein Q is OH, OR", SH, SR'", $NH_2$, NHR'", $NR_2$'", NR"OH, NR"OR'" or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2$', NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2$', NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 And v is 2, 3, 4, 5 or 6; wherein R is H or a linear or branched chain alkyl or acyl group, or an aryl group; wherein $R^2$, $R^9$ and $R^{10}$ are independently the same or different and are H or a linear or branched chain alkyl group; wherein $R^4$ is a H or linear or branched chain alkyl, alkyloxymethyl, or alkoxyethyl group, or a hydroxymethyl or hydroxyethyl group, or a linear or branched chain alkenylalkyl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

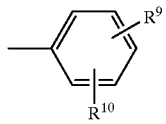

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; and wherein n is 2, 3 or 4.

The invention still further provides a compound having the structure:

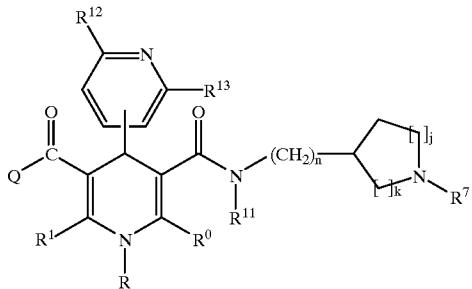

wherein Q is OH, OR", SH, SR''', NH$_2$, NHR''', NR$_2$''', NR"OH, NR"OR''' or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R''' is a linear or branched chain alkyl group, or an aryl group; wherein R is H or a linear or branched chain alkyl or acyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$ or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$, NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4 5 or 6; wherein R$^7$ is an aryl or diarylalkyl group; wherein R$^{11}$ is H or a linear chain alkyl group; wherein R$^{12}$ and R$^{13}$ are independently the same or different and are H or a linear chain alkyl group; wherein j and k are independently the same or different and are 0, 1, 2, 3 or 4; and wherein n is 2, 3 or 4.

The invention also provides a compound having the structure:

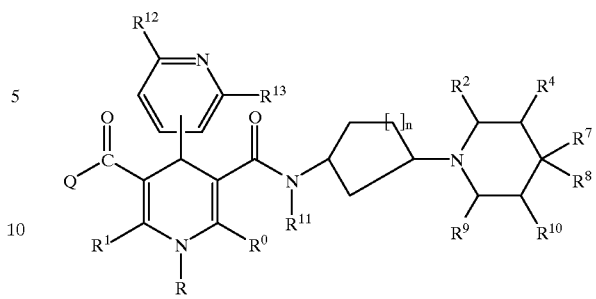

wherein Q is OH, OR", SH, SR''', NH$_2$, NHR''', NR$_2$''', NR"OH, NR"OR''' or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R''' is a linear or branched chain alkyl group, or an aryl group; wherein R is H or a linear or branched chain alkyl or acyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$ or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$, NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^2$, R$^9$ and R$^{10}$ are independently the same or different and are H or a linear or branched chain alkyl group; wherein R$^4$ is H or a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR$_2$', NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

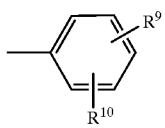

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; and wherein n is 2, 3 or 4.

In addition, the invention provides a compound having the structure:

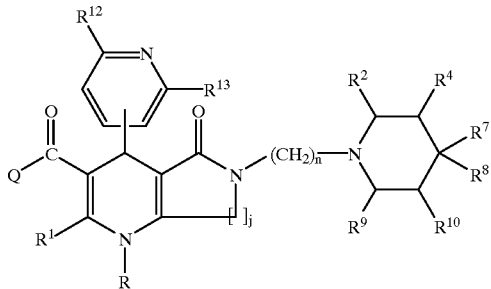
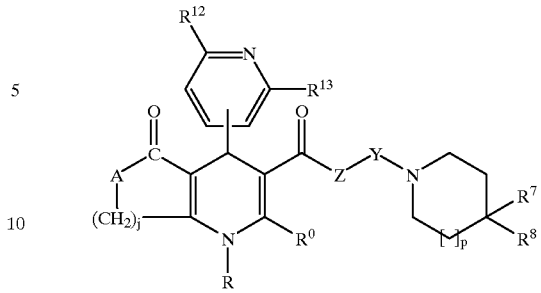

wherein Q is OH, OR'', SH, SR''', NH$_2$, NHR''', NR$_2$''', NR''OH, NR''OR''' or a linear or branched chain alkyl it group, or an arylalkyl group, or an alkenyl or alkynyl group, or an aryl group, where R'' is H, a linear or branched chain alkyl group, trialkylsilylalkyl, cyanoalkyl or an aryl group, and R''' is a linear or branched chain alkyl group, or an aryl group; wherein R is H or a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^2$, R$^9$ and R$^{10}$ are independently the same or different and are a linear or branched chain alkyl group; wherein R$^4$ is a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

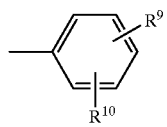

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; and wherein n is 2, 3 or 4.

The invention also provides a compound having the structure:

wherein Q is OH, OR'', SH, SR''', NH$_2$, NHR''', NR$_2$''', NR''OH, NR''OR''' or a linear or branched chain alkyl it group, or an arylalkyl group, or an alkenyl or alkynyl group, or an aryl group, where R'' is H, a linear or branched chain alkyl group, trialkylsilylalkyl, cyanoalkyl or an aryl group, and R''' is a linear or branched chain alkyl group, or an aryl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein A is CH$_2$, CR$_{a2}$, NH, NR$^a$, NCHO, NCOR$^a$, NOH, O or S, where R is a methyl, ethyl or propyl group; wherein Z is O, NH, NCHO, NCOR', NR', NOR', or CH$_2$, where R' is a methyl, ethyl or propyl group; wherein R is H or a linear or branched chain alkyl or acyl group, or an aryl group; wherein R$^0$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$,and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

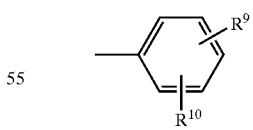

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ and R$^{13}$ are independently the same or different and are H or a linear chain alkyl group; wherein j is 1, 2, 3 or 4; wherein n is 2, 3 or 4; and wherein p is 0, 1, 2 or 3.

The invention further provides a compound having the structure:

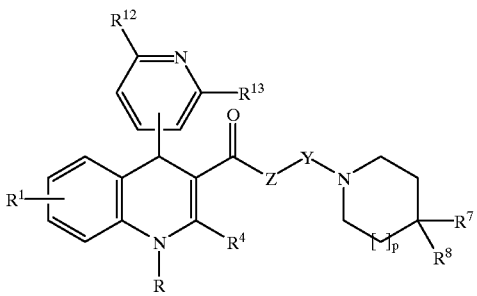

wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein R' is H, Cl, Br, I, F, NO$_2$, CN, OH, OR$^2$, OCOR$^2$, NH$_2$, NR$^2$, NHCOR$_2$, or CF$_3$, where R$^2$ is a linear or branched chain alkyl group, or an aryl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH, or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

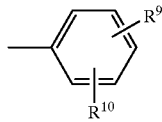

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ and R$^{13}$ are independently the same or different and are H or a linear chain alkyl group; wherein j is 1, 2, 3 or 4; wherein n is 2, 3 or 4; and wherein p is 0, 1, 2 or 3.

The invention still further provides a compound having the structure:

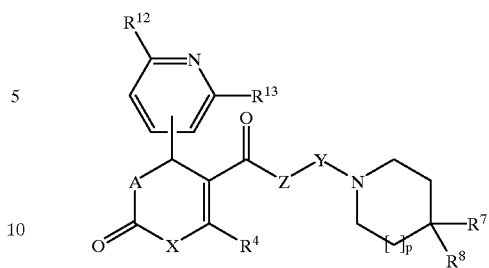

wherein A is CH$_2$, CR$_2$, NH, NR, NCHO, NCOR, NOH, O or S, where R is a methyl, ethyl or propyl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR', NR', NOR' or CH$_2$, where R' is a methyl, ethyl or propyl group; wherein X is NH, NR", O or S, where R" is H or a linear or branched chain alkyl or acyl group, or an aryl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

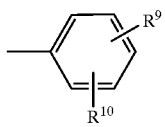

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ and R$^{13}$ are independently the same or different and are H or a linear chain alkyl group; and wherein p is 0, 1, 2 or 3.

The invention provides a compound having the structure:

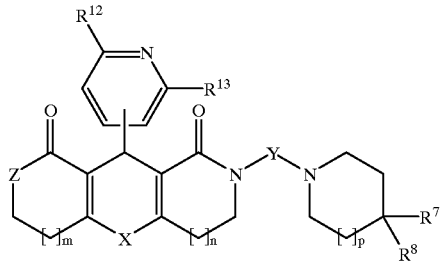

wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH₂)ₕ—CH=CH—(CH₂)ₖ—; or —(CH₂)ₕ—C≡C—(CH₂)ₖ—, where h and k are independently the same or different and are 1, 2, 3 or 4; wherein Z is O, NH, NCHO, NCOR, NR, NOR or CH₂, where R is a methyl, ethyl or propyl group; wherein X is NH, NR', O, or S, where R' is H or a linear or branched chain alkyl or acyl group, or an aryl group; wherein R⁷ and R⁸ are independently the same or different and are H, CN, CF₃, OH, OR', OCOR', NH₂, NHR', NR'₂, NHCOR', CONH₂, CONHR', CONR₂', COOH, COOR', CHO, COR', COSH, COSR', COO(CH₂)_qOH or COO(CH₂)_qOR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

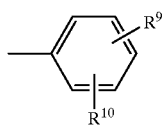

wherein R⁹ and R¹⁰ are independently the same or different and are H, Cl, Br, I, F, OH, NO₂, N₃, OR^{iv}, OCOR^{iv}, OCOOR^{iv}, OCONHR^{iv}, NH₂, NHR^{iv}, NR^{iv}₂, NHCOR^{iv}, NHCOOR^{iv} or NHCONHR^{iv}, where R' is a linear or branched chain alkyl group, and R^{iv} is a linear or branched chain alkyl group, and q is 2, 3, 4 or 5; wherein R¹² and R¹³ are independently the same or different and are H or a linear chain alkyl group; wherein m and n are independently the same or different and are 0 or 1; and wherein p is 0, 1, 2 or 3.

The invention also provides a compound having the structure:

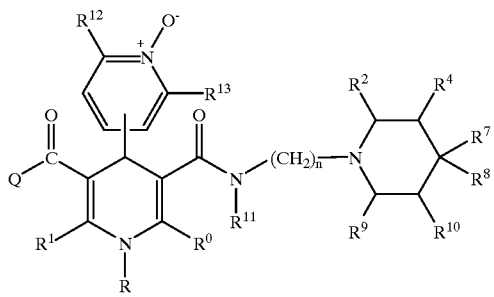

wherein Q is OH, OR", SH, SR'", NH₂, NHR'", NR₂'", NR"OH, NR"OR'" or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R is H or a linear or branched chain alkyl or acyl group, or an aryl group; wherein R⁰ and R¹ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH₂)_vW, where W is NH₂, NHR', NR₂¹, NHOH, N⁺R₃'Z⁻, NHCOR', N₃, NO₂ or CH₂W⁰(CH₂)_vW¹, or a linear or branched chain alkyl group, or an arylalkyl group, or an alkenyl or alkynyl group, or an aryl group, where R' is a linear or branched chain alkyl group, or an aryl group, where W⁰ is O, S or NH, where W¹ is NH₂, NHR', NR₂', NHOH, N⁺R₃'Z⁻, NHCOR', N₃ or NO₂, and where R' is a linear or branched chain alkyl group, or an aryl group, where Z⁻ is a pharmaceutically acceptable counterion, and t is 1, 2, 3, 4, 5 or 6 and v is 2, 3, 4, 5 or 6; wherein R², R⁹ and R¹⁰ are independently the same or different and are H or a linear or branched chain alkyl group; wherein R⁴ is H or a linear or branched chain alkyl, alkyloxymethyl, or alkoxyethyl group, or a hydroxymethyl or hydroxyethyl group, or a linear or branched chain alkenylalkyl group; wherein R⁷ and R⁸ are independently the same or different and are H, CN, CF₃, OH, OR', OCOR', NH₂, NHR', NR'₂, NHCOR', CONH₂, CONHR', CONR₂', COOH, COOR', CHO, COR', COSH, COSR', COO(CH₂)_qOH or COO(CH₂)_qOR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

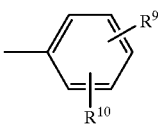

wherein R⁹ and R¹⁰ are independently the same or different and are H, Cl, Br, I, F, OH, NO₂, N₃, OR^{iv}, OCOR^{iv}, OCOOR^{iv}, OCONHR^{iv}, NH₂, NHR^{iv}, NR^{iv}₂, NHCOR^{iv}, NHCOOR^{iv} or NHCONHR^{iv}, where R' is a linear or branched chain alkyl group, and R^{iv} is a linear or branched chain alkyl group, and q is 2, 3, 4 or 5; wherein R¹¹ is H or a linear chain alkyl group; wherein R¹² and R¹³ are independently the same or different and are H or a linear chain alkyl group; and wherein n is 2, 3 or 4.

The invention further provides a compound having the structure:

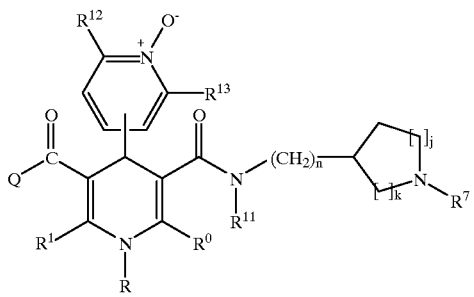

wherein Q is OH, OR", SH, SR'", NH₂, NHR'", NR₂'", NR"OH, NR"OR'" or a linear or branched chain alkyl it group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R⁰ and R¹ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH₂)_vW, where W is NH₂, NHR', NR₂', NHOH, N⁺R₃'Z⁻, NHCOR', N₃, NO₂ or CH₂W⁰(CH₂)_vW¹, or a linear or branched chain alkyl group, or an arylalkyl group, or an alkenyl or alkynyl group, or an aryl group, where R' is a linear or branched chain alkyl group, or an aryl group, where W⁰ is O, S or NH, where W¹ is NH₂, NHR', NR₂', NHOH, N⁺R₃'Z⁻, NHCOR', N₃ or NO₂, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein $R^7$ is an aryl or diarylalkyl group; wherein $R^{11}$ is H or a linear chain alkyl group; wherein $R^{12}$ and $R^{13}$ are independently the same or different and are H or a linear chain alkyl group; wherein j and k are independently the same or different and are 0, 1, 2, 3 or 4; and wherein n is 2, 3 or 4.

The invention still further provides a compound having the structure:

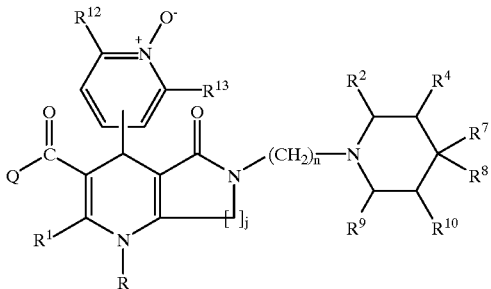

wherein Q is OH, OR''', SH, SR''', $NH_2$, NHR''', $NR_2$''', NR''OH, NR''OR''' or a linear or branched chain alkyl it group, or an arylalkyl group, or an alkenyl or alkynyl group, or an aryl group, where R'' is H, a linear or branched chain alkyl group, trialkylsilylalkyl, cyanoalkyl or an aryl group, and R''' is a linear or branched chain alkyl group, or an aryl group; wherein $R^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein $R^2$, $R^9$ and $R^{10}$ are independently the same or different and are a linear or branched chain alkyl group; wherein $R^4$ is a linear or branched chain alkyl, alkyloxymethyl, or alkoxyethyl group, or a hydroxymethyl or hydroxyethyl group, or a linear or branched chain alkenylalkyl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

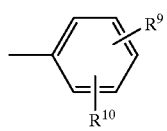

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{11}$ is H or a linear chain alkyl group; wherein $R^{12}$ and $R^{13}$ are independently the same or different and are H or a linear chain alkyl group; wherein j is 1, 2, 3 or 4; and wherein n is 2, 3 or 4.

The invention provides a compound having the structure:

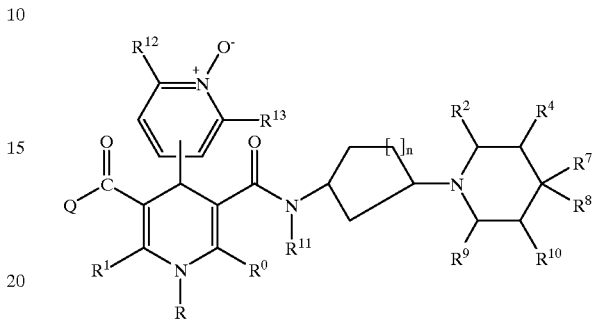

wherein Q is OH, OR'', SH, SR''', $NH_2$, NHR''', $NR_2$''', NR''OH, NR''OR''' or a linear or branched chain alkyl it group, or an arylalkyl group, or an alkenyl or alkynyl group, or an aryl group, where R'' is H, a linear or branched chain alkyl group, trialkylsilylalkyl, cyanoalkyl or an aryl group, and R''' is a linear or branched chain alkyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^2$, $R^9$ and $R^{10}$ are independently the same or different and are H or a linear or branched chain alkyl group; wherein $R^4$ is H or a linear or branched chain alkyl, alkyloxymethyl, or alkoxyethyl group, or a hydroxymethyl or hydroxyethyl group, or a linear or branched chain alkenylalkyl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_q$ OH or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

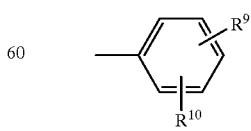

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{11}$ is H or a linear chain alkyl group; wherein R$^{12}$ and R$^{13}$ are independently the same or different and are H or a linear chain alkyl group; and wherein n is 2, 3 or 4.

The invention also provides a compound having the structure:

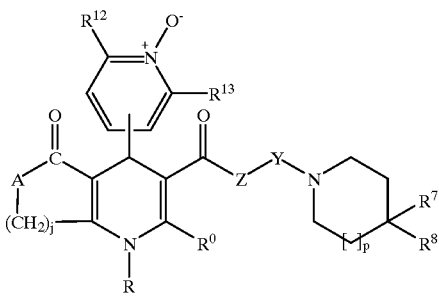

wherein R$^0$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein A is CH$_2$, CR$^a$$_2$, NH, NR$^a$, NCHO, NCOR$^a$, NOH, O or S, where R$^a$ is a methyl, ethyl or propyl group; wherein Z is O, NH, NCHO, NCOR', NR', NOR', or CH$_2$, where R' is a methyl, ethyl or propyl group; wherein R is H or a linear or branched chain alkyl or acyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

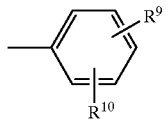

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ and R$^{13}$ are independently the same or different and are H or a linear chain alkyl group; wherein j is 1, 2, 3 or 4; wherein n is 2, 3 or 4; and wherein p is 0, 1, 2 or 3.

The invention further provides a compound having the structure:

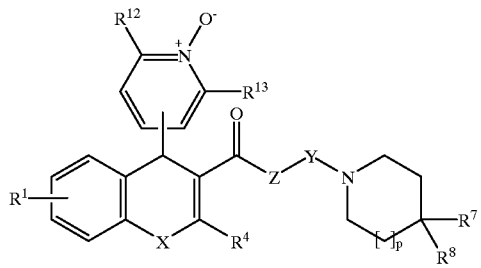

wherein X is NH, NR", O, or S, where R" is H or a linear or branched chain alkyl or acyl group, or an aryl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; or an aryl group; wherein R$^1$ is H, Cl, Br, I, F, NO$_2$, CN, OH, OR$^2$, OCOR$^2$, NH$_2$, NR$^2$, NHCOR$_2$, or CF$_3$, where R$^2$ is a linear or branched chain alkyl group, or an aryl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

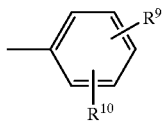

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ and R$^{13}$ are independently the same or different and are H or a linear chain alkyl group; and wherein p is 0, 1, 2 or 3.

The invention still further provides a compound having the structure:

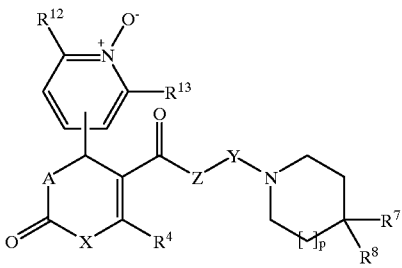

wherein A is $CH_2$, $CR_2$, NH, NR, NCHO, NCOR, NOH, O or S, where R is a methyl, ethyl or propyl group; wherein Y is —$(CH_2)_n$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$, where h and k are independently the same or different and are 1, 2, 3 or 4; wherein Z is O, NH, NCHO, NCOR', NR', NOR' or $CH_2$, where R' is a methyl, ethyl or propyl group; wherein X is NH, NR", O, or S, where R" is H or a linear or branched chain alkyl or acyl group, or an aryl group; wherein $R^4$ is H, or a linear or branched chain alkyl group, or an aryl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR'_2$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

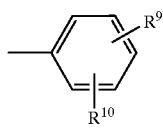

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{12}$ and $R^{13}$ are independently the same or different and are H or a linear chain alkyl group; and wherein p is 0, 1, 2 or 3.

The invention also provides a compound having the structure:

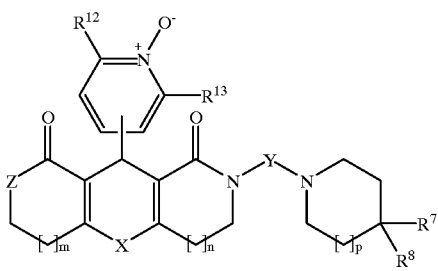

wherein Y is —$(CH_2)_n$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$—, where h and k are independently the same or different and are 1, 2, 3 or 4; wherein Z is O, NH, NCHO, NCOR, NR, NOR or $CH_2$, where R is a methyl, ethyl or propyl group; wherein X is NH, NR', O, or S, where R' is H or a linear or branched chain alkyl or acyl group, or an aryl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR'_2$, COOH, COOR', CHO, COR', COSH, COSR', $COO(CH_2)_qOH$ or $COO(CH_2)_q$ OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

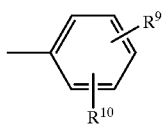

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{12}$ and $R^{13}$ are independently the same or different and are H or a linear chain alkyl group; wherein m and n are independently the same or different and are 0 or 1; and wherein p is 0, 1, 2 or 3.

The invention further provides a compound having the structure:

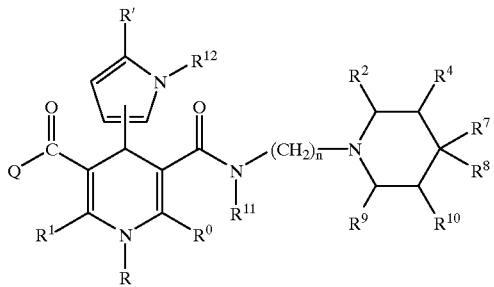

wherein Q is OH, OR', SH, SR''', $NH_2$, NHR''', $NR_2$''', NR"OH, NR"OR''', or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R''' is a linear or branched chain alkyl group, or an aryl group; wherein $R^0$, $R^1$ and R' are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2^1$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein $R^2$, $R^9$ and $R^{10}$ are independently the same or different and are H or a linear or branched chain alkyl group; wherein $R^4$ is H or a linear or branched chain alkyl, alkyloxymethyl, or alkoxyethyl group, or a hydroxymethyl or hydroxyethyl group, or a linear or branched chain alkenylalkyl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

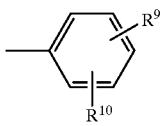

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{11}$ is H or a linear chain alkyl group; wherein $R^{12}$ is H or a linear chain alkyl or acyl group; and wherein n is 2, 3 or 4.

In addition, the invention provides a compound having the structure:

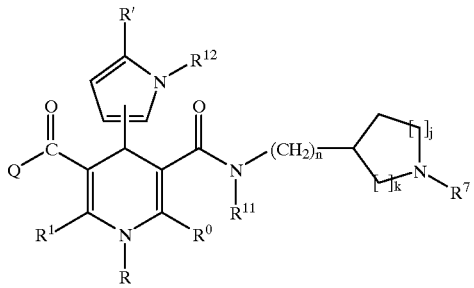

wherein Q is OH, OR'', SH, SR''', $NH_2$, NHR''', $NR_2'''$, NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein $R^0$, $R^1$ and R' are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2^1$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein $R^7$ is an aryl or diarylalkyl group; wherein $R^{11}$ is H or a linear chain alkyl group; wherein $R^{12}$ is H or a linear chain alkyl or acyl group;

wherein j and k are independently the same or different and are 0, 1, 2, 3 or 4; and wherein n is 2, 3 or 4.

The invention also provides a compound having the structure:

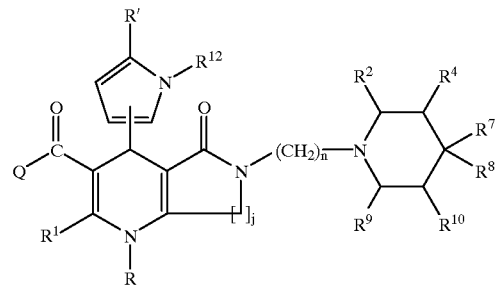

wherein Q is OH, OR'', SH, SR''', $NH_2$, NHR''', $NR_2'''$, NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein $R^1$ and R' are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^1$ and R' are independently the same or different and are H, or a linear or branched chain alkyl, alkyloxymethyl, or alkoxyethyl group, or a hydroxymethyl or hydroxyethyl group, or an aryl group; wherein $R^2$, $R^9$ and $R^{10}$ are independently the same or different and are H or a linear or branched chain alkyl group; wherein $R^4$ is H or a linear or branched chain alkyl, alkyloxymethyl, or alkoxyethyl group, or a hydroxymethyl or hydroxyethyl group, or a linear or branched chain alkenylalkyl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

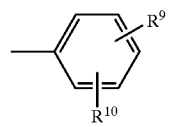

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{11}$ is H or a linear chain alkyl group; wherein $R^{12}$ is H or a linear chain alkyl or acyl group; wherein j is 1, 2, 3 or 4; and wherein n is 2, 3 or 4.

The invention further provides a compound having the structure:

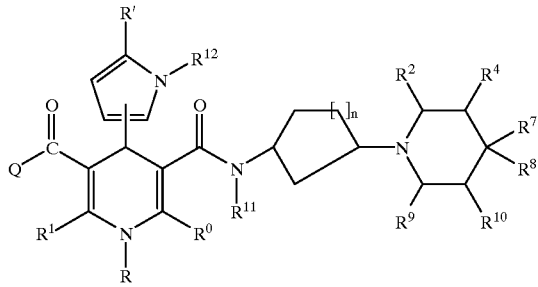

wherein Q is OH, OR", SH, SR'", $NH_2$, NHR'", $NR_2$'", NR"OH, NR"OR'", or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R'" is a linear or branched chain alkyl group, or an aryl group; wherein $R^0$, $R^1$ and R' are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^2$, $R^9$ and $R^{10}$ are independently the same or different and are H or a linear or branched chain alkyl group; wherein $R^4$ is H or a linear or branched chain alkyl, alkyloxymethyl, or alkoxyethyl group, or a hydroxymethyl or hydroxyethyl group, or a linear or branched chain alkenylalkyl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', COOH, COOR', CHO, COR', COSH, COSR', $COO(CH_2)_q$OH or $COO(CH_2)_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

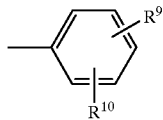

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{11}$ is H or a linear chain alkyl group; wherein $R^{12}$ is H or a linear chain alkyl or acyl group; and wherein n is 0, 1, 2, 3 or 4.

The invention further provides a compound having the structure:

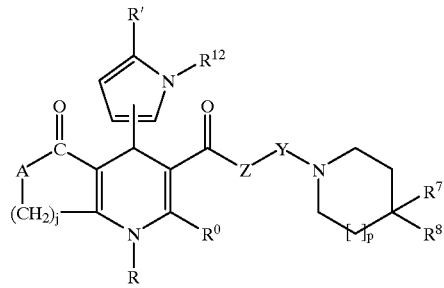

wherein Y is $-(CH_2)_n-$, where n is 1, 2, 3, 4 or 5; $-(CH_2)_h-O-(CH_2)_k-$, where h and k are independently the same or different and are 2, 3 or 4; $-(CH_2)_h-CH=CH-(CH_2)_k-$; or $-(CH_2)_h-C\equiv C-(CH_2)_k-$, where h and k are independently the same or different and are 1, 2, 3 or 4; wherein A is $CH_2$, $CR^a_2$, NH, NR, NCHO, NCOR', NOH, O or S, where $R^a$ is a methyl, ethyl or propyl group; wherein Z is O, NH, NCHO, $NCOR^b$, $NR^b$, $NOR^b$, or $CH_2$, where $R^b$ is a methyl, ethyl or propyl group; wherein R is H or a linear or branched chain alkyl or acyl group, or an aryl group; wherein $R^0$ and R' are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_q$OH or COO $(CH_2)_q$ OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

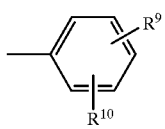

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{12}$ is H or a linear chain alkyl or acyl group; wherein j is 1, 2, 3 or 4; wherein n is 2, 3 or 4; and wherein p is 0, 1, 2 or 3.

The invention still further provides a compound having the structure:

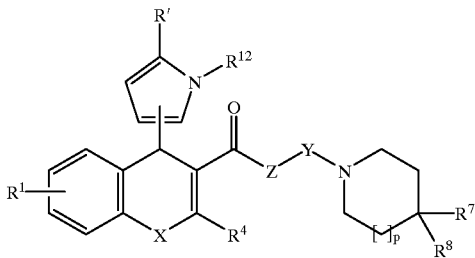

wherein X is NH, NR$^a$, O, or S, where R$^a$ is H or a linear or branched chain alkyl or acyl group, or an aryl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR', NR', NOR', or CH$_2$, where R' is a methyl, ethyl or propyl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

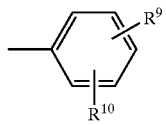

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl or acyl group; wherein j is 1, 2, 3 or 4; wherein n is 2, 3 or 4; and wherein p is 0, 1, 2 or 3.

The invention also provides a compound having the structure:

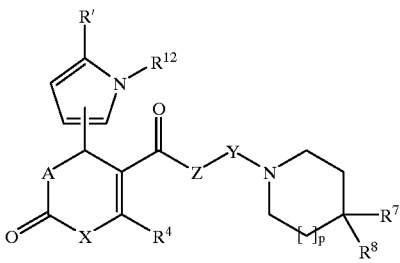

wherein A is CH$_2$, CR$_2$, NH, NR, NCHO, NCOR, NOH, O or S, where R is a methyl, ethyl or propyl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$, where h and k are independently the same or different and are 1, 2, 3 or 4; wherein Z is O, NH, NCHO, NCOR', NR', NOR' or CH$_2$, where R' is a methyl, ethyl or propyl group; wherein X is NH, NR", O, or S, where R" is H or a linear or branched chain alkyl or acyl group, or an aryl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

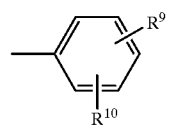

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl or acyl group; and wherein p is 0, 1, 2 or 3.

The invention provides a compound having the structure:

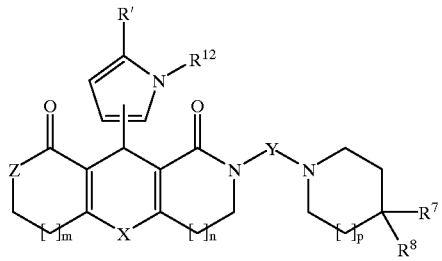

wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR', NR', NOR', or CH$_2$, where R' is a methyl, ethyl or propyl group; wherein X is NH, NR", O, or S, where R" is H or a linear or branched chain alkyl or acyl group, or an aryl group; wherein R' is H, or a methyl, ethyl or propyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

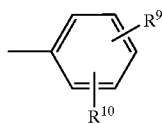

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{12}$ is H or a linear chain alkyl or acyl group; wherein m and n are independently the same or different and are 0 or 1; and wherein p is 0, 1, 2 or 3.

The invention also provides a compound having the structure:

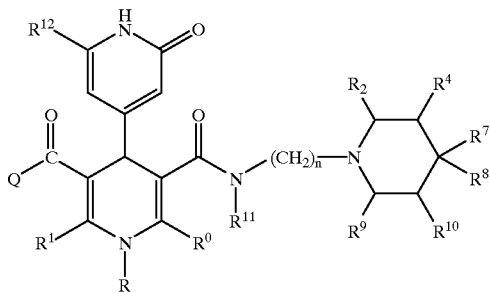

wherein Q is OH, OR", SH, SR''', $NH_2$, NHR''', $NR_2$''', NR"OH, NR"OR''', or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R''' is a linear or branched chain alkyl group, or an aryl group; wherein $R^0$, and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein $R^0$ and $R^1$ are independently the same or different and are H, or a linear or branched chain alkyl group, or an aryl group; wherein $R^2$, $R^9$ and $R^{10}$ are independently the same or different and are H or a linear or branched chain alkyl group; wherein $R^4$ is H or a linear or branched chain alkyl, alkyloxymethyl, or alkoxyethyl group, or a hydroxymethyl or hydroxyethyl group, or a linear or branched chain alkenylalkyl group; wherein $R^7$ and $R^8$ are independently the same or different and are H, CN, $CF_3$, OH, OR', OCOR', $NH_2$, NHR', $NR_2'$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

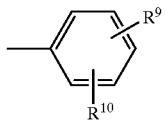

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{11}$ is H or a linear chain alkyl group; wherein $R^{12}$ is H or a linear chain alkyl group; and wherein n is 2, 3 or 4.

The invention further provides a compound having the structure:

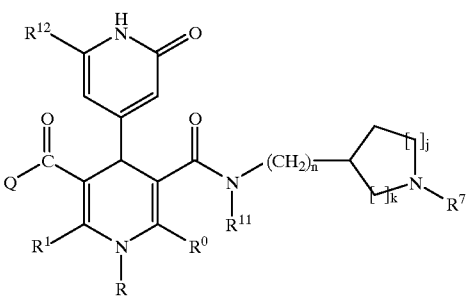

wherein Q is OH, OR", SH, SR''', $NH_2$, NHR''', $NR_2$''', NR"OH, NR"OR''', or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R''' is a linear or branched chain alkyl group, or an aryl group; wherein R is H or a linear or branched chain alkyl or acyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^7$ is an aryl or diarylalkyl group; wherein $R^{11}$ is H or a linear chain alkyl group; wherein $R^{12}$ is H or a linear chain alkyl group; wherein j and k are independently the same or different and are 0, 1, 2, 3 or 4; and wherein n is 2, 3 or 4.

The invention still further provides a compound having the structure:

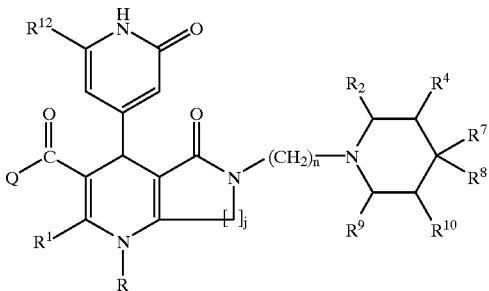

wherein Q is OH, OR", SH, SR'", NH$_2$, NHR'", NR$_2$'", NR"OH, NR"OR'", or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R'" is a linear or branched chain alkyl group, or an aryl group; wherein R is H or a linear or branched chain alkyl or acyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^2$, R$^9$ and R$^{10}$ are independently the same or different and are H or a linear or branched chain alkyl group; wherein R$^4$ is H or a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

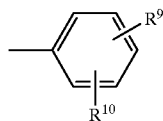

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; wherein j is 1, 2, 3 or 4; and wherein n is 2, 3 or 4.

The invention also provides a compound having the structure:

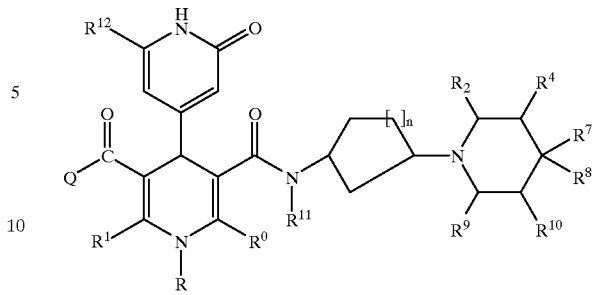

wherein Q is OH, OR", SH, SR'", NH$_2$, NHR'", NR$_2$'", NR"OH, NR"OR'", or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R'" is a linear or branched chain alkyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^2$, R$^9$ and R$^{10}$ are independently the same or different and are H or a linear or branched chain alkyl group; wherein R$^4$ is H or a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

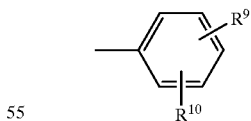

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{11}$ is H or a linear chain alkyl group; wherein R$^{12}$ is H or a linear chain alkyl or acyl group; and wherein n is 0, 1, 2, 3 or 4.

The invention further provides a compound having the structure:

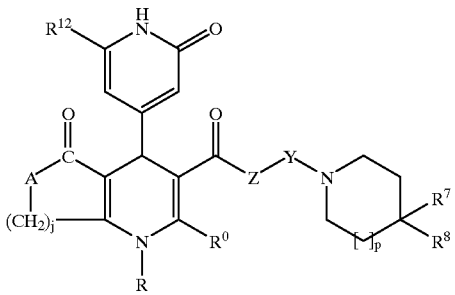

wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein A is CH$_2$, CR'$_2$, NH, NR', NCHO, NCOR', NOH, O or S, where R' is a methyl, ethyl or propyl group; wherein Z is O, NH, NCHO, NCOR", NR", NOR", or CH$_2$, where R" is a methyl, ethyl or propyl group; wherein R is H or a linear or branched chain alkyl or acyl group, or an aryl group; wherein R$^0$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

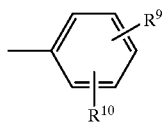

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR', NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; wherein j is 1, 2, 3 or 4; and wherein p is 0, 1, 2 or 3.

The invention also provides a compound having the structure:

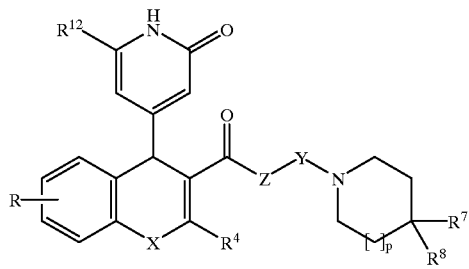

wherein X is NH, NR", O or S, where R" is H or a linear or branched chain alkyl or acyl group, or an aryl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR', NOR' or CH$_2$, where R' is a methyl, ethyl or propyl group; wherein R$^1$ is H, Cl, Br, I, F, NO$_2$, CN, OH, OR$^2$, OCOR$^2$, NH$_2$, NR$^2$, NHCOR$_2$, or CF$_3$, where R$^2$ is a linear or branched chain alkyl group, or an aryl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

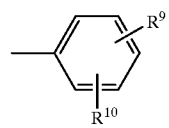

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; and wherein p is 0, 1, 2 or 3.

The invention further provides a compound having the structure:

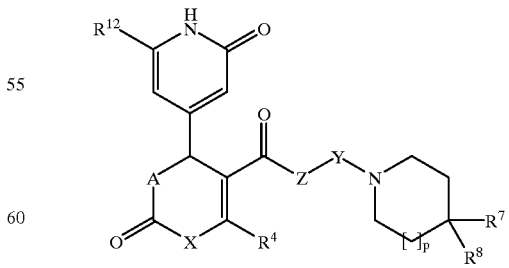

wherein A is CH$_2$, CR$_2$, NH, NR, NCHO, NCOR, NOH, O or S, where R is a methyl, ethyl or propyl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$, where h and k are independently the same or different and are 1, 2, 3 or 4; wherein Z is O, NH, NCHO, NCOR', NR', NOR' or CH$_2$, where R' is a methyl, ethyl or propyl group; wherein X is NH, NR", O or S, where R" is H or a linear or branched chain alkyl or acyl group, or an aryl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

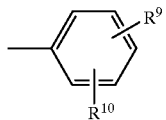

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; and wherein p is 0, 1, 2 or 3.

The invention provides a compound having the structure:

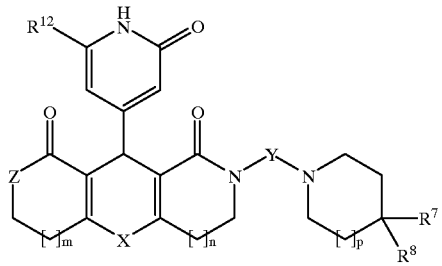

wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein X is NH, NR', O, or S, where R' is H or a linear or branched chain alkyl or acyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO (CH$_2$)$_q$ OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

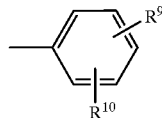

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; wherein m and n are independently the same or different and are 0 or 1; and wherein p is 0, 1, 2 or 3.

The invention also provides a compound having the structure:

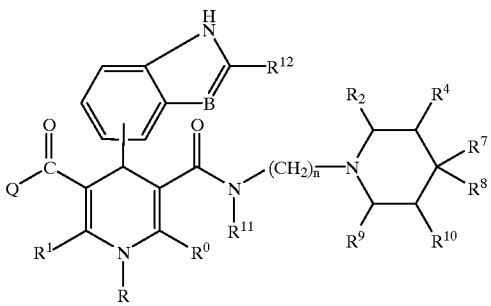

wherein B is CH or N; wherein Q is OH, OR''', SH, SR''', NH$_2$, NHR''', NR$_2$''', NR"OH, NR"OR''', or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R''' is a linear or branched chain alkyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^2$, R$^9$ and R$^{10}$ are independently the same or different and are H or a linear or branched chain alkyl group; wherein R$^4$ is H or a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

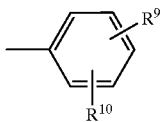

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}{}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{11}$ is H or a linear chain alkyl group; wherein $R^{12}$ is H or a linear chain alkyl group; and wherein n is 2, 3 or 4.

The invention further provides a compound having the structure:

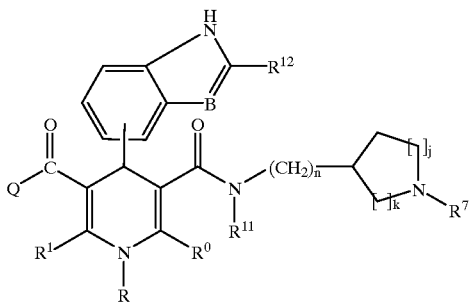

wherein B is CH or N; wherein Q is OH, OR'', SH, SR''', $NH_2$, NHR''', $NR_2'''$, NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^7$ is an aryl or diarylalkyl group; wherein $R^{11}$ is a linear chain alkyl group; wherein $R^{12}$ is H or a linear chain alkyl group; wherein j and k are independently the same or different and are 0, 1, 2, 3 or 4; and wherein n is 2, 3 or 4.

The invention still further provides a compound having the structure:

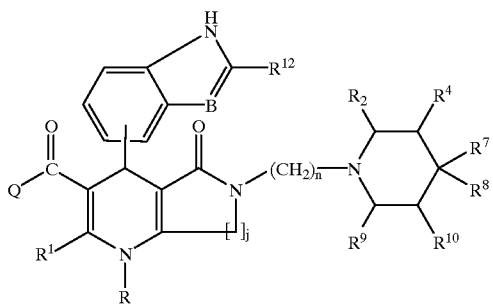

wherein B is CH or N; wherein Q is OH, OR'', SH, SR''', $NH_2$, NHR''', $NR_2'''$, NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein $R^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein $R^2$, $R^9$ and $R^{10}$ are independently the same or different and are H or a linear or branched chain alkyl group; wherein $R^4$ is H or a linear or branched chain alkyl, alkyloxymethyl, or alkoxyethyl group, or a hydroxymethyl or hydroxyethyl group, or a linear or branched chain alkenylalkyl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

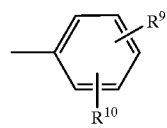

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}{}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{11}$ is H or a linear chain alkyl group; wherein $R^{12}$ is H or a linear chain alkyl group; wherein j is 1, 2, 3 or 4; and wherein n is 2, 3 or 4.

The invention also provides a compound having the structure:

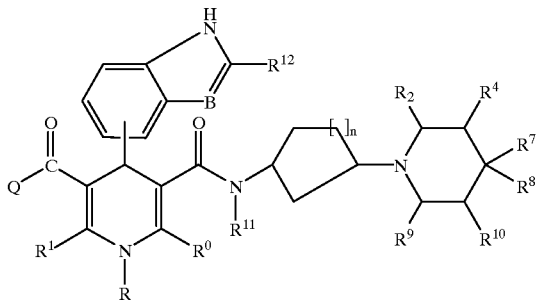
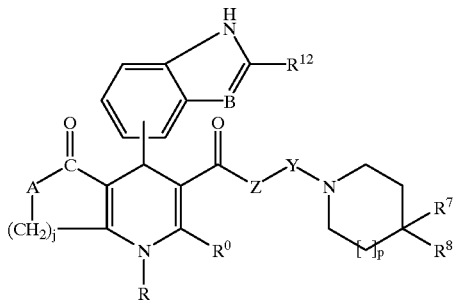

wherein B is CH or N; wherein Q is OH, OR'', SH, SR''', NH$_2$, NHR''', NR$_2$''', NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^2$, R$^9$ and R$^{10}$ are independently the same or different and are H or a linear or branched chain alkyl group; wherein R$^4$ is H or a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

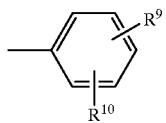

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{11}$ is H or a linear chain alkyl group; wherein R$^{12}$ is H or a linear chain alkyl or acyl group; and n is 2, 3 or 4.

The invention further provides a compound having the structure:

wherein A is CH$_2$, CR$_2$, NH, NR, NCHO, NCOR, NOH, O or S, where R is a methyl, ethyl or propyl group; wherein B is CH or N; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein R$^0$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR$^{iv}$, N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

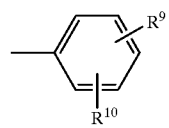

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; wherein j is 1, 2, 3 or 4; and wherein p is 0, 1, 2 or 3.

The invention still further provides a compound having the structure:

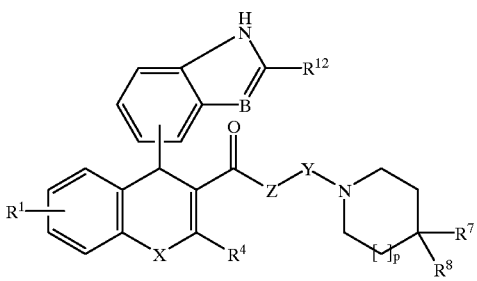

wherein B is CH or N; wherein X is NH, NR', O, or S, where R' is H or a linear or branched chain alkyl or acyl group, or an aryl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein R$^1$ is H, Cl, Br, I, F, NO$_2$, CN, OH, OR$^2$, OCOR$^2$, NH$_2$, NR$_2$, NHCOR$_2$ or CF$_3$, where R$^2$ is a linear or branched chain alkyl group, or an aryl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

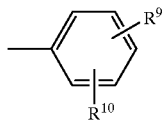

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; and wherein p is 0, 1, 2 or 3.

The invention also provides a compound having the structure:

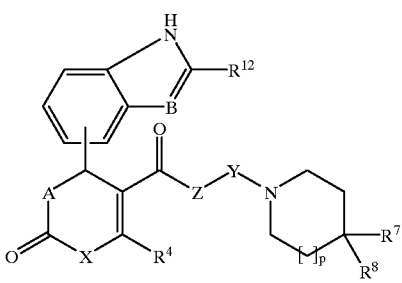

wherein A is CH$_2$, CR$_2$, NH, NR, NCHO, NCOR, NOH, O or S, where R is a methyl, ethyl or propyl group; B is CH or N; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein X is NH, NR', O or S, where R' is H or a linear or branched chain alkyl or acyl group, or an aryl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

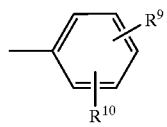

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; and wherein p is 0, 1, 2 or 3. The invention further provides a compound having the structure:

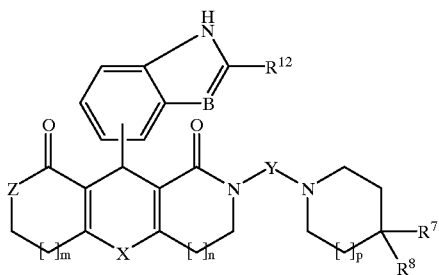

wherein B is CH or N; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein X is NH, NR', O or S, where R' is H or a linear or branched chain alkyl or acyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

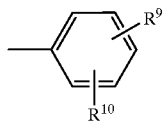

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{12}$ is H or a linear chain alkyl group; wherein m and n are independently the same or different and are 0 or 1; and wherein p is 0, 1, 2 or 3.

The invention provides a compound having the structure:

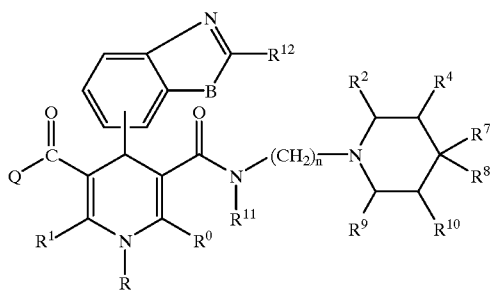

wherein B is O or S; wherein Q is OH, OR''', SH, SR''', $NH_2$, NHR''', $NR_2'''$, NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W_0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein $R^2$, $R^9$ and $R^{10}$ are independently the same or different and are H or a linear or branched chain alkyl group; wherein $R^4$ is H or a linear or branched chain alkyl, alkyloxymethyl, or alkoxyethyl group, or a hydroxymethyl or hydroxyethyl group, or a linear or branched chain alkenylalkyl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{11}$ is H or a linear chain alkyl group; wherein $R^{12}$ is H or a linear chain alkyl group; and n is 2, 3 or 4.

The invention also provides a compound having the structure:

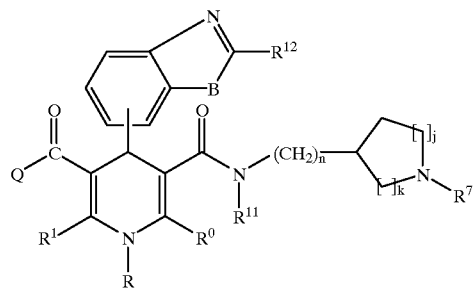

wherein B is O or S; wherein Q is OH, OR''', SH, SR''', $NH_2$, NHR''', $NR_2'''$, NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W_0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein $R^7$ is an aryl or diarylalkyl group; wherein $R^{11}$ is H or a linear chain alkyl group; wherein $R^{12}$ is H or a linear chain alkyl group; wherein j and k are independently the same or different and are 0, 1, 2, 3 or 4; and n is 2, 3 or 4.

The invention further provides a compound having the structure:

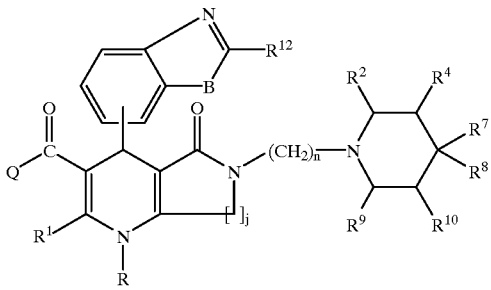

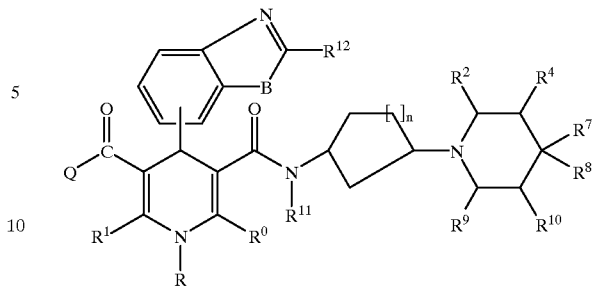

wherein B is O or S; wherein Q is OH, OR''', SH, SR''', NH$_2$, NHR''', NR$_2$''', NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^2$, R$^9$ and R$^{10}$ are independently the same or different and are H or a linear or branched chain alkyl group; wherein R$^4$ is H or a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

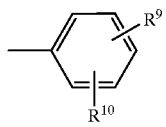

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{11}$ is H or a linear chain alkyl group; wherein R$^{12}$ is H or a linear chain alkyl group; wherein j is 1, 2, 3 or 4; and wherein n is 2, 3 or 4.

The invention still further provides a compound having the structure:

wherein B is O or S; wherein Q is OH, OR''', SH, SR''', NH$_2$, NHR''', NR$_2$''', NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$_0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^2$, R$^9$ and R$^{10}$ are independently the same or different and are H or a linear or branched chain alkyl group; wherein R$^4$ is H or a linear or branched chain alkyl, alkyloxymethyl or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

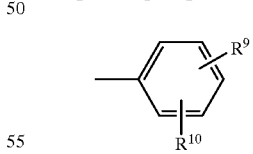

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{11}$ is H or a linear chain alkyl group; wherein R$^{12}$ is H or a linear chain alkyl or acyl group; and wherein n is 0, 1, 2, 3 or 4.

In addition, the invention provides a compound having the structure:

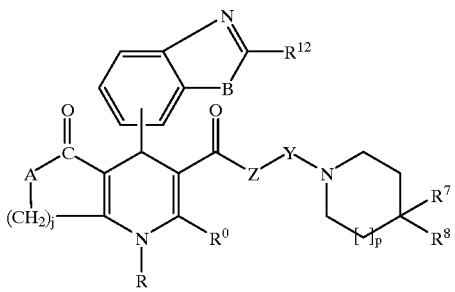

wherein B is O or S; wherein Q is OH, OR'', SH, SR''', NH$_2$, NHR''', NR$_2$''', NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein R$^0$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$_0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein A is CH$_2$, CR'$_2$, NH, NR', NCHO, NCOR', NOH, O or S, where R' is a methyl, ethyl or propyl group; wherein Z is O, NH, NCHO, NCOR$^a$, NR$^a$, NOR$^a$, or CH$_2$, where R$^a$ is a methyl, ethyl or propyl group; wherein R is H or a linear or branched chain alkyl or acyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

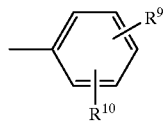

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; wherein j is 1, 2, 3 or 4; and wherein p is 0, 1, 2 or 3.

The invention also provides a compound having the structure:

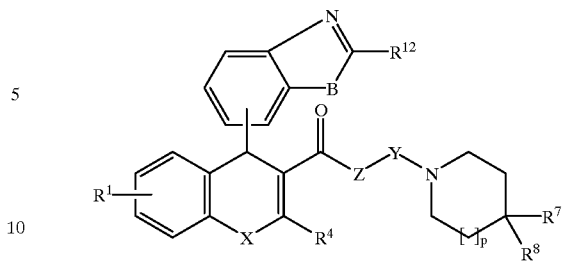

wherein B is O or S; wherein X is NH, NR', O, or S, where R' is H or a linear or branched chain alkyl or acyl group, or an aryl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—CH≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein R$^1$ is H, Cl, Br, I, F, NO$_2$, CN, OH, OR$^2$, OCOR$^2$, NH$_2$, NR$^2$, NHCOR$_2$, or CF$_3$, where R$^2$ is a linear or branched chain alkyl group, or an aryl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

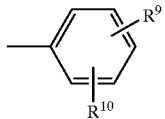

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; and wherein p is 0, 1, 2 or 3.

The invention further provides a compound having the structure:

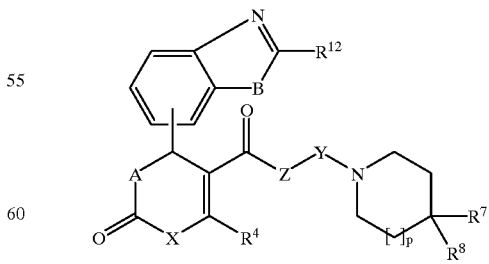

wherein A is CH$_2$, CR$_2$, NH, NR, NCHO, NCOR, NOH, O or S, where R is a methyl, ethyl or propyl group; wherein B is O or S; wherein X is NH, NR', O, or S, where R' is H or a linear or branched chain alkyl or acyl group, or an aryl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

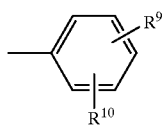

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}_2$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; and wherein p is 0, 1, 2 or 3.

The invention still further provides a compound having the structure:

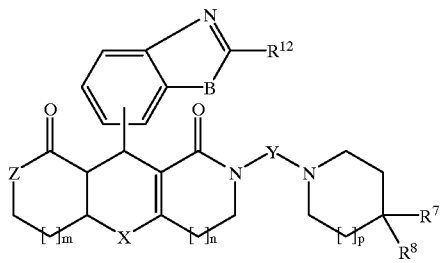

wherein B is O or S; wherein X is NH, NR', O or S, where R' is H or a linear or branched chain alkyl or acyl group, or an aryl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

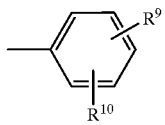

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; wherein m and n are independently the same or different and are 0 or 1; and wherein p is 0, 1, 2 or 3.

The invention provides a compound having the structure:

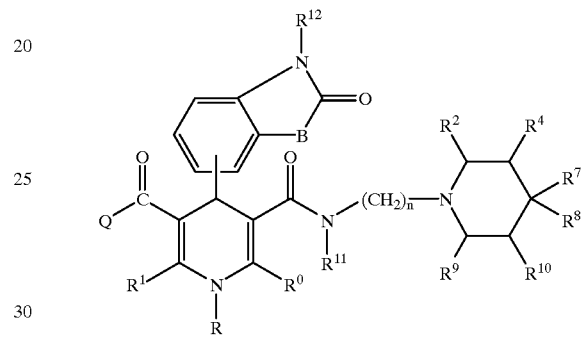

wherein B is O, S or NR$^{12}$; wherein Q is OH, OR", SH, SR'", NH$_2$, NHR'", NR$_2$'", NR"OH, NR"OR'", or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R'" is a linear or branched chain alkyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^2$, R$^9$ and R$^{10}$ are independently the same or different and are H or a linear or branched chain alkyl group; wherein R$^4$ is H or a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

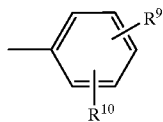

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{11}$ is H or a linear chain alkyl group; wherein $R^{12}$ is H or a linear chain alkyl group; and n is 2, 3 or 4.

The invention also provides a compound having the structure:

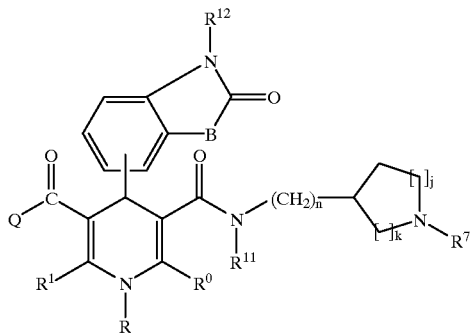

wherein B is O, S or $N^{12}$; wherein Q is OH, OR'', SH, SR''', $NH_2$, NHR''', $NR_2'''$, NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W_0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein $R^7$ is an aryl or diarylalkyl group; wherein $R^{11}$ is a linear chain alkyl group; wherein $R^{12}$ is H or a linear chain alkyl group; wherein j and k are independently the same or different and are 0, 1, 2, 3 or 4; and n is 2, 3 or 4.

The invention further provides a compound having the structure:

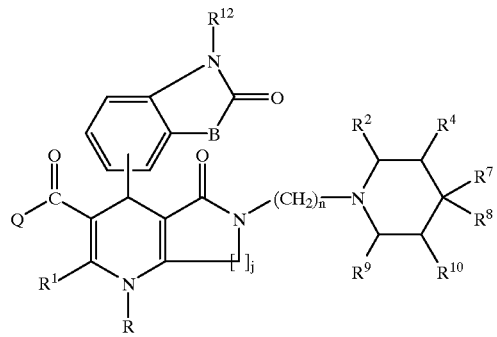

wherein B is O, S or $N^{12}$; wherein Q is OH, OR'', SH, SR''', $NH_2$, NHR''', $NR_2^{1'''}$, NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein $R^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R^{3'}Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein R is H or a linear or branched chain alkyl or acyl group; or an aryl group; wherein $R^2$, $R^9$ and $R^{10}$ are independently the same or different and are H or a linear or branched chain alkyl group; wherein $R^4$ is H or a linear or branched chain alkyl, alkyloxymethyl, or alkoxyethyl group, or a hydroxymethyl or hydroxyethyl group, or a linear or branched chain alkenylalkyl group; wherein $R^7$ and $R^8$ are independently the same or different and are H, CN, $CF_3$, OH, OR', OCOR', $NH_2$, NHR', $NR_2'$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

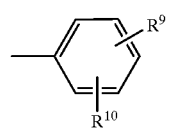

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{11}$ is H or a linear chain alkyl group; wherein $R^{12}$ is H or a linear chain alkyl group; and n is 2, 3 or 4.

The invention still further provides a compound having the structure:

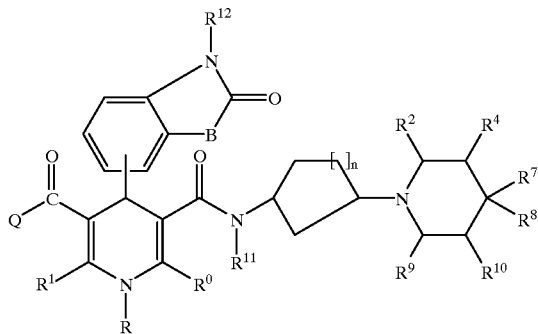
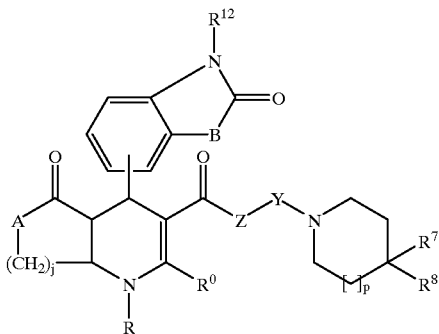

wherein B is CH or N; wherein Q is OH, OR''', SH, SR''', NH$_2$, NHR''', NR$_2$''', NR''OH, NR''OR'''$_1$, or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$_0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^2$, R$^9$ and R$^{10}$ are independently the same or different and are H or a linear or branched chain alkyl group; wherein R$^4$ is a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

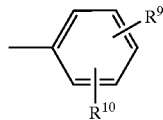

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{11}$ is H or a linear chain alkyl group; wherein R$^{12}$ is H or a linear chain alkyl or acyl group; wherein j is 1, 2, 3 or 4; and n is 0, 1, 2, 3 or 4.

The invention also provides a compound having the structure:

wherein B is O, S, or NR', where R' is H or a linear chain alkyl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein A is CH$_2$, CR'$_2$, NH, NR', NCHO, NCOR', NOH, O or S, where R' is a methyl, ethyl or propyl group; wherein Z is O, NH, NCHO, NCOR'', NR'', NOR'', or CH$_2$, where R'' is a methyl, ethyl or propyl group; wherein R is H or a linear or branched chain alkyl or acyl group, or an aryl group; wherein R$^0$ is independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$_0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO (CH$_2$)$_q$ OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

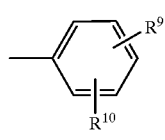

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; wherein j is 1, 2, 3 or 4; wherein n is 2, 3 or 4; and wherein p is 0, 1, 2 or 3.

The invention further provides a compound having the structure:

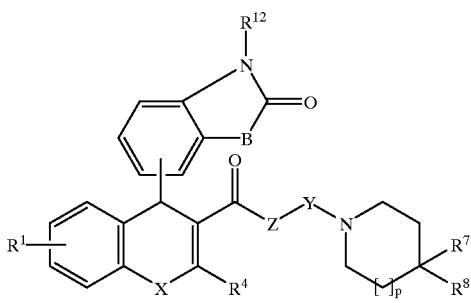

wherein B is O, S or NR', where R' is H or a linear chain alkyl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein R$^1$ is H, Cl, Br, I, F, NO$_2$, CN, OH, OR$^2$, OCOR$^2$, NH$_2$, NR$^2$, NHCOR$_2$ or CF$_3$, where R$^2$ is a linear or branched chain alkyl group, or an aryl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$, COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

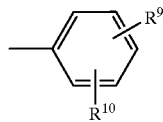

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; and wherein p is 0, 1, 2 or 3.

The invention still further provides a compound having the structure:

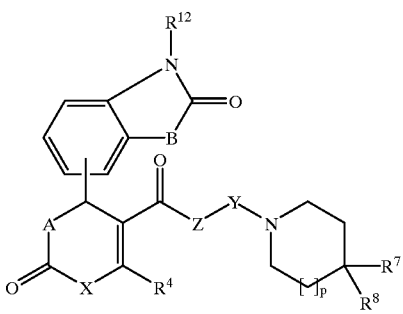

wherein A is CH$_2$, CR$_2$, NH, NR, NCHO, NCOR, NOH, O or S, where R is a methyl, ethyl or propyl group; B is O, S or NR', where R' is H or a linear chain alkyl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR", NR", NOR" or CH$_2$, where R" is a methyl, ethyl or propyl group; wherein X is NH, NR', O or S, where R' is H or a linear or branched chain alkyl or acyl group, or an aryl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

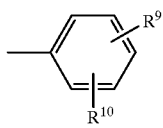

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ is H or a linear chain alkyl group; and wherein p is 0, 1, 2 or 3.

The invention also provides a compound having the structure:

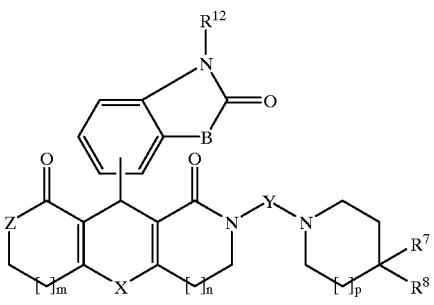

wherein B is O, S or NR', where R' is H or a linear chain alkyl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein X is NH, NR', O or S, where R' is H or a linear or branched chain alkyl or acyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO (CH$_2$)$_q$ OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

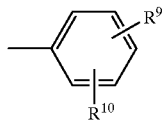

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{12}$ is H or a linear chain alkyl group; wherein m and n are independently the same or different and are 0 or 1; and wherein p is 0, 1, 2 or 3.

The invention further provides a compound having the structure:

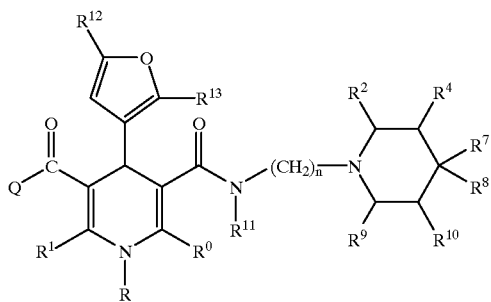

wherein Q is OH, OR", SH, SR''', $NH_2$, NHR''', $NR_2$''', NR"OH, NR"OR''', or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R''' is a linear or branched chain alkyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W^0$ is O, S or NH, where $W^1$ is $NH_2$, NHR', $NR_2$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5, or 6; wherein R is H or a linear or branched chain alkyl or acyl group, or an aryl group; wherein $R^2$, $R^9$ and $R^{10}$ are independently the same or different and are H or a linear or branched chain alkyl group; wherein $R^4$ is H or a linear or branched chain alkyl, alkyloxymethyl or alkoxyethyl group, or a hydroxymethyl or hydroxyethyl group, or a linear or branched chain alkenylalkyl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

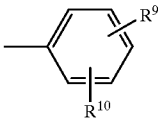

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, OCONHR', $NH_2$, $NHR^{iv}$, $NR^{iv}_2$, NHCOR', $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{11}$ is H or a linear chain alkyl group; wherein $R^{12}$ and $R^{13}$ are independently the same or different and are H or a linear chain alkyl group; and wherein n is 2, 3 or 4.

The invention still further provides a compound having the structure:

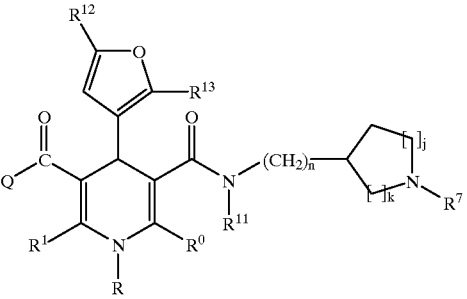

wherein Q is OH, OR", SH, SR''', $NH_2$, NHR''', $NR_2$''', NR"OH, NR"OR''', or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R''' is a linear or branched chain alkyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$, where W is $NH_2$, NHR', $NR_2'$, NHOH, $N^+R_3'Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W_0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein $R^7$ is an aryl or diarylalkyl group; wherein $R^{11}$ is a linear chain alkyl group; wherein $R^{12}$ and $R^{13}$ are independently the same or different and are H or a linear chain alkyl group; wherein j and k are independently the same or different and are 0, 1, 2, 3 or 4; and wherein n is 2, 3 or 4.

In addition, the invention provides a compound having the structure:

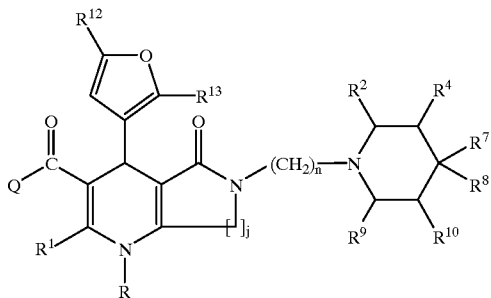

wherein Q is OH, OR", SH, SR'", NH$_2$, NHR'", NR$_2$'", NR"OH, NR"OR'", or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R'" is a linear or branched chain alkyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$_0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^2$, R$^9$ and R$^{10}$ are independently the same or different and are H or a linear or branched chain alkyl group; wherein R$^4$ is H or a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

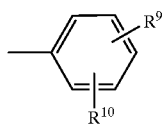

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{11}$ is H or a linear chain alkyl group; wherein R$^{12}$ and R$^{13}$ are independently the same or different and are H or a linear chain alkyl group; and wherein n is 2, 3 or 4.

The invention also provides a compound having the structure:

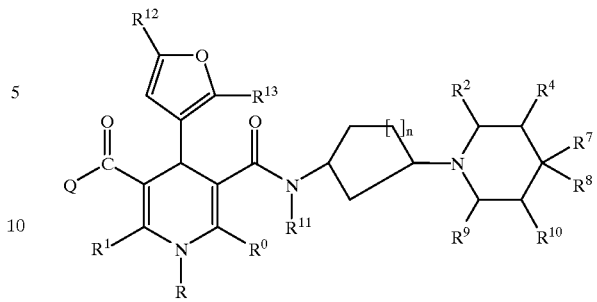

wherein Q is OH, OR", SH, SR'", NH$_2$, NHR'", NR$_2$'", NR"OH, NR"OR'", or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R'" is a linear or branched chain alkyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R$^1$ is a linear or branched chain alkyl group, or an aryl group, where W$_0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^2$, R$^9$ and R$^{10}$ are independently the same or different and are a linear or branched chain alkyl group; wherein R$^4$ is a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

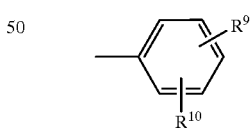

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{11}$ is H or a linear chain alkyl group; wherein R$^{12}$ and R$^{13}$ are independently the same or different and are H or a linear chain alkyl group; wherein j is 1, 2, 3 or 4; and wherein n is 0, 1, 2, 3 or 4.

The invention further provides a compound having the structure:

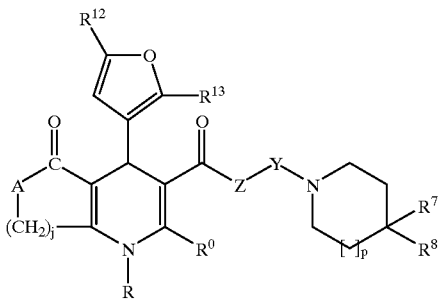

wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein A is CH$_2$, CR'$_2$, NH, NR', NCHO, NCOR', NOH, O or S, where R' is a methyl, ethyl or propyl group; wherein Z is O, NH, NCHO, NCOR'', NR'', NOR'' or CH$_2$, where R'' is a methyl, ethyl or propyl group; wherein R is H or a linear or branched chain alkyl or acyl group, or an aryl group; wherein R$^0$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR'$_2$, NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$_0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$, COOH, COOR', CHO, COR', COSH, COSR', COO(CH$_2$)$_q$OH or COO (CH$_2$)$_q$ OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

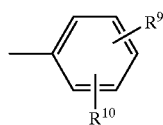

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ and R$^{13}$ are independently the same or different and are H or a linear chain alkyl group; wherein j is 1, 2, 3 or 4; wherein n is 2, 3 or 4; and wherein p is 0, 1, 2 or 3.

The invention still further provides a compound having the structure:

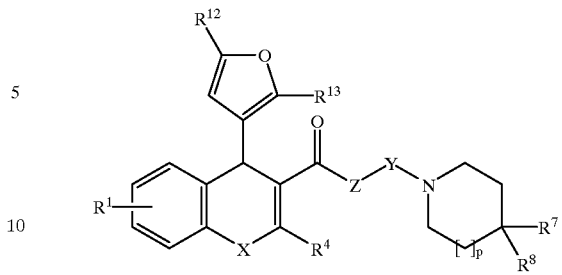

wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein R$^1$ is H, Cl, Br, I, F, NO$_2$, CN, OH, OR$^2$, OCOR$^2$, NH$_2$, NR$_2$, NHCOR$_2$, or CF$_3$, where R$^2$ is a linear or branched chain alkyl group, or an aryl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

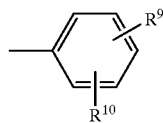

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ and R$^{13}$ are independently the same or different and are H or a linear chain alkyl group; and wherein p is 0, 1, 2 or 3.

The invention also provides a compound having the structure:

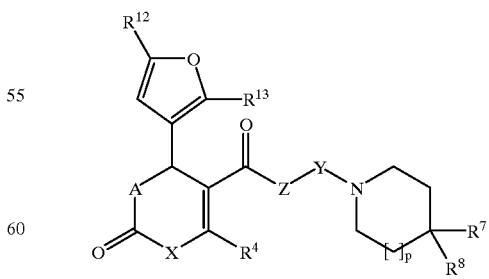

wherein A is CH$_2$, CR$_2$, NH, NR, NCHO, NCOR, NOH, O or S, where R is a methyl, ethyl or propyl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR', NR', NOR' or CH$_2$, where R' is a methyl, ethyl or propyl group; wherein X is NH, NR", O or S, where R" is H or a linear or branched chain alkyl or acyl group, or an aryl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

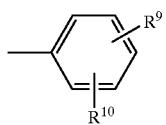

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ and R$^{13}$ are independently the same or different and are H or a linear chain alkyl group; and wherein p is 0, 1, 2 or 3.

The invention further provides a compound having the structure:

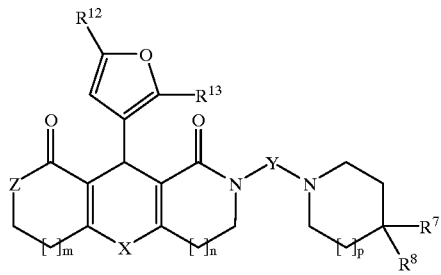

wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR, NR, NOR or CH$_2$, where R is a methyl, ethyl or propyl group; wherein X is NH, NR', O or S, where R' is H or a linear or branched chain alkyl or acyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$ OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

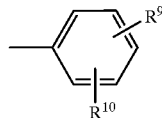

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ and R$^{13}$ are independently the same or different and are H or a linear chain alkyl group; wherein m and n are independently the same or different and are 0 or 1; and wherein p is 0, 1, 2 or 3.

The invention still further provides a compound having the structure:

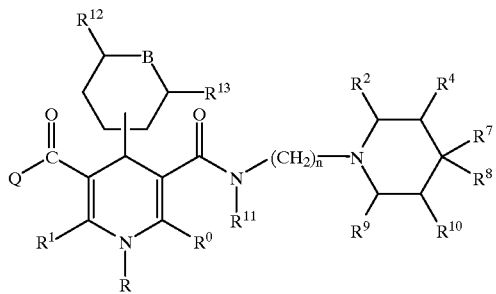

wherein B is O, S, CH$_2$, CHR$^a$, NH or NR$^b$, where R$^a$ is a linear or branched chain alkyl group, or OH, OR', NH$_2$, NR'$_2$, O(C=O)R' or NH(C=O)R", where R" is H or a linear alkyl group, and where R$^b$ is a linear or branched chain alkyl group; wherein Q is OH, OR", SH, SR'", NH$_2$, NHR'", NR$_2$'", NR"OH"NR"OR'", or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R'" is a linear or branched chain alkyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$_0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^2$, R$^9$ and R$^{10}$ are independently the same or different and are H or a linear or branched chain alkyl group; wherein R$^4$ is H or a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

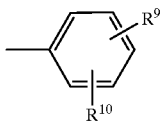

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ and R$^{13}$ are independently the same or different and are H or a linear chain alkyl group; wherein R$^{11}$ is H or a linear chain alkyl group; wherein R$^{12}$ and R$^{13}$ are independently the same or different and are H or a linear chain alkyl group; and wherein n is 2, 3 or 4.

The invention also provides a compound having the structure:

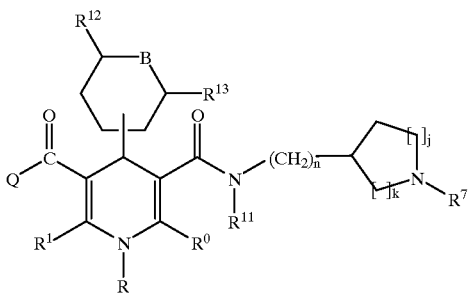

wherein B is O, S, CH$_2$, CHR$^a$, NH or NR$^b$, where R$^a$ is a linear or branched chain alkyl group, or OH, OR$^c$, NH$_2$, NR$^c$$_2$, O(C=O)R$^c$ or NH(C=O)R$^c$, where R$^c$ is H or a linear alkyl group, and where R$^b$ is a linear or branched chain alkyl group; wherein Q is OH, OR'', SH, SR''', NH$_2$, NHR''', NR$_2$''', NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$_0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^7$ is an aryl or diarylalkyl group; wherein R$^{11}$ is H or a linear chain alkyl group; wherein R$^{12}$ and R$^{13}$ are independently the same or different and are H or a linear chain alkyl group; wherein j and k are independently the same or different and are 0, 1, 2, 3 or 4; and wherein n is 2, 3 or 4.

The invention further provides a compound having the structure:

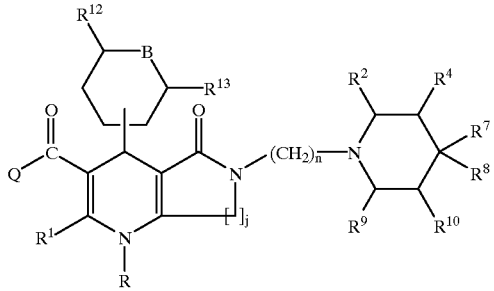

wherein B is O, S, CH$_2$, CHR$^a$, NH or NR$^b$, where R$^a$ is a linear or branched chain alkyl group, or OH, OR$^c$, NH$_2$, NR$^c$$_2$, O(C=O)R$^c$ or NH(C=O)R$^c$, where R$^c$ is H or a linear alkyl group, and where R$^b$ is a linear or branched chain alkyl group; wherein Q is OH, OR'', SH, SR''', NH$_2$, NHR''', NR$_2$''', NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$_0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^2$, R$^9$ and R$^{10}$ are independently the same or different and are H or a linear or branched chain alkyl group; wherein R$^4$ is H or a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

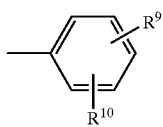

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{11}$ is H or a linear chain alkyl group; wherein R$^{12}$ and R$^{13}$ are independently the same or different and are H or a linear chain alkyl group; and wherein n is 2, 3 or 4.

The invention still further provides a compound having the structure:

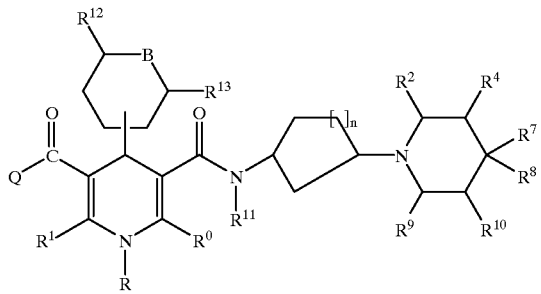

wherein B is O, S, CH$_2$, CHR$^a$, NH or NR$^b$, where R$^a$ is a linear or branched chain alkyl group, or OH, OR$^c$, NH$_2$, NR$^c_2$, O(C=O)R$^c$ or NH(C=O)R$^c$, where R$^c$ is H or a linear alkyl group, and where R$^b$ is a linear or branched chain alkyl group; wherein Q is OH, OR'', SH, SR''', NH$_2$, NHR''', NR$_2$''', NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''', is a linear or branched chain alkyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^2$, R$^9$ and R$^{10}$ are independently the same or different and are H or a linear or branched chain alkyl group; wherein R$^4$ is H or a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

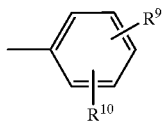

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{11}$ is H or a linear chain alkyl group; wherein R$^{12}$ and R$^{13}$ are independently the same or different and are H or a linear chain alkyl group; wherein j is 1, 2, 3 or 4; and wherein n is 0, 1, 2, 3 or 4.

In addition, the invention provides a compound having the structure:

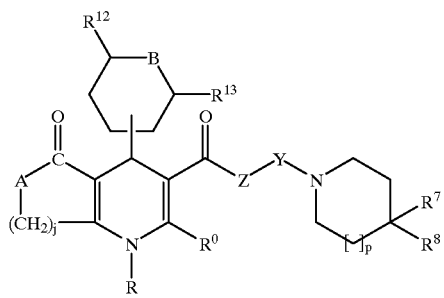

wherein B is O, S, CH$_2$, CHR$^a$, NH or NR$^b$, where R$^a$ is a linear or branched chain alkyl group, or OH, OR$^c$, NH$_2$, NR$^c_2$, O(C=O)R$^c$ or NH(C=O)R$^c$, where R$^c$ is H or a linear alkyl group, and where R$^b$ is a linear or branched chain alkyl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein A is CH$_2$, CR'$_2$, NH, NR', NCHO, NCOR', NOH, O or S, where R' is a methyl, ethyl or propyl group; wherein Z is O, NH, NCHO, NCOR'', NR'', NOR'' or CH$_2$, where R'' is a methyl, ethyl or propyl group; wherein R is H or a linear or branched chain alkyl, or acyl group, or an aryl group; wherein R$^0$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$_0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; H, or a linear or branched chain, alkoxyalkyl, azidoalkyl, aminoalkoxyalkyl, azidoalkoxyalkyl, trihaloalkoxyalkyl, aminoalkyl, hydroxyalkyl, alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$ OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

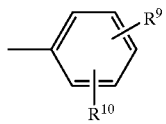

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ and R$^{13}$ are independently the same or different and are H or a linear chain alkyl group; wherein j is 1, 2, 3 or 4; wherein n is 2, 3 or 4; and wherein p is 0, 1, 2 or 3.

The invention also provides a compound having the structure:

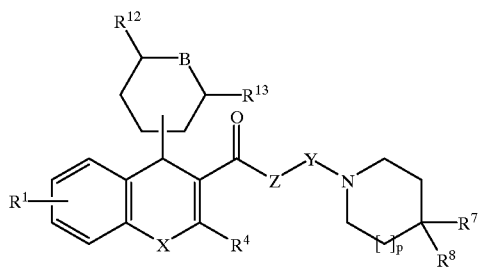

wherein B is O, S, CH$_2$, CHR$^a$, NH or NR$^b$, where R$^a$ is a linear or branched chain alkyl group, or OH, OR$^c$, NH$_2$, NR$^c_2$, O(C=O)R$^c$ or NH(C=O)R$^c$, where R$^c$ is H or a linear alkyl group, and where R$^b$ is a linear or branched chain alkyl group; wherein X is NH, NR', O or S, where R' is H or a linear or branched chain alkyl or acyl group, or an aryl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR", NR", NOR" or CH$_2$, where R" is a methyl, ethyl or propyl group; wherein R is H or a linear or branched chain alkyl or acyl group, or an aryl group; wherein R$^1$ is H, Cl, Br, I, F, NO$_2$, CN, OH, OR$^2$, OCOR$^2$, NH$_2$, NR$^2$, NHCOR$_2$ or CF$_3$, where R$^2$ is a linear or branched chain alkyl group, or an aryl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

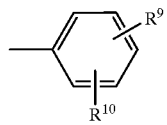

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{12}$ and R$^{13}$ are independently the same or different and are H or a linear chain alkyl group; and wherein p is 0, 1, 2 or 3.

The invention further provides a compound having the structure:

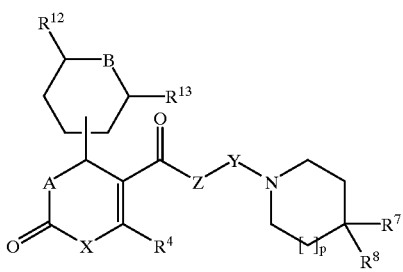

wherein A is CH$_2$, CR$_2$, NH, NR, NCHO, NCOR, NOH, O or S, where R is a methyl, ethyl or propyl group; B is O, S, CH$_2$, CHR$^a$, NH or NR$^b$, where R$^a$ is a linear or branched chain alkyl group, or OH, OR$^c$, NH$_2$, NR$^c_2$, O(C=O)R$^c$ or NH(C=O)R$^c$, where R$^c$ is H or a linear alkyl group, and where R$^b$ is a linear or branched chain alkyl group; wherein X is NH, NR', O or S, where R' is H or a linear or branched chain alkyl or acyl group, or an aryl group; wherein Y is —(CH$_2$)$_n$—, where n is 1, 2, 3, 4 or 5; —(CH$_2$)$_h$—O—(CH$_2$)$_k$—, where h and k are independently the same or different and are 2, 3 or 4; —(CH$_2$)$_h$—CH=CH—(CH$_2$)$_k$—; or —(CH$_2$)$_h$—C≡C—(CH$_2$)$_k$—, where h and k are independently the same or different and are 1, 2, 3 or 4; wherein Z is O, NH, NCHO, NCOR", NR", NOR" or CH$_2$, where R" is a methyl, ethyl or propyl group; wherein R$^4$ is H, or a linear or branched chain alkyl group, or an aryl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

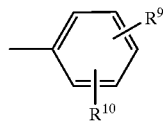

wherein R$^9$ and R$^{10}$ are independently the same or different and are H, Cl, Br, I, F, OH, NO$_2$, N$_3$, OR , OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein $R^{12}$ and $R^{13}$ are independently the same or different and are H or a linear chain alkyl group; and wherein p is 0, 1, 2 or 3.

The invention further provides a compound having the structure:

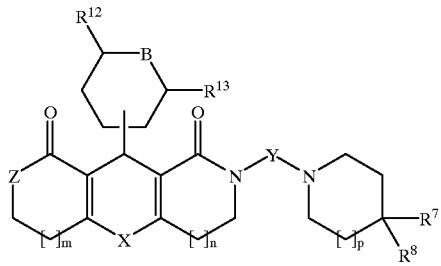

wherein B is O, S, $CH_2$, $CHR^a$, NH or $NR^b$, where $R^a$ is a linear or branched chain alkyl group, or OH, $OR^c$, $NH_2$, $NR^c_2$, $O(C=O)R^c$ or $NH(C=O)R^c$, where $R^c$ is H or a linear alkyl group, and where $R^b$ is a linear or branched chain alkyl group; wherein X is NH, NR', O or S, where R' is H or a linear or branched chain alkyl or acyl group, or an aryl group; wherein Y is —$(CH_2)_n$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$—, where h and k are independently the same or different and are 1, 2, 3 or 4; wherein Z is O, NH, NCHO, NCOR", NR", NOR" or $CH_2$, where R" is a methyl, ethyl or propyl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_q OH$ or $COO(CH_2)_q OR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

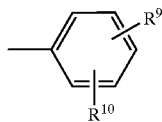

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{12}$ and $R^{13}$ are independently the same or different and are H or a linear chain alkyl group; wherein m and n are independently the same or different and are 0 or 1; and wherein p is 0, 1, 2 or 3.

The invention still further provides a compound having the structure:

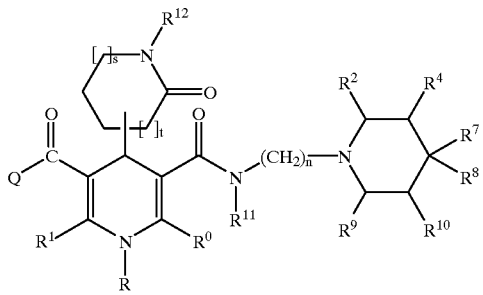

wherein Q is OH, OR", SH, SR'", $NH_2$, NHR'", $NR_2^{1'''}$, NR"OH, NR"OR'", or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R'" is a linear or branched chain alkyl group, or an aryl group; wherein $R^0$ and $R^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_t W$, where W is $NH_2$, NHR', $NR_2'$, NHOH, $N^+R_3'Z^-$, NHCOR', $N_3$, $NO_2$ or $CH_2W^0(CH_2)_v W^1$, or a linear or branched chain alkyl group, or an arylalkyl group, or an alkenyl or alkynyl group, or an aryl group, where R' is a linear or branched chain alkyl group, or an aryl group, where $W_0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein $R^2$, $R^9$ and $R^{10}$ are independently the same or different and are H or a linear or branched chain alkyl group; wherein $R^4$ is H or a linear or branched chain alkyl, alkyloxymethyl, or alkoxyethyl group, or a hydroxymethyl or hydroxyethyl group, or a linear or branched chain alkenylalkyl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_q OH$ or $COO(CH_2)_q OR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

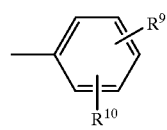

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{11}$ is H or a linear chain alkyl group; wherein $R^{12}$ is H or a linear chain alkyl group; wherein n is 2, 3 or 4; and wherein s and t are independently the same or different and are 0, 1, 2 or 3.

The invention also provides a compound having the structure:

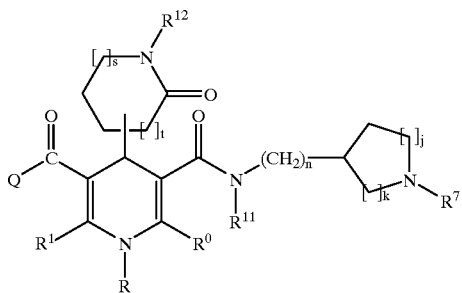

wherein Q is OH, OR'', SH, SR''', NH$_2$, NHR''', NR$_2$''', NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$_0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^7$ is an aryl or diarylalkyl group; wherein R$^{11}$ is H or a linear chain alkyl group; wherein R$^{12}$ is H or a linear chain alkyl group; wherein j and k are independently the same or different and are 0, 1, 2, 3 or 4; wherein n is 2, 3 or 4; and wherein s and t are independently the same or different and are 0, 1, 2 or 3.

The invention further provides a compound having the structure:

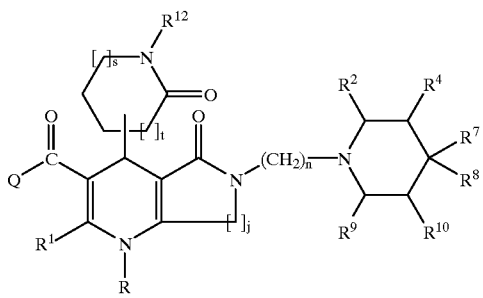

wherein Q is OH, OR'', SH, SR''', NH$_2$, NHR''', NR$_2$''', NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein R$^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$_0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein R$^2$, R$^9$ and R$^{10}$ are independently the same or different and are H or a linear or branched chain alkyl group; wherein R$^4$ is H or a linear or branched chain alkyl, alkyloxymethyl, or alkoxyethyl group, or a hydroxymethyl or hydroxyethyl group, or a linear or branched chain alkenylalkyl group; wherein R$^7$ and R$^8$ are independently the same or different and are H, CN, CF$_3$, OH, OR', OCOR', NH$_2$, NHR', NR'$_2$, NHCOR', CONH$_2$, CONHR', CONR$_2$', COOH, COOR', CHO, COR', COSH, COSR', COO(CH$_2$)$_q$OH or COO(CH$_2$)$_q$OR', or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

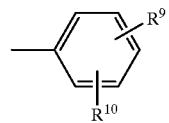

wherein R$^9$ and R$^{10}$ are independently the same or different and are H, Cl, Br, I, F, OH, NO$_2$, N$_3$, OR$^{iv}$, OCOR$^{iv}$, OCOOR$^{iv}$, OCONHR$^{iv}$, NH$_2$, NHR$^{iv}$, NR$^{iv}_2$, NHCOR$^{iv}$, NHCOOR$^{iv}$ or NHCONHR$^{iv}$, where R' is a linear or branched chain alkyl group, and R$^{iv}$ is a linear or branched chain alkyl group, and q is 2, 3, 4 or 5; wherein R$^{11}$ is H or a linear chain alkyl group; wherein R$^{12}$ is H or a linear chain alkyl group; wherein n is 2, 3 or 4; and wherein s and t are independently the same or different and are 0, 1, 2 or 3.

The invention still further provides a compound having the structure:

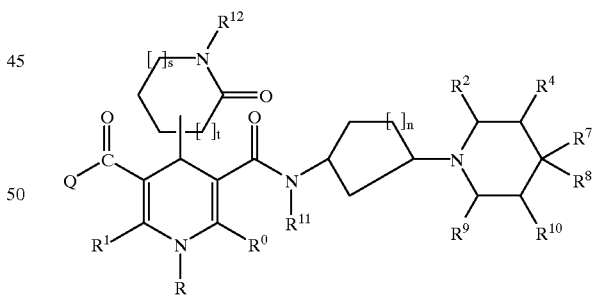

wherein Q is OH, OR'', SH, SR''', NH$_2$, NHR''', NR$_2$''', NR''OH, NR''OR''', or a linear or branched chain alkyl group, or an arylalkyl group, or an alkenyl or alkynyl group, or an aryl group, where R'' is H, a linear or branched chain alkyl group, trialkylsilylalkyl, cyanoalkyl, or an aryl group, and R''' is a linear or branched chain alkyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH$_2$)$_t$W, where W is NH$_2$, NHR', NR$_2$', NHOH, N$^+$R$_3$'Z$^-$, NHCOR', N$_3$, NO$_2$ or $CH_2W^0(CH_2)_vW^1$, or a linear or branched chain alkyl group, or an arylalkyl group, or an alkenyl or alkynyl group, or an aryl group, where R' is a linear or branched chain alkyl group, or an aryl group, where $W_0$ is O, S or NH, where $W^1$ is $NH_2$, NHR', $NR_2'$, NHOH, $N^+R_3'Z^-$, NHCOR', $N_3$ or $NO_2$, and where R' is a linear or branched chain alkyl group, or an aryl group, where $Z^-$ is a pharmaceutically acceptable counterion, and t is 1, 2, 3, 4, 5 or 6 and v is 2, 3, 4, 5 or 6; wherein R is H or a linear or branched chain alkyl or acyl group, or an aryl group; wherein $R^2$, $R^9$ and $R^{10}$ are independently the same or different and are H or a linear or branched chain alkyl group; wherein $R^4$ is H or a linear or branched chain alkyl, alkyloxymethyl, or alkoxyethyl group, or a hydroxymethyl or hydroxyethyl group, or a linear or branched chain alkenylalkyl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

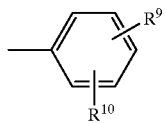

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NRv_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{11}$ is H or a linear chain alkyl group; wherein $R^{12}$ is H or a linear chain alkyl group; wherein j is 1, 2, 3 or 4; wherein n is 0, 1, 2, 3 or 4; and wherein s and t are independently the same or different and are 0, 1, 2 or 3.

The invention also provides a compound having the structure:

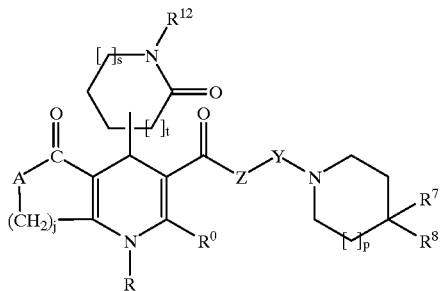

wherein Q is OH, OR', SH, SR", $NH_2$, NHR", NR'OH, NR'OR", where R' is H, or a linear or branched chain alkyl, trialkylsilylalkyl, or cyanoalkyl group, or an aryl group, and where R" is a linear or branched chain alkyl group, or an aryl group; wherein Y is $—(CH_2)_n—$, where n is 1, 2, 3, 4 or 5; $—(CH_2)_h—O—(CH_2)_k—$, where h and k are independently the same or different and are 2, 3 or 4; $—(CH_2)_h—CH=CH—(CH_2)_k—$; or $—(CH_2)_h—C\equiv C—(CH_2)_k—$, where h and k are independently the same or different and are 1, 2, 3 or 4; wherein A is $CH_2$, $CR^a_2$, NH, $NR^a$, NCHO, $NCOR^a$, NOH, O or S, where $R^a$ is a methyl, ethyl or propyl group; wherein Z is O, NH, NCHO, $NCOR^b$, $NR^b$, $NOR^b$, or $CH_2$, where $R^b$ is a methyl, ethyl or propyl group; wherein R is H or a linear or branched chain alkyl or acyl group, or an aryl group; wherein $R^0$ is H, or a linear or branched chain alkyl, alkoxyalkyl, azidoalkyl, aminoalkoxyalkyl, azidoalkoxyalkyl, trihaloalkoxyalkyl, aminoalkyl, or hydroxyalkyl group, or an aryl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

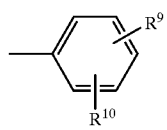

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{12}$ is H or a linear chain alkyl group; wherein j is 1, 2, 3 or 4; wherein p is 0, 1, 2 or 3; and wherein s and t are independently the same or different and are 0, 1, 2 or 3.

The invention further provides a compound having the structure:

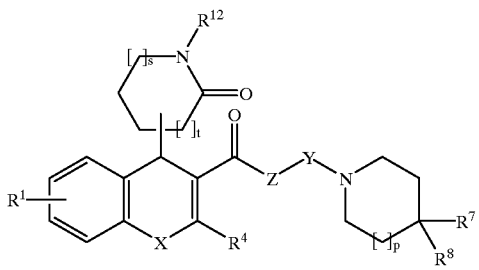

wherein X is NH, NR, O or S, where R is H or a linear or branched chain alkyl or acyl group, or an aryl group; Y is $—(CH_2)_n—$, where n is 1, 2, 3, 4 or 5; $—(CH_2)_h—O—(CH_2)_k—$, where h and k are independently the same or different and are 2, 3 or 4; $—(CH_2)_h—CH=CH—(CH_2)_k—$; or $—(CH_2)_h—C\equiv C—(CH_2)_k—$, where h and k are independently the same or different and are 1, 2, 3 or 4; wherein Z is O, NH, NCHO, NCOR', NR', NOR' or $CH_2$, where R' is a methyl, ethyl or propyl group; wherein $R^1$ is H, Cl, Br, I, F, $NO_2$, CN, OH, OR", OCOR", $NH_2$, NR", NHCOR" or $CF_3$, where R" is a linear or branched chain alkyl group, or an aryl group; wherein $R^4$ is H, or a linear or branched chain alkyl group, or an aryl group; wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

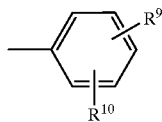

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}{}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and g is 2, 3, 4 or 5; wherein $R^{12}$ is H or a linear chain alkyl group; wherein j is 1, 2, 3 or 4; wherein p is 0, 1, 2 or 3; and wherein s and t are independently the same or different and are 0, 1, 2 or 3.

The invention also provides a compound having the structure:

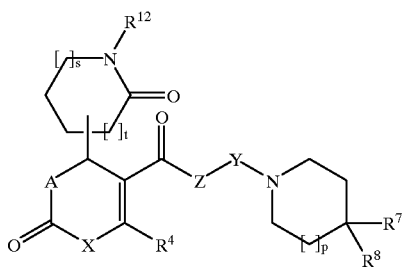

wherein A is $CH_2$, $CR_2$, NH, NR, NCHO, NCOR, NOH, O or S, where R is a methyl, ethyl or propyl group; wherein X is NH, NR', O or S, where R' is H or a linear or branched chain alkyl or acyl group, or an aryl group; wherein Y is —$(CH_2)_n$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$—, where h and k are independently the same or different and are 1, 2, 3 or 4; wherein Z is O, NH, NCHO, NCOR", NR", NOR" or $CH_2$, where R" is a methyl, ethyl or propyl group; wherein $R^4$ is H, or a linear or branched chain alkyl group, or an aryl group; wherein $R^7$ and $R^8$ are independently the same or different and are H, CN, $CF_3$, OH, OR', OCOR', $NH_2$, NHR', NR'${}_2$, NHCOR', $CONH_2$, CONHR', $CONR_2$', COOH, COOR', CHO, COR', COSH, COSR', $COO(CH_2)_q OH$ or $COO(CH_2)_q OR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

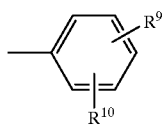

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}{}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{12}$ is H or a linear chain alkyl group; wherein j is 1, 2, 3 or 4; wherein p is 0, 1, 2 or 3; and wherein s and t are independently the same or different and are 0, 1, 2 or 3.

The invention also provides a compound having the structure:

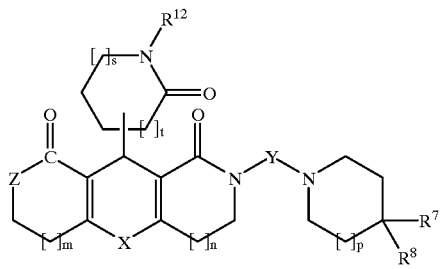

wherein X is NH, NR, O or S, where R is H or a linear or branched chain alkyl or acyl group, or an aryl group; Y is —$(CH_2)_n$—, where n is 1, 2, 3, 4 or 5; —$(CH_2)_h$—O—$(CH_2)_k$—, where h and k are independently the same or different and are 2, 3 or 4; —$(CH_2)_h$—CH=CH—$(CH_2)_k$—; or —$(CH_2)_h$—C≡C—$(CH_2)_k$—, where h and k are independently the same or different and are 1, 2, 3 or 4; wherein Z is O, NH, NCHO, NCOR', NR', NOR' or $CH_2$, where R' is a methyl, ethyl or propyl group; wherein $R^7$ and $R^8$ are independently the same or different and are H, CN, $CF_3$, OH, OR', OCOR', $NH_2$, NHR', NR'${}_2$, NHCOR', $CONH_2$, CONHR', $CONR_2$', COOH, COOR', CHO, COR', COSH, COSR', $COO(CH_2)_q OH$ or $COO(CH_2)_q OR'$, or a benzyl group, a linear or branched chain alkyl or cycloalkyl group, or are a heteroaryl group comprising a pyridyl, indolyl, indolylalkyl, quinolinyl, isoquinolinyl, pyrryl, furyl or thiophene group, or an aryl group having the structure:

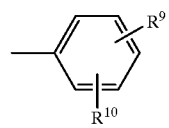

wherein $R^9$ and $R^{10}$ are independently the same or different and are H, Cl, Br, I, F, OH, $NO_2$, $N_3$, $OR^{iv}$, $OCOR^{iv}$, $OCOOR^{iv}$, $OCONHR^{iv}$, $NH_2$, $NHR^{iv}$, $NR^{iv}{}_2$, $NHCOR^{iv}$, $NHCOOR^{iv}$ or $NHCONHR^{iv}$, where R' is a linear or branched chain alkyl group, and $R^{iv}$ is a linear or branched chain alkyl group, and q is 2, 3, 4 or 5; wherein $R^{12}$ is H or a linear chain alkyl group; wherein j is 1, 2, 3 or 4; wherein m and n are independently the same or different and are 0 or 1; wherein p is 0, 1, 2 or 3; and wherein s and t are independently the same or different and are 0, 1, 2 or 3.

The invention provides a compound having the structure:

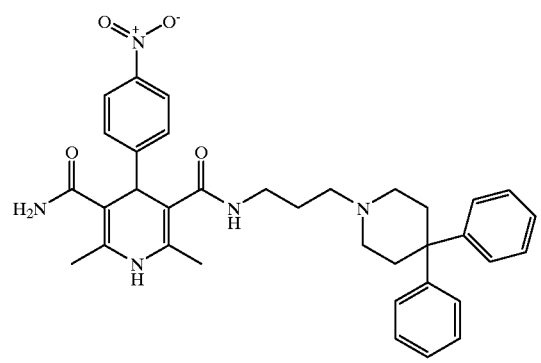

The invention also provides a compound having the structure:

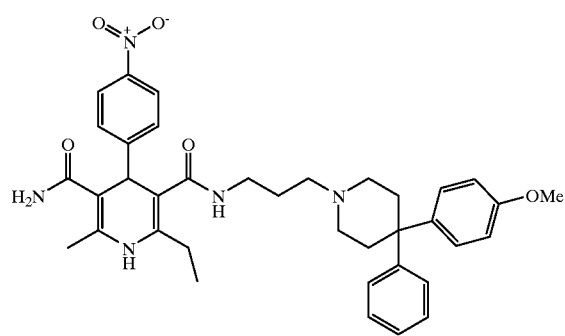

The invention further provides a compound having the structure:

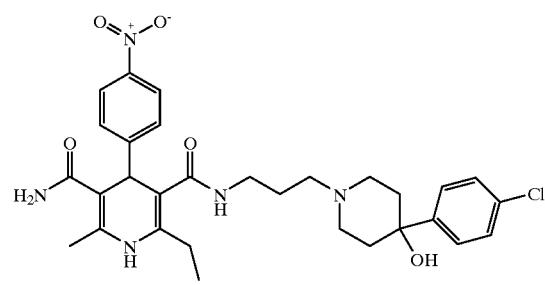

The invention also provides a compound having the structure:

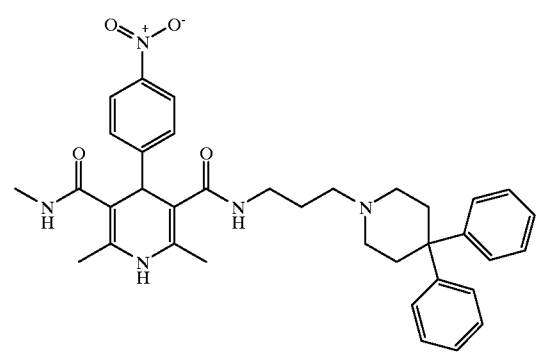

The invention further provides a compound having the structure:

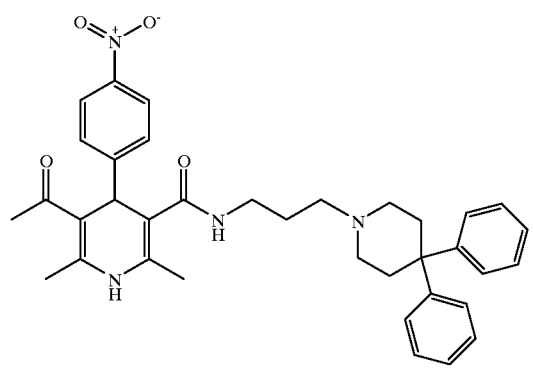

The invention also provides a compound having the structure:

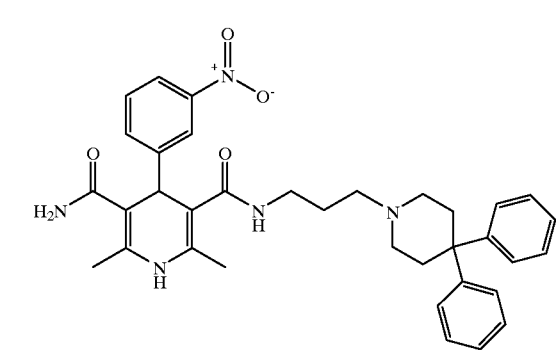

The invention provides a compound having the structure:

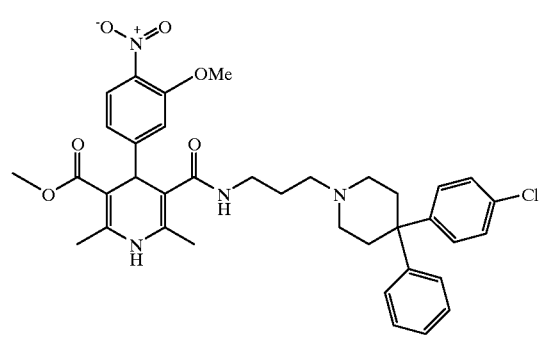

The invention further provides a compound having the structure:

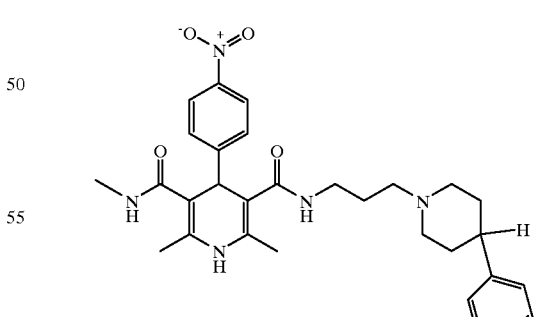

The invention additionally provides a compound having the structure:

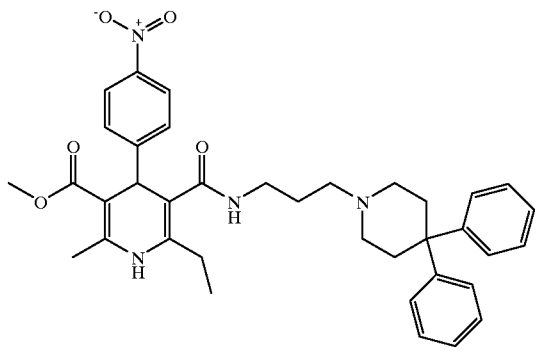

The invention further provides a compound having the structure:

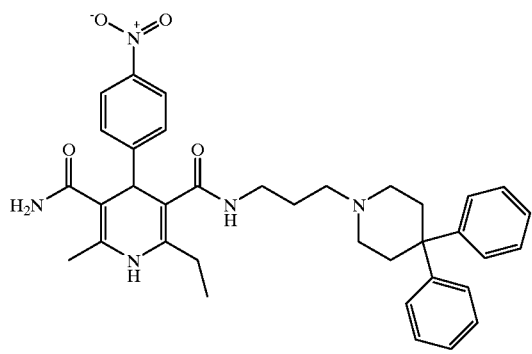

The invention also provides a compound having the structure:

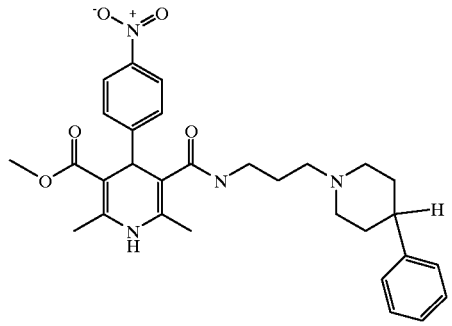

The invention provides a compound having the structure:

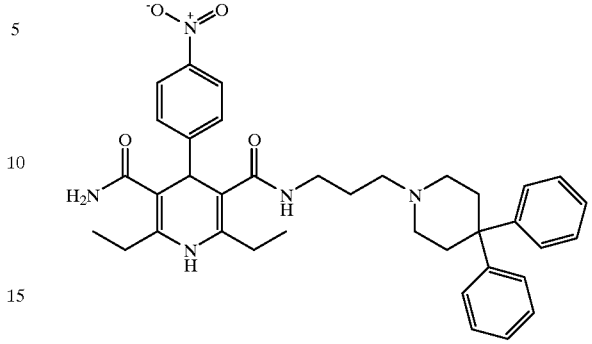

The invention also provides a compound having the structure:

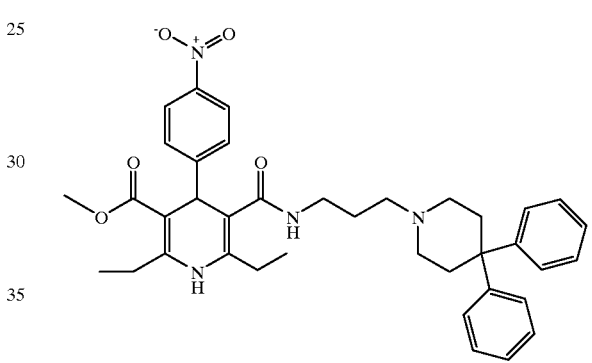

The invention further provides a compound having the structure:

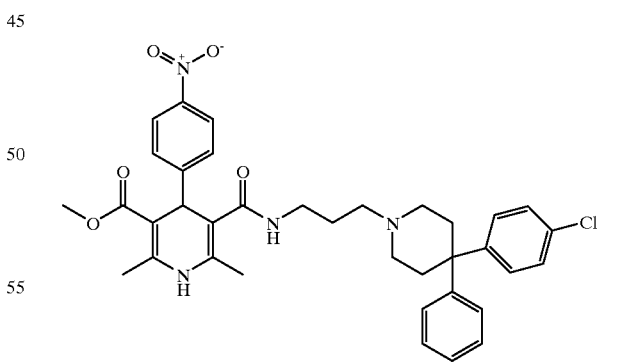

The invention also provides a compound having the structure:

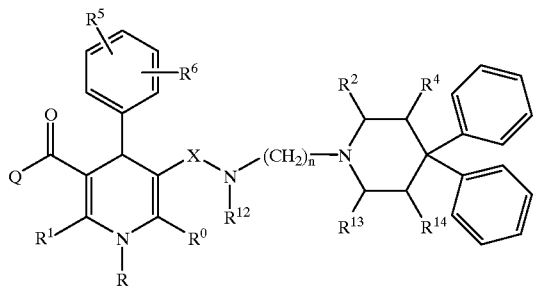

wherein X is C=O, CH₂, CR$^a_2$, NH, NR$^a$, NCHO, NCOR$^a$, NOH, O or S, where R$^a$ is a methyl, ethyl or propyl group; wherein Q is OH, OR", SH, SR''', NH₂, NHR''', NR₂''', NR"OH, NR"OR''', or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R''' is a linear or branched chain alkyl group, or an aryl group; wherein R⁰ and R¹ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH₂)$_t$W, where W is NH₂, NHR', NR₂', NHOH, N⁺R₃'Z⁻, NHCOR', N₃, NO₂ or CH₂W⁰(CH₂)$_v$W¹, or a linear or branched chain alkyl group, or an arylalkyl group, or an alkenyl or alkynyl group, or an aryl group, where R' is a linear or branched chain alkyl group, or an aryl group, where W₀ is O, S or NH, where W¹ is NH₂, NHR', NR₂', NHOH, N⁺R₃'Z⁻, NHCOR', N₃ or NO₂, and where R' is a linear or branched chain alkyl group, or an aryl group, where Z⁻ is a pharmaceutically acceptable counterion, and t is 1, 2, 3, 4, 5 or 6 and v is 2, 3, 4, 5 or 6; wherein R is H, a linear or branched chain alkyl or acyl group, or an aryl group; wherein R², R¹³, and R¹⁴ are independently the same or different and are H, or a linear or branched chain alkyl, hydroxyalkyl, alkoxyalkyl, amino alkyl or aryl group; wherein R⁴ is a linear or branched chain alkyl, alkoxyalkyl, hydroxyalkyl or a linear or branched chain alkenylalkyl group; wherein R⁵ and R⁶ are independently the same or different and are H, OH, Cl, Br, I, F, NO₂, CN, N₃, NH₂, CF₃, a linear or branched chain alkyl, alkoxy, alkoxycarbonyl, acyl, alkylsulfoxide, alkylsulfoxide, or mono- or dialkylamino group, or together constitute a methylenedioxy group; wherein R¹² is H or a linear chain alkyl group; and wherein n is 2, 3 or 4. In one embodiment, the invention provides a compound having the structure:

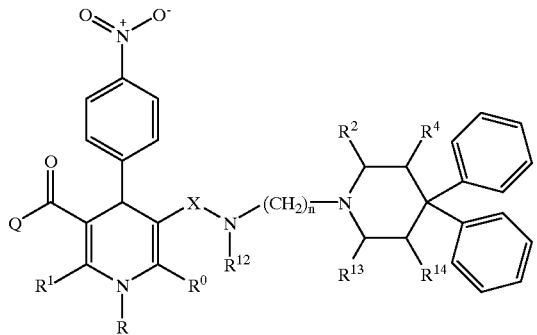

wherein X is C=O, CH₂, CR$^a_2$, NH, NR$^a$, NCHO, NCOR$^a$, NOH, O or S, where R$^a$ is a methyl, ethyl or propyl group; wherein Q is OH, OR", SH, SR''', NH₂, NHR''', NR₂''', NR"OH, NR"OR''', or a linear or branched chain alkyl group, or an arylalkyl group, or an alkenyl or alkynyl group, or an aryl group, where R" is H, a linear or branched chain alkyl group, trialkylsilylalkyl, cyanoalkyl, or an aryl group, and R''' is a linear or branched chain alkyl group, or an aryl group; wherein R⁰ and R¹ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH₂)$_t$W, where W is NH₂, NHR', NR₂', NHOH, N⁺R₃'Z⁻, NHCOR', N₃, NO₂ or CH₂W⁰(CH₂)$_v$W¹, or a linear or branched chain alkyl group, or an arylalkyl group, or an alkenyl or alkynyl group, or an aryl group, where R' is a linear or branched chain alkyl group, or an aryl group, where W₀ is O, S or NH, where W¹ is NH₂, NHR', NR₂', NHOH, N⁺R₃'Z⁻, NHCOR', N₃ or NO₂, and where R' is a linear or branched chain alkyl group, or an aryl group, where Z⁻ is a pharmaceutically acceptable counterion, and t is 1, 2, 3, 4, 5 or 6 and v is 2, 3, 4, 5 or 6; wherein R², R¹³, and R¹⁴ are independently the same or different and are H, or a linear or branched chain alkyl, hydroxyalkyl, alkoxyalkyl, amino alkyl or aryl group; wherein R⁴ is a linear or branched chain alkyl, alkoxyalkyl, hydroxyalkyl or a linear or branched chain alkenylalkyl group; wherein R¹² is H or a linear chain alkyl group; and wherein n is 2, 3 or 4. In another embodiment, the invention provides a compound having the structure:

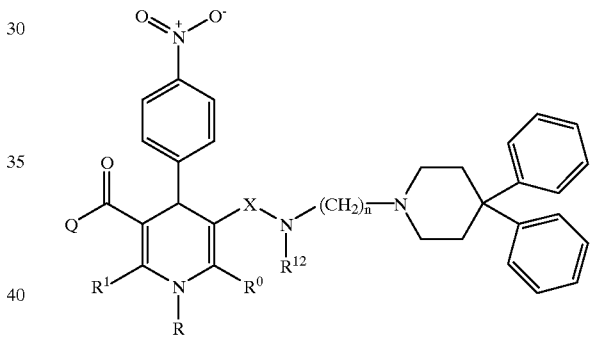

wherein X is C=O, CH₂, CR$^a_2$, NH, NR$^a$, NCHO, NCOR$^a$, NOH, O or S, where R$^a$ is a methyl, ethyl or propyl group; wherein Q is OH, OR", SH, SR''', NHZ, NHR''', NR''', NR"OH, NR"OR''' or a linear or branched chain alkyl group, or an arylalkyl group, or an alkenyl or alkynyl group, or an aryl group, where R''' is H, a linear or branched chain alkyl group, trialkylsilylalkyl, cyanoalkyl or an aryl group, and R''' is a linear or branched chain alkyl group, or an aryl group; wherein R⁰ and R¹ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or (CH₂)$_t$W, where W is NH₂, NHR', NR₂', NHOH, N⁺R₃'Z⁻, NHCOR', N₃, NO₂ or CH₂W⁰(CH₂)$_v$W¹, or a linear or branched chain alkyl group, or an arylalkyl group, or an alkenyl or alkynyl group, or an aryl group, where R' is a linear or branched chain alkyl group, or an aryl group, where W⁰ is O, S or NH, where W¹ is NH₂, NHR', NR₂', NHOH, N⁺R₃'Z⁻, NHCOR', N₃ or NO₂, and where R' is a linear or branched chain alkyl group, or an aryl group, where Z⁻ is a pharmaceutically acceptable counterion, and t is 1, 2, 3, 4, 5 or 6 and v is 2, 3, 4, 5 or 6; wherein R is H, a linear or branched chain alkyl or acyl group, or an aryl group; wherein R¹² is H or a linear chain alkyl group; and wherein n is 2, 3 or 4. In one embodiment, the invention provides a compound having the structure:

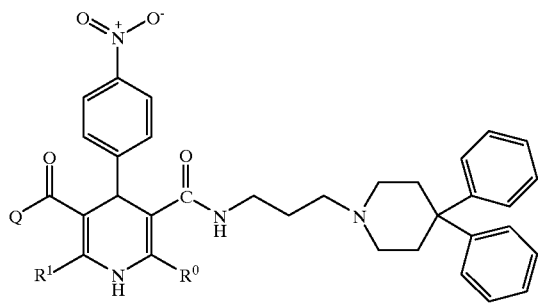

wherein Q is OH, OR", SH, SR'", NH$_2$, NHR'", NR$_2$'", NR"OH, NR"OR'" or a linear or branched chain alkyl group, or an arylalkyl group, or an alkenyl or alkynyl group, or an aryl group, where R" is H, a linear or branched chain alkyl group, trialkylsilylalkyl, cyanoalkyl or an aryl group, and R'" is a linear or branched chain alkyl group, or an aryl group; wherein R$^0$ and R$^1$ are independently the same or different and are H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl or an aryl group, or (CH$_2$)$_t$W, where W is NH$_2$, NHR', NR$_2$', NHOH, N$^+$R$_3$'Z$^-$, NHCOR', N$_3$, NO$_2$ or CH$_2$W$^0$(CH$_2$)$_v$W$^1$, or a linear or branched chain alkyl group, or an arylalkyl group, or an alkenyl or alkynyl group, or an aryl group, where R' is a linear or branched chain alkyl group, or an aryl group, where W$^0$ is O, S or NH, where W$^1$ is NH$_2$, NHR', NR$_2$', NHOH, N$^+$R$_3$'Z$^-$, NHCOR', N$_3$ or NO$_2$, and where R' is a linear or branched chain alkyl group, or an aryl group, where Z$^-$ is a pharmaceutically acceptable counterion, and t is 1, 2, 3, 4, 5 or 6 and v is 2, 3, 4, 5 or 6; and wherein R is H, a linear or branched chain alkyl or acyl group, or an aryl group.

The invention provides a compound having the structure:

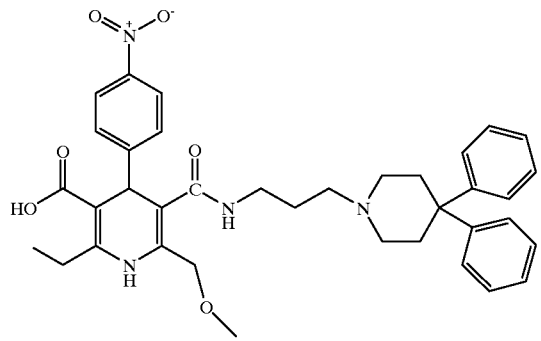

The invention also provides a compound having the structure:

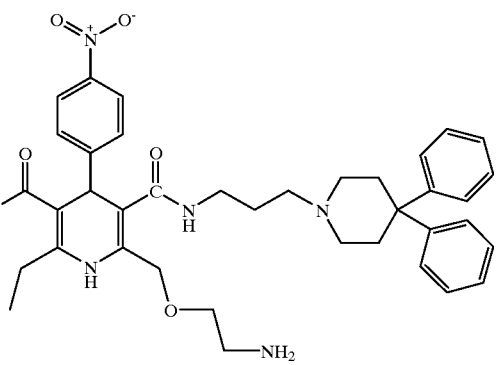

The invention further provides a compound having the structure:

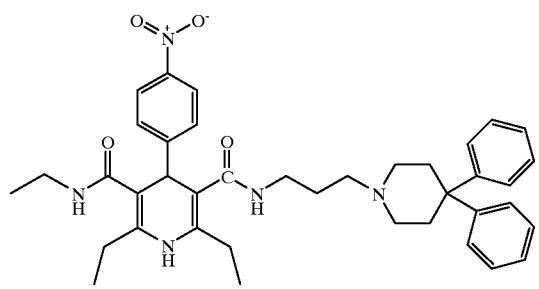

The invention still further provides the (+) and (−) enantiomer of the compound having the structure:

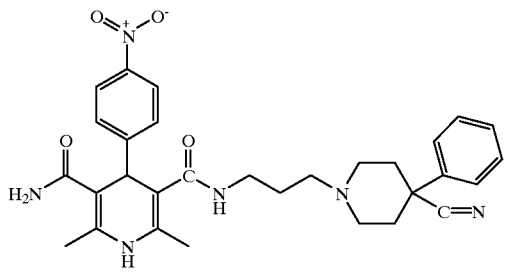

and pharmaceutically acceptable salts thereof.

The invention also provides a compound of having the structure:

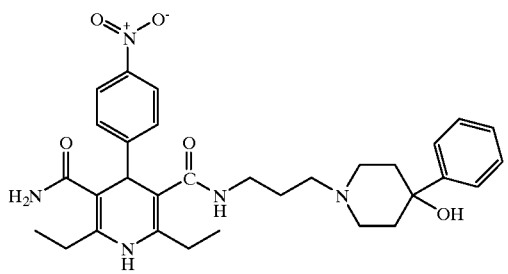

The invention additionally provides the (+) and (−) enantiomer of the compound having the structure:

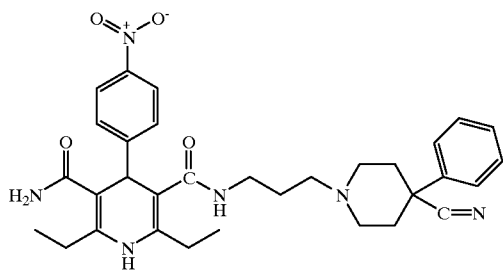

and pharmaceutically acceptable salts thereof.

The invention also provides a compound having the structure:

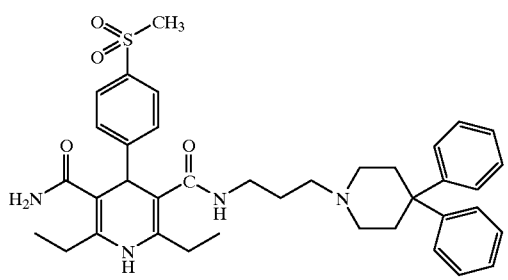

The invention provides a compound having the structure:

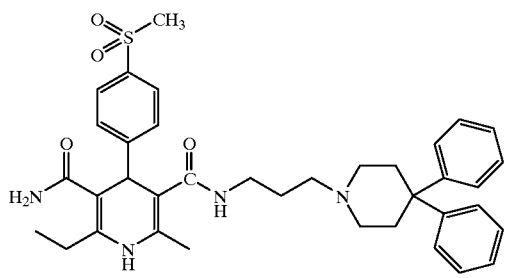

The invention also provides a compound having the structure:

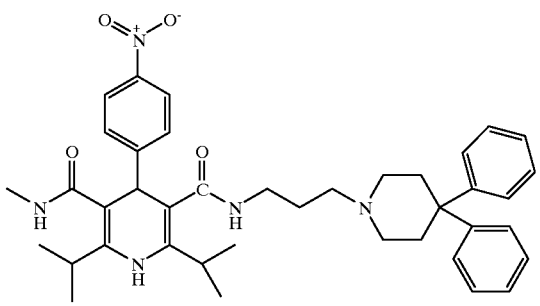

The invention additionally provides a compound having the structure:

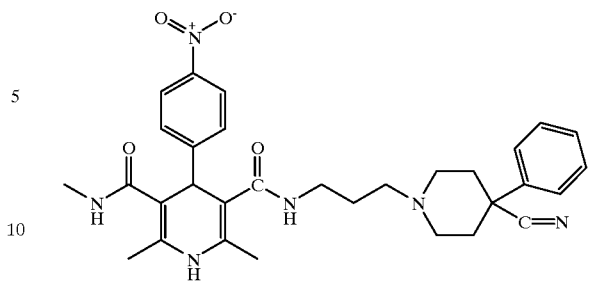

The invention provides a compound having the structure:

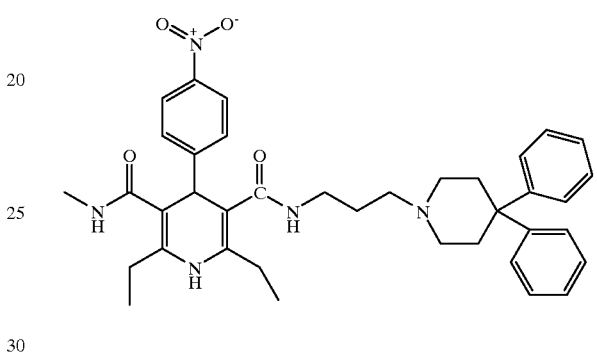

The invention also provides a compound having the structure:

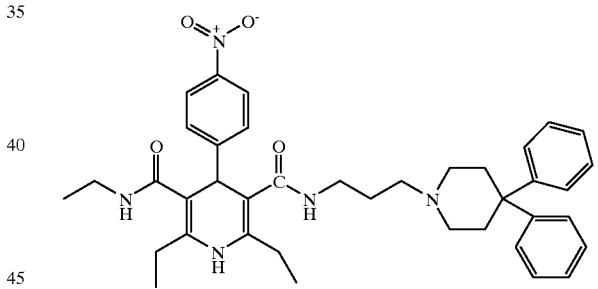

The invention further provides a compound having the structure:

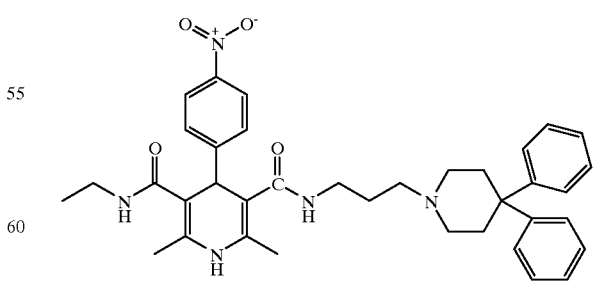

The invention further provides a compound having the structure:

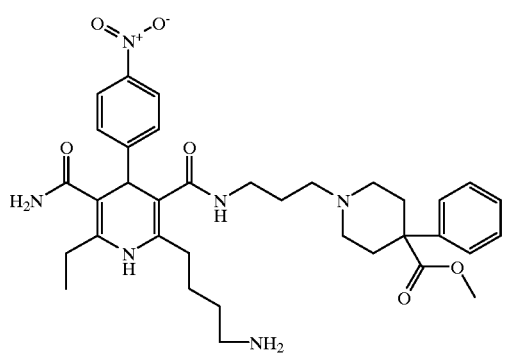

The invention also provides a compound having the structure:

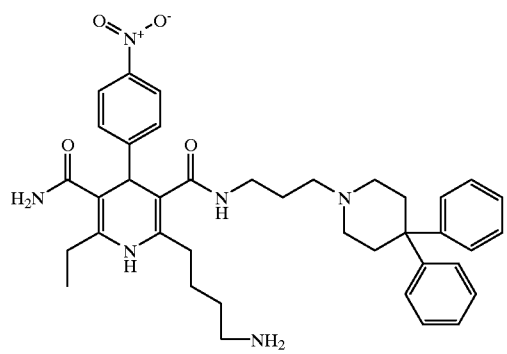

The invention provides a compound having the structure:

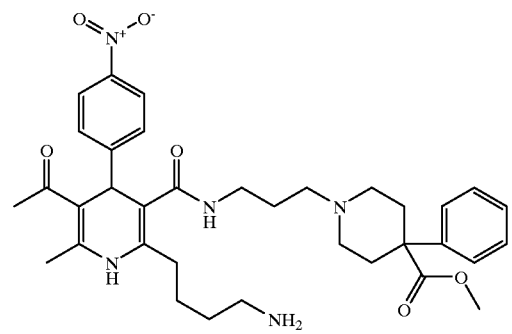

The invention further provides a compound having the structure:

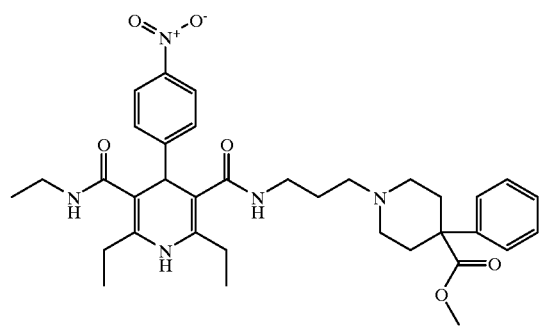

The invention also provides a compound having the structure:

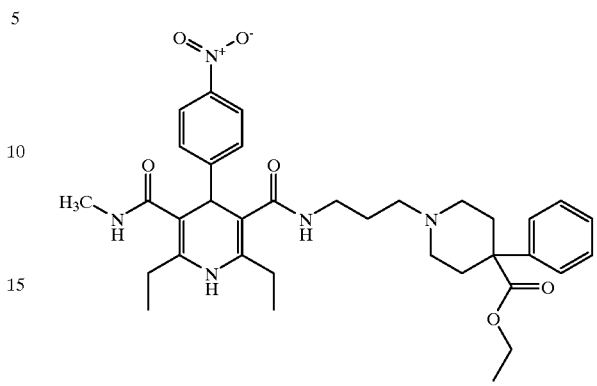

The invention further provides a compound having the structure:

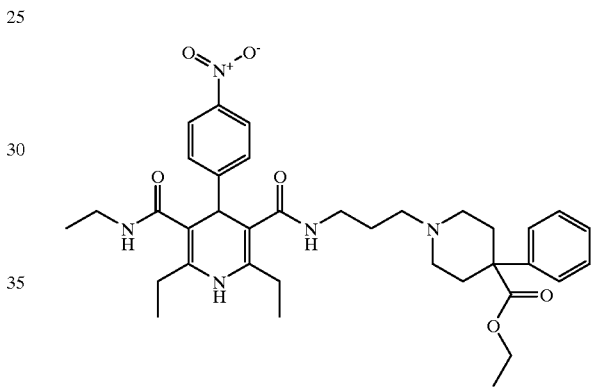

The invention still further provides a compound having the structure:

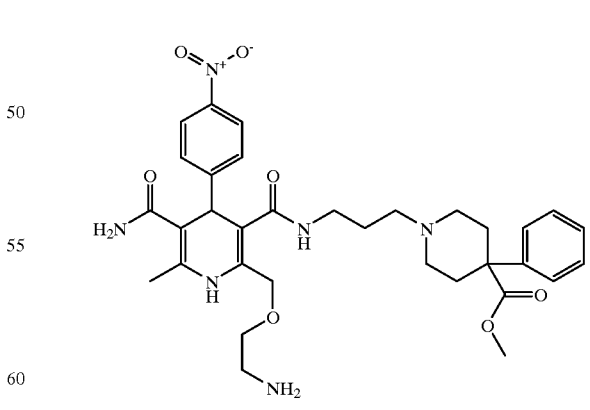

The invention also provides a compound having the structure:

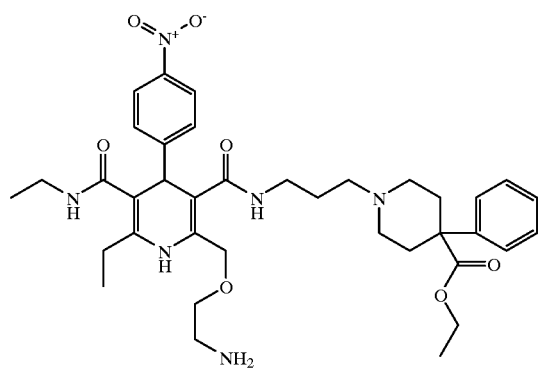

The invention further provides a compound having the structure:

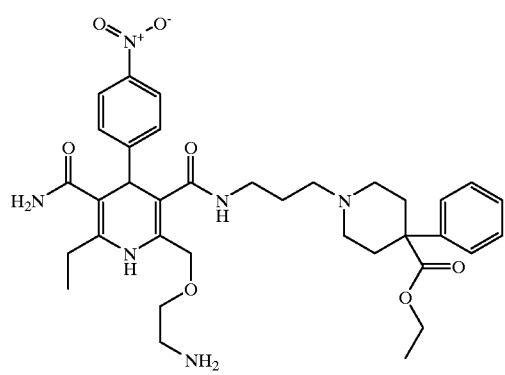

The invention also provides a compound having the structure:

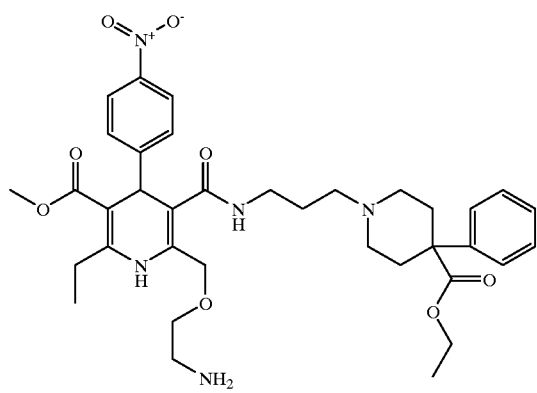

The invention further provides a compound having the structure:

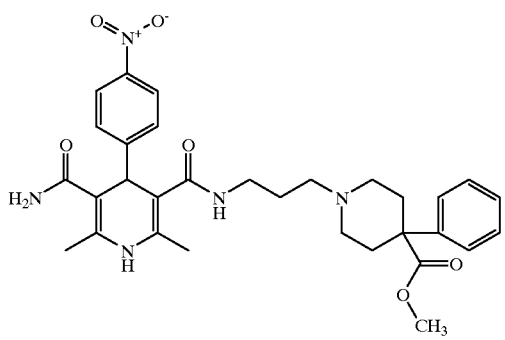

The invention still further provides a compound having the structure:

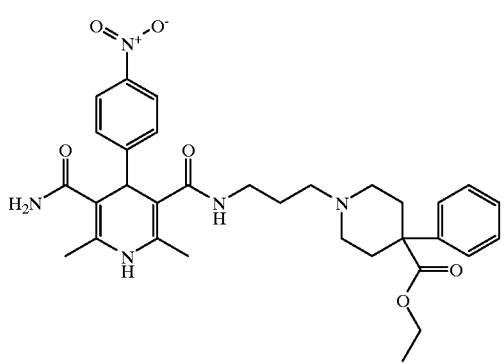

The invention also provides a compound having the structure:

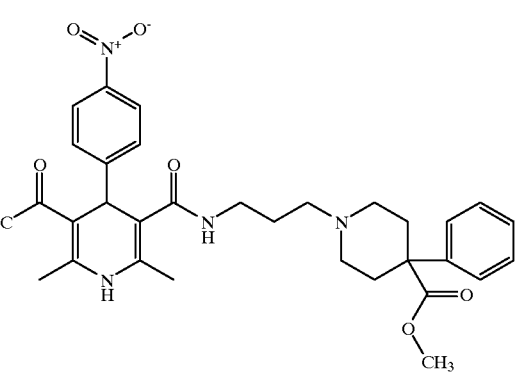

The invention further provides a compound having the structure:

The invention still further provides a compound having the structure:

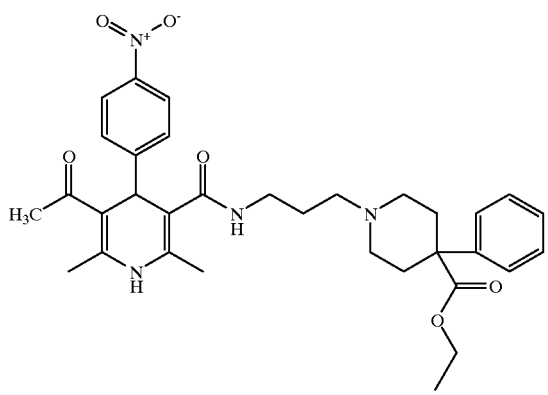

The invention further provides a compound having the structure:

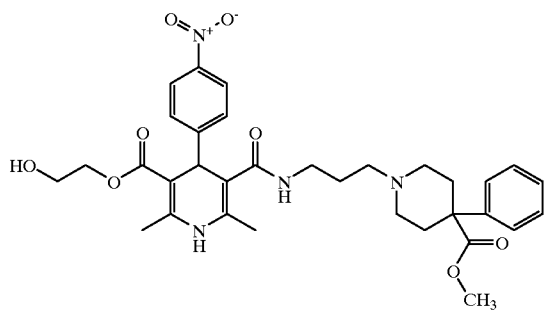

The invention also provides a compound having the structure:

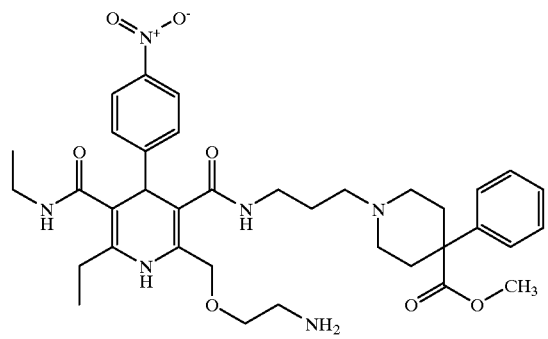

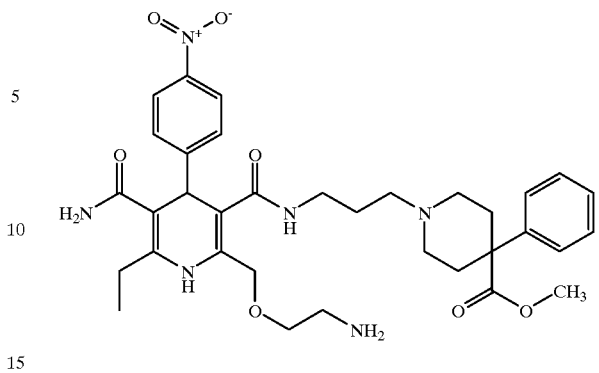

The invention additionally provides a pharmaceutical composition which comprises the compound disclosed herein in a therapeutically effective amount and a pharmaceutically acceptable carrier. The invention includes the pharmaceutical composition wherein the carrier is a solid and the composition is a tablet. In such pharmaceutical compositions, the therapeutically effective amount is an amount from about 0.1 to about 500 mg. In certain embodiments, the therapeutically effective amount is from about 1 to 60 mg. The invention also includes a pharmaceutical composition wherein the carrier is a liquid and the composition is a solution, wherein the therapeutically effective amount is an amount from about 0.1 to about 500 mg per mL of solution and in certain embodiments, the therapeutically effective amount is an amount from about 1 to about 60 mg per mL of solution. The invention further provides a pharmaceutical composition wherein the carrier is a gel and the composition is a suppository, wherein the therapeutically effective amount is an amount from about 0.1 to about 500 mg.

The invention also encompasses a method of treating benign prostatic hyperplasia in a subject which comprises administering to the subject a therapeutically effective amount of any one of the compounds disclosed herein.

The invention provides a method of lowering intraocular pressure in a subject which comprises administering to the subject a therapeutically effective amount of any one of the compounds disclosed herein.

The invention further provides a method of inhibiting cholesterol synthesis in a subject which comprises administering to the subject a therapeutically effective amount of any one of the compounds disclosed herein.

The invention has general utility in providing a method of treating diseases mediated by $\alpha_1$ receptors in a subject which comprises administering to the subject a therapeutically effective amount of any one of the compounds disclosed herein.

Throughout this application the term "compound" is used to refer both to unresolved racemic mixtures and to each of the optically resolved enantiomers in those cases where a given compound is optically active. pyridines effective to treat benign prostatic hyperplasia. The drug may be administered to a patient afflicted with benign prostatic hyperplasia by any conventional route of administration, including, but not limited to, intravenous, intramuscular, oral, subcutaneous, intratumoral, intradermal, and parenteral. The effective quantity is between 0.001 mg and 10.0 mg per kg of subject body weight.

The present invention also provides compounds useful for preparing a pharmaceutical composition comprising any of the claimed dihydropyridines disclosed herein and a pharmaceutically acceptable carrier. The composition may contain between 0.1 mg and 500 mg of the claimed compound, and may be constituted in any form suitable for the mode of administration selected. Compositions suitable for oral administration include solid forms, such as pills, capsules, granules, tablets, and powders, and liquid forms, such as solutions, syrups, elixers, and suspensions. Forms useful for parenteral administration include sterile solutions, emulsions, and suspensions.

The drug may otherwise be prepared as a sterile solid composition which may be dissolved or suspended at the time of administration using sterile water, saline, or other appropriate sterile injectible medium. Carriers are intended to include necessary and inert binders, suspending agents, lubricants, flavorants, sweeteners, preservatives, dyes, and coatings.

Optimal dosages to be administered may be determined by those skilled in the art, and will vary with the particular dihydropyridine in use, the strength of the preparation, the mode of administration, and the advancement of the disease condition. Additional factors depending on the particular patient being treated will result in a need to adjust dosages, including patient age, weight, gender, diet, and time of administration. The following Experimental Details are set forth to aid in an understanding of the invention, and are not intended, and should not be construed, to limit in any way the invention set forth in the claims which follow thereafter.

Experimental Details.

General Methods

Four general synthetic methods were used to synthesize the compounds of the invention. These methods are illustrated in Reaction Schemes 1–4. The symbols R, A, B, and C, and the variable n are defined by the Examples.

Method A:

Example 1 is illustrative of Method A, which is outlined in Reaction Scheme 1.

EXAMPLE 1

4,4-Diphenylpiperidine hydrochloride. A mixture of 4-piperidone monohydrate hydrochloride (15.0 g, 97.6 mmol, 1.00 equiv) and $AlCl_3$ (130 g, 976 mmol, 10.0 equiv) in anhydrous benzene (600 mL) was stirred at reflux for 4 hours. The mixture was cooled to room temperature, poured into ice (300 g) and water (50 mL), and filtered. The solid was washed with toluene and dried to afford 19.2 g (72%) of off-white solid, which was characterized spectroscopically.

3-(4,4-Diphenylpiperidin-1-yl)propionitrile. To a suspension of 4,4-diphenylpiperidine hydrochloride (195 mg, 0.712 mmol, 1.0 equiv) in EtOH (1.5 mL) was added $Et_3N$ (0.25 mL, 1.8 mmol, 2.6 equiv) followed by acrylonitrile (0.13 mL, 2.01 mmol, 2.8 equiv). The resulting solution was stirred at room temperature under argon for 15 minutes and then concentrated. Water was added, and the mixture was extracted three times with EtOAc. The combined organic extracts were dried over $MgSO_4$ and concentrated to give 170 mg (87%) of tan solid, which was characterized spectroscopically and used for the next reaction without purification.

1-(3-Aminopropyl)-4,4-diphenylpiperidine. To a stirred solution of 3-(4,4-diphenylpiperidin-1-yl)propionitrile (2.00 g, 6.89 mmol, 1.0 equiv) in anhydrous THF (20 mL) under argon was added a solution of $BH_3$ in THF (1.0M, 24.1 mL, 24 mmol, 3.5 equiv) at room temperature. The mixture was refluxed for 4.5 hours and then cooled to room temperature. Aqueous HCl (6N, 50 mL) was added and stirring was continued for 1 hour. The mixture was basified to pH 9 by addition of 6N aq. NaOH, extracted 3 times with $CH_2Cl_2$, dried over $MgSO_4$ and concentrated.

The residue was purified by flash chromatography ($SiO_2$, EtOAc—MeOH-isopropylamine 9:1:0 to 4:1:0.2) to give 1.35 g (66%) of tan solid, which was characterized spectroscopically.

N-(3-(4,4-Diphenylpiperidin-1-yl)propyl) acetoacetamide. Diketene (0.44 mL, 5.7 mmol, 1.3 equiv, Aldrich) was added at room temperature to a stirred solution of 1-(3-aminopropyl)-4,4-diphenylpiperidine (1.288 g, 4.37 mmol, 1.0 equiv) in anhydrous toluene (15 mL) under argon, and stirring was continued for 48 hours. The mixture was concentrated to give 1.294 g (78%) of white solid, which was used for the next reaction without purification. An analytically pure sample was obtained by flash chromatography ($SiO_2$, EtOAc—MeOH—$Et_3N$ 9:1:0 to 6:1:0.1) and characterized spectroscopically.

4-(4-Trifluoromethylphenyl)-1,4-dihydro-3-methoxycarbonyl-2,6-dimethyl-5-(3-(4,4-diphenylpiperidin-1-yl)propyl)carboxamido)pyridine (1). N-(3-(4,4-diphenylpiperidin- 1-yl)propyl)acetoacetamide (229 mg, 0.61 mmol) was mixed with methyl 3-aminocrotonate (70 mg, 0.61 mmol) and p-trifluoromethylbenzaldehyde (83 ul, d 1.275, 0.61 mmol) in 2-propanol (5 mL). The mixture was heated at reflux for 3 days. The precipitate which formed upon cooling to room temperature was filtered off to give a pale yellow solid (160 mg). Recrystallization from 2-propanol afforded white crystals (117 mg, 31% yield): mp 228–231° C. Anal. Calcd. for $C_{37}H_{40}F_3N_3O_3$: C, 70.35; H, 6.38; N, 6.65. Found: C, 70.26; H, 6.40; N, 6.51.

Method B:

Example 2 is illustrative of Method B, which is outlined in Reaction Scheme 2.

EXAMPLE 2

5-Carboxamido-1,4-dihydro-2,6-dimethyl-4-(4-nitrophenyl)-3-{N-[3-(4,4-diphenylpiperidin-1-yl)propyl]}carboxamido)pyridine (2). A solution of 3-aminocrotonamide (6.028 g, 60.21 mmol), 4-nitrobenzaldehyde (6.066 g, 40.14 mmol) and 2-cyanoethyl acetoacetate (6.227 g, 40.14 mmol) in 125 mL of EtOH was refluxed for 48 hrs. The reaction mixture was filtered and the filtrate was concentrated to give a brown oil. This brown oil was dissolved in 250 mL of $CHCl_3$ (with addition of a small amount of acetone to give a homogeneous solution), washed with water (2×100 mL) and dried over $Na_2SO_4$. After filtration and removal of solvent, the residue was dissolved into 200 mL of MeOH and treated with 100 mL 2N KOH solution at 0° C. for 30 min. The MeOH was removed in vacuo and the aqueous layer was diluted with 100 mL of water and washed with AcOEt (2×100 mL). With stirring, the aqueous layer was acidified to pH=1 by addition of 6 N hydrochloric acid. The yellow precipitate was collected by filtration, washed with 10 mL of cold water and dried in vacuo to afford 5.877 g (46.1% yield for two steps) of 5-carboxamido-1,4-dihydro-2,6-dimethyl-4-(4-nitrophenyl)pyridine-3-carboxylic acid as a yellow powder.

A suspension of 5-carboxamido-1,4-dihydro-2,6-dimethyl-4-(4-nitrophenyl)pyridine-3-carboxylic acid (150 mg, 0.473 mmol) and 1-(3-dimethylaminopropyl)-3-ethylcarbodiimide hydrochloride (90.6 mg, 0.473 mmol) in 15 mL of $CH_2Cl_2$ was stirred at 0° C. for 20 min. To this suspension was added a solution of 3-(4,4-diphenylpiperidin-1-yl)propylamine (139 mg, 0.473 mmol) in 2 mL of $CH_2Cl_2$. The mixture was stirred at refluxing conditions overnight. The formation of a clear solution indicated completion of the reaction. The mixture was washed with water (2×10 mL) followed by brine (10 mL). After drying with $Na_2SO_4$ and removal of solvent, a yellowish oil was obtained, which was precipitated from $CH_2Cl_2/Et_2O$ to afford a yellowish powder (165 mg, 58.8%): m.p. 212–215° C. Calcd. for $C_{35}H_{39}N_5O_4$: C 70.79, H 6.63, N 11.79; Found: C 71.00, H 6.79, N 11.51.

(+) and (−)-2. The enantiomers of 2 were separated on a chiral HPLC column as follows. Four injections of the racemate (16 mg per injection in 2 ml Of EtOH) were made onto a Chiralpak AS column (20×250 mm, Daicel), which was eluted with EtOH-hexane-diethylamine (10:90:0.05) at a flowrate of 9.0 ml/min with UV detection at 300 nm. The retention times for the two enantiomers were 50 ((+)-isomer) and 65 ((−)-isomer) min repectively. The desired compounds were collected and precipitated from $Et_2O/CH_2Cl_2$ to give yellowish powders.

(+)-isomer: $[\alpha]_D^{20}=+91.2°$ (c 0.32, $CHCl_3$). Calcd. for $C_{35}H_{39}N_5O_4$: C 70.79, H 6.63, N 11.79; Found: C 70.53, H 6.41, N 11.50.

(−)-isomer: $[\alpha]_D^{20}=-90.0°$ (c 0.38, $CHCl_3$). Calcd. for $C_{35}H_{39}N_5O_4$: C 70.79, H 6.63, N 11.79; Found: C 70.58, H 6.39, N 11.57.

Method C:

Example 3 is illustrative of Method C, which is outlined in Reaction Scheme 3.

EXAMPLE 3

1,4-Dihydro-3-methoxycarbonyl-2,6-dimethyl-4-(4-nitrophenyl)-5-{N-[4-(4-phenylpiperidin-1-yl)butyl]}carboxamidopyridine hydrochloride hydrate (3). A solution of 9.61 g of benzyl acetoacetate (50.0 mmol), 5.87 g of methyl 3-aminocrotonate (51.0 mmol), and 7.71 g of 4-nitrobenzaldehyde (51.0 mmol) in 200 mL of isopropanol was heated at reflux temperature for 2 days. The reaction mixture was cooled and concentrated. The crude product was charged with 250 mL of methanol and 1.10 g of 10% Pd/C, and the mixture was hydrogenated using the balloon method for 24 h. The reaction mixture was filtered through celite 545, concentrated in vacuo, partitioned between water (200 mL, containing 3.0 g of NaOH) and ethyl acetate (100 mL). The aqueous phase was washed further with 2×50 mL of ethyl acetate, and acidified with concentrated HCl (pH=2). The separated oil was extracted with 2×200 mL of ethyl acetate, and 2×200 mL of dichloromethane. The combined organic extracts were dried ($MgSO_4$), and the solvent was removed in vacuo to give 3.52 g of 1,4-dihydro-3-methoxycarbonyl-2,6-dimethyl-4-(4-nitrophenyl)-5-carboxylic acid (21%) as a yellow solid: mp 172–175° C. (decomp.); Anal. Calcd for $C_{16}H_{16}N_2O_6$: C, 57.83; H, 4.85; N, 8.43. Found: C, 58.05; H, 4.79; N, 8.26.

4-Hydroxypiperidine (10.0 g, 98.9 mmol, 1.00 equiv) and $AlCl_3$ (15.5 g, 791.2 mmol, 8.0 equiv) were stirred in refluxing benzene (350 mL) under a $CaSO_4$ drying tube for 85 hours. The mixture was cooled to room temperature and poured carefully into ice (500 g) and water (50 mL) with stirring. With ice water cooling, the pH was adjusted to 10–11 by addition of solid NaOH. The resulting mixture was extracted with EtOAc (3×250 mL). The combined organic solutions were washed with brine, dried over $MgSO_4$, and concentrated to give 6.5 g of 4-phenylpiperidine (yellow solid, 40%), which was characterized spectroscopically.

A suspension of 4-phenylpiperidine (5.20 g, 32.2 mmol, 1.00 equiv), 4-bromobutyronitrile (4.81 mL, 48.4 mmol, 1.50 equiv), potassium carbonate (11.14 g, 80.6 mmol, 2.50 equiv), and potassium iodide (266 mg, 12.9 mmol, 0.4 equiv) in n-butanol (60 mL) and 1,4-dioxane (60 mL) was stirred at reflux under argon for 48 hours. The mixture was cooled to room temperature and concentrated. The residue was purified by flash chromatography ($SiO_2$, MeOH—EtOAc 1:19) to afford 3.95 g of 4-(4-phenylpiperidin-1-yl) butyronitrile (white solid, 53%), which was characterized spectroscopically.

To a stirred solution of 4-(4-phenylpiperidin-1-yl) butyronitrile (3.81 g, 16.7 mmol, 1.0 equiv) in anhydrous THF (20 mL) under argon was added a solution of $BH_3$ in THF (1.0M, 58.5 mL, 58 mmol, 3.5 equiv) at room temperature. The mixture was refluxed for 4.5 hours and then cooled to room temperature. Aqueous HCl (6N, 100 mL) was added and stirring was continued for 2 hours at 55–60° C. The mixture was basified to pH 9 by addition of 6N aq. NaOH and extracted with $CH_2Cl_2$ (3×100 mL).

The combined organic solutions were dried over $MgSO_4$ and concentrated. The residue was dissolved in $CH_2Cl_2$ (20 mL) and treated with HCl in ether (1.0M, 35 mL). The solvents were removed, ether (200 mL) was added, the mixture was filtered, and the filter cake was washed with ether. Water (50 mL) was added to the resulting white solid, the pH was adjusted to 10–11 with 1M NaOH, and the aqueous phase was extracted with $CH_2Cl_2$ (3×100 mL). Drying over $MgSO_4$ followed by removal of solvents gave 3.54 g of 1-(4-aminobutyl)-4-phenylpiperidine (light yellow solid, 91%) which was characterized spectroscopically.

Anhydrous $CH_2Cl_2$ (15 mL) was added to a mixture of 1,4-dihydro-3-methoxycarbonyl-2,6-dimethyl-4-(4-nitrophenyl)-5-carboxylic acid (596 mg, 1.79 mmol, 1.00 equiv), 1,3-dicyclohexylcarbodiimide (554 mg, 2.68 mmol, 1.50 equiv), and 4-(N,N-dimethylamino)pyridine (241 mg, 1.97 mmol, 1.10 equiv) and the resulting solution was stirred for 1 hour at room temperature. A solution of 1-(4-aminobutyl)-4-phenylpiperidine (500 mg, 2.15 mmol, 1.20 equiv) in $CH_2Cl_2$ (3 mL) was injected and the mixture was stirred at reflux for 3 hours. The resulting suspension was cooled to room temperature, diluted with EtOAc (100 mL) and filtered. The solid was washed with EtOAc (3×5 mL). The combined filtrates were washed with saturated aqueous ammonium chloride (3×50 mL) and brine (50 mL), dried over $MgSO_4$ and concentrated. The residue was purified by flash chromatography ($SiO_2$, $CHCl_3$—$NH_3$ in MeOH (0.67M), 90:15) to afford 595 mg (61%) of yellow solid, which was characterized spectroscopically. To a solution of this product in $CH_2Cl_2$ (10 mL) was added HCl in ether (1.0M, 1.5 mL, 1.4 equiv). After removal of the solvents, the residue was dissolved in $CH_2Cl_2$ (5 mL) and added dropwise to ether (30 mL) with swirling to give, after filtration, 430 mg of 3 hydrochloride hydrate (yellow solid): m.p. 136–137° C.; Anal. Calcd. for $C_{31}H_{38}N_4O_5$, HCl 0.75 $H_2O$: C, 62.41; H, 6.84; N, 9.39. Found: C, 62.46; H, 6.76; N, 9.33.

Method D:

Example 4 is illustrative of Method D, which is outlined in Reaction Scheme 4.

EXAMPLE 4

2-Cyanoethyl 3-Oxopentanoate. A mixture of 4.86 g of ethyl propionylacetate (33.7 mmol) and 2.00 g of 3-hydroxypropionitrile (28.1 mmol) were placed in a round bottom flask (magnetically stirred) equipped with a short distillation path. The resulting mixture was gradually heated to 180–205° C. in an oil bath. The distillate was collected (1.2 mL). The mixture was then cooled to room temperature and the residue was distilled under reduced pressure to give 2.64 g of product: bp 95–98° C. (0.5 mm Hg). The product was used in the next step after spectral characterization.

5-Benzyloxycarbonyl-2-ethyl-1,4-dihydro-6-methyl-4-(4-nitrophenyl)-3-(N-(3-(4,4-diphenylpiperidin-1-yl) propyl)carboxamido)pyridine, Hydrochloride salt, Hydrate (4). A stirred solution of 19.2 g of benzyl 3-aminocrotonate (100 mmol, Davoll, J. *J. Chem. Soc.* 1953, 3802), 16.9 g of 2-cyanoethyl 3-oxopentanoate (100 mmol), and 15.1 g of 4-nitrobenzaldehyde. (100 mmol) in 100 mL of ethanol were heated at reflux temperature for 4 h, cooled, filtered and the solids were washed with 4×50 mL of acetone. To the filtrate was added 5.20 g of NaOH in 200 mL of water, and the resulting mixture was stirred at room temperature for 12 hrs. The reaction mixture was partitioned between 200 mL of additional water and 0.5 L of dichloromethane, separated, washed with 3×0.5 L of dichloromethane, acidified with concentrated HCl (pH=2), the precipitated solids were filtered, and the solids were washed with 5×50 mL of EtOAc. More solids appeared in the filtrate. The solids were filtered, and the filtrate was concentrated in vacuo. The residue was triturated with acetone, cooled to −78° C., the precipitated solids were filtered, and washed with 2×50 mL of cold acetone (−78° C.) to give 5.20 g of 3-benzyloxycarbonyl-2-ethyl-6-methyl-4-(4-nitro) phenylpyridine-5-carboxylic acid as a yellow powder (12%): mp 209–210° C.; Anal. Calcd for $C_{23}H_{22}N_2O_6 \cdot 0.5H_2O$: C, 64.03; H, 5.37; N, 6.49. Found: C, 64.39; H, 4.83; N, 6.41.

A mixture of 3.12 g of 3-benzyloxycarbonyl-2-ethyl-6-methyl-4-(4-nitro)phenylpyridine-5-carboxylic acid (6.55 mmol), 2.03 g of DCC (9.83 mmol), and 880 mg of DMAP (7.21 mmol) in 20 mL of dry dichloromethane was stirred at room temperature for 1 h. 1-(3-aminopropyl)-4,4-diphenylpiperidine (2.06 g, 7.86 mmol) was added the mixture was heated at reflux temperature for 2 hrs. The reaction mixture was cooled, filtered, and chromatographed on 400 g of silica packed with 5% MeOH—EtOAc. The column was eluted with 5% (1 L), 10% (1 L), 15% (1 L), and 20% (2 L) MeOH—EtOAc to give 3.84 g of 5-benzyloxycarbonyl-2-ethyl-1,4-dihydro-6-methyl-4-(4-nitro)phenyl-3-(N-(3-(4,4-diphenylpiperidin-1-yl)propyl) carboxamidopyridine (95%) as a yellow foamy solid. Hydrochloride Salt: The free base (72 mg) was dissolved in 2 mL of dichloromethane and added to 7 mL of 0.25M HCl in ether. The precipitate was collected, washed with 5 mL of ether, and dried to give a yellow powder: mp 195–198° C. (decomp.). Anal. Calcd for $C_{43}H_{46}N_4O_5 \cdot HCl$: C, 68.56; H, 6.56; N, 7.44. Found: C, 68.38; H, 6.20; N, 7.40.

EXAMPLE 5

1,4-Dihydro-5-methoxycarbonyl-2,6-dimethyl-3-(N-(3-(4,4-diphenylpiperidin-1-yl) propyl) carboxamido)-4-(4-pyridyl)pyridine (5). This compound was prepared according to Method A. N-(3-(4,4-diphenylpiperidin-1-yl)propyl) acetoacetamide (200 mg, 0.53 mmol) was mixed with methyl 3-aminocrotonate (61 mg, 0.53 mmol) and 4-pyridinecarboxaldehyde (51 ul, d 1.122, 0.53 mmol) in 2-propanol (5 mL). The mixture was heated at reflux for 2 days. The precipitate which formed upon cooling to room temperature was filtered off to give an almost white solid (95 mg). Recrystallization from 2-propanol afforded white crystals (63 mg, 21% yield): mp 224–226° C. (dec.). Anal. Calcd. for $C_{35}H_{40}N_4O_3$: C, 74.44; HI 7.14; N, 9.92. Found: C, 74.43; H, 7.23; N, 9.83.

EXAMPLE 6

4-Cyclohexyl-1,4-dihydro-3-methoxycarbonyl-2,,6-dimethyl-5-(N-(3-(4,4-diphenylpiperidin-1-yl)propyl) carboxamido)pyridine (6). This compound was prepared according to Method A. N-(3-(4,4-diphenylpiperidin-1-yl) propyl) acetoacetamide (200 mg, 0.53 mmol) was mixed with methyl 3-aminocrotonate (61 mg, 0.53 mmol) and cyclohexanecarboxaldehyde (64 ul, d 0.926, 0.53 mmol) in 2-propanol (5 mL). The mixture was heated at reflux for 2 days and then concentrated to a pale yellow foam. It was dissolved in chloroform and flash chromatographed over silica gel (14 g) eluting with EtOAc/Hexane/Et$_3$N (40:20:3 and then 16:4:1) to give a pale yellow foam (114 mg). It was recrystallized from acetone/hexane to afford white crystals (63 mg, 21% yield): mp 171–174° C. Anal. Calcd. for $C_{36}H_{47}N_3O_3$: C, 75.89; H, 8.31; N, 7.37. Found: C, 75.86; H, 8.09; N, 7.00.

EXAMPLE 7

4-(4-Biphenyl)-1,4-dihydro-3-methoxycarbonyl-2,6-dimethyl-5-(N-(3-(4,4-diphenylpiperidin-1-yl)propyl) carboxamido)pyridine (7). This compound was prepared according to Method A. N-(3-(4,4-diphenylpiperidin-1-yl) propyl) acetoacetamide (200 mg, 0.53 mmol) was mixed with methyl 3-aminocrotonate (61 mg, 0.53 mmol) and 4-biphenylcarboxaldehyde (96 mg, 0.53 mmol) in 2-propanol (5 mL). The mixture was heated at reflux for 3 days before it was concentrated to a yellow foam. It was dissolved in chloroform and flash chromatographed over silica gel (15 g) eluting with EtOAc/Hexane/Et$_3$N (50:10:3) to give a yellow oil which partially solidified (128 mg). It was recrystallized from EtOAc/Hexane to afford white crystals (55 mg, 16% yield): mp 136–139° C. Anal. Calcd. for $C_{42}H_{45}N_3O_3$: C, 78.84; H, 7.09; N, 6.57. Found: C, 78.54; HI 6.92; N, 6.37.

EXAMPLE 8

4-Benzyl-1,4-dihydro-3-methoxycarbonyl-2,6-dimethyl-5-(N-(3-(4,4-diphenylpiperidin-1-yl)propyl)carboxamido) pyridine (8). This compound was prepared according to Method A. N-(3-(4,4-diphenylpiperidin-1-yl)propyl) acetoacetamide (180 mg, 0.48 mmol) was mixed with methyl 3-aminocrotonate (55 mg, 0.48 mmol) and phenylacetaldehyde (62 ul, d 1.027, 90%, 0.48 mmol) in 2-propanol (5 mL). The mixture was heated at reflux for 1 day before it was concentrated to a yellow foam. It was dissolved in chloroform and flash chromatographed over silica gel (15 g) eluting with EtOAc/Hexane/Et$_3$N (15:5:2) to give a pale yellow foam (132 mg). It was recrystallized from EtOAc/Hexane to afford a white solid (81 mg, 29% yield): mp 175–177° C. Anal. Calcd. for $C_{37}H_{43}N_3O_3$: C, 76.92; H, 7.50; N, 7.27. Found: C, 76.81; H, 7.68; N, 7.07.

EXAMPLE 9

1,4-Dihydro-3-methoxycarbonyl-2,6-Dimethyl-4-(1-oxido-4-pyridyl)-5-(N-(3-(4,4-diphenylpiperidin-1-yl) propyl)carboxamido)pyridine (9). This compound was prepared according to Method A. N-(3-(4,4-diphenylpiperidin-1-yl)propyl) acetoacetamide (205 mg, 0.54 mmol) was mixed with methyl 3-aminocrotonate (62 mg, 0.54 mmol) and 4-pyridinecarboxaldehyde N-oxide (67 mg, 0.54 mmol)

in 2-propanol (5 mL). The mixture was heated at reflux for 2 days before it was concentrated to a dark green foam. It was dissolved in chloroform and flash chromatographed over silica gel (15 g) eluting with EtOAc/MeOH/Et$_3$N (10:2:1) to give a yellow foam (171 mg). Trituration with EtOAc afforded a pale yellow powder (96 mg, 31% yield): mp 206–209° C. (dec.). Anal. Calcd. for $C_{35}H_{40}N_4O_4 \cdot \frac{1}{4}$ H$_2$O: C, 71.83; H, 6.98; N, 9.57. Found: C, 71.61; H, 6.72; N, 9.36.

EXAMPLE 10

4-(4-Chlorophenyl)-1,4-dihydro-5-methoxycarbonyl-2,6-Dimethyl-5-(N-(3-(4,4-diphenylpiperidin-1-yl)propyl) carboxamido)pyridine (10). This compound was prepared according to Method A. N-(3-(4,4-diphenylpiperidin-1-yl) propyl) acetoacetamide (200 mg, 0.53 mmol) was mixed with methyl 3-aminocrotonate (61 mg, 0.53 mmol) and 4-chlorobenzaldehyde (74 mg, 0.53 mmol) in 2-propanol (5 mL). The mixture was heated at reflux for 3 days and the precipitate, after cooling to room temperature, was filtered off to give an almost white solid (134 mg). It was recrystallized twice from chloroform/hexane to afford white crystals (99 mg, 31% yield): mp 240–242° C. Anal. Calcd. for $C_{36}H_{40}ClN_3O_3 \cdot \frac{1}{2}$ H$_2$O: C, 71.21; H, 6.81; N, 6.92. Found: C, 70.83; H, 6.50; N, 6.73.

EXAMPLE 11

1,4-Dihydro-3-methoxycarbonyl-2,6-dimethyl-4-(3,4-methylenedioxyphenyl)-5-(N-(3-(4,4-diphenylpiperidin-1-yl)propyl)carboxamido)pyridine (11). This compound was prepared according to Method A. A mixture of N-(3-(4,4-diphenylpiperidin-1-yl)propyl) acetoacetamide (322 mg, 0.85 mmol), methyl 3-aminocrotonate (98 mg, 0.85 mmol) and piperonal (128 mg, 0.85 mmol) was heated at reflux in 2-propanol (7 mL) for 1 day and then in 1-butanol (7 mL) for another day. Evaporation of the solvent gave an orange foam which was dissolved in chloroform and flash chromatographed over silica gel (20 g) eluting with EtOAc/Hexane/Et$_3$N (50:10:3) to afford a yellow foam (144 mg). Recrystallization from EtOAc/Hexane gave yellow crystals (64 mg, 12% yield): mp 197–200° C. Anal. Calcd. for $C_{37}H_{41}N_3O_5$: C, 73.12; H, 6.80; N, 6.91. Found: C, 73.12; H, 6.71; N, 6.69.

EXAMPLE 12

4-(4-Cyanophenyl)-1,4-dihydro-3-methoxycarbonyl-2,6-dimethyl-5-(N-(3-(4,4-diphenylpiperidin-1-yl)propyl) carboxamido)pyridine (12). This compound was prepared according to Method A. N-(3-(4,4-diphenylpiperidin-1-yl) propyl) acetoacetamide (200 mg, 0.53 mmol) was mixed with methyl 3-aminocrotonate (61 mg, 0.53 mmol) and 4-cyanobenzaldehyde (69 mg, 0.53 mmol) in 2-propanol (5 mL). The mixture was heated at reflux for 3 days and then concentrated to a yellow oil. It was flash chromatographed over silica gel (18 g) eluting with EtOAc/Et$_3$N (10:1) to give a yellow foam (187 mg). It was recrystallized from MeOH/ether at −20° C. to afford pale yellow crystals (146 mg, 47% yield): mp 115–118° C. Anal. Calcd. for $C_{37}H_{40}N_4O_3$: C, 75.48; H, 6.85; N, 9.52. Found: C, 75.27; H, 6.82; N, 9.39.

EXAMPLE 13

1,4-Dihydro-4-(4-iodophenyl)-3-methoxycarbonyl-2,6-dimethyl-5-(N-(3-(4,4-diphenylpiperidin-1-yl)propyl) carboxamido)pyridine (13). This compound was prepared according to Method A. N-(3-(4,4-diphenylpiperidin-1-yl) propyl) acetoacetamide (186 mg, 0.49 mmol) was mixed with methyl 3-aminocrotonate (57 mg, 0.50 mmol) and 4-iodobenzaldehyde (114 mg, 0.49 mmol) in 2-propanol (5 mL) and heated at reflux for 2 days. The solution was cooled to room temperature and then refrigerated to give a pale yellow solid. It was recrystallized from 2-propanol/hexane to afford white crystals (44 mg, 13% yield): mp 228–230° C. (dec.). Anal. Calcd. for $C_{36}H_{40}IN_3O_3$: C, 62.70; H, 5.85; N, 6.09. Found: C, 62.47; H, 5.82; N, 5.92.

EXAMPLE 14

1,4-Dihydro-3-methoxycarbonyl-2,6-dimethyl-5-(N-(3-(4,4-diphenylpiperidin-1-yl)propyl)carboxamido)-4-(3-pyridyl)pyridine (14). This compound was prepared according to Method A. N-(3-(4,4-Diphenylpiperidin-1-yl)propyl) acetoacetamide (200 mg, 0.53 mmol) was mixed with methyl 3-aminocrotonate (61 mg, 0.53 mmol) and 3-pyridinecarboxaldehyde (50 ul, d 1.135, 0.53 mmol) in 2-propanol (5 mL). The mixture was heated at reflux for 3 days. The resulting precipitate was cooled to room temperature and then filtered off to give an almost white solid (115 mg). Recrystallization from MeOH at −20° C. afforded white crystals (56 mg, 19% yield): mp 244–247° C. (dec.). Anal. Calcd. for $C_{35}H_{40}N_4O_3$: C, 74.44; H, 7.14; N, 9.92. Found: C, 74.24; H, 7.16; N, 9.73.

EXAMPLE 15

4-(4-Bromophenyl)-1,4-dihydro-3-methoxycarbonyl-2,6-dimethyl-5-(N-(3-(4,4-diphenylpiperidin-1-yl)propyl) carboxamido)pyridine (15). This compound was prepared according to Method A. N-(3-(4,4-diphenylpiperidin-1-yl) propyl) acetoacetamide (181 mg, 0.48 mmol) was mixed with methyl 3-aminocrotonate (55 mg, 0.48 mmol) and 4-bromobenzaldehyde (88 mg, 0.48 mmol) in 2-propanol (5 mL) and heated at reflux for 2 days. The precipitate was filtered off and washed with 2-propanol to give an almost white solid (61 mg). It was recrystallized from ethanol at −20° C. to afford white crystals (38 mg, 12% yield): mp 244–247° C. (dec.). Anal. Calcd. for $C_{36}H_{40}BrN_3O_3$: C, 67.28; H, 6.27; N, 6.54. Found: C, 67.02; H, 6.43; N, 6.33.

EXAMPLE 16

4-(4-Chloro-3-nitrophenyl)-1,4-dihydro-3-methoxycarbonyl-2,6-dimethyl-5-(N-(3-(4,4-diphenylpiperidin-1-yl)propyl)carboxamido)pyridine (16). This compound was prepared according to Method A. N-(3-(4,4-Diphenylpiperidin-1-yl)propyl) acetoacetamide (200 mg, 0.53 mmol) was mixed with methyl 3-aminocrotonate (61 mg, 0.53 mmol) and 4-chloro-3-nitrobenzaldehyde (98 mg, 0.53 mmol) in 2-propanol (5 mL) and heated at reflux for 2 days. Then the solvent was evaporated to give a brown foam. It was dissolved in CHCl$_3$ and flash chromatographed over silica gel (17 g) eluting with EtOAc/Et$_3$N (10:1) to yield a yellow foam (182 mg). Trituration with EtOAc afforded a pale yellow solid (107 mg, 31% yield): mp 178–181° C. Anal. Calcd. for $C_{36}H_{39}ClN_4O_5$: C, 67.23; H, 6.11; N, 8.71. Found: C, 67.04; H, 6.33; N, 8.61.

EXAMPLE 17

3-(4-Phenylpiperidin-1-yl)propionitrile. Acrylonitrile (3.1 mL, 44 mmol, 2.5 equiv) was added to a solution of 4-phenylpiperidine (3.0 g, 18 mmol, 1.0 equiv) in EtOH (40 mL) and the mixture was stirred at room temperature for 1.5 hours. The volatiles were removed to give 3.8 g of pure product (brown oil, 99%), which was characterized spectroscopically.

139

1-(3-Aminopropyl)-4-phenylpiperidine. To a stirred solution of 3-(4-phenylpiperidin-1-yl)propionitrile (5.1 g, 24 mmol, 1.0 equiv) in anhydrous THF (20 mL) under argon was added a solution of $BH_3$ in THF (1.0M, 83 mL, 83 mmol, 3.5 equiv) at room temperature. The mixture was refluxed for 4.5 hours and then cooled to room temperature. Aqueous HCl (6N, 130 mL) was added and stirring was continued for 2 hours at 50–70° C. The mixture was basified to pH 9 by addition of 6N aq. NaOH and extracted with EtOAc (100 mL) and $CH_2Cl_2$ (3×100 mL). The combined organic solutions were dried over $MgSO_4$ and concentrated. The residue was dissolved in $CH_2Cl_2$ (20 mL) and treated with HCl in ether (1.0M, 50 mL). The solvents were removed, ether (250 mL) was added, the mixture was filtered, and the filter cake was washed with ether. Water (60 mL) was added to the resulting white solid, the pH was adjusted to 10–11 with 1M NaOH, and the aqueous phase was extracted three times with $CH_2Cl_2$. Drying over $MgSO_4$ followed by removal of solvents gave 4.5 g (87%) of pure product (light brown solid), which was characterized spectroscopically.

N-(3-(4-Phenylpiperidin-1-yl)propyl)acetoacetamide. Diketene (1.64 mL, 21.3 mmol, 1.50 equiv) was added at 0° C. to a stirred solution of 1-(3-aminopropyl)-4-phenylpiperidine (3.10 g, 14.2 mmol, 1.00 equiv) in anhydrous THF (30 mL) under argon, and stirring was continued at room temperature for 1 hour. The mixture was concentrated to give 4.50 g (100%) of viscous orange oil, which was characterized spectroscopically and used for the next reaction without purification.

4-(4-Chloro-3-nitrophenyl)-1,4-dihydro-3-methoxycarbonyl-2,6-dimethyl-5-(N-(3-(4-phenylpiperidin-1-yl)propyl)carboxamido)pyridine (17). This compound was prepared according to Method A. N-(3-(4-phenylpiperidin-1-yl)propyl) acetoacetamide (221 mg, 0.73 mmol) was mixed with methyl 3-aminocrotonate (84 mg, 0.73 mmol) and 4-chloro-3-nitrobenzaldehyde (136 mg, 0.73 mmol) in 2-propanol (7 mL) and heated at ref lux for 2 days. Then the solvent was evaporated to give a yellow foam. It was dissolved in $CHCl_3$ and flash chromatographed over silica gel (19 g) eluting with $EtOAc/Et_3N$ (20:1) to yield a yellow foam (194 mg). Recrystallization from EtOAc afforded yellow crystals (119 mg, 29% yield): mp 191–192° C. Anal. Calcd. for $C_{30}H_{35}ClN_4O_5$: C, 63.54; H, 6.22; N, 9.88. Found: C, 63.65; H, 6.26; N, 9.64.

EXAMPLE 18

1,4-Dihydro-4-(4-isopropylphenyl)-3-methoxycarbonyl-2,6-dimethyl-5-(N-(3-(4,4-diphenylpiperidin-1-yl)propyl) carboxamido)pyridine (18). This compound was prepared according to Method A. A solution of N-(3-(4,4-diphenylpiperidin-1-yl)propyl) acetoacetamide (200 mg, 0.528 mmol), methyl 3-aminocrotonate (62.7 mg, 0.528 mmol), and 4-isopropylbenzaldehyde (80.1 ul, 0.528 mmol) in 2-propanol(5 mL) was refluxed for 48 hrs. Then the solvent was removed, and the residue was chromatographed (Flash silica; hexane:EtOAc:$Et_3$N=50:50:3, hexane:EtOAc:$Et_3$N=10:90:6, EtOAc:$Et_3$N=10:1) to give a yellow solid. It was recrystallized from EtOAc and hexane to afford white crystals (140 mg, 44%): m. p. 163.0–163.5° C. Anal. Calcd. for $C_{39}H_{47}N_3O_3$: C, 77.32, H, 7.82, N, 6.94. Found: C, 77.29, H, 7.80, N, 6.84.

EXAMPLE 19

1,4-Dihydro-3-methoxycarbonyl-2,6-dimethyl-4-(4-methylphenyl)-5-(N-(3-(4,4-diphenylpiperidin-1-yl) propyl) carboxamido)pyridine (19). This compound was prepared according to Method A. A solution of N-(3-(4,4-diphenylpiperidin-1-yl)propyl) acetoacetamide (200 mg, 0.528 mmol), methyl 3-aminocrotonate (62.7 mg, 0.528 mmol), and 4-methylbenzaldehyde (62.3 ul, 0.528 mmol) in 2-propanol (5 mL) was refluxed for 72 hrs. Then the solvent was removed, and the residue was chromatographed (Flash silica; hexane:EtOAc:$Et_3$N=50:50:3, hexane:EtOAc:$Et_3$N=10:90:6, EtOAc:$Et_3$N=10:1) to give a yellow solid. It was recrystallized from EtOAc and hexane to afford white crystals (100 mg, 33%): m. p. 234.0–235.0° C. Anal. Calcd. for $C_{37}H_{43}N_3O_3 \cdot \frac{1}{2}H_2O$: C, 75.73, H, 7.56, N, 7.16. Found: C, 75.91, H, 7.33, N, 6.94.

EXAMPLE 20

4-(4-Fluorophenyl)-1,4-dihydro-3-methoxycarbonyl-2,6-dimethyl-5-(N-(3-(4,4-diphenylpiperidin-1-yl)propyl) carboxamido)pyridine (20). This compound was prepared according to Method A. A solution of N-(3-(4,4-diphenylpiperidin-1-yl)propyl) acetoacetamide (200 mg, 0.528 mmol), methyl 3-aminocrotonate (62.7 mg, 0.528 mmol), and 4-fluorobenzaldehyde (56.6 ul, 0.528 mmol) in 2-propanol(5 mL) was refluxed for 72 hrs. Then the solvent was removed, and the residue was chromatographed (Flash silica; hexane:EtOAc:$Et_3$N=50:50:3, hexane:EtOAc:$Et_3$N 10:90:6, EtOAc:$Et_3$N=10:1) to give white crystals (100 mg, 33%): m. p. 251.0–251.5° C. Anal. Calcd. for $C_{36}H_{43}O_3F$: C, 74.33, H, 6.93, N, 7.22, F, 3.27. Found: C, 74.08, H, 7.13, N, 6.71, F, 3.38.

EXAMPLE 21

1,4-Dihydro-3-methoxycarbonyl-4-(4-methoxyphenyl)-2,6-dimethyl-5-(N-(3-(4,4-diphenylpiperidin-1-yl)propyl) carboxamido)pyridine (21). This compound was prepared according to Method A. A solution of N-(3-(4,4-diphenylpiperidin-1-yl)propyl) acetoacetamide (200 mg, 0.528 mmol), methyl 3-aminocrotonate (62.7 mg, 0.528 mmol), and 4-methoxybenzaldehyde (64.2 ul, 0.528 mmol) in 2-propanol(5 mL) was refluxed for 96 hrs. Then the solvent was removed, and the residue was chromatographed (Flash silica; hexane:EtOAc:$Et_3$N=50:50:3, hexane:EtOAc:$Et_3$N=10:90:6, EtOAc:$Et_3$N=10:1) to give a yellow oil. It was recrystallized from EtOAc and hexane to afford white crystals (100 mg, 31%): m. p. 212.0–213.0° C. Anal. Calcd. for $C_{37}H_{43}N_3O_4$: C, 74.84, H, 7.30, N, 7.08. Found: C, 74.61, H, 7.26, N, 6.85.

EXAMPLE 22

1,4-Dihydro-3-methoxycarbonyl-2,6-dimethyl-4-(2-naphthyl)-5-(N-(3-(4 4-diphenylpiperidin-1-yl)propyl) carboxamido)pyridine (22). This compound was prepared according to Method A. A solution of N-(3-(4,4-diphenylpiperidin-1-yl)propyl) acetoacetamide (200 mg, 0.528 mmol), methyl 3-aminocrotonate (62.7 mg, 0.528 mmol), and 2-naphthaldehyde (84.0 mg, 0.528 mmol) in 2-propanol(5 mL) was refluxed for 72 hrs. Then the solvent was removed, and the residue was chromatographed (Flash silica; hexane:EtOAc:$Et_3$N=50:50:3, hexane EtOAc:$Et_3$N=10:90:6, EtOAc:$Et_3$N=10:1) to give a yellow solid. It was recrystallized from EtOAc and hexane to afford white crystals (100 mg, 31%): sublimes at R.T. Anal. Calcd. for $C_{40}H_{43}N_3O_3$: C, 78.27, H, 7.06, N, 6.85. Found: C, 78.31, H, 7.28, N, 6.64.

EXAMPLE 23

4-(3-Furyl)-1,4-dihydro-3-methoxycarbonyl-2,6-dimethyl-5-(N-(3-(4,4-diphenylpiperidin-1-yl) propyl)

carboxamido)pyridine (23). This compound was prepared according to Method A. A solution of N-(3-(4,4-diphenylpiperidin-1-yl)propyl) acetoacetamide (200 mg, 0.528 mmol), methyl 3-aminocrotonate (62.7 mg, 0.528 mmol), and 3-furaldehyde (46.7 ul, 0.528 mmol) in 2-propanol(5 mL) was refluxed for 72 hrs. Then the solvent was removed, and the residue was chromatographed (Flash silica; hexane EtOAc:Et$_3$N 50:50:3, hexane:EtOAc:Et$_3$N= 10:90:6, EtOAc:Et$_3$N=10:1) to give a yellow oil. It was recrystallized from EtOAc and hexane to afford white crystals (40 mg, 14%): m. p. 225.0–226.0° C. Anal. Calcd. for $C_{34}H_{39}N_3O_4$: C, 73.75, H, 7.10, N, 7.59. Found: C, 73.48, H, 6.92, N, 7.30.

EXAMPLE 24

4-(3, 4-Dichlorophenyl)-1,4-dihydro-3-methoxycarbonyl-2,6-dimethyl-5-(3-(4,4-diphenylpiperidin-1-yl)propylcarboxamido)pyridine (24). This compound was prepared according to Method A. A solution of N-(3-(4,4-diphenylpiperidin-1-yl)propyl) acetoacetamide (200 mg, 0.528 mmol), methyl 3-aminocrotonate (62.7 mg, 0.528 mmol), and 3,4-dichlorobenzaldehyde (92.4 mg, 0.528 mmol) in 2-propanol(5 mL) was refluxed for 72 hrs. Then the solvent was removed, and the residue was chromatographed (Flash silica; hexane:EtOAc:Et$_3$N=50:50:3, hexane:EtOAc:Et$_3$N= 10:90:6, EtOAc:Et$_3$N=10 1) to give a yellow oil. It was recrystallized from EtOAc and hexane to afford white crystals (75 mg, 23%): m. p. 177.0–178.0° C. Anal. Calcd. for $C_{36}H_{39}N_3O_3Cl_2$:C, 68.35, H, 6.21, N, 6.64, Cl, 11.20. Found: C, 68.27, H, 5.91, N, 6.45, Cl, 10.93.

EXAMPLE 25

1,4-Dihydro-3-methoxycarbonyl-4-(4-methoxycarbonylphenyl)-2,6-dimethyl-5-(N-(3-(4,4-diphenylpiperidin-1-yl)propyl)carboxamido)pyridine (25). This compound was prepared according to Method A. A solution of N-(3-(4,4-diphenylpiperidin-1-yl)propyl) acetoacetamide (200 mg, 0.528 mmol), methyl 3-aminocrotonate (62.7 mg, 0.528 mmol), and methyl 4-formylbenzoate (86.7 mg, 0.528 mmol) in 2-propanol(5 mL) was refluxed for 72 hrs. Then the solvent was removed, and the residue was chromatographed (Flash silica; hexane:EtOAc:Et$_3$N=50:50:3, hexane:EtOAc:Et$_3$N= 10:90:6, EtOAc:Et$_3$N 10:1) to give a yellow oil. It was recrystallized from EtOAc and hexane to afford yellow crystals (70 mg, 21%): m. p. 175.5–176.0° C. Anal. Calcd. for $C_{38}H_{43}N_3O_5$: C, 73.41, H, 6.97, N, 6.76. Found: C, 73.21, H, 6.81, N, 6.52.

EXAMPLE 26

1,4-Dihydro-3-methoxycarbonyl-4-(3,4-dimethoxyphenyl)-4-(3,4-Dimethoxyphenyl)-2,6-Dimethyl-5-(3-(4,4-diphenylpiperidin-1-yl)propyl)carboxamido)pyridine (26). This compound was prepared according to Method A. A solution of N-(3-(4,4-diphenylpiperidin-1-yl) propyl) acetoacetamide (200 mg, 0.528 mmol), methyl 3-aminocrotonate (62.7 mg, 0.528 mmol), and 3,4-dimethoxybenzaldehyde (87.7 mg, 0.528 mmol) in 1-butanol (5 mL) was refluxed for 84 hrs. Then the solvent was removed, and the residue was chromatographed (Flash silica; hexane:EtOAc:Et$_3$N=50:50:3, hexane EtOAc:Et$_3$N= 10:90:6, EtOAc:Et$_3$N=10:1) to give a yellow oil. It was recrystallized from EtOAc and hexane to afford white crystals (60 mg, 18%): m. p. 180.0–181.0° C. Anal. Calcd. for $C_{38}H_{45}N_3O_5$: C, 73.17, H, 7.27, N, 6.74. Found: C, 73.21, H, 7.05, N, 6.54.

EXAMPLE 27

1,4-Dihydro-3-methoxycarbonyl-4-(3,4,5-trimethoxyphenyl)-2,6-dimethyl-5-(3-(4,4-diphenylpiperidin-1-yl)propyl)carboxamido)pyridine (27). This compound was prepared according to Method A. A solution of N-(3-(4,4-diphenylpiperidin-1-yl)propyl) acetoacetamide (200 mg, 0.528 mmol), methyl 3-aminocrotonate (62.7 mg, 0.528 mmol), and 3,4,5-trimethoxybenzaldehyde (103.6 mg, 0.528 mmol) in 1-butanol (5 mL) was refluxed for 84 hrs. Then the solvent was removed, and the residue was chromatographed (Flash silica; hexane:EtOAc:Et$_3$N=50:50:3, hexane:EtOAc:Et$_3$N= 10:90:6, EtOAc:Et$_3$N=10:1) to give a yellow oil. It was recrystallized from EtOAc and hexane to afford white crystals (70 mg, 20%): m. p. 187.0–188.0° C. Anal. Calcd. for $C_{39}H_{47}N_3O_6$: C, 71.65, H, 7.25, N, 6.43. Found: C, 71.65, H, 7.28, N, 6.41.

EXAMPLE 28

1,4-Dihydro-3-methoxycarbonyl-2,6-dimethyl-4-(3-methyl-4-nitrophenyl)-5-(N-(3-(4,4-diphenylpiperidin-1-yl) propyl)carboxamido)pyridine (28). This compound was prepared according to Method A. A solution of N-(3-(4,4-diphenylpiperidin-1-yl)propyl) acetoacetamide (300 mg, 0.792 mmol), methyl 3-aminocrotonate (94.1 mg, 0.792 mmol), and 3-methyl-4-nitrobenzaldehyde (130.8 mg, 0.792 mmol) in 1-butanol(5 mL) was refluxed for 48 hrs. Then the solvent was removed, and the residue was chromatographed (Flash silica; hexane:EtOAc:Et$_3$N=50:50:3, hexane:EtOAc:Et$_3$N=10:90:6, EtOAc Et$_3$N 10:1) to give a yellow solid. It was recrystallized from EtOAc and hexane to afford white crystals (130 mg, 29%): m. p. 222.0–222.5° C. Anal. Calcd. for $C_{37}H_{42}N_4O_5$: C, 71.36, H, 6.80, N, 8.99. Found: C, 71.00, H, 7.43, N, 8.61.

EXAMPLE 29

1,4-Dihydro-3-methoxycarbonyl-4-(3-methoxy-4-nitrophenyl)-2,6-dimethyl-5-(N-(3-(4,4-diphenylpiperidin-1-yl)propyl)carboxamido)pyridine (29). This compound was prepared according to Method A. A solution of N-(3-(4,4-diphenylpiperidin-1-yl)propyl) acetoacetamide (300 mg, 0.792 mmol), methyl 3-aminocrotonate (94.1 mg, 0.792 mmol), and 3-methoxy-4-nitrobenzaldehyde (143.4 mg, 0.792 mmol) in 1-butanol (5 mL) was refluxed for 72 hrs. Then the solvent was removed, and the residue was chromatographed (Flash silica; hexane:EtOAc:Et$_3$N=50:50:3, hexane:EtOAc:Et$_3$N=10:90:6, EtOAc:Et$_3$N=10:1) to give a brown oil. It was recrystallized from EtOAc and hexane to afford brown solid (23 mg, 4.5%): m. p. 211.0–213.0° C. Anal. Calcd. for $C_{37}H_{42}N_4O_6$: C C, 69.57, H, 6.63, N, 8.77. Found: C, 69.37, H, 6.48, N, 8.58.

EXAMPLE 30

1,4-Dihydro-3-methoxycarbonyl-2,6-dimethyl-4-(3-nitrophenyl)-5-(N-(3-(4-phenylpiperidin-1-yl) propyl) carboxamido)pyridine (30). This compound was prepared according to Method A. A solution of N-(3-(4-phenylpiperidin-1-yl)propyl) acetoacetamide (300 mg, 0.992 mmol), methyl 3-aminocrotonate (117.7 mg, 0.992 mmol), and 3-nitrobenzaldehyde (149.9 mg, 0.992 mmol) in 1-butanol(5 mL) was refluxed for 6 days. Then the solvent was removed, and the residue was chromatographed (Flash silica; hexane:EtOAc:Et$_3$N=50:50:3, hexane:EtOAc:Et$_3$N= 10:90:6, EtOAc:Et$_3$N 10:1) to give a yellow oil. It was recrystallized from EtOAc and hexane to afford yellow crystals (91 mg, 17%): m. p. 78.0–80.0° C. Anal. Calcd. for C$_{30}$H$_{36}$N$_{4}$O$_{5}$:C, 67.65, H, 6.81, N, 10.52. Found: C, 67.93, H, 6.91, N, 10.11.

EXAMPLE 31

1,4-Dihydro-3-methoxycarbonyl-2,6-dimethyl-4-(4-methylphenyl)-5-(N-(3-(4-phenylpiperidin-1-yl)propyl) carboxamido)pyridine (31). This compound was prepared according to Method A. A solution of N-(3-(4-phenylpiperidin-1-yl)propyl) acetoacetamide (300 mg, 0.992 mmol), methyl 3-aminocrotonate (117.7 mg, 0.992 mmol), and p-toluadehyde (117.0 ul, d 1.019, 0.992 mmol) in 1-butanol(5 mL) was refluxed for 72 hrs. Then the solvent was removed, and the residue was chromatographed (Flash silica; hexane:EtOAc:Et$_3$N=50:50:3, hexane:EtOAc:Et$_3$N= 10:90:6, EtOAc:Et$_3$N=10:1) to give a yellow oil. It was recrystallized from EtOAc and hexane to afford yellow crystals (79 mg, 16%): m. p. 139.0–139.5° C. Anal. Calcd. for C$_{31}$H$_{39}$H$_3$N$_3$O$_3$: C, 74.22, H, 7.83, N, 8.38. Found: C, 74.19, H, 7.87, N, 8.25.

EXAMPLE 32

1,4-Dihydro-3-methoxycarbonyl-2,6-dimethyl-5-(N-(3-(4-phenylpiperidin-1-yl)propyl) carboxamido)-4-(4-pyridyl)pyridine (32). This compound was prepared according to Method A. A solution of N-(3-(4-phenylpiperidin-1-yl)propyl) acetoacetamide (300 mg, 0.992 mmol), methyl 3-aminocrotonate (117.7 mg, 0.992 mmol), and 4-pyridincarboxaldehyde (94.7 ul, d 1.122, 0.992 mmol) in 2-propanol (5 mL) was refluxed for 48 hrs. Then the solvent was removed, and the residue was chromatographed (Flash silica; hexane:EtOAc:Et$_3$N=50:50:3, hexane:EtOAc:Et$_3$N= 10:90:6, EtOAc:Et$_3$N 10:1) to give a yellow oil. It was recrystallized from EtOAc and hexane to afford light yellow crystals (220 mg, 45%): m. p. 79.0–80.0° C. Anal. Calcd. for C$_{29}$H$_{36}$N$_4$O$_3$.½H$_2$O: C, 69.99, H, 7.49, N, 11.26. Found: C, 70.18, H, 7.51, N, 11.21.

EXAMPLE 33

4-(5-Benzofurazanyl)-5-carboxamido-1,4-dihydro-2,6-dimethyl-5-(N-(3-(4,4-diphenylpiperidin-1-yl)propyl) carboxamido)pyridine (33). This compound is prepared according to Method A. A mixture of N-(3-(4,4-diphenylpiperidin-1-yl)propyl) acetoacetamide (1 equivalent), 3-aminocrotonamide (1 equivalent) and 5-benzofurazan carboxaldehyde (1 equivalent) in 2-propanol is heated at reflux for several days and then concentrated. After flash chromatography and recrystallization, the product is isolated and characterized spectroscopically.

EXAMPLE 34

4-(4-Acetamidophenyl)-5-carboxamido-1,4-dihydro-2,6-dimethyl-3-(N-(3-(4,4-diphenylpiperidin-1-yl)propyl) carboxamido)pyridine (34). This compound is prepared according to Method A. A mixture of N-(3-(4,4-diphenylpiperidin-1-yl)propyl) acetoacetamide (1 equivalent), 3-aminocrotonamide (1 equivalent) and 4-acetamidobenzaldehyde (1 equivalent) in 2-propanol is heated at reflux for several days and then concentrated. After flash chromatography and recrystallization, the product is isolated and characterized spectroscopically.

EXAMPLE 35

5-Carboxamido-1,4-dihydro-4-(4-methanesulfonylphenyl)-2,6-dimethyl-3-(N-(3-(4,4-diphenylpiperidin-1-yl)propyl)carboxamido)pyridine (35). This compound is prepared according to Method A. A mixture of N-(3-(4,4-diphenylpiperidin-1-yl)propyl) acetoacetamide (1 equivalent), 3-aminocrotonamide (1 equivalent) and 4-methanesulfonylbenzaldehyde (1 equivalent) in 2-propanol is heated at reflux for several days and then concentrated. After flash chromatography and recrystallization, the product is isolated and characterized spectroscopically.

EXAMPLE 36

5-Carboxamido-1,4-dihydro-4-(2-hydroxybenzimidazol-5-yl)- 2,6-dimethyl-3-(N-(3-(4,4-diphenylpiperidin-1-yl) propyl)carboxamido)pyridine (36). This compound is prepared according to Method A. A mixture of N-(3-(4,4-diphenylpiperidin-1-yl)propyl) acetoacetamide (1 equivalent), 3-aminocrotonamide (1 equivalent) and 2-hydroxybenzimidazole-5-carboxaldehyde (1 equivalent) in 2-propanol is heated at reflux for several days and then concentrated. After flash chromatography and recrystallization, the product is isolated and characterized spectroscopically.

EXAMPLE 37

5-Cyano-1,4-dihydro-2,6-dimethyl-4-(4-nitrophenyl)-3-{N-[3-(4,4-diphenylpiperidin-1-yl)propyl]}carboxamidopyridine (37). This compound was prepared according to Method A. The solution of 3-aminocrotononitrile (67 mg, 0.816 mmol), 4-nitrobenzaldehyde (123 mg, 0.816 mmol) and N-(3-(4,4-diphenylpiperidin-1-yl)propyl) acetoacetamide (309 mg, 0.816 mmol) in 50 mL of 2-propanol was refluxed for 48 hrs. After the solvent was removed, the residue was purified by chromatography (SiO$_2$, MeOH:CHCl$_3$, 10:90) to give a yellowish oil, which was converted into the hydrochloride salt and recrystallized from MeOH/Et$_2$O, 12 mg (2.4% yield) colorless crystals was obtained. M.p. 252° C. (dec); Calcd for C$_{35}$H$_{37}$N$_5$O$_3$.HCl.½H$_2$O: C 67.68, H 6.33, N 11.27; Found: C 67.63, H 6.29, N 10.88.

EXAMPLE 38

1,4-Dihydro-2,6-dimethyl-5-(N-methyl) carboxamido-4-(4-nitrophenyl)-3-{N-[3-(4,4-diphenylpiperidin-1-yl)propyl]}carboxamidopyridine (38). This compound was prepared according to Method A. The solution of 3-amino-N-methylcrotonamide (60.3 mg, 0.528 mmol), 4-nitrobenzaldehyde (79.8 mg, 0.528 mmol) and N-(3-(4,4-diphenylpiperidin- 1-yl)propyl) acetoacetamide (200 mg, 0.528 mmol) in 50 mL of 2-propanol was refluxed for 48 hrs. After the solvent was removed, the residue was purified by chromatography (SiO$_2$, MeOH:CHCl$_3$, 10:90) to give a yellowish oil, which was precipitated from CH$_2$Cl$_2$/Et$_2$O to afford 38 mg (7.1% yield) of yellowish powder: m.p. 134° C.; Calcd for C$_{36}$H$_{41}$N$_5$O$_4$.¼H$_2$O: C 70.62, H 6.83, N 11.44, Found: C 70.77, H 6.56, N 10.95.

EXAMPLE 39

1,4-Dihydro-2,6-dimethyl-3-(N,N-dimethyl) carboxamido-4-(4-nitrophenyl)-5-{N-[3-(4,4-diphenylpiperidin-1-yl)propyl]}carboxamidopyridine (39). This compound was prepared according to Method A. The solution of 3-amino-N,N-dimethylcrotonamide (76 mg, 0.592 mmol), 4-nitrobenzaldehyde (89 mg, 0.592 mmol) and N-(3-(4,4-diphenylpiperidin-1-yl)propyl) acetoacetamide (224 mg, 0.592 mmol) in 50 mL of 2-propanol was refluxed for 48 hrs. After the solvent was removed, the residue was purified by chromatography (SiO$_2$, MeOH:CHCl$_3$, 10:90) to give a yellowish oil, which was precipitated by AcoEt/hexane mixture to afford 30 mg (8.0% yield) of yellowish powder: M.p. 135° C.; Calcd for C$_{37}$H$_{43}$N$_5$O$_4$·½H$_2$O: C 70.45, H 7.03, N 11.10, Found: C 70.51, H 6.89, N 11.13.

EXAMPLE 40

1,4,5,6,7,8-Hexahydro-2-methyl-4-(4-nitrophenyl)-5-oxo-3-{N-[3-(4,4-diphenylpiperidin-1-yl)propyl]}carboxamidoquinoline (40). This compound was prepared according to Method A. The solution of 3-amino-2-cyclohexene-1-one (335 mg, 3.00 mmol), 4-nitrobenzaldehyde (445 mg, 3.00 mmol) and N-(3-(4,4-diphenylpiperidin-1-yl)propyl) acetoacetamide (113 mg, 3.00 mmol) in 100 mL of 2-propanol was refluxed for 72 hrs. After the solvent was removed, the residue was purified by chromatography (SiO$_2$, MeOH:CHCl$_3$, 10:90) to give a yellowish oil, which was precipitated from CH$_2$Cl$_2$/Et$_2$O to afford 127 mg (7.0% yield) of yellow powder: M.p. 143–146° C.; Calcd for C$_{37}$H$_{40}$N$_4$O$_4$·½ H$_2$O: C 72.41, H 6.73, N 9.13; Found: C 72.69, H 6.66, N 8.98.

EXAMPLE 41

3-Carboxamido-2-methyl-1,4-dihydro-6-methyl-4-(4-nitrophenyl)-3-{N-[3-(4,4-diphenylpiperidin-1-yl)propyl]}carboxamidopyridine (41). This compound was prepared according to Method A. The solution of 3-amino-2-pentenamide (219 mg, 1.91 mmol), 4-nitrobenzaldehyde (289 mg, 1.91 mmol) and N-(3-(4,4-diphenylpiperidin-1-yl)propyl) acetoacetamide (667 mg, 1.91 mmol) in 50 mL of 2-propanol was refluxed for 72 hrs. After the solvent was removed, the residue was purified by chromatography (SiO$_2$, MeOH:CHCl$_3$, 10:90) to give a yellowish oil, which was precipitated from CH$_2$Cl$_2$/Et$_2$O to afford 156 mg (13.3% yield) of yellowish powder: M.p. 120–124° C.; Calcd for C$_{36}$H$_{41}$N$_5$O$_4$·¼H$_2$O: C 70.62, H 6.83, N 11.44; Found: C 70.91, H 6.98, N 10.97.

EXAMPLE 42

5carboxamido-2,6-diethyl-1,4-dihydro-4-(4-nitrophenyl)-3-{N-[3-(4,4-diphenylpiperidin-1-yl)propyl]}carboxamidopyridine (42). This compound was prepared according to Method A. To 30 mL of boiling p-xylene was added a solution of 6-ethyl-2,2-dimethyl-2H,4H-1,3-dioxin-4-one (760 mg, 5 mmol) and 3-(4,4-diphenylpiperidin-1-yl) propylamine (1.48 g, 5 mmol) in 20 mL p-xylene dropwise in about 15 min., during which time, about 20 mL of xylene was distilled off through a condenser. Heating was continued for an additional 45 min. to distill most of the xylene. The remaining xylene was furthur removed by evaporation in vacuo. The product, propionylacetic acid N-[3-(4,4-diphenylpiperidin-1-yl)propyl]amide, was used for next reaction without further purification.

A solution of 3-amino-2-pentenamide (261 mg, 2.28 mmol), 4-nitrobenzaldehyde (345 mg, 2.28 mmol) and propionylacetic acid N-[3-(4,4-diphenylpiperidin-1-yl)propyl] amide (896 mg, 2.28 mmol) in 50 mL of EtOH was refluxed for 72 hrs. After the solvent was removed, the residue was purified by chromatography (SiO$_2$, MeOH:CHCl$_3$, 10:90) to give a yellowish oil, which was precipitated from CH$_2$Cl$_2$/Et$_2$O to afford 81 mg (5.4% yield) of yellowish powder: M.p. 119–123° C.; Calcd for C$_{37}$H$_{43}$N$_5$O$_4$·⅔H$_2$O: C 68.02, H 7.17, N 10.72; Found: C 68.05, H 6.71, N 10.89.

EXAMPLE 43

2-(Furan-3-yl)-1,4-dihydro-5-methoxycarbonyl-6-methyl-4-(4-nitrophenyl)-3-(N-(3-(4,4-diphenylpiperidin-1-yl)propyl)carboxamidopyridine, Hydrochloride Salt (43). This compound was initially prepared according to Method A, and later according to Method B (see below). Method A: A stirred solution of 191 mg of 1-(3-aminopropyl)-4,4-diphenylpiperidine (0.676 mmol), 123 mg of ethyl 3-oxo-3-(furan-3-yl)propionate (0.676 mmol), and 83 mg of dimethylaminopyridine (0.676 mmol) in 5 mL of dry toluene were heated at reflux temperature for 18 hrs, cooled, and the residue was dissolved in 30 mL of EtOAc. The resulting solution was extracted with 2×20 mL of aqueous 1N HCl solution. The combined aqueous extracts were washed with 20 mL of 1:1 EtOAc-ether, basified with NaHCO$_3$ (pH= 8–9), and extracted with 2×20 mL of EtOAc. The combined EtOAc extracts were dried (Na$_2$SO$_4$), the solvent was removed in vacuo, and the crude product was chromatographed on 100 g of silica packed with MeOH-isopropyl amine-EtOAc (1:1:98). The column was eluted with MeOH-isopropyl amine-EtOAc 1:1:98, 2:1:97, 5:1:94, 10:1:89, 20:1:79 (0.5 L each) to give N-(3-(4,4-diphenylpiperidin-1-yl)propyl 3-oxo-3-(furan-3-yl)propanamide as a slightly yellow viscous oil. The product was used in the next step after spectral characterization.

A mixture of 40 mg of N-(3-(4,4-diphenylpiperidin-1-yl) propyl 3-oxo-3-(furan-3-yl)propanamide (0.096 mmol), 11 mg of methyl 3-aminocrotonate (0.096 mmol), and 15 mg of 4-nitrobenzaldehyde (0.096 mmol) in 5 mL of isopropanol was heated at reflux temperature for 4 days, cooled, and the solvent was removed in vacuo. The crude product was applied to a preparative Thin Layer Chromatography (TLC) plate and eluted with 5% MeOH—EtOAc. A yellow band was collected. This crude product was dissolved in a minimum of EtOAc (0.5 mL) and excess HCl in ether (1 mL) was added to afford, after filtration, 5.8 mg (1% from ethyl 3-oxo-3-(furan-3-yl)propionate) of the free base as a yellow powder: mp 197–205° C. (decomp.). Anal. Calcd for C$_{38}$H$_{40}$N$_4$O$_6$·HCl: C, 66.61; H, 6.03; N, 8.18. Found: C, 66.61; H, 5.81; N, 7.94.

Method B: A mixture of 894 mg of ethyl 3-(furan-3-yl)-3-oxopropionate (4.90 mmol) and 347 mg of 3-hydroxypropionitrile (4.88 mmol) was heated in an oil bath to 180–205° C. for 0.5 hrs. The reaction mixture was cooled and distilled under reduced pressure. Three fractions were obtained. $^1$H NMR indicated that the third fraction (bp 100–140° C. (0.5 mm Hg)) was a 1:1 mixture of ethyl 3-(furan-3-yl)-3-oxopropionate and 2-cyanoethyl 3-(furan-3-yl)-3-oxopropionate. This mixture was used in the condensation step after spectral characterization.

A solution of the 3-oxoesters (approximately 1.67 mmol), 192 mg of methyl 3-aminocrotonate (1.67 mmol), and 252 mg of 4-nitrobenzaldehyde (1.67 mmol) in 5 mL of isopropanol was heated at reflux temperature for 30 hrs, cooled, and the solvent was removed in vacuo. The residue was dissolved in 15 mL of dioxane and 15 mL of water (containing 35 mg of NaOH), stirred for 0.5 hr, and concentrated in vacuo. The residue was partitioned between ethyl acetate and water (20 mL each), separated, and the aqueous extract was washed with ethyl acetate (2×20 mL). The organic solutions were discarded. The aqueous extract was acidified with concentrated HCl (pH=3), and the resulting cloudy mixture was extracted with ethyl acetate (2×30 mL). The combined organic extracts were dried (Na$_2$SO$_4$), and the solvent was removed in vacuo to give 2-(furan-3-yl)-1,4-dihydro-5-methoxycarbonyl-6-methyl-4-(4-nitro) phenylpyridine-3-carboxylic acid as a yellow oil that partially solidified under reduced pressure. A solution of 75 mg of 2-(furan-3-yl)-1,4-dihydro-5-methoxycarbonyl-6-methyl-4-(4-nitro)phenylpyridine-3-carboxylic acid (0.20 mmol) and 35 mg of carbonyldiimidazole (0.22 mmol) was stirred at room temperature for 1 hr. The solvent was removed in vacuo, and the crude product was chromatographed on 100 g of silica packed with 2% MeOH—EtOAc. The column was eluted with 3% MeOH—EtOAc to give 45 mg (58%) of 5-carboxamido-2-(furan-3-yl)-1,4-dihydro-3-(imidazol-1-yl)carbonyl-6-methyl-4-(4-nitro) phenylpyridine.

5-Carboxamido-2-(furan-3-yl)-1,4-dihydro-3-(imidazol-1-yl)carbonyl-6-methyl-4-(4-nitro)phenylpyridine was dissolved in 5 mL of dry THF and excess (1.5 equivalents) of 1-(3-aminopropyl)-4,4-diphenylpiperidine was added to the reaction mixture. The resulting mixture was heated at reflux temperature for 3 hrs and cooled to room temperature. The solvent was removed in vacuo, and the residue was dissolved in 20 mL of ethyl acetate and washed with water (3×10 mL). After removal of the solvent, the crude product was chromatographed on 50 g of silica packed with 10% MeOH—EtOAc. The column was eluted with 10% MeOH—EtOAc to give 61 mg of 2-(furan-3-yl)-1,4-dihydro-5-methoxycarbonyl-6-methyl-4-(4-nitro)phenyl-3-(N-(3-(4,4-diphenylpiperidin-1-yl)propyl)) carboxamidopyridine, which was spectroscopically identical to the product obtained by Method A.

EXAMPLE 44

Acetoacetic acid 3-(N,N-dimethyl)aminopropyl ester. Diketene (2.54 mL, 33.0 mmol, 1.30 equiv) was added to a solution of 3-(N,N-dimethyl)aminopropan-1-ol (3.00 mL, 25.4 mmol, 1.00 equiv, Aldrich) in toluene (30 mL) and the mixture was stirred at room temperature for 70 hours. The solvent was removed to afford 4.76 g of brown oil, which was characterized spectroscopically and used for the next reaction without purification.

1,4-Dihydro-3-methoxycarbonyl-2,6-dimethyl-3-{3-[(N, N-dimethyl)amino]propoxy}carbonyl-4-(4-nitrophenyl) pyridine hydrochloride (44). This compound was prepared according to Method A. A mixture of acetoacetic acid 3-(N,N-dimethyl)aminopropyl ester (0.937 g, 5.00 mmol, 1.00 equiv), methyl-3-aminocrotonate (576 mg, 5.00 mmol, 1.00 equiv) and 4-nitrobenzaldehyde (756 mg, 5.00 mmol, 1.00 equiv) in 2-propanol (30 mL) was stirred at reflux for 60 hours. After removal of the solvent, the residue was purified twice by flash chromatography on $SiO_2$ (1. EtOAc-MeOH 1:0 to 6:1; 2. $CH_2Cl_2$-isopropylamine 10:0.5) to give 888 mg of yellow solid, which was characterized spectroscopically. To a solution of this product in $CH_2Cl_2$ (10 mL) was added a solution of HCl in ether (1.0 M, 2.50 mL, 2.5 mmol, 1.2 equiv). After removal of the solvents, a solution of the residue in $CH_2Cl_2$ (5 mL) was added dropwise with swirling to 20 mL of ether. Filtration afforded 516 mg of yellow solid: m.p. 120–121° C.; Anal. Calcd. for $C_{21}H_{27}N_3O_6$.HCl: C, 55.57; H, 6.22; N, 9.26. Found: C, 55.29 H, 6.50; N, 8.55.

EXAMPLE 45

(±)-1,4-Dihydro-3-methoxycarbonyl-2,6-dimethyl-4-(4-nitrophenyl)-5-{N-[3-(4-phenylpiperidin-1-yl)propyl]}carboxamidopyridine hydrochloride hemihydrate ((±)-45). This compound was prepared according to Method A. A solution of N-(3-(4-phenylpiperidin-1-yl)propyl) acetoacetamide (4.50 g, 14.2 mmol, 1.00 equiv), methyl 3-aminocrotonate (1.68 g, 14.2 mmol, 1.00 equiv), and 4-nitrobenzaldehyde (2.15 g, 14.2 mmol, 1.00 equiv) in 2-propanol was stirred at reflux for 52 hours under argon. After removal of the solvent, the residue was purified by flash chromatography ($SiO_2$, EtOAc—MeOH—$Et_3N$ 9:1:0 to 6:1:0.1). A solution of the chromatographed product in $CH_2Cl_2$ (15 mL) was added dropwise with swirling to 250 mL of ether-hexane (1:1). Filtration of this mixture afforded 2.50 g (33%) of yellow crystalline solid, which was characterized spectroscopically. To a solution of this product (1.0 g, 1.9 mmol, 1.0 equiv) in $CH_2Cl_2$ (10 mL) was added dropwise a solution of HCl in ether (1.0M, 2.3 mL, 2.3 mmol, 1.2 equiv). After removal of the solvents, a solution of the residue in $CH_2Cl_2$ (10 mL) was added dropwise to 70 mL of ether with swirling. Filtration afforded 1.04 g of yellow solid: m.p. 159–160° C.; Anal. Calcd. for $C_{30}N_4O_5$.HCl.0.5 $H_2O$: C, 62.33; H, 6.63; N, 9.69. Found: C, 62.19; H, 6.38; N, 9.34.

(−)- and (+)-45 hydrochloride hemihydrate. The enantiomers of 45 free base were separated on a chiral HPLC column as follows. Three injections of (±)-45 free base (ca. 25 mg per injection in EtOH solution) were made onto a Chiralpak AS column (20×250 mm) which was pre-equilibrated with EtOH-hexane-diethylamine (10:90:0.017). The column was eluted with a gradient at 9.0 mL/min: hexane, 0.0–3.0 min; ramp to EtOH-hexane-diethylamine (30:70:0.05) 3.0–6.0 min and hold at final conditions. Detection was by UV absorption at 300 nm. The first major peak eluted at 19.56 min. To a solution of this product in $CH_2Cl_2$ (3 mL) was added HCl in ether (1.0M, 0.25 mL). After removal of the solvents, a solution of the residue in $CH_2Cl_2$ (2 mL) was added dropwise into ether (6 mL) with swirling to give, after filtration, 19.4 mg of yellow powder: $(\alpha)_D$=−18.4° (EtOH, 0.000711 g/mL); m.p. 160° C; Anal. Calcd. for $C_{30}H_{36}N_4O_5$HCl.0.5 $H_2$: C, 62.33; H, 6.63; N, 9.69. Found: C, 62.74; H, 6.73; N, 9.66. The second major peak, which eluted at 29.28 min, was converted to the HCl salt and precipitated as described for the (−)- enantiomer to afford 20.6 mg of yellow powder: $[\alpha]_D$=+24.4° (EtOH, 0.000753 g/mL); m.p. 161° C.; Anal. Calcd. for $C_{36}H_{40}N_4O_5$.HCl.$H_2O$: C, 62.33; H, 6.63; N, 9.69. Found: C, 62.33; H, 6.26; N, 9.51.

EXAMPLE 46

1-[3-(N-Methylamino)propyl]-4,4-diphenylpiperidine. To a stirred solution of 3-(4,4-diphenylpiperidin-1-yl) propionitrile (5.00 g, 17.2 mmol, 1.00 equiv) in $CH_2Cl_2$ (40 mL) was added HCl in ether (1.0M, 22.4 mL, 22 mmol, 1.3 equiv). After removal of the solvents, the residue and trimethyloxonium tetrafluoroborate (9.67 g, 65.4 mmol, 3.80 equiv) were stirred in refluxing anhydrous $CH_2Cl_2$ (80 mL) under argon for 44 hours. The mixture was cooled to 0° C., anhydrous MeOH (5 mL) was added, and stirring was continued for 1 hour at 0° C. The solvents were removed and the residue was dissolved in anhydrous MeOH (30 mL). Sodium borohydride (5.20 g, 138 mmol, 8.00 equiv) was added at 0° C., and stirring was continued at this temperature under argon for 2 hours. The solution was acidified to pH 1 by slow addition of 6N aqueous HCl (40 mL) at 0° C. and stirred for 3 hours at room temperature. After removal of the solvents, water (30 mL) was added and the mixture was basified to pH 9 by addition of 6N aqueous NaOH. The mixture was extracted with $CH_2Cl_2$ (3×100 mL), and the combined organic solutions were dried over $MgSO_4$ and concentrated. The residue was purified by flash chromatography ($SiO_2$, EtOAc—MeOH-isopropylamine 9:1:0 to 5:1:0.2) to give 2.18 g (41%) of yellow solid, which was characterized spectroscopically.

N-[3-(4,4-Diphenylpiperidin-1-yl)propyl-N-methylacetoacetamide. Diketene (0.98 mL, 12.7 mmol, 1.50 equiv) was added at 0° .C to a stirred solution of 1-[3-(N- methylamino)propyl]-4,4-diphenylpiperidine (2.61 g, 8.46 mmol, 1.00 equiv) in anhydrous toluene (30 mL) under argon, and stirring was continued for 1 hour. After removal of the solvent, the residue was purified by flash chromatography (SiO$_2$, EtOAc—MeOH-isopropylamine 9:1:0 to 6:1:0.1) to afford 2.97 g (89%) of brown oil, which was characterized spectroscopically.

1,4-Dihydro-3-methoxycarbonyl-2,6-dimethyl-5-[N-[3-(4,4-diphenylpiperidin-1-yl)propyl]}carboxamido-4-(4-nitrophenyl)pyridine hydrochloride hemihydrate (46). This compound was prepared according to Method A. A solution of N-[3-(4,4-diphenylpiperidin-1-yl)propyl]-N-methylacetoacetamide (1.49 g, 3.79 mmol, 1.00 equiv), methyl 3-aminocrotonate (479 mg, 4.16 mmol, 1.10 equiv), and 4-nitrobenzaldehyde (629 mg, 4.16 mmol, 1.10 equiv) in isopropanol (20 mL) was stirred at room temperature for 0.5 hour and then refluxed under argon for 60 hours. The mixture was cooled to room temperature and concentrated, and the residue was purified three times by flash chromatography on SiO$_2$ (1. EtOAc-MeOH 10:0 to 9:1; 2. CH$_2$Cl$_2$-Et$_3$N 96:4; 3. EtOAc-MeOH 19:1) to afford 210 mg of light yellow solid, which was characterized spectroscopically. To a solution of this product (190 mg, 0.305 mmol, 1.0 equiv) in CH$_2$Cl$_2$ (10 mL) was added HCl in ether (1.0M, 0.37 mL, 0.37 mmol, 1.2 equiv) with swirling. After removal of the solvents, the residue was dissolved in CH$_2$Cl$_2$ (5 mL) and added dropwise to 20 mL of ether with swirling. Filtration afforded 196 mg of yellow solid: m.p. 179–180° C.; Anal. Calcd. for C$_{37}$H$_{43}$N$_4$O$_5$.HCl.0.5 H$_2$O: C, 66.51; H, 6.64; N, 8.38. Found: C, 66.32; H, 6.58; N, 8.16.

EXAMPLE 47

4-Aminopent-3-en-2-one. Concentrated ammonium hydroxide (ca. 14.8M, 6.6 mL, 98 mmol, 1.0 equiv) was added dropwise to neat 2,4-pentanedione (10 mL, 97 mmol, 1.0 equiv) at ambient temperature. Water (5 mL) was added and the mixture was stirred for 1 hour. The solvent was removed to give 9.2 g (95%) of white solid, which was characterized spectroscopically and used for the next step without purification.

5-Acetyl-1,4-dihydro-2,6-dimethyl-4-(4-nitrophenyl)-3-{N-[3-(4,4-diphenylpiperidin-1-yl)propyl]}carboxamidopyridine (47). This compound was prepared according to Method A. A solution of N-(3-(4,4-diphenylpiperidin-1-yl)propyl)acetoacetamide (7.57 g, 20.0 mmol, 1.00 equiv), 4-aminopent-3-en-2-one (2.18 g, 22.0 mmol, 1.10 equiv), and 4-nitrobenzaldehyde (3.33 g, 22.0 mmol, 1.10 equiv) in isopropanol 30 mL) was refluxed under argon for 72 hours. The mixture was cooled to room temperature and concentrated. The residue was purified on two successive SiO$_2$ flash chromatography columns (1. EtOAc, followed by EtOAc-MeOH 19:1; 2. CH$_2$Cl$_2$-MeOH 96:4) to give 3.5 g of yellow solid. A solution of this product in CH$_2$Cl$_2$ was added dropwise to EtOAc at room temperature. Storage of the resulting mixture at –10° C. for 12 hours, followed by filtration and washing with CH$_2$Cl$_2$-EtOAc (1:1), afforded 2.10 g of yellow solid (18%), which was characterized spectroscopically. To a solution of this product (50 mg, 0.084 mmol, 1.0 equiv) in CH$_2$Cl$_2$-EtOH (1:1, 10 mL) was added HCl in ether (1.0M, 0.13 mL, 0.13 mmol, 1.5 equiv) with swirling. After removal of the solvents, the residue was dissolved in CH$_2$Cl$_2$-EtOH 1:1 (3 mL) and added dropwise to 20 mL of ether-hexane (1:1). Filtration afforded 41 mg of yellow solid: m.p. 173–174° C.; Anal. Calcd. for C$_{36}$H$_{40}$N$_4$O$_4$.HCl.H$_2$O: C, 66.81; H, 6.70; N, 8.66. Found: C, 66.44; H, 6.34; N, 8.43.

EXAMPLE 48

1-(3-Hydroxypropyl)-4-phenylpiperidine. A suspension of 4-phenylpiperidine (3.00 g, 18.6 mmol, 1.00 equiv), 3-bromopropan-1-ol (2.12 mL, 22.3 mmol, 1.20 equiv), potassium carbonate (12.8 g, 93.0 mmol, 5.00 equiv), and potassium iodide (124 mg, 0.74 mmol, 0.04 equiv) in n-butanol (50 mL) and 1,4-dioxane (50 mL) was stirred at reflux under argon for 48 hours. The mixture was cooled to room temperature and concentrated. Water (50 mL) was added and the mixture was extracted with CH$_2$Cl$_2$ (4×100 mL). The combined organic solutions were dried over MgSO$_4$ and concentrated. The residue was crystallized from ethyl acetate to give 3.36 g (82%) of tan solid, which was characterized spectroscopically.

3-(4-Phenylpiperidin-1-yl)propyl acetoacetate. Diketene (0.95 mL, 12 mmol, 1.3 equiv) was added to a solution of 1-(3-hydroxypropyl)-4-phenylpiperidine (2.08 g, 9.48 mmol, 1.0 equiv) in toluene (30 mL), and the mixture was stirred under argon for 70 hours at room temperature. Removal of solvent gave 2.88 g (100%) of light brown, viscous oil, which was characterized spectroscopically and used for the next reaction without purification.

1,4-Dihydro-5-methoxycarbonyl-2,6-dimethyl-4-(4-nitrophenyl)-3-[3-(4-phenylpiperidin-1-yl)propoxy]}carbonylpyridine hydrochloride hydrate (48). This compound was prepared according to Method A. 3-(4-Phenylpiperidin-1-yl)propyl acetoacetate (2.85 g, 9.40 mmol, 1.00 equiv), methyl 3-aminocrotonate (1.08 g, 9.40 mmol, 1.00 equiv) and 4-nitrobenzaldehyde (1.42 g, 9.40 mmol, 1.00 equiv) were stirred together in 2-propanol (50 mL) at reflux for 48 hours under argon. After removal of the solvent, the residue was purified by flash chromatography (SiO$_2$, Et$_2$O-hexane 1:1, followed by EtOAc-hexane 2:1 to 1:0) to give 1.76 g (35%) of yellow solid, which was characterized spectroscopically. This product was dissolved in CH$_2$Cl$_2$ (10 mL) and a solution of HCl in ether (1.0M, 4.5 mL, 1.4 equiv) was added. After removal of the solvents, the residue was dissolved in CH$_2$Cl$_2$ (10 mL) and added dropwise to ether (50 mL) with swirling to give, after filtration, 1.75 g of yellow solid: m.p. 139–140° C.; Anal. Calcd. for C$_{30}$H$_{35}$N$_3$O$_6$.HCl: C, 63.20; H, 6.37; N, 7.37. Found: C, 63.05 H, 6.56; N, 7.16.

EXAMPLE 49

5-Acetyl-1,4-dihydro-2,6-dimethyl-4-(4-nitrophenyl)-3-3-(4,4-diphenylpiperidin-1-yl)propoxy]carbonylpyridine hydrochloride hemihydrate (49). This compound was prepared according to Method A. A mixture of 4-aminopent-3-en-2-one (287 mg, 2.90 mmol, 1.00 equiv), 4-nitrobenzaldehyde (438 mg, 2.90 mmol, 1.00 equiv), and 3-(4-phenylpiperidin-1-yl)propyl acetoacetate (1.10 g, 2.90 mmol, 1.00 equiv) in isopropanol (30 mL) was stirred at reflux under argon for 60 hours. After removal of the solvent, the residue was purified by flash chromatography (SiO$_2$, EtOAc-hexane 1:1 to 1:0) to give 371 mg (22%) of yellow solid, which was characterized spectroscopically. This product was dissolved in CH$_2$Cl$_2$ (5 mL) and a solution of HCl in ether (1.0M, 1.0 mL, 1.6 equiv) was added. After removal of the solvents, the residue was dissolved in CH$_2$Cl$_2$ (5 mL) and added dropwise to ether (20 mL) with swirling to give, after filtration, 319 mg of yellow solid: m.p. 160.0–160.5° C.; Anal. Calcd. for C$_{36}$H$_{39}$N$_3$O$_5$HCl.0.5 H$_2$O: C, 67.75; H, 6.32; N, 6.58. Found: C, 67.62 HI 6.34; N, 6.28.

EXAMPLE 50

3-(Piperidin-1-yl) propyl acetoacetate. Diketene (1.48 mL, 19.2 mmol, 1.30 equiv) was added to a solution of 1-(3-hydroxypropyl)piperidine (2.12 g, 14.8 mmol, 1.00 equiv, Leonard, N. J.; Musker, W. K. *J. Am. Chem. Soc.* 1960, 82, 5148) in toluene (30 mL), and the mixture was stirred under argon for 72 hours at room temperature. Removal of solvent gave 3.52 g (100%) of light brown, viscous oil, which was characterized spectroscopically and used for the next reaction without purification.

1,4-Dihydro-5-methoxycarbonyl-2,6-dimethyl-4-(4-nitrophenyl)-3-[3-(piperidin-1-yl)propoxy]carbonylpyridine hydrochloride etherate (50). This compound was prepared according to Method A. 3-(Piperidin-1-yl)propyl acetoacetate (2.20 g, 9.68 mmol, 1.00 equiv), methyl 3-aminocrotonate (1.11 g, 9.68 mmol, 1.00 equiv) and 4-nitrobenzaldehyde (1.46 g, 9.68 mmol, 1.00 equiv) were stirred together in 2-propanol (50 mL) at reflux for 72 hours under argon. After removal of the solvent, the residue was purified by flash chromatography ($SiO_2$, MeOH—EtOAc 0:1 to 1:19) to give 1.71 g (39%) of yellow solid, which was characterized spectroscopically. This product was dissolved in $CHCl_2$ (15 mL) and a solution of HCl in ether (1.0M, 4.5 mL, 1.2 equiv) was added. After removal of the solvents, the residue was dissolved in $CH_2Cl_2$ (10 mL) and added dropwise to ether (70 mL) with swirling to give, after filtration, 1.78 g of yellow solid: m.p. 128–129° C.; Anal. Calcd. for $C_{24}H_{31}N_3O_6$·HCl·0.4 $Et_2O$: C, 58.72; H, 6.93; N, 8.02. Found: C, 58.44 H, 6.82; N, 7.76.

EXAMPLE 51

N-(3-(Piperidin-1-yl)propyl)acetoacetamide. Diketene (2.40 mL, 31.1 mmol, 1.50 equiv) was added at 0° C. to a stirred solution of 1-(3-aminopropyl)piperidine (2.95 g, 20.7 mmol, 1.0 equiv, Bates, R. J.; Cymerman-Craig, J.; Moyie, M.; Yong, R. J. *J. Chem. Soc.* 1956, 388) in anhydrous THF (40 mL) under argon, and stirring was continued at room temperature for 1.5 hours. The mixture was concentrated to give 4.8 g (100%) of light brown oil, which was characterized spectroscopically and used for the next reaction without purification.

1,4-Dihydro-3-methoxycarbonyl-2,6-dimethyl-4-(4-nitrophenyl)-5-{N-[3-(piperidin-1-yl-)propyl]}carboxamidopyridine hydrochloride etherate (51). This compound was prepared according to Method A. N-(3-(Piperidin-1-yl)propyl)acetoacetamide (4.53 g, 20.0 mmol, 1.00 equiv), methyl 3-aminocrotonate (2.37 g, 20.0 mmol, 1.00 equiv) and 4-nitrobenzaldehyde (3.02 g, 20.0 mmol, 1.00 equiv) were stirred together in 2-propanol (60 mL) at reflux for 60 hours under argon. After removal of the solvent, the residue was purified by flash chromatography ($SiO_2$, MeOH—EtOAc 0:1 to 1:6) to afford 2.25 g of yellow solid. A solution of this product in $CH_2Cl_2$ (10 mL) was added dropwise into ether (50 mL) with swirling. A yellow solid (1.75 g, 19%) was collected by filtration and characterized spectroscopically. This product (1.4 g) was dissolved in $CH_2Cl_2$ (10 mL) and a solution of HCl in ether (1.0M, 4.5 mL, 1.5 equiv) was added. After removal of the solvents, the residue was dissolved in $CH_2Cl_2$ (10 mL) and added dropwise to ether (80 mL) with swirling to give, after filtration, 1.38 g of yellow solid: m.p. 150.0–150.5° C.; Anal. Calcd. for $C_{24}H_{32}N_4O_5$·HCl·0.2 $Et_2O$: C, 58.66; H, 6.95; N, 11.03. Found: C, 58.31 H, 7.05; N, 10.70.

EXAMPLE 52

(4,4-Diphenylpiperidin-1-yl)acetonitrile. A suspension of 4,4-diphenylpiperidine (4.00 g, 16.9 mmol, 1.00 equiv), chloroacetonitrile (1.40 mL, 21.9 mmol, 1.30 equiv, Aldrich), potassium carbonate (4.67 g, 33.8 mmol, 2.00 equiv), and potassium iodide (561 mg, 3.38 mmol, 0.20 equiv) in n-butanol (20 mL) and 1,4-dioxane (20 mL) was stirred at reflux under argon for 48 hours. The mixture was cooled to room temperature and concentrated. The residue was purified by flash chromatography ($SiO_2$, EtOAc) to afford 4.01 g (86%) of white solid, which was characterized spectroscopically.

1-(2-Aminoethyl)-4,4-diphenylpiperidine. To a stirred solution of (4,4-diphenylpiperidin-1-yl)acetonitrile (3.90 g, 14.1 mmol, 1.0 equiv) in anhydrous THF (10 mL) under argon was added a solution of $BH_3$ in THF (1.0M, 50 mL, 50 mmol, 3.5 equiv) at room temperature. The mixture was refluxed for 4.5 hours and then cooled to room temperature and concentrated to a volume of about 30 mL. Aqueous HCl (6N, 50 mL) was added cautiously and stirring was continued for 2 hours at 50° C. The mixture was cooled to room temperature, basified to pH 10 by addition of 6N aq. NaOH, and extracted with $CH_2Cl_2$ (3×100 mL). The combined organic solutions were dried over $MgSO_4$ and concentrated. To a solution of the residue in $CH_2Cl_2$ (30 mL) was added HCl in ether (1.0M, 16 mL, 1.1 equiv). After removal of the solvents, the residue was dissolved in $CH_2Cl_2$ (10 mL) and this solution was added dropwise into ether (100 mL) with swirling. The resulting solid was filtered and washed with ether (3×50 mL). This solid was taken up in water (20 mL), which was basified to pH 10 by addition of 1M aqueous NaOH, and extracted with $CH_2Cl_2$ (3×50 mL). The combined organic solutions were dried over $MgSO_4$ and concentrated to give 3.70 g (94%) of white solid, which was characterized spectroscopically.

N-(2-(4,4-Diphenylpiperidin-1-yl)ethyl)acetoacetamide. Diketene (1.50 mL, 19.2 mmol, 1.50 equiv) was added at 0° C. to a stirred solution of 1-(2-aminoethyl)-4,4-diphenylpiperidine (3.60 g, 12.8 mmol, 1.00 equiv) in anhydrous THF (40 mL) under argon, and stirring was continued at room temperature for 1 hour. The mixture was concentrated to give 4.10 g (88%) of white solid, which was characterized spectroscopically and used for the next reaction without purification.

1,4-Dihydro-3-methoxycarbonyl-2,6-dimethyl-4-(4-nitrophenyl)-5-{N-[2-(4,4-diphenylpiperidin-1-yl)ethyl]}carboxamidopyridine hydrochloride hemihydrate (52). This compound was prepared according to Method A. N-(2-(4,4-Diphenylpiperidin-1-yl) ethyl) acetoacetamide (2.34 g, 6.41 mmol, 1.00 equiv), methyl 3-aminocrotonate (0.839 g, 7.06 mmol, 1.10 equiv) and 4-nitrobenzaldehyde (1.07 g, 7.06 mmol, 1.10 equiv) were stirred together in 2-propanol (40 mL) at reflux for 68 hours under argon. After removal of the solvent, the residue was purified by flash chromatography ($SiO_2$, MeOH—EtOAc 0:1 to 1:9) to afford 1.40 g (37%) of yellow solid, which was characterized spectroscopically. This product (1.36 g) was dissolved in $CH_2Cl_2$ (10 mL) and a solution of HCl in ether (1.0M, 3.5 mL, 1.5 equiv) was added. After removal of the solvents, the residue was dissolved in $CH_2Cl_2$ (10 mL) and added dropwise to ether (80 mL) with swirling to give, after filtration, 1.14 g of yellow solid: m.p. 170–171° C.; Anal. Calcd. for $C_{35}H_{38}N_4O_5$·HCl·0.5 $H_2O$: C, 65.67; H, 6.30; N, 8.75. Found: C, 65.67; HI 6.35; N, 8.62.

EXAMPLE 53

4-(4,4-Diphenylpiperidin-1-yl)butyronitrile. A suspension of 4,4-diphenylpiperidine (4.15 g, 17.5 mmol, 1.00 equiv), 4-bromobutyronitrile (2.10 mL, 21.0 mmol, 1.20 equiv, Aldrich), potassium carbonate (4.85 g, 35.0 mmol, 2.00 equiv), and potassium iodide (581 mg, 3.50 mmol, 0.20 equiv) in n-butanol (20 mL) and 1,4-dioxane (20 mL) was stirred at reflux under argon for 48 hours. The mixture was cooled to room temperature and concentrated. Water (50 mL) was added and the mixture was extracted with $CH_2Cl_2$ (4×150 mL). The combined organic solutions were dried over $MgSO_4$ and concentrated. The residue was purified by flash chromatography ($SiO_2$, EtOAc) to afford 4.65 g (87%) of white solid, which was characterized spectroscopically.

1-(4-Aminobutyl)-4,4-diphenylpiperidine. To a stirred solution of 4-(4,4-diphenylpiperidin-1-yl)butyronitrile (4.65 g, 15.3 mmol, 1.0 equiv) in anhydrous THF (20 mL) under argon was added a solution of $BH_3$ in THF (1.0M, 54 mL, 54 mmol, 3.5 equiv) at room temperature. The mixture was refluxed for 4.5 hours and then cooled to room temperature and concentrated to a volume of about 40 mL. Aqueous HCl (6N, 55 mL) was added cautiously at 0° C. and stirring was continued for 2 hours at 55–65° C. The mixture was cooled to 0° C., basified to pH 10 by addition of 6N aq. NaOH, and extracted with $CH_2Cl_2$ (3×100 mL). The combined organic solutions were dried over $MgSO_4$ and concentrated. To a solution of the residue in $CH_2Cl_2$ (50 mL) was added HCl in ether (1.0M, 30 mL, 2.0 equiv). After removal of the solvents, the residue was dissolved in $CH_2Cl_2$ (10 mL) and this solution was added dropwise into ether (150 mL) with swirling. The resulting solid was filtered and washed with ether (100 mL). This solid was taken up in water (30 mL), which was basified to pH 10 by addition of 1M aqueous NaOH, and extracted with $CH_2Cl_2$ (3×50 mL). The combined organic solutions were dried over $MgSO_4$ and concentrated to give 4.51 g (95%) of light brown oil, which was characterized spectroscopically.

N-(4-(4,4-Diphenylpiperidin-1-yl)butyl) acetoacetamide. Diketene (1.68 mL, 21.9 mmol, 1.50 equiv) was added at 0° C. to a stirred solution of 1-(4-aminobutyl)-4,4-diphenylpiperidine (4.50 g, 14.6 mmol, 1.00 equiv) in anhydrous THF (40 mL) under argon, and stirring was continued at room temperature for 1.5 hours. The mixture was concentrated and the residual oil washed with hexane (3×50 mL) to give 5.17 g (90%) of light yellow oil, which was characterized spectroscopically and used for the next reaction without purification.

1,4-Dihydro-3-methoxycarbonyl-2,6-dimethyl-4-(4-nitrophenyl)-5-{N-[4-(4,4-diphenylpiperidin-1-yl)butyl]}carboxamidopyridine hydrochloride hydrate (53). This compound was prepared according to Method A. N-(4-(4,4-Diphenylpiperidin-1-yl) butyl) acetoacetamide (2.86 g, 7.30 mmol, 1.00 equiv), methyl 3-aminocrotonate (0.953 g, 8.03 mmol, 1.10 equiv) and 4-nitrobenzaldehyde (1.21 g, 8.03 mmol, 1.10 equiv) were stirred together in 2-propanol (50 mL) at reflux for 72 hours under argon. After removal of the solvent, the residue was purified by flash chromatography ($SiO_2$, MeOH—EtOAc 0:1 to 1:9) to afford 1.40 g (31%) of yellow solid, which was characterized spectroscopically. This product was dissolved in $CH_2Cl_2$ (10 mL) and a solution of HCl in ether (1.0M, 3.5 mL, 1.6 equiv) was added. After removal of the solvents, the residue was dissolved in $CH_2Cl_2$ (10 mL) and added dropwise to ether (80 mL) with swirling to give, after filtration, 1.25 g of yellow solid: m.p. 166–167° C.; Anal. Calcd. for $C_{37}H_{42}N_4O_5 \cdot HCl \cdot 0.75 H_2O$: C, 66.06; H, 6.67; N, 8.33. Found: C, 66.04; H, 6.57; N, 8.09.

EXAMPLE 54

5-Carboxamido-1,4-dihydro-2,6-dimethyl-4-(4-nitrophenyl)-3-{N-[2-(4,4-diphenylpiperidin-1-yl)ethyl]}carboxamidopyridin hydrochloride hydrate (54). This compound was prepared according to Method A. N-(2-(4,4-Diphenylpiperidin-1-yl) ethyl) acetoacetamide (2.34 g, 6.41 mmol, 1.00 equiv), 3-aminocrotonamide (0.706 g, 7.05 mmol, 1.10 equiv) and 4-nitrobenzaldehyde (1.07 g, 7.05 mmol, 1.10 equiv) were stirred together in 2-propanol (40 mL) at reflux for 72 hours under argon. After removal of the solvent, the residue was purified twice by flash chromatography on $SiO_2$ (1. MeOH—EtOAc 0:1 to 1:5; 2. $CH_2Cl_2$—$NH_3$ in MeOH (1.3M) 12:1) to afford 1.19 g (32%) of yellow solid, which was characterized spectroscopically. This product (1.05 g, 1.81 mmol, 1.0 equiv) was dissolved in $CH_2Cl_2$ (10 mL) and a solution of HCl in ether (1.0M, 2.5 mL, 1.4 equiv) was added. After removal of the solvents, the residue was dissolved in $CH_2Cl_2$ (10 mL) and added dropwise to ether (80 mL) with swirling to give, after filtration, 0.857 g of yellow solid: m.p. 193–194° C.; Anal. Calcd. for $C_{34}H_{37}N_5O_4 \cdot HCl \cdot H_2O$: C, 64.39; H, 6.36; N, 11.04. Found: C, 64.33; H, 5.98; N, 10.93.

EXAMPLE 55

5-Carboxamido-1,4-dihydro-2,6-dimethyl-4-(4-nitrophenyl)-3-{N- [4-(4,4-diphenylpiperidin-1-yl) butyl]}carboxamidopyridine hydrochloride hydrate (55). This compound was prepared according to Method A. N-(4-(4,4-Diphenylpiperidin-1-yl)butyl) acetoacetamide (2.86 g, 7.30 mmol, 1.00 equiv), 3-aminocrotonamide (0.804 g, 8.03 mmol, 1.10 equiv) and 4-nitrobenzaldehyde (1.21 g, 8.03 mmol, 1.10 equiv) were stirred together in 2-propanol (50 mL) at ref lux for 72 hours under argon. After removal of the solvent, the residue was purified twice by flash chromatography on $SiO_2$ (1. MeOH—EtOAc 1:4; 2. $CHCl_3$—$NH_3$ in MeOH (0.55M) 85:15) to afford 0.460 g (10%) of yellow solid, which was characterized spectroscopically. This product was dissolved in $CH_2Cl_2$ (5 mL) and a solution of HCl in ether (1.0M, 1.0 mL, 1.4 equiv) was added. After removal of the solvents, the residue was dissolved in $CH_2Cl_2$ (10 mL) and added dropwise to ether (80 mL) with swirling to give, after filtration, 0.260 g of yellow solid: m.p. 184–185° C.; Anal. Calcd. for $C_{36}H_{41}N_5O_4 \cdot HCl \cdot H_2O$: C, 65.29; H, 6.70; N, 10.58. Found: C, 65.45; H, 6.40; N, 10.55.

EXAMPLE 56

1,4-Dihydro-2,6-dimethyl-5-(N-methyl)carboxamido-4-(4-nitrophenyl)-3-{N-[3-(4-phenylpiperidin-1-yl)propyl]}carboxamidopyridine hydrochloride hemihydrate (56). This compound was prepared according to Method A. N-(3-(4-Phenylpiperidin-1-yl)propyl)acetoacetamide (1.60 g, 5.30 mmol, 1.00 equiv), N-methyl-3-aminocrotonamide (690 mg, 6.10 mmol, 1.15 equiv) and 4-nitrobenzaldehyde (920 mg, 6.10 mmol, 1.15 equiv) were stirred together in 2-propanol (50 mL) at reflux for 78 hours under argon. After removal of the solvent, the residue was purified twice by flash chromatography on $SiO_2$ (1. MeOH—EtOAc 1:5; 2. $CHCl_3$—$NH_3$ in MeOH (0.67M) 100:15). After removal of solvents, the product was dissolved in $CH_2Cl_2$ (3 mL) and added dropwise into ether (25 mL). The resulting precipitate was filtered and washed with ether (2×20 mL) to give 242 mg (8.6%) of yellow solid, which was characterized spectroscopically. This product (205 mg, 0.386 mmol, 1.0 equiv) was dissolved in $CH_2Cl_2$ (3 mL) and a solution of HCl in ether (1.0M, 0.70 mL, 1.8 equiv) was added. After removal of the solvents, the residue was dissolved in $CH_2Cl_2$ (3 mL) and added dropwise to ether (30 mL) with swirling to give, after filtration, 189 mg of yellow solid: m.p. 165–166° C.; Anal. Calcd. for $C_{30}H_{37}N_5O_4 \cdot HCl \cdot 0.5 H_2O$: C, 62.44; H, 6.81; N, 12.14. Found: C, 62.38; H, 6.72; N, 11.86.

EXAMPLE 57

2-(2-Cyanoethyl)-1,2,3,4-tetrahydro-6,7-dimethoxyisoquinoline. A suspension of 6,7-dimethoxy-1,2, 3,4-tetrahydroisoquinoline (9.20 g, 40.1 mmol, 1.00 equiv, Aldrich), 3-bromopropionitrile (3.66 mL, 44.1 mmol, 1.10 equiv, Aldrich), potassium carbonate (33.25 g, 240.6 mmol, 6.00 equiv), and potassium iodide (266 mg, 1.60 mmol, 0.04 equiv) in n-butanol (70 mL) and 1,4-dioxane (70 mL) was stirred at reflux under argon for 48 hours. The mixture was cooled to room temperature and concentrated. The residue was purified by flash chromatography ($SiO_2$, MeOH—EtOAc 0:1 to 1:19) to afford 8.39 g of white solid (59%), which was characterized spectroscopically.

2-(3-Aminopropyl)-1,2,3,4-tetrahydro-6,7-dimethoxyisoquinoline. To a stirred solution of 2-(2-cyanoethyl)-1,2,3,4-tetrahydro-6,7-dimethoxyisoquinoline (5.70 g, 23.1 mmol, 1.0 equiv) in anhydrous THF (20 mL) under argon was added a solution of $BH_3$ in THF (1.0M, 81 mL, 81 mmol, 3.5 equiv) at room temperature. The mixture was stirred at reflux for 4.5 hours and then cooled to room temperature. Aqueous HCl (6N, 130 mL) was added cautiously at room temperature and stirring was continued for 2.5 hours at 55–60° C. The mixture was cooled to 0° C., basified to pH 10–11 by addition of 6N aq. NaOH, and extracted with $CH_2Cl_2$ (3×100 mL). The combined organic solutions were dried over $MgSO_4$ and concentrated. To a solution of the residue in $CH_2Cl_2$ (20 mL) was added HCl in ether (1.0M, 40 mL, 1.7 equiv). The resulting solution was added dropwise into ether (250 mL) with swirling. The precipitate was filtered and washed with ether (3×100 mL). This solid was taken up in water (50 mL), which was basified to pH 10 by addition of 1M aqueous NaOH, and extracted with $CH_2Cl_2$ (3×100 mL). The combined organic solutions were dried over $MgSO_4$ and concentrated to give 5.10 g (88%) of white solid, which was characterized spectroscopically.

N-[3-(1,2,3,4-tetrahydro-6,7-dimethoxyisoquinolin-2-yl)propyl]acetoacetamide. Diketene (1.41 mL, 18.3 mmol, 1.50 equiv) was added at 0° C. to a stirred solution of 2-(3-aminopropyl)-1,2,3,4-tetrahydro-6,7-dimethoxyisoquinoline (3.05 g, 12.2 mmol, 1.00 equiv) in anhydrous THF (30 mL) under argon, and stirring was continued at room temperature for 1.5 hours. The mixture was concentrated and the residual oil washed with hexane (2×100 mL) to give 4.07 g (100%) of brown oil, which was characterized spectroscopically and used for the next reaction without purification.

1,4-Dihydro-3-methoxycarbonyl-5-{N-[3-(1,2,3,4-tetrahydro-6,7-dimethoxyisoquinolin-2-yl)propyl]}carboxamido-2,6-dimethyl-4-(4-nitrophenyl)pyridine hydrochloride hydrate (57). This compound was prepared according to Method A. N-[3-(1,2,3,4-tetrahydro-6,7-Dimethoxyisoquinolin-2-yl)propyl]acetamide (2.04 g, 6.09 mmol, 1.00 equiv), methyl 3-aminocrotonate (855 mg, 7.20 mmol, 1.20 equiv) and 4-nitrobenzaldehyde (1.09 g, 7.20 mmol, 1.20 equiv) were stirred together in 2-propanol (50 mL) at reflux for 72 hours under argon.

After removal of the solvent, the residue was purified by flash chromatography ($SiO_2$, MeOH—EtOAc 1:6) to afford 510 mg (15%) of yellow solid, which was characterized spectroscopically. This product was dissolved in $CH_2Cl_2$ (10 mL) and a solution of HCl in ether (1.0M, 1.0 mL, 1.1 equiv) was added. After removal of the solvents, the residue was dissolved in $CH_2Cl_2$ (5 mL) and added dropwise to ether (30 mL) with swirling to give, after filtration, 451 mg of yellow solid: m.p. 161–162° C.; Anal. Calcd. for $C_{30}H_{36}N_4O_7 \cdot HCl \cdot 0.75\ H_2O$: C, 58.63; H, 6.31; N, 9.12. Found: C, 58.79; H, 6.20; N, 8.83.

EXAMPLE 58

5-Carboxamido-1,4-dihydro-3-{N-[3-(1,2,3,4-tetrahydro-6,7-dimethoxyisoquinolin-2-yl)propyl]}carboxamido-2,6-dimethyl-4-(4-nitrophenyl)pyridine hydrochloride (58). This compound was prepared according to Method A. N-[3-(1,2,3,4-Tetrahydro-6,7-dimethoxyisoquinolin-2-yl)propyl]acetoacetamide (2.04 g, 6.09 mmol, 1.00 equiv), 3-aminocrotonamide (721 mg, 7.20 mmol, 1.20 equiv) and 4-nitrobenzaldehyde (1.09 g, 7.20 mmol, 1.20 equiv) were stirred together in 2-propanol (50 mL) at reflux for 72 hours under argon. After removal of the solvent, the residue was purified twice by flash chromatography on $SiO_2$ (1. $CHCl_3$—$NH_3$ in MeOH (0.8M) 9:1; 2. MeOH—EtOAc 1:6) to afford 400 mg (12%) of yellow solid, which was characterized spectroscopically. This product was dissolved in $CH_2Cl_2$ (10 mL) and a solution of HCl in ether (1.0M, 1.0 mL, 1.4 equiv) was added. After removal of the solvents, the residue was dissolved in $CH_2Cl_2$ (5 mL) and added dropwise to ether (30 mL) with swirling to give, after filtration, 310 mg of yellow solid: m.p. 180–181° C.; Anal. Calcd. for $C_{29}H_{35}N_5O_6 \cdot HCl \cdot 0.3\ CH_2Cl_2$: C, 57.54; H, 6.03; N, 11.45. Found: C, 57.27; H, 5.78; N, 11.25.

EXAMPLE 59

N-(3-Bromopropyl)acetoacetamide. Diketene (1.22 mL, 15.7 mmol, 1.50 equiv) was added at room temperature to a stirred mixture of 3-bromopropylamine hydrobromide (2.30 g, 10.5 mmol, 1.00 equiv) and triethylamine (1.46 mL, 10.5 mmol, 1.00 equiv) in anhydrous THF (20 mL) under argon, and stirring was continued at room temperature for 1 hour. The solvent was removed and the residue was purified by flash chromatography ($SiO_2$, MeOH—$CH_2Cl_2$ 0:1 to 1:18) to afford a light yellow oil, 2.10 g (90%), which was characterized spectroscopically.

N-[3-(1,2,3,4-Tetrahydroisoquinolin-2-yl)propyl]acetoacetamide. A suspension of N-(3-bromopropyl)acetoacetamide (4.50 g, 20.3 mmol, 1.00 equiv), 1,2,3,4-tetrahydroisoquinoline (3.30 mL, 26.3 mmol, 1.30 equiv), $K_2CO_3$ (3.64 g, 26.3 mmol, 1.30 equiv), and KI (330 mg, 1.99 mmol, 0.10 equiv) in acetone (60 mL) was stirred at reflux for 14 hours. The mixture was cooled to room temperature, filtered, and concentrated. The residue was purified by flash chromatography ($SiO_2$, MeOH—EtOAc 0:1 to 1:9) to give 1.78 g (43%) of light yellow oil, which was characterized spectroscopically. N-(3-Bromopropyl)acetoacetamide (1.20 g) was also recovered.

1,4-Dihydro-5-{N-[3-(1,2,3,4-tetrahydroisoquinoline-2-yl)propyl]}carboxamido-3-methoxycarbonyl-2,6-dimethyl-4-(4-nitrophenyl)pyridine hydrochloride hydrate (59). This compound was prepared according to Method A. N-[3-(1,2,3,4-Tetrahydroisoquinolin-2-yl)propyl]acetoacetamide (1.78 g, 6.48 mmol, 1.00 equiv), methyl 3-aminocrotonate (924 mg, 7.77 mmol, 1.20 equiv) and 4-nitrobenzaldehyde (1.18 g, 7.77 mmol, 1.20 equiv) were stirred together in 2-propanol (50 mL) at reflux for 68 hours under argon. After removal of the solvent, the residue was purified by flash chromatography ($SiO_2$, MeOH—EtOAc 1:9) to afford 824 mg (25%) of yellow solid, which was characterized spectroscopically. This product was dissolved in $CH_2Cl_2$ (10 mL) and a solution of HCl in ether (1.0M, 2.3 mL, 1.4 equiv) was added. After removal of the solvents, the residue was dissolved in $CH_2Cl_2$ (5 mL) and added dropwise to ether (30 mL) with swirling to give, after filtration, 690 mg of yellow solid: m.p. 145–146° C.; Anal. Calcd. for $C_{28}H_{32}N_4O_5 \cdot HCl \cdot 0.25\ H_2O$: C, 61.65; H, 6.19; N, 10.27. Found: C, 61.82; H, 6.15; N, 10.15.

EXAMPLE 60

5-Carboxamido-1,4-dihydro-2,6-dimethyl-4-(4-nitrophenyl)-3-{N-[3-(4-phenylpiperidin-1-yl) propyl]

}carboxamidopyridine (60). This compound was prepared according to Method B. The suspension of 5-carboxamido-1,4-dihydro-2,6-dimethyl-2,6-dimethyl-4-(4-nitrophenyl)pyridine-3-carboxylic acid (90 mg, 0.28 mmol) and 1-(3-dimethylaminopropyl)-3-ethylcarbodiimide hydrochloride (59 mg, 0.31 mmol) in 15 mL of $CH_2Cl_2$ was stirred at 0° C. for 20 min. To this suspension was added the solution of 3-(4-phenylpiperidin-1-yl)propylamine (68 mg, 0.473 mmol) in 2 mL of $CH_2Cl_2$. The mixture was stirred at r.t. for 3 days. The mixture was washed with water (2×10 mL) followed by saturated brine (10 mL). After drying with $Na_2SO_4$ and removal of solvent, a yellowish oil was obtained, which was charged to $SiO_2$ prep-TLC and eluted with $CHCl_3$/MeOH/N; (2N in MeOH) mixture (ratio=90:8:4). The desired product was collected and precipitated from $CH_2Cl_2/Et_2O$ to afford 27 mg (18% yield) of yellowish powder: M.p. 100–105° C.; Calcd for $C_{29}H_{35}N_5O_5 \cdot \frac{3}{4}H_2O$: C 65.58, H. 6.93, N 13.19; Found: C 65.94, H 6.53, N 12.81.

EXAMPLE 61

5-Carboxamido-1,4-dihydro-2,6-dimethyl-4-(3-nitrophenyl)-3-{N-[3-(4,4-diphenylpiperidin-1-yl)propyl]}carboxamidopyridine (61). This compound was prepared according to Method B. 5-Carboxamido-3-(2-cyanoethoxy)carbonyl-1,4-dihydro-2,6-dimethyl-4-(3-nitrophenyl)pyridine was prepared by refluxing the solution of 3-aminocrotonamide (3.696 g, 36.9 mmol), 3-nitrobenzaldehyde (5.576 g, 36.9 mmol) and 2-cyanoethyl acetoacetate (2.864 g, 18.5 mmol) in 100 mL of EtOH for 48 hrs. After work up, the reaction mixture was purified by chromatography ($SiO_2$, MeOH:$CHCl_3$, 10:90) to give a yellow oil (4.762 g, 69.5% yield). The cyanoethyl ester (2.90 g, 7.83 mmol) thus prepared was hydrolyzed by 2N KOH and 5-carboxamido-1,4-dihydro-2,6-dimethyl-4-(3-nitrophenyl)pyridine-3-carboxylic acid (1.632 g, 65.7% yield) was obtained as a bright yellow powder.

A suspension of 5-carboxamido-1,4-dihydro-2,6-dimethyl-4-(3-nitrophenyl)pyridine-3-carboxylic acid (136 mg, 0.429 mmol), 1-(3-dimethylaminopropyl)-3-ethylcarbodiimide hydrochloride (82 mg, 0.429 mmol) and 3-(4,4-diphenylpiperidin-1-yl)propylamine (126 mg, 0.429 mmol) in 15 mL of $CH_2Cl_2$ was stirred at refluxing conditions overnight. The mixture was washed with water (2×10 mL) and brine (10 mL). After drying with $Na_2SO_4$ and removal of solvent, a yellowish oil was obtained, which was charged to $SiO_2$ prep-TLC and eluted with $CHCl_3$/MeOH/$NH_3$(2N in MeOH) mixture (ratio=90:8:4). The desired product was collected and precipitated from $CH_2Cl_2/Et_2O$ to afford 59, mg (23% yield) of yellowish powder: M.p. 144–148° C.; Calcd for $C_{35}H_{39}N_5O_4 \cdot \frac{3}{4}H_2O$: C 69.23, H 6.72, N 11.52; Found: C 69.16, H 6.25, N 11.32.

EXAMPLE 62

5-Carboxamido-1,4-dihydro-2,6-dimethyl-4-(3-nitrophenyl)-3-{N-[3-(4-phenylpiperidin-1-yl)propyl]}carboxamidopyridine (62). This compound was prepared according to Method B. The suspension of 5-carboxamido-1,4-dihydro-2,6-dimethyl-4-(3-nitrophenyl)pyridine-3-carboxylic acid (136 mg, 0.429 mmol), 1-(3-dimethylaminopropyl)-3-ethylcarbodiimide hydrochloride (82 mg, 0.429 mmol) and 3-(4-phenylpiperidin-1-yl)propylamine (94 mg, 0.429 mmol) in 15 mL of $CH_2Cl_2$ was stirred at refluxing conditions overnight. The mixture was washed with water (2×10 mL) and brine (10 mL). After drying with $Na_2SO_4$ and removal of solvent, a yellowish oil was obtained, which was charged to $SiO_2$ prep-TLC and eluted with $CHCl_3$/MeOH/$NH_3$(2N in MeOH) mixture (ratio=90:8:4). The desired product was collected and precipitated from $CH_2Cl_2/Et_2O$ to afford 75 mg (33% yield) of yellowish powder: M.p. 92–96° C.; Calcd for $C_{29}H_{35}N_5O_4 \cdot \frac{3}{4}H_2O$: C 65.58, H 6.93, N 13.19; Found: C 65.96, H 6.54, N 13.04.

EXAMPLE 63

1,4-Dihydro-6-methyl-4-(4-nitrophenyl)-5-{N-[3-(4-phenylpiperidin-1-yl) propyl]}carboxamido-[2,3,d]uracilylpyridine (63). This compound was prepared according to Method B. 5-(2-cyanoethoxy)carbonyl-1,4-dihydro-6-methyl-4-(4-nitrophenyl)-[2,3,d]uracilylpyridine was prepared by refluxing the solution of 4-amino-2,6-dihydroxypyrimidine (820 mg, 6.40 mmol), 4-nitrobenzaldehyde (973 mg, 6.40 mmol) and 2-cyanoethyl acetoacetate (1.00 g, 6.40 mmol) in 100 mL of 2-propanol for 72 hrs. The product, a white precipitate, was collected by filtration, washed with 10 mL of cold 2-propanol, 10 mL of cold MeOH, then dried in vacuo to give 1.19 g (46.8% yield) of white powder. The cyanoethyl ester (500 mg, 1.26 mmol) thus prepared was hydrolyzed by 2N KOH and 1,4-dihydro-6-methyl-4-(4-nitrophenyl)-(2,3,d]uracilylpyridine-5-carboxylic acid (255 mg, 58.8% yield) was obtained as a yellowish powder.

A suspension of 1,4-dihydro-6-methyl-4-(4-nitrophenyl)-[2,3,d]uracilylpyridine-5-carboxylic acid (100 mg, 0.30 mmol), 1-(3-dimethylaminopropyl)-3-ethylcarbodiimide hydrochloride (58 mg, 0.30 mmol) and 3-(4-phenylpiperidin-1-yl)propylamine (66 mg, 0.30 mmol) in 40 mL of $CH_2Cl_2$ was stirred at r.t. for 48 hrs. The mixture was washed with water (2×10 mL), followed by washed with 10% $NaHCO_3$(10 mL). After drying with $MgSO_4$ and removal of solvent, a yellowish oil was obtained, which was purified by chromatography ($SiO_2$, MeOH:$CHCl_3$, 10:90). The product was precipitated from $CH_2Cl_2/Et_2O$ to afford 21 mg (13% yield) of yellowish powder: M.p. 202–205° C.; Calcd for $C_{29}H_{32}N_6O_5$:C 63.95, H 5.92, N 15.43; Found: C 63.71, H 5.71, N 15.30.

EXAMPLE 64

1,4-Dihydro-6-methyl-4-(4-nitrophenyl)-5-{N-[3-(4,4-diphenylpiperidin-1-yl) propyl]}carboxamido-[2,3,d]uracilylpyridine (64). This compound was prepared according to Method B. The suspension of 1,4-dihydro-6-methyl-4-(4-nitrophenyl)-[2,3,d]uracilylpyridine-5-carboxylic acid (100 mg, 0.30 mmol), 1-(3-dimethylaminopropyl)-3-ethylcarbodiimide hydrochloride (58 mg, 0.30 mmol) and 3-(4,4-diphenylpiperidin-1-yl)propylamine (86 mg, 0.30 mmol) in 50 mL of $CH_2Cl_2$ was stirred at r.t. for 48 hrs. The mixture was washed with water (2×10 mL)and 10% $NaHCO_3$ (10 mL). After drying with $MgSO_4$ and removal of solvent, a yellowish oil was obtained, which was purified by chromatography ($SiO_2$, MeOH:$CHCl_3$, 10:90). The product was precipitated from $CH_2Cl_2/Et_2O$ to afford 25 mg (13% yield) of yellowish powder: M.p. 184–186° C.; Calcd for $C_{35}H_{36}N_6O_5 \cdot CO_2$: C 65.05, H 5.46, N 12.64; Found: C 65.43, H 5.69, N 12.21.

EXAMPLE 65

2-(Furan-3-yl)-1,4-dihydro-5-methoxycarbonyl-6-methyl-4-(4-nitrophenyl)-5-{N-[3-(4-phenylpiperidin-1-yl)propyl]}carboxamidopyridine hydrochloride hydrate (64). This compound was prepared according Method B from 86.8 mg of 2-(furan-3-yl)-1,4-dihydro-3-(imidazol-1-yl)carbonyl-5-methoxycarbonyl-6-methyl-4-(4-nitro)

phenylpyridine (0.200 mmol) and 65.5 mg of 1-(3-aminopropyl)-4-phenylpiperidine (0.300 mmol) in 3 mL of dry THF. The crude product was chromatographed on 100 g of silica (gradient elution: 5% to 20% MeOH—EtOAc) to give 110 mg of 2-(furan-3-yl)-1,4-dihydro-5-methoxycarbonyl-6-methyl-4-(4-nitrophenyl)-5-{N-(3-(4-phenylpiperidin-1-yl)propyl]}carboxamidopyridine as a yellow foamy solid (94%). The free base (98 mg) was dissolved in 0.5 mL of dichloromethane and added to 1 mL of 1M HCl in ether. The precipitate was collected, washed with 5 mL of ether, and dried to give a yellow powder: mp 205–210° C. (decomp.); Anal. Calcd for $C_{33}H_{36}N_4O_6 \cdot HCl \cdot 1.2\ H_2O$: C, 61.67; H, 6.18; N, 8.72. Found: C, 61.53; H, 5.71; N, 9.01.

EXAMPLE 66

5-Carboxamido-2-(furan-3-yl)-1,4-dihydro-6-methyl-4-(4-nitro)phenyl-3-{N- [N-phenylmethyl) piperidin-4-yl)}carboxamidopyridine hydrochloride hydrate (66). This compound was prepared according to Method B from 50.0 mg of 5-carboxamido-2-(furan-3-yl)-1,4-dihydro-3-(imidazol-1-yl)carbonyl-6-methyl-4-(4-nitro)phenylpyridine (0.115 mmol) and 32.9 mg of N-benzyl-4-aminopiperidine (0.173 mmol) in 3 mL of dry THF. The crude product was chromatographed on 100 g of silica (EtOAc) to give 56 mg of the free base (87%) as a yellow foamy solid. The free base (45 mg) was dissolved in 2 mL of dichloromethane and added to 3 mL of 0.33M HCl in ether. The precipitate was collected, washed with 5 mL of ether, and dried to give a yellow powder: mp 210–215° C. (decomp.); Anal. Calcd for $C_{31}H_{32}N_4O_6 \cdot HCl \cdot H_2O$: C, 60.93; H, 5.77; N, 9.17. Found: C, 60.93; HI 5.35; N, 9.07.

EXAMPLE 67

5-Carboxamido-2-(furan-3-yl)-1,4-dihydro-6-methyl-3-{N-[3-(6,7-dimethoxy-1,2,3,4-tetrahydroisoquinolin-2-yl)propyl)[}carboxamido-4-(4-nitro)phenylpyridine hydrochloride hydrate (67). This compound was prepared according to Method B from 51.1 mg of 5-carboxamido-2-(furan-3-yl)-1,4-dihydro-3-(imidazol-1-yl) carbonyl-6-methyl-4-(4-nitro)phenylpyridine (0.118 mmol) and 38.3 mg of 2-(3-aminopropyl)-1,2,3,4-tetrahydro-6,7-dimethoxyisoquinoline (0.153 mmol) in 3 mL of dry THF. The crude product was chromatographed on 100 g of silica (gradient elution: 5% to 15% MeOH—EtOAc) to give the free base as a yellow foamy solid (71%). The free base (50 mg) was dissolved in 2 mL of dichloromethane and added to 3 mL of 0.33M HCl in ether. The precipitate was collected, washed with 5 mL of ether, and dried to give a yellow powder: mp 211–221° C. (decomp.); Anal. Calcd for $C_{33}H_{36}N_4O_8 \cdot HCl \cdot 0.5H_2O$: C, 59.86; H, 5.78; N, 8.46. Found: C, 59.96; H, 5.57; N, 8.45.

EXAMPLE 68

2-Cyanoethyl 3-Oxohaeanoate. A mixture of ethyl 3-oxohexanoate (33.7 mmol) and 3-hydroxypropionitrile (28.1 mmol) were placed in a round bottom flask (magnetically stirred) equipped with a short distillation path. The resulting mixture was gradually heated to 180–205° C. in an oil bath. The distillate was collected. The mixture was then cooled to room temperature and the residue was distilled under reduced pressure to give 2-cyanoethyl 3-oxohexanoate.

1,4-Dihydro-5-methoxycarbonyl-6-methyl-4-(4-nitrophenyl)-2-propylpyridine-3-carboxylic Acid. A mixture of 2-cyanoethyl 3-oxohexanoate (11.9 mmol), methyl 3-aminocrotonate (11.9 mmol), and 4-nitrobenzaldehyde in 25 mL of isopropanol were heated at reflux temperature for 16 h, cooled, and the solvent was removed under reduced pressure. The residue was dissolved in 15 mL of dioxane (slightly warmed with a heat gun to dissolve the product) and 626 mg of NaOH in 15 mL of water was added to the reaction mixture. After 0.5 hrs, the maroon solution was concentrated to a small volume under reduced pressure, partitioned between 50 mL of water and 50 mL of ethyl acetate, separated, and the aqueous solution was washed with 2×20 mL of ethyl acetate. The aqueous extract was acidified with concentrated HCl (pH=2), and the precipitated oil was extracted with ethyl acetate (2×40 mL). The combined organic extracts were dried ($MgSO_4$), and the solvent was removed in vacuo to give the desired product as a foamy yellow solid. The acid was used in the next step without further purification.

3-(Imidazol-1-yl)carbonyl-5-methyoxycarbonyl-6-methyl-4-(4-nitro)phenyl-2-propylpyridine. A solution of 1,4-dihydro-5-methoxycarbonyl-6-methyl-4-(4-nitro)phenyl-2-propylpyridine-3-carboxylic acid (2.89 mmol) and carbonyldiimidazole (3.75 mmol) in 20 mL of anhydrous THF are stirred at room temperature for 12 hours; solvent was removed in vacuo, and the crude product was chromatographed on silica. The column was eluted with MeOH—EtOc to give the title compound as a yellow oily solid.

1,4-Dihydro-5-methoxycarbonyl-6-methyl-4- C4-nitro) phenyl-3-(N-(3-(4,4-diphenylpiperidin-1-yl)propyl) carboxamido)-2-propylpyridine (68). A solution of 3-(imidazol-1-yl)carbonyl-5-methyoxycarbonyl-6-methyl-4-(4-nitro)phenyl-2-propylpyridine (0.456 mmol) and 1-(3-aminopropyl)-4,4-diphenylpiperidine (1.06 mmol) in 5 mL of dry THF are heated at reflux temperature for 19 hrs, cooled to room temperature. The solvent was removed in vacuo and the crude product is chromatographed on 50 g of silica packed with 5% MeOH—EtOAc. The column was eluted with MeOH—EtOAc to afford the title compound as a yellow foamy solid. To this product was added HCl in ether (1M) in a minimum amount of ethyl acetate. The precipitate was collected, washed with ether (2×5 mL), and dried to give the hydrochloride salt as a yellow powder, which was characterized spectroscopically. The fumarate salt was prepared by mixing fumaric acid (8.7 mg, 0.0749 mmol) and the free base (0.0749 mmol) in 2 mL of 1:1 acetone-water. The product was purified by recrystallization.

EXAMPLE 69

2,2-Dimethyl-5-(1-oxoheptyl)-1,3-dioxane-4,6-dione. Carbonyldiimidazole (71.7 g, 0.442 mol) was added portionwise to a stirred solution of heptanoic acid (0.402 mol) in 300 mL of dry dichloromethane. The resulting mixture was stirred at room temperature for 2 hours. A solution of pyridine (35.8 mL, 0.442 mol) and Meldrum's acid (63.7 g, 0.442 mol) in 150 mL of dry dichloromethane were added over a period of 2 hours to the reaction mixture. The reaction mixture was stirred for 16 hours, quenched with 400 mL of 2N HCl (bubbling), separated, washed sequentially with 2×400 mL 2N HCl, brine (400 mL), dried ($MgSO_4$), and the solvent was removed in vacuo to give the title compound as aviscous oil. The crude product was used in the next step after spectral characterization.

2-Cyanoethyl 3-Oxonanoate: A mixture of 2,2-dimethyl-5-(1-oxoheptyl)-1,3-dioxane-4,6-dione (29.4 mmol) and 3-hydroxypropionitrile (4.48 g, 63.0 mmol) in 25 mL of dry toluene were heated at reflux temperature for 1 hour. The solvent was removed in vacuo, and the residue was chromatographed on silica gel to give the title compound as a viscous oil, which was used in the next step after spectral characterization.

2-Hexyl-1,4-dihydro-5-methoxycarbonyl-6-methyl-4-(4-nitro)phenylpyridine-3-carboxylic acid. A mixture of 2-cyanoethyl 3-oxooctanoate (11.9 mmol), methyl 3-aminocrotonate (11.9 mmol), and 4-nitrobenzaldehyde in 25 mL of isopropanol are heated at reflux temperature for 16 h, cooled, and the solvent is removed under reduced pressure. The residue is dissolved in 15 mL of dioxane and 626 mg of NaOH in 15 mL of water is added to the reaction mixture. After 0.5 hr, the solution is concentrated to a small volume under reduced pressure, partitioned between 50 mL of water and 50 mL of ethyl acetate, separated, and the aqueous solution is washed with 2×20 mL of ethyl acetate. The organic solutions are discarded. The aqueous extract is acidified with concentrated HCl (pH=2), and the precipitated oil is extracted with ethyl acetate (2×40 mL). The combined organic extracts are dried (MgSO$_4$), and the solvent is removed in vacuo to give a residue, which is characterized spectroscopically.

2-Hexyl-1,4-dihydro-3-(imidazol-1-yl)carbonyl-5-methoxycarbonyl-6-methyl-4-(4-nitro)phenylpyridine. A solution of 2-hexyl-1,4-dihydro-5-methoxycarbonyl-6-methyl-4-(4-nitro)phenylpyridine-3-carboxylic acid (2.89 mmol) and carbonyldiimidazole (3.75 mmol) in 20 mL of anhydrous THF is stirred at room temperature for 12 hrs. The solvent is removed in vacuo, and the crude product is chromatographed on silica and characterized spectroscopically.

2-Hexyl-1,4-dihydro-5-methoxycarbonyl-6-methyl-4-(4-nitro)phenyl-3-(N-(4,4-diphenylpiperidin-1-yl)propyl))carboxamidopyridine (69). This compound is prepared according to Method B. A solution of 2-hexyl-1,4-dihydro-3-(imidazol-1-yl)carbonyl-5-methoxycarbonyl-6-methyl-4-(4-nitro)phenylpyridine (0.456 mmol) and 1-(3-aminopropyl)-4,4-diphenylpiperidine (1.06 mmol) in 5 mL of dry THF are heated at reflux temperature for 19 hrs and then cooled to room temperature. The solvent is removed in vacuo. The crude product is purified by flash chromatography and characterized spectroscopically. The hydrochloride salt is prepared by addition of HCl in ether (1M) to the free base in a minimum amount of ethyl acetate. The precipitate is collected, washed with ether (2×5 mL), dried, and purified by recrystallization. The fumarate salt is prepared by mixing fumaric acid (8.7 mg, 0.0749 mmol) and the free base (0.0749 mmol) in 2 mL of 1:1 acetone-water. The product is purified by recrystallization.

EXAMPLE 70

1,4-Dihydro-4-(4-methyloxyphenyl)-5-methoxycarbonyl-6-methyl-2-propylpyridine-3-carboxylic acid. A mixture of 2-cyanoethyl 3-oxohexanoate (11.9 mmol), methyl 3-aminocrotonate (11.9 mmol), and 4-methoxybenzaldehyde in 25 mL of isopropanol is heated at reflux temperature for 16 h, cooled, and the solvent is removed under reduced pressure. The residue is dissolved in 15 mL of dioxane and 626 mg of NaOH in 15 mL of water is added to the reaction mixture. After 0.5 hrs, the solution is concentrated to a small volume under reduced pressure, partitioned between 50 mL of water and 50 mL of ethyl acetate, separated, and the aqueous solution is washed with 2×20 mL of ethyl acetate. The organic solutions are discarded. The aqueous extract is acidified with concentrated HCl (pH=2), and the precipitated oil is extracted with ethyl acetate (2×40 mL). The combined organic extracts are dried (MgSO$_4$), and the solvent is removed in vacuo to give a residue, which is characterized spectroscopically.

2-Hexyl-1,4-dihydro-3-(imidazol-1-yl)carbonyl-5-methoxycarbonyl-4-(4-methoxy)phenyl-6-methylpyridine. A solution of 1,4-dihydro-4-(4-methyloxyphenyl)-5-methoxycarbonyl-6-methyl-2-propylpyridine-3-carboxylic acid (2.89 mmol) and carbonyldiimidazole (3.75 mmol) in 20 mL of anhydrous THF are stirred at room temperature for 12 hrs. The solvent is removed in vacuo. The product is purified by flash chromatography and characterized spectroscopically.

1,4-Dihydro-5-methoxycarbonyl-6-methyl-4-(4-methoxy)phenyl-3-(N-(4,4-diphenylpiperidin-1-yl)propyl))carboxamido-2-propylpyridine (70). This compound is prepared according to Method B. A solution of 1,4-dihydro-3-(imidazol-1-yl)carbonyl-5-methoxycarbonyl-4-(4-methoxy)phenyl-6-methyl-2-propylpyridine (0.456 mmol) and 1-(3-aminopropyl)-4,4-diphenylpiperidine (1.06 mmol) in 5 mL of dry THF is heated at ref lux temperature for 19 hrs. The solvent is removed in vacuo. The crude product is purified by flash chromatography and characterized spectroscopically. The hydrochloride salt is prepared by addition of HCl in ether (1M) to the free base in a minimum amount of ethyl acetate. The precipitate is collected, washed with ether (2×5 mL), dried, and purified by recrystallization. The fumarate salt is prepared by mixing fumaric acid (8.7 mg, 0.0749 mmol) and the free base (0.0749 mmol) in 2 mL of 1:1 acetone-water. The product is purified by recrystallization.

EXAMPLE 71

4-(4-Chlorophenyl)-1,4-dihydro-5-methoxycarbonyl-6-methyl-2-propylpyridine-3-carboxylic acid. A mixture of 2-cyanoethyl 3-oxohexanoate (11.9 mmol), methyl 3-aminocrotonate (11.9 mmol), and 4-chlorobenzaldehyde in 25 mL of isopropanol is heated at reflux temperature for 16 h, cooled, and the solvent is removed under reduced pressure. The residue is dissolved in 15 mL of dioxane and 626 mg of NaOH in 15 mL of water is added to the reaction mixture. After 0.5 hrs, the solution is concentrated to a small volume under reduced pressure, partitioned between 50 mL of water and 50 mL of ethyl acetate, separated, and the aqueous solution is washed with 2×20 mL of ethyl acetate. The organic solutions are discarded. The aqueous extract is acidified with concentrated HCl (pH=2), and the precipitated oil is extracted with ethyl acetate (2×40 mL). The combined organic extracts are dried (MgSO$_4$), and the solvent is removed in vacuo to give a residue, which is characterized spectroscopically.

4-(4-Chlorophenyl)-1,4-dihydro-3-(imidazol-1-yl)carbonyl-5-methoxycarbonyl-6-methyl-2-propylpyridine. A solution of 4-(4-chlorophenyl)-1,4-dihydro-5-methoxycarbonyl-6-methyl- 2-propylpyridine-3-carboxylic acid (2.89 mmol) and carbonyldiimidazole (3.75 mmol) in 20 mL of anhydrous THF is stirred at room temperature for 12 hrs. The solvent is removed in vacuo. The product is purified by flash chromatography and characterized spectroscopically. 4-(4-Chlorophenyl)-1,4-dihydro-5-methoxycarbonyl-6-methyl-3-(N-(4,4-diphenylpiperidin-1-yl)propyl))carboxamido-2-propylpyridine (71). This compound is prepared according to Method B. A solution of 4-(4-chlorophenyl)-1,4-dihydro-3-(imidazol-1-yl)carbonyl-5-methoxycarbonyl-6-methyl-2-propylpyridine (0.456 mmol) and 1-(3-aminopropyl)-4,4-diphenylpiperidine (1.06 mmol) in 5 mL of dry THF is heated at reflux temperature for 19 hrs. The solvent is removed in vacuo. The crude product is purified by flash chromatography and characterized spectroscopically. The hydrochloride salt is prepared by addition of HCl in ether (1M) to the free base in a minimum amount of ethyl acetate. The precipitate is collected, washed with ether (2×5 mL), dried, and purified by recrystallization. The fumarate salt is prepared by mixing fumaric acid (8.7 mg, 0.0749 mmol) and the free base (0.0749 mmol) in 2 mL of 1:1 acetone-water. The product is purified by recrystallization.

EXAMPLE 72

1,4-Dihydro-5-methoxycarbonyl-6-methyl-4-(4-methyl) phenyl-2-propylpyridine-3-carboxylic acid. A mixture of 2-cyanoethyl 3-oxohexanoate (11.9 mmol), methyl 3-aminocrotonate (11.9 mmol), and 4-methylbenzaldehyde in 25 mL of isopropanol are heated at reflux temperature for 16 h, cooled, and the solvent is removed under reduced pressure. The residue is dissolved in 15 mL of dioxane and 626 mg of NaOH in 15 mL of water is added to the reaction mixture. After 0.5 hrs, the solution is concentrated to a small volume under reduced pressure, partitioned between 50 mL of water and 50 mL of ethyl acetate, separated, and the aqueous solution is washed with 2×20 mL of ethyl acetate. The organic solutions are discarded. The aqueous extract is acidified with concentrated HCl (pH=2), and the precipitated oil is extracted with ethyl acetate (2×40 mL). The combined organic extracts are dried (MgSO$_4$), and the solvent is removed in vacuo to give a residue, which is characterized spectroscopically.

1,4-Dihydro-3-(imidazol-1-yl)carbonyl-5-methoxycarbonyl-6-methyl-4-(4-methylphenyl)-2-propylpyridine. A solution of 1,4-dihydro-5-methoxycarbonyl-6-methyl-4-(4-methyl)phenyl-2-propylpyridine-3-carboxylic acid (2.89 mmol) and carbonyldiimidazole (3.75 mmol) in 20 mL of anhydrous THF is stirred at room temperature for 12 hrs. The solvent is removed in vacuo. The product is purified by flash chromatography and characterized spectroscopically.

1,4-Dihydro-5-methoxycarbonyl-6-methyl-4-(4-methylphenyl)-3-(N-(3-(4,4-diphenylpiperidin-1-yl) propyl))carboxamido-2-propylpyridine (72). This compound is prepared according to Method B. A solution of 1,4-dihydro-3-(imidazol-1-yl)carbonyl-5-methoxycarbonyl-6-methyl-4-(4-methylphenyl)-2-propylpyridine (0.456 mmol) and 1-(3-aminopropyl)-4,4-diphenylpiperidine (1.06 mmol) in 5 mL of dry THF is heated at reflux temperature for 19 hrs. The solvent is removed in vacuo. The crude product is purified by flash chromatography and characterized spectroscopically. The hydrochloride salt is prepared by addition of HCl in ether (1M) to the free base in a minimum amount of ethyl acetate. The precipitate is collected, washed with ether (2×5 mL), dried, and purified by recrystallization. The fumarate salt is prepared by mixing fumaric acid (8.7 mg, 0.0749 mmol) and the free base (0.0749 mmol) in 2 mL of 1:1 acetone-water. The product is purified by recrystallization.

EXAMPLE 73

2-Ethyl-1,4-dihydro-3-(imidazol-1-yl)carbonyl-5-methoxycarbonyl-6-methyl-4-(4-nitro)phenylpyridine. A solution of 1.00 g of 2-ethyl-1,4-dihydro-5-methoxycarbonyl-6-methyl-4-(4-methylphenyl)pyridine-3-carboxylic acid (2.89 mmol) and 609 mg of carbonyldiimidazole (3.75 mmol) in 20 mL of anhydrous THF were stirred at room temperature for 12 hrs. The solvent was removed in vacuo, and the crude product was chromatographed on 200 g of silica packed with 1% MeOH—EtOAc. The column was eluted with 1% (0.5 L), 2%, (0.5 L), and 3% (1 L) MeOH—EtOAc to give 350 mg (31%) of yellow oily solid, which was characterized spectroscopically.

2-Ethyl-1,4-dihydro-5-methoxycarbonyl-6-methyl-4-(4-nitro)phenyl-3-(N-(3-(4,4-diphenylpiperidin-1-yl)propyl)) carboxamidopyridine (73). This compound was prepared according to Method B. A solution of 181 mg of 2-ethyl-1, 4-dihydro-3-(imidazol-1-yl)carbonyl-5-methoxycarbonyl-6-methyl-4-(4-nitro)phenylpyridine (0.456 mmol) and 300 mg of 1-(3-aminopropyl)-4,4-diphenylpiperidine (1.06 mmol) in 5 mL of dry THF was heated at reflux temperature for 19 hrs and then cooled to room temperature. The solvent was removed in vacuo and the crude product was chromatographed on 50 g of silica packed with 5% MeOH—EtOAc. The column was eluted with 0.5 L of 10% and 0.5 L of 15% MeOH—EtOAc to afford 270 mg (95%) of yellow foamy solid, which was characterized spectroscopically. To a solution of this free base (124 mg) in EtOAc (0.5 mL) was added HCl in ether (1 mL, 1M). The precipitate was collected, washed with ether (2×5 mL), and dried to give a yellow powder: mp 240–245° C. (decomp.); Anal. Calcd for $C_{37}H_{42}N_4O_5 \cdot HCl \cdot H_2O$: C, 65.62; H 6.70; N, 8.27. Found: C, 65.57; H, 6.49; N, 8.31.

EXAMPLE 74

2-Ethyl-1,4-dihydro-5-methoxycarbonyl-6-methyl-4-(4-nitro)phenyl-3-(N-(3-(4-phenylpiperidin-1-yl)propyl)) carboxamidopyridine hydrochloride hydrate (74). This compound was prepared according to Method B from 97.4 mg of 2-ethyl-1,4-dihydro-3-(imidazol-1-yl)carbonyl-5-methoxycarbonyl-6-methyl-4-(4-nitro)phenylpyridine (0.246 mmol) mmol) and 80.7 mg of 1-(3-aminopropyl)-4-phenylpiperidine (0.369 mmol) in 3 mL of dry THF. The crude product was chromatographed on 100 g of silica (gradient elution: 5% to 25% MeOH—EtOAc) to give 128 mg (95%) of foamy yellow solid. This free base (45 mg) was dissolved in 2 mL of dichloromethane and added to 3 mL of 0.33M HCl in ether. The precipitate was collected, washed with 5 mL of ether, and dried to give a yellow powder: mp 209–214° C. (decomp.); Anal. Calcd for $C_{31}H_{38}N_4O_5 \cdot HCl \cdot H_2O$: C, 61.94; H, 6.87; N, 9.32. Found: C, 62.14; H, 6.37; N, 9.39.

EXAMPLE 75

2-Ethyl-1,4-dihydro-5-methoxycarbonyl-6-methyl-4-(4-nitro)phenyl-3-(N-(N-phenylmethyl) piperidin-4-yl) carboxamidopyridine hydrochloride (75). This compound was prepared according to Method B from 63.1 mg of 2-ethyl-1,4-dihydro-3-(imidazol-1-yl) carbonyl-5-methoxycarbonyl-6-methyl-4-(4-nitro) phenylpyridine (0.159 mmol) and 45.4 mg of N-benzyl-4-aminopiperidine (0.239 mmol) in 3 mL of dry THF. The crude product was chromatographed on 100 g of silica (gradient elution: 1% to 2% MeOH—EtOAc) to give 56 mg (87%) of foamy yellow solid (87%). This free base (50 mg) was dissolved in 0.5 mL of dichloromethane and added to 3 mL of 0.33M HCl in ether. The precipitate was collected, washed with 5 mL of ether, and dried to give a yellow powder: mp 221–224° C. (decomp.); Anal. Calcd for $C_{29}H_{34}N_4O_5 \cdot HCl$: C, 62.75; H, 6.36; N, 10.09. Found: C, 62.47; H, 6.06; N, 9.94.

EXAMPLE 76

5-Carboxamido-2-ethyl-1,4-dihydro-3-(N-(3-(1, 2,3,4-tetrahydro-6,7-dimethoxyisoquinolin-2-yl) propyl) )carboxamido-6-methyl-4-(4-nitro)phenylpyridine hydrochloride hydrate (76). This compound was prepared according to Method B from 64.3 mg of 5-carboxamido-2-ethyl-1,4-dihydro-3-(imidazol-1-yl)carbonyl-6-methyl-4-(4-nitro)phenylpyridine (0.162 mmol) and 69.9 mg of 2-(3-aminopropyl)-6,7-dimethoxy-1,2,3,4-tetrahydroisoquinoline (0.243 mmol) in 3 mL of dry THF. The crude product was chromatographed on 100 g of silica (gradient elution: 5% to 15% MeOH—EtOAc) to give 67 mg (71%) of foamy yellow solid. This free base (50 mg) was dissolved in 0.5 mL of dichloromethane and added to 3 mL of 0.33M HCl in ether. The precipitate was collected, washed with 5 mL of ether, and dried to give a yellow powder: mp 200–204° C. (decomp.); Anal. Calcd for $C_{31}H_{38}N_4O_7 \cdot HCl \cdot 0.8H_2O$: C, 59.15; H, 6.50; N, 8.90. Found: C, 59.27; H, 5.89; N, 9.10.

EXAMPLE 77

5-Carboxamido-2-ethyl-1,4-dihydro-6-methyl-4-(4-nitro)phenyl-3-(N-(4-(4-phenylpiperidin-1-yl) butyl )carboxamidopyridine hydrochloride hydrate (77). This compound was prepared according to Method B from 102 mg of 5-carboxamido-2-ethyl-1,4-dihydro-3-(imidazol-1-yl)carbonyl-6-methyl-4-(4-nitro)phenylpyridine (0.258 mmol) and 90.0 mg of 1-(4-aminobutyl)-4-phenylpiperidine (0.387 mmol) in 3 mL of dry THF. The crude product was chromatographed on 100 g of silica (gradient elution: 10% to 20% MeOH—EtOAc) to give 131 mg (91%) of foamy yellow solid. This free base (40 mg) was dissolved in 0.5 mL of dichloromethane and added to 3 mL of 0.33M HCl in ether. The precipitate was collected, washed with 5 mL of ether, and dried to give a yellow powder: mp 190–195° C. (decomp.); Anal. Calcd for $C_{32}H_{40}N_4O_5 \cdot HCl \cdot H_2O$: C, 62.48; H, 7.05; N, 9.11. Found: C, 62.87; H, 6.87; N, 9.15.

EXAMPLE 78

1,4-Dihydro-5-methoxycarbonyl-6-methyl-4-(4-nitrophenyl)-2-phenylpyridine-3-carboxylic acid. A solution of 5.01 g of 2-cyanoethyl 3-phenyl-3-oxopropionate (23.1 mmol), 6.98 g of 4-nitrobenzaldehyde (46.2 mmol), and 5.32 g of methyl 3-aminocrotonate (46.2 mmol) in 100 mL of isopropanol were heated at ref lux temperature for 2 days, cooled, and the solvent was removed in vacuo. The residue was dissolved in 50 mL of warm dioxane and 1.21 g of NaOH in 25 mL of water was added to the reaction mixture. The resulting maroon solution was stirred for 3 hrs. The solvent was removed in vacuo. The residue was partitioned between water (100 mL) and ethyl acetate (50 mL), separated, and washed with ethyl acetate (3×50 mL). The aqueous extract was acidified with concentrated HCl (pH 2–3), the precipitated solids were filtered, and washed with water (2×20 mL). The crude product was recrystallized from acetone-water mixture to give 5.02 g (55%) of yellow amorphous solid: mp 190–191° C.; Anal. Calcd for $C_{21}H_{18}N_2O_4$:C, 63.96; H, 4.60; N, 7.10. Found: C, 63.86; H, 4.59; N, 7.04.

1,4-Dihydro-5-methoxycarbonyl-6-methyl-4-(4-nitro)phenyl-2-phenyl-3-(N-(3-(4,4-diphenylpiperidin-1-yl)propyl))carboxamidopyridine hydrochloride hydrate (78). This compound was prepared according to Method B. A mixture of 394 mg of 1,4-dihydro-5-methoxycarbonyl-6-methyl-4-(4-nitro)phenyl-2-phenylpyridine-3-carboxylic acid (1.00 mmol), 310 mg of DCC (1.50 mmol), and 134 mg of DMAP (1.10 mmol) in 10 mL of dry dichloromethane were stirred at room temperature for 1 h. 1-(3-Aminopropyl)-4,4-diphenylpiperidine (339 mg, 1.20 mmol) was added and the mixture was heated at reflux temperature for 2 hrs. The reaction mixture was cooled, filtered, and chromatographed on 200 g of silica packed with 10% MeOH—EtOAc. The column was eluted with 10% (0.5 L), 15% (1 L), and 20% (0.5 L) MeOH—EtOAc to give 628 mg (95%) of yellow foamy solid. This free base (317 mg) was dissolved in 5 mL of dichloromethane and added to 15 mL of 0.33M HCl in ether. The precipitate was collected, washed with 5 mL of ether, and dried to give a yellow powder: mp 210–215° C, (decomp.); Anal. Calcd for $C_{41}H_{42}N_4O_5 \cdot HCl$: C, 69.63; HI 6.13; N, 7.92. Found: C, 69.33; H, 6.34; N, 7.86.

EXAMPLE 79

1,4-Dihydro-5-methoxycarbonyl-6-methyl-4-(4-nitro)phenyl-2-phenyl-3-(N-(3-(4-phenylpiperidin-1-yl)propyl))carboxamidopyridine hydrochloride (79). This compound was prepared according to Method B from 205 mg of 1,4-dihydro-5-methoxycarbonyl-6-methyl-4-(4-nitro)phenyl-2-phenylpyridine-3-carboxylic acid (0.520 mmol), 161 mg of DCC (0.780 mmol), 70 mg of DMAP (0.572 mmol), and 121 mg of 1-(4-aminobutyl)-4-phenylpiperidine (0.520 mmol) in 10 mL of dry dichloromethane. The crude product was chromatographed on 100 g of silica (gradient elution: 5% to 15% MeOH—EtOAc) to give 290 mg (96%) of foamy yellow solid. This free base (280 mg) was dissolved in 5 mL of dichloromethane and added to 15 mL of 0.33M HCl in ether. The precipitate was collected, washed with 2×5 mL of ether, and dried to give a yellow powder: mp 196–201° C. (decomp.); Anal. Calcd for $C_{36}H_{40}N_4O_5 \cdot HCl \cdot 0.5H_2O$: C, 66.10; H, 6.47; N, 8.56. Found: C, 66.07; H, 6.09; N, 8.46.

EXAMPLE 80

5-Carboxamido-1,4-dihydro-4-(4-nitro)phenyl-2-phenyl-3-(N-(3-(4,4-diphenylpiperidin-1-yl)propyl))carboxamidopyridine hydrochloride (80). This compound was prepared according to Method B from 99.0 mg of 5-carboxamido-1,4-dihydro-6-methyl-4-(4-nitro)phenyl-2-phenylpyridine-3-carboxylic acid (0.261 mmol), 80.8 mg of DCC (0.391 mmol), 35.1 mg of DMAP (0.287 mmol), and 88.4 mg of 1-(3-aminopropyl)-4,4-diphenylpiperidine (0.313 mmol) in 5 mL of dry dichloromethane (24 hrs of reflux). The crude product was chromatographed on 200 g of silica (gradient elution: 20% to 25% MeOH—EtOAc) to give 20 mg (18%) of foamy yellow solid. This free base was dissolved in 1 mL of dichloromethane and added to 2 mL of 0.5M HCl in ether. The precipitate was collected, washed with 5 mL of ether, and dried to give a yellow powder: mp 225–230° C. (decomp.); Anal. Calcd for $C_{32}H_{40}N_4O_5 \cdot HCl \cdot 0.8\ CH_2Cl_2$:C, 64.46; HI 5.78; N, 9.21. Found: C, 64.42; H, 5.76; N, 9.19.

EXAMPLE 81

5-Carboxamido-2-ethyl-1,4-dihydro-6-methyl-4-(4-nitro)phenyl-3-(N-(3-(4,4-diphenylpiperidin-1-yl)propyl))carboxamidopyridine hydrochloride (81). This compound was prepared according to Method B from 550 mg of 5-carboxamido-2-ethyl-1,4-dihydro-6-methyl-4-(4-nitrophenyl)pyridine-3-carboxylic acid (88% pure by spectral analyses) (1.46 mmol), 514 mg of DCC (2.49 mmol), 223 mg of DMAP (1.83 mmol), and 523 mg of 1-(3-aminopropyl)-4,4-diphenylpiperidine (1.99 mmol) in 20 mL of dry dichloromethane (12 hrs of ref lux). The crude product was chromatographed on 200 g of silica (gradient elution: 1:1:50 to 2:2:50 MeOH-isopropyl amine-EtOAc) to give 720 mg (74%) of foamy yellow solid (contains one equivalent of EtOAc). This free base (350 mg) was dissolved in 5 mL of dichloromethane and added to 20 mL of 0.25M HCl in ether. The precipitate was collected, washed with 3×5 mL of ether, and dried to give a yellow powder: mp 243–248° C. (decomp.); Anal. Calcd for $C_{36}H_{41}N_5O_4$·HCl·1.5$H_2O$: C, 64.42; H, 6.76; N, 10.43. Found: C, 64.32; H, 6.64; N, 10.36.

EXAMPLE 82

4-(4-Methoxyphenyl)-4-phenylpiperidine. 4-Hydroxy-4-phenylpiperidine (5.00 g, 28.2 mmol, 1.00 equiv, Aldrich) was added to a suspension of AlCl3 (18.8 g, 141 mmol, 5.00 equiv) in anhydrous anisole (100 mL). The mixture was stirred at room temperature for 1 hour and then heated to 50° C. for 3.5 hours. It was cooled to room temperature and poured cautiously into ice-water. The mixture was basified to pH 11 by addition of 6M aqueous NaOH, and extracted with EtOAc (3×75 mL). The combined organic solutions were applied directly to a flash chromatography column, which was eluted with $CH_2Cl_2$—$NH_3$ in MeOH (0.67M), 4:1 to afford 1.683 g (22%) of light yellow oil, which was characterized spectroscopically.

3-[4-(4-Methoxyphenyl)-4-phenylpiperidin-1-yl]propionitrile. Acrylonitrile (1.03 mL, 15.7 mmol, 2.50 equiv) was added at 0° C. to a solution of 4-(4-methoxyphenyl)-4-phenylpiperidine (1.68 g, 6.28 mmol, 1.00 equiv) in EtOH (20 mL) and the resulting solution was stirred for 1.5 hours at room temperature. After removal of the solvent, the residue was purified by flash chromatography ($SiO_2$, EtOAc-$CHCl_3$ 1:3) to give 1.41 g (70%) of colorless oil, which was characterized spectroscopically.

1-(3-Aminopropyl)-4-(4-methoxyphenyl)-4-phenylpiperidine. To a stirred solution of 3-[4-(4-methoxyphenyl)-4-phenylpiperidin-1-yl]propionitrile (1.41 g, 4.40 mmol, 1.0 equiv) in anhydrous THF (10 mL) under argon was added a solution of $BH_3$ in THF (1.0M, 11.0 mL, 2.5 equiv) at room temperature. The mixture was refluxed for 4.5 hours and then cooled to room temperature. Aqueous HCl (6N, 15 mL) was added and stirring was continued for 2 hours at 55–60° C. The mixture was basified to pH 9 by addition of 6N aq. NaOH and extracted with $CH_2Cl_2$ (3×75 mL). The combined organic solutions were dried over $MgSO_4$ and concentrated. The residue was dissolved in $CH_2Cl_2$ (10 mL) and treated with HCl in ether (1.0M, 9.0 mL, 2.0 equiv). The solvents were removed, ether (30 mL) was added, the mixture was filtered, and the filter cake was washed with ether (2×10 mL). Water (20 mL) was added to the resulting white solid, the pH was adjusted to 10 with 1MNaOH, and the aqueous phase was extracted with $CH_2Cl_2$ (3×40 mL). The combined organic solutions were dried over $MgSO_4$ and concentrated to give 610 mg (43%) of white solid, which was characterized spectroscopically.

5-Carboxamido-2-ethyl-1,4-dihydro-3-{N-[3-(4-methoxyphenyl)-4-phenylpiperidin-1-y)propyl]}carboxamido-6-methyl-4-(4-nitro)phenylpyridine hydrochloride hydrate (82). This compound was prepared according to Method B. Anhydrous $CH_2Cl_2$ (10 mL) was added to a mixture of 5-carboxamido-2-ethyl-1,4-dihydro-6-methyl-4-(4-nitrophenyl)pyridine-3-carboxylic acid (200 mg, 0.604 mmol, 1.00 equiv), 1-(3-dimethylaminopropyl)-3-ethylcarbodiimide hydrochloride (174 mg, 0.905 mmol, 1.50 equiv), and 4-(N,N-dimethylamino)pyridine (81 mg, 0.66 mmol, 1.1 equiv) and the resulting solution was stirred for 1 hour at room temperature. A solution of 1-(3-aminopropyl)-4-(4-methoxyphenyl)-4-phenylpiperidine (234 mg, 0.721 mmol, 1.20 equiv) in $CH_2Cl_2$ (2 mL) was injected and the mixture was stirred at reflux for 6 hours. Methylene chloride (150 mL) was added and the organic phase was washed with saturated aqueous ammonium chloride (2×40 mL), dried over $MgSO_4$ and concentrated. The residue was purified by flash chromatography ($SiO_2$, $CHCl_3$— $NH_3$ in MeOH (0.77M) 90:13) to afford 209 mg (55%) of yellow solid, which was characterized spectroscopically. To a solution of this product (200 mg, 0.310 mmol) in $CH_2Cl_2$ (10 mL) was added HCl in ether (1.0M, 0.60 mL, 1.9 equiv). After removal of the solvents, the residue was dissolved in $CH_2Cl_2$ (5 mL) and added dropwise to ether (30 mL) with swirling to give, after filtration, 150 mg of yellow solid: m.p. 183–184° C.; Anal. Calcd. for $C_{37}H_{43}N_5O_5$·HCl·1.25 $H_2O$: C, 63.78; H, 6.73; N, 10.05. Found: C, 63.80; H, 6.81; N, 9.72.

EXAMPLE 83

3-[4-(4-Chlorophenyl)-4-hydroxypiperidin-1-yl]propionitrile. Acrylonitrile (2.33 mL, 35.4 mmol, 2.50 equiv) was added at 0° C. to a solution of 4-(4-chlorophenyl)-4-hydroxypiperidine (3.00 g, 14.2 mmol, 1.00 equiv, Aldrich) in EtOH (30 mL) and the resulting solution was stirred for 1.5 hours at room temperature. The solvent was removed to give 3.71 g (99%) of white solid, which was characterized spectroscopically and used without purification for the next reaction.

1-(3-Aminopropyl)-4-(4-chlorophenyl)-4-hydroxypiperidine. To a stirred solution of 3-[4-(4-chlorophenyl)-4-hydroxypiperidin-1-yl]propionitrile (3.51 g, 13.2 mmol, 1.0 equiv) in anhydrous THF (20 mL) under argon was added a solution of $BH_3$ in THF (1.0M, 46.4 mL, 3.5 equiv) at room temperature. The mixture was refluxed for 4.5 hours and then cooled to room temperature. Aqueous HCl (6N, 30 mL) was added and stirring was continued for 2 hours at 55–60° C. The mixture was basified to pH 9 by addition of 6N aq. NaOH and extracted with $CH_2Cl_2$ (3×150 mL). The combined organic solutions were dried over $MgSO_4$ and concentrated. The residue was dissolved in $CH_2Cl_2$ (20 mL) and treated with HCl in ether (1.0M, 27.7 mL, 2.1 equiv). The solvents were removed, ether (60 mL) was added, the mixture was filtered, and the filter cake was washed with ether (2×20 mL). Water (40 mL) was added to the resulting white solid, the pH was adjusted to 10 with 1M NaOH, and the aqueous phase was extracted with $CH_2Cl_2$ (3×80 mL). The combined organic solutions were dried over $MgSO_4$ and concentrated to give 3.10 g (87%) of white solid, which was characterized spectroscopically.

5-Carboxamido-3-{N-[3-(4-(4-chlorophenyl)-4-hydroxypiperidine-1-yl)propyl]}carboxamido-2-ethyl-1,4-dihydro-6-methyl-4-(4-nitrophenyl)pyridine hydrochloride (83). This compound was prepared according to Method B. Anhydrous $CH_2Cl_2$ (10 mL) was added to a mixture of 5-carboxamido-2-ethyl-1,4-dihydro-6-methyl-4-(4-nitrophenyl)pyridine-3-carboxylic acid (200 mg, 0.604 mmol, 1.00 equiv), 1-(3-dimethylaminopropyl)-3-ethylcarbodiimide hydrochloride (174 mg, 0.905 mmol, 1.50 equiv), and 4-(N,N-dimethylamino)pyridine (81 mg, 0.66 mmol, 1.1 equiv) and the resulting solution was stirred for 1 hour at room temperature. A solution of 1-(3-aminopropyl)-4-(4-chlorophenyl)-4-phenylpiperidine (194 mg, 0.722 mmol, 1.20 equiv) in $CH_2Cl_2$ (2 mL) was injected and the mixture was stirred at reflux for 6 hours. Methylene chloride (150 mL) was added and the organic phase was washed with saturated aqueous ammonium chloride (2×40 mL), dried over $MgSO_4$ and concentrated. The residue was purified by flash chromatography ($SiO_2$, MeOH—EtOAc 1:3) to afford 71 mg (22%) of yellow solid, which was characterized spectroscopically. To a solution of this product (56 mg, 0.10 mmol) in $CH_2Cl_2$ (3 mL) was added HCl in ether (1.0M, 0.20 mL, 2.0 equiv). After removal of the solvents, the residue was dissolved in $CH_2Cl_2$ (3 mL) and added dropwise to ether (20 mL) with swirling to give, after filtration, 57 mg of yellow solid: m.p. 178–179° C.; Anal. Calcd. for $C_{30}H_{36}N_5O_5$ HCl.1.6 $CH_2Cl_2$: C, 52.79; H, 5.64; N, 9.74. Found: C, 52.70; H, 5.89; N, 10.10.

EXAMPLE 84

3-(4-Benzylpiperidin-1-yl)propionitrile. Acrylonitrile (9.37 mL, 142 mmol, 2.50 equiv) was added at 0° C. to a solution of 4-benzylpiperidine (10.0 mL, 56.9 mmol, 1.00 equiv, Aldrich) in EtOH (60 mL) and the resulting solution was stirred for 1.5 hours at room temperature. The solvent was removed to give 12.98 g (99%) of colorless oil, which was characterized spectroscopically and used without purification for the next reaction.

1-(3-Aminopropyl)-4-benzylpiperidine. To a stirred solution of 3-(4-benzylpiperidin-1-yl)propionitrile (8.20 g, 35.9 mmol, 1.0 equiv) in anhydrous THF.(20 mL) under argon was added a solution of $BH_3$ in THF (1.0N, 126 mL, 3.5 equiv) at room temperature. The mixture was refluxed for 4.5 hours, then cooled to room temperature and concentrated to a volume of about 30 mL. Aqueous HCl (6N, 80 mL) was added and stirring was continued for 2 hours at 55–60° C. The mixture was basified to pH 9 by addition of 6N aq. NaOH and extracted with $CH_2Cl_2$ (3×150 mL). The combined organic solutions were dried over $MgSO_4$ and concentrated. The residue was dissolved in $CH_2Cl_2$ (20 mL) and treated with HCl in ether (1.0M, 75 mL, 2.1 equiv). The solvents were removed, ether (60 mL) was added, the mixture was filtered, and the filter cake was washed with ether (2×30 mL). Water (40 mL) was added to the resulting white solid, the pH was adjusted to 10 with 1M NaOH, and the aqueous phase was extracted with $CH_2Cl_2$ (3×80 mL). The combined organic solutions were dried over $MgSO_4$ and concentrated to give 7.59 g (91%) of colorless oil, which was characterized spectroscopically.

5-Carboxamido-3-{N-[3-(4-benzylpiperidin-1-yl)propyl]}-carboxamido-2-ethyl-1,4-dihydro-6-methyl-4-(4-nitrophenyl)pyridine hydrchloride hydrate etherate (84). This compound was prepared according to Method B. Anhydrous $CH_2Cl_2$ (10 mL) was added to a mixture of 5-carboxamido-2-ethyl-1,4-dihydro-2-ethyl-6-methyl-4-(4-nitrophenyl)pyridine-3-carboxylic acid (200 mg, 0.604 mmol, 1.00 equiv), 1-(3-dimethylaminopropyl)-3-ethylcarbodiimide hydrochloride (174 mg, 0.905 mmol, 1.50 equiv), and 4-(N,N-dimethylamino)pyridine (81 mg, 0.66 mmol, 1.1 equiv) and the resulting solution was stirred for 1 hour at room temperature. A solution of 1-(3-aminopropyl)-4-benzylpiperidine (181 mg, 0.779 mmol, 1.29 equiv) in $CH_2Cl_2$ (2 mL) was injected and the mixture was stirred at reflux for 6 hours. Methylene chloride (150 mL) was added and the organic phase was washed with saturated aqueous ammonium chloride (3×40 mL) and concentrated. A solution of the residue in EtOAc (100 mL) was extracted with 0.1M aqueous HCl (2×100 mL) and the organic layer was discarded. The combined HCl solutions were basified to pH 10 by addition of 1M aqueous NaOH and extracted with $CH_2Cl_2$ (3×100 mL). The combined $CH_2Cl_2$ solutions were dried over $MgSO_4$ and concentrated. A solution of the residue in $CH_2Cl_2$ (2 mL) was added dropwise into ether (20 mL) to afford, after filtration, 195 mg (60%) of yellow solid, which was characterized spectroscopically. To a solution of this product (183, 0.335 mmol) in $CH_2Cl_2$ (3 mL) was added HCl in ether (1.0M, 0.65 mL, 1.9 equiv). After removal of the solvents, the residue was dissolved in $CH_2Cl_2$ (5 mL) and added dropwise to ether (30 mL) with swirling to give, after filtration, 190 mg of yellow solid: m.p. 163–164° C.; Anal. Calcd. for $C_{31}H_{39}N_5O_4$.HCl.$H_2O$.0.35 $C_4H_{10}O$: C, 62.14; H, 7.32; N, 11.18. Found: C, 62.15; H, 7.32; N, 11.11.

EXAMPLE 85

1-(3-Aminopropyl)-4,4-dicyclohexylpiperidine. A solution of 3-(4,4-diphenylpiperidin-1-yl)propionitrile (1.01 g, 3.48 mmol, 1.00 equiv) in denatured EtOH (50 mL, 5% isopropanol) was stirred at 120–130° C. in the presence of 10% Pd on activated carbon (1.00 g, Aldrich) and hydrogen at 440 psi for 15 hours. The catalyst was filtered out by use of Celite and washed with $CH_2Cl_2$ (100 mL) and MeOH (150 mL). After removal of the solvents, the residue was dissolved in $CH_2Cl_2$ (10 mL) and treated with HCl in ether (1.0M., 8.7 mmol, 2.5 equiv). The solvents were removed again and the residue was recrystallized from hot EtOH-ether (1:2). The white solid obtained from filtration of this mixture was taken up in water (40 mL), which was basified to pH 10 by addition of 1N NaOH and extracted with $CH_2Cl_2$ (3×75 mL). The combined organic solutions were dried over $MgSO_4$ and concentrated to afford 650 mg of colorless oil (61%), which was characterized spectroscopically.

5-Carboxamido-3-{N-[3-(4,4-dicyclohexylpiperidine-1-yl)-propyl]}carboxamido-2-ethyl-1,4-dihydro-6-methyl-4-(4-nitrophenyl)pyridine hydrochloride hydrate etherate (85). This compound was prepared according to Method B. Anhydrous $CH_2Cl_2$ (10 mL) was added to a mixture of 5-carboxamido-2-ethyl-1,4-dihydro-6-methyl-4-(4-nitrophenyl)pyridine-3-carboxylic acid (200 mg, 0.604 mmol, 1.00 equiv), 1-(3-dimethylaminopropyl)-3-ethylcarbodiimide hydrochloride (174 mg, 0.905 mmol, 1.50 equiv), and 4-(N,N-dimethylamino)pyridine (81 mg, 0.66 mmol, 1.1 equiv) and the resulting solution was stirred for 1 hour at room temperature. A solution of 1-(3-aminopropyl)-4,4-dicyclohexylpiperidine (181 mg, 0.779 mmol, 1.29 equiv) in $CH_2Cl_2$ (2 mL) was injected and the mixture was stirred at reflux for 6 hours. Methylene chloride (150 mL) was added and the organic phase was washed with saturated aqueous ammonium chloride (3×40 mL) and concentrated. A solution of the residue in EtOAc (100 mL) was extracted with 0.1M aqueous HCl (2×100 mL) and the organic layer was discarded. The combined HCl solutions were basified to pH 10 by addition of 1M aqueous NaOH and extracted with $CH_2Cl_2$ (3×100 mL). The combined $CH_2Cl_2$ solutions were dried over $MgSO_4$ and concentrated. A solution of the residue in $CH_2Cl_2$ (2 mL) was added dropwise into ether (20 mL) to afford, after filtration, 242 mg (65%) of yellow solid, which was characterized spectroscopically. To a solution of this product (290, 0.470 mmol) in $CH_2Cl_2$ (10 mL) was added HCl in ether (1.0M, 0.80 mL, 1.7 equiv). After removal of the solvents, the residue was dissolved in $CH_2Cl_2$ (5 mL) and added dropwise to ether (30 mL) with swirling to give, after filtration, 293 mg of yellow solid: m.p. 185–186° C.; Anal. Calcd. for $C_{36}H_{53}N_5O_4$.HCl.0.75 $H_2O$.0.35 $C_4H_{10}O$: C, 64.55; HI 8.33; N, 10.06. Found: C, 64.49; H, 8.62; N, 9.87.

EXAMPLE 86

4-Cyclohexylpiperidine. A solution of 4-phenylpyridine hydrochloride (4.50 g, 29.0 mmol, 1.00 equiv) in denatured EtOH (100 mL, 5% isopropanol) was stirred at 110–120° C. in the presence of 10% Pd on activated carbon (4.50 g, Aldrich) and hydrogen at 440 psi for 24 hours. The catalyst was filtered out by use of Celite and washed with $CH_2Cl_2$ (100 mL) and MeOH (150 mL). The filtrate was concentrated to give 5.32 g (90%) of white solid, which was characterized spectroscopically as 4-cyclohexylpiperidine hydrochloride. This white solid was taken up in water (150 mL), which was basified to pH 10 by addition of 1N NaOH and extracted with $CH_2Cl_2$ (3×200 mL). The combined organic solutions were dried over $MgSO_4$ and concentrated to afford 4.27 g of white solid (88%), which was characterized spectroscopically.

3-(4-Cyclohexylpiperidin-1-yl)propionitrile. Acrylonitrile (4.16 mL, 63.1 mmol, 2.50 equiv) was-added at 0° C. to a solution of 4-cyclohexylpiperidine (4.20 g, 25.3 mmol, 1.00 equiv) in EtOH (50 mL) and the resulting solution was stirred for 1.5 hours at room temperature. The solvent was removed to give 5.11 g (92%) of white solid, which was characterized spectroscopically and used without purification for the next reaction.

1-(3-Aminopropyl)-4-cyclohexylpiperidine. To a stirred solution of 3-(4-cyclohexylpiperidin-1-yl)propionitrile (5.11 g, 23.3 mmol, 1.0 equiv) in anhydrous THF (15 mL) under argon was added a solution of $BH_3$ in THF (1.0M, 82 mL, 3.5 equiv) at room temperature. The mixture was refluxed for 4.5 hours, then cooled to room temperature and concentrated to a volume of about 30 mL. Aqueous HCl (6N, 55 mL) was added and stirring was continued for 2 hours at 55–60° C. The mixture was basified to pH 9 by addition of 6N aq. NaOH and extracted with $CH_2Cl_2$ (3×100 mL). The combined organic solutions were dried over $MgSO_4$ and concentrated. The residue was dissolved in $CH_2Cl_2$ (20 mL) and treated with HCl in ether (1.0M, 58 mL, 2.5 equiv). The solvents were removed, ether (40 mL) was added, the mixture was filtered, and the filter cake was washed with ether (2×20 mL). Water (40 mL) was added to the resulting white solid, the pH was adjusted to 10 with 1M NaOH, and the aqueous phase was extracted with $CH_2Cl_2$ (3×80 mL). The combined organic solutions were dried over $MgSO_4$ and concentrated to give 4.63 g (88%) of colorless oil, which was characterized spectroscopically.

5-Carboxamido-3-{N-[3-(4-cyclohexylpiperidin-1-yl) propyl]}carboxamido-2-ethyl-1,4-dihydro-6-methyl-4-(4-nitrophenyl)pyridine hydrochloride hydrate (86). This compound was prepared according to Method B. Anhydrous $CH_2Cl_2$ (10 mL) was added to a mixture of 5-carboxamido-2-ethyl-1,4-dihydro-6-methyl-4-(4-nitrophenyl)pyridine-3-carboxylic acid (200 mg, 0.604 mmol, 1.00 equiv), 1-(3-dimethylaminopropyl)-3-ethylcarbodiimide hydrochloride (174 mg, 0.905 mmol, 1.50 equiv), and 4-(N,N-dimethylamino)pyridine (81 mg, 0.66 mmol, 1.1 equiv) and the resulting solution was stirred for 1 hour at room temperature. A solution of 1-(3-aminopropyl)-4-cyclohexylpiperidine (175 mg, 0.780 mmol, 1.29 equiv) in $CH_2Cl_2$ (2 mL) was injected and the mixture was stirred at reflux for 6 hours. Methylene chloride (150 mL) was added and the organic phase was washed with saturated aqueous ammonium chloride (3×40 mL) and concentrated. A solution of the residue in EtOAc (100 mL) was extracted with 0.1M aqueous HCl (2×100 mL) and the organic layer was discarded. The combined HCl solutions were basified to pH 10 by addition of 1M aqueous NaOH and extracted with $CH_2Cl_2$ (3×100 mL). The combined $CH_2Cl_2$ solutions were dried over $MgSO_4$ and concentrated. A solution of the residue in $CH_2Cl_2$ (2 mL) was added dropwise into ether (20 mL) to afford, after filtration, 203 mg (63%) of yellow solid, which was characterized spectroscopically. To a solution of this product (257, 0.478 mmol) in $CH_2Cl_2$ (10 mL) was added HCl in ether (1.0M, 0.90 mL, 1.9 equiv). After removal of the solvents, the residue was dissolved in $CH_2Cl_2$ (5 mL) and added dropwise to ether (30 mL) with swirling to give, after filtration, 260 mg of yellow solid: m.p. 167–168° C.; Anal. Calcd. for $C_{30}H_{43}N_5O_4$ HCl.0.75 $H_2O$: C, 61.32; H, 7.80; N, 11.92. Found: C, 61.16; H, 8.06; N, 11.54.

EXAMPLE 87

3-[N-(3-Bromopropyl)]carboxamido-5-carboxamido-2-ethyl-1,4-dihydro-6-methyl-4-(4-nitrophenyl)pyridine. This compound is prepared according to Method B. Anhydrous $CH_2Cl_2$ (10 mL) is added to a mixture of 5-carboxamido-2-ethyl-1,4-dihydro-6-methyl-4-(4-nitrophenyl)pyridine-3-carboxylic acid (200 mg, 0.604 mmol, 1.00 equiv), 1-(3-dimethylaminopropyl)-3-ethylcarbodiimide hydrochloride (174 mg, 0.905 mmol, 1.50 equiv), and 4-(N,N-dimethylamino)pyridine (81 mg, 0.66 mmol, 1.1 equiv) and the resulting solution is stirred for 1 hour at room temperature. To this solution is added a $CH_2Cl_2$ solution (10 mL) of 3-bromopropylamine, which is generated from 3-bromopropylamine hydrobromide (172 mg, 0.785 mmol, 1.30 equiv) by stirring for 10 minutes over solid $K_2CO_3$ followed by filtration. The reaction mixture is stirred at room temperature for 24 hours. Methylene chloride (150 mL) is added and the organic phase is washed with 0.1M aqueous HCl (3×40 mL), dried over $MgSO_4$ and concentrated. A solution of the residue in $CH_2Cl_2$ (2 mL) is added dropwise into ether (20 mL). The solid product is obtained by filtration and characterized spectroscopically.

3-{N-[3-(4-Acetyl-4-phenylpiperidin-1-yl)propyl]}carboxamido-5-carboxamido-2-ethyl-1,4-dihydro-6-methyl-4-(4-nitrophenyl)pyridine (87). A suspension of 4-acetyl-4-phenylpiperidine hydrochloride (63.7 mg, 0.266 mmol, 1.20 equiv), 3-[N-(3-bromopropyl)]carboxamido-5-carboxamido-2-ethyl-1,4-dihydro-6-methyl-4-(4-nitrophenyl)pyridine (100 mg, 0.222 mmol, 1.00 equiv), potassium carbonate (92.0 mg, 0.666 mmol, 3.00 equiv), and potassium iodide (18.4 mg, 0.111 mmol, 0.50 equiv) in acetone (1.1 mL) is stirred at reflux under argon for 15 hours. The mixture is cooled to room temperature and concentrated. The residue is diluted with EtOAc (20 mL) and extracted with 0.1N aqueous HCl (3×30 mL). The combined aqueous solutions are basified by addition of 1M aqueous NaOH and extracted with $CH_2Cl_2$ (3×50 mL). The combined $CH_2Cl_2$ solutions are dried over $MgSO_4$ and concentrated to afford the product, which is purified by flash chromatography and characterized spectroscopically.

EXAMPLE 88

2-Ethyl-1,4-dihydro-6-methyl-4-(4-nitro)phenyl-3-{N-[3-(4,4-diphenylpiperidin-1-yl)propyl]}carboxamidopyridine-5-carboxylic acid. A mixture of 2.15 g of 5-benzyloxycarbonyl-2-ethyl-1,4-dihydro-6-methyl-4-(4-nitro)phenyl-3-{N-[3-(4,4-diphenylpiperidin-1-yl)propyl]}carboxamidopyridine (3.08 mmol) and 0.510 g of 10% Pd/C in 50 mL of methanol was hydrogenated using a balloon method for 6 h, filtered through Celite 545, and the residue was washed with methanol (4×30 mL). The combined filtrates were concentrated to give 1.76 g (96%) of yellow solid, which was used in the next step without any further purification.

2-Ethyl-1,4-dihydro-6-methyl-5-(O-methylhydroxamyl) carbonyl-4-(4-nitro)phenyl-3-{N-[3-(4,4-diphenylpiperidin-1-yl)propyl]}carboxamidopyridine dihydrochloride salt (88). This compound was prepared according to Method D.

A mixture of 173 mg of 2-ethyl-1,4-dihydro-6-methyl-4-(4-nitro)phenyl-3-{N-[3-(4,4-diphenylpiperidin-1-yl) propyl]}carboxamidopyridine-5-carboxylic acid (0.284 mmol), 38.2 mg of DMAP (0.312 mmol), and 87.9 mg of DCC (0.426 mmol) in 10 mL of dry dichloromethane was stirred at room temperature for 1 h. O-Methylhydroxylamine hydrochloride (71.2 mg, 0.852 mmol) and 45.2 mg of sodium carbonate (0.426 mmol) were added and stirring was continued for 4 days. The mixture was filtered and concentrated, and the residue was dissolved in 50 mL of ethyl acetate. This solution was washed with 30 mL of saturated sodium bicarbonate solution, dried ($Na_2CO_3$), and concentrated. The residue was chromatographed on 200 g of silica packed with 5% MeOH—EtOAc. The column was eluted with 5% (0.5 L), 10% (0.5 L), 15% (0.5 L), 20% (1 L), and 25% (1 L) to give 20 mg (11%) of yellow solid, which was characterized spectroscopically. A solution of this free base (20 mg) in 0.5 mL of dichloromethane was added to 1M HCl in ether (2 mL). The precipitate was collected, washed with 5 mL of ether, and dried: mp 196–200° C.; Anal. Calcd for $C_{37}H_{43}N_5O_5.HCl.0.9\ CH_2Cl_2$:C, 60.64; H, 6.15; N, 9.33. Found: C, 60.89; H, 5.63; N, 9.30.

EXAMPLE 89

3-Ethoxycarbonyl-2-(ethoxycarbonyl)methyl-1,4-dihydro-5-methoxycarbonyl-6-methyl-4-(4-nitro)]phenylpyridine. A stirred solution of 2.02 g of diethyl 1,3-acetonedicarboxylate (10.0 mmol), 1.15 g of methyl 3-aminocrotonate (10.0 mmol), and 1.51 g of 4-nitrobenzaldehyde (10.0 mmol) in 100 mL of isopropanol was heated at reflux temperature for 3 days, cooled, and the solvent was removed in vacuo. The crude product was chromatographed on 200 g of silica packed-with 5% EtOAc-hexanes. The column was eluted with 5% to 50% EtOAc-hexanes (5% change/500 mL) to afford 2.71 g of yellow viscous oil: Anal. Calcd for $C_{21}H_{24}N_2O_8$:C, 58.23; H, 5.59; N, 6.48. Found: C, 58.17; H, 5.76; N, 6.25.

3-Ethoxycarbonyl-1,4-dihydro-5-methoxycarbonyl-6-methyl-4-(4-nitro)phenyl-2-(N-(3-(4,4,-diphenylpiperidin-1-yl)propyl)carboxamido)methylpyridine, fumarate salt (89). A solution of 803 mg of 3-ethoxycarbonyl-2-(ethoxycarbonyl)methyl-1,4-dihydro-5-methoxycarbonyl-6-methyl-4-(4-nitro)phenylpyridine (1.86 mmol) and 98 mg of NaOH (2.5 mmol) in 10 mL of 1:1 dioxane-water mixture were stirred at room temperature for 24 hrs, concentrated to a small volume, partitioned between water (10 mL) and ethyl acetate (20 mL), separated, and the aqueous layer was washed with ether (20 mL). The aqueous extract was acidified with concentrated HCl (pH=2–3), the precipitated oil was extracted with 20 mL of EtOAc, dried ($Na_2SO.$), and the solvent was removed in vacuo to afford 750 mg of 3-(carboxy)methyl-2-(ethoxycarbonyl)methyl-1,4-dihydro-5-methoxycarbonyl-6-methyl-4-(4-nitro) phenylpyridine (99.8%). The crude acid was used in the next step without any further purification.

Dicyclohexylcarbodiimide (164 mg, 0.796 mmol) was added, in one portion, to a stirred solution of 354 mg of 3-(carboxy)methyl-2-(ethoxycarbonyl)methyl-1,4-dihydro-5-methoxycarbonyl-6-methyl-4-(4-nitro)phenylpyridine (0.875 mmol) and 225 mg of 1-(3-aminopropyl)-4,4-diphenylpiperidine (0.796 mmol) in 5 mL of dry dichloromethane. Stirring was continued at room temperature for 18 h. The solvent was removed in vacuo, the residue was triturated with ether (10 mL), and the mixture was filtered. The solid was washed with ether (2×10 mL) and the filtrate was concentrated. The crude product was chromatographed on 150 g of silica packed with 10% MeOH—EtOAc. The column was eluted with 10% to 25% MeOH—EtOAc (5% change/500 mL) to afford 273 mg of product: Anal. Calcd for $C_{39}H_{44}N_4O_7.0.5EtOAc$: C, 67.91; H, 6.58; N, 8.12. Found: C, 67.88; H, 6.51; N, 8.13.

Fumarate Salt: A mixture of 51.0 mg of 3-ethoxycarbonyl-1,4-dihydro-5-methoxycarbonyl-6-methyl-4-(4-nitro) phenyl-2-(N-(3-(4,4,-diphenylpiperidin-1-yl) propyl) carboxamido)methylpyridine (0.0749 mmol) and 8.7 mg of fumaric acid (0.0749 mmol) in 2 mL of 1:1 acetone-water was heated to boiling until a homogeneous solution resulted. The reaction mixture was cooled, filtered, and the solvent was removed in vacuo to give 58.5 mg of yellow solid (98%): mp 134–137° C,; Anal. Calcd for $C_{43}H_{48}N_4O_{11}$:C, 64.81; H, 6.07; N, 7.03. Found: C, 64.61; H, 6.14; N, 6.91.

EXAMPLES 90 AND 91

2-Chloromethyl-3-ethoxycarbonyl-1,4-dihydro-5-methoxycarbonyl-6-methyl-4-(4-nitro) phenylpyridine. A stirred mixture of 1.64 g of ethyl 4-chloro-3-oxobutyrate (10.0 mmol), 1.15 g of ethyl 3-aminocrotonate (10.0 mmol), and 1.51 g of 4-nitrobenzaldehyde (10.0 mmol) in 100 mL of methanol was heated at reflux temperature for 18 hrs, cooled, and the solvent was removed in vacuo.

The crude product was initially chromatographed on 200 g of silica packed with dichloromethane and eluted with dichloromethne to 5% EtOAc-dichloromethane (1% change/500 mL) to afford a yellow oily solid which was approximately 50% pure by $^1H$ NMR spectroscopy. This was rechromatographed on 200 g of silica packed with EtOAc-hexanes (1:4). The column was eluted with 600 mL of 1:4 EtOAc-hexanes and 1 L of 1:3 EtOAc-hexanes to afford 590 mg of the desired product (15%) as an oily yellow solid: The chromatographed product was used in the next alkylation step without any further characterization (unstable product, kept in the freezer).

3-Ethoxycarbonyl-1,,4-dihydro-5-methoxycarbonyl-6-methyl-4-(4-nitro)phenyl-2-(N-(3-(4,4,-diphenylpiperidin-1-yl)propyl)amino)methylpyridine, hydrochloride (90) 1,4,7,7-Tetrahydro-3-methoxycarbonyl-6-methyl-5-oxo-4-(4-nitrophenyl)-6-(3-(4,4-diphenylpiperidin-1-yl))propylpyrrolo[3,4-b]pyridine, hydrochloride salt, (91). A stirred solution of 93 mg of 1-(3-aminopropyl)-4,4-diphenylpiperidine (0.33 mmol), 118 mg of 5-methyl-2-chloromethyl-4-(4-nitrophenyl)-3-carboethoxy-5-carbomethoxy-1,4-dihydropyridine (0.299 mmol), and 182 mg of potassium carbonate (1.32 mmol) in 5 mL of dry DMF were stirred at room temperature for 6 days. Ethyl acetate (30 mL) was added, and the organic solution was washed with water (20 mL+2×10 mL), dried ($Na_2SO_4$), and concentrated. The crude product was chromatographed on 100 g of silica packed with MeOH-isopropyl amine-EtOAc (1:1:98) . The column was eluted with MeOH-isopropyl amine-EtOAc (1:1:98 (0.5 L), 2:1:97 (0.5 L), 5:1;94 (2 L), 20:1:79 (2 L) to give 63 mg of the 3-ethoxycarbonyl-1,4-dihydro-5-methoxycarbonyl-6-ethyl-4-(4-nitro) phenyl-2-(N-(3-(4,4,-diphenylpiperidin-1-yl) propyl) amino) methylpyridine, hydrochloride (32%) and 16 mg of 1,4,7,7-Tetrahydro-3-methoxycarbonyl-6-methyl-5-oxo-4-(4-nitrophenyl)-6-(3-(4,4-diphenylpiperidin-1-yl))propylpyrrolo[3,4-b]pyridine, hydrochloride salt (9%).

Hydrochloride Salts: The hydrochloride salts were prepared by dissolving the free bases in minimum amounts of ethyl acetate (0.5 mL) and addition of an excess of 1 K HCl in ether (1 mL). Compound 90 can exist as a monohydrochloride or as a dihydrochloride salt. The monohydrochloride salt is soluble in ethyl acetate and the dihydrochloride salt is not. The two can be separated by trituration of the crude product with ethyl acetate, in which case, the monohydrochloride can be found in the ethyl acetate extract.

3-Ethoxycarbonyl-1,4-dihydro-5-methoxycarbonyl-6-methyl-4-(4-nitro)phenyl-2-(N-(3-(4,4,-diphenylpiperidin-1-yl)propyl)amino)methylpyridine, hydrochloride hydrate (90): Anal. Calcd for $C_{39}H_{44}N_4O_7 \cdot HCl \cdot H_2O$: C, 63.71; H, 6.44; N, 7.62. Found: C, 63.75; H, 6.53; N, 7.19.

3-Ethoxycarbonyl-1,4-dihydro-5-methoxycarbonyl-6-methyl-4-(4-nitrophenyl)-2-(N-(3-(4,4-diphenylpiperidin-1-yl)propyl)amino)methylpyridine, dihydrochloride: Anal. Calcd for $C_{39}H_{44}N_4O_7 \cdot 2HCl$: C, 62.15; H, 6.15; N, 7.43. Found: C, 61.75; HI 6.16; N, 7.32.

1,4,7,7-Tetrahydro-3-methoxycarbonyl-6-methyl-5-ozo-4-(4-nitrophenyl)-6-(3-(4,,4-diphenylpiperidin-1-yl))propylpyrrolo[3,4-b]pyridine, hydrochloride hydrate (91). Anal. Calcd for $C_{37}H_{38}N_4O_6 \cdot HCl \cdot H_2O$: C, 64.48; H, 6.00; N, 8.13. Found: C, 64.05; H, 6.05; N, 8.53.

EXAMPLE 92

1,4-Dihydro-5-methoxycarbonyl-1,2,6-trimethyl-4-(4-nitrophenyl)-3-3-(4,4-diphenylpiperidin-1-yl)propoxy]carbonylpyridine hydrochloride hydrate (92). Sodium hydride (60% dispersion in mineral oil, 100 mg, 2.51 mmol, 3.0 equiv) was washed with anhydrous hexane under argon, and the washings were discarded. Tetrahydrofuran (11 mL) was added and the resulting suspension was cooled to 0° C. A solution of 1,4-dihydro-5-methoxycarbonyl-2,6-dimethyl-4-(4-nitrophenyl)-3-[3-(4,4-diphenylpiperidin-1-yl)propoxy]carbonylpyridine (510 mg, 0.840 mmol, 1.0 equiv) in THF (4 mL) was added, followed by $CH_3I$ (0.156 mL, 2.51 mmol, 3.0 equiv). The resulting orange suspension was stirred at 0° C. for 2 hours and then at room temperature for 1.5 hours. Water (10 mL) was added, the pH was adjusted to 9–10 by addition of 6M aq. NaOH, and the aqueous phase, was extracted with EtOAc (4×20 mL). The combined organic solutions were dried over $MgSO_4$ and concentrated. The residue was purified by flash chromatography ($SiO_2$, EtOAc-hexane 1:1 to 1:0) to give 218 mg (42%) of yellow solid, which was characterized spectroscopically. To a solution of this product in EtOAc (5 mL) was added a solution of HCl in ether (1.0M, 0.38 mL, 1.1 equiv). The mixture was warmed to 50° C. until the solution was clear, then cooled slowly to 0° C. Filtration afforded 64 mg of yellow solid: m.p. 127–128° C.; Anal. Calcd. for $C_{37}H_{41}N_3O_6 \cdot HCl$, $H_2O$: C, 65.53; H, 6.54; N, 6.20. Found: C, 65.73 H, 6.34; N, 6.12.

EXAMPLE 93

(±)-1,4-Dihydro-3-methoxycarbonyl-2,6-dimethyl-4-(4-nitrophenyl)-5-{N-[3-(4,4-diphenylpiperidin-1-yl)propyl]} carboxamidopyridine hydrochloride hydrate ((±)-93). This compound was prepared according to Method A. A solution of N-(3-(4,4-diphenylpiperidin-1-yl)propyl)acetoacetamide (365 mg, 0.964 mmol, 1.0 equiv), methyl 3-aminocrotonate (138 mg, 1.20 mmol, 1.2 equiv, Aldrich), and 4-nitrobenzaldehyde (181 mg, 1.20 mmol, 1.2 equiv, Aldrich) in isopropanol (20 ml) was refluxed under argon for 60 hours. The mixture was cooled to room temperature and concentrated, and the residue was diluted with $CH_2Cl_2$, washed with water, dried over $MgSO_4$, and concentrated. The residue was purified by flash chromatography ($SiO_2$, EtOAc, followed by EtOAc-MeOH 19:1 and 9:1) to give 147.8 mg (25%) of yellow solid, which was characterized spectroscopically. To a solution of this product in EtOH (2 mL) was added a solution of HCl in ether (1.0M, 0.24 mL, 1.0 equiv). Addition of ethyl acetate (3 mL) followed by heating gave a clear solution. Slow cooling of this solution, followed by filtration, gave 91 mg of yellow crystalline solid: m.p. 182–183° C.; Anal. Calcd. for $C_{36}H_{40}N_4O_5 \cdot HCl \cdot H_2O$: C, 65.20; H, 6.54; N, 8.45. Found: C, 65.30; H, 6.28; N, 8.15.

(−)- and (+)-93 hydrochloride hydrate. The enantiomers of 93.HCl.$H_2O$ were separated on a chiral HPLC column as follows. Four injections of (±)-93.HCl .$H_2O$ (ca. 22.5 mg per injection in EtOH solution) were made onto a Chiralpak AS column (20×250 mm, Daicel), which was eluted with EtOH-hexane-diethylamine (30:70:0.05) at a flowrate of 8.0 mL/min with UV detection at 300 nm. The first major peak to elute (retention time 8.68 min) was further purified by flash chromatography ($SiO_2$, MeOH—$CH_2Cl_2$ 12:88). To a solution of this product in $CH_2Cl_2$ (3 mL) was added HCl in ether (1.0M, 0.25 mL). After removal of the solvents, a solution of the residue in $CH_2Cl_2$ (2 mL) was added dropwise into ether (6 mL) with swirling to give, after filtration, 18.6 mg of yellow powder: $[\alpha]_D = -30.4°$ ($CH_2Cl_2$, 0.000745 g/mL); m.p. 176° C.; Anal. Calcd. for $C_{36}H_{40}N_4O_5 \cdot HCl \cdot H_2O$: C, 65.20; H, 6.54; N, 8.45. Found: C, 65.36; H, 6.46; N, 8.42. The second major peak to elute from the chiral column (retention time 14.14 min) was reinjected into the chiral column, collected, and converted to the HCl salt and precipitated as described for the (−)-enantiomer to afford 8.5 mg of yellow powder: $[\alpha]_D = +26.6°$ ($CH_2Cl_2$, 0.001033 g/mL); m.p. 182 ° C.; Anal. Calcd. for $C_{36}H_{40}N_4O_5 \cdot HCl \cdot H_2O$: C, 65.20; H, 6.54; N, 8.45. Found: C, 65.51; H, 6.42; N, 8.36.

EXAMPLE 94

1,4-Dihydro-3-methoxycarbonyl-2,6-dimethyl-4-(4-nitrophenyl)-3-13-(4,4-diphenylpiperidin-1-yl)propoxy]carbonylpyridine hydrochloride (94). This compound was prepared according to Method A. A solution of methyl 3-aminocrotonate (265 mg, 2.3 mmol, 1.0 equiv), 4-nitrobenzaldehyde (348 mg, 2.3 mmol, 1.0 equiv), and acetoacetic acid 3-(4,4-diphenylpiperidin-1-yl)propyl] ester (872 mg, 2.3 mmol, 1.0 equiv) in isopropanol was refluxed under argon with stirring for 68 hours. Cooling and removal of solvent gave a residue, which was purified by flash chromatography ($SiO_2$, EtOAc-hexane 1:1 and 1:2 followed by EtOAc) to afford 717 mg (51%) of yellow solid, which was characterized spectroscopically. To a solution of this product (710 mg, 1.16 mmol, 1.0 equiv) in EtOH (5 mL) was added a solution of HCl in ether (1.0M, 1.5 mL, 1.5 mmol, 1.3 equiv). The solvents were removed and the residue was dissolved in $CH_2Cl_2$. This solution was added dropwise to 25 mL of ether to afford, after filtration, 500 mg of yellow crystalline solid: m.p. 152–153° C. Anal. Calcd. for $C_{36}H_{39}N_3O_6 \cdot HCl$: C, 66.92; H, 6.24; N, 6.50. Found: C, 66.70; H, 5.99; N, 6.27.

EXAMPLE 95

5-Carboxamido-1,4-dihydro-2,6-dimethyl-4-(4-nitrophenyl)pyridine-3-carboxylic acid. A solution of 3-aminocrotonamide (6.028 g, 60.21 mmol), 4-nitrobenzaldehyde (6.066 g, 40.14 mmol) and 2-cyanoethyl acetoacetate (6.227 g, 40.14 mmol) in 125 mL of EtOH was refluxed for 48 hrs. The reaction mixture was filtered and the filtrate was concentrated to give a brown oil. This brown oil was dissolved in 250 mL of $CHCl_3$ (with addition of a small amount of acetone to give a homogeneous solution), washed with water (2×100 mL) and dried over $Na_2SO_4$. After filtration and removal of solvent, the residue was dissolved into 200 mL of MeOH and treated with 100 mL 2N KOH solution at 0° C. for 30 min. The MeOH was removed in vacuo and the aqueous layer was diluted with 100 mL of water and washed with EtOAc (2×100 mL). With stirring, the aqueous layer was acidified to pH 1 by addition of 6N hydrochloric acid. The yellow precipitate was collected by filtration, washed with 10 mL of cold water and dried in vacuo to afford 5.877 g (46.1% yield for two steps) of yellow powder.

3-(4-Hydroxy-4-phenylpiperidin-1-yl)propionitrile. To a solution of 4-hydroxy-4-phenylpiperidine (3.11 g, 17.5 mmol, 1.00 equiv) in EtOH (30 mL) was added acrylonitrile (2.89 mL, 43.8 mmol, 2.50 equiv) dropwise at 0° C. The mixture was stirred at room temperature for 1.5 hours and then concentrated to afford 3.71 g (92%) of white solid, which was characterized spectroscopically.

1-(3-Aminopropyl)-4-hydroxy-4-phenylpiperidine. To a solution of 3-(4-hydroxy-4-phenylpiperidin-1-yl) propionitrile (3.71 g, 16.1 mmol, 1.00 equiv) in THF (15 mL) at room temperature was added borane-tetrahydrofuran complex (1.0M in THF, 56.3 mL, 56.3 mmol, 3.50 equiv) dropwise. The mixture was stirred at reflux for 4.5 hours and then cooled to room temperature. Aqueous HCl (6N, 85 mL) was added and the mixture was stirred at 50–70° C. for 2 hours. The mixture was basified to pH 9–10 by addition of 6N aqueous NaOH and extracted with EtOAc (75 mL) and $CH_2Cl_2$ (3×75 mL). The combined organic solutions were dried over $MgSO_4$ and concentrated. To a solution of the residue in $CH_2Cl_2$ (75 mL) was added HCl in $Et_2O$ (1.0M, 38 mL, 2.3 equiv). After removal of the solvents, the residue was triturated with $Et_2O$ (185 mL). The resulting white solid was collected by filtration and washed with Et.0. Water (50 mL) was added to this solid, and the mixture was basified to pH 10–11 by addition of 1N aqueous NaOH and extracted with $CH_2Cl_2$ (150 mL+2×75 mL). The combined $CH_2Cl_2$ solutions were dried over $MgSO_4$ and concentrated to give 3.12 g (83%) of colorless oil, which was characterized spectroscopically.

5-Carboxamido-1,4-dihydro-3-{N-[3-(4-hydroxy-4-phenylpiperidin-1-yl) propylcarboxamido]}-2,6-dimethyl-4-(4-nitrophenyl)pyridine hydrochloride hydrate (95). A mixture of 5-carboxamido-1,4-dihydro-2,6-dimethyl-4-(4-nitrophenyl)pyridine-3-carboxylic acid (200 mg, 0.63 mmol, 1.00 equiv), 1-(3-dimethylaminopropyl)-3-ethylcarbodiimide hydrochloride (181.3 mg, 0.946 mmol, 1.50 equiv) and 4-dimethylaminopyridine (84.7 mg, 0.690 mmol, 1.10 equiv) in anhydrous $CH_2C_2$ (15 mL) was stirred at room temperature under argon for 1 hour. A solution of 1-(3-aminopropyl)-4-hydroxy-4-phenylpiperidine (177 mg, 0.756 mmol, 1.20 equiv) in $CHCl_2$ (10 mL) was injected, and the mixture was stirred at reflux for 14 hours. Anhydrous DMF (8 mL) was injected, and the resulting clear solution was refluxed for an additional hour. The mixture was cooled to room temperature, diluted with $CH_2Cl_2$ (150 mL), and washed with saturated aqueous $NH_4Cl$ (3×40 mL). The organic phase was dried over $MgSO_4$ and concentrated. The residue was purified by flash chromatography ($SiO_2$, $CHCl_3$—MeOH-methanolic ammonia (2M) 100:9:7) to afford 145 mg (43%) of 95 free base as a yellow solid, which was characterized spectroscopically. To a solution of this product in $CH_2Cl_2$ (10 mL) was added HCl in ether (1.0M, 0.5 mL, 1.3 equiv). After removal of the solvents, the residue was dissolved in $CH_2Cl_2$ (5 mL) and added dropwise to ether (30 mL) with swirling to give, after filtration, 130 mg of yellow solid: m.p. 159° C. (decomp.); Anal. Calcd. for $C_{29}H_{35}N_5O_5$ HCl.1.9 $H_2O$: C, 57.64; H, 6.64; N, 11.59. Found: 35 C, 57.50; H, 6.65; N, 11.58.

EXAMPLE 96

4-Acetyl-1-(3-aminopropyl)-4-phenylpiperidine. 4-Acetyl-4-phenylpiperidine (1.53 g, 7.50 mmol, 1.00 equiv, Aldrich), 3-bromopropylamine hydrobromide (1.64 g, 7.50 mmol, 1.00 equiv) and potassium carbonate (1.24 g, 9.00 mmol, 1.20 equiv) were stirred in refluxing 1,4-dioxane (50 mL) for 12 hours. After removal of dioxane, water (50 mL) was added and the pH was adjusted to 11–12 by addition of 1N aqueous NaOH. The mixture was extracted with $CH_2Cl_2$ (100 mL+3×50 mL). The combined organic solutions were dried over $MgSO_4$ and concentrated. The residue was purified by flash chromatography (EtOAc-MeOH—$Et_3N$ 100:40:20) to give 780 mg (40%) of colorless oil, which was characterized spectroscopically.

3-{N-[3-(4-Acetyl-4-phenylpiperidin-1-yl)propyl]} carboxamido-5-carboxamido-1,4-dihydro-2,6-dimethyl-4-(4-nitrophenyl)pyridine hydrochloride sesquihydrate (96). A mixture of 5-carboxamido-1,4-dihydro-2,6-dimethyl-4-(4-nitrophenyl)pyridine-3-carboxylic acid (200 mg, 0.63 mmol, 1.00 equiv), 1-(3-dimethylaminopropyl)-3-ethylcarbodiimide hydrochloride (181.3 mg, 0.946 mmol, 1.50 equiv) and 4-dimethylaminopyridine (84.7 mg, 0.690 mmol, 1.10 equiv) in anhydrous $CH_2Cl_2$ (20 mL) was stirred at room temperature under argon for 1 hour. A solution of 4-acetyl-1-(3-aminopropyl)-4-phenylpiperidine (197 mg, 0.756 mmol, 1.20 equiv) in $CH_2Cl_2$ (10 mL) was injected, and the mixture was stirred at reflux for 6 hours. The mixture was cooled to room temperature, diluted with $CH_2Cl_2$ (150 mL), and washed with saturated aqueous $NH_4Cl$ (3×40 mL). The organic phase was dried over $MgSO_4$ and concentrated. The residue was purified by flash chromatography ($SiO_2$, $CHCl_3$—MeOH-methanolic ammonia (2M) 90:8:5) to afford 220 mg (62%) of 96 free base as a yellow solid, which was characterized spectroscopically. To a solution of this product in $CH_2Cl_2$ (10 mL) was added HCl in ether (1.0M, 0.5 mL, 1.3 equiv). After removal of the solvents, the residue was dissolved in $CH_2Cl_2$ (5 mL) and added dropwise to ether (30 mL) with swirling to give, after filtration, 190 mg of 96 hydrochloride sesquihydrate (yellow solid): m.p. 177° C. (decomp.); Anal. Calcd. for $C_{31}H_{37}N_5O_5$.HCl.1.5 $H_2O$.0.1 $Et_2O$: C, 59.79; H, 6.71; N, 11.10. Found: C, 59.86; H, 6.73; N, 10.88.

EXAMPLE 97

1-(3-Aminopropyl)-4-cyano-4-phenylpiperidine. 4-cyano-4-phenylpiperidine hydrochloride (5.01 g, 22.5 mmol, 1.00 equiv, Aldrich) was added to water (100 mL), and the solution was basified to pH 10–11 by addition of 6N aqueous NaOH. The aqueous phase was extracted with $CH_2Cl_2$ (3×100 mL). The combined organic solutions were dried over $MgSO_4$ and concentrated. To the residue were added 3-bromopropylamine hydrobromide (4.92 g, 22.5 mmol, 1.00 equiv, Aldrich), anhydrous $K_2CO_3$ (3.42 g, 24.8 mmol, 1.10 equiv), and 1,4-dioxane (100 mL). The mixture was stirred at reflux for 24 hours under a $CaSO_4$ drying tube. The solvent was removed, and the product was purified by flash chromatography ($SiO_2$, $CHCl_3$—MeOH-methanolic ammonia (2M) 100:8:4 to 100:20:8) to give 3.23 g (59%) of colorless oil, which was characterized spectroscopically.

(±)-5-Carboxamido-3-{N-[3-(4-cyano-4-phenylpiperidin-1-yl)propyl]}carboxamido-1,4-dihydro-2,6-dimethyl-4-(4-nitrophenyl)pyridine hydrochloride sesquihydrate (97). A mixture of 5-carboxamido-1,4-dihydro-2,6-dimethyl-4-(4-nitrophenyl)pyridine-3-carboxylic acid (200 mg, 0.63 mmol, 1.00 equiv), 1-(3-dimethylaminopropyl)-3-ethylcarbodiimide hydrochloride (181.3 mg, 0.946 mmol, 1.50 equiv) and 4-dimethylaminopyridine (84.7 mg, 0.690 mmol, 1.10 equiv) in anhydrous $CH_2Cl_2$ (20 mL) was stirred at room temperature under argon for 1 hour. A solution of 1-(3-aminopropyl)-4-cyano-4-phenylpiperidine (184 mg, 0.756 mmol, 1.20 equiv) in $CH_2Cl_2$ (10 mL) was injected, and the mixture was stirred at reflux for 6 hours. The mixture was cooled to room temperature, diluted with $CH_2Cl_2$ (150 mL), and washed with saturated aqueous $NH_4Cl$ (3×40 mL). The organic phase was dried over $MgSO_4$ and concentrated. The residue was purified by flash chromatography ($SiO_2$, $CHCl_3$—MeOH-methanolic ammonia (2M) 100:4:2) to afford 220 mg (64%) of 97 free base as a yellow solid, which was characterized spectroscopically. To a solution of this product (210 mg, 0.387 mmol) in $CH_2Cl_2$ (10 mL) was added HCl in ether (1.0M, 0.5 mL, 1.3 equiv). After removal of the solvents, the residue was dissolved in $CH_2Cl_2$ (5 mL) and added dropwise to ether (30 mL) with swirling to give, after filtration, 200 mg of 97 hydrochloride sesquihydrate (yellow solid): m.p. 182° C. (decomp.); Anal. Calcd. for $C_{30}H_{34}N_6O_4 \cdot HCl \cdot 1.5\ H_2O$: C, 59.45; H, 6.32; N, 13.87. Found: C, 59.35; H, 6.15; N, 13.76.

(−)- and (+)-97 hydrochloride hydrate. The enantiomers of 3 free base (700 mg) were separated in seven injections on a Chiralpak AS column (20×250 mm, Daicel), which was eluted with EtOH-hexane 20:80 at 9.0 mL/min with UV detection at 300 nm. The first major peak eluted at 27 min. To a solution of this product ($[\alpha]_D = +29.9°$ (MeOH, 0.01395 g/mL)) in EtOH (10 mL) was added HCl in ether (1.0M, 0.50 mL) at 0° C. After removal of the solvents, a solution of the residue in EtOH (2 mL) was added dropwise into ether (50 mL) with swirling to give, after filtration, 282.1 mg of yellow powder: $[\alpha]_D = -45.0°$ (MeOH, 0.0119 g/mL); m.p. 199° C. (decomp.); Anal. Calcd. for $C_{30}H_{34}N_6O_4 \cdot HCl \cdot 2.15\ H_2O$: C, 58.32; HI 6.41;

N, 13.60. Found: C, 58.49; H, 6.22; N, 13.31. The second major component eluted at 43 min $[\alpha_D] = -28.7°$ (MeOH, 0.02005 g/mL)). This product was converted to the HCl salt and precipitated as described for the other enantiomer to afford 272.9 mg of yellow powder: $[\alpha]_D = +45.3°$ MeOH, 0.01085 g/mL); m.p. 199° C. (decomp.); Anal. Calcd. for $C_{30}H_{34}N_6O_4 \cdot HCl \cdot 2.15\ H_2O$: C, 58.32; HI 6.41; N, 13.60. Found: C, 58.16; H, 6.21; N, 13.39.

EXAMPLE 98

4-(4-Methoxyphenyl)-4-phenylpiperidine. 4-Hydroxy-4-phenylpiperidine (5.00 g, 28.2 mmol, 1.00 equiv, Aldrich) was added to a suspension of $AlCl_3$ (18.8 g, 141 mmol, 5.00 equiv) in anhydrous anisole (100 mL). The mixture was stirred at room temperature for 1 hour and then heated to 50° C. for 3.5 hours. It was cooled to room temperature and poured cautiously into ice-water. The mixture was basified to pH 11 by addition of 6M aqueous NaOH, and extracted with EtOAc (3×75 mL). The combined organic solutions were applied directly to a flash chromatography column, which was eluted with $CH_2Cl_2$—$NH_3$ in MeOH (0.67M), 4:1 to afford 1.683 g (22%) of light yellow oil, which was characterized spectroscopically.

3-[4-(4-Methoxyphenyl)-4-phenylpiperidin-1-yl] propionitrile. Acrylonitrile (1.03 mL, 15.7 mmol, 2.50 equiv) was added at 0° C. to a solution of 4-(4-methoxyphenyl)-4-phenylpiperidine (1.68 g, 6.28 mmol, 1.00 equiv) in EtOH (20 mL) and the resulting solution was stirred for 1.5 hours at room temperature. After removal of the solvent, the residue was purified by flash chromatography ($SiO_2$, EtOAc-$CHCl_3$ 1:3) to give 1.41 g (70%) of colorless oil, which was characterized spectroscopically.

1-(3-Aminopropyl)-4-(4-methoxyphenyl)-4-phenylpiperidine. To a stirred solution of 3-[4-(4-methoxyphenyl)-4-phenylpiperidin-1-yl]propionitrile (1.41 g, 4.40 mmol, 1.0 equiv) in anhydrous THF (10 mL) under argon was added a solution of $BH_3$ in THF (1.0M, 11.0 mL, 2.5 equiv) at room temperature. The mixture was refluxed for 4.5 hours and then cooled to room temperature. Aqueous HCl (6N, 15 mL) was added and stirring was continued for 2 hours at 55–60° C. The mixture was basified to pH 9 by addition of 6N aqueous NaOH and extracted with $CH_2Cl_2$ (3×75 mL). The combined organic solutions were dried over $MgSO_4$ and concentrated. The residue was dissolved in $CH_2Cl_2$ (10 mL) and treated with HCl in ether (1.0M, 9.0 mL, 2.0 equiv). The solvents were removed, ether (30 mL) was added, the mixture was filtered, and the filter cake was washed with ether (2×10 mL). Water (20 mL) was added to the resulting white solid, the pH was adjusted to 10 with 1N NaOH, and the aqueous phase was extracted with $CH_2Cl_2$ (3×40 mL). The combined organic solutions were dried over $MgSO_4$ and concentrated to give 610 mg (43%) of white solid, which was characterized spectroscopically.

5-Carboxamido-1,4-dihydro-3-{N-[3-(4-(4-methoxyphenyl)-4-phenylpiperidin-1-yl)propyl]} carboxamido-2,6-dimethyl-4-(4-nitrophenyl)pyridine hydrochloride (98). A mixture of 5-carboxamido-1,4-dihydro-2,6-dimethyl-4-(4-nitrophenyl)pyridine-3-carboxylic acid (200 mg, 0.63 mmol, 1.00 equiv), 1-(3-dimethylaminopropyl)-3-ethylcarbodiimide hydrochloride (181.3 mg, 0.946 mmol, 1.50 equiv) and 4-dimethylaminopyridine (84.7 mg, 0.690 Mmol, 1.10 equiv) in anhydrous $CH_2Cl_2$ (20 mL) was stirred at room temperature under argon for 1 hour. A solution of 1-(3-aminopropyl)-4-(4-methoxyphenyl)-4-phenylpiperidine (245 mg, 0.755 mmol, 1.20 equiv) in $CH_2Cl_2$ (10 mL) was injected, and the mixture was stirred at reflux for 6 hours. The mixture was cooled to room temperature, diluted with $CH_2Cl_2$ (150 mL), and washed with saturated aqueous $NH_4Cl$ (3×40 mL). The organic phase was dried over $MgSO_4$ and concentrated. The residue was purified by flash chromatography ($SiO_2$, $CHCl_3$—MeOH-methanolic ammonia (2M) 100:4:2) to afford 275 mg (70%) of 98 free base as a yellow solid, which was characterized spectroscopically. To a solution of this product in $CH_2Cl_2$ (10 mL) was added HCl in ether (1.0M, 0.8 mL, 1.8 equiv). After removal of the solvents, the residue was dissolved in $CH_2Cl_2$ (5 mL) and added dropwise to ether (30 mL) with swirling to give, after filtration, 225 mg of 98 hydrochloride (yellow solid): m.p. 185° C. (decomp.); Anal. Calcd. for $C_{36}H_{41}N_5O_5 \cdot HCl \cdot 0.4\ CH_2Cl_2$:C, 62.98; H, 6.21; N, 10.09. Found: C, 63.02; H, 6.40; N, 9.76.

EXAMPLE 99

1-Benzyl-4-methyl-piperidin-4-ol. To a solution of 1-benzyl-4-piperidone (5.00 mL, 27.0 mmol, 1.00 equiv, Aldrich) in anhydrous ether at −78° C. under argon was added methyllithium (1.4M in $Et_2O$, 54.0 mL, 53.9 mmol, 2.00 equiv). Stirring was continued at −78° C. for 1.5 hours. Ether (200 mL) and water (40 mL) were added, and the two phases were separated. The aqueous solution was extracted with $Et_2O$ (3×50 mL). The combined organic solutions were dried over $MgSO_4$ and concentrated. The residue was purified by flash chromatography ($SiO_2$, EtOAc to EtOAc-MeOH 9:1) to give 4.81 g (87%) of colorless oil, which was characterized spectroscopically.

1-Benzyl-4-methyl-4-phenylpiperidine. 1-Benzyl-4-methylpiperidin-4-ol (4.81 g, 23.4 mmol, 1.00 equiv) was added to a suspension of $AlCl_3$ (15.62 g, 117 mmol, 5.00 equiv) in benzene (100 mL) at room temperature under argon. The mixture was stirred at reflux for 24 hours, then cooled and poured cautiously into ice water (100 g of ice plus 50 mL of water). The aqueous phase was adjusted to pH 11–12 by addition of 6N aqueous NaOH at 0° C., and extracted with EtOAc (3×100 mL). The combined organic solutions were dried over $MgSO_4$ and concentrated. The residue was purified by flash chromatography ($SiO_2$, hexane-$Et_2O$ 19:1 to 9:1 followed by hexane-EtOAc 3:1) to give 3.23 g (52%) of brown oil, which was characterized spectroscopically.

4-Methyl-4-phenylpiperidine. Freshly prepared methanolic formic acid solution (4.4% by weight, 70 mL) was added to 1-benzyl-4-methyl-4-phenylpiperidine (3.23 g, 12.2 mmol, 1.00 equiv). To the resulting solution was added palladium on carbon (10% Pd, 2.00 g). The mixture was stirred at room temperature for 24 hours. The solid was filtered out and washed with MeOH (30 mL), H2O (15 mL), $CH_2Cl_2$ (30 mL) and MeOH (15 mL). The combined filtrate and washings were concentrated, and the residue was dissolved in $CH_2Cl_2$ (50 mL) and H2O (10 mL). The aqueous phase was adjusted to pH 11 by addition of 1N aqueous NaOH. The organic phase was separated, dried over $MgSO_4$ and concentrated. The residual oil was purified by flash chromatography ($SiO_2$, $CHCl_3$—MeOH—$NH_3$ (2.0M in MeOH) 100:4:0 to 100:20:10) to afford 1.20 g of 1-benzyl-4-methyl-4-phenylpiperidine and 1.10 g (51%, 82% based on unrecovered starting material) of 4-methyl-4-phenylpiperidine, which was characterized spectroscopically.

3-Aminopropyl-4-methyl-4-phenylpiperidine. 4-Methyl-4-phenylpiperidine (1.00 g, 5.70 mmol, 1.00 equiv), 3-bromopropylamine hydrobromide (1.87 g, 8.55 mmol, 1.00 equiv) and potassium carbonate (1.97 g, 14.2 mmol, 2.5 equiv) were stirred in refluxing dioxane (20 mL) for 36 hours. After removal of the solvent, water (50 mL) was added and the pH was adjusted to 11–12 by addition of 1N aqueous NaOH. The mixture was extracted with $CH_2Cl_2$ (150 mL+3×100 mL). The combined organic solutions were dried over $MgSO_4$ and concentrated. The residue was purified by flash chromatography ($SiO_2$, $CHCl_3$-MeOH—$NH_3$ (2M in MeOH) 100:20:10) to give 241 mg (18%) of colorless oil, which was characterized spectroscopically.

5-Carboxamido-1,4-dihydro-2,6-dimethyl-3-{N-[3-(4-methyl-4-phenylpiperidin-1-yl)propyl]}carboxamido-4-(4-nitrophenyl)pyridine hydrochloride hydrate (99). A mixture of 5-carboxamido-1,4-dihydro-2,6-dimethyl-4-(4-nitrophenyl)pyridine-3-carboxylic acid (148 mg, 0.465 mmol, 1.00 equiv), 1-(3-dimethylaminopropyl)-3-ethylcarbodiimide hydrochloride (149 mg, 0.776 mmol, 1.67 equiv) and 4-dimethylaminopyridine (69.5 mg, 0.569 mmol, 1.22 equiv) in anhydrous $CH_2Cl_2$ (15 mL) was stirred at room temperature under argon for 1 hour. A solution of 3-aminopropyl-4-methyl-4-phenylpiperidine (120 mg, 0.517 mmol, 1.11 equiv) in $CH_2Cl_2$ (5 mL) was injected, and stirring was continued at reflux for 6 hours. The mixture was cooled to room temperature, diluted with $CH_2Cl_2$ (120 mL), and washed with saturated aqueous $NH_4Cl$ (3×35 mL). The organic phase was dried over $MgSO_4$ and concentrated. The residue was purified by flash chromatography ($SiO_2$, $CHCl_3$—MeOH-methanolic ammonia (2M) 100:3:1.5 to 100:4:2) to afford 135 mg (54%) of 99 free base as a yellow solid, which was characterized spectroscopically. To a solution of this product (132 mg, 0.25 mmol, 1.0 equiv) in $CH_2Cl_2$ (4 mL) and MeOH (1 mL) was added HCl in ether (1.0M, 0.5 mL, 2.0 equiv). After removal of the solvents, the residue was dissolved in $CH_2Cl_2$ (4 mL) and MeOH (1 mL) and added dropwise to ether (30 mL) with swirling to give, after filtration, 110 mg of yellow solid: m.p. 178° C. (decomp.); Anal. Calcd. for $C_{30}H_{37}N_5SO_4 \cdot HCl \cdot 1.4 H_2O$: C, 60.73; HI 6.93; N, 11.80. Found: C, 60.76; H, 6.96; N, 11.70.

EXAMPLE 100

6-Ethyl-2,2-dimethyl-2H,4H-1,3-dioxin-4-one. To a solution of 2,2-dimethyl-1,3-dioxan-4,6-dione 1 (40.4 g, 280 mmol, 1.00 equiv, Aldrich) in anhydrous $CH_2Cl_2$ (300 mL) at 0° C. under argon was added propionyl chloride (26.7 mL, 308 mmol, 1.10 equiv) followed by pyridine (45.3 mL, 560 mmol, 2.00 equiv). The resulting mixture was stirred at 0° C. for 1 hour and then at room temperature for 5 hours. The organic solution was washed with 1N aqueous HCl (2×100 mL) and water (3×100 mL), dried over $MgSO_4$ and concentrated to give 32 g of 2,2-dimethyl-5-propanoyl-1,3-dioxan-4,6-dione as a purple solid, which was characterized spectroscopically. A solution of this solid and acetone (10.3 mL, 140 mmol, 0.50 equiv) in toluene (300 mL) was stirred at reflux under argon for 1.5 hours. After removal of the solvents, the residue was distilled at reduced pressure to afford 15.0 g (34%) of colorless oil (b.p. 85–87° C./0.5 mm Hg), which was characterized spectroscopically.

3-Amino-2-pentenamide. Anhydrous ammonia gas was passed into a solution of 6-ethyl-2,,2-dimethyl-2H, 4H-1,3-dioxin-4-one (15.1 g, 96.7 mmol) in p-xylene (240 mL) at 115° C. (bath temperature) for 5 hours. The mixture was cooled to room temperature, diluted with $CHCl_3$ (145 mL), dried over $MgSO_4$, and concentrated to afford 10.05 g (91%) of light yellow oil, which was characterized spectroscopically and used for the next step without purification.

2-Cyanoethyl 3-oxopentanoate. A solution of ethyl propionylacetate (50 g, 0.35 mol, 1.0 equiv) and 3-hydroxypropionitrile (35 mL, 0.52 mol, 1.5 equiv) was heated at 190–210° C. while EtOH (19 mL) was collected by distillation. The residue was distilled in vacuo to afford 37 g (63%) of yellow oil (b.p. 120–125° C./0.4 mm Hg), which was characterized spectroscopically.

2-Cyanoethyl 2-(4-nitrophenyl)methyleno-3-oxopentanoate. In a dry flask, a mixture of 4-nitrobenzaldehyde (12.7 g, 84.3 mmol, 1.00 equiv), 2-cyanoethyl 3-oxopentanoate (15.0 g, 88.7 mmol, 1.00 equiv), piperidine (0.44 mL, 4.4 mmol, 0.05 equiv) and acetic acid (0.25 mL, 4.4 mmol, 0.05 equiv) in 2-propanol (200 mL) was stirred at room temperature under argon for 24 hours. The resulting white precipitate was collected by filtration, washed with cold 2-propanol (3×50 mL), and dried to afford 24.6 g (96%) of white solid, which was characterized spectroscopically.

5-Carboxamido-3-(2-cyanoethoxy)carbonyl-2,6-diethyl-1,4-dihydro-4-(4-nitrophenyl) pyridine. A mixture of 2-cyanoethyl 2-(4-nitrophenyl)methyleno-3-oxopentanoate (24.2 g, 80.1 mmol, 1.00 equiv) and 3-amino-2-pentenamide (10.1 g, 88.1 mmol, 1.10 equiv) in EtOH was stirred at reflux under argon for 14 hours. Removal of the solvent afforded 32.1 g (91% crude yield) of yellow solid, which was characterized spectroscopically and used for the next step without purification.

5-Carboxamido-2,6-diethyl-1,4-dihydro-4-(4-nitrophenyl)pyridine-3-carboxylic acid. Aqueous NaOH (1N, 204 mL, 204 mmol, 3.0 equiv) was added slowly with stirring at −5° C. to a solution of 5-carboxamido-3-(2-cyanoethoxy)carbonyl-2,6-diethyl-1,4-dihydro-4-(4-nitrophenyl) pyridine (27.1 g, 68.0 mmol, 1.0 equiv) in acetone (100 mL) and stirring was continued at −5–0° C. for 1 hour. Acetone was removed in vacuo at 10° C. The aqueous solution was extracted with EtOAc (2×150 mL) and CH$_2$Cl$_2$ (2×100 mL), and the organic extracts were discarded. The aqueous phase was acidified to pH 2–3 by addition of 6N aqueous HCl (ca. 340 mL) with stirring at −5–0° C., and stirring was continued for 30 minutes at 0° C. The resulting solid was collected by filtration, washed with water (2×30 mL), and dried in vacuo at room temperature to give 22.1 g (94%) of yellow solid, which was characterized spectroscopically.

5-Carboxamido-2,6-diethyl-1,4-dihydro-3-{N-[3-(4-hydroxy-4-phenylpiperidin-1-yl)propyl]}carboxamido-4-(4-nitrophenyl)pyridine hydrochloride hydrate (100). A mixture of 5-carboxamido-2,6-diethyl-1,4-dihydro-4-(4-nitrophenyl)pyridine-3-carboxylic acid (250 mg, 0.724 mmol, 1.00 equiv), 1-(3-dimethylaminopropyl)-3-ethylcarbodiimide hydrochloride (208.2 mg, 1.086 mmol, 1.50 equiv) and 4-dimethylaminopyridine (92.3 mg, 0.796 mmol, 1.10 equiv) in anhydrous CH$_2$Cl$_2$ (15 mL) was stirred at room temperature under argon for 1 hour. A solution of 1-(3-aminopropyl)-4-hydroxy-4-phenylpiperidine (203.6 mg, 0.870 mmol, 1.20 equiv) in CH$_2$Cl (10 mL) was injected, and the mixture was stirred at reflux for 14 hours. Anhydrous DMF (8 mL) was injected, and the resulting clear solution was refluxed for an additional hour. The mixture was cooled to room temperature, diluted with CH$_2$Cl$_2$ (150 mL), and washed with saturated aqueous NH$_4$Cl (3×40 mL). The organic phase was dried over MgSO$_4$ and concentrated. The residue was purified by flash chromatography (SiO$_2$, CHCl$_3$—MeOH-methanolic ammonia (2M) 100:8:6) to afford 188 mg (46%) of 100 free base as a yellow solid, which was characterized spectroscopically. To a solution of this product in CH$_2$Cl$_2$ (10 mL) was added HCl in ether (1.0M, 0.6 mL, 1.8 equiv). After removal of the solvents, the residue was dissolved in CH$_2$Cl$_2$ (5 mL) and added dropwise to ether (30 mL) with swirling to give, after filtration, 202 mg of 100 hydrochloride hydrate (yellow solid): m.p. 165° C. (decomp.); Anal. Calcd. for C$_{31}$H$_{39}$N$_5$O$_5$.HCl.1.8 H$_2$O: C, 59.05; H, 6.97; N, 11.11. Found: C, 58.98; H, 6.70; N, 11.09.

EXAMPLE 101

3-[4-(4-Chlorophenyl)-4-hydroxypiperidin-1-yl]propionitrile. Acrylonitrile (2.33 mL, 35.4 mmol, 2.50 equiv) was added at 0° C. to a solution of 4-(4-chlorophenyl)-4-hydroxypiperidine (3.00 g, 14.2 mmol, 1.00 equiv, Aldrich) in EtOH (30 mL) and the resulting solution was stirred for 1.5 hours at room temperature. The solvent was removed to give 3.71 g (99%) of white solid, which was characterized spectroscopically and used without purification for the next reaction.

1-(3-Aminopropyl)-4-(4-chlorophenyl)-4-hydroxypiperidine. To a stirred solution of 3-[4-(4-chlorophenyl)-4-hydroxypiperidin-1-yl]propionitrile (3.51 g, 13.2 mmol, 1.0 equiv) in anhydrous THF (20 mL) under argon was added a solution of BH$_3$ in THF (1.0M, 46.4 mL, 3.5 equiv) at room temperature. The mixture was refluxed for 4.5 hours and then cooled to room temperature. Aqueous HCl (6N, 30 mL) was added and stirring was continued for 2 hours at 55–60° C. The mixture was basified to pH 9 by addition of 6N aqueous NaOH and extracted with CH$_2$Cl$_2$ (3×150 mL). The combined organic solutions were dried over MgSO$_4$ and concentrated. The residue was dissolved in CH$_2$Cl$_2$ (20 mL) and treated with HCl in ether (1.0M, 27.7 mL, 2.1 equiv). The solvents were removed, ether (60 mL) was added, the mixture was filtered, and the filter cake was washed with ether (2×20 mL). Water (40 mL) was added to the resulting white solid, the pH was adjusted to 10 with 1M NaOH, and the aqueous phase was extracted with CH$_2$Cl$_2$ (3×80 mL). The combined organic solutions were dried over MgSO$_4$ and concentrated to give 3.10 g (87%) of white solid, which was characterized spectroscopically.

5-Carboxamido-2,6-diethyl-1,4-dihydro-3-{N-[3-(4-hydroxy-4-phenylpiperidin-1-yl)propyl]}carboxamido-4-(4-nitrophenyl)pyridine hydrochloride hydrate (101). A mixture of 5-carboxamido-2,6-diethyl-1,4-dihydro-4-(4-nitrophenyl)pyridine-3-carboxylic acid (250 mg, 0.724 mmol, 1.00 equiv), 1-(3-dimethylaminopropyl)-3-ethylcarbodiimide hydrochloride (208.2 mg, 1.086 mmol, 1.50 equiv) and 4-dimethylaminopyridine (92.3 mg, 0.796 mmol, 1.10 equiv) in anhydrous CH$_2$Cl$_2$ (15 mL) was stirred at room temperature under argon for 1 hour. A solution of 1-(3-aminopropyl)-4-chlorophenyl-4-hydroxypiperidine (233.5 mg, 0.870 mmol, 1.20 equiv) in CH$_2$Cl$_2$ (10 mL) was injected, and the mixture was stirred at reflux for 6 hours. The mixture was cooled to room temperature, diluted with CH$_2$Cl$_2$ (150 mL), and washed with saturated aqueous NH$_4$Cl (3×40 mL). The organic phase was dried over MgSO$_4$ and concentrated. The residue was purified by flash chromatography (SiO$_2$, CHCl$_3$—MeOH-methanolic ammonia (2M) 90:8:5) to afford 256 mg (59%) of 101 free base as a yellow solid, which was characterized spectroscopically. To a solution of this product in CH$_2$Cl$_2$ (10 mL) was added HCl in ether (1.0M, 0.8 mL, 1.9 equiv). After removal of the solvents, the residue was dissolved in CH$_2$Cl$_2$ (5 mL) and added dropwise to ether (30 mL) with swirling to give, after filtration, 224 mg of yellow solid: m.p. 164° C. (decomp.); Anal. Calcd. for C$_{31}$H$_{38}$N$_5$O$_5$.HCl.1.8 H$_2$O: C, 59.05; H, 6.97; N, 11.11. Found: C, 58.98; H, 6.70; N, 11.09.

EXAMPLE 102

5-Carboxamido-3-{H-[(4-cyano-4-phenylpiperidin-1-yl)propyl]}carboxamido-2,6-diethyl-1,4-dihydro-4-(4-nitrophenyl)pyridine hydrochloride hydrate (102). A mixture of 5-carboxamido-2,6-diethyl-1,4-dihydro-4-(4-nitrophenyl)pyridine-3-carboxylic acid (1.00 g, 2.90 mmol, 1.00 equiv), 1-(3-dimethylaminopropyl)-3-ethylcarbodiimide hydrochloride (830 mg, 4.34 mmol, 1.50 equiv) and 4-dimethylaminopyridine (389.7 mg, 3.19 mmol, 1.10 equiv) in anhydrous CH$_2$Cl$_2$ (50 mL) was stirred at room temperature under argon for 1 hour. A solution of 1-(3-aminopropyl)-4-cyano-4-phenylpiperidine (848 mg, 3.48 mmol, 1.20 equiv) in CH$_2$Cl$_2$ (10 mL) was injected, and the mixture was stirred at reflux for 6 hours. The mixture was cooled to room temperature, diluted with CH$_2$Cl$_2$ (250 mL), and washed with saturated aqueous NH$_4$Cl (3×80 mL). The organic phase was dried over MgSO$_4$ and concentrated. The residue was purified by flash chromatography (SiO$_2$, CHCl$_3$—MeOH-methanolic ammonia (2M) 100:2:1 to 100:3:1.5) to afford 1.53 g (92%) of yellow solid (102), which was characterized spectroscopically. To a solution of this product (1.51 g, 2.65 mmol, 1.00 equiv) in CH$_2$Cl$_2$ (10 mL) was added a solution of HCl in ether (1.0M, 5.2 mL, 2.0 equiv) at room temperature. After removal of the solvents, a solution of the residue in CH$_2$Cl$_2$ (10 mL) was added dropwise with swirling to ether (50 mL). The resulting precipitate was collected by filtration and dried in vacuo at 85° C. to afford 1.47 g of yellow powder: m.p. 210° C.; Anal. Calcd. for C$_{32}$H$_{38}$N$_6$O$_4$.HCl.1.2 H$_2$O: C, 61.13; H, 6.64; N. 13.37. Found: C, 61.02; H, 6.44; N, 13.12.

(−)- and (+)-102 hydrochloride hydrate. The enantiomers of 102 free base (500 mg) were separated in four injections on a Chiralpak AS column (20×250 mm, Daicel), which was eluted with EtOH-hexane 15:85 at 9.0 mL/min with UV detection at 300 nm. The first major peak eluted at 43 min.

To a solution of this product ([α]$_D$=+13.1° (EtOH, 0.0233 g/mL)) in EtOH (10 mL) was added HCl in ether (1.0M, 0.36 mL) at 0° C. After removal of the solvents, a solution of the residue in EtOH (2 mL) was added dropwise into ether (50 mL) with swirling to give, after filtration, 153.6 mg of yellow powder: [α]$_D$=−36.6° (EtOH, 0.00975 g/mL); m.p. 230° C. (decomp.); Anal. Calcd. for $C_{32}H_{38}N_6O_4$·HCl·1.57 $H_2O$: C, 60.49; H, 6.68; N, 13.23. Found: C, 60.19; H, 6.28; N, 13.01. The second major component eluted at 71 min ([α]$_D$=−17.4° (EtOH, 0.03155 g/mL)). This product was converted to the HCl salt and precipitated as described for the other enantiomer to afford 168.6 mg of yellow powder: [α]=$_D$=+28.6° (EtOH, 0.0101 g/mL); m.p. 230° C. (decomp.); Anal. Calcd. for $C_{32}H_{38}N_6O_4$·HCl·1.57 $H_2O$: C, 60.49; H, 6.68; N, 13.23. Found: C, 60.25; H, 6.34; N, 12.92.

EXAMPLE 103

4,4-bis-(4-Methoxyphenyl)piperidine. To a solution of $AlCl_3$ (26.0 g, 0.195 mmol, 6.00 equiv) in anhydrous anisole (100 mL) at 0° C. under argon was added 4-piperidone hydrate hydrochloride (5.00 g, 32.5 mmol, 1.00 equiv). stirring was continued at 0° C. for 3 hours and then at room temperature for 12 hours. The mixture was added cautiously to ice water (100 g of ice plus 50 mL of water). The aqueous phase was extracted with $Et_2O$ (3×50 mL) and the combined organic solutions were concentrated. The resulting white solid was dissolved in water (100 mL). This solution was basified to pH 11–12 by addition of 1N aqueous NaOH, and extracted with $CH_2Cl_2$ (250 mL+3×150 mL). The combined organic solutions were dried over $MgSO_4$ and concentrated to afford 9.38 g (97%) of colorless oil, which was characterized spectroscopically.

1-(3-Aminopropyl)-4,4-bis-(4-methoxyphenyl) piperidine. 4,4-bis-(4-Methoxyphenyl)piperidine (9.01 g, 30.3 mmol, 1.00 equiv), 3-bromopropylamine hydrobromide (6.66 g, 30.3 mmol, 1.00 equiv) and potassium carbonate (5.02 g, 36.3 mmol, 1.20 equiv) were stirred in refluxing anhydrous 1,4-dioxane (200 mL) for 12 hours. After removal of dioxane, water (200 mL) was added and the pH was adjusted to 11–12 by addition of 1N aqueous NaOH. The mixture was extracted with $CH_2Cl_2$ (4×200 mL). The combined organic solutions were dried over $MgSO_4$ and concentrated. The residue was purified by flash chromatography ($SiO_2$, $CHCl_3$—MeOH—$NH_3$ (2M in MeOH) 100:20:10) to give 6.50 g of 4,4-bis-(4-methoxyphenyl)piperidine and 2.70 g (25%, 90% after correction for recovered starting material) of 1-(3-aminopropyl)-4,4-bis-(4-methoxyphenyl)piperidine (colorless oil), which was characterized spectroscopically.

5-Carboxamido-2,6-diethyl-1,4-dihydro-3-{N-[3-(4,4-bis-(4-methoxyphenyl) piperidin-1-yl) propyl]}carboxamido}-4-( 4-nitrophenyl)pyridine hydrochloride (103). A mixture of 5-carboxamido-2,6-diethyl-1,4-dihydro-4-(4-nitrophenyl)pyridine-3-carboxylic acid (300 mg, 0.869 mmol, 1.00 equiv), 1-(3-dimethylaminopropyl)-3-ethylcarbodiimide hydrochloride (250.0 mg, 1.30 mmol, 1.50 equiv) and 4-dimethylaminopyridine (116.9 mg, 0.957 mmol, 1.10 equiv) in anhydrous $CH_2Cl_2$ (18 mL) was stirred at room temperature under argon for 1 hour. A solution of 1-(3-aminopropyl)-4,4-bis-(4-methoxyphenyl)piperidine (369.6 mg, 1.04 mmol, 1.20 equiv) in $CH_2Cl_2$ (12 mL) was injected, and the mixture was stirred at reflux for 6 hours. The mixture was cooled to room temperature, diluted with $CH_2Cl_2$ (180 mL), and washed with saturated aqueous $NH_4Cl$ (3×50 mL). The organic phase was dried over $MgSO_4$ and concentrated. The residue was purified by flash chromatography ($SiO_2$, $CHCl_3$—MeOH-methanolic ammonia (2M) 100:4:2 to 100:5:2.5) to afford 535 mg (90%) of 103 free base as a yellow solid, which was characterized spectroscopically. To a solution of this product (520 mg, 0.760 mmol, 1.0 equiv) in $CH_2Cl_2$ (5 mL) was added HCl in ether (1.0M, 1.5 mL, 2.0 equiv). After removal of the solvents, the residue was dissolved in $CH_2Cl_2$ (8 mL) and added dropwise to ether (50 mL) with swirling to give, after filtration, 465 mg of yellow solid: m.p. 175° C. (decomp.); Anal. Calcd. for $C_{39}H_{48}N_5O_6$·HCl·1.5 $H_2O$: C, 62.85; H, 6.90; N, 9.40. Found: C, 62.95; H, 6.80; N, 9.16.

EXAMPLE 104

1-(3-Aminopropyl)-4-phenylpiperazine. 4-Phenylpiperazine (5.00 g, 30.8 mmol, 1.00 equiv, Aldrich), 3-bromopropylamine hydrobromide (8.09 g, 37.0 mmol, 1.20 equiv) and potassium carbonate (8.51 g, 61.6 mmol, 2.00 equiv) were stirred in refluxing acetone (200 mL) and EtOH (40 mL) for 14 hours. After removal of the solvents, water (250 mL) was added and the pH was adjusted to 11–12 by addition of 1N aqueous NaOH. The mixture was extracted with $CH_2Cl_2$ (4×250 mL). The combined organic solutions were dried over $MgSO_4$ and concentrated. The residue was purified by flash chromatography ($SiO_2$, $CHCl_3$—MeOH—$NH_3$ (2M in MeOH) 100:10:5 to 100:20:10) to give 3.80 g (56%) of yellow oil, which was characterized spectroscopically.

5-Carboxamido-2,6-diethyl-1,4-dihydro-4-(4-nitrophenyl)-3-{N-[3-(4-phenylpiperazine-1-yl)propyl]}carboxamidopyridine hydrochloride hydrate (104). A mixture of 5-carboxamido-2,6-diethyl-1,4-dihydro-4-(4-nitrophenyl) pyridine-3-carboxylic acid (250 mg, 0.724 mmol, 1.00 equiv), 1-(3-dimethylaminopropyl)-3-ethylcarbodiimide hydrochloride (208 mg, 1.09 mmol, 1.50 equiv) and 4-dimethylaminopyridine (97.2 mg, 0.796 mmol, 1.10 equiv) in anhydrous $CH_2Cl_2$ (15 mL) was stirred at room temperature under argon for 1 hour. A solution of 1-(3-aminopropyl)-4-phenylpiperazine (190 mg, 0.869 mmol, 1.20 equiv) in $CH_2Cl_2$ (10 mL) was injected, and stirring was continued at reflux for 6 hours. The mixture was cooled to room temperature, diluted with $CH_2Cl_2$ (150 mL), and washed with saturated aqueous $NH_4Cl$ (3×40 mL). The organic phase was dried over $MgSO_4$ and concentrated. The residue was purified by flash chromatography ($SiO_2$, $CHCl_3$—MeOH-methanolic ammonia (2M) 100:4:2) to afford 317 mg (80%) of 104 free base as a yellow solid, which was characterized spectroscopically. To a solution of this product (302 mg, 0.550 mmol, 1.0 equiv) in $CH_2Cl_2$ (5 mL) was added HCl in ether (1.0M, 1.5 mL, 2.7 equiv). After removal of the solvents, the residue was dissolved in $CH_2Cl_2$ (5 mL) and added dropwise to ether (30 mL) with swirling to give, after filtration, 285 mg of yellow solid: m.p. 160° C. (decomp.); Anal. Calcd. for $C_{30}H_{38}N_6O_4$·HCl·1.2 $H_2O$: C, 59.58; H, 6.90; N, 13.86. Found: C, 59.49; H, 6.74; N, 13.67.

EXAMPLE 105

8-(3-Aminopropyl)-1-phenyl-1,3,8-triazaspiro[4.5] decan-4-one. 1-Phenyl-1,3,8-triazaspiro[4.5]decan-4-one (5.00 g, 21.6 mmol, 1.00 equiv), 3-bromopropylamine hydrobromide (4.73 g, 21.6 mmol, 1.00 equiv) and potassium carbonate (2.99 g, 21.6 mmol, 1.00 equiv) were stirred in refluxing dioxane (70 mL) for 24 hours. After removal of the solvent, water (50 mL) was added and the pH was adjusted to 11–12 by addition of 1N aqueous NaOH. The mixture was extracted with $CH_2Cl_2$ (200 mL+3×100 mL). The combined organic solutions were dried over $MgSO_4$ and concentrated. The residue was purified by flash chromatography (SiO$_2$, CHCl$_3$—MeOH—NH$_3$ (2M in MeOH) 100:20:10 to 100:24:12) to give 250 mg (4%) of white solid, which was characterized spectroscopically.

5-Carboxamido-2,6-diethyl-1,4-dihydro-4-(4-nitrophenyl)-3-{N-[3-(1-phenyl-4-ozo-1,3,8-triazaspiro[4.5]decan-8-yl)propyl]}carboxamidopyridine hydrochloride hydrate (105). A mixture of 5-carboxamido-2,6-diethyl-1,4-dihydro-4-(4-nitrophenyl)pyridine-3-carboxylic acid (200 mg, 0.580 mmol, 1.00 equiv), 1-(3-dimethylaminopropyl)-3-ethylcarbodiimide hydrochloride (166 mg, 0.869 mmol, 1.50 equiv) and 4-dimethylaminopyridine (77.9 mg, 0.638 mmol, 1.10 equiv) in anhydrous CH$_2$Cl$_2$ (15 mL) was stirred at room temperature under argon for 1 hour. A solution of 8-(3-aminopropyl)-1-phenyl-1, 3, 8-triazaspiro[4.5) decan-4-one (200.7 mg, 0.696 mmol, 1.20 equiv) in CH$_2$Cl$_2$ (10 mL) was injected, and stirring was continued at reflux for 6 hours. The mixture was cooled to room temperature, diluted with CH$_2$Cl$_2$ (150 mL), and washed with saturated aqueous NH$_4$Cl (3×40 mL). The organic phase was dried over MgSO$_4$ and concentrated. The residue was purified by flash chromatography (SiO$_2$, CHCl$_3$—MeOH-methanolic ammonia (2M) 100:2:1 to 100:4:2) to afford 230 mg (65%) of 105 free base as a yellow solid, which was characterized spectroscopically. To a solution of this product (215, 0.349 mmol, 1.0 equiv) in CH$_2$Cl$_2$ (5 mL) and MeOH (1 mL) was added HCl in ether (1.0M, 0.8 mL, 2.3 equiv). After removal of the solvents, the residue was dissolved in CH$_2$Cl$_2$ (5 mL) and MeOH (1 mL) and added dropwise to ether (30 mL) with swirling to give, after filtration, 165 mg of yellow solid: m.p. 187° C. (decomp.); Anal. Calcd. for C$_{33}$H$_{41}$N$_7$O$_5$.HCl.1.4 H$_2$O: C, 58.51; H, 6.67; N. 14.47. Found: C, 58.73; H, 6.80; N, 14.32.

EXAMPLE 106

5-Carboxamido-2,6-diethyl-1,4-dihydro-3-{N-[3-(4-methyl-4-phenyl piperidin-1-yl)propyl]}carboxamido-4-(4-nitrophenyl)pyridine hydrochloride hydrate (106). A mixture of 5-carboxamido-2,6-diethyl-1,4-dihydro-4-(4-nitrophenyl)pyridine-3-carboxylic acid (160 mg, 0.465 mmol, 1.00 equiv), 1-(3-dimethylaminopropyl)-3-ethylcarbodiimide hydrochloride (149 mg, 0.776 mmol, 1.67 equiv) and 4-dimethylaminopyridine (69.5 mg, 0.569 mmol, 1.22 equiv) in anhydrous CH$_2$Cl$_2$ (15 mL) was stirred at room temperature under argon for 1 hour. A solution of 3-aminopropyl-4-methyl-4-phenylpiperidine (120 mg, 0.517 mmol, 1.11 equiv) in CH$_2$Cl$_2$ (5 mL) was injected, and stirring was continued at reflux for 6 hours. The mixture was cooled to room temperature, diluted with CH$_2$Cl$_2$ (120 mL), and washed with saturated aqueous NH$_4$Cl (3×35 mL). The organic phase was dried over MgSO$_4$ and concentrated. The residue was purified by flash chromatography (SiO$_2$, CHCl$_3$—MeOH-methanolic ammonia (2M) 100:3:1.5 to 100:4:2) to afford 185 mg (71%) of 106 free base as a yellow solid, which was characterized spectroscopically.. To a solution of this product (171 mg, 0.306 mmol, 1.0 equiv) in CH$_2$Cl$_2$ (5 mL) and MeOH (1 mL) was added HCl in ether (1.0M, 0.7 mL, 2.3 equiv). After removal of the solvents, the residue was dissolved in CH$_2$Cl$_2$ (5 mL) and MeOH (1 mL) and added dropwise to ether (30 mL) with swirling to give, after filtration, 155 mg of yellow solid: m.p. 166° C. (decomp.); Anal. Calcd. for C$_{32}$H$_{41}$N$_5$O$_4$.HCl.1.2 H$_2$O: C, 62.21; H, 7.24; N, 11.34. Found: C, 62.21; H, 7.46; N, 11.26.

EXAMPLE 107

Benzylpropionylacetate. A mixture of ethylpropionyl acetate (50.0 g, 0.347 mol, 1.00 equiv) and benzyl alcohol (39.5 mL, 0.381 mol, 1.10 equiv) was stirred at 180–210° C. for ca. 3 hours while EtOH was collected by distillation (ca. 20 mL of EtOH was collected). The product was distilled (b.p. 115–120° C./0.4 mm Hg) to afford 54.8 g (76%) of colorless oil, which was characterized spectroscopically.

Benzyl 3-amino-2-pentenoate. A mixture of benzylpropionylacetate (54.80 g, 265.7 mmol) and molecular sieves (14 g, 3A, Mallinckrodt) was stirred at 50° C. for 40 hours while NH$_3$ gas was bubbled through the solution. The product was decanted to give 55.5 g of colorless oil, which was characterized spectroscopically and used for the next reaction without purification.

3-Benzyloxycarbonyl-5-(2-cyanoethoxy)carbonyl-2,6-diethyl-1,4-dihydro-4-(4-nitro)phenylpyridine. A mixture of 2-cyanoethyl 2-(4-nitrophenyl)methyleno-3-oxopentanoate (9.80 g, 32.4 mmol, 1.00 equiv) and benzyl 3-amino-2-pentenoate (7.99 g, 38.9 mmol, 1.20 equiv) in EtOH (150 mL) was stirred at reflux for 36 hours. The solvent was removed to give 15.4 g (97%) of yellow solid, which was characterized spectroscopically and used for the next reaction without purification.

3-(2-Cyanoethoxy)carbonyl-2,6-diethyl-1,4-dihydro-4-(4-nitro)phenylpyridine-5-carboxylic acid. A solution of 3-benzyloxycarbonyl-5-(2-cyanoethoxy)carbonyl-2,6-diethyl- 1,4-dihydro-4-(4-nitro)phenylpyridine (3.84 g, 7.84 mmol) in methanolic formic acid solution (4.4% by weight, 10 mL) was added to a suspension of Pd on carbon (10%, 3.84 g) in methanolic formic acid solution (4.4% by weight, 90 mL). The mixture was stirred for 20 minutes, then filtered through Celite. After removal of the solvents, a solution of the residue in CH$_2$Cl$_2$ (150 mL) was washed with 0.1N aqueous HCl (15 mL) and water (15 mL), dried over MgSO$_4$ and concentrated to give 2.95 g (94%) of yellow solid, which was characterized spectroscopically and used for subsequent reactions without purification.

5-(2-Cyanoethoxy)carbonyl-2,6-diethyl-1,4-dihydro-5-(N-methyl)carboxamido-4-(4-nitro)phenylpyridine. A mixture of 3-(2-cyanoethoxy)carbonyl-2,6-diethyl-1,4-dihydro-4-(4-nitro)phenylpyridine-5-carboxylic acid (3.70 g, 9.26 mmol, 1.00 equiv), 1-(3-dimethylaminopropyl)-3-ethylcarbodiimide hydrochloride (2.66 g, 13.9 mmol, 1.50 equiv) and 4-dimethylaminopyridine (1.24 g, 10.2 mmol, 1.10 equiv) in anhydrous CH$_2$Cl$_2$ (200 mL) was stirred at room temperature under argon for 1 hour. Aqueous methylamine (40% by weight, 1.60 mL, 18.5 mmol, 2.00 equiv) was injected, and stirring was continued for 20 hours. The resulting solution was washed with 0.1N HCl (3×50 mL), dried over MgSO$_4$ and concentrated. The residue was purified by flash chromatography (SiO$_2$, CHCl$_3$—MeOH 100:2) to afford 3.51 g (92%) of yellow solid, which was characterized spectroscopically.

2,6-Diethyl-1,4-dihydro-5-(N-methyl)carboxamido-4-nitrophenylpyridine-3-carboxylic acid. To a solution of 5-(2-cyanoethoxy) carbonyl-2,6-diethyl-1,4-dihydro-5-(N-methyl)carboxamido-4-(4-nitro)phenylpyridine (3.25 g, 7.88 mmol, 1.00 equiv) in acetone (32 mL) was added 1N aqueous NaOH (23.6 mL, 23.6 mmol, 3.00 equiv) at −5–0° C. The mixture was stirred for 3 hours at this temperature. After removal of acetone $_{in\ vacuo}$ at 10° C., the mixture was extracted with EtOAc (15 mL). The aqueous solution was cooled to 0° C. and adjusted to pH 3–4 by addition of 6N aqueous HCl. The resulting precipitate was collected by filtration, washed with water (20 mL) and dried to afford 2.51 g (89%) of yellow solid, which was characterized spectroscopically.

2,6-Diethyl-1,4-dihydro-3-{N-[3-(4-(4-methoxyphenyl)-4-phenylpiperidin-1-yl)propyl]}carboxamido-5-N-methyl)

carboxamido-4-(4-nitrophenyl)pyridine (107). A mixture of 2,6-diethyl-1,4-dihydro-5-(N-methyl) carboxamido-4-(4-nitrophenyl)pyridine-3-carboxylic acid (200 mg, 0.558 mmol, 1.00 equiv), 1-(3-dimethylaminopropyl)-3-ethylcarbodiimide hydrochloride (160 mg, 0.837 mmol, 1.50 equiv) and 4-dimethylaminopyridine (75.0 mg, 0.614 mmol, 1.10 equiv) in anhydrous $CH_2Cl_2$ (15 mL) was stirred at room temperature under argon for 1 hour. A solution of 3-aminopropyl-4-(4-methoxyphenyl)-4-phenylpiperidine (217 mg, 0.670 mmol, 1.20 equiv) in $CH_2Cl_2$ (5 mL) was injected, and stirring was continued at ref lux for 6 hours. The mixture was cooled to room temperature, diluted with $CH_2Cl_2$ (150 mL), and washed with saturated aqueous $NH_4Cl$ (3×40 mL) The organic phase was dried over $MgSO_4$ and concentrated. The residue was purified by flash chromatography ($SiO_2$, $CHCl_3$—MeOH-methanolic ammonia (2M) 100:4:2) to afford 258 mg (69%) of yellow solid: m.p. 133° C. (decomp.); Anal. Calcd. for $C_{39}H_{47}N_5O_5$.0.25 $CHCl_3$:C, 67.77; H, 6.85; N, 10.07. Found: C, 67.56; H, 7.04; N, 10.16.

EXAMPLE 108

3-(4-Methoxy-4-phenyl)piperidin-1-ylpropionitrile. In a dry flask under argon, sodium hydride (60% dispersion in mineral oil, 520 mg, 13 mmol, 3.0 equiv) was washed with three times with hexane, and the washings were discarded. The reaction flask was cooled to 0° C., a solution of 3-(4-hydroxy-4-phenyl)piperidin-1-ylpropionitrile (1.0 g, 4.3 mmol, 1.0 equiv) in anhydrous THF (20 mL) was added, and the mixture was stirred for 30 minutes. Iodomethane (0.40 mL, 6.5 mmol, 1.5 equiv) was added, and stirring was continued at 0° C. for 1 hour and at room temperature for 2 hours. Ethyl acetate (30 mL) and water (20 mL) were added cautiously. The aqueous phase was basified to pH 10–11 by addition of 1N aqueous NaOH and extracted with EtOAc (2×100 mL) and $CH_2Cl_2$ (2×100 mL). The combined organic solutions were dried over $MgSO_4$ and concentrated. The residue was purified by flash chromatography ($SiO_2$, hexane-EtOAc 2:1 to 1:1) to give 542 mg (51%) of white solid, which was characterized spectroscopically.

1-(3-Aminopropyl)-4-methoxy-4-phenylpiperidine. Boranetetrahydrofuran complex (1.0M in THF, 7.4 mL, 7.4 mmol, 3.5 equiv) was added under argon to neat 3-(4-methoxy-4-phenyl)piperidin-1-ylpropionitrile (512 mg, 2.10 mmol, 1.0 equiv). The mixture was stirred at ref lux for 5 hours and then cooled to 0° C. Aqueous HCl (6N, 8 mL) was added cautiously, and stirring was continued at room temperature overnight, then at 42° C. for 1.5 hours. The solution was basified to pH 10–11 by addition of 6N aqueous NaOH and extracted with $CH_2Cl_2$ (3×60 mL). The combined organic solutions were dried over $MgSO_4$ and concentrated. The residue was purified by flash chromatography ($SiO_2$, $CHCl_3$—MeOH—$NH_3$ (2.0M in MeOH) to give 387 mg (75%) of colorless oil, which was characterized spectroscopically.

2,6-Diethyl-1,4-dihydro-3-{N-[3-(4-methoxy-4-phenylpiperidin-1-yl)propyl]}carboxamido}-5-(N-methyl)carboxamido-4-(4-nitrophenyl)pyridine (108). A mixture of 2,6-diethyl-1,4-dihydro-5-(N-methyl)carboxamido-4-(4-nitrophenyl)pyridine-3-carboxylic acid (200 mg, 0.558 mmol, 1.00 equiv), 1-(3-dimethylaminopropyl)-3-ethylcarbodiimide hydrochloride (160 mg, 0.837 mmol, 1.50 equiv) and 4-dimethylaminopyridine (75.0 mg, 0.614 mmol, 1.10 equiv) in anhydrous $CH_2Cl_2$ (15 mL) was stirred at room temperature under argon for 1 hour. A solution of 3-aminopropyl-4-methoxy-4-phenylpiperidine (166 mg, 0.670 mmol, 1.20 equiv) in $CH_2Cl_2$ (5 mL) was injected, and stirring was continued at ref lux for 6 hours. The mixture was cooled to room temperature, diluted with $CH_2Cl_2$ (150 mL), and washed with saturated aqueous $NH_4Cl$ (3×40 mL). The organic phase was dried over $MgSO_4$ and concentrated. The residue was purified by flash chromatography ($SiO_2$, $CHCl_3$—MeOH—$NH_3$ (2M in MeOH) 100:3:1.5 to 100:4:2) to afford 230 mg (70%) of yellow solid: m.p. 240° C. (decomp.); Anal. Calcd. for $C_{33}H_{40}N_5O_5$.0.2 $CHCl_3$:C, 64.99; He 7.10; N, 11.41. Found: C, 64.94; H, 7.36; N, 11.26.

EXAMPLE 109

Diphenyl-4-piperidylmethane hydrochloride. To a solution of diphenyl-4-pyridylmethane (2.00 g, 8.15 mmol, 1.00 equiv, Aldrich) in EtOH was added Rh on carbon (5%, 0.800 g). The suspension was stirred in a bomb under $H_2$ pressure (2.7 atm) at 55–60° C. for 7 hours. The catalyst was filtered out (Celite) and washed thoroughly with $CH_2Cl_2$ and MeOH. The combined filtrate and washings were concentrated. The residue was dissolved in $CH_2Cl_2$ (5 mL) and treated with HCl in $Et_2O$ (1.0M, 10 mL). The solvents were removed and the residue was recrystallized from EtOAc—MeOH 1:2 to afford 0.96 g of white solid. This solid was added to water (30 mL), which was adjusted to pH 11 by addition of 1N aqueous NaOH, and extracted with $CH_2Cl_2$ (3×30 mL). The combined organic solutions were dried over $MgSO_4$ and concentrated to give 0.81 g (39%) of white solid, which was characterized spectroscopically.

3-(4-Diphenylmethylpiperidin-1-yl)propionitrile. To a solution of diphenyl-4-piperidylmethane (810 mg, 3.22 mmol, 1.00 equiv) in EtOH (5 mL) was added acrylonitrile (0.53 mL, 8.06 mmol, 2.50 equiv) dropwise at 0° C. The mixture was stirred at room temperature for 1.5 hours and then concentrated. The residue was purified by flash chromatography ($SiO_2$, EtOAc-hexane 9:1 to 2:1) to give 480 mg (49%) of white solid, which was characterized spectroscopically.

1-(3-Aminopropyl)-4-diphenylmethylpiperidine. Boranetetrahydrofuran complex (1.0M in THF, 5.5 mL, 5.5 mmol, 3.5 equiv) was added under argon to neat 3-(4-diphenylmethylpiperidin-1-yl)propionitrile (480 mg, 1.58 mmol, 1.00 equiv). The mixture was stirred at reflux for 5 hours and then cooled to 0° C. Aqueous HCl (6N, 6 mL) was added cautiously, and stirring was continued at room temperature overnight, then at 42° C. for 1.5 hours. The solution was basified to pH 10–11 by addition of 6N aqueous NaOH and extracted with $CH_2Cl_2$ (3×50 mL). The combined organic solutions were dried over $MgSO_4$ and concentrated. The residue was purified by flash chromatography ($SiO_2$, $CHCl_3$—MeOH—$NH_3$ (2.0M in MeOH) to give 420 mg (86%) of colorless oil, which was characterized spectroscopically.

2,6-Diethyl-1,4-dihydro-5-(N-methyl)carboxamido-4-(4-nitrophenyl)-3-{N-[3-(4-diphenyliethylpiperidin-1-yl)propyl]}carboxamidopyridine (109). A mixture of 2,6-diethyl-1,4-dihydro-5-N-methyl)carboxamido-4-(4-nitrophenyl)pyridine-3-carboxylic acid (200 mg, 0.558 mmol, 1.00 equiv), 1-(3-dimethylaminopropyl)-3-ethylcarbodiimide hydrochloride (160 mg, 0.837 mmol, 1.50 equiv) and 4-dimethylaminopyridine (75.0 mg, 0.614 mmol, 1.10 equiv) in anhydrous $CH_2Cl_2$ (15 mL) was stirred at room temperature under argon for 1 hour. A solution of 1-(3-aminopropyl)-4-diphenylmethylpiperidine (206 mg, 0.670 mmol, 1.20 equiv) in $CH_2Cl_2$ (5 mL) was injected, and stirring was continued at reflux for 6 hours. The mixture was cooled to room temperature, diluted with $CHCl_2$ (150 mL), and washed with saturated aqueous NH$_4$Cl (3×40 mL). The organic phase was dried over MgSO$_4$ and concentrated. The residue was purified by flash chromatography (SiO$_2$, CHCl$_3$—MeOH—NH$_3$ (2M in MeOH) 100:3:1.5 to 100:4:2) to afford 260 mg (72%) of yellow solid: m.p. 128° C. (decomp.); Anal. Calcd. for CH$_{39}$H$_{47}$N$_5$O$_4$.0.30 CHCl$_3$: C, 68.85; H, 6.95; N, 10.21 Found: C, 68.78; H, 7.13; N, 10.23.

EXAMPLE 110

3-Aminopropyl-4-carboxamido-4-phenylpiperidine. 4-Carboxamido-4-phenylpiperidine (700 mg, 3.43 mmol, 1.00 equiv), 3-bromopropylamine hydrobromide (900 mg, 4.11 mmol, 1.20 equiv) and potassium carbonate (1.03 g, 7.45 mmol, 2.17 equiv) were stirred in refluxing dioxane (25 mL) for 24 hours. After removal of the solvent, the residue was purified by flash chromatography (SiO$_2$, CHCl$_3$—MeOH—NH$_3$ (2M in MeOH) 100:8:4 to 100:20:8) to give 135 mg (14%) of colorless oil, which was characterized spectroscopically.

3-{N-[3-(4-Carboxamido-4-phenylpiperidin-1-yl) propyl]} carbozaxamido-2,6-diethyl-1,4-dihydro-5-(N-methyl)carboxamido-4-(4-nitrophenyl)pyridine (110). A mixture of 2,6-diethyl-1,4-dihydro-5-(N-methyl) carboxamido-4-(4-nitrophenyl)pyridine-3-carboxylic acid (126 mg, 0.352 mmol, 1.00 equiv), 1-(3-dimethylaminopropyl)-3-ethylcarbodiimide hydrochloride (102 mg, 0.530 mmol, 1.51 equiv) and 4-dimethylaminopyridine (48.0 mg, 0.393 mmol, 1.12 equiv) in anhydrous CH$_2$Cl$_2$ (7 mL) was stirred at room temperature under argon for 1 hour. A solution of 1-(3-aminopropyl)-4-carboxamido-4-phenylpiperidine (92.0 mg, 0.352 mmol, 1.00 equiv) in CH$_2$Cl$_2$ (3 mL) was injected, and stirring was continued at reflux for 6 hours. The mixture was cooled to room temperature, diluted with CH$_2$Cl$_2$ (100 mL), and washed with saturated aqueous NH$_4$Cl (3×30 mL). The organic phase was dried over NgSO$_4$ and concentrated. The residue was purified by flash chromatography (SiO$_2$, CHCl$_3$—MeOH—NH$_3$ (2M in MeOH) 100:6:3 to 100:8:4) to afford 81 mg (38%) of yellow solid: m.p. 124° C. (decomp.); Anal. Calcd. for C$_{33}$H$_{42}$N$_6$O$_5$0.35 CHCl$_3$: C, 62.15; H, 6.62; N, 13.04 Found: C, 61.90; H, 7.00; N, 12.96.

EXAMPLE 111

3-(2-Cyanoethoxy)carbonyl-2,6-diethyl-5-(N-ethyl) carboxamido-1,4-dihydro-4-(4-nitrophenyl)pyridine. A mixture of 3-(2-cyanoethoxy)carbonyl-2,6-diethyl-1,4-dihydro-4-(4-nitrophenyl)pyridine-5-carboxylic acid (2.50 g, 6.26 mmol, 1.00 equiv), 1-(3-dimethylaminopropyl)-3-ethylcarbodiimide hydrochloride (1.80 g, 9.38 mmol, 1.50 equiv) and 4-dimethylaminopyridine (0.841 g, 6.89 mmol, 1.10 equiv) in anhydrous CH$_2$Cl$_2$ (50 mL) was stirred at room temperature under argon for 1.5 hours. Aqueous ethylamine (70% by weight, 2.00 mL, 31.0 mmol, 4.95 equiv) was injected, and the mixture was stirred at reflux for 5 hours and then at room temperature for 12 hours. The resulting solution was washed with saturated aqueous NH$_3$ (3×50 mL), dried over MgSO$_4$ and concentrated. The residue was purified by flash chromatography (SiO$_2$, CHCl$_3$—MeOH—NH$_3$ (2.0M in MeOH) 90:8:4) to afford 2.11 g (79%) of yellow solid, which was characterized spectroscopically.

2,6-Diethyl-5-(N-ethyl)carboxamido-1,4-dihydro-4-(4-nitrophenyl)pyridine-3-carboxylic acid. To a solution of 3-(2-cyanoethoxy)carbonyl-2,6-diethyl-5-(N-ethyl) carboxamido-1,4-dihydro-4-(4-nitrophenyl)pyridine (2.11 g, 4.95 mmol, 1.00 equiv) in acetone (20 mL) was added 1N aqueous NaOH (14.8 mL, 14.8 mmol, 3.00 equiv) at −5–0° C. The mixture was stirred for 30 minutes at this temperature. After removal of acetone in vacuo at 10° C., the aqueous solution was cooled to 0° C. and adjusted to pH 3–4 by addition of 6N aqueous HCl. The resulting precipitate was collected by filtration, washed with water (20 mL) and dried to afford 1.09 g (59%) of yellow solid, which was characterized spectroscopically.

2,6-Diethyl-5-(N-ethyl)carboxamido-1,4-dihydro-3-{N-[3-(4-(4-methoxy)phenyl-4-phenylpiperidin-1-yl)propyl]} carboxamido-4-(4-nitrophenyl)pyridine (111). A mixture of 2,6-diethyl-5-(N-ethyl)carboxamido-1,4-dihydro-4-(4-nitrophenyl)pyridine-3-carboxylic acid (200 mg, 0.536 mmol, 1.00 equiv), 1-(3-dimethylaminopropyl)-3-ethylcarbodiimide hydrochloride (154 mg, 0.803 mmol, 1.50 equiv) and 4-dimethylaminopyridine (72.0 mg, 0.590 mmol, 1.10 equiv) in anhydrous CHCl$_2$ (5 mL) was stirred at room temperature under argon for 1.5 hours. A solution of 1-(3-aminopropyl)-4-(4-methoxyphenyl)-4-phenylpiperidine (208.7 mg, 0.643 mmol, 1.20 equiv) in CH$_2$Cl$_2$ (1 mL) was injected, and stirring was continued at reflux for 5 hours. The mixture was cooled to room temperature, diluted with CH$_2$Cl$_2$ (150 mL), and washed with saturated aqueous NH$_4$Cl (3×50 mL). The organic phase was dried over MgSO$_4$ and concentrated. The residue was purified by flash chromatography (SiO$_2$, CHCl$_3$—MeOH—NH$_3$ (2M in MeOH) 90:8:4) to afford 220 mg (60%) of yellow solid: m.p. 172° C. (decomp.); Anal. Calcd. for C$_{40}$H$_{49}$N$_5$O$_5$.0.8 CHCl$_3$: C, 63.20; H, 6.47; N, 9.03 Found: C, 63.23; H, 6.22; N, 9.11.

EXAMPLE 112

2,6-Diethyl-1,4-dihydro-4-(3-methoxyphenyl)-3,5-bis (N-(3-(4,4-diphenylpiperidin-1-yl)propyl)carboxamido)-pyridine (112). A mixture of 2-cyanoethyl propionylacetate (1.00 g, 5.91 mmol), m-anisaldehyde (1.0 ml, d 1.119, 8.22 mmol) and 3-aminocrotonamide (0.89 g, 8.89 mmol) in EtOH (9 ml) was heated at reflux overnight. Then the solvent was evaporated to give an oily residue which was suspended in chloroform and flash chromatographed over silica gel (100 g). Elution with EtOAc/Hexane (1:2, 1:1 and 3:1) gave a yellow oil (336 mg). It was dissolved in EtOH (1.5 ml) and treated with NaOH (74 mg, 1.85 mmol) in water (1 ml). The solution was stirred at room temperature overnight and then washed twice with CH$_2$Cl$_2$. Acidification of the basic layer with 5% HCl gave a precipitate which was filtered off and washed with water and EtOAc to afford an off-white solid (118 mg, 6% yield).

This solid (114 mg, 0.34 mmol) was mixed with 1-(3-dimethyl-aminopropyl)-3-ethyl-carbodiimide hydrochloride (71 mg, 0.37 mmol), 3-(4,4-diphenylpiperidin-1-yl) propylamine (108 mg, 0.37 mmol) and 4-dimethylaminopyridine (catalytic amount) in dry CH$_2$Cl$_2$ (5 ml). The mixture was stirred at room temperature overnight and then concentrated. The residue was dissolved in chloroform and flash chromatographed over silica gel (16 g) eluting with EtOAc/MeOH/Et$_3$N (20:1:1) to give a colorless oil (72 mg, 44% yield). It was recrystallized from EtOAc/Hexane to afford a white solid (31 mg): mp 166–170° C. Anal. Calcd. for C$_{58}$H$_{69}$N$_5$O$_3$.½H$_2$O: C, 77.99; H, 7.90; N, 7.84. Found: C, 77.85; H, 8.01; N, 7.76.

EXAMPLE 113

5-Carboxamido-2-ethyl-1,4-dihydro-4-(3-methoxyphenyl)-6-methyl-3-(N-(3-(4,4-diphenylpiperidin-1-yl)propyl)carbozamido)-pyridine (113). A mixture of 2-cyanoethyl propionylacetate (1.00 g, 5.91 mmol), m-anisaldehyde (1.0 ml, d 1.119, 8.22 mmol) and 3-aminocrotonamide (0.89 g, 8.89 mmol) in EtOH (9 ml) was heated at reflux overnight. Then the solvent was evaporated to give an oily residue which was suspended in chloroform and flash chromatographed over silica gel (100 g). Elution with EtOAc/Hexane (1:2, 1:1 and 3:1) and EtOAc/MeOH (10:1) afforded an orange foam (0.782 g, 36% yield).

This foam (0.782 g, 2.12 mmol) was dissolved in EtOH (3 ml) and stirred with NaOH (0.121 g 3.03 mmol) in water (2 ml) for 3 h. The solution was acidified with 5% HCl and extracted with EtOAc (2×5 ml). The extract was washed with saturated NaCl solution, dried ($MgSO_4$), filtered and concentrated to give a red gum (255 mg). It was dissolved in MeOH and flash chromatographed over silica gel (17 g) eluting with EtOAc/Hexane/MeOH (5:5:1) to give a yellow oil (88 mg, 13% yield).

This oil (85 mg, 0.27 mmol) was suspended in dry $CH_2Cl_2$ (5 ml) and treated with 1-(3-dimethylaminopropyl)-3-ethylcarbodiimide hydrochloride (52 mg, 0.27 mmol), 3-(4,4-diphenyl-piperidin-1-yl)propylamine (79 mg, 0.27 mmol) and 4-dimethylamino-pyridine (2 mg). The mixture was stirred at room temperature overnight and then the solvent was evaporated. The residue was dissolved in chloroform and flash chromatographed over silica gel (17 g) eluting with EtOAc/MeOH/Et3N (10:1:1) to give a pale yellow foam (55 mg, 35% yield). Recrystallization from EtOAc/Hexane afforded a white solid (21 mg): mp 120–123° C. Anal. Calcd. for $C_{37}H_{44}N_4O_3$: C, 74.97; H, 7.48; N, 9.45. Found: C, 74.89; H, 7.61; N, 9.40.

EXAMPLE 114

4-(4-Aminophenyl)-2-ethyl-1,4-dihydro-5-methoxycarbonyl-6-methyl-3-(N-(3-(4,4-diphenylpiperidin-1-yl)propyl)carboxamido)-pyridine (114). A solution of 2-Ethyl-1,4-dihydro-5-methoxycarbonyl-6-methyl-4-(4-nitrophenyl)-3-(N-(3-(4,4-diphenylpiperidin-1-yl)propyl)carboxamido)pyridine (135 mg, 0.22 mmol) in dry MeOH (4 ml) was treated with 10% Pd/C (20 mg) and hydrogenated at 1 atm overnight. Then more catalyst (20 mg) was added and hydrogenation was continued overnight. Filtration of the reaction mixture through Celite afforded a yellow oil. It was dissolved in chloroform and flash chromatographed over silica gel (16 g) eluting with EtOAc/Hexane/MeOH/Et3N (40:20:3:3) to give a white foam (60 mg, 47% yield). The foam was dissolved in EtOAc/Hexane and treated with 1N HCl in ether (0.3 ml). The solvent was then evaporated to afford a yellow solid: mp 169–172° C. (dec). Anal. Calcd. for $C_{37}H_{44}N_4O_3 \cdot 2HCl \cdot \frac{1}{2}H_2O$: C, 65.87; H, 7.02; N, 8.30. Found: C, 65.80; H, 7.17; N, 8.31.

EXAMPLE 115

5-Carboxamido-1,4-dihydro-4-(4-methanesufonylphenyl)-2,6-dimethyl-3-(N-(3-(4,4-diphenylpiperidin-1-yl)propyl)carboxamido)-pyridine (115). p-Methanesulfonyl-benzaldehyde (1.00 g, 5.43 mmol) was mixed with cyanoethyl acetoacetate (0.84 g, 5.41 mmol), acetic acid (16 ul, d 1.049, 0.28 mmol) and piperidine (27 ul, d 0.861, 0.27 mmol) in 2-propanol (10 mL). The mixture was stirred at room temperature overnight. The solvent was replaced by EtOH (10 mL) which was then stirred at room temperature for 2 h and then heated at reflux for 4 h. 3-Aminocrotonamide (0.543 g, 5.42 mmol) was added and the mixture heated at reflux overnight. The solvent was evaporated and the residue dissolved in EtOAc/MeOH/Et3N (20:1:1) and flash chromatographed over silica gel (105 g) eluting with the same solvent to give a yellow foam (369 mg, 17% yield).

The above foam (369 mg 0.91 mmol) was partially dissolved in EtOH (4 mL) and, with ice water bath cooling, treated with NaOH (56 mg, 1.4 mmol) in water (1 mL). The mixture was stirred at room temperature for 3 h and the EtOH was evaporated. The aqueous layer was washed with $CH_2Cl_2$ twice and then acidified with 2N HCl to afford a precipitate which was filtered off as a yellow solid (235 mg, 73% yield).

The above yellow solid (233 mg, 0.66 mmol) was mixed with 3-(4,4-diphenylpiperidin-1-yl)-propylamine (197 mg, 0.67 mmol), 1-(3-dimethylaminopropyl)-3-ethylcarbodiimide hydrochloride (129 mg, 0.67 mmol), and 4-dimethylamino-pyridine (82 mg, 0.67 mmol) in dry $CH_2Cl_2$ (8 mL) which was then heated at reflux for 7 h. More carbodiimide (63 mg, 0.33 mmol) was added and the mixture was heated at reflux overnight. It was then diluted with $CHCl_3$, washed with water twice and saturated $NH_4Cl$ thrice, dried ($MgSO_4$) filtered and concentrated to give a yellow oil (385 mg). This was dissolved in $CHCl_3$ and flash chromatographed over silica gel (20 g) eluting with EtOAc/MeOH/Et3N (20:1:1 then 20:2:1) to afford a yellow foam (209 mg). Trituration with hot EtOAc gave a pale yellow solid (140 mg, 34% yield): mp 206–209° C. Anal. Calcd. for $C_{36}H_{42}N_4O_4S \cdot \frac{3}{4}H_2O$: C,67.53; H, 6.85; N, 8.75. Found: C, 67.51; H, 6.90; N, 8.51.

EXAMPLE 116

5-Carboxamido-2,6-diethyl-1,4-dihydro-4-(4-methanesulfonylphenyl)-3-(N-(3-(4,4-diphenylpiperidin-1-yl)propyl)carboxamido)-pyridine (116). p-Methanesulfonylbenzaldehyde (0.54 g, 2.93 mmol) was mixed with 2-cyanoethyl propionylacetate (0.50 g, 2.96 mmol), acetic acid (9 μl, d 1.049, 0.16 mmol) and piperidine (14 μl, d 0.861, 0.14 mmol) in EtOH (6 mL). The suspension was stirred at room temperature overnight. A solution of 3-amino-2-propenamide (313 mg, 2.74 mmol) in EtOH (3 mL) was added and the mixture was heated at reflux overnight. The solvent was evaporated to give a yellow oil which was dissolved in $CHCl_3$ and flash chromatographed over silica gel (70 g) eluting with EtOAc/Hexane/Et3N (15:5:1 then 18:2:1) to afford a yellow foam (493 mg, 39% yield).

The above yellow foam (493 mg, 1.14 mmol) was dissolved in EtOH (5 mL), cooled by an ice water bath, and treated with NaOH (74 mg, 1.85 mmol) in water (2 mL). The solution was stirred at room temperature for 2 h and then the EtOH was evaporated. The aqueous layer was diluted with water, washed twice with $CH_2Cl_2$, cooled by an ice water bath and acidified with 2N HCl. Filtration gave a pale yellow solid (329 mg, 76% yield): up 137–140° C. (dec).

The above yellow solid (326 mg, 0.86 mmol) was mixed with 3-(4,4-diphenyl-piperidin-1-yl)-propylamine (254 mg, 0.86 mmol), 1-(3-dimethylaminopropyl)-3-ethylcarbodiimide hydrochloride (254 mg, 1.32 mmol), and 4-dimethylaminopyridine (105 mg, 0.86 mmol) in dry $CH_2Cl_2$ (12 mL) which was then heated at reflux overnight. $CHCl_3$ (6 mL) was added and the mixture was washed with water (2×5 mL) and saturated $NH_4Cl$ solution (3×5 mL), dried ($MgSO_4$), filtered and concentrated to give a pale brown foam (605 mg). It was dissolved in $CHCl_3$ and flash chromatographed over silica gel (37 g) eluting with EtOAc/MeOH/Et3N (20:1:1) to afford an off-white solid (338 mg, 60% yield). A portion (308 mg) was dissolved in EtOH and treated with fumaric acid (55 mg) in EtOH. The solvent was evaporated and the residue recrystallized from 2-propanol to give a hygroscopic pale yellow solid (217 mg). Anal. Calcd. for $C_{38}H_{46}N_4O_4S \cdot C_4H_4O_4 \cdot C_3H_8O \cdot H_2O$: C, 63.66; H, 7.12; N, 6.60. Found: C, 63.78; H, 7.01; N, 6.45.

EXAMPLE 117

5-Carboxamido-1,4-dihydro-4-(3-methoxyphenyl)-2,6-dimethyl-3-(N-(3-(4,4-diphenylpiperidin-1-yl)propyl) carboxamido)-pyridine (117). A mixture of benzyl acetoacetate (0.9 mL, 5.20 mmol), m-anisaldehyde (0.63 mL, 5.20 mmol), 3-aminocrotoamide (521 mg, 5.20 mmol) in 2-propanol (10 mL) was refluxed for 4 days. The solvent was removed and the solid residue was chromatographed (Flash silica; EtOAc:MeOH:2M $NH_3$ in MeOH=10:1:0.5) to give a solid which was chromatographed again (Flash silica, EtOAc) to give a yellow solid (643 mg, 32%).

At room temperature a suspension of Pd/C (81 mg, 10%, 0.076 mmol) in MeOH (5 mL) was flushed with argon, then treated with a solution of the above yellow solid (287 mg, 0.731 mmol) in MeOH (5 mL). The resulting mixture was flushed with $H_2$ then stirred under $H_2$ (balloon) for 3.5 hrs. The reaction mixture was filtered through celite and concentrated to afford a white solid (120 mg, 54%).

A mixture of the above white solid (120.0 mg, 0.3969 mmol), 3-(4,4-diphenylpiperidin-1-yl)propylamine (116.9 mg, 0.3969 mmol), 1-(3-dimethylaminopropyl)-3-ethylcarbodiimide hydrochloride (85.4 mg, 0.446 mmol), and 4-dimethylaminopyridine (cat) in dry $CH_2Cl_2$ (10 mL) was stirred at room temperature for 14 hrs. The reaction mixture was then washed with saturated aqueous $NaHCO_3$ solution, dried, and concentrated. The resulting material was chromatographed (Flash silica, EtOAc:MeOH:2M $NH_3$ in MeOH=10:1:0.5) to give a solid, which was recrystalized from $CH_2Cl_2$ and EtOAc to afford white crystals (40 mg, 17%) 157–3: m. p. 212.0–213.0° C. Anal. Calcd. for $C_{36}H_{42}N_4O_3$: C, 74.71, H, 7.31, N, 9.68. Found: C, 74.49, H, 7.09, N, 9.45.

EXAMPLE 118

3-Carboxamido-2-ethyl-1,4-dihydro-4-(4-methanesulfonylphenyl)-6-methyl-5-(N-(3-(4,4-diphenylpiperidin-1-yl)propyl)carboxamido)-pyridine (118). A mixture of benzyl acetoacetate (0.31 mL, 1.79 mol), 4-methylsulfonylbenzaldehyde (330 mg, 1.79 mmol), trans-3-amino-2-pentenamide (204 mg, 1.79 mmol) in 2-propanol (10 mL) was refluxed for 3 days. The solvent was removed and the liquid residue was chromatographed (Flash silica, EtOAc) to give a yellow solid (507 mg, 62%).

At R.T. a suspension of Pd/C (1.117 g, 10%, 1.07 mmol) in MeOH (5 mL) was flushed with argon, then treated with a solution of the above yellow solid (500 mg, 1.10 mmol) in MeOH (10 mL). The resulting mixture was flushed with $H_2$ then stirred under $H_2$ (balloon) for 3 hrs. The reaction mixture was filtered through celite and concentrated to afford a yellow solid (220 mg, 69%).

A mixture of this yellow solid (220 mg, 0.604 mmol), 1-(3-dimethylaminopropyl)-3-ethyl-carbodiimide hydrochloride (115 mg, 0.658 mmol), and 4-dimethylaminopyridine (80.4 mg, 0.658 mmol) in dry $CH_2Cl_2$ (10 mL) was stirred at R.T. for 1 hr and then treated with 3-(4,4-diphenylpiperidin-1-yl)propylamine (176 mg, 0.598 mmol). The reaction mixture was stirred for 14 hrs and then washed with saturated aqueous $NaHCO_3$ solution, dried, and concentrated. The resulting material was chromatographed (Flash silica, EtOAc:MeOH:2M $NH_3$ in MeOH=10:1:0.5) to give a solid, which was chromatographed again (Flash silica, EtOAc:MeOH=12:1) to give a solid. The solid was recrystalized from EtOAc and Hex to afford white crystals (81 mg, 21%) 161–5: m. p. 182.0–183.0° C. Anal. Calcd. for $C_{37}H_{44}N_4O_4S \cdot \frac{1}{3}H_2O$: C, 68.70, H, 6.95, N, 8.66, S, 4.95. Found: C, 68.71, H, 6.97, N, 8.47, S, 5.19.

EXAMPLE 119

1,4-Dihydro-2,6-dimethyl-5-(N-methyl)carboxamido-4-(4-nitrophenyl)-3-{N-[3-(4,4-diphonylpiperidin-1-yl)propyl]}carboxamidopyridine (119). A suspension of 4-nitrobenzaldehyde (5.00 g, 33.0 mmol), 2-cyanoethyl acetoacetate (5.13 g, 33.0 mmol), piperidine (140 mg, 1.65 mmol) and acetic acid (99 mg, 1.7 mmol) in 150 ml of 2-propanol was stirred at r.t. for 48 hrs. Reaction mixture was filtered, the solid collected was dried in air to give 2-[(4-nitrophenyl)methylene]-3-oxobutanoic acid 2-cyanoethyl ester as a white powder (6.08 g, 64%). A solution of 2-[(4-nitrophenyl)methylene]-3-oxobutanoic acid 2-cyanoethyl ester (4.29 g, 14.9 mmol) and 3-amino-N-methylcrotonamide (2.55 g, 22.3 mmol) in 50 ml of EtOH was refluxed for 36 hrs. After solvent was removed, the residue was dissolved in 250 ml of $CHCl_3$ washed with water (2×100 ml) and dried over $Na_2SO_4$. After filtration and removal of solvent, 3-(2-cyanoethoxy) carbonyl-1,4-dihydro-2,6-dimethyl-5-(N-methyl) carboxamido-4-(4-nitrophenyl) pyridine was obtain as a yellow powder (7.96 g, 63%). The solution of 3-(2-cyanoethoxy) carbonyl-1,4-dihydro-2,6-dimethyl-5-(N-methyl) carboxamido-4-(4-nitrophenyl) pyridine (2.00 g, 5.20 mmol) in 40 ml acetone was treated with 40 ml 1N KOH solution at 0° C. for 45 min. The acetone was removed in vacuo and aqueous layer was acidified to pH=3 by 2N hydrochloric acid, the yellow precipitation was collected by filtration, washed with 10 ml of cold water and dried in vacuo. 1.53 g (89% yield) of 1,4-dihydro-2,6-dimethyl-5-(N-methyl)carboxamido-4-(4-nitrophenyl)pyridine-3-carboxylic acid was obtained as a yellow powder.

The solution of 1,4-dihydro-2,6-dimethyl-5-(N-methyl) carboxamido-4-(4-nitrophenyl)pyridine-3-carboxylic acid (745 mg, 2.25 mmol), 1-(3-dimethylaminopropyl)-3-ethyl-carbodiimide hydrochloride (690 mg, 3.60 mmol) and 4-dimethylaminopyridine (275 mg, 2.25 mmol) in 200 ml of $CH_2Cl_2$ was stirred at r.t. for 1 hr, to the solution was added the solution of 3-(4,4-diphenylpiperidin-1-yl)propylamine (662 mg, 2.25 mmol) in 2 ml of $CH_2Cl_2$, the mixture was stirred at refluxing conditions overnight. The mixture was washed with water (50 ml), sat'd $NH_4Cl$ (3×50 ml), 50 ml 10% $K_2CO_3$ and 100 ml of sat'd brine. After drying with $Na_2SO_4$ and removal of solvent, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture. A yellowish powder (1.06 g, 77.5%) was obtained. M.p. 124° C.; Calcd. for $C_{36}H_{41}N_5O_4$: C 71.14, H 6.80, N 11.52; Found: C 70.88, H 6.55, N 11.34.

Part of 3-(2-cyanoethoxy) carbonyl-1,4-dihydro-2,6-dimethyl-5-(N-methyl) carboxamido-4-(4-nitrophenyl) pyridine was subjected to chiral chromatography and two enatiomers were separated, which were subsequentially hydrolysed and coupled with 3-(4,4-diphenylpiperidin-1-yl) propylamine to give enantiomers of 1,4-dihydro-2,6-dimethyl-5-(N-methyl) carboxamido-4-(4-nitrophenyl)-3-{N-[3-(4,4-diphenylpiperidin-1-yl)propyl]} carboxamidopyridine:

(+)-isomer: $[\alpha]_D^{20}=+88°$ (c 0.35, $CHCl_3$)
(−)-isomer: $[\alpha]_D^{20}=-84°$ (c 0.33, $CHCl_3$)

EXAMPLE 120

5-Carboxamido-2,6-diethyl-1,4-dihydro-4-(4-nitrophenyl)-3-{N-[3-(4,4-diphenylpiperidin-1-yl)propyl]}carboxanidopyridine (120). 5-Carboxamido-2,6-diethyl-1,4-dihydro-4-(4-nitrophenyl)pyridine-3-carboxylic acid was prepared in the same method illustrated in Example 119. It was obtained as a yellow powder.

The suspension of 5-carboxamido-2,6-diethyl-1,4-dihydro-4-(4-nitrophenyl)pyridine-3-carboxylic acid (400 mg, 1.16 mmol) and 1-(3-dimethylaminopropyl)-3-ethylcarbodiimide hydrochloride (225 mg, 1.16 mmol) in 50 ml of $CH_2Cl_2$ was stirred at r.t. for 1 hr, to the suspension thus formed was added the solution of 3-(4,4-diphenylpiperidin-1-yl)propylamine (310 mg, 1.05 mmol) in 2 ml of $CH_2Cl_2$, the mixture was stirred at refluxing conditions overnight. The mixture was washed with water (2×10 ml), 10 ml 10% $K_2CO_3$ and 10 ml of sat'd brine. After drying with $Na_2SO_4$ and removal of solvent, a yellowish oil was obtained, which was purified by chromatography ($SiO_2$, MeOH:$CHCl_3$:1N $NH_3$ in MeOH, 6:90:3) and precipitated by $CH_2Cl_2$/$Et_2O$ mixture. A yellowish powder (340 mg, 47.5%) was obtained. M.p. 121–123° C.; Calcd. for $C_{37}H_{43}N_5O_4$: C 71.47, H 6.97, N 11.26; Found: C 71.24, H 6.69, N 10.97.

EXAMPLE 121

5-Carboxamido-2,6-diethyl-1,4-dihydro-4-(4-nitrophenyl)-3-{N-[3-(4-phenylpiperidin-1-yl)propyl]}carboxamidopyridine (121). The suspension of 5-carboxamido-2,6-diethyl-1,4-dihydro-4-(4-nitrophenyl)pyridine-3-carboxylic acid (90 mg, 0.26 mmol) and 1-(3-dimethylaminopropyl)-3-ethylcarbodiimide hydrochloride (50 mg, 0.26 mmol) in 15 ml of $CH_2Cl_2$ was stirred at r.t. for 1 hr. to the suspension was added the solution of 3-(4,4-diphenylpiperidin-1-yl)propylamine (57 mg, 0.26 mmol) in 2 ml of $CH_2Cl_2$, the mixture was stirred at refluxing conditions overnight. The mixture was washed with water (2×10 ml), 10 ml 10% $K_2CO_3$ and 10 ml of sat'd brine. After drying with $Na_2SO_4$ and removal of solvent, a yellowish oil was obtained, which was purified by chromatography ($SiO_2$, MeOH:$CHCl_3$:1N $NH_3$ in MeOH, 6:90:3) and precipitated by $CH_2Cl_2$/$Et_2O$ mixture. A yellowish powder (86 mg, 61%) was obtained. M.p. 90–101° C.; Calcd. for $C_{31}H_{39}N_5O_4 \cdot ¾H_2O$: C 66.59, H 7.30, N 12.52; Found: C 66.89, H 6.92, N 12.30.

EXAMPLE 122

5-Carboxamido-1,4-dihydro-3-(N-{1-[2-(3-indolyl)ethyl]piperidin-4-yl})carboxamido-2,6-dimethyl-4-(4-nitrophenyl)pyridine (122). The suspension of 5-carboxamido-1,4-dihydro-2,6-dimethyl-4-(4-nitrophenyl)pyridine-3-carboxylic acid (326 mg, 1.03 mmol) and 1-(3-dimethylaminopropyl)-3-ethylcarbodiimide hydrochloride (219 mg, 1.13 mmol) in 25 ml of $CH_2Cl_2$ was stirred at r.t. for 1 hr, to the suspension was added the solution of 1-(2-(3-indolyl)ethyl]-4-aminopiperidine (250 mg, 1.03 mmol) in 2 ml of $CH_2Cl_2$, the mixture was stirred at refluxing conditions overnight. The mixture was washed with water (2×20 ml), 20 ml 10% $K_2CO_3$ and 20 ml of sat'd brine. After drying with $Na_2SO_4$ and removal of solvent, a yellowish oil was obtained, which was purified by chromatography ($SiO_2$, MeOH:$CHCl_3$:1N $NH_3$ in MeOH, 6:90:3) and precipitated by $CH_2Cl_2$/$Et_2O$ mixture. A yellowish powder (134 mg, 23.8%) was obtained. M.p. 135–138° C.; Calcd. for $C_{30}H_{34}N_6O_4 \cdot ½H_2O$: C 65.32, H 6.39, N 15.23; Found: C 65.41, H 5.96, N 15.21.

EXAMPLE 123

5-Carboxamido-2,6-diethyl-1,4-dihydro-3-(N-{1-[2-(3-indolyl)ethyl]piperidin-4-yl})carboxamido-4-(4-nitrophenyl)pyridine (123). The suspension of 5-carboxamido-2,6-diethyl-1,4-dihydro-4-(4-nitrophenyl)pyridine-3-carboxylic acid (486 mg, 1.53 mmol) and 1-(3-dimethylaminopropyl)-3-ethylcarbodiimide hydrochloride (323 mg, 1.69 mmol) in 30 ml of $CH_2Cl_2$ was stirred at r.t. for 1 hr, to the suspension was added the solution of 1-[2-(3-indolyl)ethyl]-4-aminopiperidine (373 mg, 1.53 mmol) in 3 ml of $CHCl_2$, the mixture was stirred at refluxing conditions overnight. The mixture was washed with water (2×20 ml), 20 ml 10% $K_2CO_3$ and 20 ml of sat'd brine. After drying with $Na_2SO_4$ and removal of solvent, a yellowish oil was obtained, which was purified by chromatography ($SiO_2$, MeOH:$CHCl_3$:1N $NH_3$ in MeOH, 6:90:3) and precipitated by $CH_2Cl_2$/$Et_2O$ mixture. A yellowish powder (273 mg, 31.3%) was obtained. M.p. 130–135° C.; Calcd. for $C_{32}H_{38}N_6O_4 \cdot ½H_2O$: C 66.30, H 6.78, N 14.50; Found: C 66.49, H 6.75, N 14.26.

EXAMPLE 124

5-Carboxamido-1,4-dihydro-3-(N-{3-[4-2-methoxyphenyl)piperidin-1-yl]propyl})carboxamido-2,6-dimethyl-4-(4-nitrophenyl)pyridine (124). The suspension of 5-carboxamido-1,4-dihydro-2,6-dimethyl-4-(4-nitrophenyl) pyridine-3-carboxylic acid (150 mg, 0.47 mmol) and 1-(3-dimethylaminopropyl)-3-ethylcarbodiimide hydrochloride (91 mg, 0.47 mmol) in 20 ml of $CH_2Cl_2$ was stirred at r.t. for 1 hr, to the suspension was added the solution of 1-(2-methoxyphenyl)-4-(3-aminopropyl)piperazine (118 mg, 0.47 mmol) in 3 ml of $CH_2Cl_2$, the mixture was stirred at refluxing conditions overnight. The mixture was washed with water (2×10 ml), 10 ml 10% $K_2CO_3$ and 10 ml of sat'd brine. After drying with $Na_2SO_4$ and removal of solvent, a yellowish oil was obtained, which was purified by chromatography ($SiO_2$, MeOH:$CHCl_3$:1N $NH_3$ in MeOH, 6:90:3) and precipitated by $CH_2Cl_2$/$Et_2O$ mixture. A yellow-green powder (80 mg, 31%) was obtained. M.p. 95–100° C.; Calcd. for $C_{29}H_{36}N_6O_5$: C 63.48, H 6.61, N 15.32; Found: C 63.20, H 6.64, N 15.03.

EXAMPLE 125

5-Carboxamido-2,6-diethyl-1,4-dihydro-3-(N-{3-[4-(2-methoxyphenyl)piperasin-1-yl]propyl})carboxamido-4-(4-nitrophenyl)pyridine (125). The suspension of 5-carboxamido-2,6-diethyl-1,4-dihydro-4-(4-nitrophenyl) pyridine-3-carboxylic acid (150 mg, 0.43 mmol) and 1-(3-dimethylaminopropyl)-3-ethylcarbodiimide hydrochloride (83 mg, 0.43 mmol) in 20 ml of $CH_2Cl_2$ was stirred at r.t. for 1 hr, to the suspension was added the solution of 1-(2-methoxyphenyl)-4-(3-aminopropyl)piperazine (108 mg, 0.43 mmol) in 2 ml of $CH_2Cl_2$, the mixture was stirred at refluxing conditions overnight. The mixture was washed with water (2×10 ml), 10 ml 10% $K_2CO_3$ and 10 ml of sat'd brine. After drying with $Na_2SO_4$ and removal of solvent, a yellowish oil was obtained, which was purified by chromatography ($SiO_2$, MeOH:$CHCl_3$:1N $NH_3$ in MeOH, 6:90:3) and precipitated by $CH_2Cl_2$/$Et_2O$ mixture. A yellow-green powder (160 mg, 64.5%) was obtained. M.p. 90–95° C.; Calcd. for $C_{31}H_{40}N_6O_5 \cdot ½H_2O$: C 63.57, H 7.06, N 14.35; Found: C 64.00, H 7.02, N 13.99.

EXAMPLE 126

3-{N-[3-(4-Cyano-4-phenylpiperidin-1-yl)propyl]}carboxamido-1,4-dihydro-2,6-dimethyl-5-(N-methyl)

carboxamido-4-(4-nitrophenyl)pyridine (126). The suspension of 5-carboxamido-1,4-dihydro-2,6-dimethyl-4-(4-nitrophenyl)pyridine-3-carboxylic acid (100 mg, 0.30 mmol) and 1-(3-dimethylaminopropyl)-3-ethylcarbodiimide hydrochloride (58 mg, 0.30 mmol) in 20 ml of $CH_2Cl_2$ was stirred at r.t. for 1 hr, to the suspension was added the solution of 3-(4-cyano-4-phenylpiperidin-1-yl)propylamine (69 mg, 0.30 mmol) in 2 ml of $CH_2Cl_2$, the mixture was stirred at refluxing conditions overnight. The mixture was washed with water (2×10 ml), 10 ml 10% $K_2CO_3$ and 10 ml of sat'd brine. After drying with $Na_2SO_4$ and removal of solvent, a yellowish oil was obtained, which was purified by chromatography ($SiO_2$, $MeOH:CHCl_3$:1N $NH_3$ in MeOH, 6:90:3) and precipitated by $CH_2Cl_2/Et_2O$ mixture. A yellowish powder (90 mg, 54%) was obtained. M.p. 110–115° C.; Calcd. for $C_{31}H_{36}N_6O_4$: C 66.88, H 6.52, N 15.10; Found: C 66.69, H 6.41, N 15.12.

EXAMPLE 127

5-Carboxamido-1,4-dihydro-2,6-diisopropyl-4-(4-nitrophenyl)-3-{N-[3-(4,4-diphenylpiperidin-1-yl)propyl]}carboxamidopyridine (127). To 15 ml of boiling p-xylene was added a solution of 6-(2-propyl)-2,2-dimethyl-2H,4H-1,3-dioxin-4-one (165 mg, 0.97 mmol) and 3-(4,4-diphenylpiperidin-1-yl)propylamine (285 mg, 0.97 mmol) in 10 ml p-xylene dropwise in about 15 min., during which time, about 20 ml of xylene was distilled off through a condenser. Heating was continued for an additional 45 min. to distill most xylene. The remaining xylene was further removed by evaporation in vacuo. The product, isobutanoylacetic acid N-[3-(4,4-diphenylpiperidin-1-yl)propyl]amide, was used for the next reaction without further purification.

The solution of 3-amino-4-methyl-2-pentenamide (135 mg, 1.06 mmol), 4-nitrobenzaldehyde (146 mg, 0.97 mmol) and isobutanoylacetic acid N-[3-(4,4-diphenylpiperidin-1-yl)propyl]amide (394 mg, 0.96 mmol) in 20 ml of 2-propanol was refluxed for 72 hrs. After the solvent was removed, the residue was purified by chromatography ($SiO_2$, $MeOH:CHCl_3$:1N $NH_3$ in MeOH, 6:90:3) to give a yellowish oil, which was precipitated by $CH_2Cl_2/Et_2O$ mixture. 45 mg (7.1% yield) of yellowish powder was obtained. M.p. 76–80° C.; Calcd for $C_{39}H_{47}N_5O_4 \cdot \frac{1}{2}H_2O$: C 69.21, H 7.45, N 10.35; Found: C 68.98, H 7.18, N 10.54.

EXAMPLE 128

2,6-Diethyl-1,4-dihydro-5-(N-methyl) carboxamido-4-(4-nitrophenyl)-3-{N-[3-(4,4-diphenylpiperidin-1-yl)propyl]}carboxamidopyridine (128). A suspension of 4-nitrobenzaldehyde (18.3 g, 0.118 mol), 2-cyanoethyl propionylacetate (20.0 g, 0.118 mol), piperidine (503 mg, 5.91 mmol) and acetic acid (355 mg, 5.91 mmol) in 230 ml of 2-propanol was stirred at r.t. for 48 hrs. Reaction mixture was filtered, the solid collected was dried in air to give 2-[(4-nitrophenyl)methylene]-3-oxopentanoic acid 2-cyanoethyl ester as a white powder (31.7 g, 89%). A solution of 2-[(4-nitrophenyl)methylene]-3-oxopentanoic acid 2-cyanoethyl ester (14.72 g, 48.7 mmol) and benzyl 3-aminocrotonate (10.00 g, 48.7 mmol) in 150 ml of EtOH was refluxed for 36 hrs. After solvent was removed, the residue was dissolved in 250 ml of $CHCl_3$ washed with water (2×100 ml) and dried over $Na_2SO_4$. After filtration and removal of solvent, 3-benzyloxycarbonyl-5-(2-cyanoethoxy)carbonyl-2,6-diethyl-1,4-dihydro-4-(4-nitrophenyl)pyridine was obtain as a yellow oil (23.0 g, 96%).

The solution of 3-benzyloxycarbonyl-5-(2-cyanoethoxy)carbonyl-2,6-diethyl-1,4-dihydro-4-(4-nitrophenyl)pyridine (6.30 g, 13.0 mmol) in 250 ml of 4.4% (w/w) formic acid/MeOH mixture was stirred with Pd/C (10%, 6.0 g) for 30 min., the reaction was quenched by addition of 100 ml of $CHCl_3$. The mixture was filtered and concentration of filtrate give a yellow powder, which was dissolved in $CHCl_3$, washed with water and 1N HCl. After filtration and removal of solvent, 3-(2-cyanoethoxy)carbonyl-2,6-diethyl-1,4-dihydro-4-(4-nitrophenyl)pyridine-5-carboxylic acid was obtained as a yellow powder (4.5 g, 87%).

3-(2-Cyanoethoxy)carbonyl-2,6-diethyl-1,4-dihydro-4-(4-nitrophenyl)pyridine-5-carboxylic acid (2.50 g, 6.25 mmol), 1-(3-dimethylaminopropyl)-3-ethylcarbodiimide hydrochloride (2.40 g, 12.5 mmol) and 4-dimethylaminopyridine (760 mg, 6.25 mmol) in 200 ml of $CH_2Cl_2$ was stirred at r.t. for 1 hr, to the solution was added the solution of methylamine (40% solution, 2.5 ml), the mixture was stirred at r.t. overnight. The mixture was washed with water (100 ml), sat'd $NH_4Cl$ (3×50 ml), 50 ml 10% $K_2CO_3$ and 100 ml of sat'd brine. After drying with $Na_2SO_4$ and removal of solvent, 3-(2-cyanoethoxy)carbonyl-2,6-diethyl-1,4-dihydro-5-(N-methyl)carboxamido-4-(4-nitrophenyl)pyridine was obtained as a yellowish powder (2.30 g, 89%). The solution of 3-(2-cyanoethoxy) carbonyl-2,6-diethyl-1,4-dihydro-5-(N-methyl) carboxamido- 4-(4-nitrophenyl)pyridine (890 mg, 2.15 mmol) in 15 ml acetone was treated with 10 ml 1N KOH solution at 0° C. for 45 min. The acetone was removed in vacuo and aqueous layer was acidified to pH=3 by 2N hydrochloric acid, the yellow precipitation was collected by filtration, washed with 10 ml of cold water and dried in vacuo. 510 mg (66% yield) of 3-(2-cyanoethoxy)carbonyl-2,6-diethyl-1,4-dihydro-5-(N-methyl) carboxamido-4-(4-nitrophenyl)pyridine was obtained as a yellow powder.

The solution of 2,6-diethyl-1,4-dihydro-5-(N-methyl) carboxamido-4-(4-nitrophenyl)pyridine-3-carboxylic acid (494 mg, 1.38 mmol), 1-(3-dimethylaminopropyl)-3-ethylcarbodiimide hydrochloride (476 mg, 2.50 mmol) and 4-dimethylaminopyridine (169 mg, 1.38 mmol) in 50 ml of $CH_2Cl_2$ was stirred at r.t. for 1 hr, to the solution was added the solution of 3-(4,4-diphenylpiperidin-1-yl)propylamine (405 mg, 1.38 mmol) in 2 ml of $CH_2Cl_2$, the mixture was stirred at refluxing conditions overnight. The mixture was washed with water (30 ml), sat'd $NH_4Cl$ (3×20 ml), 20 ml 10% $K_2CO_3$ and 20 ml of sat'd brine. After drying with $Na_2SO_4$ and removal of solvent, a yellowish oil was obtained, which was purified by chromatography ($SiO_2$, $MeOH:CHCl_3$:1N $NH_3$ in MeOH, 6:90:3) and precipitated by $CH_2Cl_2$/hexane mixture. A yellowish powder (700 mg, 74%) was obtained. M.p. 123–126° C.; Calcd. for $C_{38}H_{45}N_5O_4 \cdot H_2O$: C 69.81, H 7.25, N 10.71; Found: C 69.79, H 7.05, N 10.74.

EXAMPLE 129

2,6-Diethyl-5-(N-ethyl)carboxamido-1,4-dihydro-4-(4-nitrophenyl)-3-{N-[3-(4,4-diphenylpiperidin-1-yl)propyl]}carboxamidopyridine (129). The solution of 3-(2-cyanoethoxy)carbonyl-2,6-diethyl-1,4-dihydro-4-(4-nitrophenyl)pyridine-5-carboxylic acid (350 mg, 0.90 mmol), 1-(3-dimethylaminopropyl)-3-ethylcarbodiimide hydrochloride (260 mg, 13.5 mmol) and 4-dimethylaminopyridine (110 mg, 0.90 mmol) in 20 ml of $CH_2Cl_2$ was stirred at r.t. for 1 hr, to the solution was added the solution of ethylamine (0.22 ml, 70% aqueous solution), the mixture was stirred at r.t. overnight. The mixture was washed with water (10 ml), saturated aqueous $NH_4Cl$ (3×10 ml), 20 ml 10% $K_2CO_3$ and 10 ml of brine. After drying with $Na_2SO_4$ and removal of solvent, 3-(2-cyanoethoxy)

carbonyl-2,6-diethyl-5-(N-ethyl)carboxamido-1,4-dihydro-4-(4-nitrophenyl)pyridine was obtained as a yellowish powder (167 mg, 44%).

The solution of 3-(2-cyanoethoxy)carbonyl-2,6-diethyl-5- (N-ethyl)carboxamido-1,4-dihydro-4-(4-nitrophenyl) pyridine (167 mg, 0.39 mmol) in 10 ml acetone was treated with 5 ml 1N KOH solution at 0 for 45 min. The acetone was removed in vacuo and aqueous layer was acidified to ph=3 by 2N hydrochloric acid, the yellow precipitation was collected by filtration, washed with 10 ml of cold water and dried in vacuo. 118 mg (81% yield) of 2,6-diethyl-5-(N-ethyl)carboxamido-1,4-dihydro-4-(4-nitrophenyl)pyridine-3-carboxylic acid was obtained as a yellow powder.

The solution of 2,6-diethyl-5-(N-ethyl)carboxamido-1,4-dihydro-4-(4-nitrophenyl)pyridine-3-carboxylic acid (110 mg, 0.30 mmol), 1-(3-dimethylaminopropyl)-3-ethylcarbodiimide hydrochloride (104 mg, 0.54 mmol) and 4-dimethylaminopyridine (40 mg, 0.30 mmol) in 20 ml of $CH_2Cl_2$ was stirred at r.t. for 1 hr, to the solution was added the solution of 3-(4,4-diphenylpiperidin-1-yl)propylamine (88 mg, 0.30 mmol) in 2 ml of $CH_2Cl_2$, the mixture was stirred at refluxing conditions overnight. The mixture was washed with water (10 ml), sat'd $NH_4Cl$ (3×20 ml), 20 ml 10% $K_2CO_3$ and 20 ml of sat'd brine. After drying with $Na_2SO_4$ and removal of solvent, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture. A yellowish powder (115 mg, 49%) was obtained. M.p. 101–104° C.; Calcd. for $C_{39}H_{47}N_5O_4 \cdot \frac{3}{4}H_2O$: C 70.62, H 7.37, N 10.56; Found: C 70.58, H 6.90, N 10.65.

EXAMPLE 130

2,6-Diethyl-1,4-dihydro-4-(4-nitrophenyl)-5-{N-[3-(4,4-diphenylpiperidin-1-yl)propyl]}carboxamidopyridine-3-carboxylic acid (130). The solution of 3-(2-cyanoethoxy) carbonyl-2,6-diethyl-1,4-dihydro-4-(4-nitrophenyl) pyridine-5-carboxylic acid (395 mg, 1.00 mmol), 1-(3-dimethylaminopropyl)-3-ethylcarbodiimide hydrochloride (345 mg, 1.80 mmol) and 4-dimethylaminopyridine (122 mg, 1.00 mmol) in 40 ml of $CH_2Cl_2$ was stirred at r.t. for 1 hr, to the solution was added the solution of 3-(4,4-diphenylpiperidin-1-yl)propylamine (294 mg, 1.00 mmol) in 2 ml of $CH_2Cl_2$, the mixture was stirred at refluxing conditions overnight. The mixture was washed with water (20 ml), sat'd $NH_4Cl$ (3×20 ml), 20 ml 10% $K_2CO_3$ and 20 ml of sat'd brine. After drying with $Na_2SO_4$ and removal of solvent, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture. 3-(2-Cyanoethoxy)carbonyl-2,6-diethyl-1,4-dihydro-5-(4-nitrophenyl)-3-{N-[3-(4,4-diphenylpiperidin-1-yl)propyl]}carboxamidopyridine was obtained as a yellowish powder (552 mg, 82%).

The solution of 3-(2-cyanoethoxy)carbonyl-2,6-diethyl-1, 4-dihydro-5-(4-nitrophenyl)-3-{N-[3-(4,4-diphenylpiperidin-1-yl)propyl]}carboxamidopyridine (500 mg, 0.82 mmol) in 15 ml acetone was treated with 8.0 ml 1N KOH solution at 0° C. for 45 min. The acetone was removed in vacuo and aqueous layer was acidified to pH=4 by 2N hydrochloric acid, the yellow precipitation was collected by filtration and dried in vacuo. 340 mg (75% yield) of product was obtained as a yellowish powder. M.p. 154–158 (dec) °C.; Calcd. for $C_{37}H_{42}N_4O_5 \cdot \frac{3}{4}H_2O$: C 69.85, H 6.89, N 8.81; Found: C 69.82, H 6.70, N 8.88.

EXAMPLE 131

5-(N-Ethyl)carboxamido-1,4-dihydro-2,6-dimethyl-4-(4-nitrophenyl)-3-{N-[3-(4,4-diphenylpiperidin-1-yl)propyl]}carboxamidopyridine (131). A suspension of 4-nitrobenzaldehyde (10.00 g, 66.2 mol), 2-cyanoethyl acetoacetate (10.27 g, 66.2 mol), piperidine (281 mg, 3.31 mmol) and acetic acid (198 mg, 3.31 mmol) in 250 ml of 2-propanol was stirred at r.t. for 48 hrs. Reaction mixture was filtered, the solid collected and dried in air to give 2-cyanoethyl 2-[(4-nitrophenyl)methylene]-3-oxobutanate as a white powder (11.24 g, 59%).

A solution of 2-cyanoethyl 2-[(4-nitrophenyl)methylene]-3-oxobutanate (15.06 g, 52.3 mmol) and benzyl 3-aminocrotonate (10.00 g, 52.3 mmol) in 150 ml of EtOH was refluxed for 36 hrs. After solvent was removed, the residue was dissolved in 250 ml of $CHCl_3$ washed with water (2×100 ml) and dried over $Na_2SO_4$. After filtration and removal of solvent, 3-benzyloxycarbonyl-5-(2-cyanoethoxy)carbonyl-1,4-dihydro-2,6-dimethyl-4-(4-nitrophenyl)pyridine was obtain as a yellow oil (23.4 g, 97%).

The solution of 3-benzyloxycarbonyl-5-(2-cyanoethoxy) carbonyl-1,4-dihydro-2,6-dimethyl-4-(4-nitrophenyl) pyridine (3.24 g, 7.02 mmol) in 160 ml of 4.4% (w/w) formic acid/MeOH mixture was stirred with Pd/C (10%, 3.24 g) for 30 min., the reaction was quenched by addition of 10 ml of $CHCl_3$. The mixture was filtered and concentration of filtrate give a yellow powder, which was dissolved in $CHCl_3$, washed with water and 1N HCL. After drying and removal of solvent, 3-(2-cyanoethoxy)carbonyl-1,4-dihydro-2,6-dimethyl-4-(4-nitrophenyl)pyridine-5- carboxylic acid was obtained as a yellow powder (1.94 g, 75%)

The solution of 3-(2-cyanoethoxy)carbonyl-1,4-dihydro-2,6-dimethyl-4-(4-nitrophenyl)pyridine-5-carboxylic acid (500 mg, 1.35 mmol), 1-(3-dimethylaminopropyl)-3-ethylcarbodiimide hydrochloride (532 mg, 2.69 mmol) and 4-dimethylaminopyridine (164 mg, 1.35 mmol) in 50 ml of $CH_2Cl_{23}$ was stirred at r.t. for 1 hr, to the solution was added the solution of ethylamine (434 mg, 70% aqueous solution), the mixture was stirred at r.t. overnight. The mixture was washed with water (30 ml), saturated aqueous $NH_4Cl$ (3×25) ml, 25 ml of 10% aqueous $K_2CO_3$ and 30 ml of brine. After drying with $Na_2SO_4$ and removal of solvent, 3-(2-cyanoethoxy)carbonyl-5-(N-ethyl)carboxamido-1,4-dihydro-2,6-dimethyl-4-(4-nitrophenyl)pyridine was obtained as a yellowish powder (529 mg 98%).

The solution of 3-(2-cyanoethoxy) carbonyl-5-(N-ethyl) carboxamido-1,4-dihydro-2,6-dimethyl-4-(4-nitrophenyl) pyridine (535 mg, 1.35 mmol) in 10 ml acetone was treated with 10 ml 1N KOH solution at 0° C. for 45 min. The acetone was received in vacuo and aqueous layer was acidified to ph=3 by 2N hydrochloric acid, the yellow precipitation was collected by filtration, washed with 5 ml of cold water and dried in vacuo. 5-(N-ethyl)carboxamido-1, 4-dihydro-2,6-dimethyl-4-(4-nitrophenyl)pyridine-3-carboxylic acid was obtained as a yellow powder (266 mg, 57%).

The suspension of 5-(N-ethyl)carboxamido-1,4-dihydro-2,6-dimethyl-4-(4-nitrophenyl)pyridine-3-carboxylic acid (285 mg, 0.825 mmol), 1-(3-dimethylaminopropyl)-3-ethylcarbodiimide hydrochloride (315 mg, 1.65 mmol) and 4-dimethylaminopyridine (101 mg, 0.825 mmol) in 20 ml of $CH_2Cl_2$ was stirred at r.t. for 1 hr, to the solution was added the solution of 3-(4,4-diphenylpiperidin-1-yl)propylamine (243 mg, 0.825 mmol) in 2 ml of $CH_2Cl_2$, the mixture was stirred at refluxing conditions overnight. The mixture was washed with water (10 ml), sat'd $NH_4Cl$ (3×20 ml), 20 ml 10% $K_2CO_3$ and 20 ml of sat'd brine. After drying with $Na_2SO_4$ and removal of solvent, a yellowish oil was obtained, which was purified by chromatography (SiO$_2$, MeOH:CHCl$_3$:1N NH$_3$ in MeOH, 6:90:3) and precipitated by CH$_2$Cl$_2$/hexane mixture. A yellowish powder (190 mg, 37%) was obtained. M.p. 104–108° C.; Calcd. for C$_{37}$H$_{43}$N$_5$O$_4$: C 71.47, H 6.97, N 11.26; Found: C 71.21, H 6.88, N 11.27.

EXAMPLE 132

2,6-Diethyl-1,4-dihydro-3-(N-isopropyl)carboxamido-4-(4-nitrophenyl)-5-{N-[3-(4,4-diphenylpiperidin-1-yl) propyl]}carboxamidopyridine (132). The solution of 3-(2-cyanoethoxy) carbonyl-2,6-diethyl-1,4-dihydro-4-(4-nitrophenyl)pyridine-5-carboxylic acid (395 mg, 1.00 mmol), 1-(3-dimethylaminopropyl)-3-ethylcarbodiimide hydrochloride (345 mg, 1.80 mmol) and 4-dimethylaminopyridine (122 mg, 1.00 mmol) in 20 ml of CH$_2$Cl$_2$ stirred at r.t. for 1 hr, to the solution was added the solution of isopropylamine (300 mg, 5.00 mmol), the mixture was stirred at r.t. overnight. The mixture was washed with water (10 ml), saturated aqueous NH$_4$Cl (3×10 ml), 20 ml 10% K$_2$CO$_3$ and 10 ml of brine. After drying with Na$_2$SO$_4$ and removal of solvent, 3-(2-cyanoethoxy) carbonyl-2,6-diethyl-1,4-dihydro-5-(N-isopropyl) carboxamido-4-(4-nitrophenyl)pyridine was obtained as a yellowish powder (345 mg, 80%).

The solution of 3-(2-cyanoethoxy)carbonyl-2,6-diethyl-1,4-dihydro-5-(N-isopropyl)carboxamido-4-(4-nitrophenyl) pyridine (300 mg, 0.69 mmol) in 15 ml acetone was treated with 5 ml 1N KOH solution at 0° for 45 min. The acetone was removed in vacuo and aqueous layer was acidified to ph=3 by 2N hydrochloric acid, the yellow precipitation was collected by filtration, washed with 10 ml of cold water and dried in vacuo. 220 mg (83% yield) of 2,6-diethyl-1,4-dihydro-5-(N-isopropyl)carboxamido-4-(4-nitrophenyl) pyridine-3-carboxylic acid was obtained as a yellow powder.

The suspension of 2,6-diethyl-1,4-dihydro-5-(N-isopropyl)carboxamido-4-(4-nitrophenyl)pyridine-3-carboxylic acid (210 mg, 0.55 mmol), 1-(3-dimethylaminopropyl)-3-ethylcarbodiimide hydrochloride (210 mg, 1.00 mmol) and 4-dimethylaminopyridine (70 mg, 0.60 mmol) in 20 ml of CH$_2$Cl$_2$ was stirred at r.t. for 1 hr, to the solution was added the solution of 3-(4,4-diphenylpiperidin-1-yl)propylamine (161 mg, 0.55 mmol) in 2 ml of CH$_2$Cl$_2$, the mixture was stirred at refluxing conditions overnight. The mixture was washed with water (10 ml), sat'd NH$_4$Cl (3×20 ml), 20 ml 10% K$_2$CO$_3$ and 20 ml of sat'd brine. After drying with Na$_2$SO$_4$ and removal of solvent, a yellowish oil was obtained, which was purified by chromatography (SiO$_2$, MeOH:CHCl$_3$:1N NH$_3$ in MeOH, 6:90:3) and precipitated by CH$_2$Cl$_2$/hexane mixture. A yellowish powder (212 mg, 58%) was obtained. M.p. 201° C. (dec.); Calcd. for C$_{40}$H$_{49}$N$_5$O$_4$.½H$_2$O: C 71.40, H 7.49, N 10.41; Found: C 71.39, H 7.32, N 10.63.

EXAMPLE 133

2,6-Diethyl-1,4-dihydro-4-(4-nitrophenyl)-5-{N-[3-(4,4diphenylpiperidin-1-yl)propyl]}carboxamido-3-(N-propyl)carboxamidopyridine (133). The solution of 3-(2-cyanoethoxy)carbonyl-2,6-diethyl-1,4-dihydro-4-(4-nitrophenyl)pyridine-5-carboxylic acid (395 mg, 1.00 mmol), 1-(3-dimethylaminopropyl)-3-ethylcarbodiimide hydrochloride (345 mg, 1.80 mmol) and 4-dimethylaminopyridine (122 mg, 1.00 mmolin 20 ml of CH$_2$Cl$_2$ was stirred at r.t. for 1 hr, to the solution was added the solution of propylamine (300 mg, 5.00 mmol), the mixture was stirred at r.t. overnight. The mixture was washed with water (10 ml), saturated aqueous NH$_4$Cl (3×10 ml), 20 ml 10% K$_2$CO$_3$ and 10 ml of brine. After drying with diethyl-1,4-dihydro-4-(4-nitrophenyl)-5-(N-propyl) carboxamidopyridine was obtained as a yellowish powder (420 mg, 95%).

The solution of 3-(2-cyanoethoxy)carbonyl-2,6-diethyl-1,4-dihydro-4-(4-nitrophenyl)-5-(N-propyl) carboxamidopyridine (420 mg, 0.95 mmol) in 10 ml acetone was treated with 5 ml 1N KOH solution at 0° for 45 min. The acetone was removed in vacuo and aqueous layer was acidified to pH=3 by 2N hydrochloric acid, the yellow precipitation was collected by filtration, washed with 10 ml of cold water and dried in vacuo. 276 mg (75% yield) of 2,6-diethyl-1,4-dihydro-4-(4-nitrophenyl)-5-(N-propyl) carboxamidopyridine-3-carboxylic acid was obtained as a yellow powder.

The suspension of 2,6-diethyl-1,4-dihydro-4-(4-nitrophenyl)-5-(N-propyl) carboxamidopyridine-3-carboxylic acid (250 mg, 0.645 mmol), 1-(3-dimethylaminopropyl)-3-ethylcarbodiimide hydrochloride (247 mg, 1.29 mmol) and 4-dimethylaminopyridine (80 mg, 0.65 mmol) in 20 ml of CH$_2$Cl$_2$ was stirred at r.t. for 1 hr, to the solution was added the solution of 3-(4,4-diphenylpiperidin-1-yl)propylamine (190 mg, 0.645 mmol) in 2 ml of CH$_2$Cl$_2$, the mixture was stirred at refluxing conditions overnight. The mixture was washed with water (10 ml), sat'd NH$_4$Cl (3×20 ml), 20 ml 10% K$_2$CO$_3$ and 20 ml of sat'd brine. After drying with Na$_2$SO$_4$ and removal of solvent, a yellowish oil was obtained, which was purified by chromatography (SiO$_2$, MeOH:CHCl$_3$:1N NH$_3$ in MeOH, 6:90:3) and precipitated by CH$_2$Cl$_2$/hexane mixture. A yellowish powder (180 mg, 42%) was obtained. M.p. 120–123° C.; Calcd. for C$_{40}$H$_{49}$N$_5$O$_4$.H$_2$O: C 71.40, H 7.49, N 10.41; Found: C 71.14, H 7.21, N 10.51.

EXAMPLE 134

1,4-Dihydro-2,6-dimethyl-4-(4-nitrophenyl)-5-{N-[3-(4,4-diphenylpiperidin-1-yl) propyl]}carboxamido-3-(N-propyl)carboxamidopyridine (134). The solution of 3-(2-cyanoethoxy)carbonyl-1,4-dihydro-2,6-dimethyl-4-(4-nitrophenyl)pyridine-5-carboxylic acid (500 mg, 1.35 mmol), 1-(3-dimethylaminopropyl)-3-ethylaminopyridine (164 mg, 1.35 mmol) in 50 ml of CH$_2$Cl$_2$ was stirred at r.t. for 1 hr, to the solution was added the solution of propylamine (164 mg, 1.35 mmol), the mixture was stirred at r.t overnight. The mixture was washed with water (30 ml), saturated aqueous NH$_4$Cl (3×25 ml), 25 ml of 10% aqueous K$_2$CO$_3$ and 30 ml of brine. After drying with Na$_2$SO$_4$ and removal of solvent, 3-(2-cyanoethoxy) carbonyl-1,4-dihydro-2,6-dimethyl-4-(4-nitrophenyl)-5-(N-propyl) carboxamidopyridine was obtained as a yellowish powder (555 mg 100%.)

The solution of 3-(2-cyanoethoxy)carbonyl-1,4-dihydro-2,6-dimethyl-4-(4-nitrophenyl)-5-(N-propyl) carboxamidopyridine (500 mg, 1.20 mmol) in 10 ml acetone was treated with 5 ml 1N KOH solution at 0° C. for 45 min. The acetone was removed in vacuo and aqueous layer was acidified to ph=3 by 2N hydrochloric acid, the yellow precipitation was collected by filtration, washed with 5 ml of cold water and dried in vacuo. 1,4-Dihydro-2,6-dimethyl-4-(4-nitrophenyl)-5-(N-propyl)carboxamidopyridine-3-carboxylic acid was obtained as a yellow powder (275 mg, 64%).

The suspension of 1,4-dihydro-2,6-dimethyl-4-(4-nitrophenyl)-5-(N-propyl) carboxamidopyridine-3-carboxylic acid (240 mg, 0.582 mmol), 1-(3- dimethylaminopropyl)-3-ethylcarbodiimide hydrochloride (223 mg, 1.16 mmol) and 4-dimethylaminopyridine (71 mg, 0.58 mmol) in 20 ml of $CH_2Cl_2$ was stirred at r.t. for 1 hr, to the solution was added the solution of 3-(4,4-diphenylpiperidin-1-yl)propylamine (171 mg, 0.58 mmol) in 2 ml of $C_2Cl_2$, the mixture was stirred at refluxing conditions overnight. The mixture was washed with water (10 ml), sat'd $NH_4Cl$ (3×20 ml), 20 ml 10% $K_2CO_3$ and 20 ml of sat'd brine. After drying with $Na_2SO_4$ and removal of solvent, a yellowish oil was obtained, which was purified by chromatography ($SiO_2$, $MeOH:CHCl_3$:1N $NH_3$ in MeOH, 6:90:3) and precipitated by $CH_2Cl_2$/hexane mixture. A yellowish powder (190 mg, 51%) was obtained. M.p. 142–145° C.; Calcd. for $C_{38}H_{45}N_5O_4 \cdot H_2O$: C 69.81, H 7.25, N 10.71; Found: C 70.12, H 6.85, N 11.01.

EXAMPLE 135

Ethyl 4-Methyloxy-3-oxo-butanoate. A mixture of 15.8 g of ethyl 4-chloroacetoacetate (96.2 mmol) and 3.39 g of methanol (106 mmol) in 10 mL of THF were added dropwise to a stirred suspension of 4.62 g of 60% NaH (in mineral oil), 1.60 g of NaI (9.62 mmol), and 3.10 g of tetrabutylammonium bromide (9.62 mmol) in 40 mL of THF at −30° C. over a period of 1.5 hrs. The reaction mixture was then warmed to room temperature and stirred for 4 days. The reaction mixture was cooled to −30° C., quenched with 5 mL of methanol, and warmed to room temperature. The reaction mixture was poured into 0.5 L of 10% HCl solution, extracted with 2×100 mL of EtOAc, dried ($Na_2SO_4$), and the solvent was removed in vacuo. The crude product was distilled. The fraction boiling at 65–70° C. (0.3 mm Hg) was collected and used in the next experiments after spectral characterization.

3-(Bensyloxy)carbonyl-5-(2-cyanoethoxy)carbonyl-6-ethyl-1,4-dihydro-2-(methyloxy) methyl)methyl-4-(4-nitro) phenylpyridine. A mixture of 3.28 g of ethyl 4-methoxy-3-oxo-butanoate (20.5 mmol) and 4.43 g of benzyl alcohol (41.0 mmol) were heated at 140–150° C. (10–15 mm Hg) for 2 hrs. The reaction mixture was cooled, diluted with 20 mL of ethanol (denatured), 1.90 g of ammonium acetate (24.6 mmol) was added, and the resulting mixture was heated at reflux temperature for 1.5 hrs. The reaction mixture was cooled and 5.27 g of 2-cyanoethyl 2-(4-nitro)phenylmethyleno-3-oxopentanoate was added to the reaction mixture. The resulting mixture was heated at reflux temperature for 2 hrs, cooled, and solvent was removed in vacuo. The crude product was chromatographed on 550 g of silica packed with 10% EtOAc-hexane. The column was eluted with 20% (2 L), and 30% EtOAc-hexane (4 L) to give 3.08 g (30%) of the title compound as a yellow oil with solidified on standing. The product was used in the next step after spectral characterization.

5-(2-Cyanoethoxy)carbonyl-6-ethyl-1,4-dihydro-2-(methyloxy)methyl-4-(4-nitro)phenylpyridine-3-carboxylic acid. A suspension of 2.86 g of 3-(benzyloxy)carbonyl-5-(2-cyanoethoxy)carbonyl-6-ethyl-1,4-dihydro-2-(methyloxy) methyl-4-(4-nitro)phenylpyridine (5.66 mmol), 572 mg of 10% Pd/C, 70 mL of methanol, and 2.09 mL of formic acid were stirred at room temperature for 0.5 h. The reaction mixture was diluted with 30 mL of chloroform, filtered through a pad of Celite 545. The filtrate was concentrated in vacuo, and the residue was chromatographed on 250 g of silica packed with 30% EtOAc-hexane. The column was eluted with 50% to 80% EtOAc-hexane (10% change/1 L) to give 1.33 g of the title compound (57%) as a yellow oily solid. Anal. Calc. for $C_{20}H_{21}N_3O_7$: C, 57.83; H, 5.10; N, 10.12. Found: C, 57.78; H, 5.08; N, 9.99.

5-(2-Cyanoethoxy)carbonyl-6-ethyl-1,4-dihydro-2-(methoxy)methyl-4-(4-nitro)phenyl-3-(N-(3-4,4-diphenylpiperidin-1-yl)propyl))carboxamidopyridine, Hemihydrate. A solution of 433 mg of 5-(2-cyanoethoxy) carbonyl-6-ethyl-1,4-dihydro-2-(methyloxy)methyl-4-(4-nitro)phenylpyridine-3-carboxylic acid (1.04 mmol), 401 mg of 1-(dimethylaminopropyl)-3-ethylcarbodiimide hydrochloride (DMAPECD) (2.09 mmol), and 153 mg of 4-dimethylaminopyridine (DMAP) (1.25 mmol) in 5 mL of dry dichloromethane were stirred at room temperature for 1 h. The reaction mixture was charged with 328 mg of N-(3-aminopropyl)-4,4-diphenylpiperidine (1.25 mmol), and the resulting solution was heated at reflux temperature for 2 hrs. The reaction mixture was cooled, and applied to 200 g of silica packed with 5% MeOH-EtOAc. The column was eluted with 10% to 20% MeOH-EtOAc (1 L/5% change) to afford 552 mg of the title compound (77%) as a yellow foamy solid: mp 120–125° C.; Anal. Calc. for $C_{40}H_{45}N_5O_6 \cdot 0.5H_2O$: C, 68.55; H, 6.62; N, 9.99. Found: C, 68.37; H, 6.26; N, 9.98.

EXAMPLE 136

6-Ethyl-1,4-dihydro-2-(methyloxy)methyl-4-(4-nitro) phenyl-3-(N-(3-(4,4-diphenylpiperidin-1-yl)propyl)) carboxamidopyridine-5-carboxylia acid (136). A solution of 40 mg of NaOH in 2 mL of water was added to 530 mg of 5-(2-cyanoethoxy)carbonyl-6-ethyl-1,4-dihydro-2-(methyloxy)methyl-4-(4-nitro)phenyl-3-(N-(3-(4,4-diphenylpiperidin-1-yl)propyl))carboxamidopyridine (0.766 mmol) in 10 mL of dioxane. The resulting mixture was stirred at room temperature for 1 hour. The solvent was removed in vacuo, the residue was partitioned between 20 mL of water (containing 200 mg of NaOH) and EtoAc (10 mL), separated, and the organic layer was extracted with 2×5 mL of water. The combined aqueous extracts were acidified (concentrated HCl, pH=3–4), and the precipitated oil was extracted with 3×10 mL of dichloromethane. The combined organic extracts were dried ($Na_2SO_4$), and the solvent was removed in vacuo to afford 472 mg (97%) of the title compound as a yellow solid: mp 120–125° C. (decomp.); Anal. Calcd for $C_{37}H_{42}N_4O_6 \cdot 2H_2O$: C, 65.86, H, 6.87; N, 8.30. Found: C, 65.52; H, 7.05; N, 7.89.

EXAMPLE 137

5-Carboxamido-6-ethyl-1,4-dihydro-2-(methyloxy) methyl-4-(4-nitro)phenyl-3-(N-(3-(4,4-diphenylpiperidin-1-yl)propyl))carboxamidopyridine, Hemihydrate (137). A mixture of 70.0 mg of 6-ethyl-1,4-dihydro-2-(methyloxy) methyl-4-(4-nitro)phenyl-3-(N-(3-(4,4-diphenylpiperidin-1-yl)propyl)) carboxamidopyridine-5-carboxylic acid (0.110 mmol), 90.5 mg of dicyclohexylcarbodiimide (DCC) (0.435 mmol), and 16.0 mg of DMAP (0.132 mmol) in 5 mL of dry dichloromethane were stirred at room temperature for 1 hour followed by addition of 5 mL of concentrated ammonia. The resulting mixture was heated at reflux temperature for 16 hours, cooled, filtered, dichloromethane was removed in vacuo, and the residue was dissolved in 5 mL of ethyl acetate (a small amount of dichloromethane was added to make the mixture homogeneous). The ethyl acetate solution was sequentially washed with aqueous saturated ammonium chloride solution (3×2 mL), aqueous sodium carbonate solution (2 mL), dried ($Na_2SO_4$), and the solvent was removed in vacuo. The residue was chromatographed on 200 g of silica packed with $NH_3$ (2M in MeOH)—MeOH—$CHCl_3$ (1:2:40). The column was eluted with the same solvent to give 21.0 mg of the title compound as a yellow solid: mp 89° C. (decomp.); Anal. Calc. for $C_{37}H_{43}N_5O_5 \cdot 0.5$ $H_2O$: C, 68.72; H, 6.86; N, 10.83. Found: C, 68.40; H, 6.91; N, 10.41

EXAMPLE 138

Ethyl 4-(2,2,2-trifluoroethyl)oxy-3-oxobutanoate. A solution of 5.00 g of trifluoroethanol (50.0 mmol) in 5 mL of dry THF was added dropwise, over a period of 0.5 hr, to a stirred mixture of 4.00 g of 60% dispersion of NaH (100 mmol), 1.61 g of tetrabutylammonium bromide (5.0 mmol), and 830 mg of NaI (5.0 mmol) in 20 mL of dry THF (water bath). The resulting mixture was stirred for 0.5 hrs, cooled to −30° C., and a solution of 8.23 g of ethyl 4-chloro-3-oxobutanoate (50.0 mmol) in 10 mL of dry THF was added dropwise, over a period of 15 min, to the reaction mixture. The reaction mixture was warmed to 0° C. over a period of 2 hrs, and stirred at room temperature for 36 hrs. The reaction mixture was quenched with 5 mL of ethanol, partioned between 100 mL of EtOAc and 100 mL of 10% aqueous HCl solution, separated, extracted with 2×40 mL of EtOAc, the combined organic extracts were dried ($Na_2SO_4$), and the solvent was removed in vacuo. The crude product was chromatographed on 400 g of silica packed with 5% EtOAc-hexane. The column was eluted with 5 to 25% EtOAc-hexane (1 L/5% change) to afford 8.75 g (77%) of ethyl 4-(2,2,2-trifluoroethyl)oxy-3-oxobutanoate as a slightly yellow oil. The product was used in the next step after spectral characterization.

2-Cyanoethyl 4-(2,2,2-trifluoroethyl)oxy-3-ozobutanoate. A mixture of 4.04 g of ethyl 4-(2,2,2-trifluoroethyl)oxy-3-oxobutanoate (17.7 mmol) and 2.55 g of 3-hydroxypropionitrile (35.9 mmol) was heated at reflux temperature at a bath temperature of 135–150° C. at 10 torr for 6 hrs. The reflux condensor was replaced with a distillation head and the product was distilled under reduced pressure to give 4.26 g (96%) of the desired product as a viscous oil: bp 155–158° C. (1.5). The product was used in the next step after spectral characterization.

5-Carboxamido-2-((2,2,2-trifluoroethyl)oxy)methyl-1,4-dihydro-6-methyl-4-(4-nitrophenyl)pyridine-3-carboxylia acid. A mixture of 1.07 g of 2-cyanoethyl 4-(2,2,2-trifluoroethyl)oxy-3-oxobutanoate (4.23 mmol) and 391 mg of ammonium acetate (5.08 mmol) in 5 mL of ethanol were heated at reflux temperature for 15 min, cooled, 2-(4-nitro) phenylmethylenoacetoacetamide (4.23 mmol) was added to the reaction mixture. The resulting mixture was heated at reflux temperature for 4.5 hours, cooled, and a solution of 406 mg of NaOH (10.2 mmol) in 5 mL of water was added to the reaction mixture. The resulting mixture was stirred at room temperature for 0.5 hour. The solvent was removed in vacuo, and the residue was partitioned between EtOAc (20 mL) and water (20 mL containing 300 mg of NaOH), separated, and the organic layer was extracted with 2×10 mL of water (each containing 150 mg of NaOH). The combined aqueous extracts were filtered, acidified to pH 2–3 with concentrated HCl, and the separated oil was extracted with 50 and then 2×20 mL of EtOAc. The combined EtOAc extracts were dried ($MgSO_4$), and the solvent was removed in vacuo. The crude product crystallized upon trituration with ethyl acetate to give 450 mg of the title compound (26%) as a yellow crystalline solid: mp 184° C. (decomp.); Anal. Calc. for $C_{17}H_{16}N_3F_3O_6$: C, 49.16; H, 3.88; N, 10.12. Found: 48.81; H, 3.97; N, 9.80.

5-Carboxamido-2-(2,2,2-trifluoroethyl)oxy)methyl-1,4-dihydro-6-methyl-4-(4-nitro)phenyl-3-(N-(3-(4,4-diphenylpiperidin-1-yl)propyl))carboxamidopyridine (138).

A mixture of 102 mg of 6-methyl-4-(4-nitrophenyl)-2-((2,2,2-trifluoroethyl)oxy)methyl-5-carboxamido-1,4-dihydropyridine-3-carboxylic acid (0.230 mmol), 72.0 mg of 1-(3-amino)propyl-4,4-diphenylpiperidine (0.276 mmol), 119 mg of DCC (0.575 mmol), and 31.0 mg of DMAP (0.253 mmol) in 5 mL of dry dichloromethane were heated at reflux temperature for 3 hours, cooled, filtered, and the solvent was removed in vacuo. The residue was dissolved in 5 mL of EtOAc, and sequentially washed with saturated aqueous ammonium chloride solution (2×2 mL), saturated aqueous sodium carbonate solution (2 mL), dried ($Na_2SO_4$), and directly applied to 200 g of silica packed with 2N $NH_3$ (in methanol)—MeOH—$CHCl_3$ (1:2:20). The column was eluted with the same solvent system to afford 140 mg of product as a yellow solid (87%): mp 89° C. (decomp.); Anal. Calc. for $C_{37}H_{40}N_5F_3O_5$: C, 64.24; H, 5.83; N, 10.12. Found: C, 63.90; Hi 5.87; N, 9.66

EXAMPLE 139

2-Asidoethanol (see scheme infra; II): A mixture of 55.6 g of sodium azide (0.855 mol), and 81.4 g of bromoethanol (1) (0.649 mol), and 394 mg of sodium hydroxide (9.85 mmol) in 250 mL of water as stirred in a 61–64° C. bath for 24 hours. The reaction mixture was saturated with solid sodium sulfate, extracted with 250 mL and then 10×100 mL of EtOAc. The combined EtOAc extracts were dried ($Na_2SO_4$), solvent removed in vacuo, redissolved in 250 mL of EtOAc, redried ($MgSO_4$), and the solvent removed in vacuo. The crude product was distilled under reduced pressure to give 45.1 g of 2-azidoethanol (80%) as a colorless oil. The product was used in the next step after spectral characterization: bp 40–45° C. (0.5 mmHg).

t-Butyl 4-(2-Asidoethyl)oxy-3-oxobutanoate (V): (2-Azidoethyl)oxyacetia Acid (III). A solution of 50.0 g of 2-azidoethanol (574 mmol) in 100 mL of dry THF was added dropwise to a stirred (mechanical stirrer) suspension of 25.3 g of NaH (632 mmol), in 250 mL of dry THF over a period of 1 hour. The reaction mixture was charged with 18.5 g of tetrabutylammonium bromide (57.4 mmol) and 9.52 g of potassium iodide (57.4 mmol) in one portion. Finally, a solid addition funnel was used to add 73.6 g of sodium chloroacetate (632 mmol) to the reaction mixture. The resulting suspension was heated at reflux temperature for 20 hrs. The reaction mixture was quenched with 200 mL of water (added dropwise with cooling), and the THF was removed in vacuo. The resulting basic solution was washed with dichloromethane (8×200 mL). The aqueous extract was acidified to pH=1 (concentrated HCl), saturated with solid NaCl, and extracted with 6×350 mL of dichloromethane. The combined dichloromethane extracts were dried overnight over $Na_2SO_4$, solvent removed in vacuo to give 45.6 g of III as a yellow oil (55%). The product was used in the next coupling experiment after spectral characterization. Carbonyldiimidazole (9.83 g, 60.6 mmol) and (2-azidoethoxy)acetic acid (II) (8.00 g, 55.1 mmol) in 100 mL of dry dichloromethane were stirred at room temperature for 1 hour. A solution of 8.7 g of 2,2-dimethyl-1,3-dioxane-4,6-dione (60.6 mmol, Meldrum's acid) and 4.4 g of dry pyridine (55.1 mmol) in 30 mL of dry dichloromethane were added to the reaction mixture, and stirred for 16 hrs at room temperature. The reaction mixture was washed with aqueous 2N HCl solution (2×60 mL), water (2×40 mL), and brine (40 mL), dried ($MgSO_4$), and the solvent removed under reduced pressure to give 15 g of the desired product (IV) (100%). TLC showed small amounts of Meldrum's acid in the crude product. The crude product was used in the next experiment without any further purification.

A solution of 8.25 g of IV (30.4 mmol) in 20 mL of t-BuOH was heated at reflux temperature for 2.5 hrs. The reaction mixture was cooled, concentrated in vacuo (7.40 g), and the crude product was filtered through a pad of silica (eluted with EtOAc-hexane, 1:4) to give 6.11 g of t-butyl 4-(2-azidoethyl)oxy-3-oxobutanoate (V) (83%). This product was spectroscopically pure, and was used in the next experiment without any further purification or characterization.

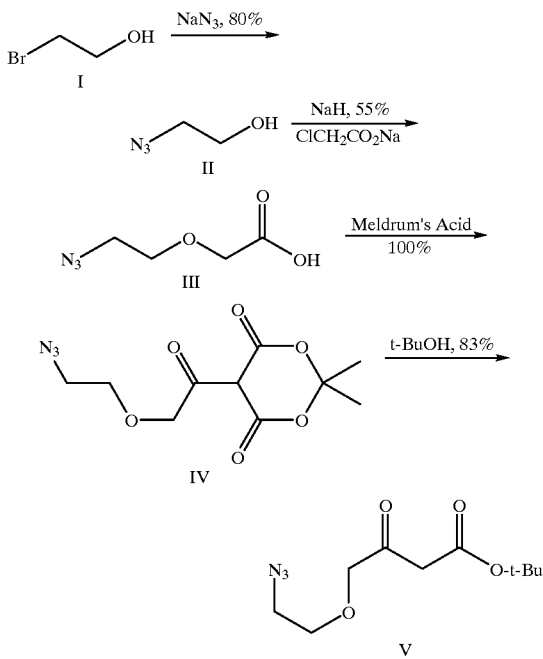

2-((2-Axidoethyl)oxy)methyl-5-(2-oyanoethoxy) carbonyl-6-ethyl-1,4-dihydro-3-(1,1-dimethylethoxy) carbonyl-4-(4-nitro)phenylpyridine. A mixture of 1.00 g of t-butyl 4-(2-azidoethoxy)-3-oxopentanoate (4.10 mmol) and concentrated ammonia (0.800 g, 24.6 mmol) in 1.5 mL of t-BUOH was stirred at room temperature 17 hours. The solvent was remove in vacuo to a give a yellow viscous oil which was used in the next step after spectral characterization. A mixture of the resulting enamide, and 0.850 g of 2-cyanoethyl 2-(4-nitro)phenylmethyleno-3-oxopentanoate in 15 mL of t-BuOH was heated at reflux temperature for 5 hrs. The reaction mixture was concentrated in vacuo, and the crude product was chromatographed on silica (EtOAc-hexane, 1:3) to give 836 mg of the title compound (56%) as a yellow viscous oil: Anal. Calc. for $C_{25}H_{30}N_6O_7$: C, 57.02; H, 5.25; N, 15.95. Found: C, 56.77; H, 5.67; N, 15.69.

2-((2-Azidoethyl)ozy)methyl-6-ethyl-1,4-dihydro-3-(1,1-dimethoxy)carbonyl-4-(4-nitro)phenylpyridine-5-carboxylic acid. A solution of 91 mg of sodium hydroxide (2.3 mmol) in 7.5 mL of water was added to a solution of 800 mg of 2-((2-azidoethyl)oxy)methyl-5-(2-cyanoethoxy) carbonyl-6-ethyl-1,4-dihydro-3-(1,1-dimethylethoxy) carbonyl-4-(4-nitro)phenylpyridine (1.52 mmol) in 7.5 mL of dioxane. The resulting mixture was stirred at room temperature for 3.5 hours. The reaction mixture was washed with ether (10 mL), and the ether extract was back-washed with water (basic at pH=9–10). The combined aqueous extracts were acidified (pH=4), and the precipitated solid was collected to give the desired acid as a yellow solid (600 mg, 83%): mp 170–173° C.; Anal. Calc. for $C_{22}H_{27}N_5O_7$: C, 55.80; H, 5.76; N, 14.78. Found: C, 2-((2-Asidoethyl)oxy)methyl-6-ethyl-1,4-dihydro-3-(1,1-dimethylethozy)carbonyl-4-(4-nitro)phenyl-5-(N-(4,4-diphenylpiperidin-1-yl)propyl))carboxamidopyridine (139). A mixture of 300 mg of 2-((2-azidoethyl)oxy)nethyl-6-ethyl-1,4-dihydro-3-(1,1-dimethylethoxy) carbonyl-4-(4-nitro)phenylpyridine-5-carboxylic acid (0.634 mmol), 182 mg of DMAPECD, and 93 mg of DMAP in 8 mL of dry dichloromethane were stirred at room temperature for 3 hrs. The reaction mixture was charged with 216 mg of N-(3-aminopropyl)-4,4-diphenylpiperidine (0.824 mmol), and heated at reflux temperature for 19 hours. The reaction mixture was concentrated in vacuo and the crude product was chromatographed (5% MeOH-EtOAc) to give 400 mg of desired product (86%) as a yellow foamy solid: mp 62–67° C.; Anal. Calc. for $C_{42}H_{51}N_7O_6$: C, 67.26; H, 6.89; N, 13.07. Found: C, 66.96; H, 6.79; N, 12.87.

EXAMPLE 140

2-((2-Aminoethyl)oxy)methyl-6-ethyl-1,4-dihydro-3-(1,1-dimethylethozy)carbonyl-4-(4-nitro)phenyl-5-(N-3-(4,4-diphenylpiperidin-1-yl)propyl))carboxamidopyridine, (140). A solution of 2-((2-azidoethyl)oxy)methyl-6-ethyl-1,4-dihydro-3-(1,1-dimethylethoxy) carbonyl-4-(4 -nitro) phenyl-5-(N-(3-(4,4-diphenylpiperdin-1-yl)propyl)) carboxamidopyridine (0.180 mmol), 57 mg of triphenylphosphine (0.22 mmol), and 5 mL of water in 3.5 mL of ethyl acetate were stirred at room temperature for 13 hours. The reaction mixture was concentrated in vacuo and the crude product was chromatographed on silica (2N $NH_3$ (in methanol)—MeOH—$CHCl_3$, 1:1:9) to give 25 mg of the title compound as a light yellow foamy solid: mp 84–89° C.; Anal. Calcd for $C_{42}H_{53}N_5O_6 \cdot 0.7H_2O$: C, 68.49; H, 7.44; N, 9.51. Found: C, 68.14; H, 7.00; N, 9.41.

EXAMPLE 141

2-((2-Azidoethyl oxy)methyl-5-(2-cyanoethoxy) carbonyl-6-ethyl-1,4-dihydro-4-(4-nitro)phenylpyridine-3-carboxylic acid. A mixture of 2.90 g of 2-((2-azidoethyl) oxy)methyl-5-(2-cyanoethoxy)carbonyl-6-ethyl-1,4-dihydro-3-(1,1-dimethylethoxy)carbonyl-4-(4-nitro) phenylpyridine (5.51 mmol) in 10 mL of formic acid was stirred for 1.5 hours, solvent removed in vacuo. The crude product was triturated with EtOAc and a small amount of hexane and the resulting precipitated yellow product was collected (700 mg): mp 150° C. (decomp.). The product was used in the following steps after spectral characterization.

2-((2-Asidoethyl)oxy)methyl-5-(2-cyanoethoxy) carbonyl-6-ethyl-1,4-dihydro-4-(4-nitro)phenyl-3-(N-3-(4,4-diphenylpiperidin-1-yl)propyl))carboxamidopyridine (141). A solution of 700 mg of 2-((2-azidoethyl)oxy)methyl-5-(2-cyanoethoxy)carbonyl-6-ethyl-1,4-dihydro-4-(4-nitro) phenylpyridine-3-carboxylic acid (1.49 mmol), 461 mg of DCC (2.23 mmol), and 145 mg of DMAP (1.19 mmol) in 10 mL of dry dichloromethane were stirred at room temperature for 1.5 hours. The reaction mixture was charged with 570 mg of N-(3-aminopropyl)-4,4-diphenylpiperidine (1.93 mmol), and the reaction mixture was stirred for 13 hours. The reaction mixture was filtered and applied to a flash chromatography column (silica, MeOH-EtOAc 5% to 10%) to give 815 mg of the desired product (73%) as a yellow foamy solid: mp 63–67° C.; Anal. Calcd for $C_{41}H_{46}N_8O_6 \cdot H_2O$: C, 64.38; H, 6.33; N, 14.65. Found: C, 64.72; H, 6.12; N, 14.62.

EXAMPLE 142

2-((2-Asidoethyl)ozy)methyl-6-ethyl-1,4-dihydro-4-(4-nitro)phenyl-3-(N-(3-(4,4-diphenylpiperidin-1-yl)propyl))

carboxamidopyridine-5-carboxylia acid (142). A solution of sodium hydroxide (30 mg) in 2 mL of water was added to a solution of 356 mg of 2-((2-azidoethyl)oxy)methyl-5-(2-cyanoethoxy)carbonyl-6-ethyl-1,4-dihydro-4-(4-nitro) phenyl-3-(N-(3-(4,4-diphenylpiperidin-1-yl)propyl)) carboxamidopyridine (0.500 mmol) in 2 mL of dioxane. The resulting mixture was stirred at room temperature for 2 hours. The solvent was removed in vacuo. The residue was dissolved in 10 mL of water and extracted with a 1:1 mixture of ether-hexane (10 mL). The aqueous extract was acidified to pH 4 (concentrated HCl), and the precipitated yellow solid was collected to give 283 mg of the title compound (82%): mp 118° C. (decomp.); Anal. Calc for $C_{38}H_{43}N_7O_6$: C, 65.78; H, 6.26; N, 14.12. Found: C, 65.55; H, 6.31; N, 13.96.

EXAMPLE 143

2-((2-Azidoethyl)ozy)methyl-5-carboxamido-6-ethyl-1, 4-dihydro-4-(4-nitro)phenyl-3-(N-(3-(4,4-diphenylpiperidin-1-yl)propyl))carboxamidopyridine (143). A solution of 600 mg of 2-((2-azidoethyl)oxy)methyl-6-ethyl-1,4-dihydro-4-(4-nitro)phenyl-3-(N-(3-(4,4-diphenylpiperidin-1-yl) propyl))carboxamidopyridine-5-carboxylic acid (0.865 mmol), DCC (357 mg, 1.73 mmol), and DMAP (85 mg, 0.692 mmol) in 15 mL of dry dichloromethane was stirred at room temperature for 2 hours. The reaction mixture was charged with 522 mg of concentrated ammonia solution, and the reaction mixture was stirred at room temperature for 3 days. The reaction mixture was filtered, concentrated in vacuo and the crude product was chromatographed (silica, MeOH-EtOAc, 1:9, 1:8, 1:4) to give 528 mg of product as a yellow foamy solid (88%): mp 88–93° C.; Anal. Calc. for $C_{38}H_{44}N_8O_5 \cdot 0.5H_2O$: C, 65.03; H, 6.46; N, 15.97. Found: C, 64.80; H, 5.96; N, 15.88.

EXAMPLE 144

2-((2-Aminoethyl)ozy)methyl-5-carboxamido-6-ethyl-1, 4-dihydro-4-(4-nitro)phenyl-3-(N-(3-(4,4-diphenylpiperidin-1-yl)propyl))carboxamidopyridine (144). A solution of 61 mg of 2-((2-azidoethyl)oxy)methyl-5-carboxamido-6-ethyl-1,4-dihydro-4-(4-nitro) phenyl-3-(N-(3-(4,4-diphenylpiperidin-1-yl)propyl)) carboxamidopyridine (0.088 mmol), triphenylphosphine (30 mg, 0.114 mmol), and water (2.5 mg, 0.141 mmol) in 1 mL EtOAc was stirred at room temperature for 3 days. The reaction mixture was concentrated in vacuo, and chromatographed (silica, $NH_3$ (2N in methanol) :MeOH:$CHCl_3$ (1:2:20)) to give 32 mg of the title compound (55%) as a yellow solid: mp 98–103° C.; Anal. Calcd for $C_{38}H_{46}N_6O_5 \cdot 1.0H_2O \cdot 0.2CH_2Cl_2$: C, 65.38; H, 6.95; N, 11.97. Found: C, 65.39; H, 6.58; N, 11.44.

Using trimethylphosphine as the reducing agent, on a large scale (3 mmol), a 93% yield of the 144 was realized. The product from this batch had the following microanalytical data: Anal. Calc. for $C_{38}H_{46}N_6O_5 \cdot 1.3 H_2O$: C, 66.12; H, 7.10; N, 12.18. Found: C, 66.17; H, 6.69; N, 12.09

The enantiomers of 144 were separated on a Chirapak AS (2×25 cm) column. The retention times on the semi-prep column were dependent on the column load. At a 60 mg load, the retention times were 128 and 228 minutes (hexane-ethanol-isopropanol (containing 3% diethylamine) 84:3:13). The retention times on the analytical Chirapak AS column (4.6 mm×25 cm), using the same solvent mixture were 34 and 54 minutes (broad peaks). The plus isomer eluted first followed by the minus isomer. The purity of the final selected enantiomeric fractions were >99.9%.

−10: $[a]_{100}$=−39.8
+10: $[a]_{100}$=+40.1

EXAMPLE 145

2-((2-Azidoethyl)ozy)methyl-6-methyl-6-ethyl-5-(N-ethyl) carbozamido-1,4-dihydro-4-(4-nitro)phenyl-3-(N-(3-(4,4-diphenylpiperidin-1-yl)propyl))carboxamidopyridine (145). A solution of 80 mg of 2-((2-azidoethyl)oxy)methyl-6-ethyl-1,4-dihydro-4-(4-nitro)phenyl-3-(N-(3-(4,4-diphenylpiperidin-1-yl)propyl))carboxamidopyridine-5-carboxylic acid (0.115 mmol), 33 mg of DMAPECD (0.173 mmol), and 31 mg of DMAP in 1 mL of dichloromethane were stirred at room temperature for 2 hours. The reaction mixture was charged with 1.15 mmol of ethylamine (70% solution in water). The reaction mixture was stirred at room temperature for 10 hours and then heated at reflux temperature for 10 hours. The reaction mixture was concentrated in vacuo, dissolved in 3 mL of ethyl acetate, with some drops of dichloromethane added to make the solution homogeneous. The resulting mixture was washed with aqueous saturated $NH_4Cl$ solution (2×2 mL), dried ($Na_2SO_4$), and the solvent removed in vacuo. The crude product was chromatographed (silica, MeOH-EtOAc, 1:9) to give 44 mg of the desired product as a yellow solid (53%): mp 82–87° C.; Anald. Calc. for $C_{40}H_{48}N_8O_5 \cdot 2.0H_2O$: C, 63.47; H, 6.92; N, 14.80. Found: C, 63.49; H, 6.24; N, 14.78.

EXAMPLE 146

2-((2-Aminoethyl)oxy)methyl-6-ethyl-5-(N-ethyl) carboxamido-1,4-dihydro-4-(4-nitro)phenyl-3-(N-(3-(4,4-diphenylpiperidin-1-yl) propyl))carboxamidopyridine (146). A solution of 30 mg of 2-((2-azidoethyl)oxy)methyl-6-ethyl-5-(N-ethyl)carboxamido-1,4-dihydro-4-(4Onitro) phenyl-3-(N-(3-(4,4-diphenylpiperidin-1-yl)propyl)) carboxamidopyridine (0.042 mmol), triphenylphosphine (17 mg, 0.063 mmol), and water (1.5 mg, 0.084 mmol) in 3 mL of EtOAc were stirred at room temperature for 19 hrs. Triphenyphosphine (2 mg) and water (1 mg) were added to the reaction mixture and stirred for 24 hrs. The reaction mixture was concentrated in vacuo, and the crude product was chromatographed on silica ($NH_3$ (2N in methanol)—MeOH—$CHCl_3$, 1:2:20) to give 13 mg of product as a yellow solid (45%: mp 115–111° C.; Anal. Calc. for $C_{40}H_{50}N_6O_5 \cdot 1.0H_2O \cdot 0.6CH_2Cl_2$: C, 63.84; H, 7.02; N, 11.00. Found: C, 63.79; H, 6.96; N, 10.81.

EXAMPLE 147

2-((2-Azidoethyl)oxy)methyl-5-(2-cyanoethoxy) carbonyl-6-ethyl-3-(N-ethyl)carboxamido-1,4-dihydro-4-(4-nitro)phenylpyridine. A solution of 150 mg of 2-((2-azidoethyl)oxy)methyl-5-(2-cyanoethoxy)carbonyl-6-ethyl-1,4-dihydro-4-(4-nitro)phenylpyridine-3-carboxylic acid (0.085 mmol), DMAPECD (92 mg, 0128 mmol), and DMAP (49 mg, 0.102 mmol) in 1.2 mL of dichloromethane was stirred at room temperature for 2.5 hours. The reaction mixture was charged with 27 mg of ethyamine (70% solution in water) and the reaction mixture was heated at reflux temperature for 4 hours. The solvent was removed in vacuo and the crude product was chromatographed (silica, EtOAc-hexane, 3:2) to give 101 mg of the desired product as a yellow solid which was used in the next experiment after spectral characterization.

2-((2-Azidoethyl)oxy)methyl-6-ethyl-3-(N-ethyl) carboxalido-1,4-dihydro-4-(4-nitro)phenylpyridine-5-carboxylic acid. A solution of 12.5 mg of NaOH in 2 mL of water was added to a solution of 104 mg of 2-((2-azidoethyl)

oxy)methyl-5-(2-cyanoethoxy)carbonyl-6-ethyl-3-(N-ethyl) carboxamido-1,4-dihydro-4-(4-(4-nitro)phenylpyridine (0.21 mmol) in 2 mL of dioxane. The resulting mixture was stirred at room temperature for 2 hours, and the solvent was removed in vacuo. The crude product was partitioned between water (5 mL) and ether (5 mL), separated, acidified (concentrated HCl, pH=5) and the precipitated oil was extracted with ethyl acetate (2×5 mL). The combined organic extracts were dried ($Na_2SO_4$), and the solvent was removed in vacuo to yield 49 mg of the desired product as a yellow solid: mp 72–77° C. The product was used in the next step after spectral characterization.

2-((2-Azidoethyl)oxy)methyl-6-ethyl-3-(N-ethyl) carboxamido-1,4-dihydro-4-(4-nitro)phenyl-5-(N-(3-(4,4-diphenylpiperidin-1-yl-)propyl))carboxamidopyridine (147). A mixture of 40 mg of 6-((2-azidoethyl)oxy)methyl-2-ethyl-3-(N-ethyl)carboxamido-1,4-dihydro-4-(4-nitro) phenylpyridine-5-carboxylic acid (0.090 mmol), DMAP-ECD (26 mg, 0.135 mmol), and DMAP (13 mg, 0.108 mmol) in 2 mL of dry dichloromethane was stirred at room temperature for 3 hours. The reaction mixture was charged with 35 mg of N-3-aminopropyl-4,4-diphenylpiperidine, and the resulting mixture was heated at reflux temperature for 17.5 hours. The reaction mixture was diluted with 2 mL of EtOAc, washed with saturated aqueous $NH_4Cl$ solution (2×2 mL), dried ($Na_2CO_3$), and the solvent was removed in vacuo. The crude product was chromatographed (silica, 10% MeOH-EtOAc) to give 30 mg of the desired product as a yellow solid (46%): mp 83–87° C.; Anal. Calc. for $C_{40}H_{48}N_8O_5 \cdot 3H_2O$: C, 62.00; H, 7.02; N, 14.46. Found: C, 61.84; H, 6.74; N, 14.75.

EXAMPLE 148

2-((2-Aminoethyl)ozy)methyl-6-ethyl-3-(N-ethyl) carboxamido-1,4-dihydro-4-(4-nitro)phenyl-5-(N-(3-(4,4-diphenylpiperidin-1-yl)propyl))carboxamidopyridine (148). A solution of 15 mg of 2-((2-azidoethyl)oxy)methyl-6-ethyl-3-(N-ethyl)carboxamido-1,4-dihydro-4-(4-nitro)phenyl-5-(N-(3-(4,4-diphenylpiperidin-1-yl)propyl)) carboxamidopyridine (0.021 mmol), triphenylphosphine (8.2 mg, 0.031 mmol), and 1.9 mg of water (0.105 mmol) in 1.5 mL of ethyl acetate were stirred at room temperature for 1 day, 2 mg of triphenylphosphine and 2 mg of water were added to the reaction mixture and stirred for one day, concentrated in vacuo, and the crude product was chromatographed (silica, $NH_3$ (2N in methanol)—MeOH—$CHCl_3$, 1:2:20) to afford 5.1 mg of the desired product as a yellow solid (28%): mp 116–120° C.; Anal. Calc. for $C_{40}H_{50}N_6O_5 \cdot 1.0H_2O \cdot 1.0Cl_2$: C, 61.72; H, 6.82; N, 10.53. Found: C, 61.95; H, 6.74; N, 10.49.

EXAMPLE 149

2-((2-Azidoethyl)oxy)methyl-3-carboxamido-5-(2-cyanoethoxy)carbonyl-6-ethyl-1,4-dihydro-4-(4-nitro) phenylpyridine. A solution of 199 mg of 2-((2-azidoethyl) oxy)methyl-5-(2-cyanoethoxy)carbonyl-6-ethyl-1,4-dihydro-4-(4-nitro)phenylpyridine-3-carboxylic acid (0.423 mmol), DMAPECD (122 mg, 0.635 mmg), and DMAP (41 mg, 0.338 mmol) in 3 mL of dry dichloromethane were stirred at room temperature 3 hours. The reaction mixture was charged with 530 mg of concentrated ammonia solution and the resulting mixture was heated at reflux temperature for 3.5 hrs. The reaction mixture was cooled, filtered and chromatographed (silica, EtOAc-hexane, 1:1, 2:1, 2.5:1) to give 55 mg of spectrally pure product along with 15 mg of slightly impure product for a combined yield of 40%: mp 114–119° C. The product was used in the next step without any further purification.

2-((2-Azidoethyloxy)methyl-3-carboxamido-6-ethyl-1,4-dihydro-4-(4-nitro)phenylpyridine-5-carboxylio acid. A solution of 12 mg of NaOH in 0.6 mL of water was added to 60 mg of 2-((2-azidoethyl)oxy)methyl-3-carboxamido-5-(2-cyanoethoxy)carbonyl-6-ethyl-1,4-dihydro-4-(4-nitro) phenylpyridine (0.127 mmol) in 2 mL of acetone. The resulting mixture was stirred at room temperature for 3.5 hours. The acetone was removed under reduced pressure, acidified with 0.2N HCl solution, filtered, the residue was dissolved in 5 mL EtOAc, dried ($Na_2SO_4$) and the solvent was removed in vacuo to yield 46 mg of the desired product (80%): mp 86° C. (decomp.). The product was used in the next step after spectral characterization.

EXAMPLE 149

2-((2-Azidoethyl)ozy)methyl-3-carboxamido-6-ethyl-1, 4-dihydro-4-(4-nitro)phenyl-5-(N-(3-(4,4-diphenylpiperidin-1-yl)propyl))carboxamidopyridine (149). A solution of 40 mg of 2-((2-azidoethyl)oxy)methyl-3-carboxamido-6-ethyl-1,4-dihydro-4-(4-nitro) phenylpyridine-5-carboxylic acid (0.096 mmol), DMAP-ECD (28 mg, 0.143 mmol), and DMAP (9 mg, 0.077 mmol) in 3 mL of dichloromethane was stirred at room temperature for 3 hours. The reaction mixture was charged with 40 mg of N-(3-aminopropyl)-4,4-diphenylpiperidine and the resulting mixture was heated at reflux temperature for 12 hrs. The reaction mixture was diluted with 3 mL of ethyl acetate, washed with aqueous saturated $NH_4Cl$ solution (2×5 mL), dried ($Na_2CO_3$), and the solvent was removed in vacuo. The crude product was chromatographed (silica, MeOH-EtOAc, 1:9 to 1:6) to afford 18 mg of spectrally pure product and 40 mg of slightly impure product for a combined yield of 88%: mp 87–91° C.; Anal. Calc. for $C_{38}H_{44}N_8O_5 \cdot 0.4H_2O$: C, 65.20; H, 6.45; N, 16.01. Found: C, 65.49; H, 6.65; N, 15.45.

EXAMPLE 150

2-((2-Aminoethyl)ozy)methyl-3-carboxamido-6-ethyl-1, 4-dihydro-4-(4-nitro)phenyl-5-(N-(3-(4,4-diphenylpiperidin-1-yl)propyl))carboxamidopyridine (150). A solution of 40 mg of 2-((2-azidoethyl)oxy)methyl-3-carboxamido-6-ethyl-1,4-dihydro-4-(4-nitro)phenyl-5-(N-(3-(4,4-diphenylpiperidin-1-yl)propyl)carboxamidopyridine (0.0577 mmol), 45 mg of triphenylphosphine (0.173 mmol), and 10 mg of water in 1.5 mL of ethyl acetate were stirred at room temperature for 13 hrs, and the crude product was chromatographed (silica, $NH_3$ (2N in methanol)—MeOH—$CHCl_3$, 1:2:20) to give 14 mg of the desired product as a yellow solid: mp 116–120° C.; Anal. Calc. for $C_{38}H_{46}N_6O_5 \cdot 1.0H_2O \cdot 1.0CH_2Cl_2$: C, 60.85; H, 6.55; N, 10.92. Found: 60.69; H, 6.51; N, 10.86.

EXAMPLE 151

2-((2-Azidoethyl)oxy)methyl-5-(2-cyanoethoxy) carbonyl-6-ethyl-1,4-dihydro-3-(N-methyl)carboxamido-4-(4-nitro)phenylpyridine. A mixture of 188 mg of 2-((2-azidoethyl)oxy)methyl-5-(2-cyanoethoxy)carbonyl-6-ethyl-1,4-dihydro-4-(4-nitro)phenylpyridine-3-carboxylic acid (0.400 mmol), 115 mg of DMAPECD (0.600 mmol), and 58.6 mg of DMAP (0.480 mmol) in 5 mL of dry dichloromethane were stirred at room temperature 2.75 hours. A solution of methylamine in water (40%, 0.40 mL, 4.80 mmol) was added, and the reaction mixture was heated at reflux temperature for 4 hours. The reaction mixture was cooled, solvent removed in vacuo, and the residue was chromatographed on 100 g of silica packed with EtOAc-hexane (3:2) to give 55 mg of the desired product as a yellow paste (29%). The product was used in the next step after spectral characterization.

2-((2-Azidoethyl)oxy)methyl-6-ethyl-1,4-dihydro-3-(N-methyl)carboxamido-4-(4-nitro)phenylpyridine-5-carboxylic acid. 2-((2-azidoethyl)oxy)methyl-5-(2-cyanoethoxy)carbonyl-6-ethyl-1,4-dihydro-3-(N-methyl)carboxamido-4-(4-nitro)phenylpyridine (50.0 mg, 0.103 mmol) was dissolved in 0.5 mL of dioxane, NaOH (6.2 mg, 0.155 mmol) in 0.5 mL of water was added to the reaction mixture, and stirred at room temperature for 2.5 hours. The reaction mixture was diluted with 2 mL of etherhexane (1:1), separated, the aqueous layer was acidified with concentrated HCl (pH=2–3), extracted with 2×2 mL of EtOAc, the combined EtOAc extracts were dried ($Na_2SO_4$), and the solvent was removed in vacuo to give 44 mg of the desired product as a yellow paste. The product was used in the next step after spectral characterization.

2-((2-Azidoethyl)oxy)methyl-6-ethyl-1,4-dihydro-3-(N-methyl)carboxamido-4-(4-nitro)phenyl-5-(N-(3-(4,4-diphenylpiperidin-1-yl)propyl))carboxamidopyridine (151). A mixture of 44.0 mg of 2-((2-azidoethyl)oxy)methyl-6-ethyl-1,4-dihydro-3-(N-methyl)carboxamido-4-(4-nitro)phenylpyridine-5-carboxylic acid (0.100 mmol), 30.0 mg of DMAPECD (0.160 mmol), and 15.0 mg of DMAP (0.120 mmol) in 2 mL of dry dichloromethane were stirred at room temperature for 2 hours. The reaction mixture was charged with 34.0 mg of N-(3-aminopropyl)-4,4-diphenylpiperidine, and the resulting mixture was heated at reflux temperature for 6 hours. The reaction mixture was cooled, and the solvent was removed in vacuo. The residue was dissolved in 5 mL of $CH_2Cl_2$-EtOAc (3:2), washed with 2×4 mL of aqueous saturated $NH_4Cl$ solution, dried ($Na_2CO_3$), and the solvent was removed in vacuo. The crude product was chromatographed on 50 g of silica packed with 10% MeOH-EtOAc to give 24.0 mg of the desired product (34%) as a yellow solid.

The hydrochloride salt was prepared by addition of a dichloromethane solution (2 mL) of the free base (24 mg) into 2 mL of 1N HCl in ether. The precipitated yellow solid was collected to give 20 mg of the desired product: Mp 200° C. (decomp.); Anal. Calcd for $C_{39}H_{46}N_8O_5 \cdot HCl \cdot 2.4CH_2Cl_2$: C, 52.50; H, 5.51; N, 11.83. Found: C, 52.67; H, 5.87; N, 11.66.

EXAMPLE 152

2-(Trimethylsilyl)ethyl Acetoacetate. A mixture of 6.70 g of 2-trimethylsilylethanol (56.7 mmol) and 8.05 g of 2,2,6-trimethyl-4H-1,3-dioxin-4-one (56.7 mmol) was placed in a round bottom flask equipped with a short distillation apparatus and heated to to drive off acetone. The calculated amount of acetone was collected, and the residue was distilled under reduced pressure. The fraction boiling at 106–110° C. (5–10 mmHg) was collected (8.52 g, 74%). The product was used in the next step after spectral characterization.

2-Trimethylsilylethyl 2-(4-nitro)phenylmethyleno-3-ozobutanoate. A mixture of 7.35 g of 2-(trimethylsilyl)ethyl acetoacetate (36.3 mmol), 5.49 g of p-nitrobenzaldehyde (36.3 mmol), 309 mg of piperidine (3.63 mmol), and 218 mg of acetic acid (3.63 mmol) in 100 mL of isopropanol was stirred at room temperature for 16 hours. The solvent was removed in vacuo, and the resulting yellow oil was placed under high vacuum (with occasional heating with a heat gun) until there was no bubbling. The resulting yellow solid was triturated with isopropanol, filtered, and washed with isopropanol to give the desired product as a pale yellow crystalline solid (11.0 g, 90%) (a mixture of E/Z isomers): mp 63–65° C.; Anal Calcd for $C_{16}H_{21}N_1Si_1O_5$: C, 57.29; H, 6.31; N, 4.18. Found: C, 57.20; H, 6.35; N, 4.22.

2-((2-Azidoethyl)ozy)methyl-3-(2-cyanoethoxy)carbonyl)-1,4-dihydro-6-methyl-5-(2-(trimethylsilylethoxy)carbonyl-4-(4-nitro)phenylpyridine. A mixture of 1.31 g of 2-cyanoethyl 4-(2-azidoethoxy)oxy-3-oxobutanoate (5.45 mmol) and 504 mg of ammonium acetate (6.54 mmol) in 5 mL of ethanol (denatured) were heated at reflux temperature for 15 min, cooled, and 1.83 g of 2-(trimethylsilyl)ethyl 2-(4-nitro) phenylmethyleno-3-oxobutanoate (5.45 mmol) was added to the reaction mixture. The resulting mixture was heated at reflux temperature for 1 hour, cooled and the solvent was removed in vacuo. The crude product was chromatographed on 400 g of silica packed with 10% EtOAc-hexane. The column was eluted with 20% (1 L), 30% (2 L), and 40% EtOAc-hexane (3 L) to afford 980 mg of pure (spectra), and 520 mg of slightly impure product for a combined yield of 49% as a yellow oily solid: Anal. calcd for $C_{25}H_{32}N_6Si_1O_7$: C, 53.94; H, 5.80; N, 15.10. Found: C, 53.80; H, 5.90; N, 15.25.

2-((2-Azidoethyl)oxy)methyl-1,4-dihydro-6-methyl-5-(2-trimethylsilylethoxy)carbonyl-4-(4-nitro)phenylpyridine-3-carboxylic acid. A solution of 48 mg of NaOH in 1 mL of water was added to 518 mg of 2-((2-azidoethyl)oxy)methyl-3-(2-cyanoethoxy)carbonyl)-1,4-dihydro-6-methyl-5-(2-trimethylsilylethoxy) carbonyl-4-(4-nitro) phenylpyridine (1.21 mmol) in 5 mL of dioxane. The reaction mixture was stirred at room temperature for 2 hrs, concentrated in vacuo, dissolved in 10 mL of ethyl acetate, washed with 2×5 mL of 1N HCl solution, dried ($Na_2SO_4$), and the solvent was removed in vacuo. The crude product was recrystallized from a mixture of EtOAc-hexane to give 399 mg of the title compound (85%) as a yellow crystalline solid: mp 145–150° C. (decomp.); Anal. Calc. for $C_{22}H_{29}N_5Si_1O_7$: C, 52.47; H, 5.81; N, 13.91. Found: C, 52.47; H, 5.61; N, 13.87.

2-((2-Azidoethyl)ozy)methyl-1,4-dihydro-6-methyl-5-(2-trimethylsilylethoxy)carbonyl-4-(4-nitro)phenyl-3-(N-(3-(4,4-diphenylpiperidin-1-yl) propyl))carboxamidopyridine (152). A mixture of 190 mg of 2-((2-azidoethyl)oxy)methyl-1,4-dihydro-6-methyl-5-(2-trimethylsilylethoxy)carbonyl-4-(4-nitro)phenylpyridine-3-carboxylic acid (0.377 mmol), 117 mg of DCC (0.566 mmol), and 51 mg of DMAP in 5 mL of dry dichloromethane was stirred at room temperature for 1 hour. The reaction mixture was charged with 119 mg of 1-(3-aminopropyl)-4,4-diphenylpiperidine (0.452 mmol) and the resulting mixture was heated at reflux temperature for 2 hours. The reaction mixture was filtered, and chromatographed on 200 g of silica packed with 2.5% MeOH-EtOAc. The column was eluted with 2.5% (0.5 L), 5% (0.5 L), 10% (1 L), and 15% MeOH-EtOAc (1 L) to give 271 mg of product as a yellow foamy solid (92%): mp 63° C. (decomp.); Anal. Calcd for $C_{42}H_{53}N_7Si_1O_6 \cdot 0.75CH_2Cl_2$: C, 61.25; H, 6.55; N, 11.72. Found: C, 61.69; H, 6.04; N, 12.13.

EXAMPLE 153

2-((2-Azidoethyl)ozy)methyl-1,4-dihydro-6-methyl-4-(4-nitro)phenyl-3-(N-(3-(4,4-diphenylpiperidin-1-yl)propyl)) carboxamidopyridine-5-carboxylic acid (153). A solution of 0.347 mmol of tetrabutylammonium fluoride (1M in THF) was added to a solution of 246 mg of 2-((2-azidoethyl)oxy) methyl-1,4-dihydro-6-methyl-5-(2-trimethylsilylethoxy) carbonyl-4-(4-nitro)phenyl-3-(N-(3-(4,4-diphenylpiperidin- 1-yl)propyl))carboxamidopyridine (0.315 mmol) in 4 mL of dry THF. After 2 hrs, 694 mL of 1N tetrabutylammonium fluoride was added to the reaction mixture and stirred for 12 hours. The solvent was removed in vacuo, and the residue was partitioned between 20 mL of EtOAc and 10 mL of water, separated and washed with 2×10 mL of water. The ethyl acetate extract was diluted with 20 mL of hexane and extracted with 3×10 mL of 0.5N NaOH solution. The combined aqueous extracts were acidified with concentrated HCl (pH 2–3) and the separated oily solid was extracted with 2×10 mL of dichloromethane. The combined organic extracts were dried ($Na_2SO_4$) and the solvent was removed in vacuo to give 192 mg of the desired product as a yellow foamy solid (89%): mp 135° C. (decomp.); Anal. Calcd for $C_{37}H_{41}N_7O_6$.0.45 $CH_2Cl_2$: C, 62.65; H, 5.88; N, 13.66. Found: C, 62.92; H, 6.00; N, 13.47.

EXAMPLE 154

2-((2-Azidoethyl)oxy)methyl-5-carboxamido-1,4-dihydro-6-methyl-4-(4-nitro)phenyl-3-(N-(3-(4,4-diphenylpiperidin-1-yl)propyl))carboxamidopyridine (154). A mixture of 161 mg of 2-((2-azidoethyl)oxy)methyl-1,4-dihydro-6-methyl-4-(4-nitro)phenyl-3-(N-(3-(4,4-diphenylpiperidin-1-yl)propyl))carboxamidopyridine-5-carboxylic acid (0.237 mmol), DCC (73 mg, 0.355 mmol), and DXAP (32 mg, 0.261 mmol) in 2 mL of dry dichloromethane was stirred at room temperature for 1 hour. The reaction mixture was charged with 100 mL of concentrated ammonia and stirred at room temperature for 16 hours. The reaction mixture was filtered, concentrated, dissolved in 5 mL of ethyl acetate, filtered, washed with aqueous saturated ammonium chloride solution (3×2 mL), and solvent removed in vacuo. The crude product was chromatographed on 200 g of silica packed with 2N $NH_3$ (in methanol)—MeOH—$CHCl_3$-$CH_2Cl_2$ (1:2:20:20). The column was eluted with the above solvent system to give 125 mg of the desired product as a yellow foamy solid (78%): mp 90–95° C. (decomp.); Anal. Calcd for $C_{37}H_{42}N_8O_5$.0.3 $CHCl_3$: C, 62.69; H, 5.97; N, 15.68. Found: C, 62.53; H, 5.32; N, 15.12.

EXAMPLE 155

2-((2-Aminoethyl)oxy)methyl-5-carboxamido-1,4-dihydro-6-methyl-4-(4-nitro)phenyl-3-(N-(3-(4,4-diphenylpiperidin-1-yl)propyl))carboxamidopyridine (155). A solution of 85 mg of 2-((2-azidoethyl)oxy)methyl-5-carboxamido-1,4-dihydro-6-methyl-4-(4-nitro)phenyl-3-(N-(3-(4,4-diphenylpiperidin-1-yl)propyl)) carboxamidopyridine (0.125 mmol), 49.3 mg of triphenylphosphine (0.188 mmol), and 7 mL of water in 2 mL of THF were stirred at room temperature for 2 days. TLC showed small amounts of the starting material in the reaction mixture. Triphenylphosphine (5 mg) was added to the reaction mixture and stirred for 1 day. The solvent was removed in vacuo, and the crude product was chromatographed on 120 g of silica packed with $NH_3$ (2M in MeOH) :MeOH:$CHCl_3$ (1:2:17). The column was eluted with 1:2:17, 1:2:15, and 1:2:10 ($NH_3$ (2 M in MeOH) :MeOH:$CHCl_3$) to give 20 mg of the desired product. The chromatographed product was dissolved in 5 mL of $CH_2Cl_2$ and 5 mL of saturated sodium carbonate mixture, separated, dried over $Na_2SO_4$, and the solvent was removed in vacuo. The residue was triturated with $CH_2Cl_2$-ether (1:2) to give a yellow solid: Anal. calc. for $C_{37}H_{44}N_6O_5$.1.4$CHCl_3$.1.4$H_2O$: C, 54.57; H, 5.75. Found: C, 54.50; H, 5.81

EXAMPLE 152

1,4-Dihydro-3-(N-isopropyl)carbozamido-2,6-dimethyl-4-(4-nitrophenyl)-5-{N[3-(4,4-diphenylpiperidin-1-yl) propyl]}carboxamidopyridine (156). A suspension of 4-nitrobenzaldehyde (10.00 g, 66.2 mol), 2-cyanoethyl acetoacetate (10.27 g, 66.2 mol), piperidine (281 mg, 3.31 mmol) and acetic acid (198 mg, 3.31 mmol) in 250 ml of 2-propanol was stirred at room temperature for 48 hrs. Reaction mixture was filtered, the solid collected and dried in air to give 2-[(4-nitrophenyl)methylene]-3 -oxobutanoic acid 2-cyanoethyl ester as a white powder (11.24 g, 59%).

A solution of 2-[(4-nitrophenyl)methylene]-3-oxobutanoic acid 2-cyanoethyl ester (15.06 g, 52.3 mmol) and benzyl 3-amino-crotonate (10.00 g, 52.3 mmol) in 150 ml of EtOH was refluxed for 36 hrs. After solvent was evaporated, the residue was dissolved in 250 ml of $CHCl_3$, washed with water (2×100 ml) and dried over $Na_2SO_4$. After filtration and evaporation of solvent, 3-benzyloxycarbonyl-5-(2-cyanoethoxy)carbonyl-1,4-dihydro-2,6-dimethyl-4-(4-nitrophenyl)pyridine was obtained as a yellow oil (23.4 g, 97%).

A solution of 3-benzyloxycarbonyl-5-(2-cyanoethoxy) carbonyl-1,4-dihydro-2,6-dimethyl-4-(4-nitrophenyl) pyridine (3.24 g, 7.02 mmol) in 160 ml of 4.4%(w/w) formic acid/NeOH mixture was stirred with Pd/C (10%, 3.24 g) for 30 min., the reaction was quenched by addition of 10 ml of $CHCl_3$. The mixture was filtered and concentrated to give a yellow powder, which was dissolved in $CHCl_3$ (100 ml), washed with water (25 ml) and aqueous 1N HCl (25 ml). After drying ($Na_2SO_4$) and evaporation of solvent, 3-(2-cyanoethoxy)carbonyl-1,4-dihydro-2,6-dimethyl-4-(4-nitrophenyl)pyridine-5-carboxylic acid was obtained as a yellow powder (1.94 g, 75%).

A solution of 3-(2-cyanoethoxy)carbonyl-1,4-dihydro-2, 6-dimethyl-4-(4-nitrophenyl)pyridine-5-carboxylic acid (473 mg, 1.35 mmol), 1-(3-dimethylaminopropyl)-3-ethylcarbodiimide hydrochloride (532 mg, 2.69 mmol) and 4-dimethylaminopyridine (164 mg, 1.35 mmol) in 50 ml of $CH_2Cl_2$ was stirred at room temperature. After 1 hr, a solution of isopropylamine (398 mg, 6.73 mmol) in 2 ml of $CH_2Cl_2$ was added and the mixture was stirred at room temperature overnight. The mixture was washed with water (30 ml), saturated aqueous $NH_4Cl$ (3×25 ml), 10% aqueous $K_2CO_3$ (25 ml) and brine (30 ml). After dried over $Na_2SO_4$ and removal of solvent in vacuo, 3-(2-cyanoethoxy) carbonyl-1,4-dihydro-5-(N-isopropyl)carboxamido-2,6-dimethyl-4-(4-nitrophenyl)pyridine was obtained as a yellowish powder (524 mg, 94%).

A solution of 3-(2-cyanoethoxy) carbonyl-1,4-dihydro-5-(N-isopropyl)carboxamido-2,6-dimethyl-4-(4-nitrophenyl) pyridine (500 mg, 1.20 mmol) in 10 ml of acetone was treated with 5 ml of 1N aqueous KOH solution at 0° C. for 45 min. The acetone was removed in vacuo and the aqueous layer was acidified to pH=3 by 2N hydrochloric acid, the resulting yellow precipitate was collected by filtration, washed with 5 ml of cold water and dried in vacuo to yield 1,4-dihydro-5-(N-isopropyl)carboxamido-2,6-dimethyl-4-(4-nitrophenyl)pyridine-3-carboxylic acid as a yellow powder (244 mg, 56%).

A solution of 1,4-dihydro-5-(N-isopropyl)carboxamido-2,6-dimethyl-4-(4-nitrophenyl)pyridine-3-carboxylic acid (240 mg, 0.67 mmol), 1-(3-dimethylaminopropyl)-3-ethylcarbodiimide hydrochloride (250 mg, 1.34 mmol) and 4-dimethylaminopyridine (80 mg, 0.67 mmol) in 20 ml of $CH_2Cl_2$ was stirred at room temperature. After 1 hr, a solution of 3-(4,4-diphenylpiperidin-1-yl)propylamine (190 mg, 0.67 mmol) in 2 ml of $CH_2Cl_2$ was added and the mixture was stirred at reflux overnight. The mixture was washed with water (10 ml), saturated aqueous $NH_4Cl$ (3×10 ml), 10% aqueous $K_2CO_3$ (10 ml) and brine (10 ml). After dried over $Na_2SO_4$ and removal of solvent in vacuo, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture. 1,4-Dihydro-3-(N-isopropyl)carboxamido-2,6-dimethyl-4-(4-nitrophenyl)-5-{N-[3-(4,4-diphenylpiperidin-1-yl)propyl]}carboxamidopyridine was obtained as a yellowish powder (263 mg, 62%). M.p. 123–125° C.; Calcd. for $C_{38}H_{45}N_5O_4$: C 71.78, H 7.13, N 11.02; Found: C 71.52, H 7.13, N 10.99.

EXAMPLE 157

6-Ethyl-5-(N-ethyl)carboxamido-1,4-dihydro-4-(4-nitrophenyl)-3-{N-[3-(4,4-diphenylpiperidin-1-yl)propyl]}carboxamido-2-propylpyridine (157). In a round-bottomed flask equipped with a distillation apparatus, a mixture of ethyl butyrylacetate (50.0 g, 0.316 mol) and 3-hydroxypropionitrile (67.4 g, 0.948 mol) was heated in a oil bath at 190° C. After most of the EtOH was distilled over, the mixture was vacuum distilled and 2-cyanoethyl butyrylacetate was collected at 125–135° C./0.1 mmHg (26.0 g, 44.9%).

A suspension of 4-nitrobenzaldehyde (16.61 g, 110 mmol), 2-cyanoethyl butyrylacetate (19.34 g, 100 mmol), piperidine (430 mg, 5.00 mmol) and acetic acid (300 mg, 5.00 mmol) in 350 ml of 2-propanol was stirred at room temperature for 48 hrs. The reaction mixture was filtered and resulting solid was air dried to give 2-[(4-nitrophenyl)methylene]-3-oxohexanoic acid 2-cyanoethyl ester as a white powder (31.0 g, 95%).

A solution of 2-[(4-nitrophenyl)methylene]-3-oxohexanoic acid 2-cyanoethyl ester (16.3 g, 50 mmol) and benzyl 3-amino-2-pentenoate (11.3 g, 55 mmol) in 250 ml of EtOH was refluxed for 36 hrs. After the solvent was removed in vacuo, the residue was dissolved in 250 ml of $CHCl_3$, washed with water (2×100 ml) and dried over $Na_2SO_4$. After filtration and evaporation of solvent, 3-benzyloxycarbonyl-5-(2-cyanoethoxy)carbonyl-6-ethyl-1,4-dihydro-4-(4-nitrophenyl)-2-propylpyridine was obtained as a yellow oil (25.1 g, 98%).

A solution of 3-benzyloxycarbonyl-5-(2-cyanoethoxy)carbonyl-6-ethyl-1,4-dihydro-4-(4-nitrophenyl)-2-propylpyridine (5.00 g, 10.0 mmol) in 150 ml of 4.4%(w/w) formic acid/MeOH mixture was stirred with Pd/C (10%, 2.50 g) at room temperature. After 40 min., the reaction was quenched by addition of 50 ml of $CHCl_3$. The mixture was filtered and concentrated in vacuo to yield a yellow powder, which was dissolved in $CHCl_3$ (150 ml), washed with 0.5N aqueous HCl (50 ml) and brine (50 ml), then dried over $Na_2SO_4$. After filtration and evaporation of solvent, 3-(2-cyanoethoxy)carbonyl-6-ethyl-1,4-dihydro-4-(4-nitrophenyl)-2-propylpyridine-5-carboxylic acid was obtained as a yellow powder (3.80 g, 93%).

A solution of 3-(2-cyanoethoxy)carbonyl-6-ethyl-1,4-dihydro-4-(4-nitrophenyl)-2-propylpyridine-5-carboxylic acid (2.50 g, 6.00 mmol), 1-(3-dimethylaminopropyl)-3-ethylcarbodiimide hydrochloride (2.30 g, 12.0 mmol) and 4-dimethylaminopyridine (0.74 g, 6.00 mmol) in 200 ml of $CH_2Cl_2$ was stirred at room temperature. After 1 hr, 4.5 ml of ethylamine (70% aqueous solution) was added to the solution and the mixture was stirred at room temperature overnight. The mixture was washed with water (200 ml), saturated aqueous $NH_4Cl$ (3×200 ml), 10% aqueous $K_2CO_3$ (200 ml) and brine (200 ml). After dried over $Na_2SO_4$ and evaporation of solvent, 3-(2-cyanoethoxy)carbonyl-6-ethyl-5-(N-ethyl)carboxamido-1,4-dihydro-4-(4-nitrophenyl)-2-propylpyridine was obtained as a yellowish powder(2.45 g, 92%).

A solution of 3-(2-cyanoethoxy)carbonyl-6-ethyl-5-(N-ethyl)carboxamido-1,4-dihydro-4-(4-nitrophenyl)-2-propylpyridine (2.40 g, 5.50 mmol) in 50 ml acetone was treated with 20 ml 1N aqueous KOH solution at 0° C. for 1 hr. The acetone was removed in vacuo and the aqueous layer was washed with $CHCl_3$ (40 ml) then acidified to pH=3 by 2N hydrochloric acid. The resulting yellow precipitate was collected by filtration, washed with 5 ml of cold water and dried in vacuo to yield 6-ethyl-5-(N-ethyl)carboxamido-1,4-dihydro-4-(4-nitrophenyl)-2-propylpyridine-3-carboxylic acid as a yellow powder (1.72 g, 82%)

A solution of 6-ethyl-5-(N-ethyl) carboxamido-1,4-dihydro-4-(4-nitrophenyl)-2-propylpyridine-3-carboxylic acid (1.50 g, 3.87 mmol), 1-(3-dimethylaminopropyl)-3-ethylcarbodiimide hydrochloride (1.48 g, 7.74 mmol) and 4-dimethylaminopyridine (670 mg, 5.10 mmol) in 50 ml of $CH_2Cl_2$ was stirred at room temperature. After 1 hr, a solution of 3-(4,4-diphenylpiperidin-1-yl)propylamine (1.14 g, 3.87 mmol) in 5 ml of $CH_2Cl_2$ was added and the mixture was stirred at reflux overnight. The mixture was washed with water (20 ml), saturated aqueous $NH_4Cl$ (3×20 ml), 10% $K_2CO_3$ (20 ml) and brine (20 ml). After dried over $Na_2SO_4$ and evaporation of solvent, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture. 6-Ethyl-5-(N-ethyl)carboxamido-1,4-dihydro-4-(4-nitrophenyl)-3-{N-[3-(4,4-diphenylpiperidin-1-yl) propyl]}carboxamido-2-propylpyridine was obtained as a yellowish powder (1.65 g, 64%). M.p. 201° C. (dec.); Calcd. for $C_{40}H_{49}N_5O_4 \cdot \frac{1}{2}H_2O$: C 71.40, H 7.49, N 10.41; Found: C 71.23, H 7.23, N 10.42.

EXAMPLE 158

6-Ethyl-5-(N-ethyl)carboxamido-1,4-dihydro-4-(4-nitrophenyl)-2-pentyl-3-{N-[3-(4,4-diphenylpiperidin-1-yl)propyl]}carboxamidopyridine (158). To a solution of 2,2-dimethyl-1,3-dioxane-4,6-dione (43.2 g, 300 mmol) and pyridine (47.5 g, 600 mmol) in 300 ml of $CH_2Cl_2$ was added hexanoyl chloride (40.4 g, 300 mmol) dropwise at 0° C. The mixture was stirred at 0° C. for 1 hr then at room temperature for 1 hr. The solution was washed with 1N aqueous HCl (300 ml), water (300 ml) and dried over $Na_2SO_4$. After evaporation of solvent, 5-hexanoyl-2,2-dimethyl-1,3-dioxane-4,6-dione was obtained as a light pink oil (35.4 g, 62%).

5-Hexanoyl-2,2-dimethyl-1,3-dioxane-4,6-dione (35.4 g, 146 mmol) was heated with 3-hydroxypropionitrile (40.0 g, 560 mmol) at 120° C. until no more $CO_2$ was released. The mixture was vacuum distilled and 2-cyanoethyl hexanoylacetate was collected at 128–145° C./0.2 mmHg (21.3 g, 69%).

A mixture of 2-cyanoethyl hexanoylacetate (21.1 g, 100 mmol), 4-nitrobenzaldehyde (16.6 g, 110 mmol), piperidine (430 mg, 5.00 mmol) and acetic acid (300 mg, 5.00 mmol) in 350 ml of 2-propanol was stirred at room temperature for 48 hrs. The resulting white precipitate was filtered and dried in the air. The product, 2-[(4-nitrophenyl)methylene]-3-oxooctanoic acid 2-cyanoethyl ester was obtained as a white powder (25.2 g, 73% yield).

A solution of 2-[(4-nitrophenyl)methylene]-3-oxooctanoic acid 2-cyanoethyl ester (6.89 g, 20 mmol) and benzyl 3-amino-2-pentenoate (4.52 g, 22 mmol) in 300 ml of EtOH was refluxed for 36 hrs. After the solvent was removed in vacuo, the residue was dissolved in 250 ml of $CHCl_3$, washed with water (2×100 ml) and dried over $Na_2SO_4$. After filtration and evaporation of solvent, 3-benzyloxycarbonyl-5-(2-cyanoethoxy)carbonyl-6-ethyl- 1,4-dihydro-4-(4-nitrophenyl)-2-pentylpyridine was obtained as a yellow oil (10.5 g, 99%).

A solution of 3-benzyloxycarbonyl-5-(2-cyanoethoxy) carbonyl-6-ethyl-1,4-dihydro-4-(4-nitrophenyl)-2-pentylpyridine (10.5 g, 20.0 mmol) in 200 ml of 4.4% (w/w) formic acid/MeOH mixture was stirred with Pd/C (10%, 3.15 g) at room temperature. After 80 min., the reaction was quenched by addition of 50 ml of $CHCl_3$. The mixture was filtered and concentrated in vacuo to give a yellow powder, which was dissolved in $CHCl_3$ (250 ml), washed with 0.5N aqueous HCl (100 ml) and brine (100 ML), then dried over $Na_2SO_4$. After filtration and evaporation of solvent, 3-(2-cyanoethoxy)carbonyl-6-ethyl-1,4-dihydro-4-(4-nitrophenyl)-2-pentylpyridine-5-carboxylic acid was obtained as a yellow powder (7.88 g, 82%).

A solution of 3-(2-cyanoethoxy)carbonyl-6-ethyl-1,4-dihydro-4-(4-nitrophenyl)-2-pentylpyridine-5-carboxylic acid (3.15 g, 6.60 mmol), 1-(3-dimethylaminopropyl)-3-ethylcarbodiimide hydrochloride (2.50 g, 13.2 mmol) and 4-dimethylaminopyridine (1.2 g, 10 mmol) in 200 ml of $CH_2Cl_2$ was stirred at room temperature. After 1 hr, 2.66 ml of ethylamine (70% aqueous solution) was added and the mixture was stirred at room temperature overnight. The mixture was washed with water (200 ml), saturated aqueous $NH_4Cl$ (3×200 ml), 10% aqueous $K_2CO_3$ (200 ml) and brine (200 ml). After dried over $Na_2SO_4$ and evaporation of solvent, 3-(2-cyanoethoxy) carbonyl-6-ethyl-5-(N-ethyl)carboxamido-1,4-dihydro-4-(4-nitrophenyl)-2-pentylpyridine was obtained as a yellowish powder(3.42 g, 100%).

A solution of 3-(2-cyanoethoxy)carbonyl-6-ethyl-5-(N-ethyl)carboxamido-1,4-dihydro-4-(4-nitrophenyl)-2-pentylpyridine (3.30 g, 6.85 mmol) in 40 ml of acetone was treated with 25 ml IN aqueous KOH solution at 0° C. for 1 hr. The acetone was removed in vacuo and the aqueous layer was washed with $CHCl_3$ (40 ml) then acidified to pH=3 by 2N hydrochloric acid. The resulting yellow precipitate was collected by filtration, washed with 5 ml of cold water and dried in vacuo to yield 6-ethyl-5-(N-ethyl)carboxamido-1,4-dihydro-4-(4-nitrophenyl)-2 -pentylpyridine-3-carboxylic acid as a yellow powder (3.00 g, 97%)

A solution of 6-ethyl-5-(N-ethyl) carboxamido-1,4-dihydro-4-(4-nitrophenyl)-2-pentylpyridine-3-carboxylic acid (1.58 g, 3.50 mmol), 1-(3-dimethylaminopropyl)-3-ethylcarbodiimide hydrochloride (1.00 g, 5.25 mmol) and 4-dimethylaminopyridine (450 mg, 3.50 mmol) in 100 ml of $CH_2Cl_2$ was stirred at room temperature. After 1 hr, a solution of 3-(4,4-diphenylpiperidin-1-yl)propylamine (1.03 g, 3.50 mmol) in 10 ml of $CH_2Cl_2$ was added and the mixture was stirred at reflux overnight. The mixture was washed with water (50 ml), saturated aqueous $NH_4Cl$ (3×50 ml), 10% aqueous $K_2CO_3$ (50 ml) and brine (50 ml). After dried over $Na_2SO_4$ and evaporation of solvent, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture. 6-Ethyl-5-(N-ethyl) carboxamido-1,4-dihydro-4-(4-nitrophenyl-2-pentyl-3-{N-[3-(4,4-diphenylpiperidin-1-yl)propyl]} carboxamidopyridine was obtained as a yellowish powder (1.21 g, 50%). M.p. 115–120° C.; Calcd. for $C_{42}H_{53}N_5O_4 \cdot \frac{1}{2}H_2O$: C 71.97, H 7.77, N 9.99; Found: C 71.99, H 7.77, N 9.86.

EXAMPLE 159

5-(N-Ethyl)carboxamido-1,4-dihydro-4-(4-nitrophenyl)-3-{N-[3-(4,4-diphenylpiperidin-1-yl)propyl]}carboxamido-2,6-dipropylpyridine (159). In a round-bottomed flask equipped with a distillation apparatus, a mixture of ethyl butyrylacetate (31.6 g, 0.20 mol) and benzyl alcohol (23.8 g, 0.220 mol) was heated with an oil bath at 190° C. After most of the EtOH was distilled over, the mixture was vacuum distilled and benzyl butyrylacetate was collected at 130–136° C./0.2 mmHg (33.5 g, 76.1%).

A mixture of benzyl butyrylacetate (22.0 g, 0.10 mol) and 10 g of 4 Å molecular sieves was treated with ammonia gas which was bubbled through the mixture for 38 hrs at 50° C. After filtration, benzyl 3-amino-2-hexenoate was obtained as a yellowish oil (21 g, 95%).

A solution of 2-[(4-nitrophenyl)methylene]-3-oxohexanoic acid 2-cyanoethyl ester (9.80 g, 30 mmol) and benzyl 3-amino-2-hexenoate (7.24 g, 33 mmol) in 150 ml of EtOH was refluxed for 36 hrs. After the solvent was removed in vacuo, the residue was dissolved in 250 ml of $CHCl_3$, washed with water (2×100 ml) and dried over $Na_2SO_4$. After filtration and evaporation of solvent, 5-benzyloxycarbonyl-3-(2-cyanoethoxy)carbonyl-1,4-dihydro-4-(4-nitrophenyl)-2,6-dipropylpyridine was obtained as a yellow oil (15.4 g, 97%).

A solution of 5-benzyloxycarbonyl-3-(2-cyanoethoxy) carbonyl-1,4-dihydro-4-4nitrophenyl)-2,6-dipropylpyridine (10.6 g, 20.4 mmol) in 200 ml of 4.4%(w/w) formic acid/ MeOH mixture was stirred with Pd/C (10%, 3.50 g) at room temperature. After 1 hr, the reaction was quenched by addition of 50 ml of $CHCl_3$. The mixture was filtered and concentrated to give a yellow powder, which was dissolved in $CHCl_3$ (250 ml), washed with 0.5N aqueous HCl (100 ml) and brine (100 ml), then dried over $Na_2SO_4$. After filtration and evaporation of solvent, 3-(2-cyanoethoxy)carbonyl-1,4-dihydro-4-(4-nitrophenyl)-2,6-dipropylpyridine-5-carboxylic acid was obtained as a yellow powder (8.04 g, 92%).

A solution of 3-(2-cyanoethoxy) carbonyl-1,4-dihydro-4-(4-nitrophenyl)-2,6-dipropylpyridine-5-carboxylic acid (4.28 g, 10.0 mmol), 1-(3-dimethylaminopropyl)-3-ethylcarbodiimide hydrochloride (3.81 g, 20.0 mmol) and 4-dimethylaminopyridine (1.6 g, 13 mmol) in 200 ml of $CH_2Cl_2$ was stirred at room temperature. After 1 hr, 3.20 g of ethylamine (70% aqueous solution) was added and the mixture was stirred at room temperature overnight. The mixture was washed with water (200 ml), saturated aqueous $NH_4Cl$ (3×200 ml), 10% aqueous $K_2CO_3$ (200 ml) and brine (200 ml). After dried over $Na_2SO_4$ and evaporation of solvent, 3-(2-cyanoethoxy) carbonyl-5-(N-ethyl) carboxamido-1,4-dihydro-4-(4-nitrophenyl)-2,6-dipropylpyridine was obtained as a yellowish powder (4.15 g, 99%).

A solution of 3-(2-cyanoethoxy)carbonyl-5-(N-ethyl) carboxamido-1,4-dihydro-4-(4-nitrophenyl)-2,6-dipropylpyridine (4.55 g, 10.0 mmol) in 50 ml of acetone was treated with 40 ml 1N aqueous KOH solution at 0° C. for 1 hr. The acetone was removed in vacuo and the aqueous layer was washed with $CHCl_3$ (40 ml) then acidified to pH=3 by 2N hydrochloric acid, the resulting yellow precipitate was collected by filtration, washed with 5 ml of cold water and dried in vacuo to yield 5-(N-ethyl)carboxamido-1,4-dihydro-4-(4-nitrophenyl)-2, 6-dipropylpyridine-3-carboxylic acid as a yellow powder (4.00 g, 100%)

A solution of 5-(N-ethyl)carboxamido-1,4-dihydro-4-(4-nitrophenyl)-2,6-dipropylpyridine-3-carboxylic acid (1.61 g, 4.00 mmol), 1-(3-dimethylaminopropyl)-3-ethylcarbodiimide hydrochloride (1.15 g, 6.00 mmol) and 4-dimethylaminopyridine (500 mg, 4.00 mmol) in 150 ml of $CH_2Cl_2$ was stirred at room temperature. After 1 hr, a solution of 3-(4,4-diphenylpiperidin-1-yl)propylamine (1.18 g, 4.00 mmol) in 10 ml of $CH_2Cl_2$ was added and the mixture was stirred at reflux overnight. The mixture was washed with water (50 ml), saturated aqueous $NH_4Cl$ (3×50 ml), 10% aqueous $K_2CO_3$ (50 ml) and brine (50 ml). After dried over $Na_2SO_4$ and evaporation of solvent, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture. 5-(N-Ethyl) carboxamido-1,4-dihydro-4-(4-nitrophenyl)-3-{N-[3-(4,4-diphenylpiperidin- 1-yl)propyl]carboxamido-2,6-dipropylpyridine was obtained as a yellowish powder (1.85 g, 68%). M.p. 123–128° C.; Calcd. for $C_{41}H_{51}N_5O_4 \cdot H_2O$: C 70.76, H 7.68, N 10.06; Found: C 70.94, H 7.56, N 10.09.

EXAMPLE 160

5-(2-Cyanoethoxycarbonyl)-1,4-dihydro-2,6-dimethyl-4-(4-nitrophenyl)-3-{N-[3-(4,4-diphenylpiperidin-1-yl)propyl]}carboxamidopyridine (160). A mixture of 2-cyanoethyl 3-aminocrotonate (247 mg, 1.60 mmol), 4--nitrobenzaldehyde (242 mg, 1.60 mmol) and N-[3-(4,4-diphenylpiperidin-1-yl)propyl]acetoacetamide (607 mg, 1.60 mmol) in 50 ml of 2-propanol was refluxed for 48 hrs. After the solvent was removed in vacuo, the residue was dissolved in 50 ml of $CHCl_3$, washed with water (25 ml) and dried over $Na_2SO_4$. After filtration and evaporation of solvent, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture. The title compound was obtained as a yellowish powder (267 mg, 26%). M.p. 93–95° C.; Calcd. for $C_{38}H_{41}N_5O_4 \cdot \frac{1}{4}H_2O$: C 69.97, H 6.41, N 10.74; Found: C 69.73, H 6.22, N 10.66.

EXAMPLE 161

1,4-Dihydro-4-(4-nitrophenyl)-5-{N-[3-(4,4-diphenylpiperidin-1-yl)propyl]}carboxamido-2,6-dipropylpyridine-3-carboxylic acid (161). A solution of 3-(2-cyanoethoxy)carbonyl-1,4-dihydro-4-(4-nitrophenyl)-2,6-dipropylpyridine-5-carboxylic acid (1.50 g, 3.60 mmol), 1-(3-dimethylaminopropyl)-3-ethylcarbodiimide hydrochloride (1.38 g, 7.20 mmol) and 4-dimethylaminopyridine (0.45 g, 3.6 mmol) in 150 ml of $CH_2Cl_2$ was stirred at room temperature. After 1 hr, a solution of 3-(4,4-diphenylpiperidin-1-yl)propylamine (1.06 g, 3.60 mmol) in 10 ml of $CH_2Cl_2$ was added and the mixture was stirred at room temperature overnight. The mixture was washed with water (100 ml), saturated aqueous $NH_4Cl$ (3×100 ml), 100 ml of 10% aqueous $K_2CO_3$ and 100 ml of brine. After drying over $Na_2SO_4$ and evaporation of solvent, 3-(2-cyanoethoxy)carbonyl-1,4-dihydro-4-(4-nitrophenyl)-5-{N-3-[(4,4-diphenylpiperidin-1-yl)propyl]}carboxamido-2,6-dipropylpyridine was obtained as a yellowish powder (640 mg, 26%).

A solution of 3-(2-cyanoethoxy)carbonyl-1,4-dihydro-4-(4-nitrophenyl)-5-{N-3-[(4,4-diphenylpiperidin-1-yl)propyl]}carboxamido-2,6-dipropylpyridine (640 mg, 0.92 mmol) in 30 ml acetone was treated with 4.6 ml 1N KOH solution at 0° C. for 1 hr. The acetone was removed in vacuo and the aqueous layer was washed with $CHCl_3$ (10 ml) then acidified to pH=3 by 2N hydrochloric acid. The resulting yellow precipitate was collected by filtration, washed with 5 ml of cold water and dried in vacuo. 1,4-Dihydro-4-(4-nitrophenyl)-5-{N-[3-(4,4-diphenylpiperidin-1-yl)propyl] }carboxamido-2,6-dipropylpyridine-3-carboxylic acid was obtained as a yellow powder (485 mg, 81%). M.p. 126–130° C; Calcd. for $C_{39}H_{46}N_4O_5 \cdot 2H_2O$: C 68.20, H 7.34, N 8.16; Found: C 68.30, H 7.01, N 8.16.

EXAMPLE 162

1,4-Dihydro-3-{N-[3-(4-hydroxy-4-phenylpiperidin-1-yl)propyl]}carboxamido-2,6-dimethyl-5-(N-methyl)carboxamido-4-(4-nitrophenyl)pyridine (162). A solution of 1,4-dihydro-2,6-dimethyl-5-(N-methyl)carboxamido-4-(4-nitrophenyl) pyridine-3-carboxylic acid (212 mg, 0.64 mmol), 1-(3-dimethylaminopropyl)-3-ethylcarbodiimide hydrochloride (253 mg, 1.28 mmol) and 4-dimethylaminopyridine (78 mg, 0.64 mmol) in 30 ml of $CH_2Cl_2$ was stirred at room temperature. After 1 hr, a solution of 3-(4-hydroxy-4-phenylpiperidin-1 -yl)propylamine (150 mg, 0.64 mmol) in 5 ml of DMF was added and the mixture was stirred at reflux overnight. After cooling to room temperature, the mixture was poured into 150 ml of hexane and a yellowish sticky oil was separated out. The oil was purified by chromatography ($SiO_2$, MeOH:$CHCl_3$:1N $NH_3$ in MeOH, 6:90:3) and precipitated by $CH_2Cl_2$/hexane mixture. The title compound was obtained as a yellowish powder (20 mg, 5.7%). M.p. 87–91° C.; Calcd. for $C_{30}H_{37}N_5O_5$: C 65.80, H 6.81, N 12.79; Found: C 66.06, H 6.90, N 12.59.

EXAMPLE 163

4-(3,4-Ethylenedioxyphenyl)-1,4-Dihydro-2,6-dimethyl-5-(N-methyl)carboxamido-3-{N-[3-(4,4-diphenylpiperidin-1-yl)propyl]}carboxamidopyridine (163). A mixture of 2-cyanoethyl acetoacetate (5.00 g, 32.2 mmol), 1,4-benzodioxan-6-carboxaldehyde (5.29 g, 32.2 mmol), piperidine (137 mg, 1.61 mmol) and acetic acid (97 mg, 1.6 mmol) in 70 ml of 2-propanol was stirred at r.t. for 48 hrs. After evaporation of solvent, the product was purified by chromatography ($SiO_2$, AcOEt: Hexane, 60:10). 2-[(3,4-Ethylenedioxyphenyl)methylene]-3-oxobutanoic acid 2-cyanoethyl ester was obtained as a yellowish oil (2.64 g, 27% yield).

A solution of 2-[(3,4-ethylenedioxyphenyl)methylene]-3-oxobutanoic acid 2-cyanoethyl ester (2.64 g, 8.76 mmol) and N-methyl 3-amino-2-pentenamide (1.00 g, 8.76 mmol) in 50 ml of EtOH was refluxed for 36 hrs. After solvent was removed in vacuo, the residue was dissolved in 50 ml of $CHCl_3$, washed with water (2×100 ml) and dried over $Na_2SO_4$. After filtration and evaporation of solvent, the product was purified by chromatography ($SiO_2$, $CHCl_3$:MeOH, 90:10). 3-(2-Cyanoethoxy)carbonyl-4-(3,4-ethylenedioxyphenyl)-1,4-dihydro-2,6-dimethyl-5-(N-methyl)carboxamidopyridine was obtained as a yellow oil (2.15 g, 62%).

The solution of 3-(2-cyanoethoxy)carbonyl-4-(3,4-ethylenedioxyphenyl)-1,4-dihydro-2,6-dimethyl-5-(N-methyl)carboxamidopyridine (2.15 g, 5.40 mmol) in 30 ml acetone was treated with 30 ml 1N KOH solution at 0° C. for 1 hr. The acetone was removed in vacuo and aqueous layer was washed with $CHCl_3$ (40 ml) then acidified to pH=3 by 2N hydrochloric acid, the yellow precipitate was collected by filtration, washed with 5 ml of cold water and dried in vacuo. 4-(3,4-Ethylenedioxyphenyl)-1,4-dihydro-2,6-dimethyl-5-(N-methyl) carboxamidopyridine-3-carboxylic acid was obtained as a yellow powder (1.00 g, 54%).

A solution of 4-(3,4-ethylenedioxyphenyl)-1,4-dihydro-2, 6-dimethyl-5-(N-methylicarboxamidopyridine-3-carboxylic acid (250 mg, 0.73 mmol), 1-(3-dimethylaminopropyl)-3-ethylcarbodiimide hydrochloride (287 mg, 1.45 mmol) and 4-dimethylaminopyridine (89 mg, 0.73 mmol) in 50 ml of $CH_2Cl_2$ was stirred at room temperature. After 1 hr, a solution of 3-(4,4-diphenylpiperidin-1-yl)propylamine (170 mg, 0.73 mmol) in 5 ml of $CH_2Cl_2$ was added and the mixture was stirred at reflux overnight. The mixture was washed with water (20 ml), saturated aqueous $NH_4Cl$ (3×20 ml), 20 ml 10% $K_2CO_3$ and 20 ml of brine. After drying over $Na_2SO_4$ and evaporation of solvent, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture. 4-(3,4-Ethylenedioxyphenyl)-1,4-Dihydro-2,6-dimethyl-5-(N-methyl)carboxamido-3-{N-[3-(4,4-diphenylpiperidin-1-yl)propyl]} carboxamidopyridine was obtained as a yellowish powder (136 mg, 30%). M.p. 115–116° C.; Calcd. for $C_{38}H_{44}N_4O_4 \cdot \frac{3}{4}H_2O$: C 71.96, H 7.23, N 8.83; Found: C 71.81, H 7.09, N 9.10.

EXAMPLE 164

4-(3,4-Ethylenedioxyphenyl)-1,4-Dihydro-3-{N-[3-(4-methoxycarbonyl-4-phenylpiperidin-1-yl)propyl]}carboxamido-2,6-dimethyl-5-[(N-methyl)carboxamido]pyridine (164). A solution of 4-(3,4-ethylenedioxyphenyl)-1,4-dihydro-2,6-dimethyl-5-[(N-methyl)carboxamido]pyridine-3-carboxylic acid (100 mg, 0.30mmol), 1-(3-dimethylaminopropyl)-3-ethylcarbodiimide hydrochloride (115 mg, 0.60 mmol) and 4-dimethylaminopyridine (73 mg, 0.60 mmol) in 30 ml of $CH_2Cl_2$ was stirred at room temperature. After 1 hr, a solution of 3-(4-methoxycarbonyl-4-phenylpiperidin-1-yl)propylamine (83.0 mg, 0.30 mmol) in 2 ml of $CH_2Cl_2$ was added and the mixture was stirred at reflux overnight. The mixture was washed with water (10 ml), saturated aqueous $NH_4Cl$ (3×10 ml), 10 ml 10% $K_2CO_3$ and 10 ml of brine. After drying over $Na_2SO_4$ and evaporation of solvent, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture. The title compound was obtained as a yellowish powder (65 mg, 36%). M.p. 101–104° C.; Calcd. for $C_{34}H_{42}N_4O_6 \cdot \frac{5}{4}H_2O$: C 65.31, H 7.17, N 8.96; Found: C 65.12, H 6.69, N 8.69.

EXAMPLE 165

2-(4-Azidobutyl)-3-{N-[3-(4-methoxycarbonyl-4-phenylpiperidin-1-yl) propyl]}carboxamido-5-carboxamido-6-ethyl-1,4-dihydro-4-(4-nitrophenyl) pyridine (165). A solution of methyl 5-bromovalerate (5.00 g, 25.6 mmol), $NaN_3$ (3.33 g, 51.2 mmol) and 15 ml of water in 40 ml of MeOH was refluxed for 3.5 hrs. The MeOH was removed in vacuo and residue was partitioned between $CHCl_3$ (200 ml) and water (50 ml). The organic layer was separated and washed with water. After drying and removal of solvent, methyl 5-azidovalerate (4.01 g, 99.7%) was obtained as a colorless oil.

Methyl 5-azidovalerate (4.01 g, 25.5 mmol) and KOH (7.58 g, 0.135 mol) were dissolved in a mixture of 70 ml of water and 90 ml of MeOH. The solution was stirred at 0° C. After 2 hrs, the MeOH was removed in vacuo. The aqueous layer was extracted by $CHCl_3$ (50 ml), acidified to pH=1 by 2N aqueous HCl and extracted by $Et_2O$ (2×100 ml). The organic layers were combined, washed with water (100 ml) and dried over $Na_2SO_4$. After filtration and evaporation of solvent, 5-azidovaleric acid (2.85 g, 77.6%) was obtained as a colorless oil.

5-Azidovaleric acid (2.00 g, 13.9 mmol) in 15 ml of toluene was treated with oxalyl chloride (3.55 g, 27.9 mmol). The mixture was stirred at 50° C. for 10 hrs. After removal of toluene in vacuo, crude 5-azidovaleric chloride was used for next reaction without further purifications.

To the solution of 2,2-dimethyl-1,3-dioxane-4,6-dione (4.45 g, 30.9 mmol) and 4-dimethylaminopyridine (7.55 g, 61.8 mmol) in 100 ml of $CH_2Cl_2$ was added the solution of crude 5-azidovaleric chloride in 10 ml of $CH_2Cl_2$ at 0° C. The mixture was stirred at 0° C. for 1 hr and at room temperature for 1 hr. The solution was washed with 1N aqueous HCl (100 ml), brine (250 ml) and dried over $Na_2SO_4$. After evaporation of solvent, 5-(5-azidopentanoyl)-2,2-dimethyl-1,3-dioxane-4,6-dione was obtained as a light pink oil (8.17 g, 98%).

5-(5-Azidopentanoyl)-2,2-dimethyl-1,3-dioxane-4,6-dione was heated with 3-hydroxypropionitrile (2.42 g, 34.0 mmol) at 80° C. until no more $CO_2$ was released. After cooling to room temperature, the mixture was diluted with 150 ml of 2-propanol, and 4-nitrobenzaldehyde (4.60 g, 30.3 mmol), piperidine (130 mg, 1.50 mmol) and acetic acid (90 mg, 1.50 mmol) were added. The mixture was stirred at room temperature for 48 hrs. The product, 7-azido-2-[(4-nitrophenyl)methylene]-3-oxoheptanoicacid2-cyanoethyl ester was obtained as a pale-yellow oil (5.73 g, 51% yield) after chromatography ($SiO_2$, Hexane: AcOEt, 2:1).

A solution of 7-azido-2-[(4-nitrophenyl)methylene]-3-oxoheptanoic acid 2-cyanoethyl ester (3.71 g, 10.0 mmol) and 3-amino-2-pentenamide (1.14 g, 10.0 mmol; this compound was prepared by bubbling ammonia gas through a solution of 6-ethyl-4H-2,2-dimethyl-1,3-dioxin-4-one in xylene at 115° C. for 2 hrs) in 50 EtOH was refluxed for 48 hrs. After the EtOH was removed in vacuo, the residue was dissolved in 150 ml of $CHCl_3$, washed with water (2×100 ml) and dried over $Na_2SO_4$. After filtration and evaporation of solvent, the product was purified by chromatography ($SiO_2$, $CHCl_3$:MeOH=5:95). 2-(4-azidobutyl)-5-carboxamido-3-(2-cyanoethoxy)carbonyl-6-ethyl-1,4-dihydro-4-(4-nitrophenyl)pyridine was obtained as a yellow powder (2.50 g, 54% yield).

A solution of 2-(4-azidobutyl)-5-carboxamido-3-(2-cyanoethoxy)carbonyl-6-ethyl-1,4-dihydro-4-(4-nitrophenyl)pyridine (1.50 g, 3.20 mmol) in 10 ml acetone was treated with 20 ml 1N aqueous KOH solution at 0° C. for 45 min. The acetone was removed in vacuo and the aqueous layer was acidified to pH=3 by 2N hydrochloric acid, the yellow precipitate was collected by filtration, washed with 10 ml of cold water and dried in vacuo. 1.20 g (90% yield) of 2-(4-azidobutyl)-5-carboxamido-6-ethyl-1,4-dihydro-4-(4-nitrophenyl)pyridine-3-carboxylic acid was obtained as a yellow powder.

A solution of 2-(4-azidobutyl)-5-carboxamido-6-ethyl-1,4-dihydro-4-(4-nitrophenyl)pyridine-3-carboxylic acid (300 mg, 0.72 mmol), 1-(3-dimethylaminopropyl)-3-ethylcarbodiimide hydrochloride (276 mg, 1.44 mmol) and 4-dimethylaminopyridine (176 mg, 1.44 mmol) in 50 ml of $CH_2Cl_2$ was stirred at room temperature. After 1 hr, a solution of 3-(4-methoxycarbonyl-4-phenylpiperidin-1-yl) propylamine (215 mg, 0.86 mmol) in 5 ml of $CH_2Cl_2$ was added and the mixture was stirred at reflux overnight. The mixture was washed with water (30 ml), saturated aqueous $NH_4Cl$ (3×30 ml), 30 ml 10% $K_2CO_3$ and 30 ml of brine. After drying over $Na_2SO_4$ and evaporation of solvent, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture. 2-(4-Azidobutyl)-3-{N-[3-(4-methoxycarbonyl-4-phenylpiperidin-1-yl)propyl]}carboxamido-5-carboxamido-6-ethyl-1,4-dihydro-4-(4-nitrophenyl)pyridine was obtained as a yellowish powder (320 mg, 66%). M.p. 74–77° C.; Calcd. for $C_{35}H_{44}N_8O_6$: C 62.48, H 6.59, N 16.66; Found: C 62.27, H 6.30, N 16.62.

EXAMPLE 166

2-(4-Aminobutyl)-5-carboxamido-6-ethyl-1,4-dihydro-3-{N-[3-(4-methoxycarbonyl-4-phenylpiperidin-1-yl) propyl]} carboxamido-4-(4-nitrophenyl)pyridine (166). A solution of 2-(4-azidobutyl)-3-{N-[3-(4-methoxycarbonyl-4-phenylpiperidin-1-yl)propyl]}carboxamido-5-carboxamido-6-ethyl-1,4-dihydro-4-(4-nitrophenyl) pyridine (280 mg, 0.42 mmol) in 5 ml of AcOEt was treated with 1.25 ml of 1M trimethylphosphine THF solution. The mixture was stirred at 0° C. for 1.5 hrs, 0.22 ml of water was then added and the mixture was stirred at room temperature for an additional 1.5 hrs. After most volatile materials were removed in vacuo, residue was dissolved into AcOEt (50 ml), washed with 6N aqueous KOH (50 ml), brine (50 ml) and dried over $K_2CO_3$. After filtration and evaporation of solvent, product was precipitated by $CH_2Cl_2$/hexane mixture. 2-(4-Aminobutyl)-3-{N-[3-(4-methoxycarbonyl-4-phenylpiperidin-1-yl)propyl]}carboxamido-5-carboxamido-6-ethyl-1,4-dihydro-4-(4-nitrophenyl)pyridine was obtained as a yellowish powder (227 mg, 84%). M.p. 75–78° C.; Calcd for $C_{35}H_{46}N_6O_6·½H_2O$: C 64.10, H 7.22, N 12.82; Found: C 63.99, H 6.82, N 12.67.

EXAMPLE 167

2-(4-Aminobutyl)-5-carboxamido-1,4-dihydro-6-methyl-4-(4-nitrophenyl)-3-{N-[3-(4,4-diphenylpiperidin-1-yl) propyl]}carboxamidopyridine (167). A solution of 7-azido-2-[(4-nitrophenyl)methylene]-3-oxoheptanoic acid 2-cyanoethyl ester (2.62 g, 7.06 mmol) and 3-aminocrotonamide (0.710 g, 7.06 mmol) in 50 EtOH was refluxed for 48 hrs. After the EtOH was removed in vacuo, the residue was dissolved in 100 ml of $CHCl_3$, washed with water (2×50 ml) and dried over $Na_2SO_4$. After filtration and evaporation of solvent, 2-(4-azidobutyl)-5-carboxamido-3-(2-cyanoethoxy) carbonyl-1,4-dihydro-6-methyl-4-(4-nitrophenyl)pyridine was obtained as a brownish oil (2.42 g, 76% yield).

A solution of 2-(4-azidobutyl)-5-carboxamido-3-(2-cyanoethoxy)carbonyl-1,4-dihydro-6-methyl-4-(4-nitrophenyl)pyridine (2.42 g, 5.34 mmol) in 15 ml acetone was treated with 25 ml 1N aqueous KOH solution at 0° C. for 1 hr. The acetone was removed in vacuo, the aqueous layer was washed with $CHCl_3$ and acidified to pH=3 by 2N hydrochloric acid, the yellow precipitate was collected by filtration, washed with 10 ml of cold water and dried in vacuo to yield 1.40 g (65% yield) of 2-(4-azidobutyl)-5-carboxamido-1,4-dihydro-6-methyl-4-(4-nitrophenyl) pyridine-3-carboxylic acid as a yellow powder.

A solution of 2-(4-azidobutyl)-5-carboxamido-1,4-dihydro-6-methyl-4-(4-nitrophenyl) pyridine-3-carboxylic acid (400 mg, 1.00 mmol), 1-(3-dimethylaminopropyl)-3-ethylcarbodiimide hydrochloride (380 mg, 2.00 mmol) and 4-dimethylaminopyridine (130 mg, 1.00 mmol) in 20 ml of $CH_2Cl_2$ was stirred at room temperature. After 1 hr, a solution of 3-(4,4-diphenylpiperidin-1-yl)propylamine (300 mg, 1.02 mmol) in 5 ml of $CH_2Cl_2$ was added and the mixture was stirred at reflux overnight. The mixture was washed with water (20 ml), saturated aqueous $NH_4Cl$ (3×20 ml), 20 ml 10% $K_2CO_3$ and 20 ml of brine. After drying over $Na_2SO_4$ and evaporation of solvent, a yellowish oil was obtained, which was purified by chromatography ($SiO_2$, MeOH:CHCl$_3$:1N NH$_3$ in MeOH, 6:90:3) and precipitated by $CH_2Cl_2$/hexane mixture. 2-(4-Azidobutyl)-5-carboxamido-1,4-dihydro-6-methyl-4-(4-nitrophenyl)-3-{N-[3-(4,4-diphenylpiperidin-1-yl)propyl]} carboxamidopyridine was obtained as a yellowish powder (420 mg, 62%). M.p. 100° C.; Calcd. for $C_{38}H_{44}N_8O_4$: C 67.44, H 6.55, N 16.56; Found: C 67.14, H 6.33, N 16.30.

A solution of 2-(4-azidobutyl)-5-carboxamido-1,4-dihydro-6-methyl-4-(4-nitrophenyl)-3-{N-[3-(4,4-diphenylpiperidin-1-yl)propyl]}carboxamidopyridine (90 mg, 0.133 mmol) in 5 ml of AcOEt was treated with 0.33 ml of 1M trimethylphosphine THF solution. The mixture was stirred at 0° C. for 1.5 hrs, 0.1 ml of water was then added and the mixture was stirred at room temperature for an additional 1.5 hrs. After most volatile materials were removed in vacuo, the residue was dissolved into AcOEt (50 ml), washed with 6N aqueous KOH (50 ml), brine (50 ml), and dried over $K_2CO_3$. After filtration and evaporation of solvent, product was precipitated by $CH_2Cl_2$/hexane mixture. 2-(4-Aminobutyl)-5-carboxamido-1,4-dihydro-6-methyl-4-(4-nitrophenyl)-3-{N-[3-(4,4-diphenylpiperidin-1-yl) propyl]}carboxamidopyridine was obtained as a yellowish powder (82 mg, 95%). M.p. 95–99° C.; Calcd for $C_{38}H_{46}N_6O_4·½H_2O$: C 69.17, H 7.18, N 12.74; Found: C 69.12, H 6.86, N 12.43.

EXAMPLE 168

2-(3-Aminopropyl)-5-carboxamido-1,4-dihydro-6-methyl-4-(4-nitrophenyl)-3-{N-[3-(4,4-diphenylpiperidin-1-yl)propyl]}carboxamidopyridine (168). A solution of ethyl 4-bromobutyrate (10.0 g, 51.3 mmol), $NaN_3$ (6.66 g, 102 mmol) and .25 ml of water in 75 ml of MeOH was refluxed for 3.5 hrs. The MeOH was removed in vacuo and residue was partitioned between $CHCl_3$ (200 ml) and water (50 ml). The organic layer was separated and washed with water. After drying and evaporation of solvent, ethyl 4-azidobutyrate (7.94 g, 98.6%) was obtained as a colorless oil.

Ethyl 4-azidobutyrate (8.06 g, 51.3 mmol) and KOH (14.4 g, 0.256 mol) were dissolved into a mixture of 100 ml of water and 120 ml of MeOH. The solution was stirred at 0° C. for 2 hrs and then MeOH was removed in vacuo. The aqueous layer was extracted by $CHCl_3$ (50 ml), acidified to pH=1 by 2N aqueous HCl and extracted by $Et_2O$ (2×100 ml). The organic layers were combined, washed with water (100 ml) and dried over $Na_2SO_4$. After filtration and evaporation of solvent, 4-azidobutyric acid (5.30 g, 80%) was obtained as a colorless oil.

4-Azidobutyric acid (2.00 g, 15.5 mmol) in 15 ml of toluene was treated with oxalyl chloride (4.92 g, 38.7 mmol). The mixture was stirred at 50° C. for 10 hrs. After removal of toluene in vacuo, crude 4-azidobutyric chloride was used for next reaction without further purifications.

To the solution of 2,2-dimethyl-1,3-dioxane-4,6-dione (3.82 g, 26.5 mmol) and pyridine (4.20 g, 53.0 mmol) in 150 ml of $CH_2Cl_2$ was added dropwise a solution of crude 4-azidobutyric chloride (3.90 g, 26.5 mmol) in 30 ml of $CH_2Cl_2$ at 0° C. The mixture was stirred at 0° C. for 1 hr then at room temperature for 1 hr. The solution was washed with 0.5N aqueous HCl (60 ml), water (60 ml) followed by brine (60 ml) and dried. After evaporation of solvent, 5-(4-azidobutanoyl)-2,2-dimethyl-1,3-dioxane-4,6-dione was obtained as a light pink oil (6.20 g, 92%).

5-(4-Azidobutanoyl)-2,2-dimethyl-1,3-dioxane-4,6-dione was heated with 3-hydroxypropionitrile (5.25 g, 72.0 mmol) at 80° C. until no more $CO_2$ was released. The reaction mixture was diluted with $CH_2Cl_2$ (100 ml), washed with water (100 ml) and brine (100 ml). After drying and evaporation of solvent, the product was purified by chromatography (SiO$_2$, CHCl$_3$:MeOH=95:5), 4-azidobutanoylacetic acid 2-cyanoethyl ester was obtained as a yellowish oil (2.86 g, 53.2%).

A mixture of 4-azidobutanoylacetic acid 2-cyanoethyl ester (2.83 g, 12.6 mmol), 4-nitrobenzaldehyde (1.91 g, 12.6 mmol), piperidine (53 mg, 0.63 mmol) and acetic acid (38 mg, 0.63 mmol) was stirred at r.t. for 48 hrs. The product, 6-azido-2-[(4-nitrophenyl)methylene]-3-oxohexanoic acid 2-cyanoethyl ester was separated out as a brownish oil (2.16 g, 48%).

A solution of 6-azido-2-[(4-nitrophenyl)methylene]-3-oxohexanoic acid 2-cyanoethyl ester (2.16 g, 6.06 mmol) and 3-aminocrotonamide (1.21 g, 12.1 mmol) in 50 EtOH was refluxed for 48 hrs. After the EtOH was removed in vacuo, the residue was dissolved in 150 ml of CHCl$_3$, washed with water (2×100 ml) and dried over Na$_2$SO$_4$. After filtration and evaporation of solvent, the product was purified by chromatography (SiO$_2$, CHCl$_3$:MeOH=95:5). 2-(3-Azidopropyl)-5-carboxamido-3-(2-cyanoethoxy)carbonyl-1,4-dihydro-6-methyl-4-(4-nitrophenyl)pyridine was obtain as a yellow powder (1.28 g, 48% yield).

A solution of 2-(3-azidopropyl)-5-carboxamido-3-(2-cyanoethoxy)carbonyl-1,4-dihydro-6-methyl-4-(4-nitrophenyl)pyridine (1.28 g, 2.91 mmol) in 20 ml acetone was treated with 15 ml 1N aqueous KOH solution at 0° C. for 45 min. The acetone was removed in vacuo and the aqueous layer was acidified to pH=3 by 2N hydrochloric acid. The resulting yellow precipitate was collected by filtration, washed with 10 ml of cold water and dried in vacuo to yield 800 mg (71% yield) of 2-(3-azidopropyl)-5-carboxamido-1,4-dihydro-6-methyl-4-(4-nitrophenyl)pyridine-3-carboxylic acid as a yellow powder.

A solution of 2-(3-azidopropyl)-5-carboxamido-1,4-dihydro-6-methyl-4-(4-nitrophenyl) pyridine-3-carboxylic acid (300 mg, 0.78 mmol), 1-(3-dimethylaminopropyl)-3-ethylcarbodiimide hydrochloride (297 mg, 1.55 mmol) and 4-dimethylaminopyridine (95 mg, 0.78 mmol) in 40 ml of CH$_2$Cl$_2$ was stirred at room temperature. After 1 hr, a solution of 3-(4,4-diphenylpiperidin-1-yl)propylamine (228 mg, 0.78 mmol) in 5 ml of CH$_2$Cl$_2$ was added and the mixture was stirred at reflux overnight. The mixture was washed with water (30 ml), saturated aqueous NH$_4$Cl (3×30 ml), 10% K$_2$CO$_3$ (30 ml) and brine (30 ml). After drying over Na$_2$SO$_4$ and evaporation of solvent, a yellowish oil was obtained, which was purified by chromatography (SiO$_2$, MeOH:CHCl$_3$:1N NH$_3$ in MeOH, 6:90:3) and precipitated by CH$_2$Cl$_2$/hexane mixture. 2-(3-Azidopropyl)-5-carboxamido-1,4-dihydro-6-methyl-4-(4-nitrophenyl)-3-{N-[3-(4,4-diphenylpiperidin-1-yl)propyl]}carboxamidopyridine was obtained as a yellowish powder (300 mg, 58%). M.p. 99° C. (dec.); Calcd. for C$_{37}$H$_{42}$N$_8$O$_4$.¾H$_2$O: C 65.71, H 6.48, N 16.57; Found: C 65.86, H 6.22, N 16.62.

A solution of 2-(3-azidopropyl)-5-carboxamido-1,4-dihydro-6-methyl-4-(4-nitrophenyl)-3-{N-[3-(4,4-diphenylpiperidin-1-yl)propyl]}carboxamidopyridine (102 mg, 0.154 mmol) in 5 ml of AcOEt was treated with 0.4 ml of 1M trimethylphosphine THF solution. The mixture was stirred at 0° C. for 1.5 hrs, then 0.1 ml of water was added and the mixture was stirred at room temperature for an additional 1.5 hrs. After most volatile materials were removed in vacuo, the residue was dissolved into AcOEt (50 ml), washed with 6N aqueous KOH (50 ml) and brine (50 ml), then dried over K$_2$CO$_3$. After filtration and evaporation of solvent, the product was precipitated by CH$_2$Cl$_2$/hexane mixture. 2-(3-Aminopropyl)-5-carboxamido-1,4-dihydro-6-methyl-4-(4-nitrophenyl)-3-{N-[3-(4,4-diphenylpiperidin-1-yl)propyl]}carboxamidopyridine was obtained as a yellowish powder (88 mg, 90%). M.p. 97–100° C.; Calcd for C$_{37}$H$_{44}$N$_6$O$_4$.½H$_2$O: C 68.82, H 7.02, N 13.01; Found: C 68.56, H 6.71, N 12.89.

EXAMPLE 169

2-(5-Aminopentyl)-5-carboxamido-1,4-dihydro-6-methyl-4-(4-nitrophenyl)-3-(N-[3-(4,4-diphenylpiperidin-1-yl) propyl]}carboxamidopyridine (169). A solution of ethyl 6-bromohexanoate (10.0 g, 44.8 mmol), NaN$_3$ (5.83 g, 89.6 mmol) and 25 ml of water in 75 ml of MeOH was refluxed for 3.5 hrs. The MeOH was removed in vacuo and the residue was partitioned between CHCl$_3$ (200 ml) and water (50 ml). The organic layer was separated and washed with water. After drying (Na$_2$SO$_4$) and evaporation of solvent, ethyl 6-azidohexanoate (8.59 g, 100%) was obtained as a colorless oil.

Ethyl 6-azidohexanoate (8.59 g, 44.8 mmol) and KOH (13.0 g, 0.231 mol) were dissolved into a mixture of 120 ml of water and 180 ml of MeOH. The solution was stirred at 0° C. for 2 hrs then MeOH was removed in vacuo. The aqueous layer was extracted by CHCl$_3$ (2×100 ml), acidified to pH=1 by 2N aqueous HCl and extracted by Et$_2$O (2×100 ml). The organic layers were combined, washed with water (100 ml) and dried over Na$_2$SO$_4$. After filtration and evaporation of solvent, 6-azidohexanoic acid (6.56 g, 93%) was obtained as a colorless oil.

6-Azidohexanoic acid (6.56 g, 41.7 mmol) in 15 ml of toluene was treated with oxalyl chloride (13.2 g, 104 mmol). The mixture was stirred at 50° C. for 10 hrs. After removal of toluene in vacuo, crude 6-azidohexanoic chloride was used for next reaction without further purification.

To a solution of 2,2-dimethyl-1,3-dioxane-4,6-dione (6.31 g, 43.8 mmol) and 4-dimethylaminopyridine (5.60 g, 45.9 mmol) in 100 ml of CH$_2$Cl$_2$ was added dropwise a solution of crude 6-azidohexanoic chloride (7.32 g, 41.7 mmol) in 30 ml of CH$_2$Cl$_2$ at 0° C. The mixture was stirred at 0° C. for 1 hr then at room temperature for 1 hr. The solution was washed with 0.5N aqueous HCl (100 ml), water (100 ml) followed by brine (100 ml) and dried over Na$_2$SO$_4$. After filtration and evaporation of solvent, 5-(6-azidohexanoyl)-2,2-dimethyl-1,3-dioxane-4,6-dione was obtained as a light red oil (12.0 g, 100%).

5-(6-Azidohexanoyl)-2,2-dimethyl-1,3-dioxane-4,6-dione was heated with 3-hydroxypropionitrile (8.90 g, 125 mmol) at 80° C. until no more CO$_2$ was released. The reaction mixture was diluted with 150 ml of 2-propanol and 4-nitrobenzaldehyde (6.30 g, 41.7 mmol), piperidine (178 mg, 2.10 mmol) and acetic acid (125 mg, 2.10 mmol) were added. The mixture was stirred at room temperature for 48 hrs. After the solvent was evaporated, the residue was dissolved into CHCl$_3$ (200 ml), washed with water (150 ml) and brine (150 ml). After drying (Na$_2$SO$_4$) and evaporation of solvent, 8-azido-2-[ (4-nitrophenyl)methylene]-3-oxooctanoic acid 2-cyanoethyl ester was obtained as a brownish oil (17.0 g, 100%).

A solution of 8-azido-2-[ (4-nitrophenyl)methylene]-3-oxooctanoic acid 2-cyanoethyl ester (4.00 g, 10.4 mmol) and 3-aminocrotonamide (2.08 g, 20.8 mmol) in 100 ml EtOH was refluxed for 48 hrs. After the EtOH was removed in vacuo, the residue was dissolved in 150 ml of CHCl$_3$, washed with water (2×100 ml) and dried over Na$_2$SO$_4$. After filtration and evaporation of solvent, the product was purified by chromatography (SiO$_2$, CHCl$_3$:MeOH=95:5). 2-(5-Azidopentyl)-5-carboxamido-3-(2-cyanoethoxy)carbonyl-1,4-dihydro-6-methyl-4-(4-nitrophenyl) pyridine was obtain as a yellow oil (2.23 g, 47% yield).

A solution of 2-(5-azidopentyl)-5-carboxamido-3-(2-cyanoethoxy)carbonyl-1,4-dihydro-6-methyl-4-(4-nitrophenyl)pyridine (2.26 g, 5.44 mmol) in 10 ml acetone was treated with 25 ml 1N aqueous KOH solution at 0° C. for 1 hr. The acetone was removed in vacuo and the aqueous layer was acidified to pH=3 by 2N hydrochloric acid, the resulting yellow precipitate was collected by filtration, washed with 10 ml of cold water and dried in vacuo to yield 1.50 g (67% yield) of 2-(5-azidopentyl)-5-carboxamido-1,4-dihydro-6-methyl-4-(4-nitrophenyl)pyridine-3-carboxylic acid as a yellow powder.

A solution of 2-(5-azidopentyl)-5-carboxamido-1,4-dihydro-6-methyl-4-(4-nitrophenyl) pyridine-3-carboxylic acid (300 mg, 0.72 mmol), 1-(3-dimethylaminopropyl)-3-ethylcarbodiimide hydrochloride (277 mg, 1.45 mmol) and 4-dimethylaminopyridine (88 mg, 0.72 mmol) in 40 ml of CH$_2$Cl$_2$ was stirred at room temperature. After 1 hr, a solution of 3-(4,4-diphenylpiperidin-1-yl)propylamine (213 mg, 0.72 mmol) in 5 ml of CH$_2$Cl$_2$ was added and the mixture was stirred at reflux overnight. The mixture was washed with water (30 ml), saturated aqueous NH$_4$Cl (3×30 ml), 10% K$_2$CO$_3$ (30 ml) and brine (30 ml). After drying over Na$_2$SO$_4$ and evaporation of solvent, a yellowish oil was obtained, which was purified by chromatography (SiO$_2$, MeOH:CHCl$_3$:1N NH$_3$ in MeOH, 6:90:3) and precipitated by CH$_2$Cl$_2$/hexane mixture. 2-(5-Azidopentyl)-5-carboxamido-1,4-dihydro-6-methyl-4-(4-nitrophenyl)-3-{N-[3-(4,4-diphenylpiperidin-1-yl)propyl]}carboxamidopyridine was obtained as a yellowish powder (300 mg, 58%). M.p. 85° C. (dec.); Calcd. for C$_{39}$H$_{46}$N$_8$O$_4$·¾H$_2$O: C 66.5, H 6.80, N 15.91; Found: C 66.45, H 6.63, N 16.03.

A solution of 2-(5-azidopentyl)-5-carboxamido-1,4-dihydro-6-methyl-4-(4-nitrophenyl)-3-{N-[3-(4,4-diphenylpiperidin-1-yl)propyl]}carboxamidopyridine (130 mg, 0.20 mmol) in 5 ml of AcOEt was treated with 0.60 ml of 1M trimethylphosphine THF solution. The mixture was stirred at 0° C. for 1.5 hrs then 0.10 ml of water was added and the mixture was stirred at room temperature for an additional 1.5 hrs. After most volatile materials were removed in vacuo, residue was dissolved into AcOEt (50 ml), washed with 6N aqueous KOH (50 ml) and brine (50 ml), then dried over K$_2$CO$_3$. After filtration and evaporation of solvent, product was precipitated by CH$_2$Cl$_2$/hexane mixture. 2-(5-Aminopentyl)-5-carboxamido-1,4-dihydro-6-methyl-4-(4-nitrophenyl)-3-{N-[3-(4,4-diphenylpiperidin-1-yl)propyl]}carboxamidopyridine was obtained as a yellowish powder (110 mg, 85%). M.p. 75–78° C.; Calcd for C$_{39}$H$_{48}$N$_6$O$_4$·½H$_2$O: C 69.52, H 7.33, N 12.47; Found: C 69.20, H 7.37, N 12.45.

EXAMPLE 170

2-(4-Aminobutyl)-1,4-dihydro-5-methoxycarbonyl-6-methyl-4-(4-nitrophenyl)-3-{N-[3-(4,4-diphenylpiperidin-1-yl)propyl]}carboxamidopyridine (170). A solution of 7-azido-2-[(4-nitrophenyl)methylene]-3-oxoheptanoicacid2-cyanoethyl ester (2.87 g, 7.73 mmol) and methyl 3-aminocrotonate (0.900 g, 7.73 mmol) in 50 ml of EtOH was refluxed for 48 hrs. After the EtOH was removed in vacuo, the residue was dissolved in 150 ml of CHCl$_3$, washed with water (2×100 ml) and dried over Na$_2$SO$_4$. After filtration and evaporation of solvent, the product was purified by chromatography (SiO$_2$, CHCl$_3$:MeOH=95:5). 2-(4-Azidobutyl)-3-(2-cyanoethoxy)carbonyl-1,4-dihydro-5-methoxycarbonyl-6-methyl-4-(4-nitrophenyl)pyridine was obtain as a yellow oil (2.43 g, 67% yield).

A solution of 2-(4-azidobutyl)-3-(2-cyanoethoxy)carbonyl-1,4-dihydro-5-methoxycarbonyl-6-methyl-4-(4-nitrophenyl)pyridine (1.38 g, 2.95 mmol) in 10 ml acetone was treated with 15 ml 1N KOH solution at 0° C. for 1 hr. The acetone was removed in vacuo and the aqueous layer was acidified to pH=3 by 2N hydrochloric acid, the resulting yellow precipitate was collected by filtration, washed with 10 ml of cold water and dried in vacuo to yield 750 mg (61% yield) of 2-(4-azidobutyl)-1,4-dihydro-5-methoxycarbonyl-6-methyl-4-(4-nitrophenyl) pyridine-3-carboxylic acid as a yellow powder.

A solution of 2-(4-azidobutyl)-1,4-dihydro-5-methoxycarbonyl-6-methyl-4-(4-nitrophenyl) pyridine-3-carboxylic acid (300 mg, 0.722 mmol), 1-(3-dimethylaminopropyl)-3-ethylcarbodiimide hydrochloride 277 mg, 1.45 mmol) and 4-dimethylaminopyridine (132 mg, 1.08 mmol) in 40 ml of CH$_2$Cl$_2$ was stirred at r.t. After 1 hr, a solution of 3-(4,4-diphenylpiperidin-1-yl)propylamine (213 mg, 0.72 mmol) in 5 ml of CH$_2$Cl$_2$ was added and the mixture was stirred at reflux overnight. The mixture was washed with water (30 ml), saturated aqueous NH$_4$Cl (3×30 ml), 10% K$_2$CO$_3$ (30 ml) and brine (30 ml). After drying over Na$_2$SO$_4$ and evaporation of solvent, a yellowish oil was obtained which was purified by chromatography (SiO$_2$, MeOH:CHCl$_3$:1N NH$_3$ in MeOH, 6:90:3) and precipitated by CH$_2$Cl$_2$/hexane mixture. 2-(4-Azidobutyl)-1,4-dihydro-5-methoxycarbonyl-6-methyl-4-(4-nitrophenyl)-3-{N-[3-(4,4-diphenylpiperidin-1-yl)propyl]}carboxamidopyridine was obtained as a yellowish powder (400 mg, 82%). M.p. 66–70° C.; Calcd. for C$_{39}$H$_{45}$N$_7$O$_5$·½H$_2$O: C 66.84, H 6.62, N 13.99; Found: C 66.80, H 6.48, N 13.89

A solution of 2-(4-azidobutyl)-1,4-dihydro-5-methoxycarbonyl-6-methyl-4-(4-nitrophenyl)-3-{N-[3-(4,4-diphenylpiperidin-1-yl)propyl]}carboxamidopyridine (200 mg, 0.29 mmol) in 5 ml of AcOEt was treated with 0.87 ml of 1M trimethylphosphine THF solution. The mixture was stirred at 0° C. for 1.5 hrs then 0.05 ml of water was added and the mixture was stirred at room temperature for an additional 1.5 hrs. After most volatile materials were removed in vacuo, residue was dissolved in 50 ml of AcOEt, washed with 6N KOH (50 ml) and brine (50 ml), then dried over K$_2$CO$_3$. After filtration and evaporation of solvent, product was precipitated by CH$_2$Cl$_2$/hexane mixture. 2-(4-Aminobutyl)-1,4-dihydro-5-methoxycarbonyl-6-methyl-4-(4-nitrophenyl)-3-{N-[3-(4,4-diphenylpiperidin-1-yl)propyl]}carboxamidopyridine was obtained as a yellowish powder (150 mg, 78%). M.p. 89–93° C.; Calcd for C$_{39}$H$_{47}$N$_5$O$_5$·¾H$_2$O: C 68.05, H 7.25, N 10.17; Found: C 68.14, H 7.08, N 10.11

EXAMPLE 171

2-(4-Aminobutyl)-5-carboxamido-6-ethyl-1,4-dihydro-4-(4-nitrophenyl)-3-{N-[3-(4,4-diphenylpiperidin-1-yl)propyl]}carboxamidopyridine (171). A solution of 2-(4-azidobutyl)-5-carboxamido-6-ethyl-1,4-dihydro-4-(4-nitrophenyl)pyridine-3-carboxylic acid (300 mg, 0.72 mmol), 1-(3-dimethylaminopropyl)-3-ethylcarbodiimide hydrochloride (276 mg, 1.44 mmol) and 4-dimethylaminopyridine (88 mg, 0.72 mmol) in 50 ml of CH$_2$Cl$_2$ was stirred at r.t. After 1 hr, a solution of 3-(4,4-diphenylpiperidin-1-yl)propylamine (215 mg, 0.72 mmol) in 5 ml of $CH_2Cl_2$ was added and the mixture was stirred at reflux overnight. The mixture was washed with water (30 ml), saturated aqueous $NH_4Cl$ (3×30 ml), 10% $K_2CO_3$ (30 ml) and brine (30 ml). After drying over $Na_2SO_4$ and evaporation of solvent, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture. 2-(4-Azidobutyl)-5-carboxamido-6-ethyl-1,4-dihydro-4-(4-nitrophenyl)-3-{N-[3-(4,4-diphenylpiperidin-1-yl)propyl]}carboxamidopyridine was obtained as a yellowish powder (312 mg, 63%). M.p. 85–89° C.; Calcd. for $C_{39}H_{46}N_8O_4$: C 67.81, H 6.71, N 16.22; Found: C 67.42, H 6.45, N 15.89

A solution of 2-(4-azidobutyl)-5-carboxamido-6-ethyl-1,4-dihydro-4-(4-nitrophenyl)-3-{N-[3-(4,4-diphenylpiperidin-1-yl)propyl]}carboxamidopyridine (310 mg, 0.45 mmol) in 5 ml of AcOEt was treated with 1.35 ml of 1M trimethylphosphine THF solution. The mixture was stirred at 0° C. for 1.5 hrs then 0.03 ml of water was added and the mixture was stirred at room temperature for an additional 1.5 hrs. After most volatile materials were removed in vacuo, residue was dissolved into AcOEt (50 ml), washed with 6N KOH (50 ml) and brine (50 ml), then dried over $K_2CO_3$. After filtration and evaporation of solvent, product was precipitated by $CH_2Cl_2$/hexane mixture. 2-(4-Aminobutyl)-5-carboxamido-6-ethyl-1,4-dihydro-4-(4-nitrophenyl)-3-{N-[3-(4,4-diphenylpiperidin-1-yl)propyl]}carboxamidopyridine was obtained as a yellowish powder (267 mg, 89%). M.p. 85–89° C.; Calcd for $C_{39}H_{48}N_6O_4$: C 70.46, H 7.28, N 12.64; Found: C 70.25, H 7.62, N 12.34.

EXAMPLE 172

2-(4-Aminobutyl)-6-ethyl-1,4-dihydro-5-(N-methyl) carboxamido-4-(4-nitrophenyl)-3-{N-[3-(4,4-diphenylpiperidin-1-yl)propyl]}carboxamidopyridine (172). A solution of 6-ethyl-2,2-dimethyl-4H-1,3-dioxin-4-one (10.0 g, 64.0 mmol) in 20 ml of xylene was bubbled with methylamine gas at 110° C. for 3 hrs. After cooling to room temperature, 5.3 ml of 1N HCl aqueous solution was added and the mixture was stirred at r.t. for 2 hrs. The organic layer was separated, the water layer was extracted by $Et_2O$ (3×30 ml). The organic layers were combined and dried ($Na_2SO_4$). After evaporation of solvent, N-methyl propionylacetamide was obtained as a colorless oil (4.25 g, 51%).

A solution of N-methyl propionylacetamide (4.25 g, 32.9 mmol) in 30 ml xylene was bubbled with ammonia gas at 110° C. for 2 hrs. After cooling to room temperature, the mixture was diluted with 30 ml of $CHCl_3$ and dried ($Na_2SO_4$). After evaporation of solvent, N-methyl 3-amino-2-pentenamide was obtained as light-gray oil (4.15 g, 98).

A solution of 7-azido-2-[(4-nitrophenyl)methylene]-3-oxoheptanoic acid 2-cyanoethyl ester (4.00 g, 10.8 mmol) and N-methyl 3-amino-2-pentenamide (1.52 g, 12.0 mmol) in 50 ml of EtOH was refluxed for 48 hrs. After the EtOH was removed in vacuo, the residue was dissolved in 150 ml of $CHCl_3$, washed with water (2×100 ml) and dried over $Na_2SO_4$. After filtration and evaporation of solvent, 2-(4-azidobutyl)-3-(2-cyanoethoxy) carbonyl-6-ethyl-1,4-dihydro-5-(N-methyl) carboxamido-4-(4-nitrophenyl) pyridine was obtain as a brown oil (5.19 g, 99% yield).

A solution of 2-(4-azidobutyl)-3-(2-cyanoethoxy) carbonyl-6-ethyl-1,4-dihydro-5-(N-methyl)carboxamido-4-(4-nitrophenyl)pyridine (5.19 g, 10.8 mmol) in 20 ml acetone was treated with 30 ml 1N KOH solution at 0° C. for 1 hr. The acetone was removed in vacuo and the aqueous layer was washed with $CHCl_3$ (20 ml) and acidified to pH=3 by 2N hydrochloric acid, the resulting yellow precipitate was collected by filtration, washed with 10 ml of cold water and dried in vacuo to yield 3.21 g (69% yield) of 2-(4-azidobutyl)-6-ethyl-1,4-dihydro-5-(N-methyl)carboxamido-4-(4-nitrophenyl)pyridine-3-carboxylic acid as a yellow powder.

A solution of 2-(4-azidobutyl)-6-ethyl-1,4-dihydro-5-(N-methyl)carboxamido-4-(4-nitrophenyl)pyridine-3-carboxylic acid (500 mg, 1.17 mmol), 1-(3-dimethylaminopropyl)-3-ethylcarbodiimide hydrochloride (450 mg, 2.34 mmol) and 4-dimethylaminopyridine (280 mg, 2.34 mmol) in 50 ml of $CH_2Cl_2$ was stirred at room temperature. After 1 hr, a solution of 3-(4,4-diphenylpiperidin-1-yl)propylamine (420 mg, 1.40 mmol) in 5 ml of $CH_2Cl_2$ was added and the mixture was stirred at reflux overnight. The mixture was washed with water (30 ml), saturated aqueous $NH_4Cl$ (3×30 ml), 10% $K_2CO_3$ (30 ml) and brine (30 ml). After drying over $Na_2SO_4$ and evaporation of solvent, a yellowish oil was obtained, which was purified by chromatography ($SiO_2$, MeOH:$CHCl_3$:1N $NH_3$ in MeOH, 6:90:3) and precipitated by $CH_2Cl$/hexane mixture. 2-(4-Azidobutyl)-6-ethyl-1,4-dihydro-5-(N-methyl) carboxamido-4-(4-nitrophenyl)-3-{N-[3-(4,4-diphenylpiperidin-1-yl)propyl]}carboxamidopyridine was obtained as a yellowish powder (449 mg, 54%). M.p. 90–93° C.; Calcd. for $C_{40}H_{48}N_8O_4 \cdot \frac{3}{4}H_2O$: C 66.88, H 6.94, N 15.66; Found: C 66.85, H 6.59, N 15.74.

A solution of 2-(4-azidobutyl)-6-ethyl-1,4-dihydro-5-(N-methyl)carboxamido-4-(4-nitrophenyl)-3-{N-[3-(4,4-diphenylpiperidin-1-yl)propyl]}carboxamidopyridine (402 mg, 0.57 mmol) in 5 ml of AcOEt was treated with 1.71 ml of 1M trimethylphosphine THF solution. The mixture was stirred at 0° C. for 1.5 hrs then 0.05 ml of water was added and the mixture was stirred at room temperature for an additional 1.5 hrs. After most volatile materials were removed in vacuo, residue was dissolved into AcOEt (50 ml), washed with 6N KOH (50 ml) and brine (50 ml), then dried over $K_2CO_3$. After filtration and evaporation of solvent, product was precipitated by $CH_2Cl_2$/hexane mixture. 2-(4-Aminobutyl)-6-ethyl-1,4-dihydro-5-(N-methyl) carboxamido-4-(4-nitrophenyl)-3-{N-[3-(4,4-diphenylpiperidin-1-yl)propyl]}carboxamidopyridine was obtained as a yellowish powder (350 mg, 90%). M.p. 105–109° C.; Calcd for $C_{40}H_{50}N_6O_4 \cdot \frac{1}{4}H_2O$: C 70.30, H 7.45, N 12.30; Found: C 70.20, H 7.31, N 12.21.

EXAMPLE 173

6-Ethyl-1,4-dihydro-2-(4-methoxybutyl)-5-(N-methyl) carboxamido-4-(4-nitrophenyl)-3-{N-[3-(4,4-diphenylpiperidin-1-yl)propyl]}carboxamidopyridine (173). A solution of methyl 5-bromovalerate (10.0 g, 51.3 mmol), NaOMe (12.3 ml of 25% solution, 53.8 mmol) in 100 ml of MeOH was refluxed for 5 hrs. The MeOH was removed in vacuo and residue was partitioned between $CHCl_3$ (200 ml) and water (50 ml). The organic layer was separated and washed with water (100 ml). After drying ($Na_2SO_4$) and evaporation of solvent, methyl 5-methoxyvalerate (7.33 g, 97.8%) was obtained as a colorless oil.

Methyl 5-methoxyvalerate (7.33 g, 50.2 mmol) and KOH (14.4 g, 0.256 mol) were dissolved into a mixture of 50 ml of water and 150 ml of MeOH. The solution was stirred at 0° C. for 2 hrs then MeOH was removed in vacuo. After washed by $CHCl_3$ (50 ml), the aqueous layer was acidified to pH=1 by 2N HCl and extracted by $Et_2O$ (2×100 ml). Organic layers were combined, washed with water (100 ml)

and dried over Na$_2$SO$_4$. After filtration and evaporation of solvent, 5-methoxyvaleric acid (5.27 g, 79.6%) was obtained as a colorless oil.

5-Methoxyvaleric acid (5.27 g, 39.9 mmol) in 15 ml of toluene was treated with oxalyl chloride (12.7 g, 99.8 mmol). The mixture was stirred at 50° C. for 10 hrs. After removal of toluene in vacuo, crude 5-methoxyvaleric chloride was used for next reaction without further purification.

To a solution of 2,2-dimethyl-1,3-dioxane-4,6-dione (5.77 g, 40.0 mmol) and 4-dimethylaminopyridine (5.86 g, 44.0 mmol) in 100 ml of CH$_2$Cl$_2$ was added dropwise the solution of crude 5-methoxyvaleric chloride (6.00 g, 39.9 mmol) in 10 ml of CH$_2$Cl$_2$ at 0° C. The mixture was stirred at 0° C. for 1 hr then at room temperature for an additional 1 hr. The solution was washed with 1N aqueous HCl (100 ml) and brine (250 ml). After dried over Na$_2$SO$_4$ and evaporation of solvent, 5-(5-methoxypentanoyl)-2,2-dimethyl-1,3-dioxane-4,6-dione was obtained as a light pink oil (9.20 g, 89%).

5-(5-Methoxypentanoyl)-2,2-dimethyl-1,3-dioxane-4,6-dione was heated with 3-hydroxypropionitrile (2.79 g, 39.2 mmol) at 80° C. until no more CO$_2$ was released. After cooling to room temperature, the mixture was diluted with 50 ml of 2-propanol and 4-nitrobenzaldehyde (5.40 g, 35.6 mmol), piperidine (150 mg, 1.78 mmol) and acetic acid (110 mg, 1.78 mmol) was added, the mixture was stirred at room temperature for 48 hrs. After evaporation of solvent, the product was purified by chromatography (SiO$_2$, MeOH:CHCl$_2$=5:95). 7-Methoxy-2-[(4-nitrophenyl)methylene]-3-oxoheptanoic acid 2-cyanoethyl ester was obtained as a pale-yellow oil (7.75 g, 60% yield).

A solution of 7-methoxy-2-[(4-nitrophenyl)methylene]-3-oxoheptanoic acid 2-cyanoethyl ester (3.87 g, 10.8 mmol) and N-methyl 3-amino-2-pentenamide (1.52 g, 11.9 mmol) in 40 ml of EtOH was refluxed for 48 hrs. After the EtOH was removed in vacuo, the residue was dissolved in 150 ml of CHCl$_3$, washed with water (2×100 ml) and dried over Na$_2$SO$_4$. After filtration and evaporation of solvent, the product was purified by chromatography (SiO$_2$i CHCl$_3$:MeOH=5:95). 3-(2-Cyanoethoxy)carbonyl-6-ethyl-1,4-dihydro-2-(4-methoxybutyl)-5-(N-methyl) carboxamido-4-(4-nitrophenyl)pyridine was obtain as a yellow oil (3.60 g, 71% yield).

A solution of 3-(2-cyanoethoxy)carbonyl-6-ethyl-1,4-dihydro-2-(4-methoxybutyl)-5-(N-methyl)carboxamido-4-(4-nitrophenyl)pyridine (3.60 g, 7.65 mmol) in 15 ml of acetone was treated with 20 ml of 1N aqueous KOH solution at 0° C. for 1 hr. The acetone was removed in vacuo and the aqueous layer was acidified to pH=3 by 2N hydrochloric acid, the resulting yellow precipitate was collected by filtration, washed with 10 ml of cold water and dried in vacuo to yield 1.99 g (63% yield) of 6-ethyl-1,4-dihydro-2-(4-methoxybutyl)-5-(N-methyl)carboxamido-4-(4-nitrophenyl)pyridine-3-carboxylic acid as a yellow powder.

A solution of 6-ethyl-1,4-dihydro-2-(4-methoxybutyl)-5-(N-methyl) carboxamido-4-(4-nitrophenyl)pyridine-3-carboxylic acid (626 mg, 1.50 mmol), 1-(3-dimethylaminopropyl)-3-ethylcarbodiimide hydrochloride (575 mg, 3.00 mmol) and 4-dimethylaminopyridine (367 mg, 3.00 mmol) in 60 ml of CH$_2$Cl$_2$ was stirred at room temperature. After 1 hr, a solution of 3-(4,4-diphenylpiperidin-1-yl)propylamine (530 mg, 1.80 mmol) in 10 ml of CH$_2$Cl$_2$ was added and the mixture was stirred at reflux overnight. The mixture was washed with water (30 ml), saturated NH$_4$Cl (3×30 ml), 30% K$_2$CO$_3$ (30 ml) and brine (30 ml). After dried over Na$_2$SO$_4$ and evaporation of solvent, a yellowish oil was obtained, which was purified by chromatography (SiO$_2$, MeOH:CHCl$_3$:1N NH$_3$ in MeOH, 6:90:3) and precipitated by CH$_2$Cl$_2$/hexane mixture. 6-Ethyl-1,4-dihydro-2-(4-methoxybutyl)-5-(N-methyl) carboxamido-4-(4-nitrophenyl)-3-{N-[3-(4,4-diphenylpiperidin-1-yl)propyl]}carboxamidopyridine was obtained as a yellowish powder (530 mg, 51%). M.p. 98–102° C.; Calcd. for C$_{41}$H$_{51}$N$_5$O$_5$.H$_2$O: C 69.17, H 7.50, N 9.84; Found: C 69.10, H 7.43, N 9.89.

EXAMPLE 174

6-Ethyl-1,4-dihydro-2-(4-methoxybutyl)-3-{N-[3-(4-methoxycarbonyl-4-phenylpiperidin-1-yl)propyl]} carboxamido-5-(N-methyl)carboxamido-4-(4-nitrophenyl) pyridine (174). A solution of 6-ethyl-1,4-dihydro-2-(4-methoxybutyl)-5-(N-methyl)carboxamido-4-(4-nitrophenyl)pyridine-3-carboxylic acid (626 mg, 1.50 mmol), 1-(3-dimethylaminopropyl)-3-ethylcarbodiimide hydrochloride (575 mg, 3.00 mmol) and 4-dimethylaminopyridine (367 mg, 3.00 mmol) in 60 ml of CH$_2$Cl$_2$ was stirred at room temperature. After 1 hr, a solution of 3-(4-methoxycarbonyl-4-phenylpiperidin-1-yl) propylamine (497 mg, 1.80 mmol) in 10 ml of CH$_2$Cl$_2$ was added and the mixture was stirred at reflux overnight. The mixture was washed with water (30 ml), saturated aqueous NH$_4$Cl (3×30 ml), 10% K$_2$CO$_3$ (30 ml) and brine (30 ml). After dried over Na$_2$SO$_4$ and evaporation of solvent, a yellowish oil was obtained, which was purified by chromatography (SiO$_2$, MeOH:CHCl$_3$:1N NH$_3$ in MeOH, 6:90:3) and precipitated by CH$_2$Cl$_2$/hexane mixture. The title compound was obtained as a yellowish powder (512 mg, 51%). M.p. 71–74° C.; Calcd. for C$_{37}$H$_{49}$N$_5$O$_7$: C 65.75, H 7.31, N 10.36; Found: C 65.47, H 7.37, N 10.22.

EXAMPLE 175

5-Carboxamido-6-ethyl-1,4-dihydro-2-(4-methoxybutyl)-4-(4-nitrophenyl)-3-{N-[3-(4,4-diphenylpiperidin-1-yl)propyl]}carboxamidopyridine (175). A solution of 7-methoxy-2-[(4-nitrophenyl)methylene]-3-oxoheptanoic acid 2-cyanoethyl ester (3.87 g, 10.8 mmol) and 3-amino-2-pentenamide (1.36 g, 11.9 mmol) in 40 ml of EtOH was refluxed for 48 hrs. After the EtOH was removed in vacuo, the residue was dissolved in 150 ml of CHCl$_3$, washed with water (2×100 ml) and dried over Na$_2$SO$_4$. After filtration and evaporation of solvent, 5-carboxamido-3-(2-cyanoethoxy)carbonyl-6-ethyl-1,4-dihydro-2-(4-methoxybutyl)-4-(4-nitrophenyl)pyridine was obtained as a yellow oil (4.00 g, 81% yield).

A solution of 5-carboxamido-3-(2-cyanoethoxy) carbonyl-6-ethyl-1,4-dihydro-2-(4-methoxybutyl)-4-(4-nitrophenyl)pyridine (4.00 g, 8.76 mmol) in 15 ml of acetone was treated with 25 ml 1N aqueous KOH solution at 0° C. for 1 hr. The acetone was removed in vacuo and the aqueous layer was washed with CHCl$_3$ (15 ml) then acidified to pH=3 by 2N hydrochloric acid, the resulting yellow precipitate was collected by filtration, washed with 10 ml of cold water and dried in vacuo to yield 1.69 g (48% yield) of 5-carboxamido-6-ethyl-1,4-dihydro-2-(4-methoxybutyl)-4-(4-nitrophenyl)pyridine-3-carboxylic acid as a yellow powder.

A solution of 5-carboxamido-6-ethyl-1,4-dihydro-2-(4-methoxybutyl)-4-(4-nitrophenyl)pyridine-3-carboxylic acid (200 mg, 0.50 mmol), 1-(3-dimethylaminopropyl)-3-ethylcarbodiimide hydrochloride (192 mg, 1.00 mmol) and 4-dimethylaminopyridine (122 mg, 1.00 mmol) in 40 ml of CH$_2$Cl$_2$ was stirred at room temperature. After 1 hr, a solution of 3-(4,4-diphenylpiperidin-1-yl) propylamine (295 mg, 1.00 mmol) in 5 ml of $CH_2Cl_2$ was added and the mixture was stirred at reflux overnight. The mixture was washed with water (20 ml), saturated aqueous $NH_4Cl$ (3×20 ml), 10% $K_2CO_3$ (20 ml) and brine (20 ml). After dried over $Na_2SO_4$ and evaporation of solvent, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture. 5-Carboxamido-6-ethyl-1,4-dihydro-2-(4-methoxybutyl)-4-(4-nitrophenyl)-3-{N-[3-(4,4-diphenylpiperidin-1-yl)propyl]}carboxamidopyridine was obtained as a yellowish powder (188 mg, 50%). M.p. 80–84° C.; Calcd. for $C_{40}H_{49}N_5O_5 \cdot \frac{1}{2}H_2O$: C 69.94, H 7.32, N 10.17; Found: C 69.56, H 7.03, N 10.19.

EXAMPLE 176

5-Acetyl-2-(4-aminobutyl)-1,4-dihydro-6-methyl-4-(4-nitrophenyl)-3-{N-[3-(4,4-diphenylpiperidin-1-yl)propyl]} carboxamidopyridine (176). A solution of 7-azido-2-[(4-nitrophenyl)methylene]-3-oxoheptanoic acid 2-cyanoethyl ester (1.12 g, 3.00 mmol) and 4-amino-3-penten-2-one (330 mg, 3.30 mmol) in 20 ml of EtOH was refluxed for 48 hrs. After the EtOH was removed in vacuo, the residue was dissolved in 150 ml of $CHCl_3$, washed with water (2×100 ml) and dried over $Na_2SO_4$. After filtration and evaporation of solvent, the product was purified by chromatography ($SiO_2$, $CHCl_3$:MeOH=5:95). 5-Acetyl-2-(4-azidobutyl)-3-(2-cyanoethoxy) carbonyl-1,4-dihydro-6-methyl-4-(4-nitrophenyl) pyridine was obtain as a yellow oil (1.05 g, 77% yield).

A solution of 5-acetyl-2-(4-azidobutyl)-3-(2-cyanoethoxy)carbonyl-1,4-dihydro-6-methyl-4-(4-nitrophenyl)pyridine (1.05 g, 2.32 mmol) in 10 ml of acetone was treated with 20 ml of 1N aqueous KOH solution at 0° C. for 1 hr. The acetone was removed in vacuo and the aqueous layer was acidified to pH=3 by 2N hydrochloric acid, the resulting yellow precipitate was collected by filtration, washed with 10 ml of cold water and dried in vacuo to yield 0.60 g (60% yield) of 5-acetyl-2-(4-azidobutyl)-1,4-dihydro-6-methyl-4-(4-nitrophenyl) pyridine-3-carboxylic acid as a yellow powder.

A solution of 5-acetyl-2-(4-azidobutyl)-1,4-dihydro-6-methyl-4-(4-nitrophenyl) pyridine-3-carboxylic acid (200 mg, 0.50 mmol), 1-(3-dimethylaminopropyl)-3-ethylcarbodiimide hydrochloride (192 mg, 1.00 mmol) and 4-dimethylaminopyridine (122 mg, 1.00 mmol) in 40 ml of $CH_2Cl_2$ was stirred at room temperature. After 1 hr, a solution of 3-(4,4-diphenylpiperidin-1-yl)propylamine (162 mg, 0.55 mmol) in 5 ml of $CH_2Cl_2$ was added and the mixture was stirred at reflux overnight. The mixture was washed with water (20 ml), saturated aqueous $NH_4Cl$ (3×20 ml), 10% $K_2CO_3$ (20 ml) and brine (20 ml). After dried over $Na_2SO_4$ and evaporation of solvent, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture. 5-Acetyl-2-(4-azidobutyl)-1,4-dihydro-6-methyl-4-(4-nitrophenyl)-3-{N-[3-(4,4-diphenylpiperidin-1-yl)propyl]}carboxamidopyridine was obtained as a yellowish powder (126 mg, 37%).

A solution of 5-acetyl-2-(4-azidobutyl)-1,4-dihydro-6-methyl-4-(4-nitrophenyl)-3-{N-[3-(4,4-diphenylpiperidin-1-yl)propyl]}carboxamidopyridine (126 mg, 0.19 mmol) in 5 ml of AcOEt was treated with 0.57 ml of 1M trimethylphosphine THF solution. The mixture was stirred at 0° C. for 1.5 hrs then 0.02 ml of water was added and the mixture was stirred at room temperature for an additional 1.5 hrs. After most volatile materials were removed in vacuo, resi-due was dissolved into 50 ml of AcOEt, washed with 6N aqueous KOH (50 ml) and brine (50 ml), then dried over $K_2CO_3$. After filtration and evaporation of solvent, product was precipitated by $CH_2Cl_2$/hexane mixture. 5-Acetyl-2-(4-aminobutyl)-1,4-dihydro-6-methyl-4-(4-nitrophenyl)-3-{N-[3-(4,4-diphenylpiperidin-1-yl)propyl]} carboxamidopyridine was obtained as a yellowish powder (112 mg, 90%). M.p. 76–79° C.; Calcd for $C_{39}H_{47}N_5O_4 \cdot \frac{3}{4}H_2O$: C 70.62, H 7.37, N 10.56; Found: C 70.56, H 6.96, N 10.40.

EXAMPLE 177

2-(4-Aminobutyl)-5-carboxamido-1,4-dihydro-3-{N-[3-(4-methoxycarbonyl-4-phenylpiperidin-1-yl)propyl]} carboxamido-6-methyl-4-(4-nitrophenyl)pyridine (177). A solution of 2-(4-azidobutyl)-5-carboxamido-1,4-dihydro-6-methyl-4-(4-nitrophenyl)pyridine-3-carboxylic acid (416 mg, 1.04 mmol), 1-(3-dimethylaminopropyl)-3- ethylcarbodiimide hydrochloride (399 mg, 2.08 mmol) and 4-dimethylaminopyridine (177 mg, 1.04 mmol) in 50 ml of $CH_2Cl_2$ was stirred at room temperature. After 1 hr, a solution of 3-(4-methoxycarbonyl-4-phenylpiperidin-1-yl) propylamine (254 mg, 1.04 mmol) in 5 ml of $CH_2Cl_2$ was added and the mixture was stirred at reflux overnight. The mixture was washed with water (20 ml), saturated aqueous $NH_4Cl$ (3×20 ml), 10% $K_2CO_3$ (20 ml) and brine (20 ml). After dried over $Na_2SO_4$ and evaporation of solvent, a yellowish oil was obtained, which was purified by chromatography ($SiO_2$, MeOH:$CHCl_3$:1N $NH_3$ in MeOH, 6:90:3) and precipitated by $CH_2Cl_2$/$Et_2O$ mixture. 2-(4-Azidobutyl)-5-carboxamido-1,4-dihydro-3-{N-[3-(4-methoxycarbonyl-4-phenylpiperidin-1-yl)propyl]} carboxamido-6-methyl-4-(4-nitrophenyl)pyridine was obtained as a yellowish powder (340 mg, 52%). M.p. 78–81° C.; calcd. for $C_{34}H_{42}N_8O_6 \cdot \frac{1}{2}Et_2O$: C 62.14, H 6.81, N 16.10; Found: C 62.42, H 6.33, N 15.85.

A solution of 2-(4-azidobutyl)-5-carboxamido-1,4-dihydro-3-{N-[3-(4-methoxycarbonyl-4-phenylpiperidin-1-yl) propyl]}carboxamido-6-methyl-4-(4-nitrophenyl) pyridine (150 mg, 0.23 mmol) in 5 ml of AcOEt was treated with 0.72 ml of 1M trimethylphosphine THF solution. The mixture was stirred at 0° C. for 1.5 hrs then 0.02 ml of water was added and the mixture was stirred at room temperature for an additional 1.5 hrs. After most volatile materials were removed in vacuo, residue was dissolved into 50 ml of AcOEt, washed with 6N KOH (50 ml) and brine (50 ml), then dried over $K_2CO_3$. After filtration and evaporation of solvent, product was precipitated by $CH_2Cl_2$/hexane mixture. 2-(4-Aminobutyl)-5-carboxamido-1,4-dihydro-3-{N-[3-(4-methoxycarbonyl-4-phenylpiperidin-1-yl) propyl]} carboxamido-6-methyl-4-(4-nitrophenyl)pyridine was obtained as a yellowish powder (110 mg, 76%). M.p. 81–84° C.; Calcd for $C_{34}H_{44}N_6O_6$: C 64.54, H 7.01, N 13.28; Found: C 64.29, H 6.87, N 13.22.

EXAMPLE 178

5-Acetyl-2-(4-aminobutyl)-1,4-dihydro-3-{N-[3-(4-methoxycarbonyl-4-phenylpiperidin-1-yl)propyl]} carboxamido-6-methyl-4-(4-nitrophenyl)pyridine (178). A solution of 5-acetyl-2-(4-azidobutyl)-1,4-dihydro-6-methyl-4-(4-nitrophenyl)pyridine-3-carboxylic acid (200 mg, 0.50 mmol), 1-(3-dimethylaminopropyl)-3-ethylcarbodiimide hydrochloride (192 mg, 1.00 mmol) and 4-dimethylaminopyridine (122 mg, 1.00 mmol) in 40 ml of $CH_2Cl_2$ was stirred at room temperature. After 1 hr, a solution of 3-(4-methoxycarbonyl-4-phenylpiperidin-1-yl)

propylamine (152 mg, 0.55 mmol) in 5 ml of $CH_2Cl_2$ was added and the mixture was stirred at reflux overnight. The mixture was washed with water (20 ml), saturated aqueous $NH_4Cl$ (3×20 ml), 10% $K_2CO_3$ (20 ml) and brine (20 ml). After dried over $Na_2SO_4$ and evaporation of solvent, a yellowish oil was obtained, which was purified by chromatography ($SiO_2$, MeOH:$CHCl_3$:1N $NH_3$ in MeOH, 6:90:3) and precipitated by $CH_2Cl_2$/hexane mixture.

A solution of 5-acetyl-2-(4-azidobutyl)-1,4-dihydro-3-{N-[3-(4-methoxycarbonyl-4-phenylpiperidin-1-yl) propyl]} carboxamido-6-methyl-4-(4-nitrophenyl)pyridine (118 mg, 0.18 mmol) in 5 ml of AcOEt was treated with 0.54 ml of 1M trimethylphosphine THF solution. The mixture was stirred at 0° C. for 1.5 hrs then 0.02 ml of water was added and the mixture was stirred at room temperature for an additional 1.5 hrs. After most volatile materials were removed in vacuo, residue was dissolved into 50 ml of AcOEt, washed with 6N KOH (50 ml) and brine (50 ml), then dried over $K_2CO_3$. After filtration and evaporation of solvent, product was precipitated by $CH_2Cl_2$/hexane mixture. 5-Acetyl-2-(4-aminobutyl)-1,4-dihydro-3-{N-[3-(4-methoxycarbonyl-4-phenylpiperidin-1-yl)propyl]} carboxamido-6-methyl-4-(4-nitrophenyl)pyridine was obtained as a yellowish powder (98 mg, 86%). M.p. 62–65° C.; Calcd for $C_{35}H_{45}N_5O_6$: C 66.54, H 7.18, N 11.09; Found: C 66.34, H 7.40, N 10.87.

EXAMPLE 179

4-Methoxycarbonyl-4-phenylpiperidine. To a stirred solution of $H_2SO_4$ (16 mL) in MeOH (400 mL), 4-phenyl-4-piperidinecarboxylic acid 4-methylbenzenesulfonate (37.7 g, 0.1 mole) was added and the mixture was stirred and refluxed for 8 hours. Excess methanol was evaporated at reduced pressure and the residue was poured into a mixture of ice and 6N NaOH. The pH was adjusted to 10–11 by adding more 6N NaOH and extracted with $CH_2Cl_2$ (3×150 mL). The combined $CH_2Cl_2$ extracts were dried ($MgSO_4$) and the solvent evaporated to leave the desired product as a viscous oil. The $^1$H-NMR showed it to be pure (20.2 g, 92%) and was used without any further purification.

3-(4-Methoxycarbonyl-4-phenylpiperidin-1-yl) propylamine. A mixture of 4-methoxycarbonyl-4-phenylpiperidine (8.5 g, 0.039 mol), 3-bromopropylamine hydrobromide (12.7 g, 0.058 mol), potassium carbonate (13.475 g, 0.0957 mole), and KI (3.24 g, 0.0195 mol) in 1,4-dioxane (200 mL) was stirred and refluxed for 24 hours. Dioxane was evaporated at reduced pressure, the residue was treated with ice-cold 6N NaOH (400 mL) and extracted with $CH_2Cl_2$ (4×120 mL). Solvent was evaporated from the combined dried ($K_2CO_3$) extracts and the residue was purified by column chromatography on silica gel using $CHCl_3$/MeOH/2M $NH_3$ in MeOH (20:2:1) as the eluent to afford the product as a viscous oil (7.8 g, 72%).

2,6-Diethyl-1,4-dihydro-3-{N-[3-(4-methoxycarbonyl-4-phenylpiperidin-1-yl)propyl]}carboxamido-5-(N-methyl) carboxamido-4-(4-nitrophenyl)pyridine (179). A mixture of 2,6-dihydro-5-(N-methyl-1,4-dihydro-5-(N-methyl) carboxamido-4-(4-nitrophenyl)pyridine-3-carboxylic acid (0.15 g, 0.417 mmol), 1-(3-dimethylaminopropyl)-3-ethylcarbodiimide hydrochloride (0.12 g, 0.626 mmol); 4-(N,N-dimethylamino)pyridine (0.056 g , 0.459 mmol), and 3-(4-methoxycarbonyl-4-phenylpiperidin-1-yl) propylamine (0.1268 g, 0.459 mmol) in $CH_2Cl_2$ (20 mL) was stirred and refluxed for 6 hours. The mixture was cooled to room temperature, diluted to 150 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (90:8:5) as the eluent to afford the product as a yellow powder (0.118 g, 46%); mp 86–87° C. Anal. Calcd for $C_{34}H_{43}N_5O_6 \cdot 0.8\ H_2O$: C, 64.60; H, 7.11; N, 11.08. Found: C, 64.63; H, 6.90; N, 10.98.

EXAMPLE 180

2,16-Diethyl-1,4-dihydro-5-(N-ethyl)carboxamido-3-{N-[3-(4-methoxycarbonyl-4-phenylpiperidin-1-yl) propyl]} carboxamido-4-(4-nitrophonyl)pyridine (180). A mixture of 2,6-diethyl-1,4-dihydro-5-(N-ethyl)carboxamido-4-(4-nitrophenyl)pyridine-3-carboxylic acid (0.1557 g, 0.417 mmol), 1-(3-dimethylaminopropyl)-3-ethylcarbodiimide hydrochloride (0.12 g, 0.626 mmol), 4-(N,N-dimethylamino)pyridine (0.056 g, 0.459 mmol), and 3-(4-methoxycarbonyl-4-phenylpiperidin-1-yl)propylamine (0.1268 g, 0.459 mmol) in $CH_2Cl_2$ (20 mL) was stirred and refluxed for 6 hours. The mixture was cooled to room temperature, diluted to 150 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (90:8:5) as the eluent to afford the product as a yellow powder (0.115 g, 43.7%); mp 217° C(d). Anal. Calcd for $C_{35}H_{45}N_5O_6 \cdot 0.1\ CHCl_3$: C, 65.49; H, 7.06; N, 10.88. Found: C, 65.23; H, 6.81; N, 10.65.

EXAMPLE 181

4-Ethoxycarbonyl-4-phenylpiperidine. To a stirred solution of $H_2SO_4$ (1.62 g, 16.56 mmol) in EtOH (200 mL), 4-phenyl-4-piperidinecarboxylic acid 4-methylbenzenesulfonate (25 g, 66.23 mmol) was added and the mixture was stirred and refluxed for 12 h. Excess ethanol was evaporated at reduced pressure and the residue was poured into a mixture of ice and 6N NaOH. The pH was adjusted to 10–11 by adding more 6N NaOH and extracted with $CH_2Cl_2$ (3×100 mL). The combined $CH_2Cl_2$ extracts were dried ($MgSO_4$) and the solvent evaporated to leave the desired product as a colorless viscous oil, the $^1$H-NMR showed it to be pure (14.68 g, 95%) and was used without any further purification.

3-(4-Ethoxycarbonyl-4-phenylpiperidin-1-yl) propylamine. A mixture of 4-ethoxycarbonyl-4-phenylpiperidine (30.5 g, 0.131 mol), 3-bromopropylamine hydrobromide (42.93 g, 0.196 mol), potassium carbonate (36.14 g, 0.241 mole), and KI (10.8 g, 0.065 mol) in 1,4-dioxane (500 mL) was stirred and refluxed for 24 hours. Dioxane was evaporated at reduced pressure, the residue was treated with ice-cold 6N NaOH (400 mL) and extracted with $CH_2Cl_2$ (4×120 mL). Solvent was evaporated from the combined dried ($K_2CO_3$) $CH_2Cl_2$ extracts and the residue was purified by column chromatography on silica gel using $CHCl_3$/MeOH/2M $NH_3$ in MeOH (20:2:1) as the eluent to afford the product as a viscous oil (24.2 g, 83.3%).

2,6-Diethyl-1,4-dihydro-3-{N-[3-(4-ethoxycarbonyl-4-phenylpiperidin- 1-yl)propyl]}carboxamido-5-(N-methyl) carboxamido-4-(4-nitrophenyl)pyridine (181). A mixture of 2,6-diethyl-1,4-dihydro-5-(N-methyl)carboxamido-4-(4-nitrophenyl)pyridine-3-carboxylic acid (0.15 g, 0.417 mmol), 1-(3-dimethylaminopropyl)-3-ethylcarbodiimide hydrochloride (0.12 g, 0.626 mmol), 4-(N,N-dimethylamino)pyridine (0.056 g, 0.459 mmol), and 3-(4-ethoxycarbonyl-4-phenylpiperidin-1-yl)propylamine (0.1333 g, 0.459 mmol) in $CH_2Cl_2$ (20 mL) was stirred and refluxed for 6 hours. The mixture was cooled to room temperature, diluted to 150 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (90:8:5) as the eluent to afford the product as a yellow powder (0.090 g, 34.2%); mp 95–97° C. Anal. Calcd for $C_{35}H_{45}N_5O_6 \cdot 0.8$ $CH_3OH$: C, 65.41; H, 7.39; N, 10.65. Found: C, 65.65; H, 7.11; N, 10.35.

EXAMPLE 182

2,6-Diethyl-1,4-dihydro-3-{N-[3-(4-Othoxycarbonyl-4-phenylpiperidin-1-yl)propyl]}carboxamido-5-(N-ethyl) carboxamido-4(4-nitrophenyl)pyridine (182). A mixture of 2,6-diethyl-1,4-dihydro-5-(N-ethyl)carboxamido-4-(4-nitrophenyl) pyridine-3-carboxylic acid (0.1557 g, 0.417 mmol), 1-(3-dimethylaminopropyl)-3-ethylcarbodiimide hydrochloride (0.12 g, 0.626 mmol), 4-(N,N-dimethylamino)pyridine (0.056 g, 0.459 mmol), and 3-(4-ethoxycarbonyl-4phenylpiperidin-1-yl)propylamine (0.1333 g, 0.459 mmol) in $CH_2Cl_2$ (20 mL) was stirred and refluxed for 6 hours. The mixture was cooled to room temperature, diluted to 150 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (90:8:5) as the eluent to afford the product as a yellow powder (0.115 g, 43%); mp 103–104° C. Anal. Calcd for $C_{36}H_{47}N_5O_6 \cdot 1.0$ $H_2O$: C, 65.14; H, 7.44; N, 10.55. Found: C, 65.02; H, 7.25; N, 10.42.

EXAMPLE 183

2-[(2-Azidoethoxy)methyl]-5-carboxamido-1,4-dihydro-3-{N-[3-(4-methoxycarbonyl-4-phenylpiperidin-1-yl) propyl]}carboxamido-6-methyl-4-($_4$-nitrophenyl)pyridine (183). A mixture of 2-[(2-azidoethoxy)methyl]-5-carboxamido-1,4-dihydro-6-methyl-4-(4-nitrophenyl) pyridine-3-carboxylic acid (0.15 g, 0.373 mmol), DCC (0.1539 g, 0.746 mmol), 4-(N,N-dimethylamino)pyridine (0.050 g 0.410 mmol), and 3-(4-methoxycarbonyl-4-phenylpiperidin-1-yl)propylamine (0.1237 g, 0.447 mmol) in $CH_2Cl_2$ (20 mL) was stirred and refluxed for 6 h. The mixture was cooled to room temperature, diluted to 150 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/ 2M $NH_3$ in MeOH (100:3:1.5) as the eluent to afford the product as a yellow powder (0.208 g, 84.5%); mp 71–72° C. Anal. Calcd for $C_{33}H_{40}N_8O_7 \cdot 1.2$ $H_2O$: C, 58.09; H, 6.26; N, 16.42. Found: C, 58.31; H, 6.25; N, 16.16.

EXAMPLE 184

2-[(2-Azidoethoxy)methyl]-5-carboxamido-1,4-dihydro-3-{N-[3-(4-(4-methoxyphenyl)-4-phenylpiperidin-1-yl) propyl]}carboxamido-6-methyl-4-(4-nitrophenyl)pyridine (184). A mixture of 2-[(2-azidoethoxy)methyl]-5-carboxamido-1,4-dihydro-6-methyl4-(4-nitrophenyl) pyridine-3 -carboxylic acid (0.15 g, 0.373 mmol), DCC (0.1539 g, 0.746 mmol), 4-(N,N-dimethylamino)pyridine (0.050 g, 0.410 mmol), and 3-{4-(4-methoxyphenyl)-4-phenylpiperidin-1yl}propylamine (0.1452 g, 0.448 mmol) in $CH_2Cl_2$ (20 mL) was stirred and refluxed for 6 hours. The mixture was cooled to room temperature, diluted to 150 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/ 2M $NH_3$ in MeOH (100:3:1.5) as the eluent to afford the product as a yellow powder (0.214 g, 81%); mp 105–107° C. Anal. Calcd for $C_{38}H_{44}N_8O_6 \cdot 0.62$ $CHCl_3$: C, 59.26; H, 5.74; N, 14.31. Found: C, 59.21; H, 5.93; N, 14.31.

EXAMPLE 185

2-[ (2-Aminoethoxy)methyl]-5-carboxamido-1,4-dihydro-3-{N-[3-(4-methoxycarbonyl-4-phenylpiperidin-1-yl)propyl]}carboxamido-6-methyl-4-(4-nitrophenyl) pyridine (185). To a stirred solution of 2-[(2-azidoethoxy) methyl]-5-carboxamido-1,4-dihydro-3-{N-[3-(4-methoxycarbonyl-4-phenylpiperidinl-yl)propyl]} carboxamido-6-methyl-4-(4-nitrophenyl)pyridine (0.165 g, 0.249 mmol) in EtOAc (5 mL) at 0° C. a solution of trimethylphosphine in THF (1M, 0.62 mL, 0.62 mmol) was added and stirred for 10 minutes. Water (0.022 mL, 1.249 mmol) was added and the mixture was allowed to warm to room temperature. After 3 hours, solvents were evaporated and the residue was purified by column chromatography on silica gel using $CHCl_3$/MeOH/2M $NH_3$ in MeOH (10:2:1) as the eluent to afford the product as a yellow powder (0.075 g, 53%); mp 121–122° C. Anal. Calcd for $C_{33}H_{42}N_6O_7 \cdot 0.66$ $CHCl_3 \cdot 0.66$ $H_2O$: C, 55.73; H, 6.11; N, 11.59. Found: C, 55.44; H, 6.31; N, 11.88.

EXAMPLE 186

2-[(2-Aminoethoxy)methyl]-5-carboxamido-1,4-dihydro-3-{-N-[3-(4-(4-methoxyphenyl)-4-phenylpiperidin-1-yl)propyl]}carboxamido-6-methyl-4-(4-nitrophenyl)pyridine (186). To a stirred solution of 2-[(2-azidoethoxy)methyl]-5-carboxamido-1,4-dihydro-3-{N-[3-(4-(4-methoxyphenyl)-4-phenylpiperidin-1-yl)propyl]} carboxamido-6-methyl-4-(4-nitrophenyl)pyridine (0.17 g, 0.239 mmol) in EtOAc (5 mL) at 0° C. a solution of trimethylphosphine in THF (1M, 0.6 mL, 0.6 mmol) was added and stirred for 10 minutes. Water (0.022 mL, 1.249 mmol) was added and the mixture was allowed to warm to room temperature. After 3 hours, solvents were evaporated and the residue was purified by column chromatography on silica gel using $CHCl_3$/MeOH/2M $NH_3$ in MeOH (10:2:1) as the eluent to afford the product as a yellow powder (0.080 g, 49%); mp 141–142° C. Anal. Calcd for $C_{38}H_{46}N_6O_6 \cdot 0.9$ $CHCl_3 \cdot 0.9NH_4Cl$: C, 55.72; H, 6.07; N, 11.52. Found: C, 55.68; H, 6.22; N, 11.31.

EXAMPLE 187

4-Dihydro-2,6-dimethyl-3-{N-[3-(4-methoxycarbonyl-4-phenylpiperidin-1-yl)propyl]}carboxamido-5-(N-methyl) carboxamido-4-(4nitrophenyl)pyridine (187). A mixture of 1,4-dihydro-2,6-dimethyl-5-(N-methyl)carboxamido-4-(4-nitrophenyl)pyridine-3-carboxylic acid (0.4839 g, 1.46 mmol), 1-(3-dimethylaminopropyl)-3-ethylcarbodiimide hydrochloride (0.5598 g, 2.92 mmol), 4-(N,N-dimethylamino)pyridine (0.2675 g, 2.19 mmol), and 3-(4-methoxycarbonyl-4-phenylpiperidin-1-yl)propylamine (0.444 g, 1.607 mmol) in $CH_2Cl_2$ (40 mL) was stirred and refluxed for 6 hours. The mixture was cooled to room temperature, diluted to 150 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (100:4:2)

as the eluent to afford the product as a yellow powder (0.605 mg, 70.3%); mp 122–123° C. Anal. Calcd for $C_{32}H_{39}N_5O_6 \cdot 0.3\ C_4H_{10}O \cdot 0.9\ H_2O$: C, 63.48; H, 7.03; N, 11.15. Found: C, 63.76; H. 7.28; N, 11.31.

EXAMPLE 188

1,4-Dihydro-2,6-dimethyl-3-{N -[3-4-ethoxycarbonyl-4-phenylpiperidin-1-yl)propyl]}carboxamido-5-(N-methyl)carboxamido-4-(4nitrophenyl)pyridine (188). A mixture of 1,4-dihydro-2,6-dimethyl-5-(N-methyl)carboxamido-4-(4-nitrophenyl) pyridine-3-carboxylic acid (0.450 g, 1.36 mmol), 1-(3-dimethylaminopropyl)-3-ethylcarbodiimide hydrochloride (0.5207 g, 2.72 mmol), 4-(N,N-dimethylamino)pyridine (0.2859 g, 2.34 mmol), and 3-(4-ethoxycarbonyl-4-phenylpiperidin-1-yl)propylamine (0.473 g, 1.63 mmol) in $CH_2Cl_2$ (40 mL) was stirred and refluxed for 6 hours. The mixture was cooled to room temperature, diluted to 210 mL with $CH_2Cl_2$, washed with saturated $NH_4Cl$ solution (3×30 mL), and dried ($MgSO_4$). Solvent was evaporated from the $CH_2Cl_2$ solution and the product was purified by flash column chromatography on silica gel using $CHCl_3/MeOH/2M\ NH_3$ in MeOH (100:3.5:1.75) as the eluent to afford the product as a yellow powder (0.600 g, 73%); mp 112–113° C. Anal. Calcd for $C_{33}H_{41}N_5O_6 \cdot 0.075\ C_6H_{12} \cdot 0.75\ H_2O$: C, 64.43; H, 7.02; N, 11.23. Found: C, 64.29; H, 7.04; N, 10.95.

EXAMPLE 189

2-[(2-Azidoethoxy)methyl]-5-(2-cyanoethoxycarbonyl)-3-{N-3-(4-ethoxycarbonyl-4-phenylpiperidin-1-yl) propyl]} carboxamido- 1,4-dihydro-6-ethyl-4-(4-nitrophenyl)pyridine. A mixture of 2-[(2-azidoethoxy)methyl]-5-(2-cyanoethoxycarbonyl)-1,4-dihydro-6-ethyl-4-(4-nitrophenyl)pyridine-3-carboxylic acid (1.06 g, 2.25 mmol), 1-(3-dimethylaminopropyl)-3-ethylcarbodiimide hydrochloride (0.864 g, 4.507 mmol), 4-(N,N-dimethylamino) pyridine (0.550 g, 4.507 mmol), and 3-(4-ethoxycarbonyl-4-phenylpiperidin-1-yl)propylamine (0.784 g, 2.7 mmol) in $CH_2Cl_2$ (20 mL) was stirred and refluxed for 6 hours. The mixture was cooled to room temperature, diluted to 150 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3/MeOH/2M\ NH_3$ in MeOH (100:3:1.5) as the eluent to afford the product as a yellow powder (1.24 g, 74%). The $^1$H-NMR showed this product to be pure and was used in the subsequent step without any further purification.

2-[(2-Azidoethoxy)methyl]-3-{N-[3-(4-ethoxycarbonyl-4-phenylpiperidin-1-yl)propyl]}carboxamido-1,4-dihydro-6-ethyl-4-(4-nitrophenyl)pyridine-5-carboxylic Acid (189). 🔲 a well-stirred solution of 2-[(2-azidoethoxy)methyl]-5-(2-cyanoethoxycarbonyl)-3-{N-[3-(4-ethoxycarbonyl-4-phenylpiperidin-1-yl)propyl]}carboxamido-1,4-dihydro-6-ethyl-4-(4-nitrophenyl)pyridine (1.29 g, 1.74 mmol) in dioxane (25 mL) at 0° C., aqueous 1N NaOH (5.21 mL, 5.21 mmol) was added and the stirring was continued. After 30 min, solvent was evaporated at reduced pressure at 0° C. and to the residue 1N HCl was added to adjust the pH to 6–7. The yellow precipitate formed was filtered and dried under vacuum. The filtrate was extracted with $CH_2Cl_2$ (10 mL), dried ($MgSO_4$) and the solvent evaporated. The combined yield was 1.18 g (96.7%); mp 109–110° C. Anal. Calcd for $C_{35}H_{43}N_7O_8 \cdot 0.4\ C_4H_8O_2 \cdot 0.6NaCl$: C, 57.82; H, 6.13; N, 12.90. Found: C, 7.66; H, 6.19; N, 12.70.

EXAMPLE 190

2-[(2-Azidoethoxy)methyl]-5-carboxamido-3-{N-[3-(4-ethoxycarbonyl-4-phenylpiperidin-1-yl)propyl]} carboxamido-1,4-dihydro-6-ethyl-4-(4-nitrophenyl)pyridine (190). A mixture of 2-[(2-azidoethoxy)methyl]-3-3-{N-[3-(4-ethoxycarbonyl-4-phenylpiperidinl-yl)propyl]} carboxamido-1,4-dihydro-6-ethyl-4-(4-nitrophenyl) pyridine-5-carboxylic acid (0.10 g, 0.145 mmol), 1-(3-dimethylaminopropyl)-3-ethylcarbodiimide hydrochloride (0.056 g, 0.29 mmol), 4-(N,N-dimethylamino)pyridine (0.0354 g, 0.29 mmol), and 40% aqueous $NH_3$ (0.064 g, 0.725 mmol) in $CH_2Cl_2$ (20 mL) was stirred overnight. The reaction mixture was diluted to 170 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3/MeOH/2M\ NH_3$ in MeOH (100:4:2) as the eluent to afford the product as a yellow powder (0.083 g, 83%); mp 63–64° C. Anal. Calcd for $C_{35}H_{44}N_8O_7 \cdot 0.3\ C_6H_{12} \cdot 0.5\ H_2O$:C, 60.53; H, 6.82; N, 15.34. Found: C, 60.69; H, 6.65; N, 15.08.

EXAMPLE 191

2-[(2-Azidoethoxy)methyl]-3-{N-[3-(4-ethoxycarbonyl-4-phenyl-piperidin-1-yl)propyl]}carboxamido-1,4-dihydro-6-ethyl-5-(N-methyl)carboxamido-4-(4-nitrophenyl) pyridine (191). A mixture of 2-[(2-azidoethoxy)methyl]-3-{N-[3-(4-ethoxycarbonyl-4-phenylpiperidin-1-yl)propyl]} carboxamido-1,4-dihydro-6-ethyl-4-(4-nitrophenyl) pyridine-5-carboxylic acid (0.10 g, 0.145 mmol), 1-(3-dimethylaminopropyl)-3 -ethylcarbodiimide hydrochloride (0.056 g, 0.29 mmol), 4-(N,N-dimethylamino)pyridine (0.0354 g, 0.29 mmol), and aqueous 40% methylamine (0.0563 g, 0.725 mmol) in $CH_2Cl_2$ (20 mL) was stirred overnight. The reaction mixture was diluted to 170 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3/MeOH/2M\ NH_3$ in MeOH (100:4:2) as the eluent to afford the product as a yellow powder (0.086 g, 84.4%); mp 67–68° C. Anal. Calcd for $C_{36}H_{46}N_8O_7 \cdot 0.4\ H_2O$:C, 60.90; H, 6.64; N, 15.78. Found: C, 60.95; H, 6.42; N, 15.42.

EXAMPLE 192

2-[(2-Aminoethoxy)methyl]-3-{N-[3-(4-ethoxycarbonyl-4-phenylpiperidin-1-yl)propyl]}carboxamido-1,4-dihydro-6-ethyl-5-(N-ethyl)carboxamido-4-(4-nitrophenyl)pyridine (192). A mixture of 2-[(2-azidoethoxy)methyl]-3-{N-[3-4-ethoxycarbonyl-4-phenylpiperidin-1-yl)propyl]} carboxamido-1,4-dihydro-6-ethyl-4-(4-nitrophenyl) pyridine-5-carboxylic acid (0.10 g, 0.145 mmol), 1-(3-dimethylaminopropyl)-3-ethylcarbodiimide hydrochloride (0.056 g, 0.29 mmol), 4-(N,N-dimethylamino)pyridine (0.0354 g, 0.29 mmol), and aqueous 70% methylamine (0.0373 g, 0.58 mmol) in $CH_2Cl_2$ (20 mL) was stirred overnight. The reaction mixture was diluted to 170 mL with $CH_2Cl_2$, washed with saturated $NH_4Cl$ solution (3×40 mL), and dried ($MgSO_4$). Solvent was evaporated from the $CH_2Cl_2$ solution, the residue was redissolved in EtOAc (5 mL) and cooled to 0° C. To this, a solution of trimethylphosphine in THF (1M, 0.32 mL, 0.32 mmol) was added and stirred for 10 minutes. Water (0.0095 mL, 0.53 mmol) was added and the mixture was allowed to warm to room temperature. After 3 hours, solvents were evaporated and the residue was purified by column chromatography on silica gel using $CHCl_3/MeOH/2M\ NH_3$ in MeOH (18:2:1) as the eluent to afford the product as a yellow powder (0.091 g, 91%); mp 112–114° C. Anal. Calcd for $C_{37}H_{50}N_6O_8 \cdot 0.18$ $C_6H_{14}$·1.8 $H_2O$:C, 61.94; H, 7.61; N, 13.38. Found: C, 61.97; H, 7.59; N, 11.19.

EXAMPLE 193

2-[(2-Aminoethoxy)methyl]-5-carboxamido-3-{N-[3-(4-ethoxycarbonyl-4-phenylpiperidin-1-yl)propyl]}carboxamido-1,4-dihydro-6-ethyl-4-(4-nitrophenyl)pyridine (193). To a stirred solution of 6-ethyl-1,4-dihydro-2-[(2-azidoethoxy)methyl]-5-carboxamido-3-{N-[3-(4-ethoxycarbonyl-4-phenylpiperidin-1-yl)propyl]}carboxamido-4-(4-nitrophenyl)pyridine (0.073 g, 0.106 mmol) in EtOAc (5 mL) at 0° C. a solution of trimethylphosphine in THF (1M, 0.32 mL, 0.32 mmol) was added and stirred for 10 minutes. Water (0.0095 mL, 0.53 mmol) was added and the mixture was allowed to warm to room temperature.

After 3 hours, solvents were evaporated and the residue was purified by column chromatography on silica gel using $CHCl_3$/MeOH/2M $NH_3$ in MeOH (25:4:2) as the eluent to afford the product as a yellow powder (0.027 g, 38.4%); mp 87–89° C. Anal. Calcd for $C_{35}H_{46}N_6O_7$·0.4 $CHCl_3$: C, 59.84; H, 6.58; N, 11.83. Found: C, 59.74; H, 6.85; N, 11.56.

EXAMPLE 194

2-[(2-Aminoethoxy)methyl]-3-{N-[3-(4-ethoxycarbonyl-4-phenylpiperidin-1-yl)propyl]}carboxamido-1,4-dihydro-6-ethyl-5-(N-methyl)carboxamido-4-(4-nitrophenyl)pyridine (194). To a stirred solution of 2-[(2-azidoethoxy)methyl]-3-{N-[3-(4-ethoxycarbonyl-4-phenylpiperidin-1-yl)propyl]}carboxamido-1,4-dihydro- 6-ethyl-5-(N-methyl)carboxamido-4-(4-nitrophenyl)pyridine (0.076 g, 0.108 mmol) in EtOAc (5 mL) at 0° C. a solution of trimethylphosphine in THF (1M, 0.32 mL, 0.32 mmol) was added and stirred for 10 minutes. Water (0.0095 mL, 0.53 mmol) was added and the mixture was allowed to warm to room temperature. After 3 hours, solvents were evaporated and the residue was purified by column chromatography on silica gel using $CHCl_3$/MeOH/2M $NH_3$ in MeOH (25:4:2) as the eluent to afford the product as a yellow powder (0.018 g, 24.6%); mp 51–53° C. Anal. Calcd for $C_{36}H_{48}N_6O_7$·0.12 $C_6H_{12}$·1.2$H_2O$: C, 62.25; H, 7.37; N, 11.86. Found: C, 62.02; H, 7.12; N, 11.58.

EXAMPLE 195

2-[(2-Azidoethoxy)methyl]-3-{N-[3-(4-ethoxycarbonyl-4-phenylpiperidin-1-yl)propyl]}carboxamido-1,4-dihydro-6-ethyl-5-methoxycarbonyl-4-(4-nitrophenyl)pyridine (195). A mixture of 2-[(2-azidoethoxy)methyl]-3-{N-[3-(4-ethoxycarbonyl-4-phenylpiperidin-1-yl)propyl]}carboxamido-1,4-dihydro-6-ethyl-4-(4-nitrophenyl)pyridine-5-carboxylic acid (0.10 g, 0.145 mmol), 1-(3-dimethylaminopropyl)-3-ethylcarbodiimide hydrochloride (0.056 g, 0.29 mmol), 4-(N,N-dimethylamino)pyridine (0.0354 g, 0.29 mmol), and methanol (0.046 g, 1.45 mmol) in $CH_2Cl_2$ (10 mL) was stirred and refluxed for 12 hours. The reaction mixture was diluted to 160 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (100:2:1) as the eluent to afford the product as a yellow powder (0.082 g, 80.4%); mp 56–57° C. Anal. Calcd for $C_{36}H_{45}N_7O_8$·0.54 $CHCl_3$: C, 57.13; H, 5.97; N, 12.76. Found: C, 57.39; H, 6.14; N, 12.41.

EXAMPLE 196

2-[(2-Aminoethoxy)methyl]-3-{N-[3-(4-ethoxycarbonyl-4-phenylpiperidin-1-yl)propyl]}carboxamido-1,4-dihydro-6-ethyl-4-(4-nitrophenyl)pyridine-5-carboxylic Acid (196). To a stirred solution of 2-[(2-azidoethoxy)methyl]-3-{N-[3-4-ethoxycarbonyl-4-phenylpiperidin-1-yl) propyl]}carboxamido-1,4-dihydro-6-ethyl-4-(4-nitrophenyl)pyridine-5-carboxylic acid (0.050 g, 0.0725 mmol) in EtOAc (5 mL) at 0° C. a solution of trimethylphosphine in THF (1M, 0.217 mL, 0.217 mmol) was added and stirred for 10 minutes. Water (0.0095 mL, 0.53 mmol) was added and the mixture was allowed to warm to room temperature. After 3 h, solvents were evaporated and the residue was purified by column chromatography on silica gel using $CHCl_3$/MeOH/2M $NH_3$ in MeOH (25:4:2) as the eluent to afford the product as a yellow powder (0.018 g, 37.4%); mp 103–105° C. Anal. Calcd for $C_{35}H_{45}N_5O_8$·0.35 $CHCl_3$: C, 60.18; H, 6.48; N, 9.93. Found: C, 60.08; H, 6.42; N, 10.07.

EXAMPLE 197

2-[(2-Aminoethoxy)methyl]-3-{N-[3-(4-ethoxycarbonyl-4-phenylpiperidin-1-yl)propyl]}carboxamido-1,4-dihydro-6-ethyl-5-methoxycarbonyl-4-(4-nitrophenyl)pyridine (197). To a stirred solution of 2-[(2-azidoethoxy)methyl]-3-{N-[3-(4-ethoxycarbonyl-4-phenylpiperidin-1-yl) propyl]}carboxamido-1,4-dihydro-6-ethyl-5-methoxycarbonyl-4-(4-nitrophenyl)pyridine (0.092 g, 0.13 mmol) in EtOAc (5 mL) at 0° C. a solution of trimethylphosphine in THF (1 M, 0.65 mL, 0.65 mmol) was added and stirred for 10 minutes. Water (0.047 mL, 2.6 mmol) was added and the mixture was allowed to warm to room temperature. After 3 hours, solvents were evaporated and the residue was purified by column chromatography on silica gel using $CHCl_3$/MeOH/2M $NH_3$ in MeOH (25:4:2) as the eluent to afford the product as a yellow powder (0.020 g, 22.7%); mp 45–47° C. Anal. Calcd for $C_{36}H_{47}N_5O_8$·0.8 $H_2O$: C, 62.47; H, 7.08; N, 10.12. Found: C, 62.58; H, 7.01; N, 9.86.

EXAMPLE 198

5-Carboxamido-1,4-dihydro-2,6-dimethyl-3-{N-[3-(4-methoxycarbonyl-4-phenylpiperidin-1-yl)propyl]}carboxamido-4-(4-nitrophenyl)pyridine (198). A mixture of 5-carboxamido-1,4-dihydro-2,6-dimethyl-4-(4-nitrophenyl)pyridine-3-carboxylic acid (0.60 g, 1.89 mmol), 1-(3-dimethylaminopropyl)-3-ethylcarbodiimide hydrochloride (0.725 g, 3.78 mmol), 4-(N,N-dimethylamino)pyridine (0.462 g, 3.78 mmol), and 3-(4-methoxycarbonyl-4-phenylpiperidin-1-yl)propylamine (0.679 g, 2.457 mmol) in $CH_2Cl_2$ (40 mL) was stirred and refluxed for 6 hours. The mixture was cooled to room temperature, diluted to 190 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (100:4:2) as the eluent to afford the product as a yellow powder (0.730 g, 67%); mp 120–121° C. Anal. Calcd for $C_{31}H_{37}N_5O_6$·0.7 $C_6H_{12}$·1.05 $H_2O$: C, 64.70; H, 7.33; N, 10.72. Found: C, 64.71; H, 7.25; N, 10.50.

EXAMPLE 199

5-Carboxamido-1,4-dihydro-21 6-dimethyl-3-{N-[3-(4-ethoxycarbonyl-4-phenylpiperidin-1-yl)propyl]}carboxamido-4-(4-nitrophenyl)pyridine (199). A mixture of 5-carboxamido-1,4-dihydro-2,6-dimethyl-4-(4-nitrophenyl)pyridine-3-carboxylic acid (0.60 g, 1.89 mmol), 1-(3-dimethylaminopropyl)-3-ethylcarbodiimide hydrochloride (0.725 g, 3.78 mmol), 4-(N,N-dimethylamino)pyridine (0.462 g, 3.78 mmol), and 3-(4-ethoxycarbonyl-4-phenylpiperidin-1-yl)propylamine (0.714 g, 2.46 mmol) in $CH_2Cl_2$ (40 mL) was stirred and refluxed for 6 hours. The mixture was cooled to room temperature, diluted to 190 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/ 2M $NH_3$ in MeOH (100:4:2) as the eluent to afford the product as a yellow powder (0.660 g, 59.3%); mp 118–120° C. Anal. Calcd for $C_{32}H_{32}N_5O_6 \cdot 0.5\ C_6H_{12} \cdot 0.5\ H_2O$: C, 65.61; H, 7.24; N, 10.93. Found: C, 65.67; H, 7.25; N, 10.69.

EXAMPLE 200

5-Carboxamido-1,4-dihydro-2,6-diethyl-3-{N-[3-(4-methoxycarbonyl4-phenylpiperidin-1-yl)propyl]}carboxamido-4-(4-nitrophenyl)pyridine (200). A mixture of 5-carboxamido-1,4-dihydro-2,6-diethyl-4-(4-nitrophenyl)pyridine-3-carboxylic acid (0.80 g, 2.415 mmol), 1-(3-dimethylaminopropyl)-3-ethylcarbodiimide hydrochloride (0.926 g, 4.289 mmol), 4-(N,N-dimethylamino)pyridine (0.524 go 4.289 mmol), and 3-(4-methoxycarbonyl-4-phenylpiperidin-1-yl) propylamine (0.80 g, 2.898 mmol) in $CH_2Cl_2$ (40 mL) was stirred and refluxed for 6 h. The mixture was cooled to room temperature, diluted to 190 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (100:4:2) as the eluent to afford the product as a yellow powder (0.950 g, 70%); mp 112–114° C. Anal. Calcd for $C_{33}H_{41}N_5O_6 \cdot 0.37\ C_4H_{10}O \cdot 0.41\ H_2O$: C, 64.86; H, 7.18; N, 10.97. Found: C, 65.13; H, 7.09; N, 10.68.

EXAMPLE 201

5-Acetyl-1,4-dihydro-2,6-dimethyl-3-{N-[3-(4-methoxycarbonyl-4-phenylpiperidin-1-yl)propyl]} carboxamido-4-(4-nitrophenyl)pyridine (201). A mixture of 5-acetyl-1,4-dihydro-2,6-dimethyl-4-(4-nitrophenyl) pyridine-3-carboxylic acid (0.70 g, 2.21 mmol), 1-(3-dimethylaminopropyl)-3-ethylcarbodiimide hydrochloride (0.849 g, 4.43 mmol), 4-(N,N-dimethylamino)pyridine (0.541 g, 4.43 mmol), and 3-(4-methoxycarbonyl-4-phenylpiperidin-1-yl)propylamine (0.732 g, 2.65 mmol) in $CH_2Cl_2$ (40 mL) was stirred and refluxed for 6 hours. The mixture was cooled to room temperature, diluted to 190 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/ 2M $NH_3$ in MeOH (100:4:2) as the eluent to afford the product as a yellow powder (0.880 g, 70%); mp 94–95° C. Anal. Calcd for $C_{32}H_{38}N_4O_6 \cdot 0.4\ H_2O$: C, 66.11; H, 6.72; N, 9.63. Found: C, 65.93; H, 6.55; N, 9.53.

EXAMPLE 202

5-Acetyl-1,4-dihydro-2,6-dimethyl-3-{N-[3-(4-ethoxycarbonyl-4-phenylpiperidin-1-yl)propyl]}carboxamido-4-(4-nitrophenyl)pyridine (202). A mixture of 5-acetyl-1,4-dihydro-2,6-dimethyl-4-(4-nitrophenyl) pyridine-3-carboxylic acid (0.70 g, 2.21 mmol), 1-(3-dimethylaminopropyl)-3-ethylcarbodiimide hydrochloride (0.849 g, 4.43 mmol), 4-(N,N-dimethylamino)pyridine (0.541 g, 4.43 mmol), and 3-(4-ethoxycarbonyl-4-phenylpiperidin-1-yl)propylamine (0.770 g, 2.65 mmol) in $CH_2Cl_2$ (40 mL) was stirred and refluxed for 6 hours. The mixture was cooled to room temperature, diluted to 190 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/ 2M $NH_3$ in MeOH (100:4:2) as the eluent to afford the product as a yellow powder (0.890 g, 68.4%); mp 87–88° C. Anal. Calcd for $C_{33}H_{40}N_4O_6 \cdot 0.6\ H_2O$: C, 66.11; H, 6.93; N, 9.35. Found: C, 65.95; H, 6.84; N, 9.22.

202 (−) and 202 (+):

(−)-5-Acetyl-1,4-dihydro-2,6-dimethyl-3-{N-[3-4-ethoxycarbonyl-4-phenylpiperidin-1-yl)propyl]}carboxamido-4-(4-nitrophenyl)pyridine and(+)-5-Acetyl-1,4-dihydro-2,6-dimethyl-3-{N-[3-(4-ethoxycarbonyl-4-phenylpiperidin-1-yl) propyl]}carboxamido-4(4-nitrophenyl)pyridine. Racemic 5-acetyl-1,4-dihydro-2,6-dimethyl-3-{N-[3-(4-ethoxycarbonyl-4-phenylpiperidin-1-yl)propyl]}carboxamido-4-(4-nitrophenyl)pyridine was separated on a chiral HPLC column Chiralpak AS (20×250 mm) as follows: The column was pre-equilibrated with 10% EtOH in hexane at 40° C. with an isocratic elution of 9 mL/minutes. The racemate (ca 20 mg) was dissolved in 1:2 ethanol/hexane (10 mL) and injected. Ten injections were made to obtain about 100 mg of each enantiomers. The first enantiomer to elute was the (−)-enantiomer (retention time, about 43 to 49 min) and the second major peak accounted for the (+)-enantiomer (retention time, about 57–67 min). Solvents were evaporated and the products were dried under vacuum. (−)-enantiomer: $[a]_D = -151.24$ (MeOH, 1.45 g/100 mL); mp 89–90° C. Anal. Calcd for $C_{33}H_{40}N_4O_6$: C, 67.33; H, 6.85; N, 9.52. Found: C, 67.12; H, 6.87; N, 9.33.

(+)-enantiomer: $[a]_D = +146.5$ (MeOH, 1.40 g/100 mL); mp 89–90° C. Anal. Calcd for $C_{33}H_{40}N_4O_6$: C, 67.33; H, 6.85; N, 9.52. Found: C, 67.09; H, 6.68; N, 9.33.

EXAMPLE 203

5-(2-Cyanoethoxycarbonyl)-1,4-dihydro-2,6-dimethyl-3-{N-[3-(4-methoxycarbonyl-4-phenylpiperidin-1-yl) propyl]} carboxamido-4-(4-nitrophenyl)pyridine (203). A mixture of 5-(2-cyanoethoxycarbonyl)-1,4-dihydro-2,6-dimethyl-4-(4-nitrophenyl)pyridine-3-carboxylic acid (1.568 g, 4.22 mmol), 1-(3-dimethylaminopropyl)-3-ethylcarbodiimide hydrochloride (1.62 g, 8.44 mmol), 4-(N,N-dimethylamino)pyridine (1.03 g, 8.44 mmol), and 3-(4-methoxycarbonyl-4-phenylpiperidin-1-yl)propylamine (1.40 g, 5.066 mmol) in $CH_2Cl_2$ (100 mL) was stirred and refluxed for 6 hours. The mixture was cooled to room temperature, diluted to 200 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (1.76 g, 66%); mp 73–74° C. Anal. Calcd for $C_{34}H_{39}N_5O_7 \cdot 0.25\ CH_2Cl_2 \cdot 1.25\ H_2O$: C, 61.59; H, 6.26; N, 10.43. Found: C, 61.23; H, 6.05; N, 10.21.

EXAMPLE 204

1,4-Dihydro-2,6-dimethyl-3-{N-[3-(4-methoxycarbonyl-4-phenylpiperidin-1-yl)propyl]}carboxamido-4-(4-nitrophenyl)pyridine-5-carboxylic acid (204). To a well-stirred solution of 5-(2-cyanoethoxycarbonyl)-1,4-dihydro-2,6-dimethyl-3-{N-[3-4-methoxycarbonyl-4-phenylpiperidin-1-yl)propyl]}carboxamido-4-(4-nitrophenyl)pyridine (1.70 g, 2.70 mmol) in dioxane (15 mL) at 0° C., aqueous 1N NaOH (5.4 mL) was added and the stirring was continued. After 30 min, most of the solvent was evaporated under reduced pressure and residue was treated with ice-cold 1N HCl to adjust the pH to 6–7. The yellow precipitate formed was filtered and dried under vacuum (1.35 g, 86%); mp 139–141° C. Anal. Calcd for $C_{31}H_{37}N_4O_7 \cdot 0.4\ CHCl_3 \cdot 1.6\ H_2O$: C, 57.74; H, 6.11; N, 8.58. Found: C, 57.98; H, 6.31; N, 10.41.

EXAMPLE 205

1,4-Dihydro-2,6-dimethyl-5-(N-ethyl)carboxamido-3-{N-[3-(4-methoxycarbonyl-4-phenylpiperidin-1-yl)propyl]}carboxamido-4-(4-nitrophenyl)pyridine (205). A mixture of 1,4-dihydro-2,6-dimethyl-3{N-[3-(4-methoxycarbonyl-4-phenylpiperidin-1-yl)propyl]}carboxamido-4-(4-nitrophenyl)pyridine-5-carboxylic acid (0.70 g, 1.222 mmol), 1-(3-dimethylaminopropyl)-3-ethylcarbodiimide hydrochloride (0.469 g, 2.445 mmol), 4-(N,N-dimethylamino)pyridine (0.299 g, 2.445 mmol), and 70% aqueous ethylamine (0.275 g, 4.277 mmol) in $CH_2Cl_2$ (40 mL) was stirred at room temperature for 14 hours, diluted to 150 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (100:4:2) as the eluent to afford the product as a yellow powder (0.36 g, 41.5%); mp 117–118° C. Anal. Calcd for $C_{33}H_{41}N_5O_6 \cdot 0.25\ C_6H_{12} \cdot 0.05\ CH_2Cl_2 \cdot 0.25\ H_2O$: C, 65.51; H, 7.10; N, 11.05. Found: c, 65.66; H, 7.34; N, 10.75.

EXAMPLE 206

1,4-Dihydro-2,6-dimethyl-5-methoxycarbonyl-3-{N-[3-(4-methoxycarbonyl-4-phenylpiperidin-1-yl)propyl]}carboxamido-4-(4-nitrophenyl)pyridine (206). A mixture of 1,4-dihydro-2,6-dimethyl-3-{N[3 (4-methoxycarbonyl-4-phenylpiperidin-1-yl)propyl]}carboxamido-4-(4-nitrophenyl)pyridine-5-carboxylic acid (0.10 g, 0.174 mmol), 1-(3-dimethylaminopropyl)-3-ethylcarbodiimide hydrochloride (0.0666 g, 0.347 mmol), 4-(N,N-dimethylamino)pyridine (0.0424 g, 0.347 mmol), and methanol (1 mL) in $CH_2Cl_2$ (40 mL) was stirred and refluxed for 14 hours and cooled. The reaction mixture was diluted to 150 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (100:4:2) as the eluent to afford the product as a yellow powder (0.045 g, 44%); mp 83–84° C. Anal. Calcd for $C_{33}H_{38}N_4O_7 \cdot 0.2\ C_6H_{12} \cdot 0.4\ H_2O$: C, 64.87; H, 6.76; N, 9.11. Found: C, 65.01; H, 6.68; N, 8.82.

EXAMPLE 207

1,4-Dihydro-2,6-dimethyl-5-(2-hydroxyethoxycarbonyl)-3-{N-[3-(4-methoxycarbonyl-4-phenylpiperidin-1-yl)propyl]}carboxamido-4-(4-nitrophenyl)pyridine (207). A mixture of 1,4-dihydro-2,6-dimethyl-3-{N-[3-(4-methoxycarbonyl-4-phenylpiperidin-1-yl)propyl]}carboxamido-4-(4-nitrophenyl)pyridine-5-carboxylic acid (0.10 g, 0.174 mmol), 1-(3-dimethylaminopropyl)-3-ethylcarbodiimide hydrochloride (0.0666 g, 0.347 mmol), 4-(N,N-dimethylamino)pyridine (0.0424 g, 0.347 mmol), and ethylene glycol (1 mL) in $CH_2Cl_2$ (40 mL) was stirred and refluxed for 14 hours and cooled. The reaction mixture was diluted to 150 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (100:4:2) as the eluent to afford the product as a yellow powder (0.052 g, 48%); mp 90–91° C. Anal. Calcd for $C_{33}H_{40}N_4O_8 \cdot 0.8\ H_2O$: C, 62.41; H, 6.60; N, 8.82. Found: C, 62.65; H, 6.86; N, 8.54.

EXAMPLE 208

1,4-Dihydro-2,6-dimethyl-5-ethoxycarbonyl-3-{N-[3-(4-methoxycarbonyl-4-phenylpiperidin-1-yl)propyl]}carboxamido-4-(4-nitrophenyl)pyridine (208). A mixture of 1,4-dihydro-2,6-dimethyl-3-{N-[3-(4-methoxycarbonyl-4-phenylpiperidin-1-yl)propyl]}carboxamido-4-(4-nitrophenyl)pyridine-5-carboxylic acid (0.10 g, 0.174 mmol), 1-(3-dimethylaminopropyl)-3-ethylcarbodiimide hydrochloride (0.0666 g, 0.347 mmol), 4-(N,N-dimethylamino)pyridine (0.0424 g, 0.347 mmol), and ethanol (1 mL) in $CH_2Cl_2$ (40 mL) was stirred and refluxed for 14 hours and cooled. The reaction mixture was diluted to 150 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (100:4:2) as the eluent to afford the product as a yellow powder (0.055 g, 53%); mp 73–75° C. Anal. Calcd for $C_{33}H_{40}N_4O_7 \cdot 0.25\ C_6H_{12} \cdot 0.5\ H_2O$: C, 65.28; H, 6.99; N, 8.83. Found: C, 65.40; H, 7.03; N, 8.66.

EXAMPLE 209

5-Carboxamido-3-{N-[3-(4-(2-cyanoethoxycarbonyl)-4-phenylpiperidin-1-yl)propyl]}carboxamido-1,4-dihydro-2,6-dimethyl-4-(4-nitrophenyl)pyridine (209). A mixture of 5-carboxamido-1,4-dihydro-2,6-dimethyl-4-(4-nitrophenyl)pyridine-3-carboxylic acid (0.415 g, 1.31 mmol), 1-(3-dimethylaminopropyl)-3-ethylcarbodiimide hydrochloride (0.502 g, 2.62 mmol), 4-(N,N-dimethylamino)pyridine (0.640 g, 5.24 mmol), and 3-{4-(2-cyanoethoxycarbonyl)-4-phenylpiperidin-1-yl}propylamine.HCl (0.508 g, 1.31 mmol) in $CH_2Cl_2$ (40 mL) was stirred and refluxed for 6 hours. The mixture was cooled to room temperature, diluted to 190 mL with $CH_2Cl_2$, washed with saturated $NH_4Cl$ solution (3×40 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (100:4:2) as the eluent to afford the product as a yellow powder (0.487 g, 60.5%); Mp 99–101° C. Anal. Calcd for $C_{33}H_{38}N_6O_6 \cdot 0.55\ CH_2Cl_2$: C, 60.93; H, 5.96; N, 12.71. Found: C, 60.94; H, 5.77; N, 12.66.

EXAMPLE 210

5-Carboxamido-3-{N-[3-(4-carboxy-4-phenyl-piperidin-1-yl)propyl]}carboxamido-1,4-dihydro-2,6-dimethyl-4-(4-nitrophenyl)pyridine (210). To a stirred solution of 5-carboxamido-3-{N-[3-(4-(2-cyanoethoxycarbonyl)-4-phenylpiperidin-1-yl)propyl]}carboxamido-1,4-dihydro-2,6-dimethyl-4-(4-nitrophenyl)pyridine (0.394 g, 0.641 mmol) in dioxane (2 mL) at 0° C., aqueous 1N sodium hydroxide (1.92 mL, 1.92 mmol) was added and the mixture was allowed to warm to room temperature. TLC analysis of the reaction mixture showed the completion of the reaction after 2 hours. Solvent was evaporated from the reaction mixture and the residue was redissolved in water (1 mL) and the pH was adjusted to 5–6 by the addition of 1N HCl. The brown precipitate formed was filtered and dried under vacuum (0.252 g, 70%); mp 208–210° C. Anal. Calcd for $C_{30}H_{35}N_5O_6 \cdot 0.43NaCl \cdot 1.0\ H_2O$: –C, 59.57; H, 6.17; N, 11.58. Found: C, 59.57; H, 6.17; N, 11.48.

EXAMPLE 211

5-Carboxamido-1,4-dihydro-2,6-dimethyl-3-{N-[3-(4-(2-methoxyethoxy)-4-phenylpiperidin-1-yl)propyl]

}carboxamido-4-(4-nitrophenyl)pyridine (211). A mixture of 5-carboxamido-3-{N-[3-(4-carboxy-4-phenylpiperidin-1-yl)propyl]}carboxamido-1,4-dihydro-2,6-dimethyl-4-(4-nitrophenyl)pyridine (0.080 g, 0.142 mmol), 1-(3-dimethylaminopropyl)-3-ethylcarbodiimide hydrochloride (0.0546 g, 0.284 mmol), 4-(N,N-dimethylamino)pyridine (0.0347 g, 0.284 mmol), and 2-methoxyethanol (0.0324 g, 0.426 mmol) in $CH_2Cl_2$ (15 mL) was stirred and refluxed for 14 hours and cooled. The reaction mixture was diluted to 50 mL with $CH_2Cl_2$, washed with saturated $NH_4Cl$ solution (3×10 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (100:4:2) as the eluent to afford the product as a yellow powder (0.032 g, 36%); mp 79–80° C. Anal. Calcd for $C_{33}H_{41}N_5O_7$: C, 63.96; H, 6.67; N, 11.30. Found: C, 64.23; H, 6.45; N, 11.03.

EXAMPLE 212

5-Carboxamido-1,4-dihydro-2,6-dimethyl-3-{N-[3-(4-(2-hydroxyethoxy)-4-phenylpiperidin-1-yl)propyl]}carboxamido-4-(4-nitrophenyl)pyridine (212). A mixture of 5-carboxamido-3-{N-[3-(4-carboxy-4-phenylpiperidin-1-yl)propyl]}carboxamido-1,4-dihydro-2,6-dimethyl-4-(4-nitrophenyl)pyridine (0.055 g, 0.098 mmol), 1-(3-dimethylaminopropyl)-3-ethylcarbodiimide hydrochloride (0.0375 g, 0.196 mmol), 4-(N,N-dimethylamino)pyridine (0.024 g, 0.196 mmol), and ethylene glycol (0.0182 g, 0.294 mmol) in $CH_2Cl_2$ (15 mL) was stirred and refluxed for 14 hours and cooled. The reaction mixture was diluted to 50 mL with $CH_2Cl_2$, washed with saturated $NH_4Cl$ solution (3×10 mL), and dried ($MgSO_4$). Solvent was evaporated from the $CH_2Cl_2$ solution and the product was purified by flash column chromatography on silica gel using $CHCl_3$/MeOH/2M $NH_3$ in MeOH (100:4:2) as the eluent to afford the product as a yellow powder (0.038 g, 64%); mp 116–118° C. Anal. Calcd for $C_{32}H_{39}N_5O_7 \cdot 0.6\ CHCl_3$: C, 57.81; H, 5.89; N, 10.34. Found: C, 57.68; H, 5.93; N, 10.23.

EXAMPLE 213

5-Carboxamido-1,4-dihydro-2,6-dimethyl-3-{N-[3-(4-phenoxy-4-phenylpiperidin-1-yl)propyl]}carboxamido-4-(4-nitrophenyl)pyridine (213). A mixture of 5-carboxamido-3-{N-[3-(4-carboxy-4-phenylpiperidin-1-yl)propyl]}carboxamido-1,4-dihydro-2,6-dimethyl-4-(4-nitrophenyl)pyridine (0.050 g, 0.098 mmol), 1-(3-dimethylaminopropyl)-3-ethylcarbodiimide hydrochloride (0.0375 g, 0.196 mmol), 4-(N,N-dimethylamino)pyridine (0.024 g, 0.196 mmol), and phenol (0.028 g, 0.294 mmol) in $CH_2Cl_2$ (15 mL) was stirred and refluxed for 14 hours and cooled. The reaction mixture was diluted to 50 mL with $CH_2Cl_2$, washed with saturated $NH_4Cl$ solution (3×10 mL), and dried ($MgSO_4$). Solvent was evaporated from the $CH_2Cl$, solution and the product was purified by flash column chromatography on silica gel using $CHCl_3$/MeOH/2M $NH_3$ in MeOH (100:4:2) as the eluent to afford the product as a yellow powder (0.048 g, 77%); mp 121–122° C. Anal. Calcd for $C_{36}H_{39}N_5O_6 \cdot 0.35\ CHCl_3$: C, 64.25; H, 5.84; N, 10.31. Found: C, 64.10; H, 5.86; N, 10.07.

EXAMPLE 214

2-((2-Azidoethyl)oxy)methyl-5-carboxamido-3-(N-(3-(4-cyano-4-phenylpiperidin-1-yl)propyl))carboxamido-1,4-dihydro-6-methyl-4-(4-nitro)phenylpyridine 2-(4-Nitrophenyl)methyleno-3-oxo-1-butanamide.

A mixture of 4- nitrobenzaldehyde (15.1 g, 100 mmol), acetoacetamide (10.1 g, 100 mmol), piperidine (0.852 g, 10 mmol), and HOAC (0.601 g, 10 mmol) in 250 mL of isopropanol were stirred at room temperature for 13 hours. The precipitated product was filtered, washed with 50 mL of isopropanol and 2×50 mL of ether, and air dried to give 20.1 g (86%) of the desired product as a slightly yellow solid: mp 148–155° C. The product was used in the next step after spectral characterization.

2-((2-Azidoethyl)oxy)methyl-5-carboxamido-1,4-dihydro-6-methyl-4-(4-nitro)phenylpyridine-3-carboxylic Acid.

A mixture of 5-((2-azidoethyl)oxy)acetyl-2,2-dimethyl-4,6-dione-1,3-dioxane (7.24 g, 26.7 mmol) and 3-hydroxypropionitrile (3.80 g, 53.4 mmol) in 50 mL of dry toluene were heated at reflux temperature for 2 hours, cooled, and the solvent was removed in vacuo. The residue was charged with ammonium acetate (2.26 g, 29.4 mmol) and ethanol (50 mL) and heated at reflux temperature for 0.5 hour. 2-(4-Nitrophenyl)methyleno-3-oxo-1-butanamide (4.38 g, 18.7 mmol) was added to the reaction mixture and heated at reflux temperature for 3 hours, cooled to room temperature, NaOH (139 mg), in 10 mL of water was added to the reaction mixture, and stirred for 3 hours. The solvent was removed in vacuo, the residue was partitioned between water (50 mL) and EtOAc (50 mL), separated, extracted with 2×50 mL of water, the combined aqueous extracts were acidified with concentrated HCl (pH=3–4), extracted with dichloromethane (3×50 mL), dried ($Na_2SO_4$), and the solvent was removed in vacuo. The crude product was precipitated from a mixture of EtOAc-hexane to give 1.15 g of the desired acid as a yellow solid: mp 160–165° C. The product was used in the next step after spectral characterization.

2-((2-Azidoethyl)oxy)methyl-5-carboxamido-3-(N-(3-(4-cyano-4-phenylpiperidin-1-yl)propyl))carboxamido-1,4-dihydro-6-methyl-4-(4-nitro)phenylpyridine (214).

A mixture of 2-(2-azidoethyl)oxy)methyl-5-carboxamido-1,4-dihydro-6-methyl-4-(4-nitro)phenylpyridine-3-carboxylic acid 150 mg, 0.373 mmol), DCC (154 mg, 0.746 mmol), DMAP (36 mg, 0.300 mmol), and 1-(3-amino)propyl-4-cyano-4-phenylpiperidine (110 mg, 0.450 mmol) in 7 mL of dry dichloromethane were stirred at reflux temperature for 3 hours. The solvent was removed in vacuo, redissolved in 10 mL of ethyl acetate, filtered, solvent removed in vacuo, and the residue was chromatographed on 300 g of silica packed with MeOH—EtOAc (1:9). The column was eluted with MeOH—EtOAc (1:9) to give 133 mg (60%) of the desired product as a yellow solid: mp 81° C. (decomp.); Anal. Calcd for $C_{32}H_{37}N_9O_5 + 0.2\ CHCl_3$: C, 59.36; H, 5.75; N, 19.35. Found: C, 59.74; H, 5.69; N, 19.08

EXAMPLE 215

2-((2-Aminoethyl)oxy)methyl-5-carboxamido-3-(N-(3-4-cyano-4-phenylpiperidin-1-yl)propyl))carboxamido-1,4-dihydro-6-methyl-4-(4-nitrophenyl)pyridine (215).

To a solution of 2-((2-azidoethyl)oxy)methyl-5-carboxamido-3-(N-(3-(4-cyano-4-phenylpiperidin-1-yl)propyl))carboxamido-1,4-dihydro-6-methyl-4-(4-nitro)phenylpyridine (100 mg, 0.160 mmol) in 5 mL of EtOAc at 0° C. was added 1M $(Me)_3P$ in THF (0.40 mL, 0.40 mmol), and water (14 mL, 0.80 mmol). The reaction mixture was stirred at room temperature for 3 hours, and the solvent was removed in vacuo. The crude product was chromatographed on 100 g of silica packed with $NH_3$ (2N in MeOH)—MeOH—$CHCl_3$ (1:2:10). The column was eluted with $NH_3$ (2N in MeOH)—MeOH—$CHCl_3$ (1:2:10) to give 77 mg (80%) of the desired product as a yellow solid: mp 101° C.

(decomp.); Anal. Calcd for $C_{38}H_{45}N_5O_6+0.5CH_2Cl_2$: C, 60.60; H, 6.26; N, 15.22. Found: C, 60.65; H, 6.12; N, 15.37.

EXAMPLE 216

2-((Azidoethyl)oxy)methyl-5-carboxamido-1,4-dihydro-6-methyl-4-(4-nitro)phenyl-3-(N-(3-(4-phenylpiperidin-1-yl)propyl))carboxamidopyridine (216).

A mixture of 2-(2-azidoethyl)oxy)methyl-5-carboxamido-1,4-dihydro-6-methyl-4-(4-nitro)phenylpyridine-3-carboxylic acid (150 mg, 0.373 mmol), DCC (154 mg, 0.746 mmol), DMAP (36 mg, 0.300 mmol), and 1-(3-amino)propyl-4-phenylpiperidine (87 mg, 0.400 mmol) in 7 mL of dry dichloromethane were stirred at reflux temperature for 4 hours, and then at room temperature for 17 hours. The solvent was removed in vacuo, redissolved in 10 mL of ethyl acetate, filtered, washed with aqueous saturated ammonium chloride solution (3×3 mL), brine (3 mL), dried ($Na_2SO_4$), solvent removed in vacuo, and the residue was chromatographed on 300 g of silica packed with MeOH—EtOAc (1:3). The column was eluted with MeOH—EtOAc (1:3) to give 133 mg (60%) of the desired product as a yellow solid: mp 76° C. (decomp.); Anal. Calcd for $C_{32}H_{37}N_9O_5+0.12CHCl_3$: C, 60.58; H, 6.23; N, 18.16. Found: C, 60.76; H, 6.22; N, 17.76.

EXAMPLE 217

2-((2-Aminoethyl)oxy)methyl-5-carboxamido-1,4-dihydro-6-methyl-3-(N-(3-(4,4-diphenylpiperidin-1-yl)propyl))carboxamido-4-(4-nitro)phenylpyridine (217).

To a solution of 2-((2-aminoethyl)oxy)methyl-5-carboxamido-1,4-dihydro-6-methyl-3-(N-(3-(4,4-diphenylpiperidin-1-yl)propyl))carboxamido-4-(4-nitro)phenylpyridine (116 mg, 0.170 mmol) in 5 mL of EtOAc at 0° C. was added 1M $(Me)_3P$ in THF (0.43 mL, 0.43 mmol), stirred at 0° C. for 10 minutes, and water (15 mL, 0.85 mmol) was added. The reaction mixture was stirred at room temperature for 2 hours, and the solvent was removed in vacuo. The crude product was chromatographed on 150 g of silica packed with $NH_3$ (2N in MeOH)—MeOH—$CHCl_3$ (1:2:10). The column was eluted with $NH_3$ (2N in MeOH)—MeOH—$CHCl_3$ (1:2:10) to give 88 mg (80%) of the desired product as a yellow solid: mp 130–140° C.; Anal. Calcd for $C_{38}H_{45}N_5O_6+0.7CH_2Cl_2$: C, 63.58; H, 6.42; N, 11.80. Found: C, 63.56; H, 6.62; N, 11.55.

EXAMPLE 218

2-((2-Aminoethyl)oxy)methyl-5-carboxamido-1,4-dihydro-6-methyl-4-(4-nitro)phenyl-3-(N-(3-(4-phenylpiperidin-1-yl)propyl))carboxamidopyridine (218).

To a solution of 2-((2-(azidoethyl)oxy)methyl-5-carboxamido-1,4-dihydro-6-methyl-4-(4-nitro)phenyl-3-(N-(3-(4-phenylpiperidin-1-yl)propyl))carboxamidopyridine (88 mg, 0.146 mmol) in 6 mL of EtOAc at 0° C. was added 1M $(Me)_3P$ in THF (0.37 mL, 0.37 mmol), and water (13 mL, 0.73 mmol) was added. After 15 minutes, a precipitate was formed which redissolved after addition of 4.5 mL of dry THF. The reaction mixture was stirred at room temperature for 4 hours, and the solvent was removed in vacuo. The crude product was chromatographed on 140 g of silica packed with $NH_3$ (2N in MeOH)—MeOH—$CHCl_3$ (1:2:10). The column was eluted with $NH_3$ (2N in MeOH)—MeOH—$CHCl_3$ (1:2:10) to give 65 mg (80%) of the desired product as a yellow solid: mp 125° C. (decomp.); Anal. Calcd for $C_{38}H_{45}N_5O_6+0.35CH_2Cl_2$: C, 62.09; H, 6.76; N, 13.86. Found: C, 62.22; H, 6.88; N, 13.51.

EXAMPLE 219

2-((2-Aminoethyl)oxy)methyl-6-ethyl-1,4-dihydro-4-(4-nitro)phenyl-3-(N-(3-(4,4-diphenylpiperidin-1-yl)propyl))carboxamidopyridine-5-carboxylic Acid (219).

To a solution of 2-((2-azidoethyl)oxy)methyl-6-ethyl-1,4-dihydro-4-(4-nitro)phenyl-3-(N-(3-(4,4-diphenylpiperidin-1-yl)propyl))carboxamidopyridine-5-carboxylic acid (38 mg, 0.055 mmol) in 4 mL of THF—EtOAc (1:3) at 0° C. was added 1M $(Me)_3P$ in THF (0.14 mL, 0.14 mmol), and water (12 mL, 0.67 mmol). The reaction mixture was stirred at room temperature for 2 hours, and the solvent was removed in vacuo. The crude product was chromatographed on 75 g of silica packed with $NH_3$ (2N in MeOH)—MeOH—$CHCl_3$ (1:2:7). The column was eluted with $NH_3$ (2N in MeOH)—MeOH—$CHCl_3$ (1:2:7) to give 30 mg (82%) of the desired product as a yellow solid. The chromatographed contained small amounts of an impurity. The product was precipitated from a mixture of EtOH—EtOAc: mp 180° C. (decomp.); Anal. Calcd for $C_{38}H_{45}N_5O_6+1.4H_2O+0.7CHCl_3$: C, 59.86; H, 6.29; N, 9.02. Found: C, 59.89; H, 6.09; N, 8.77.

EXAMPLE 220

5-(2-Cyanoethoxy)carbonyl-3-(N-(3-(4-cyano-4-phenylpiperidin-1-yl)propyl))carboxamido-6-ethyl-1,4-dihydro-2-methyloxymethyl-4-(4-nitro)phenylpyridine (220).

A mixture of 5-(2-cyanoethoxy)carbonyl-6-ethyl-1,4-dihydro-2-methyloxymethyl-4-(4-nitro)phenylpyridine-3-carboxylic acid (150 mg, 0.361 mmol), DCC (149 mg, 0.722 mmol), and DMAP (35 mg, 0.289 mmol) in 12 mL of dry dichloromethane were stirred at room temperature for 1 hour before addition of 1-(3-amino)propyl-4-cyano-4-phenylpiperidine (114 mg, 0.469 mmol). The resulting mixture was heated at reflux temperature for 3 hours. The reaction mixture was filtered, concentrated in vacuo, and the residue was chromatographed on 300 g of silica (MeOH—EtOAc, 1:29) to give 196 mg of the title compound (85%) as a yellow solid: mp 58–68° C.; Anal Calcd for $C_{35}H_{40}N_6O_6+0.7H_2O$: C, 64.34; H, 6.39; N, 12.86. Found: C, 64.69; H, 6.50; N, 12.49.

EXAMPLE 221

5-(2-Cyanoethoxy)carbonyl-6-ethyl-1,4-dihydro-2-methyloxymethyl-4-(4-nitro)phenyl-3-(N-(3-(4-phenylpiperidin-1-yl)propyl))carboxamidopyridine (221).

A mixture of 5-(2-cyanoethoxy)carbonyl-6-ethyl-1,4-dihydro-2-methyloxymethyl-4-(4-nitro)phenylpyridine-3-carboxylic acid (150 mg, 0.361 mmol), DCC (149 mg, 0.722 mmol), and DMAP (35 mg, 0.289 mmol) in 8 mL of dry dichloromethane were stirred at room temperaturre for 0.5 hour before addition of 1-(3-amino)propyl-4-phenylpiperidine (103 mg, 0.469 mmol). The resulting mixture was heated at reflux temperature for 2.5 hours. The reaction mixture was filtered, concentrated in vacuo, and the residue was chromatographed on 120 g of silica (MeOH—EtOAc, 1:9) to give 200 mg of the title compound (90%) as a yellow solid: mp 55–63° C.; Anal. Calcd for $C_{34}H_{41}N_5O_6+0.5H_2O$: C, 65.37; H, 6.78; N, 11.21. Found: C, 65.23; H, 6.77; N, 10.94.

EXAMPLE 222

3-(N-(3-(4-Cyano-4-phenylpiperidin-1-yl)propyl))carboxamido-6-ethyl-1,4-dihydro-2-methyloxymethyl-4-(4-nitro)phenylpyridine-5-carboxylic Acid (222).

To a solution of 3-(N-(3-(4-cyano-4-phenylpiperidin-1-yl)propyl))carboxamido-5-(2-cyanoethoxy)carbonyl-6- ethyl-1,4-dihydro-4-(4-nitro)phenyl-2-methyloxymethylpyridine (170 mg, 0.265 mmol in 3 mL of dioxane was added water containing NaOH (16 mg, 0.398 mmol). After 2 hours, the solvent was removed in vacuo, the residue was dissolved in water (20 mL), acidified with aqueous 1 N HCl solution (pH=3–4), and extracted with dichloromethane (3×15 mL). The combined dichloromethane extracts were dried ($Na_2SO_4$), and the solvent was removed in vacuo to give 150 mg (96%) of the desired product as a yellow solid: mp 115° C. (decomp.): Anal. Calcd for $C_{32}H_{37}N_5O_6+1.0H_2O+0.5CH_2Cl_2$: C, 60.23; H, 6.22; N, 10.81. Found: C, 60.35; H, 6.20; N, 10.76.

EXAMPLE 223

6-Ethyl-1,4-dihydro-2-methyloxymethyl-4-(4-nitro)phenyl-3-(N-(3-(4-phenylpiperidin-1-yl)propyl))carboxamidopyridine-5-carboxylic Acid (223).

To a solution of 5-(2-cyanoethoxy)carbonyl-6-ethyl-1,4-dihydro-2-methyloxymethyl-4-(4-nitro)phenyl-3-(N-(3-(4-phenylpiperidin-1-yl)propyl))carboxamidopyridine (110 mg, 0.180 mmol in 2 mL of dioxane was added 0.70 mL of water containing NaOH (11 mg, 0.270 mmol). After 2.5 hours, the solvent was removed in vacuo, the residue was dissolved in water (8 mL), acidified with aqueous 1N HCl solution (pH=5), and extracted with dichloromethane (3×8 mL). The combined dichloromethane extracts were dried ($Na_2SO_4$), and the solvent was removed in vacuo to give 100 mg (100%) of the title compound as a yellow solid: mp 88° C. (decomp.): Anal. Calcd for $C_{32}H_{37}N_5O_6+0.4CH_2Cl_2$: C, 63.21; H, 6.55; N, 9.39. Found: C, 63.21; H, 6.60; N, 8.92.

EXAMPLE 224

2-((2-Azidoethyl)oxy)methyl-6-ethyl-1,4-dihydro-5-N-methylcarboxamido-4-(4-nitro)phenyl-3-(N-(3-(4,4-diphenylpiperidin-1-yl)propyl))carboxamidopyridine (224).

A mixture of 2-((2-azidoethyl)oxy)methyl-6-ethyl-1,4-dihydro-4-(4-nitro)phenyl-3-(N-(3-(4,4-diphenylpiperidin-1-yl)propyl))carboxamidopyridine-5-carboxylic acid (100 mg, 0.144 mmol), DCC (48 mg, 0.231 mmol), and DMAP (122 mg, 14.1 mmol) in 5 mL of dry dichloromethane were stirred at room temperature for 1 hour followed by addition of 40% methylamine in water (0.123 mL, 1.44 mmol). The resulting mixture was stirred at room temperature for 18 hours. The reaction mixture was filtered, and the solvent was removed in vacuo. The crude product was dissolved in 10 mL of EtOAc, sequentially washed with aqueous saturated ammonium chloride (3×2 mL), water (2 mL), aqueous saturated sodium chloride solution (3 mL), dried ($Na_2CO_3$), and the solvent was removed in vacuo. The product was chromatographed on 100 g of silica packed with MeOH—EtOAc (1:4). The column was eluted with MeOH—EtOAc (1:4) to afford 88 mg (90%) of the desired product as a yellow solid: mp 95° C. (decomp.); Anal. Calcd for $C_{39}H_{46}8_8O_5+1.7H_2O$: C, 63.52; H, 6.75; N, 15.19. Found: C, 63.46; H, 6.32; N, 14.82.

EXAMPLE 225

2-((2-Aminoethyl)oxy)methyl-6-ethyl-1,4-dihydro-5-N-methylcarboxamido-4-(4-nitro)phenyl-3-(3-(N-(4,4-diphenylpiperidin-1-yl)propyl))carboxamidopyridine (225).

To a solution of 2-((2-azidoethyl)oxy)methyl-6-ethyl-1,4-dihydro-5-N-methylcarboxamido-4-(4-nitro)phenyl-3-(3-(N-(4,4-diphenylpiperidin-1-yl)propyl))carboxamidopyridine (75 mg, 0.11 mmol) in 5 mL of EtOAc at 0° C. was added 1M $(Me)_3P$ in THF (0.44 mL, 0.44 mmol), and water (20 mL, 1.1 mmol). The reaction mixture was stirred at room temperature for 3 hours, and the solvent was removed in vacuo. The crude product was chromatographed on 100 g of silica packed with $NH_3$ (2N in MeOH)—MeOH—$CHCl_3$ (1:2:15). The column was eluted with $NH_3$ (2N in MeOH)—MeOH—$CHCl_3$ (1 L of 1:2:17 and 1 L of 1:2:15) to give 60 mg (83%) of the desired product as a yellow solid: mp 115° C. (decomp.); Anal. Calcd for $C_{39}H_{48}N_6O_5+1.0H_2O$: C, 67.03; H, 7.21; N, 12.03. Found: C, 66.98; H, 7.18; N, 11.54.

EXAMPLE 226

2-((2-Azidoethyl)oxy)methyl-5-(2-cyanoethoxy)carbonyl-6-ethyl-1,4-dihydro-3-(N-(3-(4-methoxycarbonyl-4-phenylpiperidin-1-yl)propyl))carboxamido-4-(4-nitro)phenylpyridine (226).

A mixture of 2-((2-azidoethyl)oxy)methyl-5-(2-cyanoethoxy)carbonyl-6-ethyl-1,4-dihydro-4-(4-nitro)phenylpyridine-3-carboxylic acid (1.00 g, 2.13 mmol), DCC (877 mg, 4.25 mmol), and DMAP 208 mg, 1.70 mmol) in 40 mL of dry dichloromethane were stirred at room temperature for 15 minutes followed by addition of 1-(3-amino)propyl-4-methoxycarbonyl-4-phenylpiperidine (630 mg, 2.28 mmol). The resulting mixture was stirred at room temperature for 19 hours, filtered, and the solvent was removed in vacuo. The product was chromatographed on 750 g of silica packed with MeOH—EtOAc (1:9). The column was eluted with MeOH—EtOAc (1:9) to afford 1.33 g (84%) of the desired product as a yellow solid: mp 54–60° C.; Anal. Calcd for $C_{37}H_{44}N_8O_8$: C, 60.97; H, 6.10; N, 15.37. Found: C, 60.81; H, 6.24; N, 15.12.

EXAMPLE 227

2-((2-Azidoethyl)oxy)methyl-6-ethyl-1,4-dihydro-3-(N-(3-(4-methoxycarbonyl-4-phenylpiperidin-1-yl)propyl))carboxamido-4-(4-nitro)phenylpyridine-5-carboxylic Acid (227).

To a solution of 2-((2-azidoethyl)oxy)methyl-5-(2-cyanoethoxy)carbonyl-6-ethyl-1,4-dihydro-3-(N-(3-(4-methoxycarbonyl-4-phenylpiperidin-1-yl)propyl))carboxamido-4-(4-nitro)phenylpyridine (1.30 g, 1.78 mmol) in 10 mL of dioxane was added NaOH (75 mg, 1.87 mmol) in 5 mL of water. The reaction mixture was stirred at room temperature for 2 hours, and the solvent was removed in vacuo. The residue was dissolved in 50 mL of water, acidified with 1N HCl solution (pH=5), the precipitated solids were filtered, and dried ($MgSO_4$) to give 1.20 g (100%) of the desired product as a yellow solid: mp 110–120° C.: Anal calcd for $C_{34}H_{41}N_7O_8+1.5H_2O$: C, 58.11; H, 6.31; N, 13.95. Found: C, 58.38; H, 5.99; N, 13.85.

EXAMPLE 228

2-((2-Azidoethyl)oxy)methyl-6-ethyl-1,4-dihydro-3-(N-(3-(4-methoxycarbonyl-4-phenylpiperidin-1-yl)propyl))carboxamido-5-N-methylcarboxamido-4-(4-nitro)phenylpyridine (228).

A solution of 2-((2-azidoethyl)oxy)methyl-6-ethyl-1,4-dihydro-3-(N-(3-(4-methoxycarbonyl-4-phenylpiperidin-1-yl)propyl))carboxamido-4-(4-nitro)phenylpyridine-5-carboxylic acid (100 mg, 0.148 mmol), DCC (61 mg, 0.296 mmol), and DMAP (14 mg, 0.118 mmol) in 4 mL of dry dichloromethane were stirred at room temperature for 0.5 hour, the reaction mixture was charged with 0.13 mL of 40% $MeNH_2$ in water, and stirred at room temperature for 16 hours. The reaction mixture was filtered, the solvent was removed in vacuo, and the crude product was chromatographed on 100 g of silica packed with MeOH—EtOAc (1:6). The column was eluted with MeOH—EtOAc (1:6) to give 71 mg (70%) of the desired product as a yellow solid: mp 73–83° C.; Anal. Calcd for $C_{35}H_{44}N_8O_7+0.2H_2O$: C, 59.90; H, 6.34; N, 15.88. Found: C, 59.74; H, 6.50; N, 15.60

EXAMPLE 229

2-((2-Aminoethyl)oxy)methyl-6-ethyl-1,4-dihydro-3-(N-(3-(4-methoxycarbonyl-4-phenylpiperidin-1-yl)propyl))carboxamido-5-N-methylcarboxamido-4-(4-nitro)phenylpyridine (229).

To a solution of 2-((2-azidoethyl)oxy)methyl-6-ethyl-1,4-dihydro-3-(N-(3-(4-methoxycarbonyl-4-phenylpiperidin-1-yl)propyl))carboxamido-5-N-methylcarboxamido-4-(4-nitro)phenylpyridine (54 mg, 0.078 mmol) in 3 mL of EtOAc at 0° C. was added 1 M $(Me)_3P$ in THF (0.30 mL, 0.30 mmol), and water (14 mL, 0.78 mmol). The reaction mixture was stirred at room temperature for 4 hours, and the solvent was removed in vacuo. The crude product was chromatographed on 100 g of silica packed with $NH_3$ (2N in MeOH)—MeOH—$CHCl_3$ (1:2:15). The column was eluted with $NH_3$ (2N in MeOH)—MeOH—$CHCl_3$ (1:2:15) to give 44 mg (85%) of the desired product as a yellow solid: mp 95° C. (decomp.); Anal. Calcd for $C_{35}H_{46}N_6O_7+1.0H_2O$: C, 61.75; H, 7.11; N, 12.34. Found: C, 61.74; H, 7.10; N, 12.02.

EXAMPLE 230

2-((2-Azidoethyl)oxy)methyl-6-ethyl-5-N-ethylcarboxamido-1,4-dihydro-3-(N-(3-(4-methoxycarbonyl-4-phenylpiperidin-1-yl)propyl))carboxamido-4-(4-nitro)phenylpyridine (230).

A solution of 2-((2-azidoethyl)oxy)methyl-6-ethyl-1,4-dihydro-3-(N-(3-(4-methoxycarbonyl-4-phenylpiperidin-1-yl)propyl))carboxamido-4-(4-nitro)phenylpyridine-5-carboxylic acid (120 mg, 0.178 mmol), DCC (73 mg, 0.36 mmol), and DMAP (17 mg, 0.118 mmol) in 5 mL of dry dichloromethane were stirred at room temperature for 1.5 hours, the reaction mixture was charged with 0.144 mL of 70% $EtNH_2$ in water (1.78 mmol), and stirred at room temperature for 2 days. The reaction mixture was filtered, and the solvent was removed in vacuo. The crude product was dissolved in 10 mL of EtOAc, sequentially washed with aqueous saturated ammonium chloride (5 mL), water (5 mL), aqueous saturated sodium carbonate solution (5 mL), dried ($Na_2CO_3$), and the solvent was removed in vacuo. The crude product was chromatographed on 100 g of silica packed with MeOH—EtOAc (1:9). The column was eluted with MeOH—EtOAc (1:9) to give 50 mg (45%) of the desired product as a yellow solid: mp 70° C. (decomp.); Anal. Calcd for $C_{36}H_{46}N_8O_7+1.0H_2O$: C, 59.99; H, 6.71; N, 15.55. Found: C, 60.02; H, 6.79; N, 14.56.

EXAMPLE 231

2-((2-Azidoethyl)oxy)methyl-5-carboxamido-6-ethyl-1,4-dihydro-3-(N-(3-(4-methoxycarbonyl-4-phenylpiperidin-1-yl)propyl))carboxamido-4-(4-nitro)phenylpyridine (231).

A mixture of 2-((2-azidoethyl)oxy)methyl-6-ethyl-1,4-dihydro-3-(N-(3-(4-methoxycarbonyl-4-phenylpiperidin-1-yl)propyl))carboxamido-4-(4-nitro)phenylpyridine-5-carboxylic acid (120 mg, 0.178 mmol), DCC (73 mg, 0.36 mmol), and DMAP (17 mg, 0.118 mmol) in 5 mL of dry dichloromethane were stirred at room temperature for 1.5 hours, the reaction mixture was charged with 1.78 mL of 58% $NH_4OH$ in water (1.78 mmol), and stirred at room temperature for 2 days. The reaction mixture was filtered, the solvent was removed in vacuo. The crude product was dissolved in 10 mL of EtOAc, sequentially washed with aqueous saturated ammonium chloride (5 mL), water (5 mL), aqueous saturated sodium carbonate solution (5 mL), dried ($Na_2CO_3$), and the solvent was removed in vacuo. The crude product was chromatographed on 100 g of silica packed with MeOH—EtOAc (1:9). The column was eluted with MeOH—EtOAc (1:9) to give 50 mg (42%) of the desired product as a yellow solid: mp 70–75° C.; Anal. Calcd for $C_{34}H_{42}N_8O_7+1.0H_2O$: C, 58.95; H, 6.40; N, 16.17. Found: C, 58.86; H, 6.19; N, 15.81.

EXAMPLE 232

2-((2-Azidoethyl)oxy)methyl-6-ethyl-5-methoxycarbonyl-3-N-(3-(4-methoxycarbonyl-4-phenylpiperidin-1-yl)propyl))carboxamido-1,4-dihydro-4-(4-nitro)phenylpyridine (232).

A mixture of 2-((2-azidoethyl)oxy)methyl-6-ethyl-3-(N-(3-(4-methoxycarbonyl-4-phenylpiperidin-1-yl)propyl))carboxamido-1,4-dihydro-4-(4-nitro)phenylpyridine-5-carboxylic acid (120 mg, 0.178 mmol), DCC (73.3 mg, 0.353 mmol), and DMAP (17.4 mg, 0.142 mmol) in 5 mL of dry dichloromethane were stirred at room temperature for 2 hours, the reaction mixture was charged with methanol (72 ml, 9.6 mg, 1.78 mmol), and stirred at room temperature for 2 days. The reaction mixture was filtered, and the solvent was removed in vacuo. The crude product was chromatographed on 100 g of silica packed with MeOH—EtOAc (1:9). The column was eluted with MeOH—EtOAc (1:19) to give 91 mg (74%) of the desired product as a yellow solid: mp 50–60° C.; Anal. Calcd for $C_{35}H_{43}N_7O_8+0.5H_2O$: C, 60.16; H, 6.35; N, 14.03. Found: C, 60.33; H, 6.51; N, 13.84.

EXAMPLE 233

2-((2-Aminoethyl)oxy)methyl-6-ethyl-5-N-ethylcarboxamido-1,4-dihydro-3-(N-(3-(4-methoxycarbonyl-4-phenylpiperidin-1-yl)propyl))carboxamido-4-(4-nitro)phenylpyridine (233).

To a solution of 2-((2-Azidoethyl)oxy)methyl-6-ethyl-5-N-ethylcarboxamido-1,4-dihydro-3-(N-(3-(4-methoxycarbonyl-4-phenylpiperidin-1-yl)propyl))carboxamido-4-(4-nitro)phenylpyridine (30 mg, 0.043 mmol) in 4 mL of EtOAc at 0° C. was added 1 M $(Me)_3P$ in THF (0.17 mL, 0.17 mmol), and water (8 mL, 0.43 mmol). The reaction mixture was stirred at room temperature for 4 hours, and the solvent was removed in vacuo. The crude product was chromatographed on 100 g of silica packed with $NH_3$ (2N in MeOH)—MeOH—$CHCl_3$ (1:2:12). The column was eluted with $NH_3$ (2N in MeOH)—MeOH—$CHCl_3$ (1:2:12) to give 25 mg (86%) of the desired product as a yellow solid: mp 112° C. (decomp.); Anal. Calcd for $C_{36}H_{48}N_6O_7+0.5H_2O+0.5CH_2Cl_2$: C, 60.20; H, 6.92; N, 11.54. Found: C, 60.14; H, 7.31; N, 11.23.

EXAMPLE 234

2-((2-Aminoethyl)oxy)methyl-5-carboxamido-6-ethyl-1,4-dihydro-3-(N-(3-(4-methoxycarbonyl-4-phenylpiperidin-1-yl) propyl))carboxamido-4-(4-nitro)phenylpyridine (234).

To a solution of 2-((2-Azidoethyl)oxy)methyl-5-carboxamido-6-ethyl-1,4-dihydro-3-(N-(3-(4-methoxycarbonyl-4-phenylpiperidin-1-yl)propyl))carboxamido-4-(4-nitro)phenylpyridine (30 mg, 0.044 mmol) in 4 mL of EtOAc at 0° C. was added 1M $(Me)_3P$ in THF (0.18 mL, 0.18 mmol), and water (16 mL, 0.88 mmol).

The reaction mixture was stirred at room temperature for 4 hours, and the solvent was removed in vacuo. The crude product was chromatographed on 100 g of silica packed with $NH_3$ (2N in MeOH)—MeOH—$CHCl_3$ (1:2:15). The column was eluted with $NH_3$ (2N in MeOH)—MeOH—$CHCl_3$ (1:2:15) to give 44 mg (95%) of the desired product as a yellow solid: mp 115° C. (decomp.); Anal. Calcd for $C_{35}H_{46}N_6O_7+1.0H_2O+0.2CH_2Cl_2$: C, 60.08; H, 6.84; N, 12.29. Found: C, 60.37; H, 6.96; N, 11.98.

EXAMPLE 235

2-((2-Aminoethyl)oxy)methyl-6-ethyl-1,4-dihydro-5-methoxycarbonyl-3-(N-(3-(4-methoxycarbonyl-4-phenylpiperidin-1-yl)propyl))carboxamido-4-(4-nitro) phenylpyridine (235).

To a solution of 2-((2-azidoethyl)oxy)methyl-6-ethyl-1,4-dihydro-5-methoxycarbonyl-3-(N-(3-(4-methoxycarbonyl-4-phenylpiperidin-1-yl)propyl))carboxamido-4-(4-nitro) phenylpyridine (65 mg, 0.094 mmol) in 4 mL of EtOAc at 0° C. was added 1M $(Me)_3P$ in THF (0.38 mL, 0.38 mmol), and water (34 mL, 1.88 mmol). The reaction mixture was stirred at room temperature for 2.5 hours, and the solvent was removed in vacuo. The crude product was chromatographed on 100 g of silica packed with $NH_3$ (2N in MeOH)—MeOH—$CHCl_3$ (1:2:30). The column was eluted with $NH_3$ (2N in MeOH)—MeOH—$CHCl_3$ (1:2:15) to give 55 mg (88%) of the desired product as a yellow solid: mp 70° C. (decomp.).

The hydrochlride salt was prepared by dissolving 5 mg of 2-((2-aminoethyl)oxy)methyl-6-ethyl-1,4-dihydro-5-methoxycarbonyl-3-(N-(3-(4-methoxycarbonyl-4-phenylpiperidin-1-yl)propyl))carboxamido-4-(4-nitro) phenylpyridine in 2 mL of dichloromethane and 2 mL of 1N HCl in ether was added, the precipitated product was collected, and dried: mp 140° C. (decomp.); Anal. Calcd for $C_{35}H_{45}N_5O_8+2.0HCl+1.5H_2O$: C, 55.05; H, 6.60; N, 9.17. Found: C, 54.80; H, 6.22; N, 8.58.

EXAMPLE 236

5-Acetyl-2-((3-aminopropyl)oxy)methyl-1,4-dihydro-6-methyl-4-(4-nitro)phenyl-3-(N-(3-(4,4-diphenylpiperidin-1-yl)propyl))carboxamidopyridine (236) 3-(4-Nitrophenyl) methylenepentane-2,4-dione.

A mixture of pentane-2,4-dione (20.0 g, 200 mmol), 4-nitrobenzaldehyde (30.2 g, 200 mmol), piperidine (1.70 g, 20.0 mmol), and HOAc (1.20 g, 20.0 mmol) in 500 mL of isopropanol were heated with a heat gun until a homogeneous solution resulted. The reaction mixture was then stirred at room temperature for 18 hours. The precipitated solids were filtered, sequentially washed with isopropanol and ether, and air dried to give 28.3 g of the title compound. The filtrate also yielded 5.10 g of 3-(4-nitrophenyl) methylenepentane-2,4-dione for a combined yield of 72%: mp 90–91° C. The product was used in the next step after spectral characterization.

3-Azidopropanol.

A mixture of 3-chloropropanol (100 g, 1.06 mol), sodium azide (103 g, 1.59 mol), NaOH (636 mg, 15.9 mol), and NaI (2.39 g, 15.9 mmol) in a mixture of $H_2O$—EtOH (2:1, 750 mL) were stirred at 60–65° C. (bath temperature) for 3 days. The reaction mixture was cooled, extracted with EtOAc (3×250 mL), dried ($MgSO_4$), and the solvent was remove in vacuo. The crude product was distilled under reduced pressure to give 98.6 g (92%) of 3-azidopropanol as a colorless oil: bp 56–58 (0.2 mmHg). The product was used in the next step after spectral characterization.

(3-Azidopropyl)oxyacetic Acid.

A solution of 3-azidopropanol (70.1 g, 0.693 mol) in 100 mL of THF was added dropwise, in a period of 1.5 hours, to a mechanically stirred suspension of NaH (60% in mineral oil, 30.5 g, 0.763 mol) in 250 mL of THF. During the addition of 3-azidopropanol, a gentle reflux was maintained. This was followed by addition of solid NaI (10.4 g, 69.3 mmol), and tetrabutylammonium bromide (22.3 g, 69.3 mmol), and sodium chloroacetate (88.8 g, 0.763 mol). The reaction mixture was heated at reflux temperature for 19 hours, cooled, quenched initially with 20 mL of water (added dropwise) and then with 700 mL of water, washed with EtOAc (3×200 mL), acidified with concentrated HCl to pH=2, and extracted with dichloromethane (6×100 mL). The combined dichloromethane extracts were dried ($MgSO_4$), and the solvent was removed in vacuo to give 63.3 g (58%) of the title compound as a yellow viscous oil. The crude product was used in the next step after spectral characterization.

5-((3-Azidopropyl)oxy)acetyl-2,2-dimethyl-4,6-dione-1, 3-dioxane.

Carbonyldiimidazole (71.7 g, 0.442 mol) was added portionwise to a stirred solution of (3-azidopropyl)oxyacetic acid (63.1 g, 0.402 mol) in 300 mL of dry dichloromethane (bubbling). The resulting mixture was stirred at room temperature for 2 hours. A solution of pyridine (35.8 mL, 0.442 mol) and Meldrum's acid (63.7 g, 0.442 mol) in 150 mL of dry dichloromethane were added, over a period of 2 hours to the reaction mixture (slightly exothermic reaction). The reaction mixture was stirred for 16 hours, quenched with 400 mL of 2N HCl (bubbling), separated, washed sequentially with 2×400 mL 2N HCl, brine (400 mL), dried ($MgSO_4$), and the solvent was removed in vacuo to give 83.2 g (73%) of the title compound as a yellow viscous oil. The crude product was used in the next step after spectral characterization.

2-Cyanoethyl 3-Amino-4-((3-azidopropyl)oxy)crotonate.

A mixture of 5-((3-azidopropyl)oxy)acetyl-2,2-dimethyl-4,6-dione-1,3-dioxane (8.39 g, 29.4 mmol) and 3-hydroxypropionitrile (4.48 g, 63.0 mmol) in 25 mL of dry toluene were heated at reflux temperature for 1 hour. The solvent was removed in vacuo, the residue was charged with 35 mL of EtOH and 2.72 g of $NH_4OAc$ (35.3 mmol) and heated at reflux temperature for 20 minutes. The crude reaction mixture was divided into aliqoutes and used in the next step without any further purification or characterization.

5-Acetyl-2-((3-azidopropyl)oxy)methyl-3-(2-cyanoethoxy)carbonyl-1,4-dihydro-6-methyl-4-(4-nitro) phenylpyridine.

A solution of 2-cyanoethyl 3-Amino-4-((3-azidopropyl) oxy)crotonate (4.94 g, 19.6 mmol), 3-(4-nitrophenyl) methylenepentane-2,4-dione (4.57 g, 19.6 mmol) in 20 mL of EtOH were heated at reflux temperature for 2.5 hours. The solvent was removed in vacuo, and the crude product was chromatographed on 500 g of silica packed with 50% EtoAc-hexane. The column was eluted with increasing amounts of EtOAc (2 L/10% change) to give 7.21 g of the title compound. Spectral analysis showed the presence of impurities and 3-hydroxypropionitrile in the chromatographed product. This was used in the next deprotection step without any further purification.

5-Acetyl-2-((3-azidopropyl)oxy)methyl-1,4-dihydro-6-methyl-4-(4-nitro)phenylpyridine-3-carboxylic Acid.

A solution of 5-acetyl-2-((3-azidopropyl)oxy)methyl-3-(2-cyanoethoxy)carbonyl-1,4-dihydro-6-methyl-4-(4-nitro)

phenylpyridine (7.21 g, containing impurities), NaOH (620 mg, 15.5 mmol) in a mixture of dioxane-water (75 mL, 2:1) were stirred at room temperature for 0.5 hours. The solvent was removed in vacuo, the residue was partitioned between water (50 mL) and EtOAc (50 mL), separated, and the EtOAc wash was extracted with water (2×20 mL). The combined water extracts were acidified with concentrated HCl (pH=2–3). The precipitated oil solidified on standing. The solids were precipitated from MeOH—$H_2O$, filtered, and air dried to give 2.72 g (33% from the Meldrum's intermediate) of the title compound as a yellow solid: mp 100° C. (decomp.). The product was used in the next step after spectral characterization.

5-Acetyl-2-((3-azidopropyl)oxy)methyl-1,4-dihydro-6-methyl-4-(4-nitro)phenyl-3-(N-(3-(4,4-diphenylpiperidin-1-yl)propyl))carboxamidopyridine.

A mixture of 5-acetyl-2-((3-azidopropyl)oxy)methyl-1,4-dihydro-6-methyl-4-(4-nitro)phenylpyridine-3-carboxylic acid (416 mg, 1.00 mmol), 1-(3-amino)propyl-4,4-diphenylpiperidine (353 mg, 1.2 mmol), DCC 619 mg, 3.00 mmol), and DMAP (134 mg, 1.10 mmol) in 15 mL of dry dichloromethane were stirred at room temperature for 2 days, diluted with 10 mL of EtOAc, filtered, and chromatographed on 400 g of silica packed with MeOH—EtOAc (1:10). The column was eluted with 1:10 (1 L), 1.5:10 (1 L), 2:10 (1 L), 2:8 (3 L), to give 410 mg (59%) of the title compound as a yellow solid: mp 72–80° C.; Anal. Calcd for $C_{39}H_{45}N_7O_5+1.5H_2O$: C, 65.16; H, 6.73; N, 13.64. Found: C, 65.23; H, 6.44; N, 13.70.

5-Acetyl-2-((3-aminopropyl)oxy)methyl-1,4-dihydro-6-methyl-4-(4-nitro)phenyl- 3-(N-(3-(4,4-diphenylpiperidin-1-yl)propyl))carboxamidopyridine.

To a solution of 5-acetyl-2-((3-azidopropyl)oxy)methyl-1,4-dihydro-6-methyl-4-(4-nitro)phenyl-3-(N-(3-(4,4-diphenylpiperidin-1-yl)propyl))carboxamido pyridine (338 mg, 0.489 mmol) in 20 mL of EtOAc at 0° C. was added 1M $(Me)_3P$ in THF (1.22 mL, 1.22 mmol), and water (88 mL, 4.89 mmol). The reaction mixture was stirred at room temperature for 2 hours, and the solvent was removed in vacuo. The crude product was chromatographed on 350 g of silica packed with $NH_3$ (2N in MeOH)—MeOH—$CHCl_3$ (1:2:10). The column was eluted with $NH_3$ (2N in MeOH)—MeOH—$CHCl_3$ (1:2:10) to give 240 mg (75%) of the desired product as a yellow solid: mp 80° C. (decomp.); Anal. Calcd for $C_{36}H_{47}N_5O_5+1.5H_2O$: C, 67.61; H, 7.27; N, 10.11. Found: C, 67.23; H, 7.14; N, 10.01.

EXAMPLE 237

5-Acetyl-2-((2-aminoethyl)oxy)methyl-1,4-dihydro-6-methyl-4-(4-nitro)phenyl-3-(N-(3-(4,4-diphenylpiperidin-1-yl)propyl))carboxamidopyridine (237).

5-Acetyl-2-((2-azidoethyl)oxy)methyl-1,4-dihydro-6-methyl-4-(4-nitro)phenylpyridine-3-carboxylic acid.

A mixture of 5-((2-azidoethyl)oxy)acetyl-2,2-dimethyl-4,6-dione-1,3-dioxane (1.36 g, 5.00 mmol) and 3-hydroxypropionitrile (711 mg, 10.0 mmol) in 10 mL of dry toluene were heated at reflux temperature for 1 hour, and cooled. The residue was charged with EtOH (10 mL) and ammonium acetate (424 mg, 5.50 mmol), heated at reflux temperature for 0.5 hour, and cooled. The reaction mixture was charged with 3-(4-nitrophenyl)methylenopentane-2,4-dione (1.28 g, 5.50 mmol), and heated at reflux temperature for 2.5 hours, and cooled. Sodium hydroxide (1.00 g, 25.0 mmol) in 5 mL of water was added to the reaction mixture and stirred at room temperature for 2 hours, and the solvent was removed in vacuo. To the residue was added water (10 mL), acidified with concentrated HCl (pH=2–3), extracted with MeOH—$CH_2Cl_2$ (1:9, 5×50 mL), dried ($MgSO_4$), and the solvent was removed in vacuo. The crude product was chromatographed on 400 g of silica packed with EtOAc-hexane (1:1). The column was eluted with 80% EtOAc-hexane (2 L), EtOAc (2 L), MeOH—EtOAc (2 L) to give a product which contained many impurities. The product was partitioned between EtOAc (2 mL) and 0.05N NaOH solution (2 mL), separated, and extracted with 3×2 mL 0.05N NaOH solution. The combined aqueous extracts were acidified with concentrated HCl (pH=2–3), extracted with 5×2 mL of dichloromethane, dried ($Na_2SO_4$), and the solvent was removed in vacuo to give 50 mg (3%) of the desired product as a yellow paste. The product was used in the next step without any further purification.

5-Acetyl-2-((2-azidoethyl)oxy)methyl-1,4-dihydro-6-methyl-4-(4-nitro)phenyl-3-(N-(3-(4,4-diphenylpiperidin-1-yl)propyl))carboxamidopyridine.

A mixture of 5-acetyl-2-((2-azidoethyl)oxy)methyl-1,4-dihydro-6-methyl-4-(4-nitro)phenylpyridine-3-carboxylic acid (50 mg, 0.125 mmol), 1-(3-amino)propyl-4,4-diphenylpiperidine (44 mg, 0.149 mmol), DCC (77 mg, 0.373 mmol), and DMAP (17 mg, 0.137 mmol) in 2 mL of dry dichloromethane were stirred at room temperature for 2 days, filtered, and chromatographed on 100 g of silica packed with MeOH—EtOAc (1:9). The column was eluted with MeOH—EtOAc (10% to 20%, 1 L/5% change) to give 36 mg (41%) of the title compound as a yellow solid: mp 80–90° C. The product was used in the next step after spectral characterization.

5-Acetyl-2-((2-aminoethyl)oxy)methyl-1,4-dihydro-6-methyl- 4-nitro)phenyl-3-(N-(3-(4,4-diphenylpiperidin-1-yl)propyl))carboxamidopyridine (237).

To a solution of 5-acetyl-2-((2-azidoethyl)oxy)methyl-1,4-dihydro-6-methyl-4-(4-nitro)phenyl-3-(N-(3-(4,4-diphenylpiperidin-1-yl)propyl))carboxamido pyridine (32 mg, 0.047 mmol) in 3 mL of 1:1 THF—EtOAc at 0° C. was added 1M $(Me)_3P$ in THF (0.118 mL, 0.118 mmol), and water (8.5 mL, 0.47 mmol). The reaction mixture was stirred at room temperature for 3 hours, and the solvent was removed in vacuo. The crude product was chromatographed on 100 g of silica packed with $NH_3$ (2N in MeOH)—MeOH—$CHCl_3$ (1:2:10). The column was eluted with $NH_3$ (2N in MeOH)—MeOH—$CHCl_3$ (1:2:10) to give 10 mg (46%) of the desired product as a yellow solid: mp 100° C. (decomp.); Anal. Calcd for $C_3H_{45}N_5O_5+0.5CHCl_3$: C, 64.99; H, 6.45; N, 9.84. Found: C, 64.81; H, 6.22; N, 9.92.

EXAMPLE 238

2-((3-Aminopropyl)oxy)methyl-5-carboxamido-1,4-dihydro-6-ethyl-4-(4-nitro)phenyl-3-(N-(3-(4,4-dipheylpiperidin-1-yl)propyl))carboxamidopyridine (238).

2-((3-Azidopropyl)oxy)methyl-6-ethyl-1,4-dihydro-3-(2-trimethylsilylethoxy)carbonyl-4-(4-nitro)phenylpyridine-5-carboxylic Acid.

A mixture of 5-((3-azidopropyl)oxy)acyl-2,2-dimethyl-4,6-dione-1,3-dioxane (33.8 g, 0.119 mol) and 2-trimethylsilylethanol (30.0 g, 0.254 mol) in 100 mL of dry toluene were heated at reflux temperature for 1 hour. The reaction mixture was cooled, and the solvent was removed in vacuo. The residue was taken up in 100 mL of EtOH, ammonium acetate (11.0 g, 0.142 mol) was added to the reaction mixture and heated at reflux temperature for 0.5 hour. The reaction mixture was divided into two aliquots and used in the next experiments. 2-Cyanoethyl 3-(4-nirophenyl) methyleno-3-oxopentanoate (17.0 g, 56.2 mmol) was added to one aliquot from above and heated at reflux temperature for 2.5 hours, and cooled. The solvent was removed in vacuo. The oil was taken up in 50 mL of MeOH and water was added to oiled out the product, which was taken up in 50 mL of dioxane and NaOH (2.61 g, 65.2 mmol) in 50 mL of water was added, stirred at room temperature for 0.5 hour, and the solvent was removed in vacuo. The residue was partitioned between $CH_2Cl_2$—EtOAc (1:2, 100 mL), and $H_2O$ (50 mL), separated, and extracted with water (50 mL) and 3×50 mL of water containing 2.61 g of NaOH. The combined aqueous extracts were acidified with concentrated HCl (pH=3–4), the precipitated oil was extracted with $CHCl_3$—EtOAc (2:1, 50×7 mL), the combined organic extracts were dried ($MgSO_4$) and the solvent was removed in vacuo. The crude product was chromatographed on 400 g of silica packed with EtOAc-hexane (1:4). The column was eluted with EtOAc-hexane (20%, 2 L; 30%, 1 L; 40%, 2 L) to afford 5.60 g (18%) of the desired product as a yellow solid: mp 110° C. (decomp.). The product was used in the next step after spectral characterization.

2-((3-Azidopropyl)oxy)methyl-5-carboxamido-6-ethyl-1,4-dihydro-3-(2-trimethylsilylethoxy)carbonyl-4-(4-nitro)phenylpyridine.

A mixture of 2-((3-azidopropyl)oxy)methyl-6-ethyl-1,4-dihydro-3-(2-trimethylsilylethoxy)carbonyl-4-(4-nitro)phenylpyridine-5-carboxylic acid (390 mg, 0.734 mmol), DCC (227 mg, 1.10 mmol), and DMAP (99 mg, 0.807 mmol) in 2.5 mL of dry dichloromethane were stirred at room temperature for 1.5 hours. Ammonia (58%, 443 mg, 7.34 mmol) was added to the reaction mixture and stirred at room temperature 24 hours. The reaction mixture was filtered and chromatographed on 200 g of silica packed with MeOH—EtOAc-hexane (1:70:70). The column was eluted with the same solvent to afford 355 mg (91%) of the desired product as a yellow solid: mp 85–87° C. The product was used in the next step after spectral characterization.

2-((3-Azidopropyl)oxy)methyl-5-carboxamido-6-ethyl-1,4-dihydro-4-(4-nitro)phenylpyridine-3-carboxylic Acid.

A solution of 3.24 mmol of tetrabutylammonium fluoride (1M) in 3.24 mL of THF was added, in one portion, to a stirred solution of 2-((3-azidopropyl)oxy)methyl-5-carboxamido-6-ethyl-1,4-dihydro-3-(2-trimethylsilylethoxy)carbonyl-4-(4-nitro)phenylpyridine (532 mg, 1.00 mmol) in 41 mL of DMSO. The resulting maroon solution was was stirred at room temperature for 1 hour, poured into 50 mL of 1N aqueous HCl solution, extracted with 50 mL and then with 3×20 mL of EtOAc. The combined EtOAc extracts were washed with water (3×20 mL), dried ($Na_2SO_4$), and the solvent was removed in vacuo. The crude product was chromatographed on 200 g of silica packed with 1% MeOH—EtOAc. The column was eluted with increasing amounts of MeOH (1% to 20%, 5%/2 L change) to give 160 mg (37%) of the desired product as a yellow solid: mp 138–143° C. The product was used in the next step after spectral characterization.

2-((3-Azidopropyl)oxy)methyl-5-carboxamido-1,4-dihydro-6-ethyl-4-(4-nitro)phenyl-3-(N-(3-(4,4-dipheylpiperidin-1-yl)propyl))carboxamidopyridine.

A mixture of 2-((3-azidopropyl)oxy)methyl-5-carboxamido-6-ethyl-1,4-dihydro-4-(4-nitro)phenylpyridine-3-carboxylic acid (40 mg, 0.093 mmol), DCC (38 mg, 0.186 mmol), and DMAP (9 mg, 0.074 mmol) in 3 mL of dry dichloromethane were stirred at room temperature for 1 hour. The reaction mixture was charged with 1-(3-amino)propyl-4,4-diphenylpiperidine (34 mg, 0.12 mmol) and stirred at room temperature for 18 hours. The reaction mixture was filtered, and the solvent was removed in vacuo. The crude product was chromatographed on 100 g of silica packed with MeOH—EtOAc (1:4). The column was eluted with the same solvent to afford 50 mg (76%) of the desired product as a yellow solid: mp 90–95° C. The product was used in the next step after spectral characterization.

2-((3-Aminopropyl)oxy)methyl-5-carboxamido-1,4-dihydro-6-ethyl-4-(4-nitro)phenyl-3-(N-(3-(4,4-dipheylpiperidin-1-yl)propyl))carboxamidopyridine (238).

To a solution of 2-((azidopropyl)oxy)methyl-5-carboxamido-1,4-dihydro-6-ethyl-4-(4-nitro)phenyl-3-(N-(3-(4,4-diphenylpiperidin-1-yl)propyl))carboxamidopyridine (45 mg, 0.064 mmol) in 3 mL of EtOAc at 0° C. was added 1M $(Me)_3P$ in THF (0.16 mL, 0.16 mmol), and water (12 mL, 0.64 mmol). The reaction mixture was stirred at room temperature for 4 hours, and the solvent was removed in vacuo. The crude product was chromatographed on 100 g of silica packed with $NH_3$ (2N in MeOH)—MeOH—$CHCl_3$ (1:2:12). The column was eluted with 750 mL of $NH_3$ (2N in MeOH)—MeOH—$CHCl_3$ (1:2:10) and 500 mL of $NH_3$ (2N in MeOH)—MeOH—$CHCl_3$ (1:2:10) to give 30 mg (69%) of the desired product as a yellow solid: mp 92° C. (decomp.); Anal. Calcd for $C_{39}H_{48}N_6O_5+0.8H_2O+0.8CH_2Cl_2$: C, 62.64; H, 6.76; N, 11.09. Found: C, 62.39; H, 6.73; N, 11.19.

EXAMPLE 239

5-Acetyl-2-((2-aminoethyl)oxy)methyl-1,4-dihydro-6-methyl-4-(3,4-methylenedioxy)phenyl-3-(N-(3-(4,4-dipheylpiperidin-1-yl)propyl))carboxamidopyridine (239).

3-(3,4-Methylenedioxyphenyl)methylenepentane-2,4-dione.

A mixture of pentane-2,4-dione (20.0 g, 200 mmol), 3,4-methylenedioxybenzaldehyde (32.2 g, 200 mmol), piperidine (1.98 mL, 20.0 mmol), and HOAc (1.20 mL, 20.0 mmol) in 200 mL of isopropanol were stirred at room temperature for 3 days (no precipitate). The solvent was remove in vacuo, and the crude product was heated to 50–70° C. under reduced pressure for 0.5 hours (no solids). The crude product was chromatographed on 900 g of silica packed with 10% EtOAc-hexane. The column was eluted with increasing amounts of EtOAc (10% to 30%, 2.5%/2 L change) to give 19.1 g (41%) of the desired product as a yellow solid: mp 79–80° C. The product was used in the next step after spectral characterization.

5-Acetyl-2-((2-azidoethyl)oxy)methyl-3-(2-cyanoethoxy)carbonyl-1,4-dihydro-6-methyl-4-(3,4-methylenedioxy)phenylpyridine.

A mixture of 5-((2-azidoethyl)oxy)acetyl-2,2-dimethyl-4,6-dione-1,3-dioxane (80%, 1.50 g, 4.42 mmol) and 3-hydroxypropionitrile (629 mg, 8.85 mmol) in 10 mL of dry toluene were heated at reflux temperature for 1.5 hours. The reaction mixture was cooled, and the solvent was removed in vacuo. The crude product was charged with ammonium acetate (477 mg, 6.19 mmol) and 10 mL of ethanol and heated at reflux temperature for 0.5 hour and cooled to room temperature. The reaction mixture was charged with 3-(3,4-methylenedioxyphenyl)methylenopentane-2,4-dione (1.44 g, 6.19 mmol) and heated at reflux temperature for 5 hours. The solvent was removed in vacuo, and the crude product was chromatographed on 750 g of silica. The column was eluted with EtOAc-hexane (1:4, 2 L; 1:3, 2 L; 1:2, 2 L; 1:1, 2 L; 2:1, 2 L) to give 353 mg of spectroscopically pure and 200 mg of slightly impure product for a combined yield of 25% as a yellow paste. The crude product was used in the next deprotection step after spectral characterization.

5-Acetyl-2-((2-azidoethyl)oxy)methyl-1,4-dihydro-6-methyl-4-(3,4-methylenedioxy)phenylpyridine-3-carboxylic Acid.

This product was obtained from deprotection of two batches of 5-acetyl-2-((2-azidoethyl)oxy)methyl-3-(2-cyanoethoxy)carbonyl-1,4-dihydro-6-methyl-4-(3,4-methylenedioxy)phenylpyridine obtained from the previous experiment (340 mg and 200 mg) and were combined after completion of the reaction. A mixture of 5-acetyl-2-((2-azidoethyl)oxy)methyl-3-(2-cyanoethoxy)carbonyl-1,4-dihydro-6-methyl-4-(3,4-methylenedioxy)phenylpyridine (340 mg, 0.750 mmol; 200 mg (60%), 0.200 mmol), 1N NaOH (1.12 mL; 0.40 mL) in a mixture of dioxane (3 mL; 3 mL) were stirred at room temperature for 1.5 hours. The two batches were concentrated in vacuo, the combined batches were dissolved in 40 mL of water, washed with dichloromethane (30 mL) and EtOAc (20 mL), acidified with 1N HCl solution (pH=4–5), and extracted with dichloromethane (2×50 mL). The combined dichloromethane extracts were washed with brine (40 mL), dried ($MgSO_4$), and the solvent was removed in vacuo to give 300 mg (25%) of the title compound as a yellow paste which solidified on standing: mp 120° C. (decomp.). The product was used in the next step after spectral characterization.

5-Acetyl-2-((2-azidoethyl)oxy)methyl-1,4-dihydro-6-methyl-4-(3,4-methylenedioxy)phenyl-3-(N-(3-(4,4-dipheylpiperidin-1-yl)propyl))carboxamidopyridine.

A solution of 5-acetyl-2-((2-azidoethyl)oxy)methyl-4-(3,4-methylenedioxy)phenyl-1,4-dihydro-6-methylpyridine-3-carboxylic acid (60 mg, 0.150 mmol), DCC (62 mg, 0.300 mmol), and DMAP (15 mg, 0.120 mmol) in 3 mL of dry dichloromethane were stirred at room temperature for 20 minutes. The reaction mixture was charged with 1-(3-amino)propyl-4,4-diphenylpiperidine (53 mg, 0.180 mmol) and the reaction mixture was stirred at room temperature for 16 hours. The reaction mixture was filtered, and the solvent was removed in vacuo. The crude product was chromatographed on 300 g of silica packed with MeOH—EtOAc (1:9). The column was eluted with MeOH—EtOAc (1:9, 1.5 L; 1:4, 1 L) to give 82 mg (81%) of the title compound as a yellow solid: mp 75° C. (decomp.); Anal. Calcd for $C_{39}H_{44}N_6O_5$+$0.3H_2O$+$0.3CH_2Cl_2$: C, 66.70; H, 6.44; N, 11.88. Found: C, 66.45; H, 6.15; N, 11.80.

5-Acetyl-2-((2-aminoethyl)oxy)methyl-1,4-dihydro-6-methyl-4-(3,4-methylenedioxy)phenyl-3-(N-(3-(4,4-dipheylpiperidin-1-yl)propyl))carboxamidopyridine (239).

To a solution of 5-acetyl-2-((2-azidoethyl)oxy)methyl-4-(3,4-methylenedioxy)phenyl-1,4-dihydro-6-methyl-3-(N-(3-(4,4-diphenylpiperidin-1-yl)propyl))carboxamidopyridine (66 mg, 0.098 mmol) in 3 mL of EtOAc at 0° C. was added 1M $(Me)_3P$ in THF (0.30 mL, 0.29 mmol), and water (18 mL, 0.98 mmol). The reaction mixture was stirred at room temperature for 4 hours, and the solvent was removed in vacuo. The crude product was chromatographed on 130 g of silica packed with $NH_3$ (2N in MeOH)—MeOH—$CHCl_3$ (1:2:12). The column was eluted with 750 mL of $NH_3$ (2N in MeOH)—MeOH—$CHCl_3$ (1:2:12) and 500 mL of $NH_3$ (2N in MeOH)—MeOH—$CHCl_3$ (1:2:10) to give 52 mg (82%) of the desired product as a yellow solid: mp 80° C. (decomp.); Anal. Calcd for $C_{39}H_{46}N_4O_5$+$0.5H_2O$+$0.5CH_2Cl_2$: C, 67.56; H, 6.89; N, 7.98. Found: C, 67.24; H, 6.85; N, 8.17.

EXAMPLE 240

3-(N-3(4-Ethoxycarbonyl-4-phenylpiperidin-1-yl)propyl)carboxamido-6-ethyl-1,4-dihydro-2-(methyloxy)methyl-4-(4-nitro)phenylpyridine-5-carboxylic Acid (240).

5-(2-Cyanoethoxy)carbonyl-3-(N-3-(4-ethoxycarbonyl-4-phenylpiperidin-1-yl)propyl)carboxamido-6-ethyl-1,4-dihydro-2-(methyloxy)methyl-4-(4-nitro)phenylpyridine.

A mixture of 35 mg of 5-(2 -cyanoethoxy)carbonyl-6-ethyl-1,4-dihydro-2-(methyloxy)methyl-4-(4-nitro)phenylpyridine-3-carboxylic acid (0.084 mmol), 35 mg of DCC (0.169 mmol), and 8.2 mg of DMAP (0.067 mmol) in 3 mL of dry dichloromethane were stirred at room temperature for 1 hour before addition of 32 mg of 1-(3-amino)propyl-4-ethoxycarbonyl-4-phenylpiperidine (0.109 mmol). The resulting mixture was stirred at room temperature for 16 hours. The reaction mixture was concentrated in vacuo, and the residue was chromatographed on 180 g of silica (MeOH—EtOAc, 1:9) to give 40 mg of the title compound as a yellow solid (70%): mp 55° C. (decomp.). The product was used in the next step after spectral characterization.

3-(N-3-(4-Ethoxycarbonyl-4-phenylpiperidin-1-yl)propyl)carboxamido-6-ethyl-1,4-dihydro-2-(methyloxy)methyl-4-(4-nitro)phenylpyridine-5-carboxylic Acid (240).

To a solution of 5-(2-cyanoethoxy)carbonyl-3-(N-3-(4-ethoxycarbonyl-4-phenylpiperidin-1-yl)propyl)carboxamido-6-ethyl-1,4-dihydro-2-(methyloxy)methyl-4-(4-nitro)phenylpyridine (35 mg, 0.051 mmol in 3 mL of dioxane was added aqueous 1M NaOH (56 mL, 0.056 mmol). After 1 hour, another equivalent of NaOH was added to the reaction mixture and stirred for 1.5 hours. The solvent was removed in vacuo, the residue was dissolved in water (8 mL), washed with dichloromethane (3 mL), and ethyl acetate (3 mL). The aqueous extract was acidified with aqueous 1N HCl solution (pH=3), and extracted with dichloromethane (3×15 mL). The combined dichloromethane extracts were dried ($MgSO_4$), and the solvent was removed in vacuo to give 11 mg (34%) of the title compound as a yellow solid: mp 116–126° C.; Anal. Calcd for $C_{34}H_{42}N_4O_8$+$0.8EtOAc$+$0.4CH_2Cl_2$: C, 61.10; H, 6.71; N, 7.58. Found: C, 61.02; H, 6.95; N, 7.26.

EXAMPLE 241

5-Acetyl-2-((3-aminopropyl)oxy)methyl-1,4-dihydro-3-(N-(3-(4-methoxycarbonyl-4-phenylpiperidin-1-yl)propyl))carboxamido-6-methyl-4-(4-nitro)phenylpyridine (241).

5-Acetyl-2-((3-azidopropyl)oxy)methyl-1,4-dihydro-3-(N-(3-(4-methoxycarbonyl-4-phenylpiperidin-1-yl)propyl))carboxamido-6-methyl-4-(4-nitro)phenylpyridine.

A mixture of 5-acetyl-2-((3-azidopropyl)oxy)methyl-1,4-dihydro-6-methyl-4-(4-nitro)phenylpyridine-3-carboxylic acid (115 mg, 0.278 mmol), and DMAP (27 mg, 0.222 mmol) in 10 mL of dry dichloromethane were stirred at room temperature for 2 hours. N-3-Aminopropyl-4-methoxycarbonyl-4-phenylpiperidine (100 mg, 0.362 mmol) was added to the reaction mixture and stirred at room temperature for 2 days. The reaction mixture was filtered, solvent was removed in vacuo, and the crude product was chromatographed on 350 g of silica packed with MeOH—EtOAc (1:9). The column was eluted with the same solvent to give 124 mg (66%) of the title compound as a yellow solid: mp 54° C. (decomp.); Anal. Calcd for $C_{35}H_{43}N_7O_7$: C, 62.38; H, 6.45; N, 14.54. Found: C, 61.93; H, 6.54; N, 14.19.

5-Acetyl-2-((3-aminopropyl)oxy)methyl-1,4-dihydro-3-(N-(3-(4-methoxycarbonyl-4-phenylpiperidin-1-yl)propyl))carboxamido-6-methyl-4-(4-nitro)phenylpyridine (241).

To a solution of 5-acetyl-2-((azidopropyl)oxy)methyl-1,4-dihydro-3-(N-(3-(4-methoxycarbonyl-4-phenylpiperidin-1-yl)propyl))carboxamido-6-methyl-4-(4-nitro)phenylpyridine (95 mg, 0.141 mmol) in 4 mL of EtOAc at 0° C. was added 1M $(Me)_3P$ in THF (0.36 mL, 0.35 mmol), and water (25 mL, 1.41 mmol). The reaction mixture was stirred at room temperature for 5 hours, and the solvent was removed in vacuo. The crude product was chromatographed on 100 g of silica packed with $NH_3$ (2N in MeOH)—MeOH—$CHCl_3$ (1:2:12). The column was eluted with $NH_3$ (2N in MeOH)—MeOH—$CHCl_3$ (1:2:12) to give 72 mg (79%) of the desired product as a yellow solid: mp 70° C. (decomp.); Anal. Calcd for $C_{35}H_{45}N_5O_7+1.0H_2O+0.1CH_2Cl_2$: C, 62.52; H, 7.06; N, 10.39. Found: C, 62.61; H, 6.96; N, 10.34.

EXAMPLE 242

5-Acetyl-2-((2-aminoethyl)oxy)methyl-4-(4-fluoro)phenyl-1,4-dihydro-6-methyl-3-(N-(3-(4,4-diphenylpiperidin-1-yl)propyl))carboxamidopyridine (242).

3-(4-Fluorophenyl)methylenopentane-2,4-dione.

A mixture of pentane-2,4-dione (20.0 g, 200 mmol), 4-fluorobenzaldehyde (24.8 g, 200 mmol), piperidine (1.95 mL, 20.0 mmol), and HOAc (1.20 mL, 20.0 mmol) in 100 mL of isopropanol were heated at reflux temperature for 5 minutes, and then at room temperature for 24 hours. The reaction mixture was cooled to −78° C., filtered, and the solids were recrystallized from a mixture of $CH_2Cl_2$-hexane to give 35.2 g of 3-(4-fluorophenyl)methylenopentane-2,4-dione as a yellow crystalline solid: mp 34–35° C.; Anal. Calcd for $C_{12}H_{11}F_1O_2$: C, 69.89; H, 5.38. Found: C, 69.70; H, 5.38.

5-Acetyl-2-((2-asidoethyl)oxy)methyl-3-(2-cyanoethoxy)carbonyl-4-(4-fluoro)phenyl-1,4-dihydro-6-methylpyridine.

A mixture of 5-((2-azidoethyl)oxy)acetyl-2,2-dimethyl-4,6-dione-1,3-dioxane (1.29 g, 3.54 mmol), 3-hydroxypropionitrile (503 mg, 7.08 mmol) in 10 mL of dry toluene were heated at reflux temperature for 1.5 hours. The solvent was removed in vacuo, and the residue was dissolved in 10 mL of ethanol followed by addition of ammonium acetate (382 mg, 4.96 mmol). The reaction mixture was heated at reflux temperature for 1.5 hours, cooled, 3-(4-fluorophenyl)methylenopentane-2,4-dione (1.0 g, 4.96 mmol) was added to the reaction mixture, and heated at reflux temperature for 4 hours. Additional 3-(4-fluorophenyl)methylenopentane-2,4-dione (0.4 g) was added to the reaction mixture and heated at reflux temperature for 3 hours. The solvent was removed in vacuo, and the crude product was chromatographed on 300 g of silica. The column was eluted with EtOAc-hexane (1:2.5, 1 L; 1:2, 2 L; and 1:1, 0.5 L) to give 520 mg of the title compound (48%) as a yellow paste. The product was used in the next step after spectral characterization.

5-Acetyl-2-((2-azidoethyl)oxy)methyl-4-(4-fluoro)phenyl-1,4dihydro-6-methylpyridine-3-carboxylic Acid.

A mixture of 5-acetyl-2-((azidoethyl)oxy)methyl-3-(2-cyanoethoxy)carbonyl-4-(4-fluoro)phenyl-1,4-dihydro-6-methylpyridine (500 mg, 1.17 mmol), 1.76 mL of 1N NaOH solution (1.76 mmol), and 4 mL of dioxane were stirred at room temperature for 2 hours. The solvent was removed in vacuo, the residue dissolved in 30 mL of water, washed #with 2×15 mL of dichloromethane, 10 mL of EtOAc, acidified with 1N HCl solution (pH=4), and extracted with 3×25 mL of dichloromethane. The combined dichloromethane extracts were dried ($Na_2SO_4$), and the solvent was removed in vacuo to give 255 mg of the desired acid (40%) as a yellow solid: mp 100° C. (decomp.). The product was used in the next step after spectral characterization.

5-Acetyl-2-((2-azidoethyl)oxy)methyl-4-(4-fluoro)phenyl-1,4dihydro-6-methyl-3-(N-(3-(4,4-diphenylpiperidin-1-yl)propyl))carboxamidopyridine.

A solution of 5-acetyl-2-((2-azidoethyl)oxy)methyl-4-(4-fluoro)phenyl-1,4-dihydro-6-methylpyridine-3-carboxylic acid (60 mg, 0.161 mmol), DCC (66 mg, 0.321 mmol), and DMAP (16 mg, 0.129 mmol) in 4 mL of dry dichloromethane were stirred at room temperature for 2 hours followed by addition of 1-(3-amino)propyl-4,4-diphenylpiperidine (56.9 mg, 0.193 mmol). The resulting mixture was stirred at room temperature for 18 hours. The reaction mixture was filtered, and the solvent was removed in vacuo. The crude product was chromatographed on 50 g of silica. The column was eluted with MeOH—EtOAc (1:9) to give 70 mg of the desired product (67%) as a yellow solid: mp 68° C. (decomp.); Anal. Calcd for $C_{38}H_{43}N_6O_3F_1+1.0H_2O$: C, 68.24; H, 6.78; N, 12.57. Found: C, 68.43; H, 6.60; N, 12.46.

5-Acetyl-2-((2-aminoethyl)oxy)methyl-4-(4-fluoro)phenyl-1,4dihydro-6-methyl-3-(N-(3-(4,4-diphenylpiperidin-1-yl)propyl))carboxamidopyridine (242).

To a solution of 5-acetyl-2-((2-azidoethyl)oxy)methyl-4-(4-fluoro)phenyl-1,4-dihydro-6-methyl-3-(N-(3-(4,4-diphenylpiperidin-1-yl)propyl))carboxamidopyridine (48 mg, 0.074 mmol) in 3 mL of EtOAc at 0° C. was added 1 M $(Me)_3P$ in THF (0.19 mL, 0.19 mmol), and water (13 mL, 0.74 mmol). The reaction mixture was stirred at room temperature for 4 hours, and the solvent was removed in vacuo. The crude product was chromatographed on 100 g of silica packed with $NH_3$ (2N in MeOH)—MeOH—$CHCl_3$ (1:2:10). The column was eluted with $NH_3$ (2N in MeOH)—MeOH—$CHCl_3$ (1:2:10) to give 38 mg (82%) of the desired product as a yellow solid: mp 75° C. (decomp.); Anal. Calcd for $C_{38}H_{45}N_4O_3F_1+1.1CH_2Cl_2$: C, 65.39; H, 6.62; N, 7.80. Found: C, 65.01; H, 6.82; N, 7.85.

EXAMPLE 243

5-Carboxamido-3-(N-(3-(4-ethoxycarbonyl-4-phenylpiperidin-1-yl)propyl))carboxamido-2-((2,2,2-trifluoroethyl)oxy)methyl-1,4dihydro-6-methyl-4-(4-nitro)phenylpyridine (243).

A mixture of 5-carboxamido-2-((2,2,2-trifluoroethyl)oxy)methyl-1,4-dihydro-6-methyl-4-(4-nitro)phenylpyridine-3-carboxylic acid (45 mg, 0.109 mmol), DCC (45 mg, 0.218 mmol), and DMAP (11 mg, 0.087 mmol) in 10 mL of dry dichloromethane were stirred at room temperature for 45 minutes. 1-(3-Amino)propyl-4-ethoxycarbonyl-4-phenylpiperidine (41 mg, 0.140 mmol) was added to the reaction mixture and stirred at room temperature for 17 hours. The reaction mixture was filtered, the solvent was removed in vacuo, and the crude product was chromatographed on 200 g of silica packed with MeOH—EtOAc (1:4). The column was eluted with the same solvent to give 26 mg (47%) of the title compound as a yellow solid: mp 91° C. (decomp.); Anal. Calcd for $C_{34}H_{40}N_5F_3O_7+0.3CHCl_3$: C, 56.96; H, 5.61; N, 9.68. Found: C, 56.94; H, 5.73; N, 9.61.

EXAMPLE 244

5-Acetyl-2-((2-aminoethyl)oxy)methyl-3-(N-(3-(4-ethoxycarbonyl4-phenylpiperidin-1-yl)propyl))carboxamido-1,4-dihydro-6-methyl-4-(3,4-methylenedioxy)phenylpyridine (244).

5-Acetyl-2-((2-azidoethyl)oxy)methyl-3-(N-(3-(4-ethoxycarbonyl-4phenylpiperidin-1-yl)propyl))carboxamido-4-(3,4-methylenedioxy)phenyl-1,4-dihydro-6-methylpyridine.

A solution of 5-acetyl-2-((2-azidoethyl)oxy)methyl-4-(3,4-methylenedioxy)phenyl-1,4-dihydro-6-methylpyridine-3- carboxylic acid (60 mg, 0.150 mmol), DCC (62 mg, 0.300 mmol), and DMAP (15 mg, 0.120 mmol) in 3 mL of dry dichloromethane were stirred at room temperature for 2 hours. The reaction mixture was charged with 1-(3-amino)propyl-4-ethoxycarbonyl-4-phenylpiperidine (57 mg, 0.195 mmol) and the reaction mixture was stirred at room temperature for 16 hours. The reaction mixture was filtered, and the solvent was removed in vacuo. The crude product was chromatographed on 180 g of silica packed with MeOH—EtOAc (1:9). The column was eluted with the same solvent to give 62 mg (62%) of the title compound as a yellow solid: mp 55° C. (decomp.); Anal. Calcd for $C_{36}H_{444}N_6F_3O_7$+1.0$H_2O$+0.5EtOAc: C, 62.11; H, 6.86; N, 11.44. Found: C, 62.06; H, 6.48; N, 11.45.

5-Acetyl-2-((2-aminoethyl)oxy)methyl-3-(N-(3-4-ethoxycarbonyl-4-phenylpiperidin-1-yl)propyl))carboxamido-1,4-dihydro-6-methyl-4-(3,4-methylenedioxy)phenylpyridine (244).

To a solution of 5-acetyl-2-((2-azidoethyl)oxy)methyl-3-(N-(3-(4-ethoxycarbonyl-4-phenylpiperidin-1-yl)propyl)) carboxamido-4-(3,4-methylenedioxy)phenyl-1,4-dihydro-6-methylpyridine (45 mg, 0.067 mmol) in 3 mL of EtOAc at 0° C. was added 1M $(Me)_3P$ in THF (0.17 mL, 0.167 mmol), and water (12 mL, 0.67 mmol). The reaction mixture was stirred at room temperature for 3.5 hours, and the solvent was removed in vacuo. The crude product was chromatographed on 100 g of silica packed with $NH_3$ (2N in MeOH)—MeOH—$CHCl_3$ (1:2:10). The column was eluted with $NH_3$ (2N in MeOH)—MeOH—$CHCl_3$ (1:2:10) to give 31 mg (72%) of the desired product as a yellow solid: mp 55° C. (decomp.); Anal. Calcd for $C_{36}H_{46}N_4O_7$+1.0$H_2O$+0.3$CHCl_3$: C, 62.23; H, 6.95; N, 8.00. Found: C, 62.14; H, 6.85; N, 7.78.

EXAMPLE 245

5-Acetyl-2-((2-aminoethyl)oxy)methyl-4-(4-fluoro)phenyl-1,4-dihydro-3-(N-(3-(4-methoxycarbonyl-4-phenylpiperidin-1-yl)propyl))carboxamido-6-methylpyridine (245).

5-Acetyl-2-((2-azidoethyl)oxy)methyl-4-(4-fluoro)phenyl-1,4-dihydro-3-(N-(3-(4-methoxycarbonyl-4-phenylpiperidin-1-yl)propyl))carboxamido-6-methylpyridine.

A solution of 5-acetyl-2-((2-azidoethyl)oxy)methyl-4-(4-fluoro)phenyl-1,4-dihydro-6-methylpyridine-3-carboxylic acid (50 mg, 0.134 mmol), DCC (55 mg, 0.268 mmol), and DMAP (13 mg, 0.107 mmol) in 4 mL of dry dichloromethane were stirred at room temperature for 2 hours followed by addition of 1-(3-amino)propyl-4-methoxycarbonyl-4-phenylpiperidine (48 mg, 0.174 mmol). The resulting mixture was stirred at room temperature for 2 days. The reaction mixture was filtered, and the solvent was removed in vacuo. The crude product was chromatographed on 200 g of silica. The column was eluted with MeOH—EtOAc (1:9) to give 68 mg of the desired product (80%) as a yellow solid: mp 48° C. (decomp.); Anal. Calcd for $C_{38}H_{43}N_6O_3F_1$+0.3$CHCl_3$: C, 61.62; H, 6.23; N, 12.57. Found: C, 61.75; H, 6.47; N, 12.53.

5-Acetyl-2-((2-aminoethyl)oxy)methyl-4-(4-fluoro)phenyl-1,4-dihydro-3-(N-3-(4-methoxycarbonyl-4-phenylpiperidin-1-yl)propyl)carboxamido-6-methylpyridine (245).

To a solution of 5-acetyl-2-((2-azidoethyl)oxy)methyl-4-(4-fluoro)phenyl-1,4-dihydro-3-(N-3-(4-methoxycarbonyl-4-phenylpiperidin-1-yl)propyl)carboxamido-6-methylpyridine (52 mg, 0.0823 mmol) in 3 mL of EtOAc at 0° C. was added 1M $(Me)_3P$ in THF (0.21 mL, 0.206 mmol), and water (15 mL, 0.823 mmol). The reaction mixture was stirred at room temperature for 3.5 hours, and the solvent was removed in vacuo. The crude product was chromatographed on 100 g of silica packed with $NH_3$ (2N in MeOH)—MeOH—$CHCl_3$ (1:2:20). The column was eluted with $NH_3$ (2N in MeOH)—MeOH—$CHCl_3$ (1:2:20) to give 40 mg (85%) of the desired product as a yellow solid: mp 54° C. (decomp.); Anal. Calcd for $C_{31}H_{43}N_4O_5F_1$+0.8EtOAc+0.8$CHCl_3$: C, 57.06; H, 6.87; N, 7.61. Found: C, 57.36; H, 6.30; N, 7.40.

EXAMPLE 246

6-Ethyl-1,4-dihydro-5-(2-hydroxyethoxycarbonyl)-2-(methyloxy)methyl-4-(4-nitro)phenyl-3-(N-(3-(4,4-diphenylpiperidin-1-yl)propyl))carboxamidopyridine (246).

A solution of 50 mg of 6-ethyl-1,4-dihydro-2-(methyloxy)methyl-4-(4-nitro)phenyl-3-(N-(3-(4,4-diphenylpiperidin-1-yl)propyl))carboxamidopyridine-5-carboxylic acid (0.078 mmol), 30 mg of DMAPECD (0.157 mmol), and DMAP (19 mg, 0.157 mmol) in 3 mL of dry dichloromethane were stirred at room temperature for 2 hours before addition of ethyleneglycol (24 mg, 0.39 mmol). The reaction mixture was heated at reflux temperature for 17 hours. The reaction mixture was cooled, washed sequentially with saturated $NH_4Cl$ solution (2×5 mL), aqueous 0.1N HCl solution (3×5 mL), brine (5 mL), dried ($Na_2SO_4$), and the solvent was removed under reduced pressure. The crude product was chromatographed on 220 g of silica packed with $NH_3$ (2N in MeOH)—MeOH—$CHCl_3$ (1:2:50). The column was eluted with $NH_3$ (2N in MeOH)—MeOH—$CHCl_3$ (0.5 L of 1:2:30) to give 38 mg (75%) of the desired product as a yellow solid: mp 73° C.(decomp.); Anal. Calcd for $C_{39}H_{46}N_4O_7$+0.5 $H_2O$: C, 67.71; H, 6.85; N, 8.10. Found: C, 67.64; H, 6.96; N, 7.81.

EXAMPLE 247

6-Ethyl-1,4-dihydro-5-N-((2-methoxy)ethyl)carboxamido-2-(methyloxy)methyl-4-(4-nitro)phenyl-3-(N-(3-(4,4-diphenylpiperidin-1-yl)propyl))carboxamidopyridine (247).

A solution of 50 mg of 6-ethyl-1,4-dihydro-2-(methyloxy)methyl-4-(4-nitro)phenyl-3-(N-(3-(4,4-diphenylpiperidin-1-yl)propyl))carboxamidopyridine-5-carboxylic acid (0.078 mmol), 30.1 mg of DMAPECD (0.157 mmol), DMAP (19.2 mg, 0.157 mmol), and 2-aminoethylmethylether (29 mg, 0.390 mmol) in 3 mL of dry dichloromethane were heated at reflux temperature for 20 hours. The reaction mixture was cooled, washed sequentially with aqueous 0.1N HCl solution (3×5 mL), brine (5 mL), dried ($Na_2SO_4$), and the solvent was removed under reduced pressure. The crude product was chromatographed on 220 g of silica packed with $NH_3$ (2N in MeOH)—MeOH—$CHCl_3$ (1:2:50). The column was eluted with $NH_3$ (2N in MeOH)—MeOH—$CHCl_3$ (1:2:50) to give 38 mg (70%) of the desired product as a yellow solid: mp 70° C. (decomp.); Anal. Calcd for $C_{40}H_{49}N_5O_6$: C, 69.03; H, 7.11; N, 10.06. Found: C, 69.00; H, 7.27; N, 9.97.

EXAMPLE 248

6-Ethyl-1,4-dihydro-2-((methyl)oxy)methyl-5-N-(morpholin-4yl)carboxamido-4-(4-nitro)phenyl-3-(N-(3-(4,4-diphenylpiperidin-1-yl)propyl))carboxamidopyridine (248).

A solution of 60 mg of 6-ethyl-1,4-dihydro-2-(methyloxy)methyl-4-(4-nitro)phenyl-3-(N-(3-(4,4-diphenylpiperidin-1- yl)propyl))carboxamidopyridine-5-carboxylic acid ((0.094 mmol), 36 mg of DMAPECD (0.188 mmol), 29 mg of DMAP (0.235 mmol), and 14.4 mg of 4-aminomorpholine (0.141 mmol) in 3 mL of dry dichloromethane were heated at reflux temperature for 15 hours. The reaction mixture was cooled to room temperature, sequentially washed with aqueous 0.1N HCl solution (4×3 mL), brine (mL), dried ($Na_2CO_3$), and the solvent was removed in vacuo. The residue was chromatographed on 50 g of silica packed with $NH_3$ (2N in MeOH)—MeOH—$CHCl_3$ (1:2:50). The column was eluted with $NH_3$ (2N in MeOH)—MeOH—$CHCl_3$ (0.5 L of 1:2:50 and 1 L of 1:2:40) to give 34 mg (50%) of the desired product as a yellow solid: mp 112° C. (decomp.); Anal. Calcd for $C_{41}H_{50}N_6O_6+1.0H_2O$: C, 66.47; H, 7.07; N, 11.34. Found: C, 66.29; H, 6.94; N, 11.26.

EXAMPLE 249

1,4-Dihydro-3-methoxycarbonyl-2,6-dimethyl-4-(3-nitrophenyl)-5-(N-(3-(4,4-diphenylpiperidin- 1-yl)propyl) carboxamido)-pyridine (249).

A solution of acetoacetic acid N-(3-(4,4-diphenylpiperidin-1-yl)propyl)amide (200 mg, 0.528 mmol), methyl 3-aminocrotonate (62.7 mg, 0.528 mmol), and 3-nitrobenzaldehyde (79.8 mg, 0.528 mmol) in 2-propanol (5 ml) was refluxed for 96 hours. Then the solvent was removed, and the residue was flash chromatographed (Hexane:EtOAc:$Et_3$N=50:50:3; Hexane:EtOAc:$Et_3$N=10:90:6; and EtOAc:$Et_3$N=10:1) to give a yellow solid. It was recrystallized from EtOAc/Hexane to afford yellow crystals (96 mg, 30%): mp 192–193° C. Anal. Calcd for $C_{36}H_{40}N_4O_5$: C, 70.00, H, 6.69, N, 9.06. Found. C, 70.24, H, 6.31, N, 8.84.

EXAMPLE 250

1,4-Dihydro-3-methoxycarbonyl-2,6-dimethyl-4-(3,4-methylenedioxyphenyl)-5-(N-(3-(4-phenylpiperidin-1-yl) propyl)carboxamido)-pyridine (250).

N-(3-(4-Phenylpiperidin-1-yl)propyl)acetoacetamide (200 mg, 0.66 mmol) was mixed with methyl 3-aminocrotonate (76 mg, 0.66 mmol) and piperonal (99 mg, 0.66 mmol) in 1-butanol (5 ml). The mixture was heated at reflux temperature for 4 days and then concentrated to give a brown oil. It was dissolved in chloroform and flash chromatographed over silica gel (15 g) eluting with EtOAc/$Et_3$N (20:1) to afford a yellow oil (54 mg, 15% yield). Recrystallization from EtOAc/Hexane gave yellow crystals (19 mg): mp 161–165° C. Anal. Calcd for $C_{31}H_{37}N_3O_5$: C, 70.03; H, 7.01; N, 7.90. Found: C, 69.87; H, 7.07; N, 7.62.

EXAMPLE 251

5-Carboxamido-1,4-dihydro-2,6-dimethyl-4-(4-nitrophenyl)-3-{N-[3-(piperidin-1-yl)propyl]} carboxamidopyridine (251).

To a mixture of 5-carboxamido-1,4-dihydro-2,6-dimethyl-4-(4-nitrophenyl)pyridine-3-carboxylic acid (212 mg, 0.668 mmol, 1.00 equiv), 1-(3-dimethylaminopropyl)-3-ethylcarbodiimide hydrochloride (195 mg, 1.02 mmol, 1.52 equiv) and 4-dimethylaminopyridine (91 mg, 0.74 mmol, 1.1 equiv) in anhydrous $CH_2Cl_2$ (3 mL) was added a solution of 1-(3-amino)propylpiperidine (115.9 mg, 0.815 mmol, 1.22 equiv, Bates, R. J.; Cymerman-Craig, J.; Moyie, M.; Yong, T. J. *J. Chem. Soc.* 1956, 388). in $CH_2Cl_2$ (3.7 mL), and the mixture was stirred at room temperature under argon for 20 hours. Aqueous NaOH (1M, 50 mL) was added and the mixture was extracted with $CH_2Cl_2$-isopropanol (3:1, 3×50 mL). The combined organic solutions were dried over $Na_2SO_4$ and concentrated to give 635.7 mg of dark brown oil. This oil was purified by flash chromatography ($SiO_2$, $Cl_3CCH_3$—MeOH-methanolic ammonia (2M) 70:15:15) to afford 385 mg of a yellow oil. This yellow oil was further purified by HPLC with a 25×300 mm Waters NovaPak 6 µm $SiO_2$ radial compression column and UV detection at 252 nm. The column was eluted with the following gradient at 25 mL/min:initial conditions $CH_2Cl_2$: ($CH_2Cl_2$—MeOH—$Et_2$NH 93.8:6:0.2) 50:50, duration 30 minutes, ramped to 13:87 over 30 minutes. The pure product was obtained as a yellow solid, 167.4 mg (56%): mp 170° C.; Anal. Calcd for $C_{23}H_{31}N_5O_4 \cdot 0.1$ $CH_2Cl_2$: C, 61.65; H, 6.99; N, 15.56. Found: C, 61.61; H, 7.16; N, 15.62.

Binding affinities were measured for selected compounds of the invention at six cloned human alpha-1 and alpha-2 receptor subtypes, as well as at the L-type calcium channel. The protocols for these experiments are given below. Table 1 shows the results.

Protocol for the Determination of the Potency of $\alpha_1$ Antagonists.

The activity of compounds at the different human receptors was determined in vitro using cultured cell lines that selectively express the receptor of interest. These cell lines were prepared by transfecting the cloned cDNA or cloned genomic DNA or constructs containing both genomic DNA and cDNA encoding the human α-adrenergic receptors as follows:

$\alpha_{1A}$ Human Adrenergic Receptor.

The entire coding region of α1A (1719 bp), including 150 basepairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequence were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1A/EXJ (expression vector containing the α1A receptor gene) and the plasmid pGCcos3neo (plasmid containing the aminoglycoside transferase gene) into LM(tk⁻), CHO, and NIH3T3 cells, using calcium phosphate technique. The cells were grown, in a controlled environment (37° C., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 µg/ml streptomycin sulfate. Stable clones were then selected for resistance to the antibiotic G-418 (1 mg/ml), and membranes were harvested and assayed for their ability to bind [$^3$H]prazosin as described below (see "Radioligand Binding assays").

$\alpha_{1B}$ Human Adrenergic Receptor.

The entire coding region of α1B (1563 bp), including 200 basepairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem CDNA fragment from λ ZapII into the expression vector. Stable cell lines were selected as described above.

$\alpha_{1C}$ Human Adrenergic Receptor.

The entire coding region of α1C (1401 bp), including 400 basepairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partial overlapping fragments: a 5' 0.6 kb HincII genomic clone, a central 1.8 EcoRI hippocampal cDNA clone, and a 3' 0.6 Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above.

Radioligand Binding Assays.

Transfected cells from culture flasks were scraped into 5 ml of 5 mM Tris—HCl, 5 mM EDTA, pH 7.5, and lysed by sonication. The cell lysates were centrifuged at 1000 rpm for 5 min at 4° C., and the supernatant was centrifuged at 30,000×g for 20 min at 4° C. The pellet was suspended in 50 mM Tris—HCl, 1 mM $MgCl_2$, and 0.1% ascorbic acid at pH 7.5. Binding of the α1 antagonist [$^3$H]prazosin (0.5 nM, specific activity 76.2 Ci/mmol) to membrane preparations of LM(tk-) cells was done in a final volume of 0.25 ml and incubated at 37° C. for 20 min. Nonspecific binding was determined in the presence of 10 μM phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

$α_2$ Human Adrenergic Receptors.

To determine the potency of $α_1$ antagonists at the $α_2$ receptors, LM(tk-) cell lines stably transfected with the genes encoding the $α_{2A}$, $α_{2B}$, and $α_{2C}$ receptors were used. The cell line expressing the $α_{2A}$ receptor is designated L-$α_{2A}$, and was deposited on Nov. 6, 1992 under ATCC Accession No. CRL 11180. The cell line expressing the $α_{2B}$ receptor is designated L-NGC-$α_{2B}$, and was deposited on Oct. 25, 1989 under ATCC Accession No. CRL10275. The cell line expressing the $α_{2C}$ receptor is designated L-$α_{2C}$, and was deposited on Nov. 6, 1992 under ATCC Accession No. CRL-11181. Cell lysates were prepared as described above (see Radioligand Binding Assays), and suspended in 25 mM glycylglycine buffer (pH 7.6 at room temperature). Equilibrium competition binding assay were performed using [3H]rauwolscine (0.5 nM), and nonspecific binding was determined by incubation with 10 μM phentolamine. The bound radioligand was separated by filtration through GF/B filters using a cell harvester.

Determination of the Activity of $α_1$ Antagonists at Calcium Channels.

The potency of $α_1$ antagonists at calcium channels was determined in competition binding assays of [3H] nitrendipine to membrane fragments of rat cardiac muscle, essentially as described by Glossman and Ferry (Methods in Enzymology 109:513–550, 1985). Briefly, the tissue was minced and homogenized in 50 mM Tris—HCl (pH 7.4) containing 0.1 mM phenylmethylsulfonyl fluoride. The homogenates were centrifuged at 1000 g for 15 minutes, the resulting supernatant was centrifuged at 45,000 g for 15 minutes. The 45,000 g pellet was suspended in buffer and centrifuged a second time. Aliquots of membrane protein were incubated for 30 minutes at 37° C. in the presence of [3H]nitrendipine (1 nM), and nonspecific binding was determined in the presence of 10 μM nifedipine. The bound radioligand was separated by filtration through GF/B filters using a cell harvester.

TABLE 1

Binding Affinities at α-Adrenergic Receptors and L-Type Calcium Channels

| compound | | alpha-1 | | alpha-2 | | | Ca |
|---|---|---|---|---|---|---|---|
| | | 1a | 1b | 1c | 2a | 2b | 2c | |
| 1 | pKI | 5.59 | 6.39 | 7.52 | 5.62 | 5.48 | 6.77 | 5.18 |
| | SEM | 0.10 | 0.15 | 0.23 | 0.15 | 0.21 | 0.14 | 0.39 |
| | n | 3 | 3 | 3 | 3 | 3 | 3 | 2 |
| (±)-2 | pKI | 6.22 | 6.48 | 8.73 | 6.44 | 6.38 | 6.49 | 3.7 |
| | SEM | 0.04 | 0.08 | 0.08 | 0.03 | 0.01 | 0.02 | 0.41 |
| | n | 4 | 4 | 4 | 3 | 3 | 3 | 2 |
| (+)-2 | pKI | 6.40 | 6.35 | 7.69 | 6.52 | 6.40 | 6.53 | 4.11 |
| | SEM | 0.19 | 0.06 | 0.13 | 0.18 | 0.18 | 0.06 | |
| | n | 3 | 3 | 2 | 2 | 2 | 2 | 2 |
| (−)-2 | pKI | 6.46 | 6.39 | 8.91 | 6.83 | 6.56 | 6.78 | 2.74 |
| | SEM | 0.16 | 0.04 | 0.07 | 0.06 | 0.05 | 0.04 | |
| | n | 3 | 3 | 2 | 2 | 2 | 2 | 1 |
| 3 | pKI | 6.84 | 7.19 | 8.23 | 6.99 | 7.65 | 7.29 | 3.00 |
| | SEM | 0.02 | 0.01 | 0.04 | 0.25 | 0.02 | 0.11 | |
| | n | 3 | 3 | 3 | 3 | 3 | 3 | 1 |
| 4 | pKI | 6.71 | 6.89 | 7.17 | 6.26 | 5.99 | 6.30 | 6.01 |
| | SEM | 0.03 | 0.06 | 0.07 | 0.04 | 0.03 | 0.06 | |
| | n | 3 | 3 | 3 | 4 | 4 | 4 | 1 |
| 5 | pKI | 5.74 | 6.08 | 7.95 | 5.65 | 5.67 | 4.61 | 5.34 |
| | SEM | 0.13 | 0.12 | 0.19 | 0.03 | 0.17 | 0.17 | 0.03 |
| | n | 4 | 4 | 4 | 2 | 2 | 2 | 3 |
| 6 | pKI | 5.95 | 6.69 | 6.83 | 6.08 | 6.35 | 6.62 | 5.80 |
| | SEM | 0.15 | 0.21 | 0.27 | 0.13 | 0.14 | 0.17 | 0.10 |
| | n | 3 | 3 | 3 | 3 | 3 | 3 | 2 |
| 7 | pKI | 5.93 | 6.54 | 6.21 | 5.42 | 5.79 | 5.91 | 6.06 |
| | SEM | 0.05 | 0.04 | 0.02 | | | | |
| | n | 3 | 3 | 3 | 1 | 1 | 1 | 1 |
| 8 | pKI | 6.42 | 6.73 | 7.12 | 6.08 | 5.73 | 6.47 | 4.94 |
| | SEM | 0.05 | 0.09 | 0.03 | 0.08 | 0.01 | 0.05 | |
| | n | 3 | 3 | 3 | 2 | 2 | 2 | 1 |
| 9 | pKI | 5.77 | 6.47 | 7.62 | 5.66 | 6.26 | 5.88 | 4.72 |
| | SEM | 0.03 | 0.29 | 0.15 | 0.04 | 0.09 | 0.02 | 0.13 |
| | n | 3 | 3 | 3 | 4 | 3 | 3 | 3 |
| 10 | pKI | 6.35 | 6.91 | 8.75 | 5.63 | 5.48 | 5.91 | 5.12 |
| | SEM | 0.10 | 0.04 | 0.01 | 0.09 | 0.11 | 0.12 | 0.07 |
| | n | 3 | 3 | 3 | 3 | 3 | 3 | 2 |
| 11 | pKI | 6.52 | 6.64 | 8.95 | 5.95 | 6.06 | 6.24 | 5.64 |
| | SEM | 0.12 | 0.14 | 0.12 | 0.03 | 0.02 | 0.02 | 0.02 |
| | n | 3 | 3 | 3 | 3 | 3 | 3 | 2 |
| 12 | pKI | 6.42 | 6.82 | 8.74 | 6.11 | 5.90 | 6.06 | 5.42 |
| | SEM | 0.03 | 0.02 | 0.01 | 0.08 | | 0.04 | 0.10 |
| | n | 3 | 3 | 2 | 2 | 2 | 2 | 3 |
| 13 | pKI | 6.41 | 6.78 | 8.14 | 5.90 | 5.76 | 6.19 | 5.05 |
| | SEM | 0.08 | 0.06 | 0.15 | 0.03 | 0.05 | 0.04 | 0.06 |
| | n | 3 | 3 | 3 | 2 | 2 | 2 | 2 |
| 14 | pKI | 5.39 | 5.58 | 7.39 | 5.54 | 5.87 | 5.96 | |
| | SEM | 0.28 | 0.30 | 0.21 | 0.05 | 0.02 | 0.06 | |
| | n | 2 | 2 | 2 | 2 | 2 | 2 | |
| 15 | pKI | 6.38 | 6.78 | 8.2 | 5.61 | 5.47 | 5.95 | 5.14 |
| | SEM | 0.02 | 0.04 | 0.05 | 0.03 | 0.04 | 0.05 | |
| | n | 3 | 3 | 3 | 2 | 2 | 2 | 1 |
| 16 | pKI | 6.37 | 6.76 | 8.23 | 5.95 | 5.74 | 6.42 | 6.09 |
| | SEM | 0.01 | 0.03 | 0.07 | 0.04 | 0.15 | 0.04 | |
| | n | 3 | 3 | 3 | 2 | 2 | 2 | 1 |
| 17 | pKI | 6.90 | 7.38 | 9.27 | 6.46 | 6.85 | 7.57 | 5.00 |
| | SEM | 0.04 | 0.10 | 0.23 | 0.06 | 0.05 | 0.02 | |
| | n | 3 | 3 | 3 | 2 | 2 | 2 | 1 |
| 18 | pKI | 6.05 | 6.76 | 7.16 | 5.67 | 5.79 | 6.03 | 6.79 |
| | SEM | 0.06 | 0.10 | 0.09 | 0.03 | 0.05 | 0.06 | 0.15 |
| | n | 3 | 3 | 3 | 3 | 3 | 3 | 2 |
| 19 | pKI | 6.50 | 6.57 | 8.87 | 5.89 | 6.04 | 6.38 | 5.13 |
| | SEM | 0.04 | 0.02 | 0.21 | | | | 0.05 |
| | n | 3 | 3 | 3 | 1 | 1 | 1 | 2 |
| 20 | pKI | 5.87 | 6.92 | 8.42 | 5.75 | 5.88 | 6.09 | 5.94 |
| | SEM | 0.12 | 0.67 | 0.06 | 0.06 | 0.03 | 0.02 | 0.15 |
| | n | 3 | 3 | 3 | 2 | 2 | 2 | 3 |
| 21 | pKI | 6.31 | 6.69 | 8.15 | 5.68 | 5.97 | 6.11 | 6.00 |
| | SEM | 0.04 | 0.07 | 0.05 | 0.00 | 0.03 | 0.02 | 0.19 |
| | n | 3 | 3 | 3 | 2 | 2 | 2 | 2 |

TABLE 1-continued

Binding Affinities at α-Adrenergic Receptors and L-Type Calcium Channels

| compound | | alpha-1 | | alpha-2 | | | Ca |
|---|---|---|---|---|---|---|---|
| | | 1a | 1b | 1c | 2a | 2b | 2c |
| 22 | pKI | 6.13 | 6.86 | 7.44 | 5.80 | 6.04 | 6.20 | 6.43 |
|  | SEM | 0.06 | 0.06 | 0.03 | 0.08 | 0.22 | 0.00 | 0.14 |
|  | n | 3 | 3 | 3 | 3 | 3 | 3 | 2 |
| 23 | pKI | 6.19 | 6.67 | 7.84 | 6.02 | 6.25 | 6.33 | 6.54 |
|  | SEM | 0.06 | 0.04 | 0.07 | 0.06 | 0.03 | 0.02 | 0.02 |
|  | n | 3 | 3 | 3 | 3 | 3 | 3 | 2 |
| 24 | pKI | 6.49 | 6.94 | 8.73 | 6.04 | 5.90 | 6.8 | 5.71 |
|  | SEM | 0.03 | 0.04 | 0.06 | 0.03 | 0.01 | 0.34 | 0.09 |
|  | n | 3 | 3 | 3 | 2 | 2 | 2 | 3 |
| 25 | pKI | 6.19 | 6.48 | 7.47 | 5.82 | 6.30 | 5.99 | 5.94 |
|  | SEM | 0.09 | 0.02 | 0.08 | 0.01 | 0.33 | 0.00 | 0.16 |
|  | n | 3 | 3 | 3 | 2 | 2 | 2 | 1 |
| 26 | pKI | 6.28 | 6.36 | 8.15 | 5.67 | 6.01 | 5.83 | 7.06 |
|  | SEM | 0.03 | 0.03 | 0.21 | 0.08 | 0.05 | 0.06 |  |
|  | n | 2 | 3 | 3 | 2 | 2 | 2 | 1 |
| 27 | pKi | 6.42 | 6.49 | 8.44 | 5.71 | 5.98 | 5.92 | 6.23 |
|  | SEM | 0.04 | 0.04 | 0.16 | 0.05 | 0.06 | 0.02 |  |
|  | n | 3 | 3 | 3 | 2 | 2 | 2 | 1 |
| 28 | pKi | 6.36 | 6.62 | 8.02 | 5.64 | 5.78 | 6.20 | 4.76 |
|  | SEM | 0.06 | 0.08 | 0.10 | 0.22 | 0.09 | 0.00 |  |
|  | n | 3 | 3 | 3 | 2 | 2 | 2 | 1 |
| 29 | pKI | 6.58 | 6.85 | 8.83 | 6.16 | 6.20 | 6.40 | 4.86 |
|  | SEM | 0.05 | 0.07 | 0.08 | 0.08 | 0.10 | 0.07 |  |
|  | n | 3 | 3 | 3 | 2 | 2 | 2 | 1 |
| 30 | pKI | 6.81 | 7.27 | 8.52 | 6.93 | 6.63 | 7.31 | 7.02 |
|  | SEM | 0.01 | 0.08 | 0.41 | 0.05 | 0.10 | 0.12 | 0.09 |
|  | n | 3 | 3 | 2 | 3 | 3 | 3 | 2 |
| 31 | pKI | 6.95 | 7.69 | 8.93 | 6.80 | 6.86 | 7.28 |  |
|  | SEM | 0.06 | 0.01 | 0.12 | 0.08 | 0.10 | 0.11 |  |
|  | n | 3 | 3 | 3 | 2 | 2 | 2 |  |
| 32 | pKI | 6.13 | 6.52 | 7.88 |  |  |  | 5.80 |
|  | SEM | 0.01 | 0.05 | 0.07 |  |  |  | 0.04 |
|  | n | 2 | 2 | 2 |  |  |  | 2 |
| 37 | pKI | 6.16 | 6.70 | 7.64 | 6.15 | 5.97 | 6.24 | 5.87 |
|  | SEM |  |  |  | 0.10 | 0.00 | 0.00 |  |
|  | n | 1 | 1 | 1 | 2 | 2 | 2 | 1 |
| 38 | pKI | 6.21 | 6.38 | 8.50 | 6.40 | 6.04 | 6.49 | 5.15 |
|  | SEM | 0.08 | 0.03 | 0.09 | 0.07 | 0.02 | 0.02 | 0.11 |
|  | n | 3 | 3 | 3 | 4 | 4 | 4 | 2 |
| 39 | pKI | 5.77 | 5.93 | 7.23 | 6.02 | 5.74 | 6.09 | 4.35 |
|  | SEM | 0.06 | 0.05 | 0.01 | 0.03 | 0.02 | 0.03 | 0.12 |
|  | n | 3 | 3 | 3 | 3 | 3 | 3 | 3 |
| 40 | pKI | 6.26 | 6.56 | 7.86 | 5.73 | 5.75 | 6.01 | 4.8 |
|  | SEM | 0.05 | 0.06 | 0.01 | 0.06 | 0.07 | 0.02 | 0.11 |
|  | n | 2 | 2 | 2 | 3 | 3 | 3 | 2 |
| 41 | pKI | 6.30 | 6.53 | 8.74 | 6.37 | 6.22 | 6.36 |  |
|  | SEM | 0.07 | 0.08 | 0.03 |  |  |  |  |
|  | n | 2 | 2 | 2 | 1 | 1 | 1 |  |
| 42 | pKI | 6.35 | 6.55 | 8.90 | 6.49 | 6.64 | 6.77 |  |
|  | SEM | 0.08 | 0.02 | 0.03 |  |  |  |  |
|  | n | 2 | 2 | 2 | 1 | 1 | 1 |  |
| 43 | pKI | 6.50 | 6.74 | 8.62 | 6.18 | 6.36 | 6.40 | 4.73 |
|  | SEM | 0.06 | 0.06 | 0.21 | 0.02 | 0.00 | 0.07 |  |
|  | n | 3 | 3 | 3 | 2 | 2 | 2 | 1 |
| 44 | pKI | 5.23 | 5.08 | 5.77 |  |  |  | 4.78 |
|  | SEM | 0.09 | 0.16 | 0.08 |  |  |  | 0.04 |
|  | n | 2 | 2 | 3 |  |  |  | 2 |
| (±)-45 | pKI | 7.18 | 7.87 | 9.63 | 6.55 | 6.67 | 7.09 | 5.13 |
|  | SEM | 0.03 | 0.05 | 0.11 | 0.02 | 0.04 | 0.05 | 0.03 |
|  | n | 3 | 3 | 3 | 3 | 3 | 3 | 4 |
| (−)-45 | pKI | 7.39 | 8.04 | 9.74 | 6.47 | 6.64 | 7.86 | 5.36 |
|  | SEM | 0.13 | 0.05 | 0.07 |  |  |  |  |
|  | n | 3 | 3 | 3 | 1 | 1 | 1 | 1 |
| (+)-45 | pKI | 6.75 | 7.24 | 8.03 | 6.62 | 7.04 | 7.65 |  |
|  | SEM | 0.21 | 0.00 | 0.08 |  |  |  |  |
|  | n | 3 | 2 | 3 | 1 | 1 | 1 |  |
| 46 | pKI | 6.30 | 6.62 | 7.69 | 6.17 | 6.31 | 6.61 | 5.13 |
|  | SEM | 0.06 | 0.04 | 0.12 | 0.02 | 0.01 | 0.02 | 0.19 |
|  | n | 4 | 4 | 4 | 3 | 3 | 3 | 2 |
| 47 | pKI | 6.29 | 6.58 | 8.93 | 6.22 | 6.36 | 6.43 | 4.75 |
|  | SEM | 0.08 | 0.03 | 0.16 | 0.02 | 0.02 | 0.03 |  |
|  | n | 3 | 3 | 3 | 3 | 3 | 3 | 1 |
| 48 | pKI | 8.01 | 8.58 | 9.28 | 7.76 | 6.09 | 6.38 | 6.32 |
|  | SEM | 0.03 | 0.10 | 0.07 |  |  |  |  |
|  | n | 3 | 3 | 3 | 1 | 1 | 1 | 1 |
| 49 | pKI | 6.94 | 6.72 | 8.56 | 6.63 | 6.42 | 6.86 | 5.37 |
|  | SEM | 0.07 | 0.27 | 0.16 | 0.03 | 0.02 | 0.05 |  |
|  | n | 3 | 3 | 2 | 2 | 2 | 2 | 1 |
| 50 | pKI | 5.71 | 5.52 | 7.07 | 5.82 | 5.56 | 6.18 | 5.02 |
|  | SEM | 0.07 | 0.04 | 0.17 | 0.27 | 0.21 | 0.28 |  |
|  | n | 3 | 3 | 3 | 2 | 2 | 2 | 1 |
| 51 | pKI | 5.01 | 5.30 | 6.32 | 6.35 | 6.29 | 6.60 | 3 |
|  | SEM | 0.05 | 0.22 | 0.07 | 0.05 | 0.14 | 0.01 |  |
|  | n | 3 | 3 | 2 | 2 | 2 | 2 | 1 |
| 52 | pKI | 5.94 | 7.11 | 8.06 | 6.29 | 6.10 | 6.58 | 5.29 |
|  | SEM | 0.49 | 0.06 | 0.11 |  |  |  |  |
|  | n | 2 | 2 | 2 | 1 | 1 | 1 | 1 |
| 53 | pKI | 6.49 | 6.87 | 7.83 | 6.18 | 6.34 | 6.67 | 5.54 |
|  | SEM | 0.03 | 0.16 | 0.21 |  |  |  |  |
|  | n | 3 | 3 | 3 | 1 | 1 | 1 | 1 |
| 54 | pKI | 6.46 | 6.76 | 7.91 | 6.33 | 6.52 | 6.80 | 4.23 |
|  | SEM | 0.03 | 0.11 | 0.11 | 0.02 | 0.14 | 0.06 |  |
|  | n | 3 | 3 | 3 | 2 | 2 | 2 | 1 |
| 55 | pKI | 6.17 | 6.45 | 7.99 | 6.21 | 6.51 | 6.78 | 3 |
|  | SEM | 0.06 | 0.05 | 0.10 | 0.02 | 0.16 | 0.04 |  |
|  | n | 3 | 3 | 3 | 2 | 2 | 2 | 1 |
| 56 | pKI | 6.20 | 6.66 | 8.52 | 6.57 | 6.89 | 6.73 | 5.19 |
|  | SEM | 0.03 | 0.04 | 0.01 | 0.01 |  | 0.03 |  |
|  | n | 2 | 2 | 2 | 2 | 2 | 2 | 1 |
| 57 | pKI | 5.79 | 5.91 | 6.22 | 6.71 | 5.73 | 6.80 | 3.00 |
|  | SEM | 0.02 | 0.01 | 0.03 | 0.06 | 0.03 | 0.09 |  |
|  | n | 3 | 3 | 3 | 3 | 3 | 3 | 1 |
| 58 | pKI | 5.52 | 5.64 | 6.48 | 8.08 | 5.84 | 7.30 | 3.78 |
|  | SEM | 0.02 | 0.01 | 0.12 | 0.02 | 0.02 | 0.09 |  |
|  | n | 3 | 3 | 3 | 3 | 3 | 3 | 1 |
| 59 | pKI | 6.29 | 6.41 | 6.61 |  |  |  |  |
|  | SEM | 0.01 | 0.02 | 0.03 |  |  |  |  |
|  | n | 2 | 2 | 2 |  |  |  |  |
| 60 | pKI | 6.70 | 7.11 | 8.56 | 8.26 | 7.16 | 7.17 | 3.80 |
|  | SEM | 0.02 | 0.04 | 0.11 | 0.03 | 0.03 | 0.01 |  |
|  | n | 2 | 3 | 3 | 3 | 3 | 3 | 1 |
| 61 | pKI | 6.07 | 6.37 | 8.42 | 6.12 | 6.22 | 6.32 | 4.99 |
|  | SEM | 0.01 | 0.04 | 0.07 | 0.07 | 0.10 | 0.03 | 0.03 |
|  | n | 3 | 3 | 3 | 3 | 3 | 3 | 2 |
| 62 | pKI | 6.47 | 6.50 | 8.58 | 7.61 | 7.24 | 7.31 | 4.71 |
|  | SEM | 0.01 | 0.03 | 0.17 | 0.11 | 0.02 | 0.04 | 0.1 |
|  | n | 3 | 3 | 3 | 3 | 3 | 3 | 2 |
| 63 | pKI | 7.35 | 7.73 | 7.41 | 6.02 | 6.88 | 6.77 | 4.18 |
|  | SEM | 0.02 | 0.06 | 0.04 | 0.05 | 0.10 | 0.01 | 0.09 |
|  | n | 3 | 3 | 3 | 2 | 2 | 2 | 2 |
| 64 | pKI | 6.31 | 6.45 | 7.45 | 6.16 | 6.36 | 6.32 | 4.01 |
|  | SEM | 0.10 | 0.05 | 0.02 |  |  |  | 0.00 |
|  | n | 2 | 2 | 2 | 1 | 1 | 1 | 2 |
| 65 | pKI | 6.89 | 7.24 | 8.98 | 6.70 | 7.01 | 7.08 | 5.51 |
|  | SEM | 0.02 | 0.06 | 0.04 | 0.08 | 0.01 | 0.02 |  |
|  | n | 3 | 3 | 3 | 2 | 2 | 2 | 1 |
| 66 | pKI | 5.45 | 5.36 | 6.59 | 5.53 | 5.35 | 6.24 | 6.22 |
|  | SEM | 0.09 | 0.07 | 0.04 | 0.02 | 0.01 | 0.02 |  |
|  | n | 2 | 2 | 2 | 2 | 2 | 2 | 1 |
| 67 | pKI | 5.96 | 6.18 | 6.48 | 6.45 | 5.79 | 7.00 |  |
|  | SEM | 0.03 | 0.15 | 0.1 | 0.02 | 0.01 | 0.02 |  |
|  | n | 4 | 4 | 4 | 3 | 3 | 3 |  |
| 73 | pKI | 6.69 | 6.83 | 9.18 | 6.10 | 6.17 | 6.56 | 6.12 |
|  | SEM | 0.03 | 0.05 | 0.05 | 0.09 | 0.02 | 0.03 |  |
|  | n | 2 | 2 | 3 | 2 | 2 | 2 | 1 |
| 74 | pKI | 7.23 | 7.72 | 9.30 | 7.23 | 7.05 | 7.63 | 5.28 |
|  | SEM | 0.05 | 0.04 | 0.03 | 0.03 | 0.05 | 0.05 |  |
|  | n | 3 | 3 | 3 | 2 | 2 | 2 | 1 |
| 75 | pKI | 5.36 | 5.41 | 6.10 | 5.54 | 5.51 | 5.91 | 5.45 |
|  | SEM | 0.05 | 0.28 |  | 0.01 | 0.01 | 0.04 |  |
|  | n | 3 | 3 | 1 | 2 | 2 | 2 | 1 |
| 76 | pKI | 5.89 | 5.88 | 6.63 | 6.96 | 5.64 | 7.70 | 5.49 |
|  | SEM | 0.10 | 0.06 | 0.11 | 0.05 | 0.15 | 0.24 | 0 |
|  | n | 4 | 4 | 4 | 2 | 2 | 2 | 2 |

TABLE 1-continued

Binding Affinities at α-Adrenergic Receptors and L-Type Calcium Channels

| compound | | alpha-1 | | alpha-2 | | | Ca |
|---|---|---|---|---|---|---|---|
| | | 1a | 1b | 1c | 2a | 2b | 2c | |
| 77 | pKI | 6.83 | 7.16 | 8.30 | 6.95 | 7.08 | 7.42 | 5.94 |
| | SEM | 0.03 | 0.06 | 0.13 | 0.04 | 0.02 | 0.08 | 0.04 |
| | n | 3 | 3 | 3 | 3 | 3 | 3 | 2 |
| 78 | pKI | 6.75 | 6.96 | 8.37 | 6.14 | 6.26 | 6.82 | 5.5 |
| | SEM | 0.05 | 0.02 | 0.13 | 0.10 | 0.13 | 0.03 | 0.03 |
| | n | 3 | 3 | 3 | 3 | 3 | 3 | 2 |
| 79 | pKI | 6.99 | 7.33 | 7.76 | 6.84 | 7.28 | 7.21 | 6.17 |
| | SEM | 0.01 | 0.03 | 0.09 | 0.13 | 0.08 | 0.12 | |
| | n | 3 | 3 | 3 | 4 | 4 | 4 | 1 |
| 81 | pKI | 6.39 | 6.62 | 8.72 | 6.75 | 6.79 | 6.91 | 4.49 |
| | SEM | 0.02 | 0.02 | 0.10 | | | | 0.25 |
| | n | 3 | 3 | 2 | 1 | 1 | 1 | 2 |
| 89 | pKI | 6.46 | 6.85 | 6.30 | 5.63 | 5.71 | 6.30 | 6.09 |
| | SEM | 0.08 | 0.06 | 0.04 | 0.10 | 0.04 | 0.04 | 0.18 |
| | n | 3 | 3 | 3 | 3 | 3 | 3 | 3 |
| 90 | pKI | 6.52 | 6.87 | 7.56 | 6.13 | 6.04 | 6.79 | 6.63 |
| | SEM | 0.07 | 0.03 | 0.04 | 0.03 | | 0.35 | 0.10 |
| | n | 3 | 3 | 3 | 2 | 2 | 2 | 3 |
| 91 | pKI | 6.29 | 6.54 | 8.04 | 6.06 | 6.00 | 6.31 | 6.55 |
| | SEM | 0.25 | 0.27 | 0.05 | 0.05 | 0.05 | 0.05 | |
| | n | 3 | 3 | 3 | 3 | 3 | 3 | 1 |
| 92 | pKI | 6.68 | 7.23 | 8.51 | 5.50 | 6.14 | 6.12 | 5.38 |
| | SEM | 0.07 | 0.11 | 0.17 | | | | 0.25 |
| | n | 3 | 3 | 3 | 1 | 1 | 1 | 2 |
| (±)-93 | pKI | 5.98 | 6.57 | 8.87 | 5.48 | 5.93 | 5.88 | 6.1 |
| | SEM | 0.07 | 0.12 | 0.08 | 0.07 | 0.04 | 0.04 | 0.01 |
| | n | 3 | 3 | 3 | 2 | 2 | 2 | 2 |
| (±)-93 | pKI | 5.98 | 6.73 | 7.52 | 6.04 | 6.01 | 6.36 | 6.72 |
| | SEM | 0.5 | 0.08 | | 0.11 | 0.06 | 0.01 | |
| | n | 2 | 2 | 1 | 2 | 2 | 2 | 1 |
| (−)-93 | pKI | 6.56 | 6.95 | 8.92 | 6.13 | 6.01 | 6.27 | 5.89 |
| | SEM | | | 0.25 | 0.09 | 0.09 | 0.02 | |
| | n | 1 | 1 | 2 | 2 | 2 | 2 | 1 |
| 95 | pKi | 5.33 | 5.72 | 8.11 | 6.23 | 5.55 | 5.61 | 3.64 |
| | SEM | 0.06 | 0.09 | 0.01 | 0.08 | 0.01 | 0.03 | 0.30 |
| | n | 3 | 3 | 3 | 3 | 3 | 3 | 3 |
| 96 | pKi | 5.42 | 5.28 | 7.57 | 5.64 | 5.93 | 6.04 | 3 |
| | SEM | 0.03 | 0.06 | 0.08 | 0.03 | 0.02 | 0.05 | |
| | n | 3 | 3 | 3 | 3 | 3 | 3 | 2 |
| (±)-97 | pKi | 5.56 | 5.99 | 8.54 | 5.55 | 5.93 | 5.61 | 3 |
| | SEM | 0.11 | 0.12 | 0.09 | 0.04 | 0.11 | 0.01 | |
| | n | 4 | 4 | 4 | 3 | 3 | 3 | 3 |
| (+)-97 | pKi | 5.51 | 6.06 | 8.56 | 5.68 | 6.10 | 5.59 | 3 |
| | SEM | 0.02 | 0.18 | 0.06 | 0.02 | 0.07 | 0 | |
| | n | 3 | 3 | 2 | 3 | 3 | 3 | 1 |
| (−)-97 | pKi | 5.45 | 5.33 | 6.81 | 5.47 | 5.71 | 5.51 | 3 |
| | SEM | 0.10 | 0.06 | 0.48 | 0.13 | 0.02 | 0.02 | |
| | n | 3 | 3 | 2 | 3 | 3 | 3 | 1 |
| 98 | pKi | 5.96 | 6.52 | 8.32 | 6.45 | 6.23 | 6.37 | 3 |
| | SEM | 0.06 | 0.04 | 0.02 | 0.03 | 0.05 | 0.03 | |
| | n | 4 | 4 | 4 | 4 | 4 | 4 | 2 |
| 99 | pKi | 5.71 | 6.27 | 7.2 | 6.97 | 6.02 | 6.21 | 3 |
| | SEM | 0.03 | 0.13 | 0.32 | 0.02 | 0.01 | 0.05 | |
| | n | 3 | 3 | 3 | 2 | 2 | 2 | 2 |
| 100 | pKi | 5.31 | 5.83 | 8.36 | 6.10 | 5.54 | 5.75 | 3 |
| | SEM | 0.04 | 0.06 | 0.05 | 0.01 | 0.03 | 0.01 | |
| | n | 3 | 3 | 3 | 3 | 3 | 3 | 2 |
| 101 | pKi | 5.86 | 6.22 | 8.54 | 5.89 | 6.18 | 6.04 | 3 |
| | SEM | 0.08 | 0.04 | 0.04 | 0.02 | 0.06 | 0.04 | |
| | n | 4 | 4 | 4 | 4 | 4 | 4 | 2 |
| (±)-102 | pKi | 5.46 | 5.79 | 8.42 | 5.54 | 5.99 | 5.76 | 4.14 |
| | SEM | 0.03 | 0.02 | 0.02 | 0.02 | 0.02 | 0.04 | 0.03 |
| | n | 4 | 4 | 4 | 3 | 3 | 3 | 2 |
| (+)-102 | pKi | 5.54 | 5.91 | 8.58 | 5.41 | 5.72 | 5.48 | 3 |
| | SEM | 0.03 | 0.03 | 0.05 | 0.02 | 0.01 | 0.02 | |
| | n | 4 | 4 | 4 | 2 | 2 | 2 | 2 |
| (−)-102 | pKi | 5.17 | 5.50 | 6.95 | 5.72 | 6.23 | 5.98 | 6.26 |
| | SEM | 0.10 | 0.02 | 0.03 | 0.02 | 0.01 | 0.01 | 0.05 |
| | n | 4 | 4 | 4 | 2 | 2 | 2 | 2 |
| 103 | pKi | 5.60 | 6.74 | 7.97 | 6.31 | 6.13 | 6.57 | 6.75 |
| | SEM | 0.03 | 0.08 | 0.04 | 0.02 | 0.07 | 0.06 | 0.12 |
| | n | 3 | 3 | 3 | 3 | 3 | 3 | 2 |
| 104 | pKi | 6.88 | 7.46 | 5.49 | 8.28 | 7.25 | 7.8 | 3 |
| | SEM | 0.02 | 0.03 | 0.04 | 0.06 | 0.08 | 0.02 | |
| | n | 3 | 3 | 3 | 3 | 3 | 3 | 2 |
| 105 | pKi | 5.61 | 5.50 | 6.16 | 5.90 | 5.66 | 5.86 | 5.18 |
| | SEM | 0.25 | 0.25 | 0.20 | 0.02 | 0.01 | 0.01 | 0.29 |
| | n | 3 | 3 | 3 | 4 | 4 | 4 | 2 |
| 106 | pKi | 5.62 | 6.03 | 7.82 | 6.49 | 6.43 | 6.53 | 3 |
| | SEM | 0.04 | 0.09 | 0.03 | 0.02 | 0.07 | 0.05 | |
| | n | 4 | 4 | 4 | 3 | 3 | 3 | 2 |
| 107 | pKi | 6.06 | 6.00 | 8.23 | | | | |
| | SEM | 0.34 | 0.09 | 0.06 | | | | |
| | n | 3 | 3 | 3 | | | | |
| 108 | pKi | 5.53 | 5.38 | 8.16 | | | | |
| | SEM | 0.07 | 0.06 | 0.31 | | | | |
| | n | 3 | 3 | 3 | | | | |
| 109 | pKi | 6.07 | 6.56 | 7.18 | | | | |
| | SEM | 0.04 | 0.06 | 0.25 | | | | |
| | n | 2 | 2 | 2 | | | | |
| 110 | pKi | 4.75 | 4.50 | 5.81 | | | | |
| | SEM | 0.13 | 0.14 | 0.48 | | | | |
| | n | 3 | 3 | 3 | | | | |
| 111 | pKi | 5.75 | 6.02 | 8.24 | | | | |
| | SEM | 0.01 | 0.05 | 0.04 | | | | |
| | n | 2 | 2 | 2 | | | | |
| 112 | pKi | 7.52 | 7.63 | 7.61 | 6.59 | 6.35 | 6.57 | 7.24 |
| | SEM | 0.11 | 0.08 | 0.13 | 0.05 | 0.09 | 0.19 | 0.05 |
| | n | 3 | 3 | 3 | 3 | 3 | 3 | 2 |
| 113 | pKi | 6.16 | 6.46 | 7.75 | 6.12 | 6.78 | 6.50 | 3 |
| | SEM | 0.02 | 0.04 | 0.06 | 0.03 | 0.02 | 0.08 | |
| | n | 3 | 3 | 3 | 4 | 4 | 4 | 2 |
| 114 | pKi | 6.26 | 6.69 | 7.99 | 5.68 | 6.33 | 6.14 | 5.54 |
| | SEM | 0.13 | 0.05 | 0.04 | 0.04 | 0.03 | 0.04 | 0.1 |
| | n | 3 | 3 | 3 | 3 | 3 | 3 | 2 |
| 115 | pKi | 5.70 | 5.84 | 7.23 | 5.40 | 6.11 | 5.64 | 3 |
| | SEM | 0.01 | 0.13 | 0.05 | 0.06 | 0.03 | 0.03 | |
| | n | 3 | 3 | 3 | 3 | 3 | 3 | 2 |
| 116 | pKi | 6.73 | 6.12 | 8.41 | 5.84 | 6.43 | 6.13 | |
| | SEM | 0.44 | 0.09 | | 0.16 | 0.07 | 0.01 | |
| | n | 2 | 2 | 1 | 3 | 3 | 3 | |
| 117 | pKi | 5.68 | 6.25 | 7.56 | 6.02 | 6.36 | 6.12 | 3 |
| | SEM | 0.12 | 0.04 | 0.05 | 0.06 | 0.03 | 0.05 | |
| | n | 3 | 3 | 3 | 3 | 3 | 3 | 2 |
| 118 | pKi | 5.66 | 5.75 | 8.02 | 5.41 | 5.84 | 5.65 | 3.00 |
| | SEM | 0.06 | 0.09 | 0.10 | 0.06 | 0.02 | 0.03 | |
| | n | 3 | 3 | 3 | 3 | 3 | 3 | 1 |
| (±)-119 | pKi | 6.21 | 6.38 | 8.5 | 6.4 | 6.04 | 6.49 | 5.13 |
| | SEM | 0.08 | 0.03 | 0.09 | 0.07 | 0.02 | 0.02 | 0.11 |
| | n | 3 | 3 | 3 | 4 | 4 | 4 | 2 |
| (+)-119 | pKi | 5.89 | 6.08 | 6.42 | | | | |
| | SEM | 0.02 | 0.03 | 0.13 | | | | |
| | n | 3 | 3 | 3 | | | | |
| (−)-119 | pKi | 5.93 | 6.17 | 8.59 | | | | |
| | SEM | 0.02 | 0.03 | 0.12 | | | | |
| | n | 3 | 3 | 3 | | | | |
| 120 | pKi | 6.33 | 6.61 | 8.97 | 6.44 | 6.59 | 6.72 | 3 |
| | SEM | 0.05 | 0.04 | 0.09 | 0.03 | 0.02 | 0.03 | |
| | n | 4 | 4 | 4 | 3 | 3 | 3 | |
| 121 | pKi | 6.62 | 7.14 | 8.88 | 6.44 | 6.59 | 6.72 | 4.78 |
| | SEM | 0.08 | 0.06 | 0.04 | 0.03 | 0.02 | 0.03 | 0.15 |
| | n | 3 | 3 | 3 | 3 | 3 | 3 | 2 |
| 122 | pKi | 6.62 | 7.57 | 7.71 | 6.38 | 7.35 | 6.53 | 3 |
| | SEM | 0.17 | 0.08 | 0.17 | 0.04 | 0.04 | 0 | 0 |
| | N | 4 | 4 | 4 | 3 | 3 | 3 | 1 |
| 123 | pKi | 6.7 | 8.01 | 8.3 | 6.03 | 6.87 | 6.42 | 4.53 |
| | SEM | 0.03 | 0.09 | 0.11 | 0.02 | 0.06 | 0.01 | 0 |
| | n | 4 | 4 | 4 | 3 | 3 | 3 | 1 |
| 124 | pKi | 7.24 | 7.05 | 8.71 | 7.65 | 6.7 | 7.35 | 0 |
| | SEM | 0.06 | 0.17 | 0.05 | 0.02 | 0.04 | 0.02 | 0 |
| | n | 4 | 4 | 3 | 3 | 3 | 3 | 2 |
| 125 | pKi | 7.11 | 6.89 | 8.94 | 7.57 | 6.73 | 7.64 | 4.42 |
| | SEM | 0.09 | 0.06 | 0.08 | 0.07 | 0.03 | 0.05 | 0 |
| | N | 3 | 3 | 3 | 3 | 3 | 3 | 1 |

TABLE 1-continued

Binding Affinities at α-Adrenergic Receptors and L-Type Calcium Channels

| compound | | alpha-1 | | alpha-2 | | | Ca |
|---|---|---|---|---|---|---|---|
| | | 1a | 1b | 1c | 2a | 2b | 2c |
| 126 | pKi | 5.15 | 5.37 | 7.95 | 5.33 | 5.63 | 5.36 | 6.34 |
| | SEM | 0.01 | 0.02 | 0.06 | 0.04 | 0.02 | 0.01 | 0 |
| | n | 3 | 3 | 3 | 3 | 3 | 3 | 1 |
| 127 | pKi | 6.45 | 6.79 | 7.26 | 6.17 | 6.42 | 6.37 | 3 |
| | SEM | 0.01 | 0.09 | 0.01 | 0.01 | 0.05 | 0.03 | 0 |
| | n | 3 | 3 | 2 | 3 | 3 | 3 | 2 |
| 128 | pKi | 6.01 | 5.98 | 8.47 | 6.34 | 6.36 | 6.66 | |
| | SEM | 0.05 | 0.24 | 0.08 | 0.01 | 0.06 | 0.04 | |
| | n | 3 | 3 | 3 | 2 | 2 | 2 | |
| 129 | pKi | 6.17 | 6.29 | 8.43 | | | | 4 |
| | SEM | 0.08 | 0.23 | 0.25 | | | | |
| | n | 2 | 2 | 2 | | | | 1 |
| 130 | pKi | 6.04 | 6.38 | 7.97 | | | | |
| | SEM | 0.29 | 0.23 | 0.1 | | | | |
| | n | 3 | 3 | 3 | | | | |
| 131 | pKi | 5.83 | 6.07 | 8.34 | | | | 4 |
| | SEM | 0.35 | 0.27 | 0.47 | | | | |
| | n | 4 | 4 | 3 | | | | 1 |
| 132 | pKi | 6.11 | 6.41 | 7.24 | | | | 4.1 |
| | SEM | 0.06 | 0.19 | 0.45 | | | | |
| | n | 4 | 4 | 3 | | | | 1 |
| 135 | PKi | 6.30 | 6.75 | 6.98 | 6.18 | 6.41 | 6.47 | |
| | SEM | 0.20 | 0.16 | 0.12 | | | | |
| | n | 3 | 3 | 2 | 1 | 1 | 1 | |
| 136 | PKI | 6.08 | 6.39 | 8.46 | | | | |
| | SEM | 0.16 | 0.12 | 0.04 | | | | |
| | n | 3 | 3 | 2 | | | | |
| 139 | PKi | 6.32 | 6.85 | 7.63 | 6.08 | 5.90 | 6.51 | |
| | SEM | 0.18 | 0.11 | 0.13 | 0.05 | 0.05 | 0.01 | |
| | n | 3 | 3 | 3 | 2 | 2 | 2 | |
| 140 | PKi | 5.14 | 4.84 | 5.15 | | | | |
| | SEM | | | | | | | |
| | n | 1 | 1 | 1 | | | | |
| 141 | PKi | 7.30 | 7.48 | 8.27 | 6.22 | 6.36 | 6.45 | |
| | SEM | 0.01 | 0.09 | 0.04 | 0.07 | 0.14 | 0.01 | |
| | n | 2 | 2 | 2 | 3 | 3 | 3 | |
| 143 | PKi | 6.50 | 6.92 | 8.49 | | | | |
| | SEM | 0.07 | 0.09 | 0.07 | | | | |
| | n | 2 | 2 | 2 | | | | |
| (±)-144 | PKI | 6.20 | 6.49 | 9.19 | 6.40 | 6.05 | 6.69 | 4.90 |
| | SEM | 0.05 | 0.05 | 0.12 | 0.03 | 0.04 | 0.03 | |
| | n | 4 | 4 | 4 | 2 | 2 | 3 | 1 |
| 145 | PKi | 6.42 | 6.49 | 8.21 | | | | |
| | SEM | | | | | | | |
| | n | 1 | 1 | 1 | | | | |
| 146 | PKi | 5.73 | 5.92 | 8.43 | | | | |
| | SEM | 0.28 | 0.32 | 0.27 | | | | |
| | n | 2 | 2 | 2 | | | | |
| 147 | PKi | 6.43 | 6.59 | 7.96 | 6.06 | 5.96 | 6.60 | |
| | SEM | 0.13 | 0.11 | 0.14 | | | | |
| | n | 2 | 2 | 2 | 1 | 1 | 1 | |
| 148 | PKi | 6.34 | 5.59 | 8.53 | | | | |
| | SEM | 0.07 | 0.06 | 0.09 | | | | |
| | n | 2 | 2 | 2 | | | | |
| 149 | PKi | 6.49 | 6.61 | 8.26 | 6.30 | 6.25 | 6.59 | |
| | SEM | 0.03 | 0.00 | | 0.05 | 0.04 | 0.06 | |
| | n | 2 | 2 | 1 | 2 | 2 | 2 | |
| 150 | PKi | 6.61 | 6.84 | 8.77 | | | | |
| | SEM | 0.03 | 0.43 | 0.12 | | | | |
| | n | 2 | 2 | 2 | | | | |
| 151 | PKi | 6.20 | 6.45 | 7.91 | 6.25 | 6.27 | 6.68 | |
| | SEM | 0.06 | 0.06 | 0.03 | | | | |
| | n | 3 | 3 | 3 | 1 | 1 | 1 | |
| 152 | PKi | 6.31 | 6.66 | 6.03 | | | | |
| | SEM | 0.13 | 0.04 | 0.09 | | | | |
| | n | 2 | 2 | 2 | | | | |
| | PKI | 5.72 | 6.42 | 7.62 | | | | |
| | SEM | 0.01 | 0.08 | 0.01 | | | | |
| | n | 2 | 2 | 2 | | | | |
| 154 | PKI | 6.95 | 7.06 | 8.74 | | | | |
| | SEM | 0.01 | 0.02 | 0.15 | | | | |
| | n | 2 | 2 | 2 | | | | |
| 156 | PKI | 5.88 | 6.17 | 7.02 | 6.50 | 6.25 | 6.66 | 4.12 |
| | SEM | 0.02 | 0.06 | 0.12 | | | | |
| | n | 4 | 4 | 4 | 1 | 1 | 1 | 1 |
| 157 | PKI | 6.42 | 6.74 | 8.42 | 6.02 | 6.30 | 6.36 | 5.26 |
| | SEM | 0.04 | 0.04 | 0.16 | 0.03 | 0.05 | 0.02 | |
| | n | 3 | 3 | 3 | 2 | 2 | 2 | 1 |
| 158 | PKI | 6.42 | 6.90 | 7.81 | | | | |
| | SEM | 0.20 | 0.12 | 0.09 | | | | |
| | n | 3 | 3 | 3 | | | | |
| 159 | PKI | 6.41 | 6.75 | 8.30 | | | | 5.78 |
| | SEM | 0.03 | 0.05 | 0.13 | | | | |
| | n | 4 | 4 | 4 | | | | |
| 160 | PKI | 6.60 | 6.86 | 8.10 | 6.34 | 6.83 | 6.81 | 4.81 |
| | SEM | 0.03 | 0.04 | 0.14 | | | | |
| | n | 4 | 4 | 4 | 1 | 1 | 1 | 1 |
| 161 | PKI | 5.88 | 6.39 | 7.41 | | | | 3.00 |
| | SEM | 0.08 | 0.10 | 0.04 | | | | |
| | n | 4 | 4 | 4 | | | | 1 |
| 162 | PKI | 5.97 | 6.59 | 7.94 | 6.20 | 6.46 | 6.26 | 4.30 |
| | SEM | 0.03 | 0.05 | 0.03 | 0.01 | 0.01 | 0.00 | 0.10 |
| | n | 3 | 3 | 3 | 2 | 2 | 2 | 2 |
| 163 | PKI | 6.11 | 5.99 | 7.73 | 5.93 | 5.77 | 5.91 | |
| | SEM | 0.01 | 0.04 | 0.07 | 0.02 | 0.20 | 0.21 | |
| | n | 3 | 3 | 3 | 2 | 2 | 2 | |
| 164 | PKI | 5.53 | 5.75 | 7.64 | | | | |
| | SEM | 0.02 | 0.09 | 0.03 | | | | |
| | n | 3 | 3 | 3 | | | | |
| 165 | PKI | 5.85 | 6.24 | 9.30 | 5.52 | 5.71 | 5.82 | |
| | SEM | 0.06 | 0.05 | 0.26 | 0.06 | 0.01 | 0.02 | |
| | n | 4 | 4 | 4 | 2 | 2 | 2 | |
| 166 | PKI | 5.63 | 5.88 | 8.89 | 5.73 | 5.41 | 5.99 | 3.88 |
| | SEM | 0.02 | 0.08 | 0.15 | 0.02 | 0.02 | 0.03 | |
| | n | 3 | 3 | 3 | 4 | 4 | 4 | 1 |
| 167 | PKI | 6.50 | 6.57 | 8.36 | | | | 3.00 |
| | SEM | 0.14 | 0.05 | 0.04 | | | | 0.00 |
| | n | 3 | 3 | 3 | | | | 2 |
| 168 | PKI | 6.36 | 6.74 | 8.42 | | | | 3.77 |
| | SEM | 0.21 | 0.02 | 0.10 | | | | 0.13 |
| | n | 3 | 3 | 3 | | | | 2 |
| 169 | PKI | 6.29 | 6.64 | 8.14 | | | | 3.00 |
| | SEM | 0.24 | 0.05 | 0.13 | | | | 0.00 |
| | n | 3 | 3 | 3 | | | | 2 |
| 170 | PKI | 6.53 | 6.98 | 8.90 | 5.21 | 5.06 | 5.31 | 5.62 |
| | SEM | 0.04 | 0.05 | 0.14 | 0.54 | 0.57 | 0.84 | 0.17 |
| | n | 3 | 3 | 3 | 2 | 2 | 2 | 2 |
| 171 | PKI | 5.98 | 6.21 | 8.76 | 5.96 | 5.70 | 6.24 | 4.73 |
| | SEM | 0.03 | 0.16 | 0.13 | 0.02 | 0.06 | 0.02 | |
| | n | 3 | 3 | 3 | 2 | 2 | 2 | 1 |
| 172 | PKI | 6.09 | 6.21 | 8.55 | 5.63 | 5.46 | 6.16 | |
| | SEM | 0.53 | 0.10 | 0.03 | 0.08 | 0.04 | 0.03 | |
| | n | 3 | 3 | 2 | 2 | 2 | 2 | |
| 173 | PKI | 6.13 | 6.37 | 8.40 | 6.57 | 6.02 | 5.83 | |
| | SEM | 0.08 | 0.01 | 0.11 | 0.00 | 0.08 | 0.08 | |
| | n | 3 | 3 | 2 | 2 | 2 | 2 | |
| 174 | PKI | 5.40 | 5.72 | 8.39 | 5.70 | 6.02 | 6.17 | |
| | SEM | 0.04 | 0.03 | 0.16 | | | | |
| | n | 3 | 3 | 3 | 1 | 1 | 1 | |
| 175 | PKI | 6.34 | 6.46 | 8.29 | 6.97 | 6.66 | 6.52 | |
| | SEM | 0.02 | 0.08 | 0.04 | | | | |
| | n | 3 | 3 | 3 | 1 | 1 | 1 | |
| 176 | PKI | 6.51 | 6.80 | 8.43 | 6.01 | 5.92 | 6.14 | |
| | SEM | 0.04 | 0.07 | 0.15 | 0.04 | 0.07 | 0.11 | |
| | n | 3 | 3 | 3 | 2 | 2 | 2 | |
| 177 | PKI | 5.85 | 6.12 | 8.33 | 5.78 | 5.54 | 6.08 | 4.03 |
| | SEM | 0.06 | 0.05 | 0.09 | 0.13 | 0.07 | 0.02 | |
| | n | 4 | 4 | 4 | 2 | 2 | 2 | 1 |
| 178 | PKI | 6.08 | 6.38 | 8.59 | 6.04 | 6.12 | 6.40 | |
| | SEM | 0.04 | 0.08 | 0.05 | 0.15 | 0.16 | 0.03 | |
| | n | 3 | 3 | 3 | 2 | 2 | 2 | |
| 179 | PKI | 5.38 | 5.97 | 8.48 | 5.48 | 5.73 | 5.84 | 3.00 |
| | SEM | 0.07 | 0.16 | 0.10 | 0.01 | 0.04 | 0.00 | |
| | n | 3 | 3 | 3 | 2 | 2 | 2 | 1 |

TABLE 1-continued

Binding Affinities at α-Adrenergic Receptors and L-Type Calcium Channels

| compound | | alpha-1 | | alpha-2 | | | Ca |
|---|---|---|---|---|---|---|---|
| | | 1a | 1b | 1c | 2a | 2b | 2c |
| 180 | PKI | 5.52 | 6.07 | 8.44 | 5.16 | 5.44 | 5.24 | 3.00 |
| | SEM | 0.06 | 0.09 | 0.10 | 0.07 | 0.18 | 0.45 | |
| | n | 3 | 3 | 3 | 2 | 2 | 2 | 1 |
| 181 | PKI | 5.46 | 5.97 | 8.39 | | | | 3.00 |
| | SEM | 0.04 | 0.03 | 0.05 | | | | |
| | n | 3 | 3 | 3 | | | | 1 |
| 182 | PKI | 5.47 | 5.95 | 8.65 | 5.66 | 6.04 | 5.94 | 3.45 |
| | SEM | 0.04 | 0.08 | 0.05 | 0.16 | 0.07 | 0.04 | 0.29 |
| | n | 3 | 3 | 3 | 2 | 2 | 2 | 2 |
| 183 | PKI | 6.30 | 6.64 | 9.07 | 5.98 | 6.14 | 6.36 | 41.3 |
| | SEM | 0.02 | 0.05 | 0.10 | 0.06 | 0.01 | 0.08 | 0.35 |
| | n | 3 | 3 | 3 | 2 | 2 | 2 | 2 |
| 184 | PKI | 6.13 | 6.76 | 8.02 | | | | 4.91 |
| | SEM | 0.06 | 0.13 | 0.08 | | | | 0.27 |
| | n | 3 | 2 | 2 | | | | 3 |
| 185 | PKI | 5.72 | 6.03 | 8.50 | 6.56 | 5.89 | 6.45 | 3.23 |
| | SEM | 0.08 | 0.10 | 0.03 | 0.02 | 0.03 | 0.11 | |
| | n | 4 | 4 | 4 | 3 | 3 | 3 | 2 |
| 186 | PKI | 5.68 | 6.32 | 8.20 | 6.45 | 5.80 | 6.58 | 5.19 |
| | SEM | 0.12 | 0.14 | 0.06 | 0.08 | 0.10 | 0.03 | 0.05 |
| | n | 3 | 3 | 3 | 2 | 2 | 2 | 2 |
| 187 | | 5.15 | 5.29 | 6.27 | 8.46 | 5.91 | 5.65 | 5.29 | 3.29 |
| | SEM | 0.06 | 0.10 | 0.09 | 0.22 | 0.07 | 0.02 | 0.14 |
| | n | 3 | 3 | 3 | 3 | 3 | 3 | 2 |
| 188 | PKI | 5.25 | 5.41 | 8.21 | | | | 3.00 |
| | SEM | 0.08 | 0.04 | 0.01 | | | | 0.00 |
| | n | 3 | 3 | 3 | | | | 2 |
| 189 | PKI | 5.33 | 5.85 | 7.58 | | | | |
| | SEM | 0.09 | 0.26 | 0.05 | | | | |
| | n | 3 | 3 | 3 | | | | |
| 190 | PKI | 5.87 | 6.15 | 8.27 | | | | |
| | SEM | 0.03 | 0.03 | 0.11 | | | | |
| | n | 3 | 3 | 3 | | | | |
| 191 | PKI | 5.71 | 5.87 | 8.09 | | | | |
| | SEM | 0.10 | 0.14 | 0.08 | | | | |
| | n | 3 | 3 | 3 | | | | |
| 192 | PKI | 5.52 | 5.73 | 8.51 | 5.43 | 5.21 | 5.83 | |
| | SEM | 0.01 | 0.02 | 0.11 | 0.08 | 0.01 | 0.04 | |
| | n | 3 | 3 | 3 | 2 | 2 | 2 | |
| 193 | PKI | 5.54 | 5.76 | 8.80 | 5.99 | 5.62 | 6.20 | |
| | SEM | 0.01 | 0.04 | 0.07 | 0.05 | 0.10 | 0.07 | |
| | n | 3 | 3 | 3 | 2 | 2 | 2 | |
| 194 | PKI | 5.31 | 5.57 | 8.43 | 5.50 | 5.24 | 5.97 | |
| | SEM | 0.05 | 0.02 | 0.08 | 0.04 | 0.00 | 0.04 | |
| | n | 4 | 4 | 4 | 2 | 2 | 2 | |
| 195 | PKI | 6.54 | 6.89 | 8.15 | | | | |
| | SEM | 0.01 | 0.09 | 0.06 | | | | |
| | n | 4 | 4 | 4 | | | | |
| 196 | PKI | 5.17 | 5.44 | 7.41 | 5.08 | 5.33 | 5.51 | |
| | SEM | 0.11 | 0.05 | 0.10 | 0.12 | 0.14 | 0.09 | |
| | n | 3 | 3 | 3 | 2 | 2 | 2 | |
| 197 | PKI | 6.60 | 6.83 | 9.26 | 5.83 | 5.63 | 6.29 | 5.20 |
| | SEM | 0.01 | 0.02 | 0.11 | 0.09 | 0.01 | 0.12 | |
| | n | 4 | 4 | 4 | 2 | 2 | 2 | 1 |
| 198 | PKI | 5.35 | 5.56 | 9.08 | 5.95 | 5.97 | 5.61 | 3.75 |
| | SEM | 0.02 | 0.04 | 0.09 | 0.19 | 0.02 | 0.01 | |
| | n | 4 | 4 | 4 | 3 | 3 | 3 | 1 |
| 199 | PKI | 53.0 | 5.57 | 8.55 | 5.65 | 6.04 | 5.56 | 3.58 |
| | SEM | 0.03 | 0.04 | 0.09 | 0.09 | 0.03 | 0.08 | |
| | n | 4 | 4 | 4 | 3 | 3 | 3 | 1 |
| 200 | PKI | 5.48 | 5.70 | 8.36 | 5.26 | 5.97 | 5.79 | 3.00 |
| | SEM | 0.05 | 0.04 | 0.06 | 0.04 | 0.02 | 0.02 | |
| | n | 3 | 3 | 3 | 2 | 2 | 2 | 1 |
| 201 | PKI | 5.65 | 5.93 | 8.59 | 5.35 | 5.92 | 5.49 | 4.17 |
| | SEM | 0.01 | 0.05 | 0.05 | 0.02 | 0.09 | 0.08 | 0.01 |
| | n | 3 | 3 | 3 | 2 | 2 | 2 | 2 |
| 202 | PKI | 5.66 | 5.85 | 8.57 | 5.35 | 6.04 | 5.67 | 3.58 |
| | SEM | 0.04 | 0.09 | 0.10 | 0.08 | 0.00 | 0.04 | 0.29 |
| | n | 3 | 3 | 3 | 2 | 2 | 2 | 2 |
| 202− | PKI | 5.81 | 5.87 | 8.79 | | | | |
| | SEM | 0.06 | 0.11 | 0.08 | | | | |
| | n | 2 | 2 | 2 | | | | |
| 202+ | PKI | 5.79 | 5.81 | 8.02 | | | | |
| | SEM | 0.08 | 0.02 | 0.02 | | | | |
| | n | 2 | 2 | 2 | | | | |
| 203 | PKI | 6.12 | 6.28 | 8.32 | | | | |
| | SEM | 0.03 | 0.04 | 0.04 | | | | |
| | n | 3 | 3 | 3 | | | | |
| 204 | PKI | 4.54 | 4.54 | 7.23 | 5.93 | 5.77 | 5.91 | |
| | SEM | 0.03 | 0.04 | 0.21 | | | | |
| | n | 3 | 3 | 3 | 1 | 1 | 1 | |
| 205 | PKI | 5.32 | 5.51 | 8.32 | | | | |
| | SEM | 0.03 | 0.04 | 0.08 | | | | |
| | n | 3 | 3 | 3 | | | | |
| 206 | PKi | 5.94 | 6.16 | 8.44 | | | | |
| | SEM | 0.05 | 0.08 | 0.12 | | | | |
| | n | 3 | 3 | 3 | | | | |
| 207 | PKI | 5.73 | 5.83 | 8.62 | 6.14 | 6.02 | 5.75 | |
| | SEM | 0.06 | 0.07 | 0.10 | 0.12 | 0.05 | 0.08 | |
| | n | 3 | 3 | 3 | 2 | 2 | 2 | |
| 208 | PKI | 6.13 | 6.41 | 8.43 | 5.57 | 5.90 | 6.01 | |
| | SEM | 0.13 | 0.08 | 0.17 | 0.03 | 0.02 | 0.01 | |
| | n | 3 | 3 | 3 | 2 | 2 | 2 | |
| 209 | PKI | 5.17 | 5.44 | 8.41 | 5.78 | 6.46 | 5.70 | 4.53 |
| | SEM | 0.02 | 0.04 | 0.16 | 0.02 | 0.07 | 0.02 | |
| | n | 3 | 3 | 3 | 2 | 2 | 2 | 1 |
| 210 | PKI | 4.14 | 4.35 | 7.03 | 4.96 | 4.63 | 4.66 | 6.03 |
| | SEM | 4.14 | 0.01 | 0.13 | 0.12 | 0.09 | 0.09 | |
| | n | 2 | 2 | 2 | 3 | 3 | 3 | 1 |
| 211 | PKI | 5.50 | 5.80 | 8.27 | 5.58 | 5.68 | 5.71 | |
| | SEM | 0.02 | 0.11 | 0.04 | 0.01 | 0.00 | 0.06 | |
| | n | 3 | 3 | 3 | 2 | 2 | 2 | |
| 212 | PKI | 4.95 | 5.27 | 8.03 | 5.58 | 5.57 | 5.44 | |
| | SEM | 0.03 | 0.04 | 0.08 | 0.05 | 0.05 | 0.04 | |
| | n | 3 | 3 | 3 | 2 | 2 | 2 | |
| 213 | PKI | 6.23 | 6.81 | 8.22 | 6.00 | 6.70 | 5.75 | |
| | SEM | 0.04 | 0.08 | 0.02 | 0.02 | 0.05 | 0.16 | |
| | n | 3 | 3 | 3 | 2 | 2 | 2 | |
| 214 | PKI | 5.59 | 6.11 | 8.21 | | | | |
| | SEM | 0.04 | 0.10 | 0.03 | | | | |
| | n | 3 | 3 | 3 | | | | |
| 215 | PKI | 5.47 | 5.90 | 8.44 | | | | |
| | SEM | 0.09 | 0.15 | 0.06 | | | | |
| | n | 3 | 3 | 3 | | | | |
| 216 | PKI | 7.22 | 8.15 | 8.77 | | | | 6.00 |
| | SEM | 0.07 | 0.13 | 0.08 | | | | |
| | n | 3 | 3 | 3 | | | | 1 |
| 217 | PKI | 6.11 | 6.35 | 8.61 | | | | 5.09 |
| | SEM | 0.17 | 0.15 | 0.11 | | | | 0.11 |
| | n | 4 | 3 | 3 | | | | 2 |
| 218 | PKI | 6.78 | 7.75 | 8.86 | | | | 4.12 |
| | SEM | 0.05 | 0.15 | 0.11 | | | | 0.56 |
| | n | 3 | 3 | 3 | | | | 2 |
| 219 | PKI | 5.57 | 5.91 | 7.52 | | | | 3.24 |
| | SEM | 0.01 | 0.08 | 0.04 | | | | 0.12 |
| | n | 3 | 3 | 3 | | | | 2 |
| 220 | PKI | 5.67 | 6.28 | 8.01 | | | | 3.36 |
| | n | 4 | 4 | 4 | | | | 2 |
| 221 | PKI | 6.73 | 7.28 | 8.21 | | | | 4.85 |
| | SEM | 0.02 | 0.07 | 0.07 | | | | 0.07 |
| | n | 4 | 4 | 4 | | | | 3 |
| 222 | PKI | 4.85 | 5.17 | 7.38 | | | | 3.55 |
| | SEM | 0.05 | 0.06 | 0.04 | | | | 0.13 |
| | n | 4 | 4 | 4 | | | | 3 |
| 223 | PKI | 6.05 | 6.76 | 7.46 | | | | 3.56 |
| | SEM | 0.04 | 0.05 | 0.05 | | | | 0.28 |
| | n | 4 | 4 | 4 | | | | 2 |
| 224 | PKI | 6.18 | 6.58 | 8.16 | | | | 4.82 |
| | SEM | 0.02 | 0.05 | 0.11 | | | | 0.13 |
| | n | 3 | 3 | 3 | | | | 2 |
| 225 | PKI | 5.79 | 6.30 | 8.40 | 5.69 | 5.60 | 6.38 | 5.59 |
| | SEM | 0.04 | 0.01 | 0.17 | 0.15 | 0.13 | 0.18 | 0.08 |
| | n | 3 | 3 | 3 | 2 | 2 | 2 | 3 |

TABLE 1-continued

Binding Affinities at α-Adrenergic Receptors and L-Type Calcium Channels

| compound | | alpha-1 | | | alpha-2 | | | Ca |
|---|---|---|---|---|---|---|---|---|
| | | 1a | 1b | 1c | 2a | 2b | 2c | |
| 226 | PKI | 6.65 | 7.01 | 7.96 | | | | 5.06 |
| | SEM | 0.05 | 0.03 | 0.07 | | | | 0.04 |
| | n | 3 | 3 | 3 | | | | 2 |
| 227 | PKI | 5.29 | 5.58 | 7.63 | | | | 4.15 |
| | SEM | 0.03 | 0.04 | 0.07 | | | | 0.21 |
| | n | 3 | 3 | 3 | | | | 2 |
| 228 | PKI | 5.46 | 5.83 | 7.78 | | | | 4.47 |
| | SEM | 0.13 | 0.12 | 0.20 | | | | 0.10 |
| | n | 3 | 3 | 3 | | | | 2 |
| 229 | PKI | 5.38 | 5.86 | 8.15 | 5.52 | 5.27 | 6.05 | 4.00 |
| | SEM | 0.05 | 0.04 | 0.01 | 0.09 | 0.07 | 0.07 | 0.04 |
| | n | 3 | 3 | 3 | 2 | 2 | 2 | 2 |
| 230 | PKI | 5.75 | 6.16 | 8.06 | | | | 5.04 |
| | SEM | 0.05 | 0.11 | 0.16 | | | | 0.10 |
| | n | 3 | 3 | 3 | | | | 2 |
| 231 | PKI | 5.91 | 6.30 | 8.36 | | | | 3.41 |
| | SEM | 0.03 | 0.03 | 0.14 | | | | 0.20 |
| | n | 3 | 3 | 2 | | | | 2 |
| 232 | PKI | 6.38 | 6.66 | 8.12 | | | | 6.16 |
| | SEM | 0.18 | 0.16 | 0.03 | | | | |
| | n | 2 | 2 | 2 | | | | 1 |
| 233 | PKI | 5.39 | 5.79 | 8.67 | 5.32 | 5.06 | 5.78 | 6.59 |
| | SEM | 0.03 | 0.04 | 0.04 | 0.03 | 0.01 | 0.03 | |
| | n | 2 | 2 | 2 | 2 | 2 | 2 | 1 |
| 234 | PKI | 5.56 | 5.89 | 8.79 | 5.91 | 5.31 | 6.08 | 3.40 |
| | SEM | 0.03 | 0.07 | 0.18 | 0.04 | 0.01 | 0.00 | 0.02 |
| | n | 3 | 3 | 3 | 2 | 2 | 2 | 2 |
| 235 | PKI | 6.55 | 6.66 | 8.68 | 5.62 | 5.53 | 5.99 | 3.78 |
| | SEM | 0.03 | 0.01 | 0.12 | 0.01 | 0.05 | 0.01 | 0.23 |
| | n | 3 | 3 | 3 | 2 | 2 | 2 | 3 |
| 236 | PKI | 6.46 | 6.69 | 8.60 | | | | |
| | SEM | 0.02 | 0.08 | 0.02 | | | | |
| | n | 3 | 3 | 3 | | | | |
| 237 | PKI | 6.42 | 6.70 | 8.58 | 6.10 | 6.07 | 6.49 | |
| | SEM | 0.03 | 0.06 | 0.02 | | | | |
| | n | 3 | 3 | 3 | 1 | 1 | 1 | |
| 238 | PKI | 6.08 | 6.25 | 8.55 | 6.17 | 6.05 | 6.60 | |
| | SEM | | | | | | | |
| | n | 1 | 1 | 1 | 1 | 1 | 1 | |
| 239 | PKI | 6.56 | 6.59 | 8.69 | 6.08 | 6.12 | 6.58 | |
| | SEM | | | | | | | |
| | n | 1 | 1 | 1 | 1 | 1 | 1 | |
| 240 | PKI | 5.00 | 5.35 | 7.57 | 4.73 | 5.20 | 4.93 | |
| | SEM | | | | | | | |
| | n | 1 | 1 | 1 | 1 | 1 | 1 | |
| 241 | PKI | 5.84 | 6.31 | 8.36 | 5.80 | 5.93 | 6.40 | |
| | SEM | | | | | | | |
| | n | 1 | 1 | 1 | 1 | 1 | 1 | |
| 242 | PKI | 6.65 | 7.08 | 8.40 | 5.85 | 6.03 | 6.59 | |
| | SEM | | | | | | | |
| | n | 1 | 1 | 1 | 1 | 1 | 1 | |
| 243 | PKI | 5.82 | 6.12 | 8.24 | 5.65 | 6.01 | 5.97 | |
| | SEM | | | | | | | |
| | n | 1 | 1 | 1 | 1 | 1 | 1 | |
| 244 | PKI | 6.07 | 62.9 | 8.46 | 5.99 | 5.67 | 7.01 | |
| | SEM | | | | | | | |
| | n | 1 | 1 | 1 | 1 | 1 | 1 | |
| 245 | PKI | 6.01 | 6.45 | 8.30 | 5.98 | 5.56 | 6.50 | |
| | SEM | | | | | | | |
| | n | 1 | 1 | 1 | 1 | 1 | 1 | |
| 246 | PKI | 6.50 | 6.76 | 8.56 | 6.17 | 6.51 | 5.62 | |
| | SEM | | | | | | | |
| | n | 1 | 1 | 1 | 1 | 1 | 1 | |
| 247 | PKI | 6.01 | 6.04 | 7.61 | 6.23 | 6.32 | 6.52 | |
| | SEM | | | | | | | |
| | n | 1 | 1 | 1 | 1 | 1 | 1 | |
| 248 | PKI | 5.53 | 5.82 | 6.76 | 6.00 | 5.94 | 6.28 | |
| | SEM | | | | | | | |
| | n | 1 | 1 | 1 | 1 | 1 | 1 | |
| 249 | PKI | 6.37 | 6.63 | 9.41 | 5.81 | 5.91 | 6.25 | 7.51 |
| | SEM | 0.03 | 0.09 | 0.09 | 0.06 | 0.02 | 0.03 | 0.12 |
| | n | 3 | 3 | 2 | 3 | 3 | 3 | 3 |
| 250 | PKI | 6.22 | 7.16 | 8.96 | 6.91 | 7.40 | 7.44 | 4.88 |
| | SEM | 0.41 | 0.06 | 0.12 | 0.05 | 0.04 | 0.06 | |
| | n | 3 | 3 | 3 | 2 | 2 | 2 | 1 |
| 251 | PKI | 5.49 | 4.49 | 5.47 | | | | |
| | SEM | 0.10 | 0.00 | 0.10 | | | | |
| | n | 2 | 2 | 2 | | | | |

Several of the compounds of the invention showed in vitro efficacy in blocking the contraction of the human prostate induced by phenylepherine, a selective alpha-1 adrenergic agonist. The protocol for these experiments is given below. Table 2 shows the results.

Functional Properties of $\alpha_1$ Antagonists in the Human Prostate.

The efficacy of $\alpha_1$ adrenergic antagonists for the treatment of benign prostatic hyperplasia (BPH) is related to their ability to elicit relaxation of prostate smooth muscle. An index of this efficacy can be obtained by determining the potency of $\alpha_1$ antagonists to antagonize the contraction of human prostatic tissue induced by an $\alpha_1$ agonist "in vitro". Furthermore, by comparing the potency of subtype selective $\alpha_1$ antagonists in binding assays using human $\alpha_1$ receptors with their potency to inhibit agonist-induced smooth muscle contraction, it is possible to determine which of the $\alpha_1$ adrenergic receptor subtypes is involved in the contraction of prostate smooth muscle.

Methods.

Prostatic adenomas were obtained at the time of surgery from patients with symptomatic BPH. These were cut into longitudinal strips of 15 mm long and 2–4 mm wide, and suspended in 5 ml organ baths containing Krebs buffer (pH 7.4). The baths were maintained at 37° C. and continuously oxygenated with 5% $CO_2$ and 95% $O_2$. Isometric tension was measured with a Grass Instrument FT03 force transducer interfaced with a computer. Tissue strips were contracted with varying concentrations of phenylephrine after incubating for 20 minutes in the absence and presence of at least three different concentrations of antagonist. Dose-response curves for phenylephrine were constructed, and the antagonist potency ($pA_2$) was estimated by the dose-ratio method. The concentration of some antagonists in the tissue bath was assessed by measuring the displacement of [3H]prazosin by aliquots of the bath medium, using membrane preparations of the cloned human $\alpha_{1C}$ receptor. This control was necessary to account for losses of antagonist due to adsorption to the tissue bath and/or metabolism during the time the antagonists were equilibrated with the prostate tissue.

TABLE 2

In Vitro Human Prostate Model

| Compound | $pK_i$ |
|---|---|
| (±)-2 | 9.23 ± 0.18 |
| (±)-45 | 8.07 ± 0.13 |
| (±)-93 | 7.28 ± 0.4 |

Several of the compounds of the invention showed in vivo efficacy in blocking the contraction of the canine prostate induced by phenylepherine. The protocol for these experiments is given below. Table 3 shows the results (Diane Felsen, et. al. The Journal of Urology 1989, 141, 1230–1233).

Protocol for In Vivo Evaluation of Compounds in Canine Prostate.

Adult male mongrel dogs more than one year of age were chosen for the model. After induction of general anesthesia using sodium pentobarbital (25 mg/Kg i.v.), the animals were intubated and allowed to breathe spontaneously. An arterial catheter was inserted via the femoral artery to monitor blood pressure and i.v. line was inserted into the leg for fluid and drug administration. A constant saline infusion was maintained at 40 to 50 mL/h. Next, a seven cm lower abdominal incision was made one cm lateral to the penis. The bladder, prostate and a short segment of urethra were identified and isolated, without damage to the nerves or blood vessels. A cystotomy incision was made through which the pressure catheter was inserted and positioned in the prostatic urethra. The cystotomy was not closed, but the wound edges were sutured to stop bleeding. The tip of the catheter was positioned just distal to the prostate and secured in place with an O-silk tie around the urethra. A second holding suture at the bladder neck secured the catheter in place.

An esophageal pressure catheter (Arndorfer Med. Spec. Inc., Greendale, Wis.), used to measure closing pressures along the esophagus was easily adoptable to our study. Fluid, either water or saline, was pumped by a Harvard infusion pump at 0.1 mL/min through a Gould pressure transducer into the catheter. The fluid exists at a port in the catheter which is in the prostatic urethra. Occlusion of the port, by contraction of the prostate, blocks the flow and a pressure wave is created. This pressure is transmitted back through the catheter to the transducer which is attached to a Gould recorder. Squeezing the prostate gland caused an increase in urethral pressure which verified the correct position in the urethra.

The compounds were tested as follows: A dose response curve was first generated for phenylephrine alone, in doses ranging from one µg/Kg to 50 µg/Kg. The absolute rise in urethral pressure was recorded for each dose and the next dose given when the urethral pressure returned to baseline. Phenylephrine dose response curves were generated in all animals tested. Increasing doses of compounds were then given, and the phenylephrine dose response curve repeated in the prepense of each dose of the compound. No animal received more than one compound; four animals were used to test each compound. To test for tachyphylaxis, four separate dogs were challenged with repeated phenylephrine doses for six hrs, the usual length of each experiment. From the dose-effect data, the inhibition constant ($K_i$) and the median-effect dose ($ED_{50}$) were calculated. Both the $K_i$ and $ED_{50}$ values given are calculated by using microcomputer software and an IBM-PC.

TABLE 3

In Vivo Dog Prostate Model

| Compound | $K_i$ (nmol/Kg) |
|---|---|
| (±)-2 | 1.9 |
| (±)-45 | 12 |
| (±)-93 | 7.6 |

TABLE 4

Potency of Selected α1 Antagonists to Block Phenylephrine-Induced Contraction of Human Prostate

| Compound | pA2 |
|---|---|
| (+)-102 | 10.43 ± 0.14 |
| 97 | 9.12 ± 0.13 |
| 38 | 8.98 ± 0.06 |
| 42 | 8.92 ± 0.08 |
| 81 | 8.60 ± 0.03 |
| 73 | 8.56 ± 0.07 |
| 128 | 8.21 ± 0.06 |

TABLE 5

Ability of Selected α1 Antagonists to Inhibit Phenylephrine-Induced Increases in Urethral Pressure and Arterial Pressure in Anesthetized Dogs

| Compound | Urethral Pressure $K_i$ (nmol/kg) |
|---|---|
| 97 | 10 ± 2.0 |
| 42 | 9 ± 2.5 |
| 38 | 8 ± 1.5 |

What is claimed is:
1. A compound having the structure:

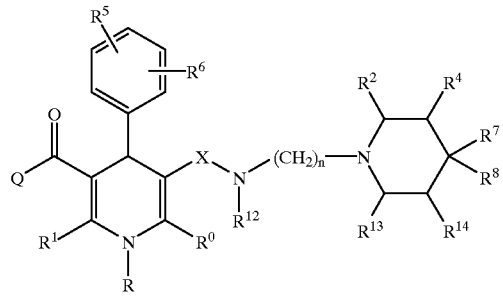

wherein X is C=O, $CH_2$, $CR^a{}_2$, NH, $NR^a$, NCHO, $NCOR^a$, NOH, O, or S;

wherein $R^a$ is a methyl, ethyl, or propyl group;

wherein Q is SH, SR''', $NH_2$, NHR''', $NR_2$''', NR"OH, NR"OR''', or a linear or branched chain alkyl group, or an arylalkyl group, or an alkenyl or alkynyl group, or an aryl group;

wherein R" is H, a linear or branched chain alkyl group, cyanoalkyl, or an aryl group;

wherein R''' is a linear or branched chain alkyl group, or an aryl group;

wherein R is H, a linear or branched chain alkyl or acyl group, or an aryl group;

wherein $R^0$ is H, methyl, ethyl, straight chained or branched propyl, an alkoxyalkyl, azidoalkyl, aminoalkoxyalkyl, azidoalkoxyalkyl, trihaloalkoxyalkyl, aminoalkyl, hydroxyalkyl or an aryl group, or $(CH_2)_tW$;

wherein $R^1$ is H, a linear or branched chain alkyl, an alkoxyalkyl, azidoalkyl, aminoalkoxyalkyl, azidoalkoxyalkyl, trihaloalkoxyalkyl, aminoalkyl, hydroxyalkyl, or an aryl group, or $(CH_2)_tW$;

wherein W is $NH_2$, NHR', $NR_2$', NHOH, $N^+R_3$'$Z^-$, NHCOR', $N_3$, $NO_2$ or $CH_2W^0(CH_2)_vW^1$, or a linear or branched chain alkyl group, or an arylalkyl group, or an alkenyl or alkynyl group, or an aryl group;

wherein R' is a linear or branched chain alkyl group, or an aryl group;

wherein $W^0$ is O, S, or NH;

wherein $W^1$ is $NH_2$, NHR', $NR_2'$, NHOH, $N^+R_3'Z^-$, NHCOR', $N_3$, or $NO_2$;

wherein $Z^-$ is a pharmaceutically acceptable counterion;

wherein t is 1, 2, 3, 4, 5, or 6;

wherein v is 2, 3, 4, 5, or 6;

wherein $R^2$, $R^{13}$, and $R^{14}$ are independently the same or different and are H, or a linear or branched chain alkyl, hydroxyalkyl, alkoxyalkyl, amino alkyl, or aryl group;

wherein $R^4$ is H, a linear or branched chain alkyl, alkoxyalkyl, hydroxyalkyl, or a linear or branched chain alkenylalkyl group;

wherein $R^5$ and $R^6$ are independently the same or different and are H, OH, Cl, Br, I, F, $NO_2$, CN, $NH_2$, $N_3$, $CF_3$, a linear or branched chain alkyl, alkoxy, alkoxycarbonyl, acyl, alkylsulfoxide, or mono- or dialkylamino group, or together constitute a methylenedioxy group;

wherein $R^7$ and $R^8$ are independently the same or different and are H, CN, $CF_3$, OH, OR', OCOR', $NH_2$, NHR', $NR'_2$, NHCOR', $CONH_2$, CONHR', $CONR_2'$, COOH, COOR', CHO, COR', COSH, COSR', $COO(CH_2)_qOH$ or $COO(CH_2)_qOR'$, or a benzyl group, a linear or branched chain alkyl or cycloalkyl group, or are a heteroaryl group consisting of a pyridyl, indolyl, indolylalkyl, quinolinyl, isoquinolinyl, pyrryl, furyl or thiophene group, or an aryl group having the structure:

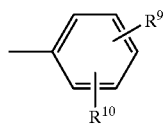

wherein $R^9$ and $R^{10}$ are independently the same or different and are H, Cl, Br, I, F, OH, $NO_2$, $N_3$, $Or^{iv}$, $OCOR^{iv}$, $OCOOR^{iv}$, $OCONHR^{iv}$, $NH_2$, $NHR^{iv}$, $NR^{iv}_2$, $NHCOR^{iv}$, $NHCOOR^{iv}$, or $NHCONHR^{iv}$;

wherein $R^{iv}$ is a linear or branched chain alkyl group;

wherein q is 2, 3, 4, or 5;

wherein $R^{12}$ is H or a linear chain alkyl group; and wherein n is 2, 3, or 4.

2. The compound of claim 1, wherein the compound is selected from the group consisting of:

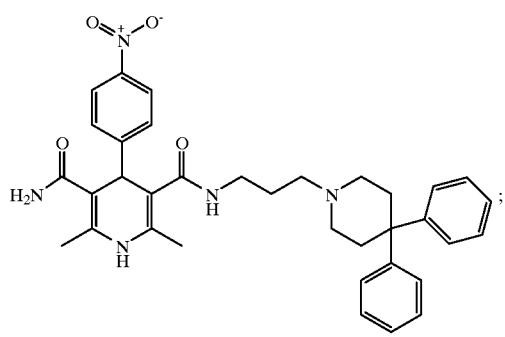

-continued

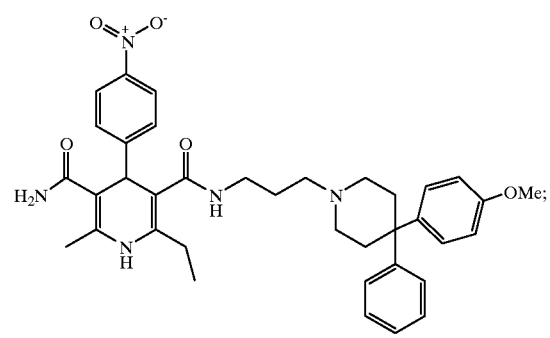

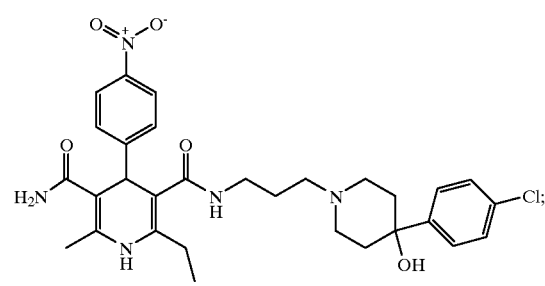

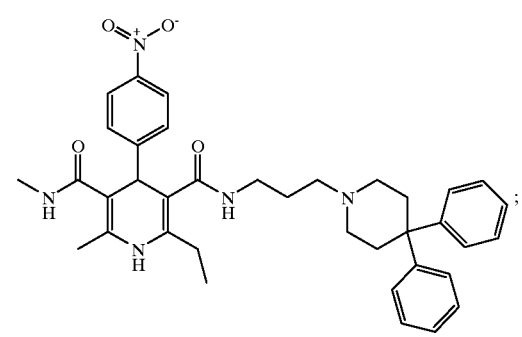

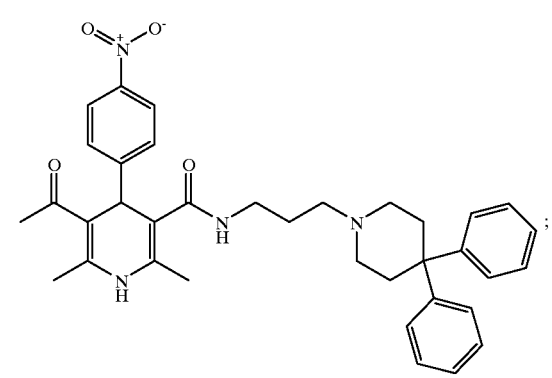

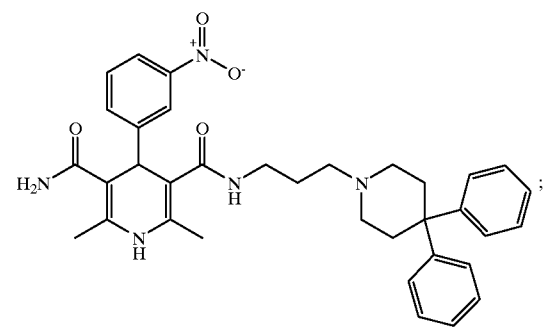

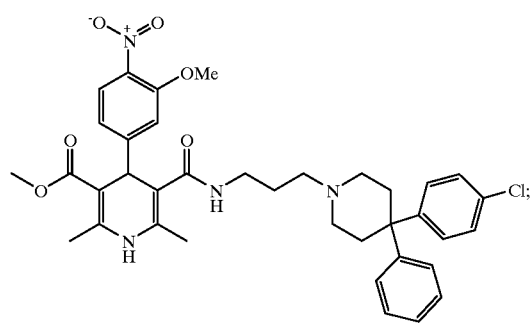
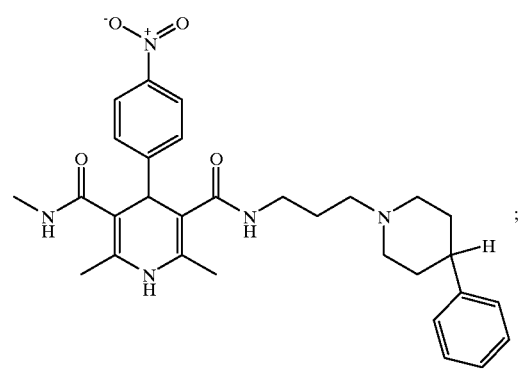
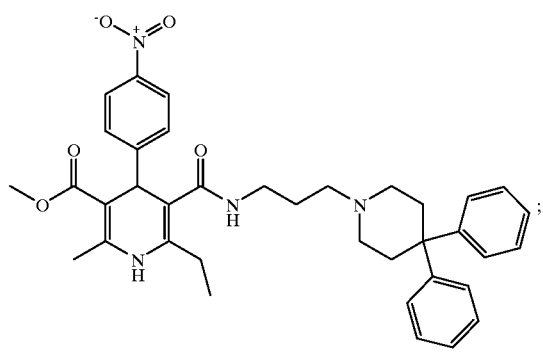
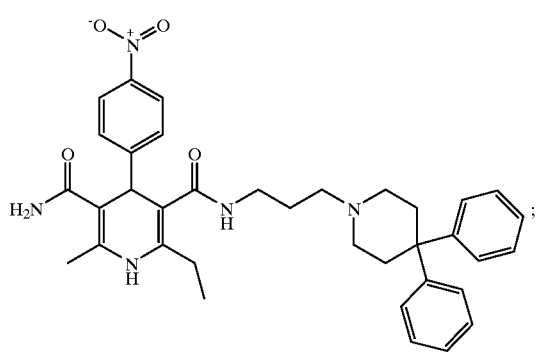
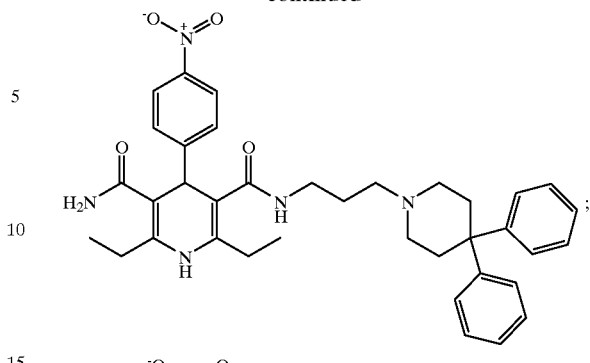
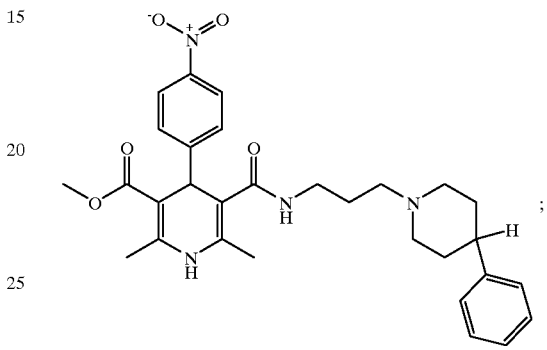
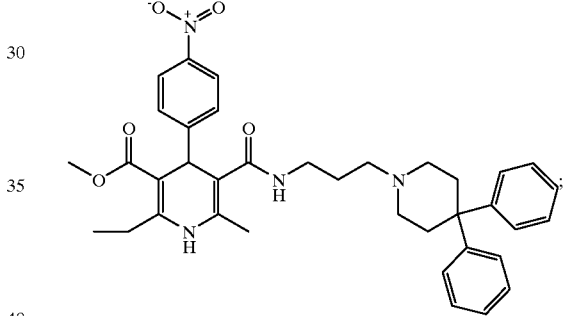
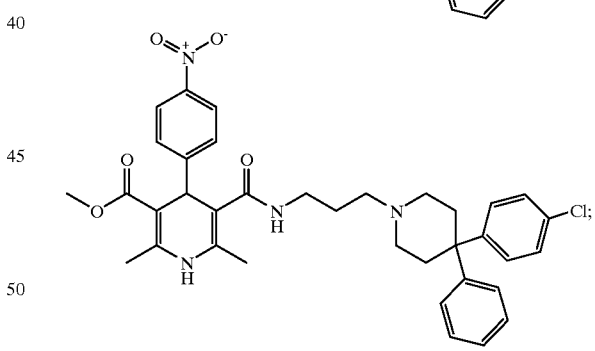
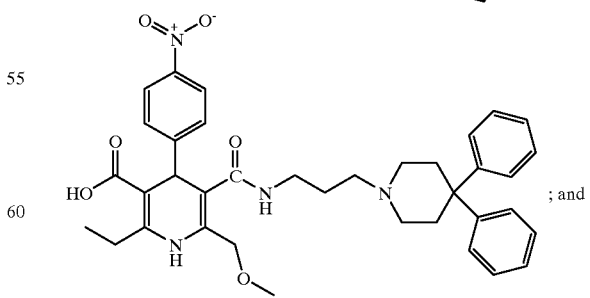

-continued

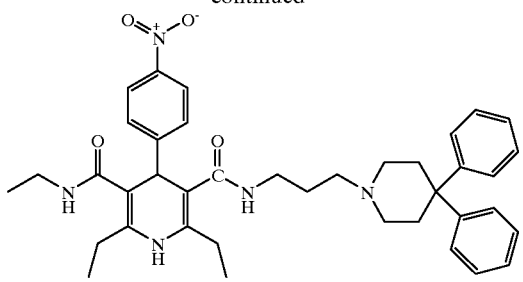

3. The compound of claim 1 having the structure:

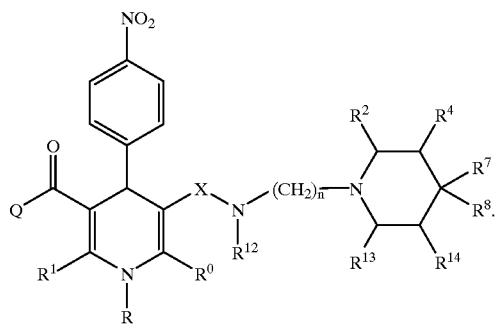

4. The compound of claim 1 having the structure:

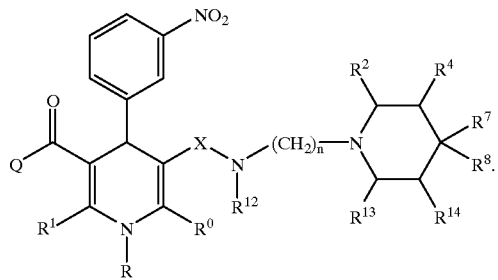

5. The compound of claim 1 having the structure:

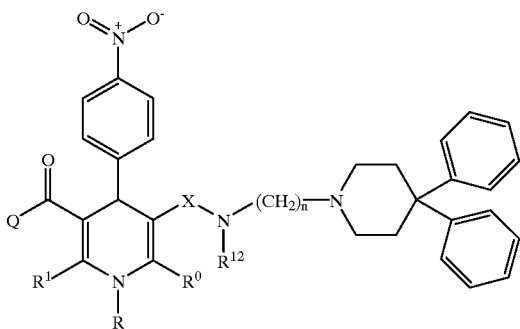

6. The compound of claim 5 having the structure:

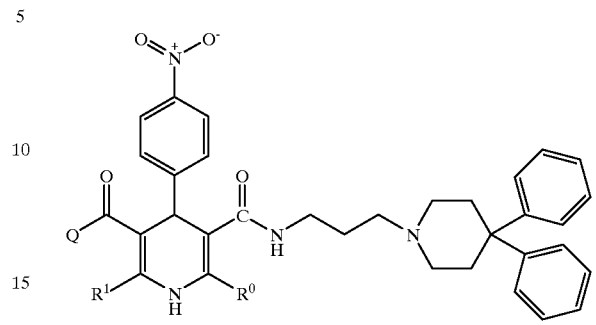

7. A pharmaceutical composition which comprises the compound of claim 1 in a therapeutically effective amount and a pharmaceutically acceptable carrier.

8. The pharmaceutical composition of claim 7 wherein the carrier is a solid and the composition is a tablet.

9. The pharmaceutical composition of claim 8 wherein the therapeutically effective amount is an amount from about 0.1 to about 500 mg.

10. The pharmaceutical composition of claim 9 wherein the therapeutically effective amount is from about 1 to 60 mg.

11. The pharmaceutical composition of claim 8, wherein the carrier is a liquid and the composition is a solution.

12. The pharmaceutical composition of claim 11 wherein the therapeutically effective amount is an amount from about 0.1 to about 500 mg per mL of solution.

13. The pharmaceutical composition of claim 12 wherein the therapeutically effective amount is an amount from about 1 to about 60 mg per mL of solution.

14. The pharmaceutical composition of claim 8, wherein the carrier is a gel and the composition is a suppository.

15. The pharmaceutical composition of claim 14, wherein the therapeutically effective amount is an amount from about 0.1 to about 500 mg.

16. A method of treating benign prostatic hyperplasia in a subject which comprises administering to the subject a therapeutically effective amount of any one of the compounds of claim 1.

* * * * *

UNITED STATES PATENT AND TRADEMARK OFFICE
CERTIFICATE OF CORRECTION

PATENT NO. : 6,211,198 B1  
DATED : April 3, 2001  
INVENTOR(S) : Charles Gluchowski et al.

Page 1 of 1

It is certified that error appears in the above-identified patent and that said Letters Patent is hereby corrected as shown below:

<u>Title page,</u>  
Inventors, change "Mohammed R. Marzabadi" to -- Mohammad R. Marzabadi --

<u>Column 287, claim 2,</u>  
Lines 50-51, change "2. The compound of claim 1, wherein the compound is selected from the group consisting of:" to -- 2. A compound selected from the group consisting of: --

Signed and Sealed this

Sixteenth Day of April, 2002

Attest:

JAMES E. ROGAN  
*Director of the United States Patent and Trademark Office*

*Attesting Officer*